(12) United States Patent
Reynolds et al.

(10) Patent No.: US 11,913,006 B2
(45) Date of Patent: Feb. 27, 2024

(54) PLANTS PRODUCING MODIFIED LEVELS OF MEDIUM CHAIN FATTY ACIDS

(71) Applicant: Commonwealth Scientific and Industrial Research Organisation, Acton (AU)

(72) Inventors: Kyle B. Reynolds, Acton (AU); Thomas Vanhercke, Kaleen (AU); Anna El Tahchy, Moncrieff (AU); Qing Liu, Giralang (AU); Surinder S. Singh, Downer (AU); James R. Petrie, Goulburn (AU)

(73) Assignee: NUSEED GLOBAL INNOVATION LTD., Manchester (GB)

( * ) Notice: Subject to any disclaimer, the term of this patent is extended or adjusted under 35 U.S.C. 154(b) by 872 days.

(21) Appl. No.: 16/355,215

(22) Filed: Mar. 15, 2019

(65) Prior Publication Data
US 2019/0284567 A1    Sep. 19, 2019

(30) Foreign Application Priority Data

Mar. 16, 2018   (AU) ............................... 2018201932
Mar. 16, 2018   (CA) ..................................... 2998211

(51) Int. Cl.
  *C12N 15/82*       (2006.01)
  *C12N 9/10*        (2006.01)
  (Continued)

(52) U.S. Cl.
  CPC .......... *C12N 15/8247* (2013.01); *C10G 3/00* (2013.01); *C10L 1/02* (2013.01); *C10L 1/026* (2013.01);
  (Continued)

(58) Field of Classification Search
  CPC ... C10G 3/00; C10L 1/02; C10L 1/026; C10L 2200/0476; C12N 15/52; C12N 15/8247;
  (Continued)

(56) References Cited

U.S. PATENT DOCUMENTS 6,329,518 B1   12/2001   Green
7,619,105 B2   11/2009   Green
(Continued)

OTHER PUBLICATIONS

Reynolds, Kyle B. (2015), "Metabolic engineering of medium-chain fatty acid biosynthesis in *Nicotiana benthamiana* plant leaf lipids," Frontiers in Plant Science, 6(164):1-14.
(Continued)

*Primary Examiner* — Latosha Hines
(74) *Attorney, Agent, or Firm* — Gary J. Gershik

(57) ABSTRACT

The present invention relates to methods of producing industrial products from plant lipids, particularly from vegetative parts of plants. In particular, the present invention provides oil products such as biofuel, and processes for producing these products, as well as plants having an increased level medium chain fatty acids such as lauric acid and myristic acid. In one particular embodiment, the present invention relates to combinations of modifications in a fatty acid thioesterase and one or more acyltransferases. In an embodiment, the present invention relates to a process for extracting lipids. In another embodiment, the lipid is converted to one or more hydrocarbon products in harvested plant vegetative parts to produce alkyl esters of the fatty acids which are suitable for use as a renewable biofuel.

33 Claims, 13 Drawing Sheets

Figure 1:
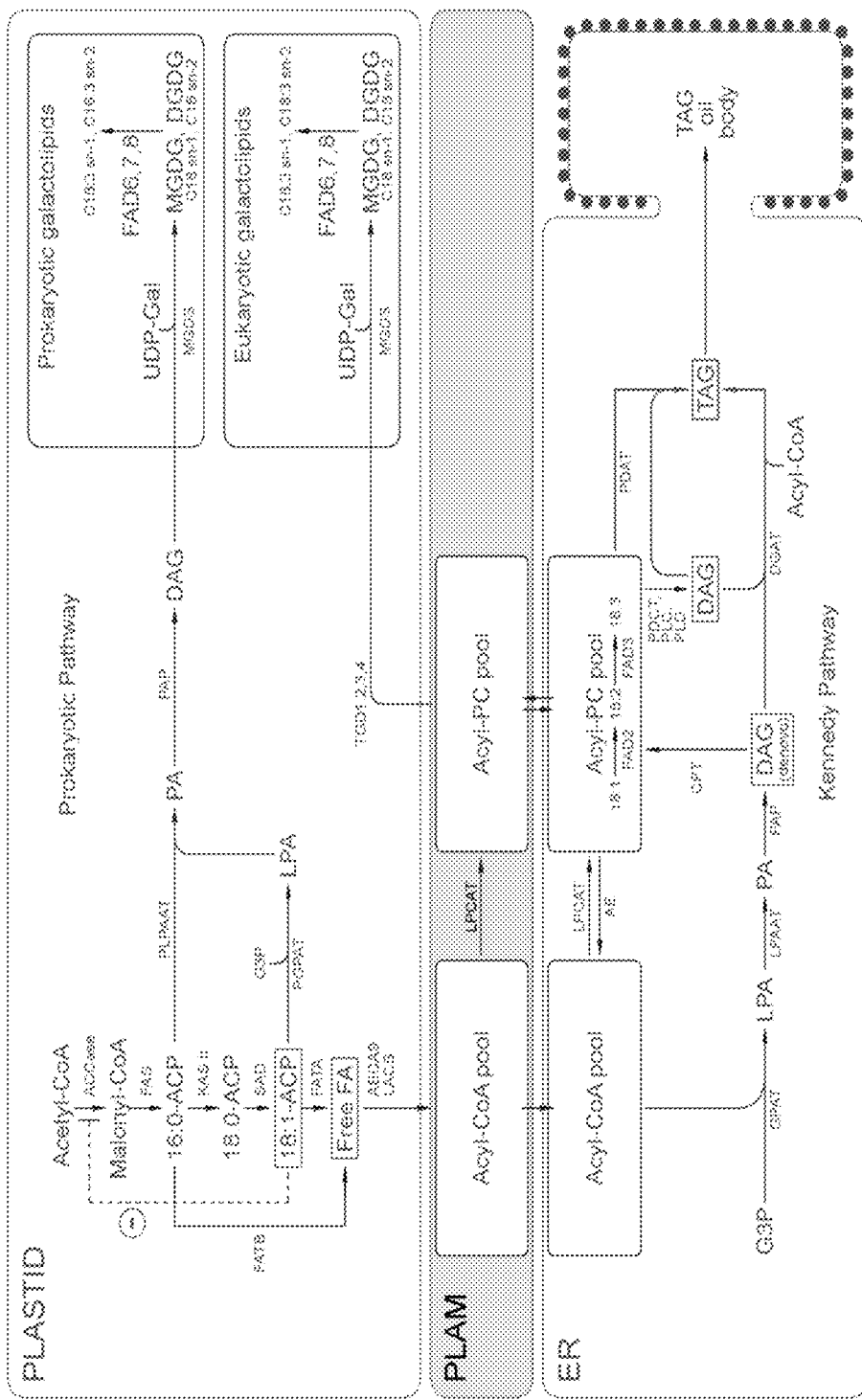

Specification includes a Sequence Listing.

(51) Int. Cl.
*C10L 1/02* (2006.01)
*C12N 9/16* (2006.01)
*C12N 15/52* (2006.01)
*C10G 3/00* (2006.01)

(52) U.S. Cl.
CPC ............. *C12N 9/1029* (2013.01); *C12N 9/16* (2013.01); *C12N 15/52* (2013.01); *C10L 2200/0476* (2013.01); *C12Y 203/01158* (2013.01); *C12Y 301/02014* (2013.01)

(58) Field of Classification Search
CPC ................... C12N 9/1029; C12N 9/16; C12Y 203/01158; C12Y 301/02014; Y02E 50/10; Y02P 30/20
See application file for complete search history.

(56) References Cited

U.S. PATENT DOCUMENTS

| | | | |
|---|---|---|---|
| 7,642,346 B2 | 1/2010 | Chaudhary | |
| 7,834,248 B2 | 11/2010 | Green | |
| 8,071,341 B2 | 12/2011 | Singh | |
| 8,921,652 B2 | 12/2014 | Liu | |
| 9,057,075 B2 | 6/2015 | Liu | |
| 9,512,438 B2 | 12/2016 | Vanhercke | |
| 9,976,107 B2 | 5/2018 | Petrie | |
| 10,246,718 B2 | 4/2019 | Vanhercke | |
| 10,260,021 B2 | 4/2019 | Zaplin | |
| 10,335,386 B2 | 7/2019 | Petrie | |
| 10,513,717 B2 | 12/2019 | Damcevski | |
| 10,570,405 B2 | 2/2020 | Devine | |
| 10,781,463 B2 | 9/2020 | Singh | |
| 10,793,507 B2 | 10/2020 | Petrie | |
| 10,800,729 B2 | 10/2020 | Petrie | |
| 10,876,127 B2 | 12/2020 | Wood | |
| 10,925,293 B2 | 2/2021 | Petrie | |
| 11,124,737 B2 | 9/2021 | Wood | |
| 11,166,479 B2 | 11/2021 | Miller | |
| 11,220,698 B2 | 1/2022 | Singh | |
| 2011/0126325 A1 | 5/2011 | Zhou | |
| 2011/0218348 A1 | 9/2011 | Zhou | |
| 2013/0164798 A1* | 6/2013 | Vanhercke | C10L 1/026 44/605 |
| 2016/0002566 A1* | 1/2016 | Vanhercke | C10L 1/08 554/162 |
| 2017/0058304 A1 | 3/2017 | Singh | |
| 2017/0349528 A1 | 12/2017 | Petrie | |
| 2019/0017063 A1 | 1/2019 | Mitchell | |
| 2019/0185871 A1 | 6/2019 | Zhou | |
| 2019/0203125 A1 | 7/2019 | Vanhercke | |
| 2019/0284567 A1 | 9/2019 | Reynolds | |
| 2019/0300894 A1 | 10/2019 | Vanhercke | |
| 2020/0080022 A1 | 3/2020 | Vanhercke | |
| 2020/0190531 A1 | 6/2020 | Devine | |
| 2020/0315115 A1 | 10/2020 | Belide | |
| 2021/0108220 A1 | 5/2021 | Wood | |
| 2021/0246097 A1 | 8/2021 | Petrie | |

OTHER PUBLICATIONS

Reynolds, Kyle B. (2017), "A reconfigured Kennedy pathway which promotes efficient accumulation of medium-chain fatty acids in leaf oils," Plant Biotechnology Journal, 15:1397-1408.

Reynolds, Kyle B. (2017). Metabolic Engineering for Medium Chain Fatty Acids in Plant Leaf Lipids. Thesis (BSc. Medical Science). Charles Sturt University.

Tahchy, Anna El et al. (2017), "Thioesterase overexpression in *Nicotiana benthamiana* leaf increases the fatty acid flux into triacylgycerol," FEBS Letters, 591:448-456.

Mar. 21, 2023 First Examination Report issued in connection with Canadian Patent Application No. 2,998,211.

\* cited by examiner

SEQUENCE LISTING

<160> NUMBER OF SEQ ID NOS: 152

<210> SEQ ID NO 1
<211> LENGTH: 520
<212> TYPE: PRT
<213> ORGANISM: Arabidopsis thaliana

<400> SEQUENCE: 1

```
Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Leu Ile
    130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
            180                 185                 190

Phe Thr Val Glu Lys Leu Val Leu Gln Lys Tyr Ile Ser Glu Pro Val
        195                 200                 205

Val Ile Phe Leu His Ile Ile Ile Thr Met Thr Glu Val Leu Tyr Pro
    210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
            260                 265                 270

Asn Pro Glu Val Ser Tyr Tyr Val Ser Leu Lys Ser Leu Ala Tyr Phe
        275                 280                 285

Met Val Ala Pro Thr Leu Cys Tyr Gln Pro Ser Tyr Pro Arg Ser Ala
    290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                325                 330                 335

Val Arg Asn Ser Lys His Pro Leu Lys Gly Asp Leu Leu Tyr Ala Ile
            340                 345                 350

Glu Arg Val Leu Lys Leu Ser Val Pro Asn Leu Tyr Val Trp Leu Cys
        355                 360                 365
```

Met Phe Tyr Cys Phe Phe His Leu Trp Leu Asn Ile Leu Ala Glu Leu
    370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
                405                 410                 415

Met Val Arg His Ile Tyr Phe Pro Cys Leu Arg Ser Lys Ile Pro Lys
            420                 425                 430

Thr Leu Ala Ile Ile Ala Phe Leu Val Ser Ala Val Phe His Glu
        435                 440                 445

Leu Cys Ile Ala Val Pro Cys Arg Leu Phe Lys Leu Trp Ala Phe Leu
    450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
            500                 505                 510

Met Asn Arg Lys Gly Ser Met Ser
        515                 520

<210> SEQ ID NO 2
<211> LENGTH: 3
<212> TYPE: PRT
<213> ORGANISM: Artificial Sequence
<220> FEATURE:
<223> OTHER INFORMATION: conserved sequence

<400> SEQUENCE: 2

Tyr Phe Pro
1

<210> SEQ ID NO 3
<211> LENGTH: 4
<212> TYPE: PRT
<213> ORGANISM: Artificial Sequence
<220> FEATURE:
<223> OTHER INFORMATION: conserved sequence

<400> SEQUENCE: 3

His Pro His Gly
1

<210> SEQ ID NO 4
<211> LENGTH: 4
<212> TYPE: PRT
<213> ORGANISM: Artificial Sequence
<220> FEATURE:
<223> OTHER INFORMATION: conserved sequence

<400> SEQUENCE: 4

Glu Pro His Ser
1

<210> SEQ ID NO 5
<211> LENGTH: 24
<212> TYPE: PRT
<213> ORGANISM: Artificial Sequence
<220> FEATURE:
<223> OTHER INFORMATION: conserved sequence
<220> FEATURE:
<221> NAME/KEY: MISC_FEATURE
<222> LOCATION: (2)..(2)

-continued

```
<223> OTHER INFORMATION: any amino acid
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (6)..(6)
<223> OTHER INFORMATION: Lysine (K) or Arginine (R)
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: MISC_FEATURE
<222> LOCATION: (9)..(11)
<223> OTHER INFORMATION: any amino acid
<220> FEATURE:
<221> NAME/KEY: MISC_FEATURE
<222> LOCATION: (13)..(15)
<223> OTHER INFORMATION: any amino acid
<220> FEATURE:
<221> NAME/KEY: MISC_FEATURE
<222> LOCATION: (16)..(16)
<223> OTHER INFORMATION: Leucine (L) or Valine (V)
<220> FEATURE:
<221> NAME/KEY: MISC_FEATURE
<222> LOCATION: (19)..(21)
<223> OTHER INFORMATION: any amino acid
<220> FEATURE:
<221> NAME/KEY: MISC_FEATURE
<222> LOCATION: (24)..(24)
<223> OTHER INFORMATION: Glutamic Acid (E) or Glutamine (Q)

<400> SEQUENCE: 5

Arg Xaa Gly Phe Xaa Xaa Xaa Ala Xaa Xaa Xaa Gly Xaa Xaa Xaa Xaa
1               5                   10                  15

Val Pro Xaa Xaa Xaa Phe Gly Xaa
            20

<210> SEQ ID NO 6
<211> LENGTH: 8
<212> TYPE: PRT
<213> ORGANISM: Artificial Sequence
<220> FEATURE:
<223> OTHER INFORMATION: conserved sequence
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (5)..(7)
<223> OTHER INFORMATION: any amino acid

<400> SEQUENCE: 6

Phe Leu Xaa Leu Xaa Xaa Xaa Asn
1               5

<210> SEQ ID NO 7
<211> LENGTH: 15
<212> TYPE: PRT
<213> ORGANISM: Artificial Sequence
<220> FEATURE:
<223> OTHER INFORMATION: conserved sequence

<400> SEQUENCE: 7

Gly Asp Leu Val Ile Cys Pro Glu Gly Thr Thr Cys Arg Glu Pro
1               5                   10                  15

<210> SEQ ID NO 8
<211> LENGTH: 6
```

```
<212> TYPE: PRT
<213> ORGANISM: Artificial Sequence
<220> FEATURE:
<223> OTHER INFORMATION: conserved sequence
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (5)..(5)
<223> OTHER INFORMATION: Threonine (T) or Valine (V)
<220> FEATURE:
<221> NAME/KEY: MISC_FEATURE
<222> LOCATION: (6)..(6)
<223> OTHER INFORMATION: Leucine (L) or Valine (V)

<400> SEQUENCE: 8

Asp Xaa Asp Xaa Xaa Xaa
1               5

<210> SEQ ID NO 9
<211> LENGTH: 26
<212> TYPE: PRT
<213> ORGANISM: Artificial Sequence
<220> FEATURE:
<223> OTHER INFORMATION: conserved sequence
<220> FEATURE:
<221> NAME/KEY: MISC_FEATURE
<222> LOCATION: (2)..(20)
<223> OTHER INFORMATION: any amino acid
<220> FEATURE:
<221> NAME/KEY: MISC_FEATURE
<222> LOCATION: (18)..(20)
<223> OTHER INFORMATION: present or absent
<220> FEATURE:
<221> NAME/KEY: MISC_FEATURE
<222> LOCATION: (21)..(21)
<223> OTHER INFORMATION: Glycine (G) or Serine (S)
<220> FEATURE:
<221> NAME/KEY: MISC_FEATURE
<222> LOCATION: (22)..(22)
<223> OTHER INFORMATION: Aspartic Acid (D) or Serine (S)
<220> FEATURE:
<221> NAME/KEY: MISC_FEATURE
<222> LOCATION: (23)..(25)
<223> OTHER INFORMATION: any amino acid
<220> FEATURE:
<221> NAME/KEY: MISC_FEATURE
<222> LOCATION: (26)..(26)
<223> OTHER INFORMATION: Aspartic Acid (D) or Asparagine (N)

<400> SEQUENCE: 9

Lys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 10
<211> LENGTH: 393
<212> TYPE: PRT
<213> ORGANISM: Sorghum bicolor

<400> SEQUENCE: 10

Met Ala Ser Pro Asn Pro Glu Ala Ala Ala Gly Leu Gln Thr Val Ala
1               5                   10                  15

Val Ala Ala Gly Gly Gly Glu Gly Gly Ser Ser Ser Ser Leu Gly Ala
            20                  25                  30
```

Val Ala Gly Ala Ala Val Ser Ser Gly Glu Leu Val Pro Arg
            35                  40                  45

Arg Ser Leu Ala Val Arg Lys Glu Arg Val Cys Thr Ala Lys Glu Arg
 50                  55                  60

Ile Ser Arg Met Pro Pro Cys Ala Ala Gly Lys Arg Ser Ser Ile Tyr
 65                  70                  75                  80

Arg Gly Val Thr Arg His Arg Trp Thr Gly Arg Tyr Glu Ala His Leu
                 85                  90                  95

Trp Asp Lys Ser Thr Trp Asn Gln Asn Gln Asn Lys Lys Gly Lys Gln
                100                 105                 110

Gly Ala Tyr Asp Asp Glu Glu Ala Ala Arg Ala Tyr Asp Leu Ala
            115                 120                 125

Ala Leu Lys Tyr Trp Gly Ala Gly Thr Gln Ile Asn Phe Pro Val Ser
130                 135                 140

Asp Tyr Ala Arg Asp Leu Glu Glu Met Gln Met Ile Ser Lys Glu Asp
145                 150                 155                 160

Tyr Leu Val Ser Leu Arg Arg Gln Leu His Asn Ser Arg Trp Asp Thr
                165                 170                 175

Ser Leu Gly Leu Gly Asn Asp Tyr Met Ser Leu Ser Cys Gly Lys Asp
            180                 185                 190

Ile Met Leu Asp Gly Lys Phe Ala Gly Ser Phe Gly Leu Glu Arg Lys
            195                 200                 205

Ile Asp Leu Thr Asn Tyr Ile Arg Trp Trp Leu Pro Lys Lys Thr Arg
210                 215                 220

Gln Ser Asp Thr Ser Lys Thr Glu Glu Ile Ala Asp Glu Ile Arg Ala
225                 230                 235                 240

Ile Glu Ser Ser Met Gln Gln Thr Glu Pro Tyr Lys Leu Pro Ser Leu
                245                 250                 255

Gly Leu Gly Ser Pro Ser Lys Pro Ser Ser Val Gly Leu Ser Ala Cys
            260                 265                 270

Ser Ile Leu Ser Gln Ser Asp Ala Phe Lys Ser Phe Leu Glu Lys Ser
            275                 280                 285

Thr Lys Leu Ser Glu Glu Cys Thr Leu Ser Lys Glu Ile Val Glu Gly
290                 295                 300

Lys Thr Val Ala Ser Val Pro Ala Thr Gly Tyr Asp Thr Gly Ala Ile
305                 310                 315                 320

Asn Ile Asn Met Asn Glu Leu Leu Val Gln Arg Ser Thr Tyr Ser Met
                325                 330                 335

Ala Pro Val Met Pro Thr Pro Met Lys Thr Thr Trp Ser Pro Ala Asp
            340                 345                 350

Pro Ser Val Asp Pro Leu Phe Trp Ser Asn Phe Val Leu Pro Ser Ser
            355                 360                 365

Gln Pro Val Thr Met Ala Thr Ile Thr Thr Thr Asn Glu Val Ser
370                 375                 380

Ser Ser Asp Pro Phe Gln Ser Gln Glu
385                 390

<210> SEQ ID NO 11
<211> LENGTH: 428
<212> TYPE: PRT
<213> ORGANISM: Lupinus angustifolius

<400> SEQUENCE: 11

Met Ala Ser Ser Ser Ser Asp Pro Gly Lys Ser Glu Ile Gly Gly Gly

```
  1               5                   10                  15
Ala Ala Glu Thr Ser Glu Ala Ala Val Ala Val Ala Val Thr Asn
             20                  25                  30
Asp Gln Ser Leu Leu Tyr Arg Gly Leu Lys Ala Lys Lys Glu Arg
             35                  40                  45
Gly Cys Thr Ala Lys Glu Arg Ile Ser Lys Met Pro Pro Cys Ala Ala
         50                  55                  60
Gly Lys Arg Ser Ser Ile Tyr Arg Gly Val Thr Arg His Arg Trp Thr
 65                  70                  75                  80
Gly Arg Tyr Glu Ala His Leu Arg Asp Lys Ser Thr Trp Asn Gln Asn
                 85                  90                  95
Gln Asn Lys Lys Gly Lys Gln Val Tyr Leu Gly Ala Tyr Asp Asp Glu
             100                 105                 110
Glu Ala Ala Arg Ala Tyr Asp Leu Ala Ala Leu Lys Tyr Trp Gly
             115                 120                 125
Pro Gly Thr Leu Ile Asn Phe Pro Val Thr Asp Tyr Thr Arg Asp Leu
 130                 135                 140
Glu Glu Met Gln Asn Val Ser Arg Glu Glu Tyr Leu Ala Ser Leu Arg
 145                 150                 155                 160
Arg Lys Ser Ser Gly Phe Ser Arg Gly Ile Ser Lys Tyr Arg Ala Leu
                 165                 170                 175
Ser Ser Arg Trp Glu Pro Ser Tyr Ser Arg Phe Ala Gly Ser Asp Tyr
             180                 185                 190
Phe Asn Ser Met His Tyr Gly Ala Gly Asp Ser Ala Ala Glu Ser
             195                 200                 205
Glu Tyr Ala Ser Gly Phe Cys Ile Glu Arg Lys Ile Asp Leu Thr Gly
 210                 215                 220
His Ile Lys Trp Trp Gly Ser Asn Lys Ser Arg Gln Pro Asp Ala Gly
 225                 230                 235                 240
Thr Arg Leu Ser Glu Glu Lys Arg His Gly Phe Ala Gly Asp Ile Cys
                 245                 250                 255
Ser Glu Pro Lys Thr Leu Glu Gln Lys Val Gln Pro Thr Glu Pro Tyr
             260                 265                 270
Gln Met Pro Glu Leu Gly Arg Ser His Asn Glu Lys Lys His Arg Ser
             275                 280                 285
Ser Ala Val Ser Ala Leu Ser Ile Leu Ser Gln Ser Ala Ala Tyr Lys
             290                 295                 300
Ser Leu Gln Glu Lys Ala Ser Lys Lys Gln Glu Asn Ser Thr Asp Asn
 305                 310                 315                 320
Asp Glu Asn Glu Asn Lys Asn Thr Val Asn Lys Leu Asp His Gly Lys
                 325                 330                 335
Ala Val Glu Lys Ser Ser Asn His Asp Gly Gly Ser Asp Arg Val Asp
             340                 345                 350
Ile Glu Ile Gly Thr Thr Gly Ala Leu Ser Leu Gln Arg Asn Ile Tyr
             355                 360                 365
Pro Leu Thr Pro Phe Leu Ser Ala Pro Leu Leu Thr Ala Tyr Asn Thr
 370                 375                 380
Val Asp Pro Ser Leu Val Asp Pro Val Leu Trp Thr Ser Leu Val Pro
 385                 390                 395                 400
Met Leu Ser Ala Gly Leu Ser Cys Pro Thr Gln Val Thr Lys Thr Glu
                 405                 410                 415
Thr Ser Ser Ser Tyr Thr Ile Phe Gln Pro Glu Gly
             420                 425
```

<210> SEQ ID NO 12
<211> LENGTH: 440
<212> TYPE: PRT
<213> ORGANISM: Ricinus communis

<400> SEQUENCE: 12

```
Met Ala Ser Ser Ser Ser Asp Pro Gly Leu Lys Pro Glu Leu Gly Gly
1               5                   10                  15

Gly Ser Gly Gly Glu Ser Ser Glu Ala Val Ile Ala Asn Asp Gln Leu
            20                  25                  30

Leu Leu Tyr Arg Gln Leu Lys Lys Pro Lys Lys Glu Arg Gly Cys Thr
        35                  40                  45

Ala Lys Glu Arg Ile Ser Lys Met Pro Pro Cys Thr Ala Gly Lys Arg
    50                  55                  60

Ser Ser Ile Tyr Arg Gly Val Thr Arg His Arg Trp Thr Gly Arg Tyr
65                  70                  75                  80

Glu Ala His Leu Trp Asp Lys Ser Thr Trp Asn Gln Asn Gln Asn Lys
                85                  90                  95

Lys Gly Lys Gln Gly Ala Tyr Asp Asp Glu Glu Ala Ala Ala Arg Ala
            100                 105                 110

Tyr Asp Leu Ala Ala Leu Lys Tyr Trp Gly Pro Gly Thr Leu Ile Asn
        115                 120                 125

Phe Pro Val Thr Asp Tyr Ser Arg Asp Leu Glu Glu Met Gln Asn Val
    130                 135                 140

Ser Arg Glu Glu Tyr Leu Ala Ser Leu Arg Arg Lys Ser Ser Gly Phe
145                 150                 155                 160

Ser Arg Gly Ile Ser Lys Tyr Arg Gly Leu Ser Ser Gln Trp Asp Ser
                165                 170                 175

Ser Phe Gly Arg Met Pro Gly Ser Glu Tyr Phe Ser Ser Ile Asn Tyr
            180                 185                 190

Gly Ala Ala Asp Asp Pro Ala Ala Glu Ser Glu Tyr Val Gly Ser Leu
        195                 200                 205

Cys Phe Glu Arg Lys Ile Asp Leu Thr Ser Tyr Ile Arg Trp Trp Gly
    210                 215                 220

Phe Asn Lys Thr Arg Glu Ser Val Ser Lys Ser Ser Asp Glu Arg Lys
225                 230                 235                 240

His Gly Tyr Gly Glu Asp Ile Ser Glu Leu Lys Ser Ser Glu Trp Ala
                245                 250                 255

Val Gln Ser Thr Glu Pro Tyr Gln Met Pro Arg Leu Gly Met Pro Asp
            260                 265                 270

Asn Gly Lys Lys His Lys Cys Ser Lys Ile Ser Ala Leu Ser Ile Leu
        275                 280                 285

Ser His Ser Ala Ala Tyr Lys Asn Leu Gln Glu Lys Ala Ser Lys Lys
    290                 295                 300

Gln Glu Asn Cys Thr Asp Asn Asp Glu Lys Glu Asn Lys Lys Thr Asn
305                 310                 315                 320

Lys Met Asp Tyr Gly Lys Ala Val Glu Lys Ser Thr Ser His Asp Gly
                325                 330                 335

Ser Asn Glu Arg Leu Gly Ala Ala Leu Gly Met Ser Gly Gly Leu Ser
            340                 345                 350

Leu Gln Arg Asn Ala Tyr Gln Leu Ala Pro Phe Leu Ser Ala Pro Leu
        355                 360                 365

Leu Thr Asn Tyr Asn Ala Ile Asp Pro Leu Val Asp Pro Ile Leu Trp
```

```
               370                 375                 380
Thr Ser Leu Val Pro Val Leu Pro Ala Gly Phe Ser Arg Asn Ser Glu
385                 390                 395                 400

Val Gly Met Gly Leu Gln Ile Val Ser Cys His Lys Asp Arg Asp Lys
                405                 410                 415

Phe Asn Leu Tyr Leu Leu Ser Ala Gly Val Ser Thr Phe Leu Leu
            420                 425                 430

Leu Val Val His Trp Arg Phe Cys
            435                 440

<210> SEQ ID NO 13
<211> LENGTH: 428
<212> TYPE: PRT
<213> ORGANISM: Lupinus angustifolius

<400> SEQUENCE: 13

Met Ala Ser Ser Ser Asp Pro Gly Lys Ser Glu Ile Gly Gly Gly
1               5                   10                  15

Ala Ala Glu Thr Ser Glu Ala Ala Val Ala Val Ala Val Thr Asn
                20                  25                  30

Asp Gln Ser Leu Leu Tyr Arg Gly Leu Lys Lys Ala Lys Lys Glu Arg
            35                  40                  45

Gly Cys Thr Ala Lys Glu Arg Ile Ser Lys Met Pro Pro Cys Ala Ala
50                  55                  60

Gly Lys Arg Ser Ser Ile Tyr Arg Gly Val Thr Arg His Arg Trp Thr
65                  70                  75                  80

Gly Arg Tyr Glu Ala His Leu Arg Asp Lys Ser Thr Trp Asn Gln Asn
                85                  90                  95

Gln Asn Lys Lys Gly Lys Gln Val Tyr Leu Gly Ala Tyr Asp Asp Glu
            100                 105                 110

Glu Ala Ala Ala Arg Ala Tyr Asp Leu Ala Ala Leu Lys Tyr Trp Gly
        115                 120                 125

Pro Gly Thr Leu Ile Asn Phe Pro Val Thr Asp Tyr Thr Arg Asp Leu
130                 135                 140

Glu Glu Met Gln Asn Val Ser Arg Glu Glu Tyr Leu Ala Ser Leu Arg
145                 150                 155                 160

Arg Lys Ser Ser Gly Phe Ser Arg Gly Ile Ser Lys Tyr Arg Ala Leu
                165                 170                 175

Ser Ser Arg Trp Glu Pro Ser Tyr Ser Arg Phe Ala Gly Ser Asp Tyr
            180                 185                 190

Phe Asn Ser Met His Tyr Gly Ala Gly Asp Asp Ser Ala Ala Glu Ser
        195                 200                 205

Glu Tyr Ala Ser Gly Phe Cys Ile Glu Arg Lys Ile Asp Leu Thr Gly
    210                 215                 220

His Ile Lys Trp Trp Gly Ser Asn Lys Ser Arg Gln Pro Asp Ala Gly
225                 230                 235                 240

Thr Arg Leu Ser Glu Glu Lys Arg His Gly Phe Ala Gly Asp Ile Cys
                245                 250                 255

Ser Glu Pro Lys Thr Leu Glu Gln Lys Val Gln Pro Thr Glu Pro Tyr
            260                 265                 270

Gln Met Pro Glu Leu Gly Arg Ser His Asn Glu Lys Lys His Arg Ser
        275                 280                 285

Ser Ala Val Ser Ala Leu Ser Ile Leu Ser Gln Ser Ala Ala Tyr Lys
    290                 295                 300
```

```
Ser Leu Gln Glu Lys Ala Ser Lys Lys Gln Glu Asn Ser Thr Asp Asn
305                 310                 315                 320

Asp Glu Asn Glu Asn Lys Asn Thr Val Asn Lys Leu Asp His Gly Lys
                325                 330                 335

Ala Val Glu Lys Ser Ser Asn His Asp Gly Gly Ser Asp Arg Val Asp
            340                 345                 350

Ile Glu Ile Gly Thr Thr Gly Ala Leu Ser Leu Gln Arg Asn Ile Tyr
        355                 360                 365

Pro Leu Thr Pro Phe Leu Ser Ala Pro Leu Leu Thr Ala Tyr Asn Thr
    370                 375                 380

Val Asp Pro Ser Leu Val Asp Pro Val Leu Trp Thr Ser Leu Val Pro
385                 390                 395                 400

Met Leu Ser Ala Gly Leu Ser Cys Pro Thr Gln Val Thr Lys Thr Glu
                405                 410                 415

Thr Ser Ser Ser Tyr Thr Ile Phe Gln Pro Glu Gly
            420                 425
```

<210> SEQ ID NO 14
<211> LENGTH: 11
<212> TYPE: PRT
<213> ORGANISM: Artificial Sequence
<220> FEATURE:
<223> OTHER INFORMATION: conserved sequence
<220> FEATURE:
<221> NAME/KEY: MISC_FEATURE
<222> LOCATION: (4)..(4)
<223> OTHER INFORMATION: Threonine (T) or Serine (S)

<400> SEQUENCE: 14

```
Arg Gly Val Xaa Arg His Arg Trp Thr Gly Arg
1               5                   10
```

<210> SEQ ID NO 15
<211> LENGTH: 8
<212> TYPE: PRT
<213> ORGANISM: Artificial Sequence
<220> FEATURE:
<223> OTHER INFORMATION: conserved sequence
<220> FEATURE:
<221> NAME/KEY: MISC_FEATURE
<222> LOCATION: (1)..(1)
<223> OTHER INFORMATION: Phenylalanine (F) or Tyrosine (Y)

<400> SEQUENCE: 15

```
Xaa Glu Ala His Leu Trp Asp Lys
1               5
```

<210> SEQ ID NO 16
<211> LENGTH: 9
<212> TYPE: PRT
<213> ORGANISM: Artificial Sequence
<220> FEATURE:
<223> OTHER INFORMATION: conserved sequence

<400> SEQUENCE: 16

```
Asp Leu Ala Ala Leu Lys Tyr Trp Gly
1               5
```

<210> SEQ ID NO 17
<211> LENGTH: 8
<212> TYPE: PRT
<213> ORGANISM: Artificial Sequence
<220> FEATURE:
<223> OTHER INFORMATION: conserved sequence
<220> FEATURE:

```
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (5)..(5)
<223> OTHER INFORMATION: Serine (S) or Alanine (A)
<220> FEATURE:
<221> NAME/KEY: MISC_FEATURE
<222> LOCATION: (8)..(8)
<223> OTHER INFORMATION: any amino acid

<400> SEQUENCE: 17

Ser Xaa Gly Phe Xaa Arg Gly Xaa
1               5

<210> SEQ ID NO 18
<211> LENGTH: 14
<212> TYPE: PRT
<213> ORGANISM: Artificial Sequence
<220> FEATURE:
<223> OTHER INFORMATION: conserved sequence
<220> FEATURE:
<221> NAME/KEY: MISC_FEATURE
<222> LOCATION: (3)..(3)
<223> OTHER INFORMATION: Histidine (H) or Glutamine (Q)
<220> FEATURE:
<221> NAME/KEY: MISC_FEATURE
<222> LOCATION: (6)..(6)
<223> OTHER INFORMATION: Arginine (R) or Lysine (K)
<220> FEATURE:
<221> NAME/KEY: MISC_FEATURE
<222> LOCATION: (13)..(13)
<223> OTHER INFORMATION: Arginine (R) or Lysine (K)

<400> SEQUENCE: 18

His His Xaa Asn Gly Xaa Trp Glu Ala Arg Ile Gly Xaa Val
1               5                   10

<210> SEQ ID NO 19
<211> LENGTH: 9
<212> TYPE: PRT
<213> ORGANISM: Artificial Sequence
<220> FEATURE:
<223> OTHER INFORMATION: conserved sequence
<220> FEATURE:
<221> NAME/KEY: MISC_FEATURE
<222> LOCATION: (7)..(7)
<223> OTHER INFORMATION: any amino acid

<400> SEQUENCE: 19

Gln Glu Glu Ala Ala Ala Xaa Tyr Asp
1               5

<210> SEQ ID NO 20
<211> LENGTH: 11142
<212> TYPE: DNA
<213> ORGANISM: Artificial Sequence
<220> FEATURE:
<223> OTHER INFORMATION: TDNA sequence

<400> SEQUENCE: 20
tcctgtggtt ggcatgcaca tacaaatgga cgaacggata aaccttttca cgccctttta      60
aatatccgat tattctaata aacgctcttt tctcttaggt ttacccgcca atatatcctg     120
tcaaacactg atagtttaaa ctgaaggcgg gaaacgacaa tctgctagtg gatctcccag     180
tcacgacgtt gtaaaacggg cgccctagaa tctaattatt ctattcagac taaattagta     240
taagtatttt tttaatcaat aaataataat taataattta ttagtaggag tgattgaatt     300
```

```
tataatatat ttttttttaat catttaaaga atcttatatc tttaaattga caagagtttt    360
aaatggggag agtgttatca tatcacaagt aggattaatg tgttatagtt tcacatgcat    420
tacgataagt tgtgaaagat aacattatta tatataacaa tgacaatcac tagcgatcga    480
gtagtgagag tcgtcttatt acactttctt ccttcgatct gtcacatggc ggcggcccga    540
attctcacac aaggtagttg caagacactg aagtggtggt agtggtagta gaagaagcag    600
aatcggtaga aaggcaagac aatggagaag atgaagatgg tggagattct cttcccacaa    660
cgcagcaatc aaggttttca aggttaaggc actcgtgctt tccatcatcg aacatgaagt    720
cgatgttatc ctcgaaagca agctcgttga agagttctgg gtactcaatt gggttctcgt    780
tagcaaggtt ttgatcggta aggaatgggg agaatccagt atccatcatg cagaagttcc    840
aagcaagttc gttgttatct ccgcacctat ccatttccat gatggtggaa gaatcaatgc    900
agcagttaac aacggcagct tcctcagaat atcccacaat ttcagcctct tgttgctcag    960
ccttctcttc ctctttttct tcttcctctt gaggtggttc ctcaacgtat tgttgcttaa   1020
cctcttccct aggttcctct ttagcttctc tagtctcaac ctcttgctta gcctcaacaa   1080 gaatacctc ttgatggtta gcctggttaa ctgggaatgg gaaaacgccc ttcttcttaa    1140
gcctgtcgat gtagttggag atatcgaagt tggtaacagc gttagcacct ctgtactcaa   1200
tagcagccat atcataagca gctgcagcct cttcttgagt gttgtaagtt ccgaggtaga   1260
ggtacttgtt tccgaaaact cttccaatcc tagcttccca tcttccgtta tgatgatgcc   1320
tagcaactcc cctatactta gaaactcccc tagagaatcc agatgactgc cttctaaggg   1380
aagcaagata ctcttctttg gtcaccctct gcatctcttc aagttctttg gtgtaagtct   1440
cagctgggaa gttaagaatg gtatctgggc cccaatactt aagagcagca agatcatagg   1500
tatgagcagc agcctcttca gaatcataag ctccaaggta aacctgcttg cccttcttgt   1560
tttggatgga gttccaagag gacttatccc aaaggtgagc ttcgaatctt ccagtccatc   1620 tatgccagt aacacctctg tagatagatg accttctggt agaagctgga gaagttgggt    1680
tatgagactt atcgccagat ggagatgact tcttagccct cttagctctc tttggtcttg   1740
gagcttcaga ttgaattggg ctagaggtag tagtagaaga ggacactgaa gaagatggag   1800
aactagagca ggtagaggta gtgagcctct tcttcatgaa ttctgttctt ctttactctt   1860
tgtgtgactg aggtttggtc tagtgctttg gtcatctata tataatgata acaacaatga   1920
gaacaagctt tggagtgatc ggagggtcta ggatacatga gattcaagtg gactaggatc   1980
tacaccgttg gattttgagt gtggatatgt gtgaggttaa ttttacttgg taacggccac   2040
aaaggcctaa ggagaggtgt tgagacccct atcggcttga accgctggaa taatgccacg   2100
tggaagataa ttccatgaat cttatcgtta tctatgagtg aaattgtgtg atggtggagt   2160
ggtgcttgct cattttactt gcctggtgga cttggcccct tccttatggg gaatttatat   2220
tttacttact atagagcttt catacctttt ttttaccttg gatttagtta atatataatg   2280
gtatgattca tgaataaaaa tgggaaattt ttgaatttgt actgctaaat gcataagatt   2340
aggtgaaact gtggaatata tattttttc atttaaaagc aaaatttgcc ttttactaga    2400
attataaata tagaaaaata tataacattc aaataaaaat gaaataaga actttcaaaa    2460 aacagaacta tgtttaatgt gtaaagatta gtcgcacatc aagtcatctg ttacaatatg   2520
ttacaacaag tcataagccc aacaaagtta gcacgtctaa ataaactaaa gagtccacga   2580
aaatattaca aatcataagc ccaacaaagt tattgatcaa aaaaaaaaaa cgcccaacaa   2640
agctaaacaa agtccaaaaa aaacttctca agtctccatc ttcctttatg aacattgaaa   2700
```

```
actatacaca aaacaagtca gataaatctc tttctgggcc tgtcttccca acctcctaca   2760
tcacttccct atcggattga atgttttact tgtacctttt ccgttgcaat gatattgata   2820
gtatgtttgt gaaaactaat agggttaaca atcgaagtca tggaatatgg atttggtcca   2880
agattttccg agagctttct agtagaaagc ccatcaccag aaatttacta gtaaaataaa   2940
tcaccaatta ggtttcttat tatgtgccaa attcaatata attatagagg atatttcaaa   3000
tgaaaacgta tgaatgttat tagtaaatgg tcaggtaaga cattaaaaaa atcctacgtc   3060
agatattcaa ctttaaaaat tcgatcagtg tggaattgta caaaaatttg ggatctacta   3120
tatatatata atgctttaca acacttggat ttttttttgg aggctggaat ttttaatcta   3180
catatttgtt ttggccatgc accaactcat tgtttagtgt aatactttga ttttgtcaaa   3240
tatatgtgtt cgtgtatatt tgtataagaa tttctttgac catatacaca cacacatata   3300
tatatatata tatatattat atatcatgca cttttaattg aaaaaataat atatatatat   3360
atagtgcatt ttttctaaca accatatatg ttgcgattga tctgcaaaaa tactgctaga   3420
gtaatgaaaa atataatcta ttgctgaaat tatctcagat gttaagtttt tcttaaagta   3480
aattctttca aattttagct aaaagtcttg taataactaa agaataatac acaatctcga   3540
ccacggaaaa aaaacacata ataaatttgg ggcccctaga atctaattat tctattcaga   3600
ctaaattagt ataagtattt ttttaatcaa taaataataa ttataatttt attagtagga   3660
gtgattgaat ttataatata ttttttttaa tcatttaaag aatcttatat ctttaaattg   3720
acaagagttt taaatgggga gagtgttatc atatcacaag taggattaat gtgttatagt   3780
ttcacatgca ttacgataag ttgtgaaaga taacattatt atatataaca atgacaatca   3840
ctagcgatcg agtagtgaga gtcgtcttat tacactttct tccttcgatc tgtcacatgg   3900
cggcggcccg cggccgcttc attactcgag ccaggaggat ggatcgatgc tggtctgaga   3960
ccctgctacc ggttgctgac tgaactgctc ggcacggtcc ttcatttcac gggccttgct   4020
cgccaacttt gtcttggccg actccaactg atccgctccg ggtggatgtt tccccgtcag   4080
gtaacggtag atccaggaca gcacagacag agcggcaaca ccaaatcccc cgcttgccag   4140
aaaacccgct cccaacagga agatggtgat gactgcagat cagaaaaact cagattaatc   4200
gacaaattcg atcgcacaaa ctagaaacta acaccagatc tagatagaaa tcacaaatcg   4260
aagagtaatt attcgacaaa actcaaatta tttgaacaaa tcggatgata tctatgaaac   4320
cctaatcgag aattaagatg atatctaacg atcaaaccca gaaatcgtc ttcgatctaa   4380 gattaacaga atctaaacca aagaacatat acgaaattgg gatcgaacga aaacaaaatc   4440
gaagattttg agagaataag gaacacagaa atttacctgc agggaccagt acaggcgaga   4500
agatcaccag gagaggtgtg gcgattgtca gcgcaatgac cgttccagcc agggtcaacc   4560
cggataacac caacaggcta cctccggcag taaccgcggt cgctgccttt acaacacgct   4620
gagcacgcgg ttgcagttgc aagtgggggg cacgtgtttg ttgctgctgc ccgtagtgct   4680
ctgccatggt ttttttttaac ggagcaagcg gccgctgttc ttctttactc tttgtgtgac   4740
tgaggtttgg tctagtgctt tggtcatcta tatataatga taacaacaat gagaacaagc   4800
tttggagtga tcggagggtc taggatacat gagattcaag tggactagga tctacaccgt   4860
tggattttga gtgtggatat gtgtgaggtt aatttttactt ggtaacggcc acaaaggcct   4920
aaggagaggt gttgagaccc ttatcggctt gaaccgctgg aataatgcca cgtggaagat   4980
aattccatga atcttatcgt tatctatgag tgaaattgtg tgatggtgga gtggtgcttg   5040
```

```
ctcattttac ttgcctggtg gacttggccc tttccttatg gggaatttat attttactta    5100
ctatagagct ttcatacctt tttttttacct tggatttagt taatatataa tggtatgatt    5160
catgaataaa aatgggaaat ttttgaattt gtactgctaa atgcataaga ttaggtgaaa    5220
ctgtggaata tatatttttt tcatttaaaa gcaaaatttg cctttttacta gaattataaa    5280
tatagaaaaa tatataacat tcaaataaaa atgaaaataa aactttcaa aaaacagaac     5340
tatgttttaat gtgtaaagat tagtcgcaca tcaagtcatc tgttacaata tgttacaaca   5400
agtcataagc ccaacaaagt tagcacgtct aaataaacta aagagtccac gaaaatatta    5460
caaatcataa gcccaacaaa gttattgatc aaaaaaaaaa aacgcccaac aaagctaaac    5520
aaagtccaaa aaaaacttct caagtctcca tcttcctttta tgaacattga aaactataca   5580
caaaacaagt cagataaatc tctttctggg cctgtcttcc caacctccta catcacttcc    5640
ctatcggatt gaatgtttta cttgtacctt ttccgttgca atgatattga tagtatgttt    5700
gtgaaaacta atagggttaa caatcgaagt catggaatat ggatttggtc caagattttc    5760
cgagagcttt ctagtagaaa gcccatcacc agaaatttac tagtaaaata aatcaccaat    5820
taggtttctt attatgtgcc aaattcaata taattataga ggatatttca aatgaaaacg    5880
tatgaatgtt attagtaaat ggtcaggtaa gacattaaaa aaatcctacg tcagatattc    5940
aactttaaaa attcgatcag tgtggaattg tacaaaaatt tgggatctac tatatatata   6000
taatgcttta caacacttgg attttttttt ggaggctgga attttttaatc tacatatttg    6060
ttttggccat gcaccaactc attgtttagt gtaatacttt gattttgtca aatatatgtg    6120
ttcgtgtata tttgtataag aatttctttg accatataca cacacacata tatatatata    6180
tatatatatt atatatcatg cacttttaat tgaaaaaata atatatatat atatagtgca    6240
ttttttctaa caaccatata tgttgcgatt gatctgcaaa aatactgcta gagtaatgaa    6300
aaatataatc tattgctgaa attatctcag atgttaagat tttcttaaag taaattctttt   6360
caaattttag ctaaaagtct tgtaataact aagaataat acacaatctc gaccacggaa     6420
aaaaaacaca taataaattt gggcgcgccg cgtattggct agagcagctt gccaacatgg    6480
tggagcacga cactctcgtc tactccaaga atatcaaaga tacagtctca gaagaccaaa    6540
gggctattga gacttttcaa caaagggtaa tatcgggaaa cctcctcgga ttccattgcc    6600
cagctatctg tcacttcatc aaaaggacag tagaaaagga aggtggcacc tacaaatgcc    6660
atcattgcga taaggaaag gctatcgttc aagatgcctc tgccgacagt ggtcccaaag     6720
atggaccccc acccacgagg agcatcgtgg aaaaagaaga cgttccaacc acgtcttcaa    6780
agcaagtgga ttgatgtgat aacatggtgg agcacgacac tctcgtctac tccaagaata    6840
tcaaagatac agtctcagaa gaccaaaggg ctattgagac ttttcaacaa agggtaatat    6900
cgggaaacct cctcggattc cattgcccag ctatctgtca cttcatcaaa aggacagtag    6960
aaaaggaagg tggcacctac aaatgccatc attgcgataa aggaaaggct atcgttcaag    7020
atgcctctgc cgacagtggt cccaaagatg gaccccacc cacgaggagc atcgtggaaa     7080
aagaagacgt tccaaccacg tcttcaaagc aagtggattg atgtgatatc tccactgacg    7140
taagggatga cgcacaatcc cactatcctt cgcaagacct tcctctatat aaggaagttc    7200
atttcatttg gagaggacac gctgaaatca ccagtctctc tctacaaatc tatctctgcg    7260
atcgcatggc gattttggat tctgctggcg ttactacggt gacggagaac ggtggcggag    7320
agttcgtcga tcttgatagg cttcgtcgac ggaaatcgag atcggattct tctaacggac    7380
ttcttctctc tggttccgat aataattctc cttcggatga tgttggagct cccgccgacg    7440
```

```
ttagggatcg gattgattcc gttgttaacg atgacgctca gggaacagcc aatttggccg    7500
gagataataa cggtggtggc gataataacg gtggtggaag aggcggcgga gaaggaagag    7560
gaaacgccga tgctacgttt acgtatcgac cgtcggttcc agctcatcgg agggcgagag    7620
agagtccact tagctccgac gcaatcttca aacagagcca tgccggatta ttcaacctct    7680
gtgtagtagt tcttattgct gtaaacagta gactcatcat cgaaaatctt atgaagtatg    7740
gttggttgat cagaacggat ttctggttta gttcaagatc gctgcgagat tggccgcttt    7800
tcatgtgttg tatatccctt tcgatctttc ctttggctgc ctttacggtt gagaaattgg    7860
tacttcagaa atacatatca gaacctgttg tcatctttct tcatattatt atcaccatga    7920
cagaggtttt gtatccagtt tacgtcaccc taaggtgtga ttctgctttt ttatcaggtg    7980
tcactttgat gctcctcact tgcattgtgt ggctaaagtt ggtttcttat gctcatacta    8040
gctatgacat aagatcccta gccaatgcag ctgataaggc caatcctgaa gtctcctact    8100
acgttagctt gaagagcttg gcatatttca tggtcgctcc cacattgtgt tatcagccaa    8160
gttatccacg ttctgcatgt atacggaagg gttgggtggc tcgtcaattt gcaaaactgg    8220
tcatattcac cggattcatg ggatttataa tagaacaata tataaatcct attgtcagga    8280
actcaaagca tcctttgaaa ggcgatcttc tatatgctat tgaaagagtg ttgaagcttt    8340
cagttccaaa tttatatgtg tggctctgca tgttctactg cttcttccac ctttggttaa    8400
acatattggc agagcttctc tgcttcgggg atcgtgaatt ctacaaagat tggtggaatg    8460
caaaaagtgt gggagattac tggagaatgt ggaatatgcc tgttcataaa tggatggttc    8520
gacatatata cttcccgtgc ttgcgcagca agataccaaa gacactcgcc attatcattg    8580
ctttcctagt tctgcagtc tttcatgagc tatgcatcgc agttccttgt cgtctcttca    8640
agctatgggc ttttcttggg attatgtttc aggtgccttt ggtcttcatc acaaactatc    8700
tacaggaaag gtttggctca acggtgggga acatgatctt ctggttcatc ttctgcattt    8760
tcggacaacc gatgtgtgtg cttctttatt accacgacct gatgaaccga aaaggatcga    8820
tgtcatgagc gatcgcgatc gttcaaacat ttggcaataa agtttcttaa gattgaatcc    8880
tgttgccggt cttgcgatga ttatcatata atttctgttg aattacgtta agcatgtaat    8940
aattaacatg taatgcatga cgttatttat gagatgggtt tttatgatta gagtcccgca    9000
attatacatt taatacgcga tagaaaacaa atatatagcgc gcaaactagg ataaattatc    9060
gcgcgcggtg tcatctatgt tactagatcc ctgcagggcg tattggctag agcagcttgc    9120
caacatggtg gagcacgaca ctctcgtcta ctccaagaat atcaaagata cagtctcaga    9180
agaccaaagg gctattgaga cttttcaaca agggtaata tcgggaaacc tcctcggatt    9240
ccattgccca gctatctgtc acttcatcaa aaggacagta gaaaggaag gtggcaccta    9300 caaatgccat cattgcgata aaggaaaggc tatcgttcaa gatgcctctg ccgacagtgg    9360
tcccaaagat ggaccccac ccacgaggag catcgtggaa aaagaagacg ttccaaccac    9420
gtcttcaaag caagtggatt gatgtgataa catggtggag cacgacactc tcgtctactc    9480
caagaatatc aaagatacag tctcagaaga ccaaagggct attgagactt ttcaacaaag    9540
ggtaatatcg gaaacctcc tcggattcca ttgcccagct atctgtcact tcatcaaaag    9600
gacagtagaa aaggaaggtg gcacctacaa atgccatcat tgcgataaag gaaaggctat    9660
cgttcaagat gcctctgccg acagtggtcc caaagatgga ccccacccca cgaggagcat    9720
cgtggaaaaa gaagacgttc caaccacgtc ttcaaagcaa gtggattgat gtgatatctc    9780
```

```
cactgacgta agggatgacg cacaatccca ctatccttcg caagaccttc ctctatataa    9840
ggaagttcat ttcatttgga gaggacacgc tgaaatcacc agtctctctc tacaaatcta    9900
tctctctcga gatgattgaa caagatggat tgcacgcagg ttctccggcc gcttgggtgg    9960
agaggctatt cggctatgac tgggcacaac agacaatcgg ctgctctgat gccgccgtgt   10020
tccggctgtc agcgcagggg aggccggttc tttttgtcaa gaccgacctg tccggtgccc   10080
tgaatgaact tcaagacgag gcagcgcggc tatcgtggct ggccacgacg ggcgttcctt   10140
gcgcagctgt gctcgacgtt gtcactgaag cgggaaggga ctggctgcta ttgggcgaag   10200
tgccggggca ggatctcctg tcatctcacc ttgctcctgc cgagaaagta tccatcatgg   10260
ctgatgcaat gcggcggctg catacgcttg atccggctac ctgcccattc gaccaccaag   10320
cgaaacatcg catcgagcga gcacgtactc ggatggaagc cggtcttgtc gatcaggatg   10380
atctggacga agagcatcag ggctcgcgc cagccgaact gttcgccagg ctcaaggcgc   10440
gcatgcccga cggcgaggat ctcgtcgtga ctcatggcga tgcctgcttg ccgaatatca   10500
tggtggaaaa tggccgcttt tctggattca tcgactgtgg ccggctgggt gtggcggacc   10560
gctatcagga catagcgttg gctacccgtg atattgctga agagcttggc ggcgaatggg   10620
ctgaccgctt cctcgtgctt tacggtatcg ccgctcccga ttcgcagcgc atcgccttct   10680
atcgccttct tgacgagttc ttctgaaacg cgtgatcgtt caaacatttg gcaataaagt   10740
ttcttaagat tgaatcctgt tgccggtctt gcgatgatta tcatataatt tctgttgaat   10800
tacgttaagc atgtaataat taacatgtaa tgcatgacgt tatttatgag atgggttttt   10860
atgattagag tcccgcaatt atacatttaa tacgcgatag aaaacaaaat atagcgcgca   10920
aactaggata aattatcgcg cgcggtgtca tctatgttac tagatcgacg tccgtacggt   10980
taaaaccacc ccagtacatt aaaaacgtcc gcaatgtgtt attaagttgt ctaagcgtca   11040
atttgtttac accacaatat atcctgccac cagccagcca acagctcccc gaccggcagc   11100
tcggcacaaa atcaccactc gatacaggca gcccatcagt cc                       11142
```

<210> SEQ ID NO 21  
<211> LENGTH: 16749  
<212> TYPE: DNA  
<213> ORGANISM: Artificial Sequence  
<220> FEATURE:  
<223> OTHER INFORMATION: vector sequence

<400> SEQUENCE: 21

```
gcttcctcgt gctttacggt atcgccgctc ccgattcgca gcgcatcgcc ttctatcgcc      60
ttcttgacga gttcttctga aacgcgtgat cgttcaaaca tttggcaata aagtttctta     120
agattgaatc ctgttgccgg tcttgcgatg attatcatat aatttctgtt gaattacgtt     180
aagcatgtaa taattaacat gtaatgcatg acgttattta tgagatgggt ttttatgatt     240
agagtcccgc aattatacat ttaatacgcg atagaaaaca aaatatagcg cgcaaactag     300
gataaattat cgcgcgcggt gtcatctatg ttactagatc gacgtccgta cggttaaaac     360
caccccagta cattaaaaac gtccgcaatg tgttattaag ttgtctaagc gtcaatttgt     420
ttacaccaca atatatcctg ccaccagcca gccaacagct ccccgaccgg cagctcggca     480
caaaatcacc actcgataca ggcagcccat cagtccacta gactctcacc gggctggttg     540
ccctcgccgc tgggctggcg gccgtctatg ccctgcaaa cgcgccagaa acgccgtcga     600
agccgtgtgc gagacaccgc agccgccggc gttgtggata cctcgcggaa aacttggccc     660
tcactgacag atgaggggcg gacgttgaca cttgaggggc cgactcaccc ggcgcggcgt     720
```

```
tgacagatga ggggcaggct cgatttcggc cggcgacgtg gagctgggca gcctcgcaaa      780
tcggcgaaaa cgcctgattt tacgcgagtt tcccacagat gatgtggaca agcctgggga      840
taagtgccct gcggtattga cacttgaggg gcgcgactac tgacagatga ggggcgcgat      900
ccttgacact tgagggggcag agtgctgaca gatgaggggc gcacctattg acatttgagg     960
ggctgtccac aggcagaaaa tccagcattt gcaagggttt ccgcccgttt ttcggccacc     1020
gctaacctgt cttttaacct gcttttaaac caatatttat aaaccttgtt tttaaccagg     1080
gctgcgccct gtgcgcgtga ccgcgcacgc cgaaggggggg tgcccccccct tctcgaaccc   1140 tcccggcccg ctctcgcgtt ggcagcatca cccataattg tggtttcaaa atcggctccg     1200
tcgatactat gttatacgcc aactttgaaa acaactttga aaagctgtt ttctggtatt      1260 taaggtttta gaatgcaagg aacagtgaat tggagttcgt cttgttataa ttagcttctt     1320
ggggtattta aatactgtag aaaagaggaa ggaaataata aatggctaaa atgagaatat     1380
caccggaatt gaaaaaactg atcgaaaaat accgctgcgt aaaagatacg gaaggaatgt     1440
ctcctgctaa ggtatataag ctggtgggag aaaatgaaaa cctatattta aaaatgacgg     1500
acagccggta taagggacc acctatgatg tggaacggga aaaggacatg atgctatggc      1560
tggaaggaaa gctgcctgtt ccaaaggtcc tgcaccttga acggcatgat ggctggagca     1620
atctgctcat gagtgaggcc gatggcgtcc tttgctcgga agagtatgaa gatgaacaaa     1680
gccctgaaaa gattatcgag ctgtatgcgg agtgcatcag gctctttcac tccatcgaca     1740
tatcggattg tcccctatacg aatagcttag acagccgctt agccgaattg gattacttac    1800
tgaataacga tctggccgat gtggattgcg aaaactggga agaagacacc ccatttaaag     1860
atccgcgcga gctgtatgat tttttaaaga cggaaaagcc cgaagaggaa cttgtctttt     1920
cccacggcga cctgggagac agcaacatct ttgtgaaaga tggcaaagta agtggcttta     1980
ttgatcttgg gagaagcggc agggcggaca agtggtatga cattgccttc tgcgtccggt     2040
cgatcaggga ggatattggg gaagaacagt atgtcgagct attttttgac ttactgggga    2100
tcaagcctga ttgggagaaa ataaaatatt atattttact ggatgaattg ttttagtacc     2160
tagatgtggc gcaacgatgc tggcgacaag caggagcgca ccgacttctt ccgcatcaag     2220
tgttttggct ctcaggccga ggcccacggc aagtatttgg gcaaggggtc gctggtattc     2280
gtgcagggca agattcggaa taccaagtac gagaaggacg ccagacggt ctacgggacc      2340 gacttcattg ccgataaggt ggattatctg gacaccaagg caccaggcgg atcaaatcag     2400
gaataagggc acattgcccc ggcgtgagtc ggggcaatcc cgcaaggagg gtgaatgaat     2460
cggacgtttg accggaaggc atacaggcaa gaactgatcg acgcggggtt ttccgccgag     2520
gatgccgaaa ccatcgcaag ccgcaccgtc atgcgtgcgc cccgcgaaac cttccagtcc     2580
gtcggctcga tggcccagca agctacggcc aagatcgagc gcgacagcgt gcaactggct     2640 cccccctgccc tgcccgcgcc atcggccgcc gtggagcgtt cgcgtcgtct cgaacaggag    2700
gcggcaggtt tggcgaagtc gatgaccatc gacacgcgag gaactatgac gaccaagaag     2760
cgaaaaaccg ccggcgagga cctggcaaaa caggtcagcg aggccaagca agccgcgttg     2820
ctgaaacaca cgaagcagca gatcaaggaa atgcagcttt ccttgttcga tattgcgccg     2880
tggccggaca cgatgcgagc gatgccaaac gacacggccc gctctgccct gttcaccacg     2940
cgcaacaaga aaatcccgcg cgaggcgctg caaaacaagg tcattttcca cgtcaacaag     3000
gacgtgaaga tcacctacac cggcgtcgag ctgcggccg acgatgacga actggtgtgg     3060
```

```
cagcaggtgt tggagtacgc gaagcgcacc cctatcggcg agccgatcac cttcacgttc    3120
tacgagcttt gccaggacct gggctggtcg atcaatggcc ggtattacac gaaggccgag    3180
gaatgcctgt cgcgcctaca ggcgacggcg atgggcttca cgtccgaccg cgttgggcac    3240
ctggaatcgg tgtcgctgct gcaccgcttc cgcgtcctgg accgtggcaa gaaaacgtcc    3300
cgttgccagg tcctgatcga cgaggaaatc gtcgtgctgt ttgctggcga ccactacacg    3360
aaattcatat gggagaagta ccgcaagctg tcgccgacgg cccgacggat gttcgactat    3420
ttcagctcgc accgggagcc gtacccgctc aagctggaaa ccttccgcct catgtgcgga    3480
tcggattcca cccgcgtgaa gaagtggcgc gagcaggtcg gcgaagcctg cgaagagttg    3540
cgaggcagcg gcctggtgga cacgccctgg gtcaatgatg acctggtgca ttgcaaacgc    3600
tagggccttg tggggtcagt tccggctggg ggttcagcag ccagcgcttt actgagatcc    3660
tcttccgctt cctcgctcac tgactcgctg cgctcggtcg ttcggctgcg gcgagcggta    3720
tcagctcact caaaggcggt aatacggtta tccacagaat caggggataa cgcaggaaag    3780
aacatgtgag caaaaggcca gcaaaaggcc aggaaccgta aaaaggccgc gttgctggcg    3840
tttttccata ggctccgccc ccctgacgag catcacaaaa atcgacgctc aagtcagagg    3900
tggcgaaacc cgacaggact ataaagatac caggcgtttc cccctggaag ctccctcgtg    3960
cgctctcctg ttccgaccct gccgcttacc ggatacctgt ccgcctttct cccttcggga    4020
agcgtggcgc tttctcatag ctcacgctgt aggtatctca gttcggtgta ggtcgttcgc    4080
tccaagctgg gctgtgtgca cgaaccccc gttcagcccg accgctgcgc cttatccggt    4140
aactatcgtc ttgagtccaa cccggtaaga cacgacttat cgccactggc agcagccact    4200
ggtaacagga ttagcagagc gaggtatgta ggcggtgcta cagagttctt gaagtggtgg    4260
cctaactacg gctacactag aagaacagta tttggtatct gcgctctgct gaagccagtt    4320
accttcggaa aaagagttgg tagctcttga tccggcaaac aaaccaccgc tggtagcggt    4380
ggttttttg tttgcaagca gcagattacg cgcagaaaaa aaggatctca agaagatcct    4440
ttgatctttt ctacggggtc tgacgctcag tggaacgaaa actcacgtta agggattttg    4500
gtcatgagat tatcaaaaag gatcttcacc tagatccttt tggatctcct gtggttggca    4560
tgcacataca aatggacgaa cggataaacc ttttcacgcc cttttaaata tccgattatt    4620
ctaataaacg ctcttttctc ttaggtttac ccgccaatat atcctgtcaa acactgatag    4680
tttaaactga aggcgggaaa cgacaatctg ctagtggatc tcccagtcac gacgttgtaa    4740
aacgggcgtc tgcgatcgct gaagttccta cttttcag agaataggaa cttcggaata    4800
ggaacttccc atgggatcta gtaacataga tgacaccgcg cgcgataatt tatcctagtt    4860
tgcgcgctat attttgtttt ctatcgcgta ttaaatgtat aattgcggga ctctaatcat    4920
aaaaacccat ctcataaata acgtcatgca ttacatgtta attattacat gcttaacgta    4980
attcaacaga aattatatga taatcatcgc aagaccggca acaggattca atcttaagaa    5040
actttattgc caaatgtttg aacgatcacg ctagcggata acaatttcac acagggatat    5100
cactagtaaa aggtaccgag ctcctgcagt atcgatgcgg ccgcaaagtc gacgaattct    5160
cattagcaga actcaagatg ctgatcctct ggaacgttga acttgagctt gtgttcctcg    5220
aaaagcttgc acaactcttt gatgtaacgc tggtgaagtc tatcaacttc ctctctagaa    5280
ggctgaggag tcatttgaac ctcgataggc tttccaacga tagtagtgat aggctgtctg    5340
aaaggcatga gtccgaaaga gtattggaaa actccccttc catggaaaag tggaaggctg    5400
attcccataa tcttttggag tctgttctgg atccatctaa gccaagttcc aggagtgttc    5460
```

```
tcaacctggt tgaagaggtt gttctctccg aatgagaaga taggaacaag agcagcacca    5520
tgcataagag caagtctgat gaatccctta cggttcttca agagaagtct gtaagcacca    5580
ggtctagcat caagagcctc ttgagcacct ccaacgatga tagcaagaag gtttccacca    5640 cccttctctgc taaggatgtg atcagcagaa actttctcgc tagacacgag tccaccagac    5700
atgatgtaat ctctgaagaa tggagccctg aaccaaacgg taagcatcat aaggtaggat    5760
ctgattccag ggaacaaaga ggtgaatcca gtagactcag tacagaggtt aaggaaagca    5820
ccagcagcaa gaacaccatg aggatggaat ccagcaatgt agttacggct aggatcaagc    5880
tcagcagtct taacgagaga cacagggaag taatccttca tgtacttcca gatggccaat    5940
cttctgaaga attggatagg tctaccacct tgtctaggct tatcccaatc caagtaccac    6000
caggtagcgt aaagaacaga gaaaagccag aacctggtga acaagagtcc aacgaagata    6060
acgatgcaga gttgagcaag agcaaggaat gagaaaaccc actgaagaac agcgaaagtc    6120
tgcaatcttc tctcccaagg aacaagaagt ggagcgaact cgaccatgaa ttcagtcccc    6180
cgtgttctct ccaaatgaaa tgaacttcct tatatagagg aagggtcttg cgaaggatag    6240
tgggattgtg cgtcatccct tacgtcagtg gagatatcac atcaatccac ttgctttgaa    6300
gacgtggttg gaacgtcttc tttttccacg atgctcctcg tgggtggggg tccatctttg    6360
ggaccactgt cggcagaggc atcttcaacg atggcctttc ctttatcgca atgatggcat    6420
ttgtaggagc caccttcctt ttccactatc ttcacaataa agtgacagat agctgggcaa    6480
tggaatccga ggaggtttcc ggatattacc ctttgttgaa aagtctcaat tgcccttttgg    6540 tcttctgaga ctgtatcttt gatatttttg gagtagacaa gtgtgtcgtg ctccaccatg    6600
ttgacgaaga ttttcttctt gtcattgagt cgtaagagac tctgtatgaa ctgttcgcca    6660
gtctttacgg cgagttctgt taggtcctct atttgaatct ttgactccat gggatccaag    6720
ggccctagaa tctaattatt ctattcagac taaattagta taagtatttt tttaatcaat    6780
aaataataat taataattta ttagtaggag tgattgaatt tataatatat tttttttaat    6840
catttaaaga atcttatatc tttaaattga caagagtttt aaatggggag agtgttatca    6900
tatcacaagt aggattaatg tgttatagtt tcacatgcat tacgataagt tgtgaaagat    6960
aacattatta tatataacaa tgacaatcac tagcgatcga gtagtgagag tcgtcttatt    7020
acactttctt ccttcgatct gtcacatggc ggcggcccga attctcacac aaggtagttg    7080
caagacactg aagtggtggt agtggtagta gaagaagcag aatcggtaga aaggcaagac    7140
aatggagaag atgaagatgg tggagattct cttcccacaa cgcagcaatc aaggttttca    7200
aggttaaggc actcgtgctt tccatcatcg aacatgaagt cgatgttatc ctcgaaagca    7260
agctcgttga agagttctgg gtactcaatt gggttctcgt tagcaaggtt ttgatcggta    7320
aggaatgggg agaatccagt atccatcatg cagaagttcc aagcaagttc gttgttatct    7380
ccgcacctat ccatttccat gatggtggaa gaatcaatgc agcagttaac aacggcagct    7440
tcctcagaat atcccacaat ttcagcctct tgttgctcag ccttctcttc ctcttttttct    7500 tcttcctctt gaggtggttc ctcaacgtat tgttgcttaa cctcttccct aggttcctct    7560
ttagcttctc tagtctcaac ctcttgctta gcctcaacaa gaatacctc ttgatggtta    7620 gcctggttaa ctgggaatgg gaaaacgccc ttcttcttaa gcctgtcgat gtagttggag    7680
atatcgaagt tggtaacagc gttagcacct ctgtactcaa tagcagccat atcataagca    7740
gctgcagcct cttcttgagt gttgtaagtt ccgaggtaga ggtacttgtt tccgaaaact    7800
```

```
cttccaatcc tagcttccca tcttccgtta tgatgatgcc tagcaactcc cctatactta   7860
gaaactcccc tagagaatcc agatgactgc cttctaaggg aagcaagata ctcttctttg   7920
gtcaccctct gcatctcttc aagttctttg gtgtaagtct cagctgggaa gttaagaatg   7980
gtatctgggc cccaatactt aagagcagca agatcatagg tatgagcagc agcctcttca   8040
gaatcataag ctccaaggta aacctgcttg cccttcttgt tttggatgga gttccaagag   8100
gacttatccc aaaggtgagc ttcgaatctt ccagtccatc tatgcctagt aacacctctg   8160
tagatagatg accttctggt agaagctgga gaagttgggt tatgagactt atcgccagat   8220
ggagatgact tcttagccct cttagctctc tttggtcttg gagcttcaga ttgaattggg   8280
ctagaggtag tagtagaaga ggacactgaa gaagatggag aactagagca ggtagaggta   8340
gtgagcctct tcttcatgaa ttcactagtg attaaatttt gttggtgctt tgagcatata   8400
acaagcatgg tatatatagg cacgtaaaca agttgagaaa ttttactttg agtttgacat   8460
aaccaataaa agttagtgct gtttattacc tcactcagtt tgcaccgcaa ctgtcgttag   8520
tgatgtttac ctttccttt tctattattt attagtatta taatatat atatatgtgt   8580 gatgagactt gaaattgttt agcaccgcaa atgtccttct tgaggggagg ttttctttg    8640 ctgaggttgg ggtgtcacat acccccct ctatggactc aacgtccttg ctgaggttta    8700
ccccacacta catgagattt ttctagactc aatactatga tatttctcgc cttatcggaa   8760
ttggttaaac tcagttgaag ttagggtcat atcgataaaa ttgacacatg atcgactctg   8820
atattaaaca gattctctcc ctcgaacctc actcactttc cttttctat tctttattag    8880 tattatataa tagatccgtt ccaaccattc acgtacataa gaagagagat atttttttt    8940 aatggactaa catgacaaat aaaacaaaca aaggagtaat gatcactaca acaaattaga   9000
ttatgaggga caaataattt catcatctat aaatcatgtt tcgtcactaa aaattttgtg   9060
tgacgaaaaa gatttcgtca atcagttgtc actaaaaata tacaaagacg atttaatgat   9120
gtttaccttt cctttctat tctttattag tattatataa taaatatatg tgtgatgaga   9180
cttgaaattg tttagcaccg caaatgtcct tgttgaaggg aggttttctt tgctgaggt    9240 tggggtgtca catacccccc ctctatggac tgaacgtcct tttgaggtt tattttacac    9300 tgcatgagat ttttctagat tcaacattat gatttctaga ctcaacacta cgatcgtcac   9360
taaagactat ttttatata taaaaaaat actttgtcct taaatgtata aattagggat    9420
aaatttatta ttataaaaaa ggttaataat tttgtgatta aatctattat tttgtcactg   9480
aaagtgtttg cttttaccga cgacatatat gtcactaaat attatcataa gtagtgacaa   9540
ttacaattgt cacaaaataa aaaaattat tcatattcaa caaaaaggg tactacgaca    9600 atacattttt tgtcactgaa agtaatcaag ttgtgataaa ttaatttatt taatgacaaa   9660
aatatttgta tcaaaattca cccatgatca tataataaaa ataactaaaa ttatactaaa   9720
gcataaatga caagaaaatc taactaaaac atatcaaata ttactcctaa acaaagacat   9780
ataagtaaaa atttcttcca aagtatcaat aacgtggtga cacatagctt gcaatcaatc   9840
ttgcttcaat tttcacccttt tatacctgta aaagaaaga gaaataaaa caatgattta    9900 aaaatcgaat tcccgcggcc cctagaatct aattattcta ttcagactaa attagtataa   9960 gtatttttt aatcaataaa taataattaa taatttatta gtaggagtga ttgaatttat   10020
aatatatttt ttttaatcat ttaaagaatc ttatatcttt aaattgacaa gagttttaaa  10080
tggggagagt gttatcatat cacaagtagg attaatgtgt tatagtttca catgcattac   10140
gataagttgt gaaagataac attattatat ataacaatga caatcactag cgatcgagta  10200
```

```
gtgagagtcg tcttattaca ctttcttcct tcgatctgtc acatggcggc ggcccgcggc  10260
cgcttcatta ctcgagccag gaggatggat cgatgctggt ctgagaccct gctaccggtt  10320
gctgactgaa ctgctcggca cggtccttca tttcacgggc cttgctcgcc aactttgtct  10380
tggccgactc caactgatcc gctccgggtg gatgtttccc cgtcaggtaa cggtagatcc  10440
aggacagcac agacagagcg gcaacaccaa atccccgct tgccagaaaa cccgctccca  10500
acaggaagat ggtgatgact gcagatcaga aaaactcaga ttaatcgaca aattcgatcg  10560
cacaaactag aaactaacac cagatctaga tagaaatcac aaatcgaaga gtaattattc  10620
gacaaaactc aaattatttg aacaaatcgg atgatatcta tgaaaccta atcgagaatt  10680
aagatgatat ctaacgatca aacccagaaa atcgtcttcg atctaagatt aacagaatct  10740
aaaccaaaga acatatacga aattgggatc gaacgaaaac aaaatcgaag attttgagag  10800
aataaggaac acagaaattt acctgcaggg accagtacag gcgagaagat caccaggaga  10860
ggtgtggcga ttgtcagcgc aatgaccgtt ccagccaggg tcaacccgga taacaccaac  10920
aggctacctc cggcagtaac cgcggtcgct gcctttacaa cacgctgagc acgcggttgc  10980
agttgcaagt gggggcacg tgtttgttgc tgctgcccgt agtgctctgc catggaaatt  11040
ttgttggtgc tttgagcata taacaagcat ggtatatata ggcacgtaaa caagttgaga  11100
aattttactt tgagtttgac ataaccaata aaagttagtg ctgtttatta cctcactcag  11160
tttgcaccgc aactgtcgtt agtgatgttt acctttcctt tttctattat ttattagtat  11220
tatataatat atatatatgt gtgatgagac ttgaaattgt ttagcaccgc aaatgtcctt  11280
cttgagggga ggttttcttt tgctgaggtt ggggtgtcac atacaccccc ctctatggac  11340
tcaacgtcct tgctgaggtt tacccacac tacatgagat ttttctagac tcaatactat  11400
gatatttctc gccttatcgg aattggttaa actcagttga agttagggtc atatcgataa  11460
aattgacaca tgatcgactc tgatattaaa cagattctct ccctcgaacc tcactcactt  11520
tcctttttct attctttatt agtattatat aatagatccg ttccaaccat tcacgtacat  11580
aagaagagag atattttttt ttaatggact aacatgacaa ataaaacaaa caaaggagta  11640
atgatcacta caacaaatta gattatgagg gacaaataat ttcatcatct ataaatcatg  11700
tttcgtcact aaaaattttg tgtgacgaaa aagatttcgt caatcagttg tcactaaaaa  11760
tatacaaaga cgatttaatg atgtttacct ttcctttttct attctttatt agtattatat  11820
aataaatata tgtgtgatga gacttgaaat tgtttagcac cgcaaatgtc cttgttgaag  11880
ggaggttttc ttttgctgag gttgggggtgt cacatacacc ccctctatgg actgaacgtc  11940
ctttttgagg tttatttttac actgcatgag attttttctag attcaacatt atgatttcta  12000
gactcaacac tacgatcgtc actaaagact attttttata tataaaaaaa atactttgtc  12060
cttaaatgta taaattaggg ataaatttat tattataaaa aaggttaata attttgtgat  12120
taaatctatt attttgtcac tgaaagtgtt tgcttttacc gacgacatat atgtcactaa  12180
atattatcat aagtagtgac aattacaatt gtcacaaaat aaaaaaaatt attcatattc  12240
aacaaaaaag ggtactacga caatacattt tttgtcactg aaagtaatca agttgtgata  12300
aattaatttta tttaatgaca aaaatatttg tatcaaaatt cacccatgat catataataa  12360
aaataactaa aattatacta aagcataaat gacaagaaaa tctaactaaa acatatcaaa  12420
tattactcct aaacaaagac atataagtaa aaatttcttc caaagtatca ataacgtggt  12480
gacacatagc ttgcaatcaa tcttgcttca attttcacct tttatacctg taaaaagaaa  12540
```

-continued

```
gagaaaataa aacaatgatt taaaggcgcg ccgcgtattg gctagagcag cttgccaaca    12600
tggtggagca cgacactctc gtctactcca agaatatcaa agatacagtc tcagaagacc    12660
aaagggctat tgagactttt caacaaaggg taatatcggg aaacctcctc ggattccatt    12720
gcccagctat ctgtcacttc atcaaaagga cagtagaaaa ggaaggtggc acctacaaat    12780
gccatcattg cgataaagga aaggctatcg ttcaagatgc ctctgccgac agtggtccca    12840
aagatggacc cccacccacg aggagcatcg tggaaaaaga agacgttcca accacgtctt    12900
caaagcaagt ggattgatgt gataacatgg tggagcacga cactctcgtc tactccaaga    12960
atatcaaaga tacagtctca gaagaccaaa gggctattga acttttcaa caaagggtaa    13020 tatcgggaaa cctcctcgga ttccattgcc cagctatctg tcacttcatc aaaaggacag    13080
tagaaaagga aggtggcacc tacaaatgcc atcattgcga taaggaaag gctatcgttc    13140 aagatgcctc tgccgacagt ggtcccaaag atggaccccc acccacgagg agcatcgtgg    13200
aaaaagaaga cgttccaacc acgtcttcaa agcaagtgga ttgatgtgat atctccactg    13260
acgtaaggga tgacgcacaa tcccactatc cttcgcaaga ccttcctcta tataaggaag    13320
ttcatttcat ttggagagga cacgctgaaa tcaccagtct ctctctacaa atctatctct    13380
gcgatcgcat ggcgatttg gattctgctg gcgttactac ggtgacggag aacggtggcg    13440
gagagttcgt cgatcttgat aggcttcgtc gacggaaatc gagatcggat tcttctaacg    13500
gacttcttct ctctggttcc gataataatt ctccttcgga tgatgttgga gctcccgccg    13560
acgttaggga tcggattgat tccgttgtta acgatgacgc tcagggaaca gccaatttgg    13620
ccggagataa taacggtggt ggcgataata acggtggtgg aagaggcggc ggagaaggaa    13680
gaggaaacgc cgatgctacg tttacgtatc gaccgtcggt tccagctcat cggagggcga    13740
gagagagtcc acttagctcc gacgcaatct tcaaacagag ccatgccgga ttattcaacc    13800
tctgtgtagt agttcttatt gctgtaaaca gtagactcat catcgaaaat cttatgaagt    13860
atggttggtt gatcagaacg gatttctggt ttagttcaag atcgctgcga gattggccgc    13920
ttttcatgtg ttgtatatcc ctttcgatct ttcctttggc tgcctttacg gttgagaaat    13980
tggtacttca gaaatacata tcagaacctg ttgtcatctt tcttcatatt attatcacca    14040
tgacagaggt tttgtatcca gtttacgtca ccctaaggtg tgattctgct ttttatcag    14100 gtgtcacttt tgatgctcctc acttgcattg tgtggctaaa gttggtttct tatgctcata    14160
ctagctatga cataagatcc ctagccaatg cagctgataa ggccaatcct gaagtctcct    14220
actacgttag cttgaagagc ttggcatatt tcatggtcgc tcccacattg tgttatcagc    14280
caagttatcc acgttctgca tgtatacgga agggttgggt ggctcgtcaa tttgcaaaac    14340
tggtcatatt caccggattc atgggattta aatagaaca atatataat cctattgtca    14400 ggaactcaaa gcatcctttg aaaggcgatc ttctatatgc tattgaaaga gtgttgaagc    14460
tttcagttcc aaatttatat gtgtggctct gcatgttcta ctgcttcttc cacctttggt    14520
taaacatatt ggcagagctt ctctgcttcg gggatcgtga attctacaaa gattggtgga    14580
atgcaaaaag tgtgggagat tactggagaa tgtggaatat gcctgttcat aaatggatgg    14640
ttcgacatat atacttcccg tgcttgcgca gcaagatacc aaagacactc gccattatca    14700
ttgctttcct agtctctgca gtctttcatg agctatgcat cgcagttcct tgtcgtctct    14760
tcaagctatg ggcttttctt gggattatgt ttcaggtgcc tttggtcttc atcacaaact    14820
atctacagga aaggtttggc tcaacggtgg ggaacatgat cttctggttc atcttctgca    14880
ttttcggaca accgatgtgt gtgcttcttt attaccacga cctgatgaac cgaaaaggat    14940
```

```
cgatgtcatg agcgatcgcg atcgttcaaa catttggcaa taaagtttct taagattgaa    15000
tcctgttgcc ggtcttgcga tgattatcat ataatttctg ttgaattacg ttaagcatgt    15060
aataattaac atgtaatgca tgacgttatt tatgagatgg ttttttatga ttagagtccc    15120
gcaattatac atttaatacg cgatagaaaa caaaatatag cgcgcaaact aggataaatt    15180
atcgcgcgcg gtgtcatcta tgttactaga tccctgcagg gcgtattggc tagagcagct    15240
tgccaacatg gtggagcacg acactctcgt ctactccaag aatatcaaag atacagtctc    15300
agaagaccaa agggctattg agacttttca acaagggta atatcgggaa acctcctcgg    15360
attccattgc ccagctatct gtcacttcat caaaaggaca gtagaaaagg aaggtggcac    15420
ctacaaatgc catcattgcg ataaaggaaa ggctatcgtt caagatgcct ctgccgacag    15480
tggtcccaaa gatggacccc cacccacgag gagcatcgtg gaaaagaag acgttccaac     15540
cacgtcttca aagcaagtgg attgatgtga taacatggtg gagcacgaca ctctcgtcta    15600
ctccaagaat atcaaagata cagtctcaga agaccaaagg gctattgaga cttttcaaca    15660
aagggtaata tcgggaaacc tcctcggatt ccattgccca gctatctgtc acttcatcaa    15720
aaggacagta gaaaaggaag gtggcaccta caaatgccat cattgcgata aggaaaggc    15780
tatcgttcaa gatgcctctg ccgacagtgg tcccaaagat gaccccac ccacgaggag     15840
catcgtggaa aaagaagacg ttccaaccac gtcttcaaag caagtggatt gatgtgatat    15900
ctccactgac gtaagggatg acgcacaatc ccactatcct tcgcaagacc ttcctctata    15960
taaggaagtt catttcattt ggagaggaca cgctgaaatc accagtctct ctctacaaat    16020
ctatctctct cgagatgatt gaacaagatg gattgcacgc aggttctccg gccgcttggg    16080
tggagaggct attcggctat gactgggcac aacagacaat cggctgctct gatgccgccg    16140
tgttccggct gtcagcgcag ggaggccgg ttcttttttgt caagaccgac ctgtccggtg     16200
ccctgaatga acttcaagac gaggcagcgc ggctatcgtg gctggccacg acgggcgttc    16260
cttgcgcagc tgtgctcgac gttgtcactg aagcgggaag ggactggctg ctattgggcg    16320
aagtgccggg gcaggatctc ctgtcatctc accttgctcc tgccgagaaa gtatccatca    16380
tggctgatgc aatgcggcgg ctgcatacgc ttgatccggc tacctgccca ttcgaccacc    16440
aagcgaaaca tcgcatcgag cgagcacgta ctcggatgga agccggtctt gtcgatcagg    16500
atgatctgga cgaagagcat caggggctcg cgccagccga actgttcgcc aggctcaagg    16560
cgcgcatgcc cgacggcgag gatctcgtcg tgactcatgg cgatgcctgc ttgccgaata    16620
tcatggtgga aaatggccgc ttttctggat tcatcgactg tggccggctg ggtgtggcgg    16680
accgctatca ggacatagcg ttggctaccc gtgatattgc tgaagagctt ggcggcgaat    16740
gggctgacc                                                             16749
```

<210> SEQ ID NO 22
<211> LENGTH: 137
<212> TYPE: DNA
<213> ORGANISM: Artificial Sequence
<220> FEATURE:
<223> OTHER INFORMATION: linker sequence

<400> SEQUENCE: 22

```
atttaaatgc ggccgcgaat tcgtcgattg aggacgtccc tactagacct gctggacctc    60
ctcctgctac ttactacgat tctctcgctg tgcatatggt cagtcatgcc cgggcctgca   120
ggcggccgca tttaaat                                                  137
```

<210> SEQ ID NO 23
<211> LENGTH: 434
<212> TYPE: DNA
<213> ORGANISM: Artificial Sequence
<220> FEATURE:
<223> OTHER INFORMATION: hpRNAi

<400> SEQUENCE: 23

```
gtgagcaatg aaccaagatt tatcaatacc gttactttttg atagcaaaga gggttctcct      60
actcttgtta tggtccacgg atatggtgcc tctcagggtt tcttctttcg gaattttttat    120
gcccttgcga ggcatttcaa agttattgct attgatcagc ttggctgggg tggttcaagc    180
aggcctgact tcacatgcag aagtacagaa gagactgaag attggtttat tgattccttt    240
gaggagtggc gcaaagccaa aaaccttagc aactttatttt tgcttgggca ctccttttgga    300
gggtatgtcg ctgcaaaata tgctctcaag catccagagc atgttcagca gttgattctg    360
gtaggaccag ctggatttac atcagagact gaacatatgt ccgagcggct tacccagttt    420
agagcaaacat ggaa                                                     434
```

<210> SEQ ID NO 24
<211> LENGTH: 593
<212> TYPE: DNA
<213> ORGANISM: Artificial Sequence
<220> FEATURE:
<223> OTHER INFORMATION: hpRNAi

<400> SEQUENCE: 24

```
actgctgatg ctgtcaggca gtatctatgg ttgtttgagg agcataatgt tcttgaattc       60
ctcgtacttg ctggagatca tctatatcga atggattatg aaaagttcat tcaagcccac    120
agagaaacag atgctgatat tactgttgcc gcactgccaa tggatgaaaa gcgagccact    180
gcatttggtc tcatgaagat tgacgaagaa ggacgcatta ttgaatttgc agagaaaccg    240
aaaggagagc aattgaaagc aatgaaagtg gatactacca tttttaggtct tgatgatgag    300
agagctaaag agatgccttt tatcgcaagt atgggtatat atgtcattag caaagatgtg    360
atgttaaaact tacttcgtga taagttccct ggtgccaatg attttggcag tgaagttatt    420
cctggtgcaa cttcgcttgg gatgagagtg caagcttatt tatatgatgg atactgggaa    480
gatattggta ccatcgaagc tttctacaat gccaattttgg gcattaccaa aaagccagtc    540
ccagatttta gcttctatga ccgatcagct ccaatctaca cccaacctcg ata            593
```

<210> SEQ ID NO 25
<211> LENGTH: 5
<212> TYPE: PRT
<213> ORGANISM: Artificial Sequence
<220> FEATURE:
<223> OTHER INFORMATION: lipase motif
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (4)..(4)
<223> OTHER INFORMATION: any amino acid

<400> SEQUENCE: 25

Gly Xaa Ser Xaa Gly
1               5

<210> SEQ ID NO 26

```
<211> LENGTH: 6
<212> TYPE: PRT
<213> ORGANISM: Artificial Sequence
<220> FEATURE:
<223> OTHER INFORMATION: acyltransferase motif
<220> FEATURE:
<221> NAME/KEY: MISC_FEATURE
<222> LOCATION: (2)..(5)
<223> OTHER INFORMATION: any amino acid

<400> SEQUENCE: 26

His Xaa Xaa Xaa Xaa Asp
1               5

<210> SEQ ID NO 27
<211> LENGTH: 7
<212> TYPE: PRT
<213> ORGANISM: Artificial Sequence
<220> FEATURE:
<223> OTHER INFORMATION: probable lipid binding motif
<220> FEATURE:
<221> NAME/KEY: MISC_FEATURE
<222> LOCATION: (2)..(4)
<223> OTHER INFORMATION: any amino acid

<400> SEQUENCE: 27

Val Xaa Xaa Xaa His Gly Phe
1               5

<210> SEQ ID NO 28
<211> LENGTH: 584
<212> TYPE: PRT
<213> ORGANISM: Arabidopsis thaliana

<400> SEQUENCE: 28

Met Asn Ser Met Asn Asn Trp Leu Gly Phe Ser Leu Ser Pro His Asp
1               5                   10                  15

Gln Asn His His Arg Thr Asp Val Asp Ser Ser Thr Thr Arg Thr Ala
                20                  25                  30

Val Asp Val Ala Gly Gly Tyr Cys Phe Asp Leu Ala Ala Pro Ser Asp
            35                  40                  45

Glu Ser Ser Ala Val Gln Thr Ser Phe Leu Ser Pro Phe Gly Val Thr
    50                  55                  60

Leu Glu Ala Phe Thr Arg Asp Asn Asn Ser His Ser Arg Asp Trp Asp
65                  70                  75                  80

Ile Asn Gly Gly Ala Cys Asn Thr Leu Thr Asn Asn Glu Gln Asn Gly
                85                  90                  95

Pro Lys Leu Glu Asn Phe Leu Gly Arg Thr Thr Thr Ile Tyr Asn Thr
            100                 105                 110

Asn Glu Thr Val Val Asp Gly Asn Gly Asp Cys Gly Gly Gly Asp Gly
        115                 120                 125

Gly Gly Gly Gly Ser Leu Gly Leu Ser Met Ile Lys Thr Trp Leu Ser
    130                 135                 140

Asn His Ser Val Ala Asn Ala Asn His Gln Asp Gly Asn Gly Ala
145                 150                 155                 160

Arg Gly Leu Ser Leu Ser Met Asn Ser Ser Thr Ser Asp Ser Asn Asn
                165                 170                 175

Tyr Asn Asn Asn Asp Asp Val Val Gln Glu Lys Thr Ile Val Asp Val
            180                 185                 190

Val Glu Thr Thr Pro Lys Lys Thr Ile Glu Ser Phe Gly Gln Arg Thr
        195                 200                 205
```

```
Ser Ile Tyr Arg Gly Val Thr Arg His Arg Trp Thr Gly Arg Tyr Glu
    210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Lys Ala Ala
            245                 250                 255

Arg Ala Tyr Asp Leu Ala Ala Leu Lys Tyr Trp Gly Pro Thr Thr Thr
                260                 265                 270

Thr Asn Phe Pro Leu Ser Glu Tyr Glu Lys Val Glu Glu Met Lys
            275                 280                 285

His Met Thr Arg Gln Glu Tyr Val Ala Ser Leu Arg Arg Lys Ser Ser
290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Glu Ala Ala Glu Ala
            340                 345                 350

Tyr Asp Ile Ala Ala Ile Lys Phe Arg Gly Leu Ser Ala Val Thr Asn
                355                 360                 365

Phe Asp Met Asn Arg Tyr Asn Val Lys Ala Ile Leu Glu Ser Pro Ser
370                 375                 380

Leu Pro Ile Gly Ser Ser Ala Lys Arg Leu Lys Asp Val Asn Asn Pro
385                 390                 395                 400

Val Pro Ala Met Met Ile Ser Asn Asn Val Ser Glu Ser Ala Asn Asn
                405                 410                 415

Val Ser Gly Trp Gln Asn Thr Ala Phe Gln His His Gln Gly Met Asp
            420                 425                 430

Leu Ser Leu Leu Gln Gln Gln Glu Arg Tyr Val Gly Tyr Tyr Asn
435                 440                 445

Gly Gly Asn Leu Ser Thr Glu Ser Thr Arg Val Cys Phe Lys Gln Glu
    450                 455                 460

Glu Glu Gln Gln His Phe Leu Arg Asn Ser Pro Ser His Met Thr Asn
465                 470                 475                 480

Val Asp His His Ser Ser Thr Ser Asp Ser Val Thr Val Cys Gly
            485                 490                 495

Asn Val Val Ser Tyr Gly Gly Tyr Gln Gly Phe Ala Ile Pro Val Gly
                500                 505                 510

Thr Ser Val Asn Tyr Asp Pro Phe Thr Ala Ala Glu Ile Ala Tyr Asn
            515                 520                 525

Ala Arg Asn His Tyr Tyr Ala Gln His Gln Gln Gln Gln Ile
530                 535                 540

Gln Gln Ser Pro Gly Gly Asp Phe Pro Val Ala Ile Ser Asn Asn His
545                 550                 555                 560

Ser Ser Asn Met Tyr Phe His Gly Glu Gly Gly Glu Gly Ala Pro
                565                 570                 575

Thr Phe Ser Val Trp Asn Asp Thr
            580

<210> SEQ ID NO 29
<211> LENGTH: 336
<212> TYPE: DNA
<213> ORGANISM: Artificial Sequence
<220> FEATURE:
<223> OTHER INFORMATION: inducible promoter
```

```
<400> SEQUENCE: 29
tcgatagttg tgatagttcc cacttgtccg tccgcatcgg catccgcagc tcgggatagt     60
tccgacctag gattggatgc atgcggaacc gcacgagggc ggggcggaaa ttgacacacc    120
actcctctcc acgcaccgtt caagaggtac gcgtatagag ccgtatagag cagagacgga    180
gcactttctg gtactgtccg cacgggatgt ccgcacggag agccacaaac gagcggggcc    240
ccgtacgtgc tctcctaccc caggatcgca tccccgcata gctgaacatc tatataaaga    300
cccccaaggt tctcagtctc accaacatca tcaacc                              336

<210> SEQ ID NO 30
<211> LENGTH: 2466
<212> TYPE: DNA
<213> ORGANISM: Artificial Sequence
<220> FEATURE:
<223> OTHER INFORMATION: inducer

<400> SEQUENCE: 30
atggccgaca ctagaagaag gcagaaccac tcttgtgacc catgccgtaa gggcaagaga     60
agatgtgatg ctccagagaa ccgtaacgag gctaatgaga acggatgggt gtcatgctct    120
aactgcaaga ggtggaacaa ggactgcacc ttcaactggc ttagctccca aggtctaag    180 gctaagggtg ctgctccaag agctaggact aagaaggcta ggactgctac tactacctcc    240
gagccttcta cttccgctgc tactattcca actcccgagt ccgataatca cgatgctcca    300
ccagtgatca actcccacga tgctttgcca tcttggactc agggacttct ttctcaccct    360
ggcgatctct tcgacttctc ccattctgct attccagcta acgctgagga tgctgctaac    420
gtgcaatctg atgctccatt cccatgggat cttgctatcc caggcgattt ctctatggga    480
cagcaacttg agaagcccct ctccccattg tctttccagg ctgttcttct tccaccacac    540
tccccaaaca ctgatgatct cattcgtgag cttgaggaac agactaccga tccagattcc    600
gtgactgaca ctaactccgt tcagcaagtt gctcaggatg ctctctttg gtctgatagg    660 cagtctccac tcctcccaga aaacagtttg tgcatggctt ccgactctac cgctagaagg    720
tatgctaggt ccaccatgac caagaacctc atgaggatct accacgactc catggaaaac    780
gccctttctt gctggcttac tgagcacaac tgcccatact ccgaccagat ttcttacctc    840
ccaccaaagc aaagggctga gtggggacca aattggtcta acaggatgtg cattagggtg    900
tgcaggctcg atagggtgtc aacttctctt agaggaaggg ctctctccgc tgaagaagat    960
aaggctgctg ctagggcact tcaccttgct attgtggctt tcgcttctca gtggactcaa   1020
catgctcaaa ggggagctgg acttaacgtc ccagctgata ttgctgctga cgagcgttct   1080
attaggcgta acgcttggaa tgaggctagg catgcacttc agcacactac tggaatccca   1140
tccttcaggg tgatcttcgc caacatcatc ttcagcctca ctcagtccgt gctcgatgat   1200
gatgagcaac atggaatggg agctaggctc gataagcttc tcgagaatga tggtgctcca   1260
gtgttcctcg agactgctaa taggcagctc tacaccttca ggcacaagtt cgctaggatg   1320
cagagaaggg gtaaggcttt caataggctt cctggtggat ccgtggcttc tacttcgct   1380 ggaattttcg agactccac ccctcatctc gagtctccac aacttgatcc agtggtggct    1440
tctgaggaac acaggtctac tctgtctctc atgttctggc tcgggatcat gttcgacact   1500
ctgtctgctg ctatgtacca gaggccactt gttgtgtccg atgaggactc ccagatctct   1560
tctgcttctc caccaagaag aggtgccgag actcctatta accttgattg ctgggagcca   1620
```

-continued

```
ccaaggcagg tcccatctaa tcaagagaag tctgatgtgt ggggcgacct gttccttagg    1680
acttctgatt ctttgcccga ccacgagtcc cacactcaaa tttctcaacc agctgctagg    1740
tggccatgca cttatgaaca agctgctgct gctctctcct ctgctactcc tgttaaggtg    1800
ttgctttaca ggcgtgtgac tcagctccag actttgttgt ataggggagc ttctccagct    1860
aggcttgagg ctgctattca gaggactctc tacgtgtaca accactggac tgctaagtac    1920
cagccattca tgcaggattg cgttgccaac catgagcttc tcccatccag gatccagtct    1980
tggtacgtga tccttgatgg acactggcac cttgctgcta tgcttttggc tgatgtgctc    2040
gagtccatcg acagggattc ctactccgat atcaaccaca tcgacctcgt gactaagctc    2100
aggcttgata acgctcttgc tgtgtctgct ctcgctaggt catctcttag aggccaagaa    2160
ctcgatccag gcaaggcttc tccaatgtac aggcacttcc acgactccct tactgaggtt    2220
gcattccttg ttgagccatg gactgtggtg ctcatccact catttgctaa ggctgcttac    2280
atcctcctcg attgccttga tcttgatggt cagggaaacg ctctcgctgg ataccttcaa    2340
cttaggcaga actgcaacta ctgcatcagg gctctccagt tccttggccg taagtctgat    2400
atggctgctc tcgtggctaa ggatcttgag aggggactca acggaaaggt cgacagcttc    2460
ctctaa                                                                2466
```

<210> SEQ ID NO 31
<211> LENGTH: 208
<212> TYPE: PRT
<213> ORGANISM: Arabidopsis thaliana

<400> SEQUENCE: 31

```
Met Thr Ser Ser Val Ile Val Ala Gly Ala Gly Asp Lys Asn Asn Gly
1               5                   10                  15

Ile Val Val Gln Gln Pro Pro Cys Val Ala Arg Glu Gln Asp Gln
            20                  25                  30

Tyr Met Pro Ile Ala Asn Val Ile Arg Ile Met Arg Lys Thr Leu Pro
        35                  40                  45

Ser His Ala Lys Ile Ser Asp Asp Ala Lys Glu Thr Ile Gln Glu Cys
    50                  55                  60

Val Ser Glu Tyr Ile Ser Phe Val Thr Gly Glu Ala Asn Glu Arg Cys
65                  70                  75                  80

Gln Arg Glu Gln Arg Lys Thr Ile Thr Ala Glu Asp Ile Leu Trp Ala
                85                  90                  95

Met Ser Lys Leu Gly Phe Asp Asn Tyr Val Asp Pro Leu Thr Val Phe
            100                 105                 110

Ile Asn Arg Tyr Arg Glu Ile Glu Thr Asp Arg Gly Ser Ala Leu Arg
        115                 120                 125

Gly Glu Pro Pro Ser Leu Arg Gln Thr Tyr Gly Asn Gly Ile Gly
    130                 135                 140

Phe His Gly Pro Ser His Gly Leu Pro Pro Gly Pro Tyr Gly Tyr
145                 150                 155                 160

Gly Met Leu Asp Gln Ser Met Val Met Gly Gly Arg Tyr Gln
                165                 170                 175

Asn Gly Ser Ser Gly Gln Asp Glu Ser Ser Val Gly Gly Ser Ser
            180                 185                 190

Ser Ser Ile Asn Gly Met Pro Ala Phe Asp His Tyr Gly Gln Tyr Lys
        195                 200                 205
```

<210> SEQ ID NO 32

<211> LENGTH: 278
<212> TYPE: PRT
<213> ORGANISM: Zea mays

<400> SEQUENCE: 32

Met Asp Ser Ser Ser Phe Leu Pro Ala Ala Gly Ala Glu Asn Gly Ser
1               5                   10                  15

Ala Ala Gly Gly Ala Asn Asn Gly Gly Ala Ala Gln Gln His Ala Ala
                20                  25                  30

Pro Ala Ile Arg Glu Gln Asp Arg Leu Met Pro Ile Ala Asn Val Ile
            35                  40                  45

Arg Ile Met Arg Arg Val Leu Pro Ala His Ala Lys Ile Ser Asp Asp
50                  55                  60

Ala Lys Glu Thr Ile Gln Glu Cys Val Ser Glu Tyr Ile Ser Phe Ile
65                  70                  75                  80

Thr Gly Glu Ala Asn Glu Arg Cys Gln Arg Glu Gln Arg Lys Thr Ile
                85                  90                  95

Thr Ala Glu Asp Val Leu Trp Ala Met Ser Arg Leu Gly Phe Asp Asp
            100                 105                 110

Tyr Val Glu Pro Leu Gly Ala Tyr Leu His Arg Tyr Arg Glu Phe Glu
        115                 120                 125

Gly Asp Ala Arg Gly Val Gly Leu Val Pro Gly Ala Ala Pro Ser Arg
130                 135                 140

Gly Gly Asp His His Pro His Ser Met Ser Pro Ala Ala Met Leu Lys
145                 150                 155                 160

Ser Arg Gly Pro Val Ser Gly Ala Ala Met Leu Pro His His His His
                165                 170                 175

His His Asp Met Gln Met His Ala Ala Met Tyr Gly Gly Thr Ala Val
            180                 185                 190

Pro Pro Pro Ala Gly Pro Pro His His Gly Gly Phe Leu Met Pro His
        195                 200                 205

Pro Gln Gly Ser Ser His Tyr Leu Pro Tyr Ala Tyr Glu Pro Thr Tyr
    210                 215                 220

Gly Gly Glu His Ala Met Ala Ala Tyr Tyr Gly Gly Ala Ala Tyr Ala
225                 230                 235                 240

Pro Gly Asn Gly Gly Ser Gly Asp Gly Ser Gly Ser Gly Gly Gly Gly
                245                 250                 255

Gly Ser Ala Ser His Thr Pro Gln Gly Ser Gly Gly Leu Glu His Pro
            260                 265                 270

His Pro Phe Ala Tyr Lys
        275

<210> SEQ ID NO 33
<211> LENGTH: 234
<212> TYPE: PRT
<213> ORGANISM: Arabidopsis thaliana

<400> SEQUENCE: 33

Met Glu Arg Gly Gly Phe His Gly Tyr Arg Lys Leu Ser Val Asn Asn
1               5                   10                  15

Thr Thr Pro Ser Pro Pro Gly Leu Ala Ala Asn Phe Leu Met Ala Glu
                20                  25                  30

Gly Ser Met Arg Pro Pro Glu Phe Asn Gln Pro Asn Lys Thr Ser Asn
            35                  40                  45

Gly Gly Glu Glu Glu Cys Thr Val Arg Glu Gln Asp Arg Phe Met Pro
50                  55                  60

-continued

Ile Ala Asn Val Ile Arg Ile Met Arg Arg Ile Leu Pro Ala His Ala
65                  70                  75                  80

Lys Ile Ser Asp Asp Ser Lys Glu Thr Ile Gln Glu Cys Val Ser Glu
            85                  90                  95

Tyr Ile Ser Phe Ile Thr Gly Glu Ala Asn Glu Arg Cys Gln Arg Glu
            100                 105                 110

Gln Arg Lys Thr Ile Thr Ala Glu Asp Val Leu Trp Ala Met Ser Lys
            115                 120                 125

Leu Gly Phe Asp Asp Tyr Ile Glu Pro Leu Thr Leu Tyr Leu His Arg
            130                 135                 140

Tyr Arg Glu Leu Glu Gly Glu Arg Gly Val Ser Cys Ser Ala Gly Ser
145                 150                 155                 160

Val Ser Met Thr Asn Gly Leu Val Val Lys Arg Pro Asn Gly Thr Met
            165                 170                 175

Thr Glu Tyr Gly Ala Tyr Gly Pro Val Pro Gly Ile His Met Ala Gln
            180                 185                 190

Tyr His Tyr Arg His Gln Asn Gly Phe Val Phe Ser Gly Asn Glu Pro
            195                 200                 205

Asn Ser Lys Met Ser Gly Ser Ser Gly Ala Ser Gly Ala Arg Val
            210                 215                 220

Glu Val Phe Pro Thr Gln Gln His Lys Tyr
225                 230

<210> SEQ ID NO 34
<211> LENGTH: 312
<212> TYPE: PRT
<213> ORGANISM: Arabidopsis thaliana

<400> SEQUENCE: 34

Met Val Asp Glu Asn Val Glu Thr Lys Ala Ser Thr Leu Val Ala Ser
1               5                   10                  15

Val Asp His Gly Phe Gly Ser Gly Ser Gly His Asp His His Gly Leu
            20                  25                  30

Ser Ala Ser Val Pro Leu Leu Gly Val Asn Trp Lys Lys Arg Arg Met
            35                  40                  45

Pro Arg Gln Arg Arg Ser Ser Ser Phe Asn Leu Leu Ser Phe Pro
50                  55                  60

Pro Pro Met Pro Pro Ile Ser His Val Pro Thr Pro Leu Pro Ala Arg
65                  70                  75                  80

Lys Ile Asp Pro Arg Lys Leu Arg Phe Leu Phe Gln Lys Glu Leu Lys
            85                  90                  95

Asn Ser Asp Val Ser Ser Leu Arg Arg Met Ile Leu Pro Lys Lys Ala
            100                 105                 110

Ala Glu Ala His Leu Pro Ala Leu Glu Cys Lys Glu Gly Ile Pro Ile
            115                 120                 125

Arg Met Glu Asp Leu Asp Gly Phe His Val Trp Thr Phe Lys Tyr Arg
            130                 135                 140

Tyr Trp Pro Asn Asn Asn Ser Arg Met Tyr Val Leu Glu Asn Thr Gly
145                 150                 155                 160

Asp Phe Val Asn Ala His Gly Leu Gln Leu Gly Asp Phe Ile Met Val
            165                 170                 175

Tyr Gln Asp Leu Tyr Ser Asn Tyr Val Ile Gln Ala Arg Lys Ala
            180                 185                 190

Ser Glu Glu Glu Glu Val Asp Val Ile Asn Leu Glu Glu Asp Asp Val

```
            195                 200                 205
Tyr Thr Asn Leu Thr Arg Ile Glu Asn Thr Val Val Asn Asp Leu Leu
    210                 215                 220

Leu Gln Asp Phe Asn His His Asn Asn Asn Asn Asn Asn Asn Ser Asn
225                 230                 235                 240

Ser Asn Ser Asn Lys Cys Ser Tyr Tyr Tyr Pro Val Ile Asp Asp Val
                245                 250                 255

Thr Thr Asn Thr Glu Ser Phe Val Tyr Asp Thr Thr Ala Leu Thr Ser
            260                 265                 270

Asn Asp Thr Pro Leu Asp Phe Leu Gly Gly His Thr Thr Thr Thr Asn
        275                 280                 285

Asn Tyr Tyr Ser Lys Phe Gly Thr Phe Asp Gly Leu Gly Ser Val Glu
    290                 295                 300

Asn Ile Ser Leu Asp Asp Phe Tyr
305                 310

<210> SEQ ID NO 35
<211> LENGTH: 321
<212> TYPE: PRT
<213> ORGANISM: Brassica napus

<400> SEQUENCE: 35

Met Met Ala Asp Glu Asn Val Glu Thr Lys Ala Ser Thr Leu Ile Ala
1               5                   10                  15

Ser Val Gly His Gln Gly His Gly Phe Gly Ser Gly Ser Gly Gly His
                20                  25                  30

His Gly Leu Ser Ala Ser Val Pro Leu Leu Gly Val Asn Ser Lys Lys
            35                  40                  45

Arg Arg Met Pro Arg Gln Arg Arg Ser Ser Ser Phe Asn Leu Leu
    50                  55                  60

Ser Leu Pro Pro Pro Met Pro Leu Ser Pro His Val Pro Thr Pro Leu
65                  70                  75                  80

Ser Ala Arg Lys Ile Asp Pro Arg Lys Leu Arg Phe Leu Phe Gln Lys
                85                  90                  95

Glu Leu Lys Asn Ser Asp Val Ser Ser Leu Arg Arg Met Ile Leu Pro
            100                 105                 110

Lys Lys Ala Ala Glu Ala His Leu Pro Ala Leu Glu Cys Lys Glu Gly
        115                 120                 125

Ile Pro Ile Arg Met Glu Asp Leu Asp Gly Leu His Val Trp Thr Phe
    130                 135                 140

Lys Tyr Arg Tyr Trp Pro Asn Asn Asn Ser Arg Met Tyr Val Leu Glu
145                 150                 155                 160

Asn Thr Gly Asp Phe Val Asn Ala His Gly Leu Gln Leu Gly Asp Phe
                165                 170                 175

Ile Met Val Tyr Leu Asp Leu Asp Ser Asn Asn Tyr Val Ile Gln Ala
            180                 185                 190

Arg Lys Ala Ser Glu Glu Glu Glu Glu Asp Val Thr Ile Ile
        195                 200                 205

Glu Glu Asp Asp Val Tyr Thr Asn Leu Thr Lys Ile Glu Asn Thr Val
    210                 215                 220

Val Asn Asp Leu Leu Ile Gln Asp Phe Asn His His Asn Asp Asn Ser
225                 230                 235                 240

Ser Asn Asn Asn Ser Asn Asn Ile Asn Asn Asn Lys Cys Ser Tyr
                245                 250                 255
```

Tyr Tyr Pro Val Ile Asp Asp Ile Thr Thr Asn Thr Ala Ser Phe Val
            260                 265                 270

Tyr Asp Thr Thr Thr Leu Thr Ser Asn Asp Ser Pro Leu Asp Phe Leu
        275                 280                 285

Gly Gly His Thr Thr Thr Thr Thr Asn Thr Tyr Tyr Ser Lys Phe Gly
290                 295                 300

Ser Phe Glu Gly Leu Gly Ser Val Glu Asn Ile Ser Leu Asp Asp Phe
305                 310                 315                 320

Tyr

<210> SEQ ID NO 36
<211> LENGTH: 314
<212> TYPE: PRT
<213> ORGANISM: Medicago truncatula

<400> SEQUENCE: 36

Met Met Met Asp Glu Gly Glu Gly Lys Lys Lys Val Val Gln Lys
1               5                   10                  15

Thr Glu Ala Cys Gly Phe Met Ala Gly Val Glu Asp Glu Leu Gly Phe
                20                  25                  30

Val Asn Val Lys Gly Asp Asn Asn Gly Ser Gly Gln Arg Ile His
            35                  40                  45

His Asp His Gly Phe Val Ala Ala Ala Phe Gly Thr Val His Arg Lys
50                  55                  60

Lys Arg Met Ala Arg Gln Arg Arg Ser Ser Ser Thr Ile Thr Ile
65              70                  75                  80

His Leu Lys Asn Leu Pro Ser Ser Thr Thr Thr Thr Thr Thr Thr
                85                  90                  95

Thr Ser His Val Pro Ile Ser Pro Ile Pro Pro Leu Phe His Ser Leu
            100                 105                 110

Pro Pro Ala Arg Glu Ile Asp His Arg Arg Leu Arg Phe Leu Phe Gln
        115                 120                 125

Lys Glu Leu Lys Asn Ser Asp Val Ser Ser Leu Arg Arg Met Val Leu
130                 135                 140

Pro Lys Lys Ala Ala Glu Ala Phe Leu Pro Val Leu Glu Ser Lys Glu
145                 150                 155                 160

Gly Ile Leu Leu Ser Met Asp Asp Leu Asp Gly Leu His Val Trp Ser
                165                 170                 175

Phe Lys Tyr Arg Phe Trp Pro Asn Asn Asn Ser Arg Met Tyr Val Leu
            180                 185                 190

Glu Asn Thr Gly Asp Phe Val Ser Thr His Gly Leu Arg Phe Gly Asp
        195                 200                 205

Ser Ile Met Val Tyr Gln Asp Asn Gln Asn His Asn Tyr Val Ile Gln
210                 215                 220

Ala Lys Lys Ala Cys Asp Gln Asp Glu Tyr Met Glu Glu Ala Asn Asp
225                 230                 235                 240

Thr Ile Asn His Ile Phe Val Asp Asp Tyr Glu Val Asn Lys Ser Cys
                245                 250                 255

Phe Asp Val Ala Tyr Pro Ala Met Asn Asp Thr Ser Met Ser Phe Ile
            260                 265                 270

Tyr Asp Thr Thr Ile Ser Asn Asp Ser Pro Leu Asp Phe Leu Gly Gly
        275                 280                 285

Ser Met Thr Asn Tyr Ser Arg Ile Gly Ser Val Glu Thr Phe Gly Ser
290                 295                 300

Val Glu Asn Leu Ser Leu Asp Asp Phe Tyr
305                 310

<210> SEQ ID NO 37
<211> LENGTH: 3275
<212> TYPE: DNA
<213> ORGANISM: Arabidopsis thaliana

<400> SEQUENCE: 37

| | | | | | |
|---|---|---|---|---|---|
| ggttggctat | atggtccaaa | ttttgatttg | caatatgaga | ttgcacagag | agaacaatct | 60 |
| ttcattatga | ttaattattg | tacaagtaac | aaacaccaat | ctccgatata | ctttggctct | 120 |
| ttagcacatt | gttatgctag | aagttagcgg | aaatctatat | gttgttaaac | gcagcgttta | 180 |
| aattgaacag | tgtaatttac | cttgaaattt | taagactaca | tgctgtttag | aatttcagat | 240 |
| gaaaacatct | tgatgtttta | gaaatccacg | tgggaatagc | gtaaaatctt | atccaacgaa | 300 |
| cttatttttgg | ttttgttgta | tttgtgcaag | tcgtcacgct | aatcgaaaaa | agaaaagaaa | 360 |
| aaaagaagcc | gtcatgatcg | gccatttctc | ggccgagtct | gagtctgact | ctgcgtccgt | 420 |
| gtcaccatta | tcagatcgag | cctgtcttat | ctcgttgcga | ttccctatgc | aaaaatcttc | 480 |
| ttctttttt | tattcccccca | tttatctctg | atctcttctc | tcttctcaag | taaacctctc | 540 |
| tgcttcacgt | ctcttctttt | cttgtcgatt | ttccccagat | aatcagttga | aacacaccc | 600 |
| aaattcatct | tcgaatcaat | aatggatata | agtaatgagg | ctagtgtcga | tcccttttcg | 660 |
| attggaccat | catctatcat | gggtcgaacc | attgcttca | gagtcttgtt | ctgtagatca | 720 |
| atgtcacagc | ttaggcgtga | tctctttcgg | ttcttgttgc | attggtttct | tagatttaag | 780 |
| ctgaccgttt | caccgtttgt | gtcgtggttt | catcctcgga | accctcaagg | gattttagcg | 840 |
| gtggttacaa | tcattgcctt | tgtgttgaaa | cgatacacga | atgtgaaaat | aaaggcggaa | 900 |
| atggcttacc | ggaggaagtt | tggaggaat | atgatgcgga | cggctttgac | ttatgaggaa | 960 |
| tgggctcatg | ctgctaagat | gttagagaag | gaaacaccaa | agatgaatga | atctgatctt | 1020 |
| tatgatgaag | agttggttaa | gaacaagctt | caggagcttc | gtcatcgtcg | ccaagaaggc | 1080 |
| tcacttagag | acattatgtt | ttgtatgaga | gctgatttgg | tgaggaatct | cggtaatatg | 1140 |
| tgtaattcgg | agcttcataa | aggtagactt | caggttccta | gacatatcaa | agagtacatt | 1200 |
| gatgaggtgt | ctactcagtt | gagaatggtt | tgtaactctg | attcagagga | gctttcttta | 1260 |
| gaagagaagc | tttcttttat | gcatgaaaca | cggcatgcct | tggtagaaac | ggcttttgctt | 1320 |
| ttgagtggtg | gggcttctct | tggtgcgttt | catgttggtg | tggttaggac | tttggttgag | 1380 |
| cataagcttt | tacctcgaat | aattgctggt | tctagtgttg | gatccatcat | ttgtgctgtt | 1440 |
| gtggcctcaa | ggtcttggcc | agaactacag | agtttctttg | agaattcttt | gcattcttta | 1500 |
| cagttctttg | atcagctcgg | aggcgtgttc | tcaatagtga | aacgggtaat | gacacaaggg | 1560 |
| gctctacacg | atatcagaca | gttgcaatgt | atgcttagaa | acctcacaag | caatctcaca | 1620 |
| ttccaagaag | cttatgacat | gacaggaagg | attctcggga | tcaccgtttg | ctccccaaga | 1680 |
| aagcatgaac | ctcctcggtg | tcttaactat | ttgacttcgc | ctcatgtggt | tatatggagc | 1740 |
| gcagtgactg | cttcttgtgc | ttttcctggt | ctctttgaag | ctcaagagct | aatggctaaa | 1800 |
| gatcgaagtg | gagagatcgt | accgtatcat | ccacctttca | atttggatcc | agaagtaggc | 1860 |
| actaaatcat | catctggacg | ccggtggaga | gatggtagtt | tggaggttga | tttaccaatg | 1920 |
| atgcagctta | agaactgtt | caatgtcaat | catttattg | tgagccaagc | caatcctcac | 1980 |
| attgctccat | tactgcgtct | aaaggattta | gttcgagctt | atggtggtag | attcgcagct | 2040 |

```
aagctcgcgc atctagtgga gatggaggtc aaacatagat gcaaccaggt attagagctc    2100
ggttttcctc tcggtggact cgcaaagctt tttgctcagg agtgggaagg tgatgttaca    2160
gttgtaatgc ctgctactct tgctcagtac tcgaagatta tacaaaatcc gactcatgtc    2220
gagcttcaga aagcggctaa ccaaggaaga agatgcactt gggagaagct ctcagccata    2280
aaatcaaact gcgggatcga gcttgcgctt gatgattctg tagctattct taaccatatg    2340
cggaggctca agaaaagtgc ggagagagcc gccactgcca cgtcttcgtc tcatcacgga    2400
ttggcttcaa ccaccagatt caatgcttca agaagaatcc catcttggaa cgtccttgcc    2460
agagagaact caacaggctc actggatgat ctagtcactg acaataacct ccacgcttct    2520
tcgggcagga atttaagcga cagtgaaaca gagagcgtgg agttgagttc ttggacaaga    2580
actggtggac ctttaatgag aacagcttct gctaataagt tcattgattt tgttcagagt    2640
cttgatatcg acattgcatt ggtcagagga tttagtagca gtcccaattc tccagcagtt    2700
cctcctggtg gctcgtttac tccaagcccg agatccatag cggctcattc ggatatcgaa    2760
tcaaacagca atagcaacaa tcttggaaca agcacttcaa gcataacagt tactgaaggt    2820
gatcttctac agcctgagag aacgagtaac ggatttgtgt taaacgtcgt taaaagagag    2880
aacttgggaa tgccatcgat tgggaaccaa aatacagagt taccagagag tgtacagctc    2940
gatataccgg agaaggagat ggattgtagc tctgtatcag aacacgaaga agatgataac    3000
gacaatgaag aagaacataa cggctcgagt ctggttactg tttcttcaga agattccggt    3060
ttacaagaac cggtgtctgg tagtgttata gatgcttaga gtgtgattga ttcaagtgag    3120
tatagattct taattaaatt tgcagagttt ccaaagggtt tagtgcacca cttgtgtatg    3180
tttgtattgc ttattgtttg aaattcattt gtgaaatcga aatatatctg taaattcaga    3240
aaatattctc tcatccatta caaaatattt gagtc                              3275
```

<210> SEQ ID NO 38
<211> LENGTH: 2724
<212> TYPE: DNA
<213> ORGANISM: Sorghum bicolor

<400> SEQUENCE: 38

```
atggatgaca tcgccagcga ggcgccggtg ggggcgttcg ccatcggccc gtccacggcg     60
ctgggccgcg ccgtcgcgct ccgggtgctg ctctgcggct ccgcggcgcg cctgcggcac    120
cgcctggccg cggcgctccg cgccgcgctg cccgtcgcgg cggcgtggct gcaccgcgcg    180
gacaacacgc gcgggatcct gctcgccgtc tgcgccgtcg cgctcctgct gcggggccga    240
cgcggcaggg ccgggctgcg ggcgagggtg cagtccgcct accgccgcaa gttctggcgg    300
aacatgatgc gcgccgcgct cacctacgag gagtgggcgc acgcggcgcg gatgctggag    360
cgcgaggccg cccgcgccg cgccagcgac gccgacctct acgacgagga gctcgtccgc    420
aataagctcc gcgagctcag gcaccggcgc cacgagggat cgctcaggga catcgtcttc    480
tgcatgcgcg cggacctgct caggaacctc ggcaatatgt gcaaccccga actgcacaaa    540
gggaggctgc aggtgcctag actcataaag gaatacattg aggaagtatc tactcaactg    600
aaaatggtct gtgattctga ttcagatgag ttgcctcttg aagagaaact cgcatttatg    660
catgagacaa ggcatgcctt tggtagaaca gccttgctgc taagtggagg tgcttcattg    720
ggatcctttc atgtgggtgt tgttaaaacc ttggtagagc ataaactttt gccaaggata    780
atttcaggat caagtgttgg ctcgataatg tgttctatag tagcaacaag atcatggcct    840
gagctggaga gcttttttga agagtggcat tccctgaaat tttttgatca gatgggtgga    900
```

| | | | |
|---|---|---|---|
| atctttcctg tggttaaaag aattttgacg caaggcgctg ttcatgatat aaggcacttg | 960 |
| caggtgcttt tgagaaacct taccagcaat ttgacatttc aagaagctta tgacatgact | 1020 |
| ggtcggattc ttgttgtcac cgtgtgttct ccaaggaagc atgagccgcc tcgatgccta | 1080 |
| aactatttaa catcacctca tgttcttatc tggagtgcag taacagcttc ctgtgctttt | 1140 |
| cctggacttt tgaggccca agaattgatg gcaaaagata gatttggtca aaccattcct | 1200 |
| ttccatgctc cattcttatt aggcatagaa gaacgaactg ttgctccaac cgccgctgg | 1260 |
| agagatggga gcttagaaag cgatttaccc atgaagcaat tgaaggaact attcaatgtg | 1320 |
| aatcatttca tagtaagcca agccaatcct cacatagctc cgctgttgag actaaaggaa | 1380 |
| atcgtcaggg cttatggagg cagcttcgct gccaagcttg ctgaacttgc tgagatggaa | 1440 |
| gtcaaacata ggtgtaatca agttttggaa cttggatttc ctctaggagg attagctaaa | 1500 |
| ttatttgctc aagattggga aggcgatgtt acagttgtta tgccagccac tcttgcgcag | 1560 |
| tattccaaga tgatacagaa cccatcttat gctgagcttc agaaggctgc gaatcaaggt | 1620 |
| aggagatgca cttgggaaaa gctatcagcc atcagggcaa attgtgctat tgagcttgca | 1680 |
| ctggatgaat gtgttgccct cctgaaccac ttgcgtaggc taaagaggag tgcagaaaga | 1740 |
| gcatccgcat cgcaaggata tggtccagca atcaggttct gcccatctag gaggattcca | 1800 |
| tcctggaatc tcatagcaag agaaaattca actggttctc ttgaagaaga atgcttaca | 1860 |
| tctcctcaag gacctggagg agttgctgga acatctacca gaaaccagta tcctcagaga | 1920 |
| agtgcacatg agagcagcga cagtgaatct gagagtattg atttacactc ttggacaaga | 1980 |
| agtggtggcc ctcttatgag gacaacctca gccaataaat tcatcagctt tgttcagaat | 2040 |
| cttgagatcg acacagaatc cagaacaatt ccatcgaggg aagacataac tgatcttgtg | 2100 |
| acaccaaatg ctggtacctt ggcagctcat gcagtgagta gagaagcaat cgataggagc | 2160 |
| ttggacaatt cagctttaga tatccatgat accagtaccc ctagatcgac atttggccct | 2220 |
| tcaacaagta ttgtggtttc tgaaggtgac ttgttgcagc ctgaaaagat tgaaaatggt | 2280 |
| attttgttta atgttgtaag gagggatact ctgctcgggt ctagtagtgg agttgagtct | 2340 |
| caaggatctc ctcgggaacc agatgttgaa acagtacaga cggagtgcct tgatggcgtg | 2400 |
| tctacttctg atgatgatga tgacaaggaa ctaaatgcca ttgatgatgg aggaactagt | 2460 |
| cccatgagca gaaataatct acaacatcag gggtcctcac tggaagaaaa attataccat | 2520 |
| ccctcttcct taaattctga agacgagaca aacacaaaca aaccagaagc tgcatcgatt | 2580 |
| tttgatatat gtacagatat gcatccggca tctattagcc tacctgaagg gtcttcagaa | 2640 |
| aagacagaac tggaaacaac aaagattcct gatgacaatt cagctgttat gaatgatgaa | 2700 |
| gttgcctcag gtgctggtaa ctaa | 2724 |

<210> SEQ ID NO 39
<211> LENGTH: 3470
<212> TYPE: DNA
<213> ORGANISM: Nicotiana benthamiana

<400> SEQUENCE: 39

| | | |
|---|---|---|
| gttatctgat ccaaacttct gactttttct attttccgaa tccctatgtt ttttaataaa | 60 |
| tccatctctg ccattgcagt gatatattca tttattgtta tcaccttctt catttattgg | 120 |
| tccctctgtg ttttccatat attgaaggag aaaacattaa ctttatgcga ttttgtagtt | 180 |
| tttctggttg attcctacaa cccctttttga cattgatctt gtgggttaca aaaaacattg | 240 |

```
aatctttatg tcaaaatttg atctttgtat ttcattttaa attgaaattt gattttgggg      300
ggtattaagg attcttttgt cggttgattt tgtgccttt ttgccaagtt cttgtcggtc       360
tctgagctga atttccataa tttgacaaaa agaaaaggct aaagcagaaa ggttgggagt      420
ttctttcttt gacttcaga aactaaggta ttttctttga tctaattctt gttaatatct       480
ggttcaatct gattccgttg aatcttgtga atagcctttg tttccctatt gtcagaaaat     540
tatttccttt tcactttcct cgactctcag aagttagtac aatctttgtt ctgctaaatc     600
ttgtgaataa cctttagctt agagttttag gtatctgtat attgggttct cttaacatt      660
agcctagaag ccttctctag gattagtccc ccttttcatt gagatggata taagtaatga    720
ggctacaatt gacttctttt ccattggacc tactacgata ttgggtcgaa caatcgcctt    780
tagagtgttg ttctgtaaat caatttcaca attgaagcat cacctatttc atttcttgat    840
atattacttg tacaaattca agaatggttt gtcatactac ttgacaccct tgatctcgtg    900
gttgcaccct cgtaatccac aaggaatatt ggcattggta acgcttctcg ccttcttgtt    960
gaggcgatac acgaatgtaa aaatcaaggc tgagatggcc tataggagga agttttggag   1020
gaatatgatg agatctgcat tgacttatga ggagtgggct catgctgcca agatgctaga   1080
taaagagacc cctaaaatga atgaggcaga tctttatgat gtagaattag ttcgaaataa   1140
actccaagag cttcgacatc gtaggcaaga gggttctatg agggatatca tattctgtat   1200
gagagctgac cttgttagga atcttggtaa tatgtgtaat ccagaacttc acaagggaag   1260
gcttcatgtg cctagactga ttaaggatta tattgatgag gtttcaactc agttgagaat   1320
ggtatgcgac tctgattcgg aggagcttct cttggaagag aagcttgctt tcatgcatga   1380
aacaagacat gcctttggta ggacagcttt gcttttaagt ggaggtgctt ctttaggagc   1440
tttccatgtg ggcgtggtga aaacacttgt agaacacaaa ctgatgccac ggataattgc   1500
tggttcaagt gtcggctcga ttatgtgctc catagttgca actcgatctt ggcctgagct   1560
ccagagtttt tcgaggact cctggcactc tttgcaattt ttcgatcagt tgggtgggat    1620
ttttactatt tcaggaggg tcatgaccca gggtgctgta catgagatca gacagctgca    1680
ggtgctgtta cgtaatctca cgaataatct tactttccaa gaagcctatg acatgactgg   1740
tagagttctg gggattactg tttgctcgcc taggaaacat gaacctccta gatgcttgaa   1800
ctacttgact tcacctcatg ttgttatatg gagtgccgtt accgcttctt gtgccttttcc  1860
tggtctcttc gaagctcaag aacttatggc aaaggataga agtggagatc ttgttccata   1920
tcacccacca tttcatttgg gtcctgatgc cacttctagt gcatctgctc gtcgttggag   1980
ggatggtagc ttggaggttg atttgccaat gatgcagcta aaggagctct tcaatgtcaa   2040
tcactttatt gtgagccagg cgaatccgca tattgctcca ctgctgagga tcaaagagtt    2100
tgtaagagct tatggaggca actttgctgc caagcttgct caacttacgg aaatggaggt    2160
gaagcacaga tgcaatcagg tattagaact tggttttccc ttgggaggat tagcaaagct    2220
ttttgctcaa gaatgggagg gtgatgtaac tgttgtaatg cctgccactc tagctcagta    2280
ctcaaaaatc atacagaatc cctcgactct ggagctgcaa aaagcagcaa atcaaggaag    2340
aaggtgcact tggaaaaac tctcagccat gaaagcaaac tgtggaattg agcttgcact     2400
tgatgaatgc gttgctatac tgaatcacat gcgtagactg aaaaggagtg ctgagagggc   2460
ggctgctgct tcacatggct tggcaagcac tgtcagattt aacacttcca gaagaattcc   2520
ttcttggaac tgcattgcac gagagaactc aacaggctcc cttgaagatt ttcttgcgga    2580
tgttgctgct tcacatcatc aaggaggcag tggttcgggg gcgcatgtta accgtagttg   2640
```

| | |
|---|---|
| gcgaacgcac cggaatgcac atgatggtag tgacagtgag ccggaaaatg tggaccttaa | 2700 |
| ttcttggaca agatcgggtg gtcctttgat gaggacaaca tcagctgata agtttattga | 2760 |
| ctttgtccag aacttggaaa ttggttcgcg attgaacaaa ggattgacta ttgacctcaa | 2820 |
| caatattatt cctcgatgg caagcaggga ccatttctcc ccgagcccaa gggtaacaac | 2880 |
| acctgataga agttcagata cagaatttga tcaaagagat tttagttaca gggtccctgc | 2940 |
| gagtagttca agcattatgg taggcgaagg tgaccttctg cagcctgaaa ggactaacag | 3000 |
| cggtattgtc ttcaatgtgg taaggaaagg agacttgacc ccatcgaaca gaagccttga | 3060 |
| ttcagaaaat aatagttccg tgcaggatgc agttgctgag tgcgtgcaac ttgaaagtcc | 3120 |
| agaaaaggag atggatatta gctcagtatc ggaggatggt gagaatgatg ttgggcaagg | 3180 |
| aagtagggta aatgaagttg attgtagtaa aaatcgttca tcaatcggtg atggcaacga | 3240 |
| taagcaagtt attgatactt gagagtttag ctttgattat tctacacagg ccattcgaat | 3300 |
| tatttttat actcaaatgg agcttctttc agagctaaca cactcagaat tggggttgta | 3360 |
| aatagtgcaa gtagcaaatc tgtaataaat gtttagtgta gtcatcaccc ttctactagt | 3420 |
| tcaaagtggc tcagttcaat tcaaattcag aacttcgata attcatgttt | 3470 |

```
<210> SEQ ID NO 40
<211> LENGTH: 713
<212> TYPE: DNA
<213> ORGANISM: Nicotiana benthamiana

<400> SEQUENCE: 40
```

| | |
|---|---|
| tgtatgagag ctgaccttgt taggaatctt ggtaatatgt gtaatccaga acttcacaag | 60 |
| ggaaggcttc atgtgcctag actgattaag gattatattg atgaggtttc aactcagttg | 120 |
| agaatggtat gcgactctga ttcggaggag cttctcttgg aagagaagct tgctttcatg | 180 |
| catgaaacaa gacatgcctt tggtaggaca gctttgcttt taagtggagg tgcttctttta | 240 |
| ggagctttcc atgtgggcgt ggtgaaaaca cttgtagaac acaaactgat gccacggata | 300 |
| attgctggtt caagtgtcgg ctcgattatg tgctccatag ttgcaactcg atcttggcct | 360 |
| gagctccaga gttttttcga ggactcctgg cactcttttgc aattttttcga tcagttgggt | 420 |
| gggatttttta ctattttcag gagggtcatg acccagggtg ctgtacatga gatcagacag | 480 |
| ctgcaggtgc tgttacgtaa tctcacgaat aatcttactt tccaagaagc ctatgacatg | 540 |
| actggtagag ttctggggat tactgtttgc tcgcctagga acatgaaccc tcctagatgc | 600 |
| ttgaactact tgacttcacc tcatgttgtt atatggagtg ccgttaccgc ttcttgtgcc | 660 |
| tttcctggtc tcttcgaagc tcaagaactt atggcaaagg atagaagtgg aga | 713 |

```
<210> SEQ ID NO 41
<211> LENGTH: 1500
<212> TYPE: DNA
<213> ORGANISM: Arabidopsis thaliana

<400> SEQUENCE: 41
```

| | |
|---|---|
| cgaaaaaaga agtagaatat atatatatat atatatatat atatatattc | 60 |
| gtgtggacat cataaatgcc taaatgataa tagttgattt cgagttttat tttcgttact | 120 |
| tccaatcaaa ttctccttgc accatattta tttttttact gtgagaacat ataagtat | 180 |
| atattggaat tacgtatccg agaggttttt gcatatttcg tttatttatt ttcgatatcc | 240 |
| acactactgt attattaaaa atttgaaaaa ttcaactagg gcttttcatc ttctctagaa | 300 |

```
ttattcgttt atttatgtcg atgtccacac tattattaaa ataaaacgag aggatatggt    360
tggatcatcc aagtttcgtt tatgactctt tgttcattta caaacgttta gttttccact    420
taagttttga aaagagttaa tttccaatat attcggcaca gttttcaag tgtattcatc     480 tgttttttt tttttggtt ggctatatgg tccaaatttt gatttgcaat atgagattgc     540
acagagagaa caatctttca ttatgattaa ttattgtaca agtaacaaac accaatctcc    600
gatatacttt ggctctttag cacattgtta tgctagaagt tagcggaaat ctatatgttg    660
ttaaacgcag cgtttaaatt gaacagtgta atttaccttg aaatttaag actacatgct    720 gtttagaatt tcagatgaaa acatcttgat gttttagaaa tccacgtggg aatagcgtaa    780
aatcttatcc aacgaactta ttttggtttt gttgtatttg tgcaagtcgt cacgctaatc    840 gaaaaagaa aagaaaaaaa gaagccgtca tgatcggcca tttctcggcc gagtctgagt    900
ctgactctgc gtccgtgtca ccattatcag atcgagcctg tcttatctcg ttgcgattcc    960
ctatgcaaaa atcttcttct tttttttatt cccccattta tctctgatct cttctctctt   1020
ctcaagtaaa cctctctgct tcacgtctct tcttttcttg tcgattttcc ccagataatc    1080
aggtaaataa ggctactttc ttatttgatc tggtggtctt tgtgttgaaa tctctgggtt    1140
ttctctgttg atttcaaagt tctctctttt ttttttgtt tactgggtgc tgtgaaaaat     1200
gatcttgtca aagtctcctc ttttcatcga attgaaactc taattagaaa aaagatcata    1260
acttttatta aaaaaatgag tttgcttttgc ttaattttgc gaattgcttc atagattcat    1320
tgattagcct atttggggta acaaaaaaa gctgacacgg tttcagattc caaaaataga    1380
tcatgactct gtttcttctc tgcagaggtt ttaataaata tatgcttctt ctcatgagtt    1440
ctcgtttttt ttgtcaccett cgcagttgaa aacacaccca aattcatctt cgaatcaata   1500
```

<210> SEQ ID NO 42
<211> LENGTH: 2871
<212> TYPE: DNA
<213> ORGANISM: Artificial Sequence
<220> FEATURE:
<223> OTHER INFORMATION: Nucleotide sequence of the complement of the pSSU-Oleosin gene in the T-DNA of pJP3502. In order (complementary sequences): Glycine max Lectin terminator 348nt, 3' exon 255nt, UBQ10 intron 304nt, 5' exon 213nt, SSU promoter

<400> SEQUENCE: 42

```
ggcccctaga atctaattat tctattcaga ctaaattagt ataagtattt ttttaatcaa     60
taaataataa ttaataattt attagtagga gtgattgaat ttataatata ttttttttaa    120
tcatttaaag aatcttatat cttaaattg acaagagttt taaatgggga gagtgttatc    180
atatcacaag taggattaat gtgttatagt ttcacatgca ttacgataag ttgtgaaaga    240
taacattatt atatataaca atgacaatca ctagcgatcg agtagtgaga gtcgtcttat    300
tacactttct tccttcgatc tgtcacatgg cggcggcccg cggccgcttc attactcgag    360
ccaggaggat ggatcgatgc tggtctgaga ccctgctacc ggttgctgac tgaactgctc    420
ggcacggtcc ttcatttcac gggccttgct cgccaacttt gtcttggccg actccaactg    480
atccgctccg ggtggatgtt tccccgtcag gtaacggtag atccaggaca gcacagacag    540
agcggcaaca ccaaatcccc cgcttgccag aaaacccgct cccaacagga agatggtgat    600
gactgcagat cagaaaaact cagattaatc gacaaattcg atcgcacaaa ctagaaacta    660
acaccagatc tagatagaaa tcacaaatcg aagagtaatt attcgacaaa actcaaatta    720
tttgaacaaa tcggatgata tctatgaaac cctaatcgag aattaagatg atatctaacg    780
```

| | | |
|---|---|---|
| atcaaaccca gaaaatcgtc ttcgatctaa gattaacaga atctaaacca agaacatat | 840 | |
| acgaaattgg gatcgaacga aaacaaaatc gaagattttg agagaataag gaacacagaa | 900 | |
| atttacctgc agggaccagt acaggcgaga agatcaccag gagaggtgtg gcgattgtca | 960 | |
| gcgcaatgac cgttccagcc agggtcaacc cggataacac caacaggcta cctccggcag | 1020 | |
| taaccgcggt cgctgccttt acaacacgct gagcacgcgg ttgcagttgc aagtgggggg | 1080 | |
| cacgtgtttg ttgctgctgc ccgtagtgct ctgccatgtt ttttttttaac ggagcaagcg | 1140 | |
| gccgctgttc ttctttactc tttgtgtgac tgaggtttgg tctagtgctt tggtcatcta | 1200 | |
| tatataatga taacaacaat gagaacaagc tttggagtga tcggagggtc taggatacat | 1260 | |
| gagattcaag tggactagga tctacaccgt tggattttga gtgtggatat gtgtgaggtt | 1320 | |
| aattttactt ggtaacggcc acaaaggcct aaggagaggt gttgagaccc ttatcggctt | 1380 | |
| gaaccgctgg aataatgcca cgtggaagat aattccatga atcttatcgt tatctatgag | 1440 | |
| tgaaattgtg tgatggtgga gtggtgcttg ctcattttac ttgcctggtg gacttggccc | 1500 | |
| tttccttatg gggaatttat attttactta ctatagagct ttcataccct ttttttacct | 1560 | |
| tggatttagt taatatataa tggtatgatt catgaataaa aatgggaaat ttttgaattt | 1620 | |
| gtactgctaa atgcataaga ttaggtgaaa ctgtggaata tatatttttt tcatttaaaa | 1680 | |
| gcaaatttg cctttactta gaattataaa tatagaaaaa tataataacat tcaaataaaa | 1740 | |
| atgaaaataa gaactttcaa aaaacagaac tatgtttaat gtgtaaagat tagtcgcaca | 1800 | |
| tcaagtcatc tgttacaata tgttacaaca agtcataagc ccaacaaagt tagcacgtct | 1860 | |
| aaataaacta aagagtccac gaaaatatta caaatcataa gcccaacaaa gttattgatc | 1920 | |
| aaaaaaaaaa aacgcccaac aaagctaaac aaagtccaaa aaaaacttct caagtctcca | 1980 | |
| tcttcccttta tgaacattga aaactataca caaacaagt cagataaatc tctttctggg | 2040 | |
| cctgtcttcc caacctccta catcacttcc ctatcggatt gaatgttttta cttgtacctt | 2100 | |
| ttccgttgca atgatattga tagtatgttt gtgaaaacta atagggttaa caatcgaagt | 2160 | |
| catggaatat ggatttggtc caagattttc cgagagcttt ctagtagaaa gcccatcacc | 2220 | |
| agaaatttac tagtaaaata aatcaccaat taggtttctt attatgtgcc aaattcaata | 2280 | |
| taattataga ggatatttca aatgaaaacg tatgaatgtt attagtaaat ggtcaggtaa | 2340 | |
| gacattaaaa aaatcctacg tcagatattc aactttaaaa attcgatcag gtgtggaattg | 2400 | |
| tacaaaaatt tgggatctac tatatatata taatgctttta caacacttgg atttttttttt | 2460 | |
| ggaggctgga atttttaatc tacatatttg tttttggccat gcaccaactc attgtttagt | 2520 | |
| gtaatacttt gattttgtca aatatatgtg ttcgtgtata tttgtataag aatttctttg | 2580 | |
| accatataca cacacacata tatatatata tatatatatt atatatcatg cacttttaat | 2640 | |
| tgaaaaaata atatatatat atatagtgca tttttttctaa caaccatata tgttgcgatt | 2700 | |
| gatctgcaaa aatactgcta gagtaatgaa aaatataatc tattgctgaa attatctcag | 2760 | |
| atgttaagat tttcttaaag taaattcttt caaatttag ctaaaagtct tgtaataact | 2820 | |
| aaagaataat acacaatctc gaccacggaa aaaaacaca taataaattt g | 2871 | |

<210> SEQ ID NO 43
<211> LENGTH: 362
<212> TYPE: PRT
<213> ORGANISM: Arabidopsis thaliana

<400> SEQUENCE: 43

Met Leu Lys Leu Ser Cys Asn Val Thr Asp Ser Lys Leu Gln Arg Ser

```
            1               5                   10                  15
        Leu Leu Phe Phe Ser His Ser Tyr Arg Ser Asp Pro Val Asn Phe Ile
                        20                  25                  30

Arg Arg Arg Ile Val Ser Cys Ser Gln Thr Lys Lys Thr Gly Leu Val
                        35                  40                  45

Pro Leu Arg Ala Val Val Ser Ala Asp Gln Gly Ser Val Val Gln Gly
                50                      55                  60

Leu Ala Thr Leu Ala Asp Gln Leu Arg Leu Gly Ser Leu Thr Glu Asp
        65                  70                  75                  80

Gly Leu Ser Tyr Lys Glu Lys Phe Val Val Arg Ser Tyr Glu Val Gly
                        85                  90                  95

Ser Asn Lys Thr Ala Thr Val Glu Thr Ile Ala Asn Leu Leu Gln Glu
                        100                 105                 110

Val Gly Cys Asn His Ala Gln Ser Val Gly Phe Ser Thr Asp Gly Phe
                    115                 120                 125

Ala Thr Thr Thr Thr Met Arg Lys Leu His Leu Ile Trp Val Thr Ala
                    130                 135                 140

Arg Met His Ile Glu Ile Tyr Lys Tyr Pro Ala Trp Gly Asp Val Val
        145                 150                 155                 160

Glu Ile Glu Thr Trp Cys Gln Ser Glu Gly Arg Ile Gly Thr Arg Arg
                        165                 170                 175

Asp Trp Ile Leu Lys Asp Ser Val Thr Gly Glu Val Thr Gly Arg Ala
                    180                 185                 190

Thr Ser Lys Trp Val Met Met Asn Gln Asp Thr Arg Arg Leu Gln Lys
                        195                 200                 205

Val Ser Asp Asp Val Arg Asp Glu Tyr Leu Val Phe Cys Pro Gln Glu
                    210                 215                 220

Pro Arg Leu Ala Phe Pro Glu Glu Asn Asn Arg Ser Leu Lys Lys Ile
        225                 230                 235                 240

Pro Lys Leu Glu Asp Pro Ala Gln Tyr Ser Met Ile Gly Leu Lys Pro
                    245                 250                 255

Arg Arg Ala Asp Leu Asp Met Asn Gln His Val Asn Asn Val Thr Tyr
                    260                 265                 270

Ile Gly Trp Val Leu Glu Ser Ile Pro Gln Glu Ile Val Asp Thr His
                    275                 280                 285

Glu Leu Gln Val Ile Thr Leu Asp Tyr Arg Arg Glu Cys Gln Gln Asp
                    290                 295                 300

Asp Val Val Asp Ser Leu Thr Thr Thr Ser Glu Ile Gly Gly Thr
        305                 310                 315                 320

Asn Gly Ser Ala Thr Ser Gly Thr Gln Gly His Asn Asp Ser Gln Phe
                        325                 330                 335

Leu His Leu Leu Arg Leu Ser Gly Asp Gly Gln Glu Ile Asn Arg Gly
                        340                 345                 350

Thr Thr Leu Trp Arg Lys Lys Pro Ser Ser
                        355                 360

<210> SEQ ID NO 44
        <211> LENGTH: 367
        <212> TYPE: PRT
        <213> ORGANISM: Arabidopsis thaliana

<400> SEQUENCE: 44

Met Leu Lys Leu Ser Cys Asn Val Thr Asp His Ile Asn Leu Phe
        1               5                   10                  15
```

```
Ser Asn Ser Arg Arg Ile Phe Val Pro Val His Arg Gln Thr Arg Pro
            20                  25                  30

Ile Ser Cys Phe Gln Leu Lys Lys Glu Pro Leu Arg Ala Ile Leu Ser
        35                  40                  45

Ala Asp His Gly Asn Ser Ser Val Arg Val Ala Asp Thr Val Ser Gly
    50                  55                  60

Thr Ser Pro Ala Asp Arg Leu Arg Phe Gly Arg Leu Met Glu Asp Gly
65                  70                  75                  80

Phe Ser Tyr Lys Glu Lys Phe Ile Val Arg Ser Tyr Glu Val Gly Ile
                85                  90                  95

Asn Lys Thr Ala Thr Ile Glu Thr Ile Ala Asn Leu Leu Gln Glu Val
            100                 105                 110

Ala Cys Asn His Val Gln Asn Val Gly Phe Ser Thr Asp Gly Phe Ala
        115                 120                 125

Thr Thr Leu Thr Met Arg Lys Leu His Leu Ile Trp Val Thr Ala Arg
130                 135                 140

Met His Ile Glu Ile Tyr Lys Tyr Pro Ala Trp Ser Asp Val Val Glu
145                 150                 155                 160

Ile Glu Thr Trp Cys Gln Ser Glu Gly Arg Ile Gly Thr Arg Arg Asp
                165                 170                 175

Trp Ile Leu Lys Asp Cys Ala Thr Gly Glu Val Ile Gly Arg Ala Thr
            180                 185                 190

Ser Lys Trp Val Met Met Asn Gln Asp Thr Arg Arg Leu Gln Arg Val
        195                 200                 205

Thr Asp Glu Val Arg Asp Glu Tyr Leu Val Phe Cys Pro Pro Glu Pro
210                 215                 220

Arg Leu Ala Phe Pro Glu Glu Asn Asn Ser Ser Leu Lys Lys Ile Pro
225                 230                 235                 240

Lys Leu Glu Asp Pro Ala Gln Tyr Ser Met Leu Gly Leu Lys Pro Arg
                245                 250                 255

Arg Ala Asp Leu Asp Met Asn Gln His Val Asn Asn Val Thr Tyr Ile
            260                 265                 270

Gly Trp Val Leu Glu Ser Ile Pro Gln Glu Ile Ile Asp Thr His Glu
        275                 280                 285

Leu Lys Val Ile Thr Leu Asp Tyr Arg Arg Glu Cys Gln Gln Asp Asp
290                 295                 300

Ile Val Asp Ser Leu Thr Thr Ser Glu Thr Pro Asn Glu Val Val Ser
305                 310                 315                 320

Lys Leu Thr Gly Thr Asn Gly Ser Thr Thr Ser Ser Lys Arg Glu His
                325                 330                 335

Asn Glu Ser His Phe Leu His Ile Leu Arg Leu Ser Glu Asn Gly Gln
            340                 345                 350

Glu Ile Asn Arg Gly Arg Thr Gln Trp Arg Lys Lys Ser Ser Arg
        355                 360                 365

<210> SEQ ID NO 45
<211> LENGTH: 412
<212> TYPE: PRT
<213> ORGANISM: Arabidopsis thaliana

<400> SEQUENCE: 45

Met Val Ala Thr Ser Ala Thr Ser Ser Phe Phe Pro Val Pro Ser Ser
1               5                   10                  15

Ser Leu Asp Pro Asn Gly Lys Gly Asn Lys Ile Gly Ser Thr Asn Leu
            20                  25                  30
```

Ala Gly Leu Asn Ser Ala Pro Asn Ser Gly Arg Met Lys Val Lys Pro
                 35                  40                  45

Asn Ala Gln Ala Pro Pro Lys Ile Asn Gly Lys Lys Val Gly Leu Pro
 50                  55                  60

Gly Ser Val Asp Ile Val Arg Thr Asp Thr Glu Thr Ser Ser His Pro
 65                  70                  75                  80

Ala Pro Arg Thr Phe Ile Asn Gln Leu Pro Asp Trp Ser Met Leu Leu
                 85                  90                  95

Ala Ala Ile Thr Thr Ile Phe Leu Ala Ala Glu Lys Gln Trp Met Met
                 100                 105                 110

Leu Asp Trp Lys Pro Arg Arg Ser Asp Met Leu Val Asp Pro Phe Gly
                 115                 120                 125

Ile Gly Arg Ile Val Gln Asp Gly Leu Val Phe Arg Gln Asn Phe Ser
                 130                 135                 140

Ile Arg Ser Tyr Glu Ile Gly Ala Asp Arg Ser Ala Ser Ile Glu Thr
145                 150                 155                 160

Val Met Asn His Leu Gln Glu Thr Ala Leu Asn His Val Lys Thr Ala
                 165                 170                 175

Gly Leu Leu Gly Asp Gly Phe Gly Ser Thr Pro Glu Met Phe Lys Lys
                 180                 185                 190

Asn Leu Ile Trp Val Val Thr Arg Met Gln Val Val Asp Lys Tyr
                 195                 200                 205

Pro Thr Trp Gly Asp Val Val Glu Val Asp Thr Trp Val Ser Gln Ser
210                 215                 220

Gly Lys Asn Gly Met Arg Arg Asp Trp Leu Val Arg Asp Cys Asn Thr
225                 230                 235                 240

Gly Glu Thr Leu Thr Arg Ala Ser Ser Val Trp Val Met Met Asn Lys
                 245                 250                 255

Leu Thr Arg Arg Leu Ser Lys Ile Pro Glu Glu Val Arg Gly Glu Ile
                 260                 265                 270

Glu Pro Tyr Phe Val Asn Ser Asp Pro Val Leu Ala Glu Asp Ser Arg
                 275                 280                 285

Lys Leu Thr Lys Ile Asp Asp Lys Thr Ala Asp Tyr Val Arg Ser Gly
                 290                 295                 300

Leu Thr Pro Arg Trp Ser Asp Leu Asp Val Asn Gln His Val Asn Asn
305                 310                 315                 320

Val Lys Tyr Ile Gly Trp Ile Leu Glu Ser Ala Pro Val Gly Ile Met
                 325                 330                 335

Glu Arg Gln Lys Leu Lys Ser Met Thr Leu Glu Tyr Arg Arg Glu Cys
                 340                 345                 350

Gly Arg Asp Ser Val Leu Gln Ser Leu Thr Ala Val Thr Gly Cys Asp
                 355                 360                 365

Ile Gly Asn Leu Ala Thr Ala Gly Asp Val Glu Cys Gln His Leu Leu
                 370                 375                 380

Arg Leu Gln Asp Gly Ala Glu Val Val Arg Gly Arg Thr Glu Trp Ser
385                 390                 395                 400

Ser Lys Thr Pro Thr Thr Thr Trp Gly Thr Ala Pro
                 405                 410

<210> SEQ ID NO 46
<211> LENGTH: 345
<212> TYPE: PRT
<213> ORGANISM: Arabidopsis thaliana

```
<400> SEQUENCE: 46

Met Phe Ile Ala Val Glu Val Ser Pro Val Met Glu Asp Ile Thr Arg
1               5                   10                  15

Gln Ser Lys Lys Thr Ser Val Glu Asn Glu Thr Gly Asp Asp Gln Ser
                20                  25                  30

Ala Thr Ser Val Val Leu Lys Ala Lys Lys Arg Arg Ser Gln Pro
            35                  40                  45

Arg Asp Ala Pro Pro Gln Arg Ser Ser Val His Arg Gly Val Thr Arg
        50                  55                  60

His Arg Trp Thr Gly Arg Tyr Glu Ala His Leu Trp Asp Lys Asn Ser
65                  70                  75                  80

Trp Asn Glu Thr Gln Thr Lys Lys Gly Arg Gln Val Tyr Leu Gly Ala
                85                  90                  95

Tyr Asp Glu Glu Asp Ala Ala Arg Ala Tyr Asp Leu Ala Ala Leu
            100                 105                 110

Lys Tyr Trp Gly Arg Asp Thr Ile Leu Asn Phe Pro Leu Cys Asn Tyr
            115                 120                 125

Glu Glu Asp Ile Lys Glu Met Glu Ser Gln Ser Lys Glu Glu Tyr Ile
    130                 135                 140

Gly Ser Leu Arg Arg Lys Ser Ser Gly Phe Ser Arg Gly Val Ser Lys
145                 150                 155                 160

Tyr Arg Gly Val Ala Lys His His Asn Gly Arg Trp Glu Ala Arg
                165                 170                 175

Ile Gly Arg Val Phe Gly Asn Lys Tyr Leu Tyr Leu Gly Thr Tyr Ala
            180                 185                 190

Thr Gln Glu Glu Ala Ala Ile Ala Tyr Asp Ile Ala Ala Ile Glu Tyr
        195                 200                 205

Arg Gly Leu Asn Ala Val Thr Asn Phe Asp Ile Ser Arg Tyr Leu Lys
    210                 215                 220

Leu Pro Val Pro Glu Asn Pro Ile Asp Thr Ala Asn Asn Leu Leu Glu
225                 230                 235                 240

Ser Pro His Ser Asp Leu Ser Pro Phe Ile Lys Pro Asn His Glu Ser
                245                 250                 255

Asp Leu Ser Gln Ser Gln Ser Ser Glu Asp Asn Asp Arg Lys
            260                 265                 270

Thr Lys Leu Leu Lys Ser Ser Pro Leu Val Ala Glu Glu Val Ile Gly
            275                 280                 285

Pro Ser Thr Pro Pro Glu Ile Ala Pro Pro Arg Arg Ser Phe Pro Glu
        290                 295                 300

Asp Ile Gln Thr Tyr Phe Gly Cys Gln Asn Ser Gly Lys Leu Thr Ala
305                 310                 315                 320

Glu Glu Asp Asp Val Ile Phe Gly Asp Leu Asp Ser Phe Leu Thr Pro
                325                 330                 335

Asp Phe Tyr Ser Glu Leu Asn Asp Cys
            340                 345

<210> SEQ ID NO 47
<211> LENGTH: 303
<212> TYPE: PRT
<213> ORGANISM: Arabidopsis thaliana

<400> SEQUENCE: 47

Met Ala Lys Val Ser Gly Arg Ser Lys Lys Thr Ile Val Asp Asp Glu
1               5                   10                  15
```

```
Ile Ser Asp Lys Thr Ala Ser Ala Ser Glu Ser Ala Ser Ile Ala Leu
             20                  25                  30

Thr Ser Lys Arg Lys Arg Lys Ser Pro Pro Arg Asn Ala Pro Leu Gln
         35                  40                  45

Arg Ser Pro Tyr Arg Gly Val Thr Arg His Arg Trp Thr Gly Arg
 50                  55                  60

Tyr Glu Ala His Leu Trp Asp Lys Asn Ser Trp Asn Asp Thr Gln Thr
 65                  70                  75                  80

Lys Lys Gly Arg Gln Val Tyr Leu Gly Ala Tyr Asp Glu Glu Ala
                 85                  90                  95

Ala Ala Arg Ala Tyr Asp Leu Ala Ala Leu Lys Tyr Trp Gly Arg Asp
             100                 105                 110

Thr Leu Leu Asn Phe Pro Leu Pro Ser Tyr Asp Glu Asp Val Lys Glu
             115                 120                 125

Met Glu Gly Gln Ser Lys Glu Glu Tyr Ile Gly Ser Leu Arg Arg Lys
             130                 135                 140

Ser Ser Gly Phe Ser Arg Gly Val Ser Lys Tyr Arg Gly Val Ala Arg
145                 150                 155                 160

His His His Asn Gly Arg Trp Glu Ala Arg Ile Gly Arg Val Phe Ala
                 165                 170                 175

Thr Gln Glu Glu Ala Ala Ile Ala Tyr Asp Ile Ala Ala Ile Glu Tyr
             180                 185                 190

Arg Gly Leu Asn Ala Val Thr Asn Phe Asp Val Ser Arg Tyr Leu Asn
             195                 200                 205

Pro Asn Ala Ala Ala Asp Lys Ala Asp Ser Asp Ser Lys Pro Ile Arg
 210                 215                 220

Ser Pro Ser Arg Glu Pro Glu Ser Ser Asp Asn Lys Ser Pro Lys
225                 230                 235                 240

Ser Glu Glu Val Ile Glu Pro Ser Thr Ser Pro Glu Val Ile Pro Thr
                 245                 250                 255

Arg Arg Ser Phe Pro Asp Asp Ile Gln Thr Tyr Phe Gly Cys Gln Asp
             260                 265                 270

Ser Gly Lys Leu Ala Thr Glu Glu Asp Val Ile Phe Asp Cys Phe Asn
     275                 280                 285

Ser Tyr Ile Asn Pro Gly Phe Tyr Asn Glu Phe Asp Tyr Gly Pro
 290                 295                 300

<210> SEQ ID NO 48
<211> LENGTH: 445
<212> TYPE: PRT
<213> ORGANISM: Avena sativa

<400> SEQUENCE: 48

Met Lys Arg Ser Pro Pro Ala Pro Pro Ala Ala Pro Pro Pro
1               5                   10                  15

Gln Pro Ser Pro Ser Ser Ser Pro Ala Cys Ser Pro Ser Pro Ser
             20                  25                  30

Ser Ser Ser Cys Pro Ser Ser Ser Asp Ser Ser Ser Ile Val Ile Pro
         35                  40                  45

Arg Lys Arg Ala Arg Thr Gln Lys Ala Ala Ser Gly Lys Pro Lys Ala
 50                  55                  60

Lys Ala Ser Ala Lys Arg Pro Lys Lys Asp Ala Ser Arg Ser Ser Lys
65                  70                  75                  80

Glu Thr Asp Ala Asn Gly Ala Ala Ala Ala Gly Lys Arg Ser Ser
                 85                  90                  95
```

Ile Tyr Arg Gly Val Thr Arg His Arg Trp Thr Gly Arg Phe Glu Ala
            100                 105                 110
His Leu Trp Asp Lys Asn Cys Phe Thr Ser Val Gln Asn Lys Lys Lys
            115                 120                 125
Gly Arg Gln Val Tyr Leu Gly Ala Tyr Asp Thr Glu Asp Ala Ala Ala
130                 135                 140
Arg Ala Tyr Asp Leu Ala Ala Leu Lys Tyr Trp Gly Ser Glu Thr Ile
145                 150                 155                 160
Leu Asn Phe Ser Val Glu Asp Tyr Ala Lys Glu Met Pro Glu Met Glu
                165                 170                 175
Ala Val Ser Arg Glu Glu Tyr Leu Ala Ala Leu Arg Arg Ser Ser
                180                 185                 190
Gly Phe Ser Arg Gly Val Ser Lys Tyr Arg Gly Val Ala Arg His His
                195                 200                 205
His Asn Gly Arg Trp Glu Ala Arg Ile Gly Arg Val Leu Gly Asn Lys
            210                 215                 220
Tyr Leu Tyr Leu Gly Thr Phe Asp Thr Gln Glu Glu Ala Ala Lys Ala
225                 230                 235                 240
Tyr Asp Leu Ala Ala Ile Glu Tyr Arg Gly Ala Asn Ala Val Thr Asn
                245                 250                 255
Phe Asp Ile Ser Cys Tyr Leu Asp Gln Pro Gln Leu Leu Ala Gln Leu
                260                 265                 270
Gln Gln Gly Pro Gln Val Val Pro Ala Leu Gln Glu Glu Leu Gln His
            275                 280                 285
Asp Val Gln His Asp Leu Gln Asn Asp Asn Ala Val Gln Glu Leu Asn
            290                 295                 300
Ser Gly Glu Val Gln Met Pro Gly Ala Met Asp Glu Pro Ile Ala Leu
305                 310                 315                 320
Asp Asp Ser Thr Glu Cys Ile Asn Thr Pro Phe Glu Phe Asp Phe Ser
                325                 330                 335
Val Glu Glu Asn Leu Trp Ser Pro Cys Met Asp Tyr Glu Leu Asp Ala
                340                 345                 350
Ile Leu Gly Asn Asn Thr Ser Asn Ser Ala Asn Met Asn Glu Trp Phe
            355                 360                 365
Asn Asp Ser Thr Phe Glu Ser Asn Ile Gly Cys Leu Phe Glu Gly Cys
            370                 375                 380
Ser Asn Ile Asp Asp Cys Ser Ser Lys His Cys Ala Asp Leu Ala
385                 390                 395                 400
Ala Phe Asp Phe Phe Lys Glu Gly Asp Asp Asn Asp Phe Ser Asn Met
                405                 410                 415
Glu Met Glu Ile Thr Pro Gln Ala Asn Asp Val Ser Cys Pro Pro Asn
            420                 425                 430
Asp Val Ser Cys Pro Pro Lys Met Ile Thr Val Cys Asn
            435                 440                 445

<210> SEQ ID NO 49
<211> LENGTH: 420
<212> TYPE: PRT
<213> ORGANISM: Sorghum bicolor

<400> SEQUENCE: 49

Met Asp Met Glu Arg Ser Gln Gln Gln Lys Ser Pro Thr Glu Ser Pro
1               5                   10                  15

Pro Pro Pro Ser Pro Ser Ser Ser Ser Ser Ser Val Ser Ala Asp Thr

```
            20                  25                  30
Val Leu Pro Pro Gly Lys Arg Arg Ala Ala Thr Thr Ala Lys
         35                  40                  45

Ala Lys Ala Gly Ala Lys Pro Lys Arg Ala Arg Lys Asp Ala Ala
     50                  55                  60

Ala Ala Asp Pro Pro Pro Pro Ala Ala Ala Ala Gly Lys Arg
 65                  70                  75                  80

Ser Ser Val Tyr Arg Gly Val Thr Arg His Arg Trp Thr Gly Arg Phe
                 85                  90                  95

Glu Ala His Leu Trp Asp Lys His Cys Leu Ala Ala Leu His Asn Lys
                100                 105                 110

Lys Lys Gly Arg Gln Val Tyr Leu Gly Ala Tyr Asp Ser Glu Glu Ala
            115                 120                 125

Ala Ala Arg Ala Tyr Asp Leu Ala Ala Leu Lys Tyr Trp Gly Pro Glu
        130                 135                 140

Thr Leu Leu Asn Phe Pro Val Glu Asp Tyr Ser Ser Glu Met Pro Glu
145                 150                 155                 160

Met Glu Gly Val Ser Arg Glu Tyr Leu Ala Ser Leu Arg Arg Arg
                165                 170                 175

Ser Ser Gly Phe Ser Arg Gly Val Ser Lys Tyr Arg Gly Val Ala Arg
            180                 185                 190

His His His Asn Gly Arg Trp Glu Ala Arg Ile Gly Arg Val Phe Gly
        195                 200                 205

Asn Lys Tyr Leu Tyr Leu Gly Thr Phe Asp Thr Gln Glu Glu Ala Ala
    210                 215                 220

Lys Ala Tyr Asp Leu Ala Ala Ile Glu Tyr Arg Gly Val Asn Ala Val
225                 230                 235                 240

Thr Asn Phe Asp Ile Ser Cys Tyr Leu Asp His Pro Leu Phe Leu Ala
                245                 250                 255

Gln Leu Gln Gln Glu Pro Gln Val Val Pro Ala Leu Asn Gln Glu Ala
            260                 265                 270

Gln Pro Asp Gln Ser Glu Thr Glu Thr Ile Ala Gln Glu Ser Val Ser
        275                 280                 285

Ser Glu Ala Lys Thr Pro Asp Asp Asn Ala Glu Pro Asp Asn Ala
290                 295                 300

Glu Pro Asp Asp Ile Ala Glu Pro Leu Ile Thr Val Asp Asp Ser Ile
305                 310                 315                 320

Glu Glu Ser Leu Trp Ser Pro Cys Met Asp Tyr Glu Leu Asp Thr Met
                325                 330                 335

Ser Arg Ser Asn Phe Gly Ser Ser Ile Asn Leu Ser Glu Trp Phe Asn
            340                 345                 350

Asp Ala Asp Phe Asp Ser Asn Ile Gly Cys Leu Phe Asp Gly Cys Ser
        355                 360                 365

Ala Val Asp Glu Gly Gly Lys Asp Gly Val Gly Leu Ala Asp Phe Ser
    370                 375                 380

Leu Leu Glu Asp Phe Ser Leu Phe Glu Ala Gly Asp Gly Gln Leu Lys
385                 390                 395                 400

Asp Val Leu Ser Asp Met Glu Glu Gly Ile Gln Pro Pro Thr Met Ile
                405                 410                 415

Ser Val Cys Asn
            420

<210> SEQ ID NO 50
```

<211> LENGTH: 395
<212> TYPE: PRT
<213> ORGANISM: Zea mays

<400> SEQUENCE: 50

```
Met Glu Arg Ser Gln Arg Gln Ser Pro Pro Pro Ser Pro Ser Ser
1               5                   10                  15

Ser Ser Ser Ser Val Ser Ala Asp Thr Val Leu Val Pro Pro Gly Lys
            20                  25                  30

Arg Arg Arg Ala Ala Thr Ala Lys Ala Gly Ala Glu Pro Asn Lys Arg
            35                  40                  45

Ile Arg Lys Asp Pro Ala Ala Ala Ala Gly Lys Arg Ser Ser Val
50                  55                  60

Tyr Arg Gly Val Thr Arg His Arg Trp Thr Gly Arg Phe Glu Ala His
65                  70                  75                  80

Leu Trp Asp Lys His Cys Leu Ala Ala Leu His Asn Lys Lys Lys Gly
                85                  90                  95

Arg Gln Val Tyr Leu Gly Ala Tyr Asp Ser Glu Glu Ala Ala Ala Arg
            100                 105                 110

Ala Tyr Asp Leu Ala Ala Leu Lys Tyr Trp Gly Pro Glu Thr Leu Leu
            115                 120                 125

Asn Phe Pro Val Glu Asp Tyr Ser Ser Glu Met Pro Glu Met Glu Ala
130                 135                 140

Val Ser Arg Glu Glu Tyr Leu Ala Ser Leu Arg Arg Arg Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
            180                 185                 190

Leu Tyr Leu Gly Thr Phe Asp Thr Gln Glu Glu Ala Ala Lys Ala Tyr
            195                 200                 205

Asp Leu Ala Ala Ile Glu Tyr Arg Gly Val Asn Ala Val Thr Asn Phe
210                 215                 220

Asp Ile Ser Cys Tyr Leu Asp His Pro Leu Phe Leu Ala Gln Leu Gln
225                 230                 235                 240

Gln Glu Pro Gln Val Val Pro Ala Leu Asn Gln Glu Pro Gln Pro Asp
            245                 250                 255

Gln Ser Glu Thr Gly Thr Thr Glu Gln Glu Pro Glu Ser Ser Glu Ala
            260                 265                 270

Lys Thr Pro Asp Gly Ser Ala Glu Pro Asp Glu Asn Ala Val Pro Asp
            275                 280                 285

Asp Thr Ala Glu Pro Leu Thr Thr Val Asp Asp Ser Ile Glu Glu Gly
290                 295                 300

Leu Trp Ser Pro Cys Met Asp Tyr Glu Leu Asp Thr Met Ser Arg Pro
305                 310                 315                 320

Asn Phe Gly Ser Ser Ile Asn Leu Ser Glu Trp Phe Ala Asp Ala Asp
            325                 330                 335

Phe Asp Cys Asn Ile Gly Cys Leu Phe Asp Gly Cys Ser Ala Ala Asp
            340                 345                 350

Glu Gly Ser Lys Asp Gly Val Gly Leu Ala Asp Phe Ser Leu Phe Glu
            355                 360                 365

Ala Gly Asp Val Gln Leu Lys Asp Val Leu Ser Asp Met Glu Glu Gly
370                 375                 380

Ile Gln Pro Pro Ala Met Ile Ser Val Cys Asn
```

385          390          395

<210> SEQ ID NO 51
<211> LENGTH: 430
<212> TYPE: PRT
<213> ORGANISM: Triadica sebifera

<400> SEQUENCE: 51

Met Ala Ser Ser Ser Asp Pro Val Leu Lys Ala Glu Leu Gly Ser
1               5                   10                  15

Ser Gly Gly Gly Cys Ser Ser Gly Gly Gly Glu Ser Ser Glu Ala
                20                  25                  30

Val Ile Ala Asn Asp Gln Leu Leu Tyr Arg Gly Leu Lys Lys Pro
            35                  40                  45

Lys Lys Glu Arg Gly Cys Thr Ala Lys Glu Arg Ile Ser Lys Met Pro
50                  55                  60

Pro Cys Thr Ala Gly Lys Arg Ser Ser Ile Tyr Arg Gly Val Thr Arg
65                  70                  75                  80

His Arg Trp Thr Gly Arg Tyr Glu Ala His Leu Trp Asp Lys Ser Thr
                85                  90                  95

Trp Asn Gln Asn Gln Lys Lys Gly Lys Gln Val Tyr Leu Gly Ala
                100                 105                 110

Tyr Asp Asp Glu Glu Ala Ala Ala Arg Ala Tyr Asp Leu Ala Ala Leu
            115                 120                 125

Lys Tyr Trp Gly Pro Gly Thr Leu Ile Asn Phe Pro Val Thr Asp Tyr
130                 135                 140

Thr Arg Asp Leu Glu Glu Met Gln Asn Met Ser Arg Glu Glu Tyr Leu
145                 150                 155                 160

Ala Ser Leu Arg Arg Lys Ser Ser Gly Phe Ser Arg Gly Ile Ser Lys
                165                 170                 175

Tyr Arg Gly Leu Ser Ser Arg Trp Glu Ser Ser Val Gly Arg Met Pro
            180                 185                 190

Gly Ser Glu Tyr Phe Ser Ser Ile Asn Tyr Val Asp Asp Pro Ala Ala
        195                 200                 205

Glu Ser Glu Tyr Val Gly Ser Leu Cys Phe Glu Arg Lys Ile Asp Leu
    210                 215                 220

Thr Ser Tyr Ile Lys Trp Trp Gly Leu Asn Lys Thr Arg Gln Ala Glu
225                 230                 235                 240

Ser Ile Ser Lys Ser Ala Glu Glu Thr Lys Pro Gly Cys Ala Glu Asp
                245                 250                 255

Ile Gly Gly Glu Leu Lys Thr Thr Glu Trp Ala Ile Gln Pro Thr Glu
            260                 265                 270

Pro Tyr Gln Met Pro Arg Leu Gly Met Pro Val His Val Lys Lys His
        275                 280                 285

Lys Gly Ser Lys Ile Ser Ala Leu Ser Val Leu Ser Gln Ser Ala Ala
    290                 295                 300

Phe Lys Ser Leu Gln Glu Lys Ala Ser Lys Lys Gln Glu Asn Ser Thr
305                 310                 315                 320

Asp Asn Asp Glu Asn Glu Asn Lys Asn Thr Asn Thr Asn Lys Ile Asp
                325                 330                 335

Tyr Gly Lys Ala Val Glu Thr Ser Ala Ser His Asp Ser Ser Asn Glu
            340                 345                 350

Arg Pro Val Thr Ala Leu Gly Met Ser Gly Gly Leu Ser Leu Lys Arg
        355                 360                 365

Asn Val Tyr Gln Leu Thr Pro Phe Leu Ser Ala Pro Leu Leu Thr Asn
370                 375                 380

Tyr Gly Thr Ile Asp Gln Leu Val Asp Pro Ile Leu Trp Ala Ser Leu
385                 390                 395                 400

Val Pro Val Leu Pro Thr Gly Leu Ser Arg Asn Pro Glu Val Thr Lys
                405                 410                 415

Thr Glu Thr Ser Ser Thr Tyr Thr Phe Phe Arg Pro Glu Glu
                420                 425                 430

<210> SEQ ID NO 52
<211> LENGTH: 1531
<212> TYPE: DNA
<213> ORGANISM: Solanum tuberosum

<400> SEQUENCE: 52

| | | | | |
|---|---|---|---|---|
| ttttaaatca | ttgttttatt | ttctctttct | ttttacaggt ataaaaggtg | aaaattgaag | 60 |
| caagattgat | tgcaagctat | gtgtcaccac | gttattgata ctttggaaga | aatttttact | 120 |
| tatatgtctt | tgtttaggag | taatatttga | tatgttttag ttagattttc | ttgtcattta | 180 |
| tgctttagta | taattttagt | tatttttatt | atatgatcat gggtgaattt | tgatacaaat | 240 |
| attttttgtca | ttaaataaat | taatttatca | caacttgatt actttcagtg | acaaaaaatg | 300 |
| tattgtcgta | gtacccttttt | tgttgaata | tgaataattt tttttatttt | gtgacaattg | 360 |
| taattgtcac | tacttatgat | aatatttagt | gacatatatg tcgtcggtaa | aagcaaacac | 420 |
| tttcagtgac | aaaataatag | atttaatcac | aaaattatta acctttttta | taataataaa | 480 |
| tttatcccta | atttatacat | ttaaggacaa | agtatttttt ttatatataa | aaaatagtct | 540 |
| ttagtgacga | tcgtagtgtt | gagtctagaa | atcataatgt tgaatctaga | aaaatctcat | 600 |
| gcagtgtaaa | ataaacctca | aaaggacgt | tcagtccata gagggggtgt | atgtgacacc | 660 |
| ccaacctcag | caaaagaaaa | cctcccttca | acaaggacat ttgcggtgct | aaacaatttc | 720 |
| aagtctcatc | acacatatat | ttattatata | atactaataa agaatagaaa | aggaaaggta | 780 |
| aacatcatta | aatcgtcttt | gtatattttt | agtgacaact gattgacgaa | atctttttcg | 840 |
| tcacacaaaa | tttttagtga | cgaaacatga | tttatagatg atgaaattat | ttgtccctca | 900 |
| taatctaatt | tgttgtagtg | atcattactc | ctttgtttgt tttatttgtc | atgttagtcc | 960 |
| attaaaaaaa | aatatctctc | ttcttatgta | cgtgaatggt tggaacggat | ctattatata | 1020 |
| atactaataa | agaatagaaa | aggaaagtg | agtgaggttc gagggagaga | atctgtttaa | 1080 |
| tatcagagtc | gatcatgtgt | caattttatc | gatatgaccc taacttcaac | tgagtttaac | 1140 |
| caattccgat | aaggcgagaa | atatcatagt | attgagtcta gaaaaatctc | atgtagtgtg | 1200 |
| gggtaaacct | cagcaaggac | gttgagtcca | tagaggggg tgtatgtgac | accccaacct | 1260 |
| cagcaaaaga | aaacctcccc | tcaagaagga | catttgcggt gctaaacaat | ttcaagtctc | 1320 |
| atcacacata | tatatatatt | atataatact | aataaataat agaaaaagga | aaggtaaaca | 1380 |
| tcactaacga | cagttgcggt | gcaaactgag | tgaggtaata aacagcacta | acttttattg | 1440 |
| gttatgtcaa | actcaaagta | aaatttctca | acttgtttac gtgcctatat | ataccatgct | 1500 |
| tgttatatgc | tcaaagcacc | aacaaaattt | a | | 1531 |

<210> SEQ ID NO 53
<211> LENGTH: 1970
<212> TYPE: DNA
<213> ORGANISM: Zea mays

<400> SEQUENCE: 53

```
ggtaccttt ttcccagaga taaatgtgga atagctctac aaacaaacgg catgatgctg      60
acacttggat ggcgaccttg caatcccaag aactattgca tacggttgcc agtcgacaaa     120
tatctacgcc atgcatggct acggtcggaa tacaccgtag cggcgggtaa ctcgccgata     180
ccgtccacgt gtccttggat gcccggtcgc tgatacttct ggtcttctgg acatgcacca     240
agacaatcaa gtgattcaac cttaatttaa cataatataa ataatacgta acatccaact     300
gacgtgttca cctatagaga atattccttc tgattctact ttcagaatga tgccgttgcc     360
gtgtatcgag caagtactct cactcgaagt atcttatctc ccacatccag cacaaaaatc     420
ttctgttcgt ggcaaatctt gtggcggttg aacgaaagaa tgctatataa gtagctatag     480
agaacgtatt atgtgtaaac caaccgttca gtgtaaatcg tgtgtaaata gtcatgttaa     540
ttttttggcg gcagatcaag tacaaactgt atgcctcgga taaacatgta caaaccacaa     600
cactggccac tagatctata tccaacgttc ataaccatcc atccctctct gctgcactct     660
gcaaacaagc cccccatctc gtagcaaca tcttgtctcc gacaagctct cgatgtagtg      720
gaggccctcc accgcaatat cctagtgtat gatgttggag aagcgactcc taaataatgg     780
tggcaagatg ttgctaggtt tgtagccata gcctcaatct aagatcatcc caagccatgg     840
gacctgattc tacgaggcct acaaccaggc atgacacgtc gtctacccac tcttgtgcat     900
catcggtcac ttgatctgac ttggttccta accacttacc ctaggttcca agccctaag      960 tttctcgtat attgttagtc attcttagtg ggagttttat gtgtatttca ttcctgttaa    1020
atagcatgcc aactaagcaa acatgatgat ataaatgca atctaataaa aagatatatg     1080
agtgggtttc ataaaaaagg gagagagttt catgaggagt gaaactctga atacagatac    1140
tgatatgaca gctttaaaag tagtgttatg aaatcatcat tgagaaatgg tattagcact    1200
caatcgattt ctacgctgtc aattgtcatg agcacaattt tcacccaaag aggcacacca    1260
gcaatgtccg cttgtagtgt ccgagacgtt gctccatcgc cgtcgtcttg tttctgtgcg    1320
ctccattcaa tgcggcaagt ggctcaatcc caagcggtcg tcgcctccca gccccagcag    1380
caaaatatct tcccatgcgg ccatgccttg aaaattggaa tagattctct agattcaccg    1440
ccgcgtcatc ttcactactt tctcactggc ccaatcagca tctccttctc cgagctcaat    1500
catgctcagt caagcgtcac caatggcgtc acggttggtt ttgtcactgt ctgcatgcaa    1560
gggtattttg cttcgcaagt gtaaatggaa atggatcta aacaactgca ctgcaccaat     1620
tttggaacgc ggaaccgaga gtctgtttgg gttcgtttga aacgcgctga tgtttctcat    1680
tttttaatag atgtagttac ctgatactat ttaagttgga cgatcaaacg actgtgtcaa    1740
gtgtgattaa gaaaagcatc gaaaataaaa tttatcgcca taaaaagtta aaaacagtgg    1800
ataatagtag gacctcataa tagaaaaaat tatcaaacgg aatggagggg cccaacgcag    1860
tatatagcag ccgggtggtg ccggacatcc gacgctcgtg ccagcaggcc attcttctcg    1920
ccttactccc tcacagaacc cagtaaaata tcgccagtcc cgccgtcgag                1970
```

<210> SEQ ID NO 54
<211> LENGTH: 584
<212> TYPE: DNA
<213> ORGANISM: Aeluropus littoralis

<400> SEQUENCE: 54

```
cccaagcttg accgatgcac acgctacctg ccaaggctcc ctccatccgc actctgcatc      60
gtcgcttcgg cgtaaacttc cacgtagtac ttgtacgatt ctagctagac ccagtgcgcc    120
```

```
caccctaccg ccggcgagcg ggcccccatc tcgcgccagg cttccatgcg ggtccaccgt    180
ggaccagccc tacgccgaac cgagcccatc cctccaccct ttcaccgcca agcgggaccc    240
gcgttggacc tttccgcttg gctggccccc accagcgtcc acgcgggcca acggcctcgc    300
gaaatggatc tccacacgac aaaccaaaac gagaagaaaa taaatggaaa ggaaagaaac    360
ggatcgccac gcgttccaga ggcgtccgct aaccacccga ttatgcttgc gcagcgtgcg    420
taacctcgtc gtggggttaa tccgggtggc cggatcggga agccacggc ctttataacc     480 catccctgcc ggatcgaacc ggtaccggaa acaaaaacag ggggagaaaa aaagttcttc    540
gcgaggaagg aaaaggaaaa gtcgcgtgcc gtcctcgccc acag                     584
```

<210> SEQ ID NO 55
<211> LENGTH: 928
<212> TYPE: DNA
<213> ORGANISM: Agrobacterium rhizogenes

<400> SEQUENCE: 55

```
ttagcgaaag gatgtcaaaa aaggatgccc ataattggga ggagtggggt aaagcttaaa     60
gttggcccgc tattggattt cgcgaaagcg gcattggcaa acgtggagat tgctgcattc    120
aagtactttt ttctattttc tggttaagat gtaaagtatt gccacaatca tattaattac    180
taacattgta tatgtaatat agtgcggaaa ttatctatgc caaaatgatg tattaataat    240
agcaataata atatgtgtta atcttttttca atcgggaata cgtttaagcg attatcgtgt    300
tgaataaatt attccaaaag gaaatacatg gttttggaga acctgctata gatatatgcc    360
aaatttacac tagtttagtg ggtgcaaaac tattatctct gtttctgagt ttaataaaaa    420
ataaataagc agggcgaata gcagttagcc taagaaggaa tggtggccat gtacgtgctt    480
ttaagagacc ctataataaa ttgccagctg tgttgctttg gtgccgacag gcctaacgtg    540
gggtttagct tgacaaagta gcgccttttcc gcagcataaa taaggtagg cgggtgcgtc     600 ccattattaa aggaaaaagc aaaagctgag attccataga ccacaaacca ccattattgg    660
aggacagaac ctattccctc acgtgggtcg ctagctttaa acctaataag taaaaacaat    720
taaaagcagg caggtgtccc ttctatattc gcacaacgag gcgacgtgga gcatcgacag    780
ccgcatccat taattaataa atttgtggac ctatacctaa ctcaaatatt tttattattt    840
gctccaatac gctaagagct ctggattata aatagtttgg atgcttcgag ttatgggtac    900
aagcaacctg tttcctactt tgttacca                                        928
```

<210> SEQ ID NO 56
<211> LENGTH: 512
<212> TYPE: PRT
<213> ORGANISM: Elaeis guineensis

<400> SEQUENCE: 56

```
Met Ala Val Ser Lys Asn Pro Glu Thr Leu Ala Pro Asp Gln Glu Pro
1               5                   10                  15

Ser Lys Glu Ser Asp Leu Arg Arg Arg Pro Ala Ser Ser Pro Ser Ser
            20                  25                  30

Thr Ala Ala Ser Pro Ala Val Pro Asp Ser Ser Ser Arg Thr Ser Ser
        35                  40                  45

Ser Ile Thr Gly Ser Trp Thr Thr Ala Leu Asp Gly Asp Ser Gly Ala
    50                  55                  60

Gly Ala Val Arg Ile Gly Asp Pro Lys Asp Arg Ile Gly Glu Ala Asn
65                  70                  75                  80
```

```
Asp Ile Gly Glu Lys Lys Ala Cys Ser Gly Glu Val Pro Val Gly
                85                  90                  95

Phe Val Asp Arg Pro Ser Ala Pro Val His Val Arg Val Glu Ser
                100                 105                 110

Pro Leu Ser Ser Asp Thr Ile Phe Gln Gln Ser His Ala Gly Leu Leu
                115                 120                 125

Asn Leu Cys Val Val Val Leu Ile Ala Val Asn Ser Arg Leu Ile Ile
            130                 135                 140

Glu Asn Leu Met Lys Tyr Gly Leu Leu Ile Gly Ser Gly Phe Phe Phe
145                 150                 155                 160

Ser Ser Arg Leu Leu Arg Asp Trp Pro Leu Leu Ile Cys Ser Leu Thr
                165                 170                 175

Leu Pro Val Phe Pro Leu Gly Ser Tyr Met Val Glu Lys Leu Ala Tyr
                180                 185                 190

Lys Lys Phe Ile Ser Glu Pro Val Val Ser Leu His Val Ile Leu
                195                 200                 205

Ile Ile Ala Thr Ile Met Tyr Pro Val Phe Val Ile Leu Arg Cys Asp
            210                 215                 220

Ser Pro Ile Leu Ser Gly Ile Asn Leu Met Leu Phe Val Ser Ser Ile
225                 230                 235                 240

Cys Leu Lys Leu Val Ser Tyr Ala His Ala Asn Tyr Asp Leu Arg Ser
                245                 250                 255

Ser Ser Asn Ser Ile Asp Lys Gly Ile His Lys Ser Gln Gly Val Ser
                260                 265                 270

Phe Lys Ser Leu Val Tyr Phe Ile Met Ala Pro Thr Leu Cys Tyr Gln
                275                 280                 285

Pro Ser Tyr Pro Arg Thr Thr Cys Ile Arg Lys Gly Trp Val Ile Cys
            290                 295                 300

Gln Leu Val Lys Leu Val Ile Phe Thr Gly Val Met Gly Phe Ile Ile
305                 310                 315                 320

Glu Gln Tyr Ile Asp Pro Ile Ile Lys Asn Ser Gln His Pro Leu Lys
                325                 330                 335

Gly Asn Val Leu Asn Ala Met Glu Arg Val Leu Lys Leu Ser Ile Pro
                340                 345                 350

Thr Leu Tyr Val Trp Leu Cys Val Phe Tyr Cys Thr Phe His Leu Trp
            355                 360                 365

Leu Asn Ile Leu Ala Glu Leu Leu Cys Phe Gly Asp Arg Glu Phe Tyr
            370                 375                 380

Lys Asp Trp Trp Asn Ala Lys Thr Ile Glu Glu Tyr Trp Arg Met Trp
385                 390                 395                 400

Asn Met Pro Val His Lys Trp Met Leu Arg His Val Tyr Leu Pro Cys
                405                 410                 415

Ile Arg Asn Gly Ile Pro Lys Gly Val Ala Met Val Ile Ser Phe Phe
            420                 425                 430

Ile Ser Ala Ile Phe His Glu Leu Cys Ile Gly Ile Pro Cys His Ile
                435                 440                 445

Phe Lys Phe Trp Ala Phe Ile Gly Ile Met Phe Gln Val Pro Leu Val
                450                 455                 460

Ile Leu Thr Lys Tyr Leu Gln Asn Lys Phe Lys Ser Ala Met Val Gly
465                 470                 475                 480

Asn Met Ile Phe Trp Phe Phe Ser Ile Tyr Gly Gln Pro Met Cys
                485                 490                 495

Val Leu Leu Tyr Tyr His Asp Val Met Asn Arg Lys Val Gly Thr Glu
```

<210> SEQ ID NO 57
<211> LENGTH: 74
<212> TYPE: PRT
<213> ORGANISM: Glycine max

<400> SEQUENCE: 57

Met Ala Asp Ile Asp Arg Ser Phe Asp Asn Asn Val Ser Ala Val Ser
1               5                   10                  15

Thr Glu Lys Ser Ser Gln Val Ser Asp Val Glu Phe Ser Glu Ala Glu
            20                  25                  30

Glu Ile Leu Ile Ala Met Val Tyr Asn Leu Val Gly Glu Arg Trp Ser
        35                  40                  45

Leu Ile Ala Gly Arg Ile Pro Gly Arg Thr Ala Glu Glu Ile Glu Lys
    50                  55                  60

Tyr Trp Thr Ser Arg Phe Ser Thr Ser Gln
65                  70

<210> SEQ ID NO 58
<211> LENGTH: 146
<212> TYPE: PRT
<213> ORGANISM: Arabidopsis thaliana

<400> SEQUENCE: 58

Met Gly Ser Leu Gln Met Gln Thr Ser Pro Glu Ser Asp Asn Asp Pro
1               5                   10                  15

Arg Tyr Ala Thr Val Thr Asp Glu Arg Lys Arg Lys Arg Met Ile Ser
            20                  25                  30

Asn Arg Glu Ser Ala Arg Arg Ser Arg Met Arg Lys Gln Lys Gln Leu
        35                  40                  45

Gly Asp Leu Ile Asn Glu Val Thr Leu Leu Lys Asn Asp Asn Ala Lys
    50                  55                  60

Ile Thr Glu Gln Val Asp Glu Ala Ser Lys Lys Tyr Ile Glu Met Glu
65                  70                  75                  80

Ser Lys Asn Asn Val Leu Arg Ala Gln Ala Ser Glu Leu Thr Asp Arg
                85                  90                  95

Leu Arg Ser Leu Asn Ser Val Leu Glu Met Val Glu Glu Ile Ser Gly
            100                 105                 110

Gln Ala Leu Asp Ile Pro Glu Ile Pro Glu Ser Met Gln Asn Pro Trp
        115                 120                 125

Gln Met Pro Cys Pro Met Gln Pro Ile Arg Ala Ser Ala Asp Met Phe
    130                 135                 140

Asp Cys
145

<210> SEQ ID NO 59
<211> LENGTH: 268
<212> TYPE: PRT
<213> ORGANISM: Arabidopsis thaliana

<400> SEQUENCE: 59

Met Gly Arg Gly Lys Ile Glu Ile Lys Arg Ile Glu Asn Ala Asn Ser
1               5                   10                  15

Arg Gln Val Thr Phe Ser Lys Arg Arg Ser Gly Leu Leu Lys Lys Ala
            20                  25                  30

Arg Glu Leu Ser Val Leu Cys Asp Ala Glu Val Ala Val Ile Val Phe
        35                  40                  45

Ser Lys Ser Gly Lys Leu Phe Glu Tyr Ser Ser Thr Gly Met Lys Gln
            50                  55                  60

Thr Leu Ser Arg Tyr Gly Asn His Gln Ser Ser Ala Ser Lys Ala
 65                  70                  75                  80

Glu Glu Asp Cys Ala Glu Val Asp Ile Leu Lys Asp Gln Leu Ser Lys
                85                  90                  95

Leu Gln Glu Lys His Leu Gln Leu Gln Gly Lys Gly Leu Asn Pro Leu
            100                 105                 110

Thr Phe Lys Glu Leu Gln Ser Leu Glu Gln Gln Leu Tyr His Ala Leu
            115                 120                 125

Ile Thr Val Arg Glu Arg Lys Glu Arg Leu Leu Thr Asn Gln Leu Glu
            130                 135                 140

Glu Ser Arg Leu Lys Glu Gln Arg Ala Glu Leu Glu Asn Glu Thr Leu
145                 150                 155                 160

Arg Arg Gln Val Gln Glu Leu Arg Ser Phe Leu Pro Ser Phe Thr His
                165                 170                 175

Tyr Val Pro Ser Tyr Ile Lys Cys Phe Ala Ile Asp Pro Lys Asn Ala
            180                 185                 190

Leu Ile Asn His Asp Ser Lys Cys Ser Leu Gln Asn Thr Asp Ser Asp
            195                 200                 205

Thr Thr Leu Gln Leu Gly Leu Pro Gly Glu Ala His Asp Arg Arg Thr
210                 215                 220

Asn Glu Gly Glu Arg Glu Ser Pro Ser Ser Asp Ser Val Thr Thr Asn
225                 230                 235                 240

Thr Ser Ser Glu Thr Ala Glu Arg Gly Asp Gln Ser Ser Leu Ala Asn
                245                 250                 255

Ser Pro Pro Glu Ala Lys Arg Gln Arg Phe Ser Val
            260                 265

<210> SEQ ID NO 60
<211> LENGTH: 437
<212> TYPE: PRT
<213> ORGANISM: Arabidopsis thaliana

<400> SEQUENCE: 60

Met Glu Phe Glu Ser Val Phe Lys Met His Tyr Pro Tyr Leu Ala Ala
1               5                   10                  15

Val Ile Tyr Asp Asp Ser Ser Thr Leu Lys Asp Phe His Pro Ser Leu
            20                  25                  30

Thr Asp Asp Phe Ser Cys Val His Asn Val His His Lys Pro Ser Met
            35                  40                  45

Pro His Thr Tyr Glu Ile Pro Ser Lys Glu Thr Ile Arg Gly Ile Thr
 50                  55                  60

Pro Ser Pro Cys Thr Glu Ala Phe Gly Ala Cys Phe His Gly Thr Ser
 65                  70                  75                  80

Asn Asp His Val Phe Phe Gly Met Ala Tyr Thr Thr Pro Pro Thr Ile
                85                  90                  95

Glu Pro Asn Val Ser His Val Ser His Asp Asn Thr Met Trp Glu Asn
            100                 105                 110

Asp Gln Asn Gln Gly Phe Ile Phe Gly Thr Glu Ser Thr Leu Asn Gln
            115                 120                 125

Ala Met Ala Asp Ser Asn Gln Phe Asn Met Pro Lys Pro Leu Leu Ser
            130                 135                 140

Ala Asn Glu Asp Thr Ile Met Asn Arg Arg Gln Asn Asn Gln Val Met

Ile Lys Thr Glu Gln Ile Lys Lys Asn Lys Arg Phe Gln Met Arg
145                 150                 155                 160

Arg Ile Cys Lys Pro Thr Lys Ala Ser Ile Ile Lys Gly Gln Trp
            165                 170                 175

Thr Pro Glu Glu Asp Lys Leu Leu Val Gln Leu Val Asp Leu His Gly
        180                     185                 190

Thr Lys Lys Trp Ser Gln Ile Ala Lys Met Leu Gln Gly Arg Val Gly
    195                     200                 205

Lys Gln Cys Arg Glu Arg Trp His Asn His Leu Arg Pro Asp Ile Lys
210                 215                 220

Lys Asp Gly Trp Thr Glu Glu Asp Ile Leu Ile Lys Ala His
225                 230                 235                 240

Lys Glu Ile Gly Asn Arg Trp Ala Glu Ile Ala Arg Lys Leu Pro Gly
            245                 250                 255

Arg Thr Glu Asn Thr Ile Lys Asn His Trp Asn Ala Thr Lys Arg Arg
        260                     265                 270

Gln His Ser Arg Arg Thr Lys Gly Lys Asp Glu Ile Ser Leu Ser Leu
    275                     280                 285

Gly Ser Asn Thr Leu Gln Asn Tyr Ile Arg Ser Val Thr Tyr Asn Asp
290                 295                 300

305                 310                 315                 320

Asp Pro Phe Met Thr Ala Asn Ala Asn Ala Asn Ile Gly Pro Arg Asn
            325                 330                 335

Met Arg Gly Lys Gly Lys Asn Val Met Val Ala Val Ser Glu Tyr Asp
        340                     345                 350

Glu Gly Glu Cys Lys Tyr Ile Val Asp Gly Val Asn Asn Leu Gly Leu
    355                     360                 365

Glu Asp Gly Arg Ile Lys Met Pro Ser Leu Ala Ala Met Ser Ala Ser
370                 375                 380

Gly Ser Ala Ser Thr Ser Gly Ser Ala Ser Gly Ser Gly Ser Val
385                 390                 395                 400

Thr Met Glu Ile Asp Glu Pro Met Thr Asp Ser Trp Met Val Met His
            405                 410                 415

Gly Cys Asp Glu Val Met Met Asn Glu Ile Ala Leu Leu Glu Met Ile
        420                     425                 430

Ala His Gly Arg Leu
    435

<210> SEQ ID NO 61
<211> LENGTH: 359
<212> TYPE: PRT
<213> ORGANISM: Arabidopsis thaliana

<400> SEQUENCE: 61

Met Tyr His Gln Asn Leu Ile Ser Ser Thr Pro Asn Gln Asn Ser Asn
1               5                   10                  15

Pro His Asp Trp Asp Ile Gln Asn Pro Leu Phe Ser Ile His Pro Ser
            20                  25                  30

Ala Glu Ile Pro Ser Lys Tyr Pro Phe Met Gly Ile Thr Ser Cys Pro
        35                  40                  45

Asn Thr Asn Val Phe Glu Glu Phe Gln Tyr Lys Ile Thr Asn Asp Gln
    50                  55                  60

Asn Phe Pro Thr Thr Tyr Asn Thr Pro Phe Pro Val Ile Ser Glu Gly
65                  70                  75                  80

```
Ile Ser Tyr Asn Met His Asp Val Gln Glu Asn Thr Met Cys Gly Tyr
                85                  90                  95

Thr Ala His Asn Gln Gly Leu Ile Ile Gly Cys His Glu Pro Val Leu
            100                 105                 110

Val His Ala Val Val Glu Ser Gln Gln Phe Asn Val Pro Gln Ser Glu
            115                 120                 125

Asp Ile Asn Leu Val Ser Gln Ser Glu Arg Val Thr Glu Asp Lys Val
            130                 135                 140

Met Phe Lys Thr Asp His Lys Lys Asp Ile Ile Gly Lys Gly Gln
145                 150                 155                 160

Trp Thr Pro Thr Glu Asp Glu Leu Leu Val Arg Met Val Lys Ser Lys
                165                 170                 175

Gly Thr Lys Asn Trp Thr Ser Ile Ala Lys Met Phe Gln Gly Arg Val
            180                 185                 190

Gly Lys Gln Cys Arg Glu Arg Trp Asn His Leu Arg Pro Asn Ile
            195                 200                 205

Lys Lys Asn Asp Trp Ser Glu Glu Asp Gln Ile Leu Ile Glu Val
            210                 215                 220

His Lys Ile Val Gly Asn Lys Trp Thr Glu Ile Ala Lys Arg Leu Pro
225                 230                 235                 240

Gly Arg Ser Glu Asn Ile Val Lys Asn His Trp Asn Ala Thr Lys Arg
                245                 250                 255

Arg Leu His Ser Val Arg Thr Lys Ser Asp Ala Phe Ser Pro Arg
            260                 265                 270

Asn Asn Ala Leu Glu Asn Tyr Ile Arg Ser Ile Thr Ile Asn Asn Asn
            275                 280                 285

Ala Leu Met Asn Arg Glu Val Asp Ser Ile Thr Ala Asn Ser Glu Ile
            290                 295                 300

Asp Ser Thr Arg Cys Glu Asn Ile Val Asp Glu Val Met Asn Leu Asn
305                 310                 315                 320

Leu His Ala Thr Thr Ser Val Tyr Val Pro Glu Gln Ala Val Leu Thr
                325                 330                 335

Trp Gly Tyr Asp Phe Thr Lys Cys Tyr Glu Pro Met Asp Asp Thr Trp
            340                 345                 350

Met Leu Met Asn Gly Trp Asn
        355

<210> SEQ ID NO 62
<211> LENGTH: 386
<212> TYPE: PRT
<213> ORGANISM: Arabidopsis thaliana

<400> SEQUENCE: 62

Met Ser Lys Arg Pro Pro Asp Pro Val Ala Val Leu Arg Gly His
1               5                   10                  15

Arg His Ser Val Met Asp Val Ser Phe His Pro Ser Lys Ser Leu Leu
            20                  25                  30

Phe Thr Gly Ser Ala Asp Gly Glu Leu Arg Ile Trp Asp Thr Ile Gln
            35                  40                  45

His Arg Ala Val Ser Ser Ala Trp Ala His Ser Arg Ala Asn Gly Val
            50                  55                  60

Leu Ala Val Ala Ala Ser Pro Trp Leu Gly Glu Asp Lys Ile Ile Ser
65                  70                  75                  80

Gln Gly Arg Asp Gly Thr Val Lys Cys Trp Asp Ile Glu Asp Gly Gly
                85                  90                  95
```

Leu Ser Arg Asp Pro Leu Leu Ile Leu Glu Thr Cys Ala Tyr His Phe
            100                 105                 110

Cys Lys Phe Ser Leu Val Lys Pro Lys Asn Ser Leu Gln Glu Ala
            115                 120                 125

Glu Ser His Ser Arg Gly Cys Asp Gln Asp Gly Gly Asp Thr Cys
130                 135                 140

Asn Val Gln Ile Ala Asp Asp Ser Glu Arg Ser Glu Glu Asp Ser Gly
145                 150                 155                 160

Leu Leu Gln Asp Lys Asp His Ala Glu Gly Thr Thr Phe Val Ala Val
                165                 170                 175

Val Gly Glu Gln Pro Thr Glu Val Glu Ile Trp Asp Leu Asn Thr Gly
            180                 185                 190

Asp Lys Ile Ile Gln Leu Pro Gln Ser Ser Pro Asp Glu Ser Pro Asn
            195                 200                 205

Ala Ser Thr Lys Gly Arg Gly Met Cys Met Ala Val Gln Leu Phe Cys
    210                 215                 220

Pro Pro Glu Ser Gln Gly Phe Leu His Val Leu Ala Gly Tyr Glu Asp
225                 230                 235                 240

Gly Ser Ile Leu Leu Trp Asp Ile Arg Asn Ala Lys Ile Pro Leu Thr
                245                 250                 255

Ser Val Lys Phe His Ser Glu Pro Val Leu Ser Leu Ser Val Ala Ser
            260                 265                 270

Ser Cys Asp Gly Gly Ile Ser Gly Gly Ala Asp Asp Lys Ile Val Met
    275                 280                 285

Tyr Asn Leu Asn His Ser Thr Gly Ser Cys Thr Ile Arg Lys Glu Ile
            290                 295                 300

Thr Leu Glu Arg Pro Gly Val Ser Gly Thr Ser Ile Arg Val Asp Gly
305                 310                 315                 320

Lys Ile Ala Ala Thr Ala Gly Trp Asp His Arg Ile Arg Val Tyr Asn
                325                 330                 335

Tyr Arg Lys Gly Asn Ala Leu Ala Ile Leu Lys Tyr His Arg Ala Thr
            340                 345                 350

Cys Asn Ala Val Ser Tyr Ser Pro Asp Cys Glu Leu Met Ala Ser Ala
    355                 360                 365

Ser Glu Asp Ala Thr Val Ala Leu Trp Lys Leu Tyr Pro Pro His Lys
370                 375                 380

Ser Leu
385

<210> SEQ ID NO 63
<211> LENGTH: 292
<212> TYPE: PRT
<213> ORGANISM: Arabidopsis thaliana

<400> SEQUENCE: 63

Met Glu Pro Pro Gln His Gln His His His Gln Ala Asp Gln Glu
1               5                   10                  15

Ser Gly Asn Asn Asn Asn Lys Ser Gly Ser Gly Gly Tyr Thr Cys
            20                  25                  30

Arg Gln Thr Ser Thr Arg Trp Thr Pro Thr Thr Glu Gln Ile Lys Ile
            35                  40                  45

Leu Lys Glu Leu Tyr Tyr Asn Asn Ala Ile Arg Ser Pro Thr Ala Asp
    50                  55                  60

Gln Ile Gln Lys Ile Thr Ala Arg Leu Arg Gln Phe Gly Lys Ile Glu

```
                65                  70                  75                  80
Gly Lys Asn Val Phe Tyr Trp Phe Gln Asn His Lys Ala Arg Glu Arg
                85                  90                  95

Gln Lys Lys Arg Phe Asn Gly Thr Asn Met Thr Thr Pro Ser Ser Ser
            100                 105                 110

Pro Asn Ser Val Met Met Ala Ala Asn Asp His Tyr His Pro Leu Leu
        115                 120                 125

His His His His Gly Val Pro Met Gln Arg Pro Ala Asn Ser Val Asn
    130                 135                 140

Val Lys Leu Asn Gln Asp His His Leu Tyr His His Asn Lys Pro Tyr
145                 150                 155                 160

Pro Ser Phe Asn Asn Gly Asn Leu Asn His Ala Ser Ser Gly Thr Glu
                165                 170                 175

Cys Gly Val Val Asn Ala Ser Asn Gly Tyr Met Ser Ser His Val Tyr
            180                 185                 190

Gly Ser Met Glu Gln Asp Cys Ser Met Asn Tyr Asn Asn Val Gly Gly
        195                 200                 205

Gly Trp Ala Asn Met Asp His His Tyr Ser Ser Ala Pro Tyr Asn Phe
    210                 215                 220

Phe Asp Arg Ala Lys Pro Leu Phe Gly Leu Glu Gly His Gln Glu Glu
225                 230                 235                 240

Glu Glu Cys Gly Gly Asp Ala Tyr Leu Glu His Arg Arg Thr Leu Pro
                245                 250                 255

Leu Phe Pro Met His Gly Glu Asp His Ile Asn Gly Gly Ser Gly Ala
            260                 265                 270

Ile Trp Lys Tyr Gly Gln Ser Glu Val Arg Pro Cys Ala Ser Leu Glu
        275                 280                 285

Leu Arg Leu Asn
    290

<210> SEQ ID NO 64
<211> LENGTH: 453
<212> TYPE: PRT
<213> ORGANISM: Brassica napus

<400> SEQUENCE: 64

Met Asp Leu Gly Ser Val Thr Gly Asn Val Asn Gly Ser Pro Ser Leu
1               5                   10                  15

Lys Glu Leu Arg Glu Ser Lys Gln Asp Arg Ser Glu Phe Asp Gly Glu
            20                  25                  30

Asp Cys Leu Gln Gln Ser Ser Lys Leu Ala Arg Thr Ile Ala Glu Asp
        35                  40                  45

Lys His Leu Pro Ser Ser Tyr Ala Ala Ala Tyr Ser Arg Pro Met Ser
    50                  55                  60

Phe His Gln Gly Ile Pro Leu Ala Arg Ser Ala Ser Leu Leu Ser Ser
65                  70                  75                  80

Asp Ser Arg Arg Gln Glu His Met Leu Ser Phe Ser Asp Lys Pro Glu
                85                  90                  95

Ala Phe Asp Phe Ser Lys Tyr Val Gly Leu Asp Asn Asn Lys Asn Ser
            100                 105                 110

Leu Ser Pro Phe Leu His Gln Leu Pro Pro Tyr Cys Arg Thr Pro
        115                 120                 125

Gly Gly Gly Tyr Gly Ser Gly Gly Met Met Met Ser Met Gln Gly Lys
    130                 135                 140
```

Gly Pro Phe Thr Leu Thr Gln Trp Ala Glu Leu Glu Gln Gln Ala Leu
145                 150                 155                 160

Ile Tyr Lys Tyr Ile Thr Ala Asn Val Pro Val Pro Ser Ser Leu Leu
            165                 170                 175

Ile Ser Ile Gln Lys Ser Phe Tyr Pro Tyr Arg Ser Phe Pro Pro Ser
            180                 185                 190

Ser Phe Gly Trp Gly Thr Phe His Leu Gly Phe Ala Gly Gly Lys Met
        195                 200                 205

Asp Pro Glu Pro Gly Arg Cys Arg Arg Thr Asp Gly Lys Lys Trp Arg
    210                 215                 220

Cys Ser Lys Asp Ala Val Pro Asp Gln Lys Tyr Cys Glu Arg His Ile
225                 230                 235                 240

Asn Arg Gly Arg His Arg Ser Arg Lys Pro Val Glu Val Gln Pro Gly
                245                 250                 255

Gln Thr Ala Ala Ser Lys Ala Ala Val Ala Ser Arg Asn Thr Ala
        260                 265                 270

Ser Gln Ile Pro Asn Asn Arg Val Gln Asn Val Ile Tyr Pro Ser Thr
    275                 280                 285

Val Asn Leu Pro Pro Lys Glu Gln Arg Asn Asn Asn Ser Ser Phe
290                 295                 300

Gly Phe Gly His Val Thr Ser Pro Ser Leu Leu Thr Ser Ser Tyr Leu
305                 310                 315                 320

Asp Phe Ser Ser Asn Gln Asn Lys Pro Glu Glu Leu Lys Ser Asp Trp
                325                 330                 335

Thr Gln Leu Ser Met Ser Ile Pro Val Ala Ser Ser Ser Pro Ser Ser
        340                 345                 350

Thr Ala Gln Asp Lys Thr Thr Leu Ser Pro Leu Arg Leu Asp Leu Pro
    355                 360                 365

Ile Gln Ser Gln Gln Glu Thr Leu Glu Ala Val Arg Lys Val Asn Thr
370                 375                 380

Trp Ile Pro Ile Ser Trp Gly Asn Ser Leu Gly Gly Pro Leu Gly Glu
385                 390                 395                 400

Val Leu Asn Ser Thr Thr Ser Ser Pro Thr Leu Gly Ser Ser Pro Thr
                405                 410                 415

Gly Val Leu Gln Lys Ser Thr Phe Cys Ser Leu Ser Asn Ser Ser Ser
        420                 425                 430

Val Thr Ser Pro Val Ala Asp Asn Asn Arg Asn Asn Asn Val Asp Tyr
    435                 440                 445

Phe His Tyr Thr Thr
    450

<210> SEQ ID NO 65
<211> LENGTH: 461
<212> TYPE: PRT
<213> ORGANISM: Brassica napus

<400> SEQUENCE: 65

Met Asp Leu Gly Ser Val Thr Gly Asn Val Asn Gly Ser Pro Gly Leu
1               5                   10                  15

Lys Glu Leu Arg Gly Ser Lys Gln Asp Arg Ser Gly Phe Asp Gly Glu
            20                  25                  30

Asp Cys Leu Gln Gln Ser Ser Lys Leu Ala Arg Thr Ile Ala Glu Asp
        35                  40                  45

Lys His Leu Pro Ser Ser Tyr Ala Ala Tyr Ser Arg Pro Met Ser Phe
    50                  55                  60

```
His Gln Gly Ile Pro Leu Thr Arg Ser Ala Ser Leu Leu Ser Ser Asp
 65                  70                  75                  80

Ser Arg Arg Gln Glu His Met Leu Ser Phe Ser Asp Lys Pro Glu Ala
                 85                  90                  95

Phe Asp Phe Ser Lys Tyr Val Gly Leu Asp Asn Asn Lys Asn Ser Leu
            100                 105                 110

Ser Pro Phe Leu His Gln Leu Pro Pro Tyr Cys Arg Ser Ser Gly
        115                 120                 125

Gly Gly Tyr Gly Ser Gly Gly Met Met Met Ser Met Gln Gly Lys Gly
        130                 135                 140

Pro Phe Thr Leu Thr Gln Trp Ala Glu Leu Glu Gln Gln Ala Leu Ile
145                 150                 155                 160

Tyr Lys Tyr Ile Thr Ala Asn Val Pro Val Pro Ser Ser Leu Leu Ile
                165                 170                 175

Ser Ile Gln Lys Ser Phe Tyr Pro Tyr Arg Ser Phe Pro Pro Ser Ser
            180                 185                 190

Phe Gly Trp Gly Thr Phe His Leu Gly Phe Ala Gly Gly Lys Met Asp
        195                 200                 205

Pro Glu Pro Gly Arg Cys Arg Arg Thr Asp Gly Lys Lys Trp Arg Cys
210                 215                 220

Ser Lys Asp Ala Val Pro Glu Gln Lys Tyr Cys Glu Arg His Ile Asn
225                 230                 235                 240

Arg Gly Arg His Arg Ser Arg Lys Pro Val Glu Val Gln Pro Gly Gln
                245                 250                 255

Thr Ala Ala Ser Lys Ala Val Ala Ser Arg Asp Thr Ala Ser Gln Ile
                260                 265                 270

Pro Ser Asn Arg Val Gln Asn Val Ile Tyr Pro Ser Asn Val Asn Leu
                275                 280                 285

Gln Pro Lys Glu Gln Arg Asn Asn Asp Asn Ser Pro Phe Gly Phe Gly
        290                 295                 300

His Val Thr Ser Ser Ser Leu Leu Thr Ser Ser Tyr Leu Asp Phe Ser
305                 310                 315                 320

Ser Asn Gln Glu Lys Pro Ser Gly Asn His His Asn Gln Ser Ser Trp
                325                 330                 335

Pro Glu Glu Leu Lys Ser Asp Trp Thr Gln Leu Ser Met Ser Ile Pro
                340                 345                 350

Val Ala Ser Ser Ser Pro Ser Ser Thr Ala Gln Asp Lys Thr Ala Leu
                355                 360                 365

Ser Pro Leu Arg Leu Asp Leu Pro Ile Gln Ser Gln Gln Glu Thr Leu
        370                 375                 380

Glu Ser Ala Arg Lys Val Asn Thr Trp Ile Pro Ile Ser Trp Gly Asn
385                 390                 395                 400

Ser Leu Gly Gly Pro Leu Gly Glu Val Leu Asn Ser Thr Thr Ser Ser
                405                 410                 415

Pro Thr Leu Gly Ser Ser Pro Thr Gly Val Leu Gln Lys Ser Thr Phe
                420                 425                 430

Cys Ser Leu Ser Asn Ser Ser Val Thr Ser Pro Ile Ala Asp Asn
                435                 440                 445

Asn Arg Asn Asn Asn Val Asp Tyr Phe His Tyr Thr Thr
450                 455                 460

<210> SEQ ID NO 66
<211> LENGTH: 409
```

```
<212> TYPE: PRT
<213> ORGANISM: Arabidopsis thaliana

<400> SEQUENCE: 66

Met Glu Ala Arg Pro Val His Arg Ser Gly Ser Arg Asp Leu Thr Arg
1               5                   10                  15

Thr Ser Ser Ile Pro Ser Thr Gln Lys Pro Ser Pro Val Glu Asp Ser
            20                  25                  30

Phe Met Arg Ser Asp Asn Asn Ser Gln Leu Met Ser Arg Pro Leu Gly
        35                  40                  45

Gln Thr Tyr His Leu Leu Ser Ser Ser Asn Gly Gly Ala Val Gly His
    50                  55                  60

Ile Cys Ser Ser Ser Ser Ser Gly Phe Ala Thr Asn Leu His Tyr Ser
65                  70                  75                  80

Thr Met Val Ser His Glu Lys Gln Gln His Tyr Thr Gly Ser Ser Ser
                85                  90                  95

Asn Asn Ala Val Gln Thr Pro Ser Asn Asn Asp Ser Ala Trp Cys His
            100                 105                 110

Asp Ser Leu Pro Gly Gly Phe Leu Asp Phe His Glu Thr Asn Pro Ala
        115                 120                 125

Ile Gln Asn Asn Cys Gln Ile Glu Asp Gly Gly Ile Ala Ala Ala Phe
    130                 135                 140

Asp Asp Ile Gln Lys Arg Ser Asp Trp His Glu Trp Ala Asp His Leu
145                 150                 155                 160

Ile Thr Asp Asp Pro Leu Met Ser Thr Asn Trp Asn Asp Leu Leu
                165                 170                 175

Leu Glu Thr Asn Ser Asn Ser Asp Ser Lys Asp Gln Lys Thr Leu Gln
                180                 185                 190

Ile Pro Gln Pro Gln Ile Val Gln Gln Pro Ser Pro Ser Val Glu
    195                 200                 205

Leu Arg Pro Val Ser Thr Thr Ser Ser Asn Ser Asn Asn Gly Thr Gly
210                 215                 220

Lys Ala Arg Met Arg Trp Thr Pro Glu Leu His Glu Ala Phe Val Glu
225                 230                 235                 240

Ala Val Asn Ser Leu Gly Gly Ser Glu Arg Ala Thr Pro Lys Gly Val
                245                 250                 255

Leu Lys Ile Met Lys Val Glu Gly Leu Thr Ile Tyr His Val Lys Ser
                260                 265                 270

His Leu Gln Lys Tyr Arg Thr Ala Arg Tyr Arg Pro Glu Pro Ser Glu
            275                 280                 285

Thr Gly Ser Pro Glu Arg Lys Leu Thr Pro Leu Glu His Ile Thr Ser
        290                 295                 300

Leu Asp Leu Lys Gly Ile Gly Ile Thr Glu Ala Leu Arg Leu Gln
305                 310                 315                 320

Met Glu Val Gln Lys Gln Leu His Glu Gln Leu Glu Ile Gln Arg Asn
                325                 330                 335

Leu Gln Leu Arg Ile Glu Glu Gln Gly Lys Tyr Leu Gln Met Met Phe
            340                 345                 350

Glu Lys Gln Asn Ser Gly Leu Thr Lys Gly Thr Ala Ser Thr Ser Asp
        355                 360                 365

Ser Ala Ala Lys Ser Glu Gln Glu Asp Lys Lys Thr Ala Asp Ser Lys
    370                 375                 380

Glu Val Pro Glu Glu Glu Thr Arg Lys Cys Glu Glu Leu Glu Ser Pro
385                 390                 395                 400
```

Gln Pro Lys Arg Pro Lys Ile Asp Asn
            405

<210> SEQ ID NO 67
<211> LENGTH: 1173
<212> TYPE: DNA
<213> ORGANISM: Sapium sebiferum L.

<400> SEQUENCE: 67

| | | | |
|---|---|---|---|
| tgccaatagc cagccaataa aacatctaca cgttttcaca cggcttttca tcacagccgt | 60 |
| tgtttttctc atctcactcc gtgccttcat cttcatcctc ttctcctctc tctctgtctc | 120 |
| tatatgtata gaagcgttag atgtcttgcg ttgttaacca attcattttt cgctttctgc | 180 |
| ttcttctaat attataagaa agtttgattc ttcttcttgt caatctttgt tcgcggcttt | 240 |
| taacgatatc cgctaaagga aatttgaaat ttcaattatg gccgatggaa acgtcaattc | 300 |
| gcaagaacag atggctaagc aggaggaaca gaggctgaag tatttggagt ttgtacaagt | 360 |
| ggctgcaata catgctgtgg tgaccttcac aaacctctat gtttatgcca aaaacaagtc | 420 |
| gggtccattg aagcccggtg ttgagactgt tgaaggtacg gtcaagagtg tggttggacc | 480 |
| tgtttatggc aagttccatg atgttcccat tgaggttctc aagtttgtcg atcgcaagat | 540 |
| tgatcaatct gtaagcagcc tagacagccg tgtgcctcca gttgtgaagc agttatcggc | 600 |
| ccaagcattt tcagtggctc gcgaagcccc agtggctgct cgtgctgtgg cttctgaagt | 660 |
| gcagactgct ggagtgaagg aaactgcatc tgggttggca agaactctgt acttcaaata | 720 |
| tgaacccaag gccaaggagc tatacaccaa gtatgaacca aaagcggaac agtgtgctgc | 780 |
| ctctgcctgg cgtaagctca atcaactccc agtcttccct catgtagctc aggttgttat | 840 |
| gccaacagca gcttattgtt ctgaaaagta caaccaggca gtacttacca ccgctgagaa | 900 |
| aggatacaga gtgtcctctt atttgccttt tgtgcccact gagagaattg ctaagttgtt | 960 |
| taggaatgag gcacctgaat ctacccccttt ccttttccaat tgagcaagat gctgataaat | 1020 |
| gattcacaat ggacatgtgg acagaataaa aatctttgga tattatatgg tactgtgtat | 1080 |
| ttcaaggttc aagattactc tctacaatgt gtgaattttt gtttcagatg acttaattct | 1140 |
| tgttcattca ttatatatat atatatatat ata | 1173 |

<210> SEQ ID NO 68
<211> LENGTH: 241
<212> TYPE: PRT
<213> ORGANISM: Sapium sebiferum L.

<400> SEQUENCE: 68

Met Ala Asp Gly Asn Val Asn Ser Gln Glu Gln Met Ala Lys Gln Glu
1               5                   10                  15

Glu Gln Arg Leu Lys Tyr Leu Glu Phe Val Gln Val Ala Ala Ile His
            20                  25                  30

Ala Val Val Thr Phe Thr Asn Leu Tyr Val Tyr Ala Lys Asn Lys Ser
        35                  40                  45

Gly Pro Leu Lys Pro Gly Val Glu Thr Val Glu Gly Thr Val Lys Ser
    50                  55                  60

Val Val Gly Pro Val Tyr Gly Lys Phe His Asp Val Pro Ile Glu Val
65                  70                  75                  80

Leu Lys Phe Val Asp Arg Lys Ile Asp Gln Ser Val Ser Ser Leu Asp
                85                  90                  95

Ser Arg Val Pro Pro Val Val Lys Gln Leu Ser Ala Gln Ala Phe Ser

|  |  | 100 |  |  | 105 |  |  | 110 |  |  |  |
|--|--|--|--|--|--|--|--|--|--|--|--|

Val Ala Arg Glu Ala Pro Val Ala Arg Ala Val Ala Ser Glu Val
              115                        120                      125

Gln Thr Ala Gly Val Lys Glu Thr Ala Ser Gly Leu Ala Arg Thr Leu
130                      135                        140

Tyr Phe Lys Tyr Glu Pro Lys Ala Lys Glu Leu Tyr Thr Lys Tyr Glu
145                  150                        155                        160

Pro Lys Ala Glu Gln Cys Ala Ala Ser Ala Trp Arg Lys Leu Asn Gln
              165                        170                        175

Leu Pro Val Phe Pro His Val Ala Gln Val Val Met Pro Thr Ala Ala
                 180                        185                        190

Tyr Cys Ser Glu Lys Tyr Asn Gln Ala Val Leu Thr Thr Ala Glu Lys
            195                        200                        205

Gly Tyr Arg Val Ser Ser Tyr Leu Pro Phe Val Pro Thr Glu Arg Ile
        210                        215                        220

Ala Lys Leu Phe Arg Asn Glu Ala Pro Glu Ser Thr Pro Phe Leu Ser
225                      230                        235                        240

Asn

<210> SEQ ID NO 69
<211> LENGTH: 1252
<212> TYPE: DNA
<213> ORGANISM: Sapium sebiferum L.

<400> SEQUENCE: 69

```
ctactttttcc ctagcattag tattctaggc cccactctgt agattcctcc agctgcctga    60
tctaattttt tatcaactct tgaccgttcg atcatcccaa cggctcagat tcactagtac   120
ttttctcaca ccgtatctcc gattctccat gactccatcg atataaatcg cagtgctcat   180
caactgaatt ctcgaaattg cggttacaag ctgctataag aagcgaaaag aaacgctgag   240
aaacaggatc cgttcctcct ccctcgtttt ttactcctta caagatggag accgagaaga   300
agattcctga attgaagcac ttagggttcg tgaggatggc tgctattcag tcactgattt   360
gcgtctcgaa tctctacgat tacgcgaagc ataactcagg acctttgaga tccactgttg   420
gaaccgtgga gggtgccgta accaccgtag taggtccagt ttaccagaaa ttcaaagacc   480
ttcctgatga tcttcttgta tatgttgata agaaggtgga tgaaggaaca cacaagtttg   540
ataagcatgc tccacctatt gctaagaagg ctgcgagcca agcccatagt ttgtttcata   600
tagccttgga gaaggtcgaa aaactcgtgc aggaggctcg tgcaggagga cctcgtgctg   660
ctctgcattt tgtggctaca gagtcgaagc acttggcgtt gacccaatct gtgaagctgt   720
atagtaaact taatcagttc cctgtcattc acactgttac agatgtaacc cttcccacag   780
ctactcactg gtcagataag tataaccata cccttatgga cctgaccgg aagggttata   840
cgatctttgg ttatttgcct ttggttccta ttgatgacat atctaagaca tttaaacaaa   900
gtaaagcaga ggagaaagaa aatgcaacta cgcataaatc tgattcatcg gattccgact   960
aaacggttgc catcatgtct aatgggtgtg gtttgttaag tatagtggtt tgcgaaaatg  1020
ttctagggtt tatgagcctg ctcgaaagat gctgagaaat ggaaatctgt actatttagg  1080
agttttccg tactataata atgagtatga atggtttgta aattctgcct tgtgctttct  1140
cgacaagtat atcatgcttc tattttttac tactacttac tggactactg aattgtctca  1200
taattgtccc tagtgtctaa ttaaatatca cctccaaaat attattgaaa aa           1252
```

<210> SEQ ID NO 70
<211> LENGTH: 225
<212> TYPE: PRT
<213> ORGANISM: Sapium sebiferum L.

<400> SEQUENCE: 70

```
Met Glu Thr Glu Lys Lys Ile Pro Glu Leu Lys His Leu Gly Phe Val
1               5                   10                  15

Arg Met Ala Ala Ile Gln Ser Leu Ile Cys Val Ser Asn Leu Tyr Asp
                20                  25                  30

Tyr Ala Lys His Asn Ser Gly Pro Leu Arg Ser Thr Val Gly Thr Val
                35                  40                  45

Glu Gly Ala Val Thr Thr Val Val Gly Pro Val Tyr Gln Lys Phe Lys
    50                  55                  60

Asp Leu Pro Asp Asp Leu Leu Val Tyr Val Lys Lys Val Asp Glu
65                  70                  75                  80

Gly Thr His Lys Phe Asp Lys His Ala Pro Pro Ile Ala Lys Lys Ala
                85                  90                  95

Ala Ser Gln Ala His Ser Leu Phe His Ile Ala Leu Glu Lys Val Glu
                100                 105                 110

Lys Leu Val Gln Glu Ala Arg Ala Gly Gly Pro Arg Ala Ala Leu His
                115                 120                 125

Phe Val Ala Thr Glu Ser Lys His Leu Ala Leu Thr Gln Ser Val Lys
        130                 135                 140

Leu Tyr Ser Lys Leu Asn Gln Phe Pro Val Ile His Thr Val Thr Asp
145                 150                 155                 160

Val Thr Leu Pro Thr Ala Thr His Trp Ser Asp Lys Tyr Asn His Thr
                165                 170                 175

Leu Met Asp Leu Thr Arg Lys Gly Tyr Thr Ile Phe Gly Tyr Leu Pro
                180                 185                 190

Leu Val Pro Ile Asp Asp Ile Ser Lys Thr Phe Lys Gln Ser Lys Ala
            195                 200                 205

Glu Glu Lys Glu Asn Ala Thr Thr His Lys Ser Asp Ser Ser Asp Ser
    210                 215                 220

Asp
225
```

<210> SEQ ID NO 71
<211> LENGTH: 938
<212> TYPE: DNA
<213> ORGANISM: Sapium sebiferum L.

<400> SEQUENCE: 71

```
gagtattcac actctggcct gattgggttt gctataaagg gcgatcgttg caacgctcca      60
tattgtctac ttggttttgt ttcaaatctc atcattttgt aaatttgcga cagtgtagcg     120
ttttctagga aaaaggttgc taaaggaaag tagttatcaa accgcagaaa tggcggaatc     180
cgaacttaat caacacacag atatggttca agatgatgat aaaaaactca agtatctaga     240
ttttgtacaa gtggccgcga tctatgttgt ggtttgtttc tctagtatct atgaatatgc     300
taaggaaaac tccggtccac taaaaccagg ggtccaagcc gttgagtgta ccgtcaaaac     360
tgtaataagt ccggtttacg agaagtttcg cgacgtacct tttgaactcc ttaaattcgt     420
cgatcgtaaa gttgacaact ctctaggcga gttggacagg cacgtgccgt cgctggtgaa     480
gcaggcatca agccaagctc gagctgtggc tagtgaaatt caacatgctg gattggtaga     540
cgcaactaag aacattgcga agacgatgta tacaaagtat gaactgacgg cttggcagct     600
```

```
ctactgcaaa tacaagccgg tggctaagcg ttacgcggtg tcgacctggc gctcattgaa      660
ccagcttcct ctgtttcctc aagcggctca gattgcaatc ccaactgctg cttcgtggtc      720
tgagaaatac aataagatgg ttcgttacac gaaagataga ggatatccag cggcggtgta      780
tctgccattg atctcggttg agaggattgc caaggtgttc aatgaagact taaacgggcc      840
caccgtccct accaatggat catccgccgc agcacaatag ttttcatttt atgtatttat      900
gtcagattga agacgctccg gagattttga aaacctga                             938
```

<210> SEQ ID NO 72
<211> LENGTH: 194
<212> TYPE: PRT
<213> ORGANISM: Sapium sebiferum L.

<400> SEQUENCE: 72

```
Met Ala Glu Ser Glu Leu Asn Gln His Thr Asp Met Val Gln Asp Asp
1               5                   10                  15

Asp Lys Lys Leu Lys Tyr Leu Asp Phe Val Gln Val Ala Ala Ile Tyr
            20                  25                  30

Val Val Val Cys Phe Ser Ser Ile Tyr Glu Tyr Ala Lys Glu Asn Ser
        35                  40                  45

Gly Pro Leu Lys Pro Gly Val Gln Ala Val Glu Cys Thr Val Lys Thr
    50                  55                  60

Val Ile Ser Pro Val Tyr Glu Lys Phe Arg Asp Val Pro Phe Glu Leu
65                  70                  75                  80

Leu Lys Phe Val Asp Arg Lys Val Asp Asn Ser Leu Gly Glu Leu Asp
                85                  90                  95

Arg His Val Pro Ser Leu Val Lys Gln Ala Ser Ser Gln Ala Arg Ala
            100                 105                 110

Val Ala Ser Glu Ile Gln His Ala Gly Leu Val Asp Ala Thr Lys Asn
        115                 120                 125

Ile Ala Lys Thr Met Tyr Thr Lys Tyr Glu Leu Thr Ala Trp Gln Leu
    130                 135                 140

Tyr Cys Lys Tyr Lys Pro Val Ala Lys Arg Tyr Ala Val Ser Thr Trp
145                 150                 155                 160

Arg Ser Leu Asn Gln Leu Pro Leu Phe Pro Gln Ala Ala Gln Ile Ala
                165                 170                 175

Ile Pro Thr Ala Ala Ser Trp Ser Glu Lys Tyr Asn Lys Met Val Arg
            180                 185                 190

Tyr Thr
```

<210> SEQ ID NO 73
<211> LENGTH: 2526
<212> TYPE: DNA
<213> ORGANISM: Sorghum bicolor

<400> SEQUENCE: 73

```
atggacgagt ccggggaagc gagcgtcggc tccttcagga tcggcccgtc gacgctgctg      60
ggccgcgggg tggcgctccg cgtgcttctc ttcagctcgc tgtggcgcct gcgggcgcgc     120
gcgtacgccg ccatctcgcg cgtgcgcagc gcggtgctgc cggtggcggc gtcctggctt     180
cacctcagga acacccacgg cgtcctcctc atggtcgtcc tcttcgccct ctccctgagg     240
aagctctccg gcgcgcggtc gcgggcggcg ctcgcgcgcc ggcgcaggca gtacgagaag     300
gccatgctgc atgccgggac gtacgaggtc tgggcccgcg ccgccaatgt gctcgacaag     360
```

```
atgtctgatc aggtccatga ggcggatttc tatgacgagg agctgatcag gaacaggctt    420
gaggacctcc ggaggcggag ggaggacggg tcgctgcggg acgtggtgtt ctgtatgcgc    480
ggcgatcttg ttaggaactt ggggaacatg tgcaatcctg aacttcacaa gggcaggcta    540
gaggttccta agcttataaa ggaatacatt gaagaggttt ctattcaact aagaatggtg    600
tgcgaatctg acactgatga gttgctattg ggagagaagc ttgcctttgt tcaggagacc    660
aggcatgcct ttgggaggac agccctactc ttaagtgggg gtgcttcact ggggtctttc    720
catgtaggtg tagtgaaaac attggttgag cataagcttc tgcctcggat tatagcagga    780
tcaagcgttg gttccattat atgttcgatt gttgctaccc ggacatggcc tgagattgag    840
agcttcttca cagactcatt acagaccttg cagttctttg ataggatggg tggaattttt    900
gcagtgatga ggcgagtcac cactcatggt gcactgcatg acattagcca gatgcaaagg    960
cttctgaggg atctcacaag taacttaaca tttcaagagg cttatgacat gactggccgt   1020
gtccttggga tcaccgtttg ctctcctaga aaaaatgagc acccccgctg cctcaactat   1080
ctgacgtcgc cgcacgttgt tatttggagt gctgtaactg cctcttgtgc atttcctggg   1140
ctctttgaag ctcaggaact gatggcgaag gatagattcg gcaacatagt tcccttccat   1200
gcacccttg ccacagatcc tgaacaaggt cctggagcat caaagcgccg gtggagagat   1260
gggagcctgg aaatggattt gcccatgatg agactcaagg agttgtttaa tgtaaaccat   1320
ttcattgtga gccaaactaa tcctcacatt tctcccctcc tccgaatgaa agagcttgtt   1380
agagtctatg gagggcgctt tgctggaaag cttgctcgtc ttgctgagat ggaggttaag   1440
tatcgatgta accaaatcct agagattggt cttccaatgg gaggacttgc aaaattgttt   1500
gctcaggact gggagggtga tgtcaccatg gttatgccgg caacagtagc tcagtatttg   1560
aagattattc agaatccaac atatgcggag ctccaaatgg ctgccaacca aggccgcagg   1620
tgtacatggg agaagctctc tgcaatcaga gcaaactgtg ccatcgaact tgcattggat   1680
gaatctatag cagtttttaaa ccacaaacgg aggctaaaaa gaagcatgga gaggacagag   1740
gctgctttgc agggtcattc taactatgtt cgactcaaaa ctccaaggag ggtaccatca   1800
tggagctgca tcagtcgaga gaattcttca gaatctctct cggaagagat ttcagcagtt   1860
gctacttcaa ccgcgcagca aggtgctgct cttgttgtcg gcacagccac tctttctcac   1920
catgttcgac gcaattctca tgacggaagt gagagtgaat cagaaaccat tgaccttaat   1980
tcctggacca ggagtggtgg gcctctaatg aggacagcat ctgctgacat gttcatcagt   2040
ttcatccata accttgagat tgacacgaa ttaagtaggc cctgtactgt ggagggtggt   2100
actgcaggta tttcgtcaga atctaccttc ccaaatgatc cacaaccgaa caatggctca   2160
agtgttacta ctccaggtag atgcacgaaa aattctgaga ccgaggcata cgacactgtc   2220
aacaccagag ccagtcaggc ttctactccc acaagcatcg ctgtttctga aggagatttg   2280
ctgcagcctg aaagcattgc tgacggtatc ctgcttaaca ttgtgaaaag agatgccttg   2340
caggctcaaa atgacagcgt aactgaattg gccgaaagct cctgcactga acatatgcg    2400
gaaacttgtg acaccatctc agggtctggc actgctgaag ataacaagga tactgctgac   2460
tcaagcaatc actcacttga tattgatgct tttgtagttt cgcatcaacc ttcagctgat   2520
gattag                                                              2526
```

<210> SEQ ID NO 74
<211> LENGTH: 3099
<212> TYPE: DNA
<213> ORGANISM: Triticum aestivum

<400> SEQUENCE: 74

```
atgcccgcgc ctgcaggtgc gtgcagccaa gccccaccgc tcgccttcta ttccgcgtcc      60
cctagcttgg cccggccctg ctccgatcca aggccgcggc ggtggcccag tgccctctcc     120
ctcctgccac gccgtccgcc gcccatggac gtcatcacca acgaggcgcg cgtgggggcg     180
ttcgcgatcg gcccgtccac ggcggcgggg cgcgcgctcg cgctgcgcgt gctcctctgc     240
ggctcgctgg cgcggctgcg gcaccgcctc gccgccgcgc tgcgcgccgc ggcgccgctg     300
gcggcggcct ggctgcaccc gcgccacaac gcgcggggga tcctgctcgc cgtctgcgcc     360
gtcgcgctgc tgctgcgcgg ccgcggggc gcgccgggg tgcgcgcgcg ggtgcagtcc      420
gcctaccgcc gcaagttctg gcggaacatg atgcgcgccg cgctcaccta cgaggagtgg     480
gcgcacgccg cgcggatgct cgagcgggag acgccgcgcc gcgtcaccga cgccgacctc     540
tacgacgagg agctcgtgtg caacaagctc cgtgagctca ggcaccgccg tcaggagggc     600
tcgctcaggg acatcgtctt ctgcatgcgc gccgatctgc tcaggaacct tggtaacatg     660
tgcaaccccg agctccacaa gttgaggctg caggtgccta aaaccatcaa ggagtacatt     720
gaggaggtat ctactcaact gaaaatggtt tgcaattctg attcggacga gttaccctt      780
gaagagaaac tggcatttat gcatgagaca agacatgcct ttggtagatc ggccctactg     840
ctaagtggag gtgcttcatt tggctctttc catgtgggtg ttgtgaaaac cttggtagag     900
cataagcttc tacctaggat tatttcagga tcaagcgttg gcgcaataat gtgtgctatt     960
gtagccacac ggtcatggcc agaactagag agttttttg aggagtggca ttccttgaaa    1020
ttctttgacc agatgggtgg gatctttcct gtatttaaaa gaattttgac gcatggagcg    1080
gttcatgaca ttaggcactt gcagacgcag ttgagaaatc ttacaagcaa tttgacattt    1140
caagaggcat atgacatgac tggccgggtt ctcgttgtta ctgtgtgttc tccaagaaaa    1200
catgagccac cacgatgcct gaactatttg acatcacctc atgttctcat ttggagtgca    1260
gtaactgctt cctgtgcttt tcctggactt tttgaggccc aggagttgat ggccaaagat    1320
agattcggag aaacagttcc ttttcatgct ccattcttgt tgggtgtgga ggaacgagct    1380
gacgctgcta cacggcgctg gagagatggc agcttagaaa gtgatttacc catgaagcaa    1440
ttgaaggaat tattcaacgt aaatcacttc atagtaagcc aagccaatcc tcacattgct    1500
ccattactga gactaaagga gatcatcagg gcttacggag gcagctttgc tgcaaagctt    1560
gctgaacttg ctgagatgga agttaagcat aggttcaatc aagttctgga acttggattt    1620
ccattaggag gaatagctaa gttgtttgct caacattggg aaggtgatgt gacaatcgtt    1680
atgccagcca cacttgctca gtattcgaag atcatacaga atccttcgta ttctgagctt    1740
cagaaagccc caagtcaggg taggcgatgc acttgggaaa agctctctgc tatcagggca    1800
aactgcgcta ttgagcttgc attagatgaa tgtgttgccc tcctgaacca catgcgtagg    1860
ctgaagagaa gtgcagaaag agcagctgct tcacaaggat atggtgctac aattagactc    1920
tgtccatcta aaggattccc atcatggaat ctcatagcaa gagaaaattc aactggttct    1980
ctcgatgagg aaatgctcac atgtcccact gttacgagcc atcaagcagt tggagggact    2040
gctgggccat ctaacagaaa tcaccatctc caacatagta tgcatgatag cagtgacagt    2100
gaatctgaga gtatagactt gaactcatgg acgagaagtg gtggccctct catgagaaca    2160
gcctcagcta taaattcat cagctttgtt cagaaccttg agattgacac agaattcaga    2220
acaatttcac caaggggag cgaaggtgat attgttacac cgaatagtaa cttatttgct    2280
```

```
ggtcacccaa ttggtagaga gccagttgat aaccatccag ggcctgctac tcctggtagg    2340
acctcaggca attcaggttg cgatcctcat gatactcctg ttcctaggtc tccatttggt    2400 cttttccacaa gtatcatggt ccctgaaggt gacttgctgc agccggaaaa gattgagaat   2460
ggtattttat tcaatgttgt gagaagggat gctcttgtag cgactactag cggagttgaa    2520
cctcatggat cttcacagga agcagatgtg gaaactgtac cgaccgagtg cctttatggt    2580
gcttcggatg acgacgacga caacgtggaa ctgaatgctg atcatgaagc attatctgac    2640
cctggagatc agagatcctc agttgcagga aacctagatc cgtccacttc catggattgt    2700
caagctgatg aaacaagtac tactcgatca gaagctccat ctctctttaa tatctgtgtg    2760
gagattcctc cagcaaccat gatcagagaa aatagtcggc ccgacgagcc ttcttcagac    2820
ataagactgg agattgtaaa gacagaatgc cctgatgaga attcagctgc tgggaacgat    2880
gaagttggct cagttcctgc caataaagaa tcttcctatt gttctcagac agctgaaaat    2940
agacagcagc atcaagttga tatgggatct gtgaactcct gtagtgtttc agtttcagaa    3000
gatgataggc atgtcagcct catttcgaac gagaaaccag ttactacttc cagtggcgga    3060
gcggagagta tgacatctgg aagaaatgaa gctgactag                           3099
```

<210> SEQ ID NO 75
<211> LENGTH: 2198
<212> TYPE: DNA
<213> ORGANISM: Artificial Sequence
<220> FEATURE:
<223> OTHER INFORMATION: S. bicolor SDP1 hpRNAi fragment

<400> SEQUENCE: 75

```
gcggcggcgt ggctgcaccc gcgcgacaac acgcgcggga tcctgctcgc cgtctgcgcc      60
gtcgcgctgg gtgcagtccg cctaccgccg caagttctgg cggaacatga tgcgcgccgc    120
gctcacctac gaggagtggg cgcacgcggc gcggatgctt ggagtgcagt aacagcttcc    180
tgtgcttttc ctggactttt tgaggcccac catctaggag gattccatcc tggaatctca    240
tagcaagaga aaattcaact ggttctctat gtgcaatcct gaacttcaca agggcaggct    300
agaggttcct aagcttataa aggaatacat tgaagaggtt tctattcaac taagaatggt    360
gtgcgaatct gacactgatg agttgctatt gggagagaag cttgcctttg ttcaggagac    420
caggcatgcc tttgggagga cagccctact cttaagtggg ggtgcttcac tggggtcttt    480
ccatgtaggt gtagtgaaaa cattggttga gcataagctt ctgcctcgga ttatagcagg    540
atcaagaagg gtggacccag ctttcttgta caaagtggtc tcgaggaatt cggtacccca    600
gcttggtaag gaaataatta ttttctttt tccttttagt ataaaatagt taagtgatgt     660
taattagtat gattataata atatagttgt tataattgtg aaaaaataat ttataaatat    720
attgtttaca taaacaacat agtaatgtaa aaaaatatga caagtgatgt gtaagacgaa    780
gaagataaaa gttgagagta agtatattat ttttaatgaa tttgatcgaa catgtaagat    840
gatatactag cattaatatt tgttttaatc ataaatagtaa ttctagctgg tttgatgaat    900
taaatatcaa tgataaaata ctatagtaaa aataagaata aataaattaa aataatatttt   960 ttttatgatt aatagtttat tatataatta aatatctata ccattactaa atattttagt    1020
ttaaaagtta ataaatattt tgttagaaat tccaatctgc ttgtaattta tcaataaaca    1080
aaatattaaa taacaagcta aagtaacaaa taatatcaaa ctaatagaaa cagtaatcta    1140
atgtaacaaa acataatcta atgctaatat aacaaagcgc aagatctatc attttatata    1200 gtattattttt caatcaacat tcttattaat ttctaaataa tacttgtagt tttattaact    1260
```

-continued

| | |
|---|---|
| tctaaatgga ttgactatta attaaatgaa ttagtcgaac atgaataaac aaggtaacat | 1320 |
| gatagatcat gtcattgtgt tatcattgat cttacatttg gattgattac agttgggaag | 1380 |
| ctgggttcga aatcgataag cttgcgctgc agttatcatc atcatcatag acacacgaaa | 1440 |
| taaagtaatc agattatcag ttaaagctat gtaatatttg cgccataacc aatcaattaa | 1500 |
| aaaatagatc agtttaaaga aagatcaaag ctcaaaaaaa taaaaagaga aaagggtcct | 1560 |
| aaccaagaaa atgaaggaga aaaactagaa atttacctgc acaagcttgg atcctctaga | 1620 |
| ccactttgta caagaaagct gggtccaccc ttcttgatcc tgctataatc cgaggcagaa | 1680 |
| gcttatgctc aaccaatgtt ttcactacac ctacatggaa agaccccagt gaagcacccc | 1740 |
| cacttaagag tagggctgtc ctcccaaagg catgcctggt ctcctgaaca aaggcaagct | 1800 |
| tctctcccaa tagcaactca tcagtgtcag attcgcacac cattcttagt tgaatagaaa | 1860 |
| cctcttcaat gtattccttt ataagcttag gaacctctag cctgcccttg tgaagttcag | 1920 |
| gattgcacat agagaaccag ttgaattttc tcttgctatg agattccagg atggaatcct | 1980 |
| cctagatggt gggcctcaaa aagtccagga aaagcacagg aagctgttac tgcactccaa | 2040 |
| gcatccgcgc cgcgtgcgcc cactcctcgt aggtgagcgc ggcgcgcatc atgttccgcc | 2100 |
| agaacttgcg gcggtaggcg gactgcaccc agcgcgacgg cgcagacggc gagcaggatc | 2160 |
| ccgcgcgtgt tgtcgcgcgg gtgcagccac gccgccgc | 2198 |

<210> SEQ ID NO 76
<211> LENGTH: 22
<212> TYPE: DNA
<213> ORGANISM: Artificial
<220> FEATURE:
<223> OTHER INFORMATION: Oligonucleotide primer

<400> SEQUENCE: 76

| | |
|---|---|
| ttttaacgat atccgctaaa gg | 22 |

<210> SEQ ID NO 77
<211> LENGTH: 23
<212> TYPE: DNA
<213> ORGANISM: Artificial
<220> FEATURE:
<223> OTHER INFORMATION: Oligonucleotide primer

<400> SEQUENCE: 77

| | |
|---|---|
| aatgaatgaa caagaattaa gtc | 23 |

<210> SEQ ID NO 78
<211> LENGTH: 22
<212> TYPE: DNA
<213> ORGANISM: Artificial
<220> FEATURE:
<223> OTHER INFORMATION: Oligonucleotide primer

<400> SEQUENCE: 78

| | |
|---|---|
| cttttctcac accgtatctc cg | 22 |

<210> SEQ ID NO 79
<211> LENGTH: 25
<212> TYPE: DNA
<213> ORGANISM: Artificial
<220> FEATURE:
<223> OTHER INFORMATION: Oligonucleotide primer

<400> SEQUENCE: 79

```
agcatgatat acttgtcgag aaagc                                    25

<210> SEQ ID NO 80
<211> LENGTH: 18
<212> TYPE: DNA
<213> ORGANISM: Artificial
<220> FEATURE:
<223> OTHER INFORMATION: Oligonucleotide primer

<400> SEQUENCE: 80
gcgacagtgt agcgtttt                                            18

<210> SEQ ID NO 81
<211> LENGTH: 25
<212> TYPE: DNA
<213> ORGANISM: Artificial
<220> FEATURE:
<223> OTHER INFORMATION: Oligonucleotide primer

<400> SEQUENCE: 81
atacataaaa tgaaaactat tgtgc                                    25

<210> SEQ ID NO 82
<211> LENGTH: 2631
<212> TYPE: DNA
<213> ORGANISM: Saccharum hybrid

<400> SEQUENCE: 82
ctgcgacagc tagaggcgcc accgcgtcct agcttcctcc aacttctcgt cggagatccc    60
ttcagggatg cccaatgcca ccgcccctaa gtcaacctgc gggagctgga gcttcgccag   120
ggtcagagct gcggcagcac cctggtagac cgcattcctg atgacccgcg gggtgcgctc   180
catgaagaag tgcattcgcc caaccaagtc gagtgggtcg cctggagggg cggggaagc    240
aaaacgttgc atgcacctag cgccctggca gcgagctcct gtagtatcac ctgcgtcgcc   300
tccagctcat gctcgcaagc ctccaggcg gcccggcagt gctccaacac tttcgcctcc    360
tcctacagct ccttccacat gcagtcgtgc tccgcacgca ccttctccac cttttactc    420
ttttctttct cttttcttgg cccatctttg gtattttcac aaatgtcccc ctacaaatga   480
taaatcacca aaactcatgg agcttgctag ttataaactc taattctaag tttggtgttt   540
atttgagtgg attttgtgtg aaagttggtg gttagaaata ggagttaagg accgccaaca   600
agatccccca cacttagccc tttgctcatc ctcgagtaaa gttcaaggac taaggtggaa   660
catctcctca aatggtacga tgcctgcata aagttattc caagcctcac ctatacatgt    720
gaactttgaa gtgtctacca cgccatcttg ggtggttgag aaatggaaca gatcagaatc   780
cagtcatctt tacctctctt gcttagataa cttgggtttt tgtaaggttt tcaaatttaa   840
aacatagtct tgctcctcaa atgattctct catatagctc aatgtgtatg gtttctcacc   900
aaggcaatgt tttgcctctt ttcatcctac ttctaatatt tcttttgtgg agcttagggt   960
agggaatgaa aaggaagcat acttgcattg catatgttac taagtcaaaa accaaatctg  1020
aggagaagca agtcatacaa tctgatcaag atgtgcaagt gtgtggatat gtggattaag  1080
ataactcctg tttattcatg ctctcctcct aataaactt tagagggcat ggcaatcttt   1140
gcatgggcct tcatgagctc atcgtatgtc taagcatgga gctcatcatt tatataagca  1200
tggtgatacc aaaattactc cttttgagca tgtttatatt taggaggacg ttttacctgt  1260
tgaggtaaat ctgaacgcta ataaatcggc taagcaaaat aatttatcac ctgttgattc  1320
taacaatttg atgatggaca atattgatga ggtgactgac aaatgattga aggctttaaa  1380
```

```
ggagattgag aaggataaat ctacaataaa aatgtaaaga agaaagcatt caaagtgtga    1440
gatctggtgt ggaagactat tttgcctctt gggggtaaaa gacaacaagt ttagtaagtg    1500
gcctcaaaat tgggagggcc catgcaagat tgttaaagta attgttttgg attgacggag    1560
gcatttcaag gtgatcatct acctagagct ctcaatggga ggtgctcgaa gacatattac    1620
ccatgtgtat ggcaagatgt ttagctagta actgactgat agtgtaaacg atctccaatg    1680
gggcaagaca tattacctaa ggccaggctg ttttttgcaa gttcgagtag gatatagaga    1740
ttctcgtgcg agttgtaaac gatctccaat ggggcaagac atcctaccct atatatagtg    1800
aaggggcagt agctgattga gaatcaatca atcaagcaca atataattta ttaattttt    1860 attcaaaccc aattttttc cttttccaac cctaattata gttttccttt tgcctctagg    1920
acaaattgac gtgttccggg tatcctgctg aattaagaac aaccctaggt gcacctgtcc    1980
cgatagagtc ccacctgggt aggcattcat agggattcgt gtatttcctg caaaaaagcg    2040
attaagctgg cttctaaaac tggctaggcc ggattctgtg gccttcacta ccaggtgatt    2100
ttcatgtgat ccgtgcattc tagcactttg ctatgtaacc caaacttaag tcgacaacta    2160
taaatatgct acttgcagga tgttatcacg acacaactcc taatctacgg aagcctaagt    2220
ttagttttgc tcggagacaa gcaattgtgg ccagtcacta tagctacgtc agagggtagt    2280
gggagcagtt gcgtcgttgg attgaaaaca ggtggatcgt atcagatatt atgcattcac    2340
atggacagta aatgtggtac agtaacttcg caaacaataa aatctgtcac aatttattag    2400
tgcactcctc tgacgtaaat gcttctacgt cagaggattt gattccgagg gccgctgcac    2460
ccatcactaa tgacggtctt tacccatcat catggaccat tgttcacatc catgctatca    2520
ctgtcgtcct gtccatgcac tgcagccctc tataaatact ggcatccctc ccccgttcac    2580
agatcacaca acacaagcaa gaaataaacg gtagctgcca taactagtac a    2631
```

<210> SEQ ID NO 83
<211> LENGTH: 2907
<212> TYPE: DNA
<213> ORGANISM: Saccharum hybrid

<400> SEQUENCE: 83

```
gcataggcat tgtaaaagcg gtatgcctct tcttcagtgc agaatttcat accaacctta     60
ggtatcctgt cttccataga attttctacc tgagtaggtt cggtctggtt ggatttgtag    120
cgggtttcat gcaaaataag ttagaaatcg tgcaaacttg caatggaggt taaatttgaa    180
atatatttgc atagacaaaa caaatataga ttatgaatgg taatccaata tgacttgcat    240
tttctaactc tattgctact gtgccagatg aagaatgttg atctggagaa gttttgtgag    300
aatgtgacaa caacgggagg tcatatcaag attctgggta cccgcggaga atcggcctcc    360
atgtagttag cctcgtcagg catggggga attggctgag atgcccccat gtagtcgtca    420
ggcatggaga gtactggctg agatgccatt gttgtgtaga tcgagagaaa cgagaagaat    480
gctagtctaa taatacccct tccgtatgcta accaactatt ataattggca ccattttca    540 catgctagcg ccttttgcct gctttattta attcaattgg gtccgataag catgtgaacg    600
tgggagacgg ttccgtcgga cggctccgtt ttcttgtagc gtacggcgtg gacggagaaa    660
aggtgagggc ctatctctaa aggggaacga atggatggtg acacgtgtg gggagacacc    720 gaagggacat gccgaggagg cacacaagct tcagcaggcg tctccagact ctcagaagaa    780
gaagaagctc acggcacggt tgcggctggt tcttgctgtc gctgtctcgt ggtgcacgtt    840
```

```
tctgtgatca cgctgaaatc gaccggccgg cggaccaaca ggaggtcagc tcggccactc      900
cgtctccgag cgcatgagtg caccgttcgt ccgcggttcc tttctctgtg gtgccgtgca      960
cgcctctgcg ttcaccggca ccctgaaacc aatcagaacg ttcccttta aggggaaagg     1020
gacaagtctg ataacctctc tgtttccatc gtcctctaac cgcgaagagc ggacgcacaa     1080
gacttagagt ctatttgttc gaaattttt actctcacaa aagctagctt ttatagacgg     1140
gcataaaagc tatcatgtcg accggcacgt ttaatattta acttatacca tatgaatatc     1200
atgtcgaact atgaggatga tacttttctg aacgtgattg cgtgagttat taaattgtac     1260
ttttagttgt ttgagcatga aggtctgaac tatgaattta tgatgtattg tggcttgtga     1320
gctactccgc tctacatttt agttggtatca taaatattat tatattatca tataaatttg     1380
atcaacttga gatgctttga ctcttcaaga ttcttggaat gacttatcat ttggggtagg     1440
gagtaggttt ctaaggccag tctcagtggg gtttcatcag agtttcatgg acattaaata     1500
agctgatgtg acaccgtatt gatgaagaga gagatgataa gagtttcatg cgagtagaga     1560
gagtttcatg gggatgaaac tcttcttcac tgtttccaaa atatagatgc attggtaaga     1620
gggccatgaa atctctagtg acactgacct aagatgagat tgactctagc actatgtttc     1680
aaaatctgca tgcatgcatg ctttgaatat tgtaacctca cattaactcc cctcacacat     1740
gcatgcaaac gggcggtgca cgcaaaagaa ttgagtgaag atgcacatga aaaataagta     1800
aaatgctttg gcttcatcac ccggcttaaa tgctcgacaa aaaacacgt cggtagtcaa     1860
ggttgtgcct aacaaactgg ggttcacatg taaaacacgt tcatgcctta gaaacggcct     1920
ggagggatta gatacaactt caattatatc ttagggcccc tccaatattg tcagctctaa     1980
actagtttta tgtgtcacgg tggaggagag ggaggctaaa aatataatct tgagctaacg     2040
tgaagagaag agctatttt ttttgctccc caatacatga tagatacaat atgagagaaa     2100
aaatatatga ataaagaaca ctttacatgc cagccataca atatgagatt tcatctaaga     2160
gccaacacct gactcgtact gttgaaggtg tcctagttgg agtggtcgat cttttagttg     2220
ttagtagtgt aagacctagt ttagtgctct tttcttgtct aggtttatgt tgtgttttgg     2280
ctgccaagtg ttgaacaact caaggtaagg tcccatctaa ttctaaaatg atgccaaata     2340
aagatagatt acaaagttaa acgacggaaa aactctaaaa taggatggaa agttttgtag     2400
agtaataatt ggtatgaagt ggcgaagtcg accacaacca acataaaga gttaaatgca     2460
tggtaggctc ttgatcttgt ctggaggtgc cacttaggtc cacaaactct caaattgcat     2520
ttttgacacc ctaatgttat tcaagtgtgc cacttagatc tacaaactct caaaatgcat     2580
ttctgatacc ctagtgttgt tcaagtgtgt cacttaggca agaaaagtta gataattttg     2640
ataagctatg ggaccaaatt aatttatgta tgcatgctcg aactagttga tgatgatgga     2700
ccccataata gacactagtt catgggctgg tttccttgta tagtactagc tagtataact     2760
ttttcaagtt gtagctacta ctttagctta tactccgcat attacaatca aatagaattc     2820
ggaagtacta taaacgggag cctataaatg gagacgtttt gcatcatgag gctataacaa     2880
cttgagcaaa aacagaagcc gtgcgcc                                          2907
```

<210> SEQ ID NO 84
<211> LENGTH: 1141
<212> TYPE: DNA
<213> ORGANISM: Saccharum hybrid

<400> SEQUENCE: 84

```
actataggc acgcgtggtc gacggcccgg gctggtctgg ttttggcctc ttttagttac       60
```

```
taaattgcca aaaagagtga ctaaaaagtg actaaactga tttagtcctc tagtcaaggg    120
actaaaccag ctaaaagaca tccgctgccc ctcattaatg cacagaagga gagagagagg    180
gagagggagg acattttggt ctttatatag tagctttaat ggactttagt acctagatcc    240
aaaccggtag tgactaaagt ttagtccttg aactgaactt taatccaggg acatggaacc    300
aaacatgccc ttaactttt tttattctaa tccctcttac attcacttgt ctcacaaagt     360
ggcaagtcat ttgccaccct cactaccagt ggcgactggt taaatatcct catgtttggt    420
tttttttagt aaccaaatac tgcaagctat tgggaaaaaa ggcaaaaaat tatctccttg    480
cttatagttg tataatccat gatccggcaa ttgtttgtta cggagatcct gaatcctctg    540
acgtagagtt taatcaattt tagctcaaga ataatacact ataaagtgga tatgacaatc    600
accgtagtac ttatttatct tgtagtagta tactgtattc gacctgcgat tatgataaag    660
gcatcagaaa ctagagtact ttctagaatc tttagtcagt ttctgtaaga tgaacgtgac    720
taggaaactt atactgttgc aatcctctga cattctctga ttgaaactcg gtttccaaaa    780
atcatatgtt actaaacaaa acatatctaa ccaaatacta tgtggtagtg tagatttata    840
tgctgtgtac tgaaagtgac gtcaagtata gtagtggcag agactcaaaa gatacctgcg    900
gattctgaat accacaacca taaaaaacag gatgatgtta tacttgtccc cttccatgat    960
acaggactgt ttagtaattt cccaaacagc ccataataca ttctgcaccc tttattaaac   1020
ctctactagc tacaacatct tactccatct tgtctagttg acaagttct ctctttcttg    1080 gctgactcca acttactaca ccgcaacttc ttgtgccctt gttccaacca tcacaattga   1140
g                                                                   1141
```

<210> SEQ ID NO 85
<211> LENGTH: 4438
<212> TYPE: DNA
<213> ORGANISM: Saccharum hybrid

<400> SEQUENCE: 85

```
aagtacaaac gtagactctg acatacacgc acgtagactc tgacatacac gcataaacga     60
acgaagaatg ttattattta tgttttgagt gggaatattt ggtactgcta tgattcacgt    120
gtgtaaggaa ggattcaaga agaaaggatg cgtttagttc gcgaaaattt ttgactttta    180
ccactatagc actttcgttt gtatttgtta attagtgtcc aatcatggac taattagact    240
caaaagatcc gtctcgtggt tttaaaccaa actgtgtaat taatttttt tatctatatt     300 taatgctcca tatatgtgtc aaatattcga tataacgaag aatcttgaaa attttttagga   360 actaaacatg ccaaagtgt tgtcccgact gagaaacttt ggaagcagaa taaaggctca    420
aaggaacatt taaagaaga ggatgatata taatcaaaag tggcgacaaa gaagtgtgta    480
cgacccactc gagattgacg aaggacagct tctttgttct tttgtgtgtt actgaatatg    540
taataatctt gtatagattg gttttaaaa tacggtggca aattaaagac gatatcactt     600
acaaagacat ggacaatgtg gaggggccaa agttatata aacgacacgc cgaatcggtg    660
atgaacacca catgcctccc ataaagacgg tgtatcaatc tttgatataa tgggtatccg    720
tttgaggcgg catttatact tgatctagtg aaattacaag gagaggaaaa gaagtttaag    780
agaatgataa tgataatgaa aaaatcgga ggaaaaagaa catgaacaaa gcaagaggag     840
atagccgtgc acacaaaata gagataattt cctcttagaa ctatgaaaac ttcctcttct    900
ttctgcaaca ctgatttgag ttttttgttct ctatctagca tttcagtcca tcttgatgtc   960
```

```
aagtgacatg taaaaagacg tattgccccc attgctgttt taaattgtct ccacacttga   1020
caacaattta atgagttgtt aaaatattat gtgtgtttat ggccaattat acttttagt    1080 tttgagtttt tcatgaagtc attaagatgc taaaaataat ataaagttgt caatgcttgt   1140
cggaagcccc aatatgtgac taaaatgctg ctaaaagttt atagcatttt tttaaaaatc   1200
taaacaaatt gaaaaagaa atccaaacta gaaattgtag atcttatcga aaactataag    1260
ttttatataa aaggcgactt tatctaacac cacacaagaa agatgtgctt tttctaagaa   1320
gacaagtctt agtatgtgat taatatgcta ctgaaaattt atattatttt taagcatttt   1380
aataacctca aatggaaaca tacaaaacta agttgcagat cttatcaaga gctataattt   1440
ttatataaaa tgtatattta ataacacca tacaagaaag atatatgatt ttttctaaga    1500
cgacaaagct ttgtatgcaa tttaatatgt tgctaaaaaa tcatattatt ttttttatca   1560
tcttaacgtc ctcaaataaa aaaaaatcag actagttggt atagacctca tcgaggctac   1620 aattttttata aaaactcaac ttcatccggt gttgtaaaa aatgatataa ttttttcctag  1680 atagagcgtt gccataagtg tattttggtc aagaaatata tgtatactta ttaatgaaat   1740
cctaacaaaa tactttaa aatctgacgg aaatgttgga taggaaacaa aagcttaaat     1800
caatgctaaa tagggaagtt ttcatcatag ttataatgag tgatttctcc acaaaatatg   1860
atgtaccaca tgttaaatat tactcgcgca caaataatca gagcatatta ctttcatagc   1920
gtggtcgtgg ccatggccta gacttggttg tggacgtctc acttcaccaa ttgatagaaa   1980
aaaaacattt ataagaaaga aaagatacag aaaccatcac acgcgacaac atgacttgcc   2040
gaaacacaaa accaaaaccc aaactcgaga agatgctttc gagaaaaagc ctgaaaagaa   2100
aaaaaatttg cacgtaaaat caaattcgga cggcgaagag ggcaaacgag acagacaact   2160
gggtccactt gctgataaaa aagagagaga ggagggccca cttgccggcg ggcaccctc    2220 agactgtctc caacaatact gacgcaaaca gaagacgcat tggatgcaat gcgttgcgct   2280
gtggcaaaaa attaggtacc tatttctagt gtattccaac agagaacgca aaagaagatg   2340
ccgtactgcg ccatgcattc atgtgggacc ggggaggatg cgggcaacag cagtttgcac   2400
gacccattgg ccggagcatg cgacgtatat ttgcgttgcg cctcgcttcc tacgcaaaat   2460
gtgtcgttgg tatgcctacc ctgttggagg gcgttttctt ctgctaaagt aacgtggagc   2520
acgcatttgc gtaggctgtt ggagatagtc tcaccacgcg gtgaccggac caggccaatt   2580
cccgagccca aaagaaaaa agcacacaca cagagacaca cgctctcgct ctcgcctccc    2640
tgacgctgga tttaagcaga gcagggagca gaggtgcaac cgcccaccac gatctcccct   2700
cccgcacgcc ccgcgggcag acccagccaa ggcaaggcag ccgcgaaccg gagcacgccg   2760
gccggtgtcg cctcccgcgc cggcggcctg ctgctcgctc gccctcgctt ccgcattgga   2820
tcacgcggcg gttggcgact tggtggtgtc tgctgctggt gattgcgcct agccggccga   2880
cgcggagacg tgaggcgct gctcttcgct tctctcccca ctgctcccct cagcggtttc    2940
tctctccctg ttatgcgtgg aggagccctg ccccgcgga acggaagcct ccgccggatc    3000
tctgttacgc cgcggttact gcctcgccct ggatttgaac ttgtttcgta attttcccttt  3060 gctgcgcttc tcgatttcgg ggaggggttc tgccggcagc tctgccgctc cacctgactt   3120
ggggaccttt ctatgttccg cgacagcagc attgatgatc tgcttgtctc ttgagttttt   3180
ttttcgtgcg atgcatcgag cgcgtgggga cacgatcacg cctgatgggc ggtagtccgc   3240
gatccgcatt tctgaatccc ggcgcctagc cgaggtgcct cggtgcttcc tggttgcctt   3300
gctgctattc ccttcttcgg atccgctctc gtacggctgg cacggtggtt gcggccttag   3360
```

```
aatttcgtgg cggcggtttg gttggattgg tgatgctgct ccgtccgcat ttatgaagga    3420
atgttctcca aacttttaag ctgctcgtgt actcggagta ttgaattgcc tgttccttgc    3480
cgctatagga ggccctgggc cagcctaccc cgctttgggt tgtgattggt gatttccggc    3540
agctgttatt gtttcatgat tcgtgtgggg aaaaaaagtt ttttggttc acgagtggtt     3600
tctggtgcat gttttgacaa gttttctatg atgctggtac tgtctttacc cctgctagag    3660
tagtttggtg gtgcgttttc ctattaggtg ggaatttaat cactttccca ctttatcgta    3720
tctctactat ggtaaccatc ttttggcaat tttgattggt atagtcatgt ttaagataag    3780
cttttgaatt caatgatctt gccgttcatt agctagcact taattttgta gagctgcttg    3840
gatcaccaaa gtgccgctca atcttgttca agtgcctatg atatatggga ttctgatgga    3900
actcttagca gtcgtgtcct taggcagtcg gcaccttgat aaggttccaa gagttcaatc    3960
ttacggaaga aatagtgagc ttgatctgag ttcagatcgg ttgtcttcac acttcacgat    4020
taattaccac gttttttaagg tgtgcattct cacttcttta cttccatcgt caatcttctt   4080
aactggttgg gttggaggtg tggtcatgca cccaaccaca taggttgagt cctcttcaac    4140
tcgaatttag gtgcctattt ttttcttaat aaaaaaggcc acctgattct ccttggttgg    4200
tcacattttt ttcttaataa aaaaaggcca cctcaatgtt tctccttta gcttgagcac     4260
tttttctgga tctcctcttt cttcttaatt ctgatccaag tgtcatcagc gttatattta    4320
tttgaacctg cttgcttttg taagcctgat cagtttgcaa agttactag aacaatttaa     4380
ccatctgtgc ttgttatttc tgcaggcatc aagtttctaa caatttgaag tacctaaa     4438
```

<210> SEQ ID NO 86
<211> LENGTH: 145
<212> TYPE: PRT
<213> ORGANISM: Sesamum indicum

<400> SEQUENCE: 86

```
Met Ala Glu His Tyr Gly Gln Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Gln Gln Pro Val Ala Gly Ser Gln Thr
    130                 135                 140

Ser
145
```

<210> SEQ ID NO 87
<211> LENGTH: 382
<212> TYPE: PRT

<213> ORGANISM: Cinnamomum camphora

<400> SEQUENCE: 87

```
Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Gln Thr Ser Leu Lys Met Ile Asn Gly
        35                  40                  45

Thr Lys Phe Ser Tyr Thr Glu Ser Leu Lys Lys Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Asn Pro Pro Gln Leu Leu
                85                  90                  95

Asp Asp His Phe Gly Pro His Gly Leu Val Phe Arg Arg Thr Phe Ala
            100                 105                 110

Ile Arg Ser Tyr Glu Val Gly Pro Asp Arg Ser Thr Ser Ile Val Ala
        115                 120                 125

Val Met Asn His Leu Gln Glu Ala Ala Leu Asn His Ala Lys Ser Val
130                 135                 140

Gly Ile Leu Gly Asp Gly Phe Gly Thr Thr Leu Glu Met Ser Lys Arg
145                 150                 155                 160

Asp Leu Ile Trp Val Val Lys Arg Thr His Val Ala Val Glu Arg Tyr
                165                 170                 175

Pro Ala Trp Gly Asp Thr Val Glu Val Glu Cys Trp Val Gly Ala Ser
            180                 185                 190

Gly Asn Asn Gly Arg Arg His Asp Phe Leu Val Arg Asp Cys Lys Thr
        195                 200                 205

Gly Glu Ile Leu Thr Arg Cys Thr Ser Leu Ser Val Met Met Asn Thr
    210                 215                 220

Arg Thr Arg Arg Leu Ser Lys Ile Pro Glu Glu Val Arg Gly Glu Ile
225                 230                 235                 240

Gly Pro Ala Phe Ile Asp Asn Val Ala Val Lys Asp Glu Glu Ile Lys
                245                 250                 255

Lys Pro Gln Lys Leu Asn Asp Ser Thr Ala Asp Tyr Ile Gln Gly Gly
            260                 265                 270

Leu Thr Pro Arg Trp Asn Asp Leu Asp Ile Asn Gln His Val Asn Asn
    275                 280                 285

Ile Lys Tyr Val Asp Trp Ile Leu Glu Thr Val Pro Asp Ser Ile Phe
290                 295                 300

Glu Ser His His Ile Ser Ser Phe Thr Ile Glu Tyr Arg Arg Glu Cys
305                 310                 315                 320

Thr Met Asp Ser Val Leu Gln Ser Leu Thr Thr Val Ser Gly Gly Ser
                325                 330                 335

Ser Glu Ala Gly Leu Val Cys Glu His Leu Leu Gln Leu Glu Gly Gly
            340                 345                 350

Ser Glu Val Leu Arg Ala Lys Thr Glu Trp Arg Pro Lys Leu Thr Asp
    355                 360                 365

Ser Phe Arg Gly Ile Ser Val Ile Pro Ala Glu Ser Ser Val
370                 375                 380
```

<210> SEQ ID NO 88
<211> LENGTH: 417

<212> TYPE: PRT
<213> ORGANISM: Cocos nucifera

<400> SEQUENCE: 88

```
Met Val Ala Ser Val Ala Ala Ser Ala Phe Phe Pro Thr Pro Ser Phe
1               5                   10                  15

Ser Ser Thr Ala Ser Ala Lys Ala Ser Lys Thr Ile Gly Glu Gly Ser
            20                  25                  30

Glu Ser Leu Asp Val Arg Gly Ile Val Ala Lys Pro Thr Ser Ser Ser
        35                  40                  45

Ala Ala Met Gln Gly Lys Val Lys Ala Gln Ala Val Pro Lys Ile Asn
    50                  55                  60

Gly Thr Lys Val Gly Leu Lys Thr Glu Ser Gln Lys Ala Glu Glu Asp
65                  70                  75                  80

Ala Ala Pro Ser Ser Ala Pro Arg Thr Phe Tyr Asn Gln Leu Pro Asp
                85                  90                  95

Trp Ser Val Leu Leu Ala Ala Val Thr Thr Ile Phe Leu Ala Ala Glu
            100                 105                 110

Lys Gln Trp Thr Leu Leu Asp Trp Lys Pro Arg Arg Pro Asp Met Leu
        115                 120                 125

Thr Asp Ala Phe Ser Leu Gly Lys Ile Val Gln Asp Gly Leu Ile Phe
    130                 135                 140

Arg Gln Asn Phe Ser Ile Arg Ser Tyr Glu Ile Gly Ala Asp Arg Thr
145                 150                 155                 160

Ala Ser Ile Glu Thr Leu Met Asn His Leu Gln Glu Thr Ala Leu Asn
                165                 170                 175

His Val Arg Asn Ala Gly Leu Leu Gly Asp Gly Phe Gly Ala Thr Pro
            180                 185                 190

Glu Met Ser Lys Arg Asn Leu Ile Trp Val Val Thr Lys Met Gln Val
        195                 200                 205

Leu Val Glu His Tyr Pro Ser Trp Gly Asp Val Val Glu Val Asp Thr
    210                 215                 220

Trp Val Gly Ala Ser Gly Lys Asn Gly Met Arg Arg Asp Trp His Val
225                 230                 235                 240

Arg Asp Tyr Arg Thr Gly Gln Thr Ile Leu Arg Ala Thr Ser Val Trp
                245                 250                 255

Val Met Met Asn Lys His Thr Arg Lys Leu Ser Lys Met Pro Glu Glu
            260                 265                 270

Val Arg Ala Glu Ile Gly Pro Tyr Phe Val Glu His Ala Ala Ile Val
        275                 280                 285

Asp Glu Asp Ser Arg Lys Leu Pro Lys Leu Asp Asp Thr Ala Asp
    290                 295                 300

Tyr Ile Lys Trp Gly Leu Thr Pro Arg Trp Ser Asp Leu Asp Val Asn
305                 310                 315                 320

Gln His Val Asn Asn Val Lys Tyr Ile Gly Trp Ile Leu Glu Ser Ala
                325                 330                 335

Pro Ile Ser Ile Leu Glu Asn His Glu Leu Ala Ser Met Thr Leu Glu
            340                 345                 350

Tyr Arg Arg Glu Cys Gly Arg Asp Ser Val Leu Gln Ser Leu Thr Ala
        355                 360                 365

Ile Ser Asn Asp Cys Thr Gly Gly Leu Pro Glu Ala Ser Ile Glu Cys
    370                 375                 380

Gln His Leu Leu Gln Leu Glu Cys Gly Ala Glu Ile Val Arg Gly Arg
385                 390                 395                 400
```

-continued

```
Thr Gln Trp Arg Pro Arg Arg Ala Ser Gly Pro Thr Ser Ala Gly Ser
            405                 410                 415
Ala

<210> SEQ ID NO 89
<211> LENGTH: 423
<212> TYPE: PRT
<213> ORGANISM: Cocos nucifera

<400> SEQUENCE: 89

Met Val Ala Ser Ile Ala Ala Ser Ala Phe Phe Pro Thr Pro Ser Ser
1               5                   10                  15

Ser Ser Ser Ala Ala Ser Ala Lys Ala Ser Lys Thr Ile Gly Glu Gly
            20                  25                  30

Pro Gly Ser Leu Asp Val Arg Gly Ile Val Ala Lys Pro Thr Ser Ser
            35                  40                  45

Ser Ala Ala Met Gln Glu Lys Val Lys Val Gln Pro Val Pro Lys Ile
        50                  55                  60

Asn Gly Ala Lys Val Gly Leu Lys Val Glu Thr Gln Lys Ala Asp Glu
65                  70                  75                  80

Glu Ser Ser Pro Ser Ser Ala Pro Arg Thr Phe Tyr Asn Gln Leu Pro
                85                  90                  95

Asp Trp Ser Val Leu Leu Ala Ala Val Thr Thr Ile Phe Leu Ala Ala
            100                 105                 110

Glu Lys Gln Trp Thr Leu Leu Asp Trp Lys Pro Arg Arg Pro Asp Met
            115                 120                 125

Leu Ala Asp Ala Phe Gly Leu Gly Lys Ile Val Gln Asp Gly Leu Val
        130                 135                 140

Phe Lys Gln Asn Phe Ser Ile Arg Ser Tyr Glu Ile Gly Ala Asp Arg
145                 150                 155                 160

Thr Ala Ser Ile Glu Thr Leu Met Asn His Leu Gln Glu Thr Ala Leu
                165                 170                 175

Asn His Val Lys Ser Ala Gly Leu Met Gly Asp Gly Phe Gly Ala Thr
            180                 185                 190

Pro Glu Met Ser Lys Arg Asn Leu Ile Trp Val Val Thr Lys Met Arg
            195                 200                 205

Val Leu Ile Glu Arg Tyr Pro Ser Trp Gly Asp Val Val Glu Val Asp
        210                 215                 220

Thr Trp Val Gly Pro Thr Gly Lys Asn Gly Met Arg Arg Asp Trp His
225                 230                 235                 240

Val Arg Asp His Arg Ser Gly Gln Thr Ile Leu Arg Ala Thr Ser Val
                245                 250                 255

Trp Val Met Met Asn Lys Asn Thr Arg Lys Leu Ser Lys Val Pro Glu
            260                 265                 270

Glu Val Arg Ala Glu Ile Gly Pro Tyr Phe Val Glu Arg Ala Ala Ile
            275                 280                 285

Val Asp Glu Asp Ser Arg Lys Leu Pro Lys Leu Asp Glu Asp Thr Thr
        290                 295                 300

Asp Tyr Ile Lys Lys Gly Leu Thr Pro Arg Trp Gly Asp Leu Asp Val
305                 310                 315                 320

Asn Gln His Val Asn Asn Val Lys Tyr Ile Gly Trp Ile Leu Glu Ser
                325                 330                 335

Ala Pro Ile Ser Ile Leu Glu Asn His Glu Leu Ala Ser Met Ser Leu
            340                 345                 350
```

-continued

```
Glu Tyr Arg Arg Glu Cys Gly Arg Asp Ser Val Leu Gln Ser Leu Thr
            355                 360                 365

Ala Val Ser Asn Asp Leu Thr Asp Gly Leu Val Glu Ser Gly Ile Glu
        370                 375                 380

Cys Gln His Leu Leu Gln Leu Glu Cys Gly Thr Glu Leu Val Lys Gly
385                 390                 395                 400

Arg Thr Glu Trp Arg Pro Lys His Ser Pro Ala Leu Gly Asn Met Gly
                405                 410                 415

Pro Thr Pro Gly Gly Ser Ala
            420

<210> SEQ ID NO 90
<211> LENGTH: 414
<212> TYPE: PRT
<213> ORGANISM: Cocos nucifera

<400> SEQUENCE: 90

Met Val Ala Ser Val Ala Ala Ser Ser Phe Phe Pro Val Pro Ser
1               5                   10                  15

Ser Ser Ser Ala Ser Ala Lys Ala Ser Arg Gly Ile Pro Asp Gly
                20                  25                  30

Leu Asp Val Arg Gly Ile Val Ala Lys Pro Ala Ser Ser Ser Gly Trp
        35                  40                  45

Met Gln Ala Lys Ala Ser Ala Arg Ala Ile Pro Lys Ile Asp Asp Thr
    50                  55                  60

Lys Val Gly Leu Arg Thr Asp Val Glu Glu Asp Ala Ala Ser Thr Ala
65                  70                  75                  80

Arg Arg Thr Ser Tyr Asn Gln Leu Pro Asp Trp Ser Met Leu Leu Ala
                85                  90                  95

Ala Ile Arg Thr Ile Phe Ser Ala Ala Glu Lys Gln Trp Thr Leu Leu
            100                 105                 110

Asp Ser Lys Lys Arg Gly Ala Asp Ala Val Ala Asp Ala Ser Gly Val
        115                 120                 125

Gly Lys Met Val Lys Asn Gly Leu Val Tyr Arg Gln Asn Phe Ser Ile
    130                 135                 140

Arg Ser Tyr Glu Ile Gly Val Asp Lys Arg Ala Ser Val Glu Ala Leu
145                 150                 155                 160

Met Asn His Phe Gln Glu Thr Ser Leu Asn His Cys Lys Cys Ile Gly
                165                 170                 175

Leu Met His Gly Gly Phe Gly Cys Thr Pro Glu Met Thr Arg Arg Asn
            180                 185                 190

Leu Ile Trp Val Val Ala Lys Met Leu Val His Val Glu Arg Tyr Pro
        195                 200                 205

Trp Trp Gly Asp Val Val Gln Ile Asn Thr Trp Ile Ser Ser Ser Gly
    210                 215                 220

Lys Asn Gly Met Gly Arg Asp Trp His Val His Asp Cys Gln Thr Gly
225                 230                 235                 240

Leu Pro Ile Met Arg Gly Thr Ser Val Trp Val Met Met Asp Lys His
                245                 250                 255

Thr Arg Arg Leu Ser Lys Leu Pro Glu Glu Val Arg Ala Glu Ile Thr
            260                 265                 270

Pro Phe Phe Ser Glu Arg Asp Ala Val Leu Asp Asp Asn Gly Arg Lys
        275                 280                 285

Leu Pro Lys Phe Asp Asp Asp Ser Ala Ala His Val Arg Arg Gly Leu
```

```
                    290                 295                 300

Thr Pro Arg Trp His Asp Phe Asp Val Asn Gln His Val Asn Asn Val
305                 310                 315                 320

Lys Tyr Val Gly Trp Ile Leu Glu Ser Val Pro Val Trp Met Leu Asp
                    325                 330                 335

Gly Tyr Glu Val Ala Thr Met Ser Leu Glu Tyr Arg Arg Glu Cys Arg
                340                 345                 350

Met Asp Ser Val Gln Ser Leu Thr Ala Val Ser Ser Asp His Ala
            355                 360                 365

Asp Gly Ser Pro Ile Val Cys Gln His Leu Leu Arg Leu Glu Asp Gly
            370                 375                 380

Thr Glu Ile Val Arg Gly Gln Thr Glu Trp Arg Pro Lys Gln Gln Ala
385                 390                 395                 400

Arg Asp Leu Gly Asn Met Gly Leu His Pro Thr Glu Ser Lys
                405                 410

<210> SEQ ID NO 91
<211> LENGTH: 419
<212> TYPE: PRT
<213> ORGANISM: Cuphea lanceolata

<400> SEQUENCE: 91

Met Val Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
                20                  25                  30

Ser Pro Thr Phe Lys Pro Lys Ser Ile Pro Asn Ala Gly Phe Gln Val
            35                  40                  45

Lys Ala Asn Ala Ser Ala His Pro Lys Ala Asn Gly Ser Ala Val Asn
50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
                100                 105                 110

Leu Asp Arg Lys Ser Lys Arg Pro Asp Met Leu Val Asp Ser Val Gly
                115                 120                 125

Leu Lys Ser Ile Val Arg Asp Gly Leu Val Ser Arg Gln Ser Phe Leu
            130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
                180                 185                 190

Asp Leu Ile Trp Val Leu Thr Lys Met Gln Ile Met Val Asn Arg Tyr
            195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255
```

-continued

```
Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
        275                 280                 285

Lys Leu His Lys Phe Asp Val Lys Thr Gly Asp Ser Ile Arg Lys Gly
        290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asn Gly Gly Arg Ser Gln Tyr Lys His Leu Leu Arg Leu Glu Asp Gly
        370                 375                 380

Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Ala Ser

<210> SEQ ID NO 92
<211> LENGTH: 419
<212> TYPE: PRT
<213> ORGANISM: Cuphea viscosissima

<400> SEQUENCE: 92

Met Val Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Ser Ile Val Arg Asp Gly Leu Val Ser Arg His Ser Phe Ser
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Thr Ile Asn His Cys Lys Ser Leu
                165                 170                 175

Gly Leu His Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205
```

```
Pro Thr Trp Gly Asp Thr Val Glu Ile Asn Thr Trp Phe Ser Gln Ser
210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
            245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
            275                 280                 285

Lys Leu Arg Lys Phe Asp Val Lys Thr Gly Asp Ser Ile Arg Lys Gly
290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
            355                 360                 365

Asn Gly Gly Arg Ser Gln Tyr Lys His Leu Leu Arg Leu Glu Asp Gly
            370                 375                 380

Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Val Ser

<210> SEQ ID NO 93
<211> LENGTH: 382
<212> TYPE: PRT
<213> ORGANISM: Umbellularia californica

<400> SEQUENCE: 93

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
130                 135                 140

Gly Ile Leu Gly Asp Gly Phe Gly Thr Thr Leu Glu Met Ser Lys Arg
145                 150                 155                 160
```

Asp Leu Met Trp Val Val Arg Arg Thr His Val Ala Val Glu Arg Tyr
            165                 170                 175

Pro Thr Trp Gly Asp Thr Val Glu Val Glu Cys Trp Ile Gly Ala Ser
        180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
        210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
        290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
        355                 360                 365

Ser Phe Arg Gly Ile Ser Val Ile Pro Ala Glu Pro Arg Val
        370                 375                 380

<210> SEQ ID NO 94
<211> LENGTH: 308
<212> TYPE: PRT
<213> ORGANISM: Cocos nucifera

<400> SEQUENCE: 94

Met Asp Ala Ser Gly Ala Ser Ser Phe Leu Arg Gly Arg Cys Leu Glu
1               5                   10                  15

Ser Cys Phe Lys Ala Ser Phe Gly Met Ser Gln Pro Lys Asp Ala Ala
            20                  25                  30

Gly Gln Pro Ser Arg Arg Pro Ala Asp Ala Asp Asp Phe Val Asp Asp
        35                  40                  45

Asp Arg Trp Ile Thr Val Ile Leu Ser Val Val Arg Ile Ala Ala Cys
50                  55                  60

Phe Leu Ser Met Met Val Thr Thr Ile Val Trp Asn Met Ile Met Leu
65                  70                  75                  80

Ile Leu Leu Pro Trp Pro Tyr Ala Arg Ile Arg Gln Gly Asn Leu Tyr
                85                  90                  95

Gly His Val Thr Gly Arg Met Leu Met Trp Ile Leu Gly Asn Pro Ile
            100                 105                 110

Thr Ile Glu Gly Ser Glu Phe Ser Asn Thr Arg Ala Ile Tyr Ile Cys
        115                 120                 125

Asn His Ala Ser Leu Val Asp Ile Phe Leu Ile Met Trp Leu Ile Pro
    130                 135                 140

Lys Gly Thr Val Thr Ile Ala Lys Lys Glu Ile Ile Trp Tyr Pro Leu
145                 150                 155                 160

```
Phe Gly Gln Leu Tyr Val Leu Ala Asn His Gln Arg Ile Asp Arg Ser
                165                 170                 175

Asn Pro Ser Ala Ala Ile Glu Ser Ile Lys Glu Val Ala Arg Ala Val
            180                 185                 190

Val Lys Lys Asn Leu Ser Leu Ile Ile Phe Pro Glu Gly Thr Arg Ser
        195                 200                 205

Lys Thr Gly Arg Leu Leu Pro Phe Lys Lys Gly Phe Ile His Ile Ala
    210                 215                 220

Leu Gln Thr Arg Leu Pro Ile Val Pro Met Val Leu Thr Gly Thr His
225                 230                 235                 240

Leu Ala Trp Arg Lys Asn Ser Leu Arg Val Arg Pro Ala Pro Ile Thr
                245                 250                 255

Val Lys Tyr Phe Ser Pro Ile Lys Thr Asp Asp Trp Glu Glu Glu Lys
            260                 265                 270

Ile Asn His Tyr Val Glu Met Ile His Ala Leu Tyr Val Asp His Leu
        275                 280                 285

Pro Glu Ser Gln Lys Pro Leu Val Ser Lys Gly Arg Asp Ala Ser Gly
    290                 295                 300

Arg Ser Asn Ser
305

<210> SEQ ID NO 95
<211> LENGTH: 356
<212> TYPE: PRT
<213> ORGANISM: Arabidopsis thaliana

<400> SEQUENCE: 95

Met Asp Val Ala Ser Ala Arg Ser Ile Ser Ser His Pro Ser Tyr Tyr
1               5                   10                  15

Gly Lys Pro Ile Cys Ser Ser Gln Ser Ser Leu Ile Arg Ile Ser Arg
            20                  25                  30

Asp Lys Val Cys Cys Phe Gly Arg Ile Ser Asn Gly Met Thr Ser Phe
        35                  40                  45

Thr Thr Ser Leu His Ala Val Pro Ser Glu Lys Phe Met Gly Glu Thr
    50                  55                  60

Arg Arg Thr Gly Ile Gln Trp Ser Asn Arg Ser Leu Arg His Asp Pro
65                  70                  75                  80

Tyr Arg Phe Leu Asp Lys Lys Ser Pro Arg Ser Gln Leu Ala Arg
                85                  90                  95

Asp Ile Thr Val Arg Ala Asp Leu Ser Gly Ala Ala Thr Pro Asp Ser
            100                 105                 110

Ser Phe Pro Glu Pro Glu Ile Lys Leu Ser Ser Arg Leu Arg Gly Ile
        115                 120                 125

Phe Phe Cys Val Val Ala Gly Ile Ser Ala Thr Phe Leu Ile Val Leu
    130                 135                 140

Met Ile Ile Gly His Pro Phe Val Leu Leu Phe Asp Pro Tyr Arg Arg
145                 150                 155                 160

Lys Phe His His Phe Ile Ala Lys Leu Trp Ala Ser Ile Ser Ile Tyr
                165                 170                 175

Pro Phe Tyr Lys Ile Asn Ile Glu Gly Leu Glu Asn Leu Pro Ser Ser
            180                 185                 190

Asp Thr Pro Ala Val Tyr Val Ser Asn His Gln Ser Phe Leu Asp Ile
        195                 200                 205

Tyr Thr Leu Leu Ser Leu Gly Lys Ser Phe Lys Phe Ile Ser Lys Thr
```

```
Gly Ile Phe Val Ile Pro Ile Ile Gly Trp Ala Met Ser Met Met Gly
225                 230                 235                 240

Val Val Pro Leu Lys Arg Met Asp Pro Arg Ser Gln Val Asp Cys Leu
                245                 250                 255

Lys Arg Cys Met Glu Leu Leu Lys Lys Gly Ala Ser Val Phe Phe Phe
            260                 265                 270

Pro Glu Gly Thr Arg Ser Lys Asp Gly Arg Leu Gly Ser Phe Lys Lys
        275                 280                 285

Gly Ala Phe Thr Val Ala Ala Lys Thr Gly Val Ala Val Val Pro Ile
    290                 295                 300

Thr Leu Met Gly Thr Gly Lys Ile Met Pro Thr Gly Ser Glu Gly Ile
305                 310                 315                 320

Leu Asn His Gly Asn Val Arg Val Ile Ile His Lys Pro Ile His Gly
                325                 330                 335

Ser Lys Ala Asp Val Leu Cys Asn Glu Ala Arg Ser Lys Ile Ala Glu
            340                 345                 350

Ser Met Asp Leu
        355

<210> SEQ ID NO 96
<211> LENGTH: 1539
<212> TYPE: DNA
<213> ORGANISM: Artificial Sequence
<220> FEATURE:
<223> OTHER INFORMATION: Codon optimised sequence

<400> SEQUENCE: 96
atggctgtgt ccaagaaccc agagactctc gctccagatc aagagccatc caaagagtct      60
gatcttaggc gtaggccagc ttcctctcca tcttctactg ctgcttctcc agctgtgcca     120
gattcctcat ctaggacttc cagttccatc actggctctt ggactactgc tctcgatggt     180
gattctggtg ctggtgctgt taggatcgga gatccaaagg ataggatcgg cgaggctaac     240
gatatcggcg aaaagaaaaa ggcttgctcc ggtgaggttc cagtgggatt tgttgataga     300
ccatctgctc cagtgcacgt gagagttgtt gagtctcctc tctcctccga tacaatcttc     360
cagcagtctc acgctggact cctcaatctt tgcgtggtgg tgcttatcgc tgtgaactcc     420
aggctcatta tcgagaacct tatgaagtac ggcctcctca tcggctccgg atttttcttc     480
tcatctcgtt tgctcaggga ttggcctctc cttatctgct ctcttactct cccagtgttc     540
ccactcggat cctacatggt tgagaagctc gcttacaaga agttcatctc cgagccagtg     600
gtggtgtctc ttcacgtgat cctcatcatt gctactatca tgtaccctgt gttcgtgatt     660
ctcaggtgcg attccccaat cctctccgga atcaacctca tgcttttcgt gtcctccatc     720
tgcctcaagc tcgtttctta cgctcacgct aactacgatc tcaggtcctc ctccaactcc     780
atcgataagg gaatccacaa gtcccagggc gtgtccttca gtctctcgt gtactttatc     840 atggctccaa cactctgcta ccagccatct tacccaagga ctacttgcat taggaagggc     900
tgggttatct gccagcttgt gaagctcgtg atcttcactg gtgtgatggg cttcatcatc     960
gagcagtaca tcgatccaat catcaagaac tcccagcacc cactcaaggg aaacgtgttg    1020
aacgctatgg aaagggtgct caagctctcc atcccaacac tttacgtgtg gctctgcgtg    1080
ttctactgca ctttccacct ctggctcaat atcctgctg agcttctttg cttcggcgat    1140
cgtgagttct acaaggattg gtggaacgct aagactatcg aagagtactg gcgtatgtgg    1200
```

```
aacatgccag tgcacaagtg gatgcttagg cacgtttacc tcccatgcat ccgtaacggt    1260
attccaaagg gtgtggctat ggtgatctcc ttcttcatct ctgctatctt ccacgagttg    1320
tgcatcggaa tcccatgcca catcttcaag ttctgggctt tcatcggcat catgttccag    1380
gtgccactcg ttatcctcac taagtacctc cagaacaagt tcaagtccgc tatggtgggc    1440
aacatgattt tctggttctt tttctcaatc tacggccagc caatgtgcgt gctcctttac    1500
taccacgatg tgatgaatag gaaggtgggc actgagtaa                           1539
```

<210> SEQ ID NO 97
<211> LENGTH: 371
<212> TYPE: PRT
<213> ORGANISM: Cocos nucifera

<400> SEQUENCE: 97

```
Met Val Glu Leu Arg Ser Ser Ser Glu Met Asp Leu Asp Arg Pro
1               5                  10                  15

Asn Ile Glu Glu Tyr Leu Thr Thr Asp Ser Ile Gln Glu Ser Pro Lys
            20                  25                  30

Lys Leu His Leu Arg Asp Leu Leu Asp Ile Ser Pro Thr Leu Thr Glu
        35                  40                  45

Ala Thr Gly Ala Ile Val Asp Asp Ser Phe Thr Arg Cys Phe Lys Ser
    50                  55                  60

Asn Pro Pro Glu Pro Trp Asn Trp Asn Val Tyr Leu Phe Pro Leu Trp
65                  70                  75                  80

Cys Leu Gly Val Ile Ile Arg Tyr Gly Ile Leu Phe Pro Leu Arg Val
                85                  90                  95

Ala Ile Leu Thr Ala Gly Trp Leu Val Phe Ala Ala Phe Ile Pro
            100                 105                 110

Val His Phe Leu Leu Thr Ala His Asn Lys Trp Arg Arg Lys Ile Glu
        115                 120                 125

Arg Lys Leu Val Glu Met Ile Cys Ser Val Phe Val Ala Ser Trp Thr
    130                 135                 140

Gly Val Val Lys Tyr His Gly Pro Arg Pro Ser Met Arg Pro Gln Gln
145                 150                 155                 160

Val Phe Val Ala Asn His Thr Ser Met Ile Asp Phe Ile Ile Leu Glu
                165                 170                 175

Gln Met Thr Ala Phe Ala Val Ile Met Gln Lys His Pro Gly Trp Val
            180                 185                 190

Gly Phe Ile Gln Lys Thr Ile Leu Glu Gly Val Gly Cys Ile Trp Phe
        195                 200                 205

Asn Arg Thr Glu Ser Lys Asp Arg Glu Val Val Ala Arg Lys Leu Arg
    210                 215                 220

Glu His Ile His Gly Ala Asp Asn Asn Pro Leu Leu Ile Phe Pro Glu
225                 230                 235                 240

Gly Thr Cys Val Asn Asn His Tyr Thr Val Met Phe Lys Lys Gly Ala
                245                 250                 255

Phe Glu Leu Gly Cys Ala Val Cys Pro Val Ala Ile Lys Tyr Asn Lys
            260                 265                 270

Ile Phe Val Asp Ala Phe Trp Asn Ser Lys Lys Gln Ser Phe Thr Met
        275                 280                 285

His Leu Phe His Leu Met Thr Ser Trp Ala Val Val Cys Asp Val Trp
    290                 295                 300

Tyr Leu Glu Pro Gln Tyr Ile Arg Pro Gly Glu Thr Pro Ile Glu Phe
305                 310                 315                 320
```

```
Ala Glu Arg Val Arg Asp Met Ile Ser Val Arg Ala Gly Leu Lys Lys
            325                 330                 335

Val Pro Trp Asp Gly Tyr Leu Lys Tyr Phe Arg Pro Ser Pro Lys Leu
            340                 345                 350

Thr Glu Arg Lys Gln Gln Ile Phe Ala Glu Ser Val Leu Gln Arg Leu
            355                 360                 365

Glu Glu Lys
    370

<210> SEQ ID NO 98
<211> LENGTH: 376
<212> TYPE: PRT
<213> ORGANISM: Arabidopsis thaliana

<400> SEQUENCE: 98

Met Ser Ser Thr Ala Gly Arg Leu Val Thr Ser Lys Ser Glu Leu Asp
1               5                   10                  15

Leu Asp His Pro Asn Ile Glu Asp Tyr Leu Pro Ser Gly Ser Ser Ile
            20                  25                  30

Asn Glu Pro Arg Gly Lys Leu Ser Leu Arg Asp Leu Leu Asp Ile Ser
            35                  40                  45

Pro Thr Leu Thr Glu Ala Ala Gly Ala Ile Val Asp Asp Ser Phe Thr
    50                  55                  60

Arg Cys Phe Lys Ser Asn Pro Pro Glu Pro Trp Asn Trp Asn Ile Tyr
65                  70                  75                  80

Leu Phe Pro Leu Tyr Cys Phe Gly Val Val Arg Tyr Cys Ile Leu
                85                  90                  95

Phe Pro Leu Arg Cys Phe Thr Leu Ala Phe Gly Trp Ile Ile Phe Leu
                100                 105                 110

Ser Leu Phe Ile Pro Val Asn Ala Leu Leu Lys Gly Gln Asp Arg Leu
            115                 120                 125

Arg Lys Lys Ile Glu Arg Val Leu Val Glu Met Ile Cys Ser Phe Phe
            130                 135                 140

Val Ala Ser Trp Thr Gly Val Val Lys Tyr His Gly Pro Arg Pro Ser
145                 150                 155                 160

Ile Arg Pro Lys Gln Val Tyr Val Ala Asn His Thr Ser Met Ile Asp
                165                 170                 175

Phe Ile Val Leu Glu Gln Met Thr Ala Phe Ala Val Ile Met Gln Lys
            180                 185                 190

His Pro Gly Trp Val Gly Leu Leu Gln Ser Thr Ile Leu Glu Ser Val
            195                 200                 205

Gly Cys Ile Trp Phe Asn Arg Ser Glu Ala Lys Asp Arg Glu Ile Val
        210                 215                 220

Ala Lys Lys Leu Arg Asp His Val Gln Gly Ala Asp Ser Asn Pro Leu
225                 230                 235                 240

Leu Ile Phe Pro Glu Gly Thr Cys Val Asn Asn Tyr Thr Val Met
                245                 250                 255

Phe Lys Lys Gly Ala Phe Glu Leu Asp Cys Thr Val Cys Pro Ile Ala
            260                 265                 270

Ile Lys Tyr Asn Lys Ile Phe Val Asp Ala Phe Trp Asn Ser Arg Lys
            275                 280                 285

Gln Ser Phe Thr Met His Leu Leu Gln Leu Met Thr Ser Trp Ala Val
            290                 295                 300

Val Cys Glu Val Trp Tyr Leu Glu Pro Gln Thr Ile Arg Pro Gly Glu
```

```
                305                 310                 315                 320
Thr Gly Ile Glu Phe Ala Glu Arg Val Arg Asp Met Ile Ser Leu Arg
                    325                 330                 335

Ala Gly Leu Lys Lys Val Pro Trp Asp Gly Tyr Leu Lys Tyr Ser Arg
                340                 345                 350

Pro Ser Pro Lys His Ser Glu Arg Lys Gln Gln Ser Phe Ala Glu Ser
                355                 360                 365

Ile Leu Ala Arg Leu Glu Glu Lys
                370                 375

<210> SEQ ID NO 99
<211> LENGTH: 371
<212> TYPE: PRT
<213> ORGANISM: Elaeis guineensis

<400> SEQUENCE: 99

Met Val Glu Leu Arg Ser Ser Ser Glu Met Asp Leu Asp Arg Pro
1               5                   10                  15

Asn Ile Glu Glu Tyr Leu Pro Pro Thr Pro Ser Lys Asn Pro Pro Lys
                20                  25                  30

Lys Leu His Leu Arg Asp Leu Leu Asp Ile Ser Pro Thr Leu Thr Glu
            35                  40                  45

Ala Ala Gly Ala Ile Val Asp Asp Ser Phe Thr Arg Cys Phe Lys Ser
        50                  55                  60

Asn Pro Pro Glu Pro Trp Asn Trp Asn Val Tyr Leu Phe Pro Leu Trp
65                  70                  75                  80

Cys Leu Gly Val Ile Ile Arg Tyr Gly Ile Leu Phe Pro Leu Arg Val
                85                  90                  95

Ala Ile Leu Thr Ala Gly Trp Leu Val Phe Ala Ala Phe Ile Pro
            100                 105                 110

Val His Phe Leu Leu Thr Ala His Asn Lys Trp Arg Arg Lys Ile Glu
        115                 120                 125

Arg Lys Leu Val Glu Met Ile Cys Ser Val Phe Val Ala Ser Trp Thr
130                 135                 140

Gly Val Val Lys Tyr His Gly Pro Arg Pro Ser Met Arg Pro Gln Gln
145                 150                 155                 160

Val Phe Val Ala Asn His Thr Ser Met Ile Asp Phe Ile Ile Leu Glu
                165                 170                 175

Gln Met Thr Ala Phe Ala Val Ile Met Gln Lys His Pro Gly Trp Val
            180                 185                 190

Gly Phe Ile Gln Lys Thr Ile Leu Glu Gly Val Gly Cys Ile Trp Phe
        195                 200                 205

Asn Arg Thr Glu Ser Lys Asp Arg Glu Val Val Ala Arg Lys Leu Arg
210                 215                 220

Glu His Ile His Gly Ala Asp Asn Asn Pro Leu Leu Ile Phe Pro Glu
225                 230                 235                 240

Gly Thr Cys Val Asn Asn His Tyr Thr Val Met Phe Lys Lys Gly Ala
                245                 250                 255

Phe Glu Leu Gly Cys Ala Val Cys Pro Val Ala Ile Lys Tyr Asn Lys
            260                 265                 270

Ile Phe Val Asp Ala Phe Trp Asn Ser Lys Lys Gln Ser Phe Thr Met
        275                 280                 285

His Leu Phe His Leu Met Thr Ser Trp Ala Val Val Cys Asp Val Trp
        290                 295                 300
```

Tyr Leu Glu Pro Gln Tyr Ile Arg Pro Gly Glu Thr Pro Ile Glu Phe
305                 310                 315                 320

Ala Glu Arg Val Arg Asp Met Ile Ser Ile Arg Ala Gly Leu Lys Lys
            325                 330                 335

Val Pro Trp Asp Gly Tyr Leu Lys Tyr Phe Arg Pro Ser Pro Lys Leu
            340                 345                 350

Thr Glu Arg Lys Gln Gln Ile Phe Ala Glu Ser Val Leu Gln Arg Leu
            355                 360                 365

Glu Glu Lys
    370

<210> SEQ ID NO 100
<211> LENGTH: 371
<212> TYPE: PRT
<213> ORGANISM: Phoenix dactylifera

<400> SEQUENCE: 100

Met Val Gly Leu Arg Ser Ser Ser Glu Met Asp Leu Asp Arg Pro
1               5                   10                  15

Asn Ile Glu Glu Tyr Leu Thr Thr Asp Ser Ile Glu Glu Ser Pro Lys
            20                  25                  30

Lys Leu His Leu Arg Asp Leu Leu Asp Ile Ser Pro Thr Leu Thr Glu
            35                  40                  45

Ala Ala Gly Ala Ile Val Asp Asp Ser Phe Thr Arg Cys Phe Lys Ser
        50                  55                  60

Asn Pro Pro Glu Pro Trp Asn Trp Asn Val Tyr Leu Phe Pro Leu Trp
65                  70                  75                  80

Cys Leu Gly Val Ile Ile Arg Tyr Gly Ile Leu Phe Pro Leu Arg Val
                85                  90                  95

Ala Val Leu Thr Ala Gly Trp Leu Val Phe Phe Ala Ala Phe Ile Pro
            100                 105                 110

Ala His Phe Leu Leu Thr Ala His Asn Lys Trp Arg Arg Lys Ile Glu
        115                 120                 125

Arg Lys Leu Val Glu Met Ile Cys Ser Val Phe Val Ala Ser Trp Thr
130                 135                 140

Gly Val Val Lys Tyr His Gly Pro Arg Pro Ser Met Arg Pro Gln Gln
145                 150                 155                 160

Val Phe Val Ala Asn His Thr Ser Met Ile Asp Phe Ile Ile Leu Glu
                165                 170                 175

Gln Met Thr Ala Phe Ala Val Ile Met Gln Lys His Pro Gly Trp Val
            180                 185                 190

Gly Phe Ile Gln Lys Thr Ile Leu Glu Gly Val Gly Cys Ile Trp Phe
        195                 200                 205

Asn Arg Thr Glu Ser Lys Asp Arg Glu Val Val Ala Arg Lys Leu Arg
210                 215                 220

Glu His Ile Gln Gly Ala Asp Asn Asn Pro Leu Leu Ile Phe Pro Glu
225                 230                 235                 240

Gly Thr Cys Val Asn Asn His Tyr Thr Val Met Phe Lys Lys Gly Ala
                245                 250                 255

Phe Glu Leu Gly Cys Ala Val Cys Pro Val Ala Ile Lys Tyr Asn Lys
            260                 265                 270

Ile Phe Val Asp Ala Phe Trp Asn Ser Lys Lys Gln Ser Phe Thr Met
        275                 280                 285

His Leu Phe His Leu Met Thr Ser Trp Ala Val Val Cys Asp Val Trp
290                 295                 300

```
Tyr Leu Glu Pro Gln Tyr Ile Arg Pro Gly Glu Thr Pro Ile Glu Phe
305                 310                 315                 320

Ala Glu Arg Val Arg Asp Met Ile Ser Val Arg Ala Gly Leu Arg Lys
            325                 330                 335

Val Pro Trp Asp Gly Tyr Leu Lys Tyr Phe Arg Pro Ser Pro Lys Leu
            340                 345                 350

Thr Glu Arg Lys Gln Gln Ile Phe Ala Glu Ser Val Leu Gln Arg Leu
            355                 360                 365

Glu Glu Lys
    370

<210> SEQ ID NO 101
<211> LENGTH: 371
<212> TYPE: PRT
<213> ORGANISM: Musa acuminata

<400> SEQUENCE: 101

Met Ala Gly Leu Ala Thr Ser Ser Thr Glu Met Asp Leu Asp Arg Pro
1               5                   10                  15

Asn Ile Asp Glu Tyr Leu Thr Val Glu Ser Ile Arg Glu Ala Pro Lys
            20                  25                  30

Lys Leu His Leu Arg Asp Leu Leu Asp Ile Ser Pro Thr Leu Lys Glu
        35                  40                  45

Ala Ala Gly Ala Ile Val Asp Asp Ser Phe Thr Arg Cys Phe Lys Ser
    50                  55                  60

Asn Pro Ser Glu Pro Trp Asn Trp Asn Ile Tyr Leu Phe Pro Leu Trp
65                  70                  75                  80

Cys Leu Gly Val Val Ile Arg Tyr Gly Ile Leu Phe Pro Phe Arg Val
                85                  90                  95

Ile Ile Leu Val Ala Gly Trp Ile Val Phe Phe Ala Ala Phe Ser Leu
            100                 105                 110

Val His Phe Leu Leu Gly Glu His Asn Lys Trp Lys Arg Glu Ile Glu
        115                 120                 125

Arg Lys Leu Val Glu Met Ile Cys Ser Val Phe Val Ala Ser Trp Thr
130                 135                 140

Ala Val Ile Lys Tyr His Gly Pro Arg Pro Ser Met Arg Pro Gln Gln
145                 150                 155                 160

Val Phe Val Ala Asn His Thr Ser Met Ile Asp Phe Ile Ile Leu Glu
                165                 170                 175

Gln Met Thr Ala Phe Ala Val Ile Met Gln Lys His Pro Gly Trp Val
            180                 185                 190

Gly Phe Ile Gln Lys Ile Ile Val Glu Ser Leu Gly Cys Ile Trp Phe
        195                 200                 205

Asn Arg Thr Glu Ala Lys Asp Arg Glu Ile Val Ala Arg Lys Leu Arg
210                 215                 220

Glu His Ile Gln Gly Val Asp Asn Asn Pro Leu Leu Ile Phe Pro Glu
225                 230                 235                 240

Gly Thr Cys Val Asn Asn His Tyr Thr Val Met Phe Lys Lys Gly Ala
                245                 250                 255

Phe Glu Leu Gly Cys Ala Val Cys Pro Val Ala Ile Lys Tyr Asn Lys
            260                 265                 270

Ile Phe Val Asp Ala Phe Trp Asn Ser Lys Lys Gln Ser Phe Thr Met
        275                 280                 285

His Leu Val Gln Leu Met Thr Ser Trp Ala Val Val Cys Asp Val Trp
```

```
                290                 295                 300
Tyr Leu Glu Pro Gln Tyr Ile Arg Pro Gly Glu Thr Pro Ile Glu Phe
305                 310                 315                 320

Ala Glu Arg Val Gln Asp Met Ile Ser Val Arg Ala Gly Leu Lys Lys
                325                 330                 335

Val Pro Trp Asp Gly Tyr Leu Lys Tyr Phe Arg Pro Ser Pro Lys Leu
                340                 345                 350

Ile Glu Arg Lys Gln Gln Ile Phe Ala Glu Ser Val Leu Gln Arg Leu
                355                 360                 365

Glu Glu Lys
        370

<210> SEQ ID NO 102
<211> LENGTH: 372
<212> TYPE: PRT
<213> ORGANISM: Ananas comosus

<400> SEQUENCE: 102

Met Ala Glu Ala Leu Gly Ser Ser Ser Ala Glu Met Asp Leu Asp Arg
1               5                   10                  15

Pro Asn Leu Glu Glu Tyr Leu Pro Thr Asp Ser Ile Gln Asp Ser Pro
                20                  25                  30

Lys Asn Leu His Leu Arg Asp Leu Leu Asp Ile Ser Pro Thr Leu Thr
            35                  40                  45

Glu Ala Ala Gly Ala Ile Val Asp Asp Ser Phe Thr Arg Cys Phe Lys
    50                  55                  60

Ser Asn Pro Pro Glu Pro Trp Asn Trp Asn Ile Tyr Leu Phe Pro Leu
65                  70                  75                  80

Trp Cys Leu Gly Val Val Arg Tyr Gly Ile Leu Phe Pro Leu Arg
                85                  90                  95

Val Ala Val Leu Ala Ile Gly Trp Ile Val Phe Phe Ser Ala Phe Phe
                100                 105                 110

Pro Val His Phe Leu Leu Lys Gly Tyr Pro Lys Trp Arg Arg Lys Leu
            115                 120                 125

Glu Arg Lys Leu Val Glu Met Met Cys Ser Val Phe Val Ala Ser Trp
    130                 135                 140

Thr Gly Val Val Lys Tyr His Gly Pro Arg Pro Ser Thr Arg Pro His
145                 150                 155                 160

Gln Val Phe Val Ala Asn His Thr Ser Met Ile Asp Phe Ile Ile Leu
                165                 170                 175

Glu Gln Met Thr Ala Phe Ala Val Ile Met Gln Lys His Pro Gly Trp
                180                 185                 190

Val Gly Phe Ile Gln Lys Thr Ile Leu Glu Ser Val Gly Cys Ile Trp
            195                 200                 205

Phe Asn Arg Thr Glu Ser Lys Asp Arg Gly Val Val Gly Arg Lys Leu
    210                 215                 220

Arg Glu His Val Gln Gly Val Asp Asn Asn Pro Leu Leu Ile Phe Pro
225                 230                 235                 240

Glu Gly Thr Cys Val Asn Asn His Tyr Thr Val Met Phe Lys Lys Gly
                245                 250                 255

Ala Phe Glu Leu Gly Cys Ala Val Cys Pro Ile Ala Ile Lys Tyr Asn
                260                 265                 270

Lys Ile Phe Val Asp Ala Phe Trp Asn Ser Lys Lys Gln Ser Phe Thr
            275                 280                 285
```

```
Met His Leu Val Arg Leu Met Thr Ser Trp Ala Val Val Cys Asp Val
    290                 295                 300

Trp Tyr Leu Glu Pro Gln Tyr Leu Arg Pro Gly Glu Thr Pro Ile Glu
305                 310                 315                 320

Phe Ala Glu Arg Val Arg Asp Met Ile Ser Ala Arg Ala Gly Leu Lys
                325                 330                 335

Lys Val Pro Trp Asp Gly Tyr Leu Lys Tyr Phe Arg Pro Ser Pro Lys
            340                 345                 350

His Thr Glu Arg Lys Gln Gln Ile Phe Ala Glu Ser Ile Leu Arg Arg
        355                 360                 365

Leu Glu Arg Lys
    370

<210> SEQ ID NO 103
<211> LENGTH: 370
<212> TYPE: PRT
<213> ORGANISM: Asparagus officinalis

<400> SEQUENCE: 103

Met Ala Gly Leu Glu Ser Ser Ala Gly Ile Asp Val Asp Pro Pro
1               5                   10                  15

Asn Ile Glu Asp Tyr Leu Thr Ser Asp Ala Leu His Gln Pro His Lys
                20                  25                  30

Lys Leu Gln Leu Lys Asp Leu Leu Asp Ile Ser Pro Thr Leu Thr Glu
            35                  40                  45

Ala Ala Gly Ala Ile Val Asp Asp Ser Phe Thr Arg Cys Phe Lys Ser
        50                  55                  60

Asn Pro Pro Glu Pro Trp Asn Trp Asn Val Tyr Leu Phe Pro Leu Trp
65                  70                  75                  80

Cys Leu Gly Val Val Arg Tyr Gly Ile Leu Phe Pro Leu Arg Val
                85                  90                  95

Met Thr Leu Ala Ala Gly Trp Ile Val Phe Phe Ser Ala Phe Leu Pro
            100                 105                 110

Val His Tyr Leu Met Lys Gly Gln Asn Lys Trp Lys Asn Asn Ile Glu
        115                 120                 125

Arg Lys Leu Val Glu Met Ile Cys Ser Val Phe Val Ala Ser Trp Thr
130                 135                 140

Gly Val Val Arg Tyr His Gly Pro Arg Pro Ser Met Arg Pro Gln Gln
145                 150                 155                 160

Val Phe Val Ala Asn His Thr Ser Met Ile Asp Phe Ile Ile Leu Glu
                165                 170                 175

Gln Met Ala Ala Phe Ala Val Ile Met Gln Lys His Pro Gly Trp Val
            180                 185                 190

Gly Phe Leu Gln Thr Thr Ile Leu Glu Ser Ile Gly Ser Ile Trp Phe
        195                 200                 205

Asn Arg Thr Glu Ala Lys Asp Arg Glu Val Val Ala Arg Lys Leu Arg
210                 215                 220

Glu His Thr Glu Gly Asp Asn Asn Pro Leu Leu Ile Phe Pro Glu Gly
225                 230                 235                 240

Thr Cys Val Asn Asn Asp Tyr Thr Val Met Phe Lys Lys Gly Ala Phe
                245                 250                 255

Glu Leu Gly Cys Ala Val Cys Pro Val Ala Ile Lys Tyr Asn Lys Ile
            260                 265                 270

Phe Val Asp Ala Phe Trp Asn Ser Lys Lys Gln Ser Phe Thr Met His
        275                 280                 285
```

```
Leu Met Arg Leu Met Thr Ser Trp Ala Val Val Cys Asp Val Trp Tyr
    290                 295                 300

Leu Glu Pro Gln Tyr Leu Lys Pro Gly Glu Thr Ser Ile Glu Phe Ala
305                 310                 315                 320

Glu Arg Val Arg Asp Met Ile Ser Val Arg Ala Gly Leu Arg Lys Val
                325                 330                 335

Pro Trp Asp Gly Tyr Leu Lys Tyr Phe Arg Pro Ser Pro Lys Leu Thr
            340                 345                 350

Glu Arg Lys Gln Gln Ile Phe Ala Glu Ser Val Leu Arg Arg Leu Glu
        355                 360                 365

Glu Lys
    370

<210> SEQ ID NO 104
<211> LENGTH: 370
<212> TYPE: PRT
<213> ORGANISM: Oryza brachyantha

<400> SEQUENCE: 104

Met Ala Ser Ser Val Ala Gly Asp Ile Glu Leu Asp Arg Pro Asn
1               5                   10                  15

Leu Glu Asp Tyr Leu Pro Pro Asp Ser Leu Pro Gln Glu Ser Pro Gly
                20                  25                  30

Asn Leu His Leu Arg Asp Leu Asp Ile Ser Pro Val Leu Thr Glu
            35                  40                  45

Ala Ala Gly Ala Ala Val Asp Asp Ser Phe Thr Arg Cys Phe Lys Ser
50                  55                  60

Asn Ser Pro Glu Pro Trp Asn Trp Asn Ile Tyr Leu Phe Pro Leu Trp
65                  70                  75                  80

Cys Leu Gly Val Val Ile Arg Tyr Gly Ile Leu Phe Pro Leu Arg Gly
                85                  90                  95

Leu Thr Leu Leu Val Gly Trp Ile Ala Phe Phe Ala Ala Phe Phe Ser
            100                 105                 110

Val His Phe Leu Phe Lys Gly Gln Lys Met Arg Ser Lys Ile Glu Arg
        115                 120                 125

Lys Leu Val Glu Met Met Cys Ser Val Phe Val Ala Ser Trp Thr Gly
130                 135                 140

Val Ile Lys Tyr His Gly Pro Arg Pro Ser Thr Arg Pro His Gln Val
145                 150                 155                 160

Phe Val Ala Asn His Thr Ser Met Ile Asp Phe Ile Ile Leu Glu Gln
                165                 170                 175

Met Thr Ala Phe Ala Val Ile Met Gln Lys His Pro Gly Trp Val Gly
            180                 185                 190

Phe Ile Gln Lys Thr Ile Leu Glu Ser Val Gly Cys Ile Trp Phe Asn
        195                 200                 205

Arg Asn Asp Leu Lys Asp Arg Glu Val Val Ala Lys Lys Leu Arg Asp
210                 215                 220

His Val Gln His Pro Asp Asn Pro Leu Leu Ile Phe Pro Glu Gly
225                 230                 235                 240

Thr Cys Val Asn Asn Gln Tyr Thr Val Met Phe Lys Lys Gly Ala Phe
                245                 250                 255

Glu Leu Gly Cys Ala Val Cys Pro Ile Ala Ile Lys Tyr Asn Lys Ile
            260                 265                 270

Phe Val Asp Ala Phe Trp Asn Ser Lys Lys Gln Ser Phe Thr Met His
```

```
                    275                 280                 285
Leu Val Arg Leu Met Thr Ser Trp Ala Val Cys Asp Val Trp Tyr
    290                 295                 300
Leu Glu Pro Gln Tyr Leu Lys Glu Gly Glu Thr Ala Ile Gln Phe Ala
305                 310                 315                 320
Glu Arg Val Arg Asp Met Ile Ala Ala Ala Gly Leu Lys Lys Val
                        325                 330                 335
Pro Trp Asp Gly Tyr Leu Lys His Asn Arg Pro Ser Pro Lys His Thr
                340                 345                 350
Glu Glu Lys Gln Arg Ile Phe Ala Asp Ser Val Leu Gln Arg Leu Glu
            355                 360                 365
Glu Ser
    370

<210> SEQ ID NO 105
<211> LENGTH: 370
<212> TYPE: PRT
<213> ORGANISM: Oryza sativa

<400> SEQUENCE: 105

Met Ala Thr Ser Ser Val Ala Gly Asp Ile Glu Leu Asp Arg Pro Asn
1               5                   10                  15
Leu Glu Asp Tyr Leu Pro Ser Asp Ser Leu Pro Gln Glu Phe Pro Arg
                20                  25                  30
Asn Leu His Leu Arg Asp Leu Leu Asp Ile Ser Pro Val Leu Thr Glu
            35                  40                  45
Ala Ala Gly Ala Ile Val Asp Asp Ser Phe Thr Arg Cys Phe Lys Ser
    50                  55                  60
Asn Ser Pro Glu Pro Trp Asn Trp Asn Ile Tyr Leu Phe Pro Leu Trp
65                  70                  75                  80
Cys Leu Gly Val Val Ile Arg Tyr Gly Ile Leu Phe Pro Leu Arg Gly
                85                  90                  95
Leu Thr Leu Leu Val Gly Trp Leu Ala Phe Ala Ala Phe Phe Pro
                100                 105                 110
Val His Phe Leu Leu Lys Gly Gln Lys Met Arg Ser Lys Ile Glu Arg
            115                 120                 125
Lys Leu Val Glu Met Met Cys Ser Val Phe Val Ala Ser Trp Thr Gly
130                 135                 140
Val Ile Lys Tyr His Gly Pro Arg Pro Ser Thr Arg Pro His Gln Val
145                 150                 155                 160
Phe Val Ala Asn His Thr Ser Met Ile Asp Phe Ile Ile Leu Glu Gln
                165                 170                 175
Met Thr Ala Phe Ala Val Ile Met Gln Lys His Pro Gly Trp Val Gly
            180                 185                 190
Phe Ile Gln Lys Thr Ile Leu Glu Ser Val Gly Cys Ile Trp Phe Asn
        195                 200                 205
Arg Asn Asp Leu Lys Asp Arg Glu Val Val Ala Lys Lys Leu Arg Asp
    210                 215                 220
His Val Gln His Pro Asp Ser Asn Pro Leu Leu Ile Phe Pro Glu Gly
225                 230                 235                 240
Thr Cys Val Asn Asn Gln Tyr Thr Val Met Phe Lys Lys Gly Ala Phe
                245                 250                 255
Glu Leu Gly Cys Ala Val Cys Pro Ile Ala Ile Lys Tyr Asn Lys Ile
            260                 265                 270
```

```
Phe Val Asp Ala Phe Trp Asn Ser Lys Lys Gln Ser Phe Thr Met His
            275                 280                 285

Leu Val Arg Leu Met Thr Ser Trp Ala Val Val Cys Asp Val Trp Tyr
        290                 295                 300

Leu Glu Pro Gln Tyr Leu Arg Asp Gly Glu Thr Ala Ile Glu Phe Ala
305                 310                 315                 320

Glu Arg Val Arg Asp Met Ile Ala Ala Arg Ala Gly Leu Lys Lys Val
                325                 330                 335

Pro Trp Asp Gly Tyr Leu Lys His Asn Arg Pro Ser Pro Lys His Thr
            340                 345                 350

Glu Glu Lys Gln Arg Ile Phe Ala Asp Ser Val Leu Arg Arg Leu Glu
        355                 360                 365

Glu Ser
    370

<210> SEQ ID NO 106
<211> LENGTH: 363
<212> TYPE: PRT
<213> ORGANISM: Nelumbo nucifera

<400> SEQUENCE: 106

Met Asp Leu Asp Arg Pro Asn Ile Glu Glu Tyr Leu Pro Ser Glu Ala
1               5                   10                  15

Ile Gln Glu Ser Asn Gly Lys Leu His Leu Arg Asp Leu Leu Asp Ile
            20                  25                  30

Ser Pro Thr Leu Thr Glu Ala Ala Gly Ala Ile Val Asp Asp Ser Phe
        35                  40                  45

Thr Arg Cys Phe Lys Ser Asn Pro Ser Glu Pro Trp Asn Trp Asn Val
50                  55                  60

Tyr Leu Phe Pro Leu Trp Cys Phe Gly Val Val Val Arg Tyr Gly Ile
65                  70                  75                  80

Leu Phe Pro Val Arg Val Leu Val Leu Thr Ile Gly Trp Ile Ile Phe
                85                  90                  95

Leu Ser Ser Phe Ile Pro Ala His Phe Leu Leu Arg Ser His Asp Lys
            100                 105                 110

Trp Arg Lys Lys Ile Glu Arg Tyr Leu Val Glu Leu Ile Cys Ser Phe
        115                 120                 125

Phe Val Ala Ser Trp Thr Gly Val Val Lys Tyr His Gly Pro Arg Pro
130                 135                 140

Ser Met Arg Pro Lys Gln Val Phe Val Ala Asn His Thr Ser Met Ile
145                 150                 155                 160

Asp Phe Ile Val Leu Glu Gln Met Thr Ala Phe Ala Val Ile Met Gln
                165                 170                 175

Lys His Pro Gly Trp Val Gly Leu Leu Gln Ser Thr Ile Leu Glu Ser
            180                 185                 190

Val Gly Cys Ile Trp Phe Asn Arg Ala Glu Ala Lys Asp Arg Glu Ile
        195                 200                 205

Val Ala Arg Lys Leu Arg Asp His Ile Gln Gly Val Asp Asn Asn Pro
210                 215                 220

Leu Leu Ile Phe Pro Glu Gly Thr Cys Val Asn Asn His Tyr Thr Val
225                 230                 235                 240

Met Phe Lys Lys Gly Ala Phe Glu Leu Gly Cys Thr Val Cys Pro Ile
                245                 250                 255

Ala Ile Lys Tyr Asn Lys Ile Phe Val Asp Ala Phe Trp Asn Ser Lys
            260                 265                 270
```

```
Lys Gln Ser Phe Thr Met His Leu Leu His Leu Met Thr Ser Trp Ala
        275                 280                 285

Val Val Cys Asp Val Trp Tyr Leu Glu Pro Gln Asn Ile Arg Pro Gly
        290                 295                 300

Glu Thr Pro Ile Glu Phe Ala Glu Arg Val Arg Asp Ile Ile Ser Val
305                 310                 315                 320

Arg Ala Gly Leu Lys Lys Val Pro Trp Asp Gly Tyr Leu Lys Tyr Ser
                325                 330                 335

Arg Pro Ser Pro Lys His Arg Glu Arg Lys Gln Gln Arg Phe Val Glu
                340                 345                 350

Ser Val Leu Gln Arg Leu Glu Lys Lys Gly Lys
        355                 360

<210> SEQ ID NO 107
<211> LENGTH: 376
<212> TYPE: PRT
<213> ORGANISM: Vitis vinifera

<400> SEQUENCE: 107

Met Ala Asn Ala Pro Asp Asn Lys Leu Thr Ser Ser Ser Ser Glu Leu
1               5                   10                  15

Asp Leu Asp Arg Pro Asn Leu Glu Asp Tyr Leu Pro Ser Gly Ser Met
                20                  25                  30

Gln Glu Pro Arg Gly Lys Leu Arg Leu Arg Asp Leu Leu Asp Ile Ser
            35                  40                  45

Pro Thr Leu Thr Glu Ala Ala Gly Ala Ile Val Asp Asp Ser Phe Thr
    50                  55                  60

Arg Cys Phe Lys Ser Asn Pro Pro Glu Pro Trp Asn Trp Asn Val Tyr
65                  70                  75                  80

Leu Phe Pro Leu Trp Cys Leu Gly Val Val Ile Arg Tyr Gly Ile Leu
                85                  90                  95

Phe Pro Thr Arg Val Leu Val Leu Thr Leu Gly Trp Ile Ile Phe Leu
            100                 105                 110

Ser Ser Phe Ile Pro Val His Phe Leu Leu Lys Gly Asn Asp Lys Leu
        115                 120                 125

Arg Lys Lys Leu Glu Arg Cys Leu Val Glu Leu Ile Cys Ser Phe Phe
130                 135                 140

Val Ala Ser Trp Thr Gly Val Val Lys Tyr His Gly Pro Arg Pro Ser
145                 150                 155                 160

Arg Arg Pro Gln Gln Val Phe Val Ala Asn His Thr Ser Met Ile Asp
                165                 170                 175

Phe Ile Val Leu Glu Gln Met Thr Ala Phe Ala Val Ile Met Gln Lys
            180                 185                 190

His Pro Gly Trp Val Gly Leu Leu Gln Ser Thr Ile Leu Glu Ser Val
        195                 200                 205

Gly Cys Ile Trp Phe Asn Arg Thr Glu Ala Lys Asp Arg Glu Ile Val
    210                 215                 220

Ala Arg Lys Leu Arg Asp His Val Gln Gly Ala Asp Asn Asn Pro Leu
225                 230                 235                 240

Leu Ile Phe Pro Glu Gly Thr Cys Val Asn Asn His Tyr Thr Val Met
                245                 250                 255

Phe Lys Lys Gly Ala Phe Glu Leu Gly Cys Thr Val Cys Pro Ile Ala
            260                 265                 270

Ile Lys Tyr Asn Lys Ile Phe Val Asp Ala Phe Trp Asn Ser Lys Lys
```

-continued

```
                275                 280                 285
Gln Ser Phe Thr Met His Leu Leu Gln Leu Met Thr Ser Trp Ala Val
    290                 295                 300
Val Cys Asp Val Trp Tyr Leu Glu Pro Gln Thr Leu Lys Pro Gly Glu
305                 310                 315                 320
Thr Pro Ile Glu Phe Ala Glu Arg Val Arg Asp Ile Ile Ser Leu Arg
                325                 330                 335
Ala Gly Leu Lys Lys Val Pro Trp Asp Gly Tyr Leu Lys Tyr Ser Arg
            340                 345                 350
Pro Ser Pro Lys His Arg Glu Gln Lys Gln Gln Ser Phe Ala Asp Ser
        355                 360                 365
Val Leu Arg Arg Leu Glu Glu Lys
    370                 375

<210> SEQ ID NO 108
<211> LENGTH: 373
<212> TYPE: PRT
<213> ORGANISM: Nicotiana tomentosiformis

<400> SEQUENCE: 108

Met Asn Met Asn Lys Leu Lys Thr Ser Ser Glu Leu Asp Leu Asp
1               5                   10                  15
Arg Pro Asn Leu Glu Asp Tyr Leu Pro Thr Gly Ser Ile Pro Glu Pro
                20                  25                  30
His Gly Lys Leu Arg Leu Arg Asp Leu Ile Asp Ile Ser Pro Thr Leu
            35                  40                  45
Thr Glu Ala Ala Gly Ala Ile Val Asp Asp Ser Phe Thr Arg Cys Phe
        50                  55                  60
Lys Ser Asn Pro Pro Glu Pro Trp Asn Trp Asn Ile Tyr Leu Phe Pro
65                  70                  75                  80
Leu Trp Cys Leu Gly Val Val Arg Tyr Gly Ile Leu Phe Pro Ile
                85                  90                  95
Arg Val Ile Val Leu Thr Ile Gly Trp Ile Ile Phe Leu Ser Cys Tyr
                100                 105                 110
Ile Pro Val His Phe Leu Leu Lys Gly His Asp Lys Phe Arg Lys Lys
            115                 120                 125
Leu Glu Arg Cys Leu Val Glu Leu Ile Cys Ser Phe Phe Val Ala Ser
        130                 135                 140
Trp Thr Gly Val Val Lys Tyr His Gly Pro Arg Pro Ser Ile Arg Pro
145                 150                 155                 160
Lys Gln Val Phe Val Ala Asn His Thr Ser Met Ile Asp Phe Ile Val
                165                 170                 175
Leu Glu Gln Met Thr Ala Phe Ala Val Ile Met Gln Lys His Pro Gly
            180                 185                 190
Trp Val Gly Leu Leu Gln Ser Thr Ile Leu Glu Gly Val Gly Cys Ile
        195                 200                 205
Trp Phe Asn Arg Ser Glu Ala Lys Asp Arg Glu Ile Val Ala Arg Lys
210                 215                 220
Leu Arg Gln His Val Glu Gly Ala Asp Asn Pro Leu Leu Ile Phe
225                 230                 235                 240
Pro Glu Gly Thr Cys Val Asn Asn His Tyr Thr Val Met Phe Lys Lys
                245                 250                 255
Gly Ala Phe Glu Leu Gly Cys Thr Val Cys Pro Val Ala Ile Lys Tyr
            260                 265                 270
```

```
Asn Lys Ile Phe Val Asp Ala Phe Trp Asn Ser Arg Lys Gln Ser Phe
            275                 280                 285

Thr Met His Leu Leu Gln Leu Met Thr Ser Trp Ala Val Val Cys Asp
    290                 295                 300

Val Trp Tyr Leu Glu Pro Gln Asn Ile Arg Pro Gly Glu Thr Pro Ile
305                 310                 315                 320

Glu Phe Ala Glu Arg Val Arg Asp Ile Ile Ser Ala Arg Ala Gly Leu
                325                 330                 335

Lys Lys Val Pro Trp Asp Gly Tyr Leu Lys Tyr Ser Arg Pro Ser Pro
                340                 345                 350

Lys His Arg Glu Arg Lys Gln Gln Ser Phe Ala Glu Ser Val Leu Arg
            355                 360                 365

Arg Leu Glu Glu Lys
    370

<210> SEQ ID NO 109
<211> LENGTH: 375
<212> TYPE: PRT
<213> ORGANISM: Jatropha curcas

<400> SEQUENCE: 109

Met Ala Thr Pro Gly Lys Leu Lys Thr Ser Ser Glu Leu Asp Leu
1               5                   10                  15

Asp Arg Pro Asn Ile Glu Asp Tyr Leu Pro Ser Gly Val Ser Ile Gln
            20                  25                  30

Glu Pro Arg Gly Lys Leu Arg Leu Arg Asp Leu Leu Asp Ile Ser Pro
        35                  40                  45

Thr Leu Thr Glu Ala Ala Gly Ala Ile Val Asp Asp Thr Phe Thr Arg
    50                  55                  60

Cys Phe Lys Ser Asn Pro Pro Glu Pro Trp Asn Trp Asn Ile Tyr Leu
65                  70                  75                  80

Phe Pro Leu Trp Cys Cys Gly Val Val Cys Arg Tyr Gly Ile Leu Phe
                85                  90                  95

Pro Ile Arg Val Leu Val Leu Thr Ile Gly Trp Ile Ile Phe Leu Ser
            100                 105                 110

Cys Tyr Ile Pro Val His Phe Leu Leu Lys Gly His Asp Lys Leu Arg
        115                 120                 125

Lys Lys Leu Glu Arg Cys Leu Val Glu Leu Ile Cys Ser Phe Phe Val
130                 135                 140

Ala Ser Trp Thr Gly Val Val Lys Tyr His Gly Pro Arg Pro Ser Ile
145                 150                 155                 160

Arg Pro Lys Gln Val Phe Val Ala Asn His Thr Ser Met Ile Asp Phe
                165                 170                 175

Ile Ile Leu Glu Gln Met Thr Ala Phe Ala Val Ile Met Gln Lys His
            180                 185                 190

Pro Gly Trp Val Gly Leu Leu Gln Ser Thr Ile Leu Glu Ser Val Gly
        195                 200                 205

Cys Ile Trp Phe Asn Arg Ser Glu Ala Lys Asp Arg Glu Ile Val Thr
    210                 215                 220

Lys Lys Leu Arg Asp His Val Gln Gly Ala Asp Asn Asn Pro Leu Leu
225                 230                 235                 240

Ile Phe Pro Glu Gly Thr Cys Val Asn Asn His Tyr Thr Val Met Phe
                245                 250                 255

Lys Lys Gly Ala Phe Glu Leu Gly Cys Thr Val Cys Pro Ile Ala Ile
            260                 265                 270
```

```
Lys Tyr Asn Lys Ile Phe Val Asp Ala Phe Trp Asn Ser Arg Lys Gln
            275                 280                 285

Ser Phe Thr Thr His Leu Leu Gln Leu Met Thr Ser Trp Ala Val Val
        290                 295                 300

Cys Asp Val Trp Tyr Leu Glu Pro Gln Asn Leu Lys Pro Gly Glu Thr
305                 310                 315                 320

Pro Ile Glu Phe Ala Glu Arg Val Arg Asp Ile Ile Ser Val Arg Ala
                325                 330                 335

Gly Leu Lys Lys Val Pro Trp Asp Gly Tyr Leu Lys Tyr Ser Arg Pro
            340                 345                 350

Ser Pro Lys His Arg Glu Arg Lys Gln Gln Ser Phe Ala Glu Ser Val
            355                 360                 365

Leu Gln Arg Leu Glu Glu Lys
            370                 375

<210> SEQ ID NO 110
<211> LENGTH: 376
<212> TYPE: PRT
<213> ORGANISM: Glycine max

<400> SEQUENCE: 110

Met Asn Asn Ser Gly Thr Pro Lys Ser Ser Ser Glu Leu Asp Leu
1               5                   10                  15

Asp Arg Pro Asn Ile Glu Asp Tyr Leu Pro Ser Gly Ser Thr Ile Gln
            20                  25                  30

Gln Glu Pro His Gly Lys Leu Phe Leu His Asp Leu Leu Asn Ile Ser
        35                  40                  45

Pro Thr Leu Ser Glu Ala Ala Gly Ala Ile Val Asp Asp Ser Phe Thr
    50                  55                  60

Arg Cys Phe Lys Ser Asn Pro Pro Glu Pro Trp Asn Trp Asn Val Tyr
65                  70                  75                  80

Leu Phe Pro Leu Trp Cys Phe Gly Val Val Ile Arg Tyr Leu Ile Leu
                85                  90                  95

Phe Pro Ile Arg Val Ile Gly Leu Thr Ile Gly Trp Ile Ile Phe Leu
            100                 105                 110

Ser Ser Phe Ile Pro Val His Phe Leu Leu Lys Gly His Asp Lys Leu
        115                 120                 125

Arg Arg Ser Ile Glu Arg Ser Leu Val Glu Met Met Cys Ser Phe Phe
130                 135                 140

Val Ala Ser Trp Thr Gly Val Val Lys Tyr His Gly Pro Arg Pro Ser
145                 150                 155                 160

Arg Arg Pro Lys Gln Val Phe Val Ala Asn His Thr Ser Met Ile Asp
                165                 170                 175

Phe Ile Ile Leu Glu Gln Met Thr Ala Phe Ala Val Ile Met Gln Lys
            180                 185                 190

His Pro Gly Trp Val Gly Leu Leu Gln Ser Thr Ile Leu Glu Ser Leu
        195                 200                 205

Gly Cys Ile Trp Phe Asn Arg Thr Glu Ala Lys Asp Arg Glu Ile Val
    210                 215                 220

Ala Arg Lys Leu Arg Asp His Val Gln Gly Ala Asp Asn Asn Pro Leu
225                 230                 235                 240

Leu Ile Phe Pro Glu Gly Thr Cys Val Asn Asn His Tyr Thr Val Met
                245                 250                 255

Phe Lys Lys Gly Ala Phe Glu Leu Gly Cys Thr Val Cys Pro Val Ala
```

```
                  260                 265                 270
Ile Lys Tyr Asn Lys Ile Phe Val Asp Ala Phe Trp Asn Ser Arg Lys
                275                 280                 285

Gln Ser Phe Thr Met His Leu Leu Gln Leu Met Thr Ser Trp Ala Val
    290                 295                 300

Val Cys Asp Val Trp Tyr Leu Glu Pro Gln Asn Leu Lys Pro Gly Glu
305                 310                 315                 320

Thr Pro Ile Glu Phe Ala Glu Arg Val Arg Asp Ile Ile Ser Val Arg
                325                 330                 335

Ala Gly Leu Lys Lys Val Pro Trp Asp Gly Tyr Leu Lys Tyr Ser Arg
            340                 345                 350

Pro Ser Pro Lys His Arg Glu Arg Lys Gln Gln Asn Phe Ala Glu Ser
        355                 360                 365

Val Leu Arg Arg Trp Glu Glu Lys
        370                 375

<210> SEQ ID NO 111
<211> LENGTH: 371
<212> TYPE: PRT
<213> ORGANISM: Sesamum indicum

<400> SEQUENCE: 111

Met Ser Lys Leu Asn Thr Ser Ser Ser Glu Leu Asp Phe Asp Arg Pro
1               5                   10                  15

Asn Ile Glu Asp Tyr Leu Pro Ser Gly Ser Ile Gln Glu Pro His Gly
            20                  25                  30

Lys Leu Arg Leu Arg Asp Leu Leu Asp Ile Ser Pro Thr Leu Thr Glu
        35                  40                  45

Ala Ala Gly Ala Ile Val Asp Asp Ser Phe Thr Arg Cys Phe Lys Ser
    50                  55                  60

Asn Pro Pro Glu Pro Trp Asn Trp Asn Ile Tyr Leu Phe Pro Leu Trp
65                  70                  75                  80

Cys Leu Gly Val Val Ile Arg Tyr Gly Leu Leu Phe Pro Leu Arg Val
                85                  90                  95

Ile Val Leu Thr Ile Gly Trp Ile Ile Phe Leu Ser Cys Tyr Phe Pro
            100                 105                 110

Val His Phe Leu Leu Arg Gly His Asp Lys Leu Arg Lys Arg Leu Glu
        115                 120                 125

Arg Gly Leu Val Glu Leu Ile Cys Ser Phe Phe Val Ala Ser Trp Thr
    130                 135                 140

Gly Val Val Lys Tyr His Gly Pro Arg Pro Ser Met Arg Pro Lys Gln
145                 150                 155                 160

Val Phe Val Ala Asn His Thr Ser Met Ile Asp Phe Ile Val Leu Glu
                165                 170                 175

Gln Met Thr Ala Phe Ala Val Ile Met Gln Lys His Pro Gly Trp Val
            180                 185                 190

Gly Leu Leu Gln Ser Thr Ile Leu Glu Ser Leu Gly Cys Ile Trp Phe
        195                 200                 205

Asn Arg Ser Glu Ser Lys Asp Arg Glu Ile Val Ala Lys Lys Leu Arg
    210                 215                 220

Glu His Val His Asp Ala Asp Asn Asn Pro Leu Leu Ile Phe Pro Glu
225                 230                 235                 240

Gly Thr Cys Val Asn Asn His Tyr Thr Val Met Phe Lys Lys Gly Ala
                245                 250                 255
```

```
Phe Glu Leu Gly Cys Thr Val Cys Pro Ile Ala Ile Lys Tyr Asn Lys
                260                 265                 270

Ile Phe Val Asp Ala Phe Trp Asn Ser Arg Lys Gln Ser Phe Thr Thr
            275                 280                 285

His Leu Leu Gln Leu Met Thr Ser Trp Ala Val Val Cys Asp Val Trp
        290                 295                 300

Tyr Leu Glu Pro Gln Asn Leu Lys Pro Gly Glu Thr Pro Ile Glu Phe
305                 310                 315                 320

Ala Glu Arg Val Arg Asp Ile Ile Ser Val Arg Ala Gly Leu Arg Lys
                325                 330                 335

Val Pro Trp Asp Gly Tyr Leu Lys Tyr Ser Arg Pro Ser Pro Lys His
            340                 345                 350

Arg Glu Arg Lys Gln Gln Ser Phe Ala Glu Ser Ile Leu Arg Arg Leu
        355                 360                 365

Glu Glu Lys
    370

<210> SEQ ID NO 112
<211> LENGTH: 364
<212> TYPE: PRT
<213> ORGANISM: Brachypodium distachyon

<400> SEQUENCE: 112

Met Ala Ser Ser Leu Asp Ala Pro Asn Leu Asp Asp Tyr Leu Pro Thr
1               5                   10                  15

Asp Ser Leu Pro Gln Glu Pro Pro Arg Ser Leu Asn Leu Arg Asp Leu
            20                  25                  30

Leu Asp Ile Ser Pro Val Leu Thr Glu Ala Ala Gly Ala Ile Val Asp
        35                  40                  45

Asp Ser Phe Thr Arg Cys Phe Lys Ser Asn Ser Pro Glu Pro Trp Asn
    50                  55                  60

Trp Asn Ile Tyr Leu Phe Pro Leu Trp Cys Phe Gly Val Val Val Arg
65                  70                  75                  80

Tyr Gly Leu Leu Phe Pro Leu Arg Val Leu Thr Leu Gly Leu Gly Trp
                85                  90                  95

Met Val Phe Phe Ala Ala Phe Pro Val His Phe Leu Leu Lys Gly
            100                 105                 110

Gln Asn Lys Leu Arg Ser Lys Ile Glu Arg Lys Leu Val Glu Met Met
        115                 120                 125

Cys Ser Val Phe Val Ala Ser Trp Thr Gly Val Ile Lys Tyr His Gly
    130                 135                 140

Pro Arg Pro Ser Ser Arg Pro Tyr Gln Val Phe Val Ala Asn His Thr
145                 150                 155                 160

Ser Met Ile Asp Phe Ile Ile Leu Glu Gln Met Thr Ala Phe Ala Val
                165                 170                 175

Ile Met Gln Lys His Pro Gly Trp Val Gly Phe Ile Gln Lys Thr Ile
            180                 185                 190

Leu Glu Ser Val Gly Cys Ile Trp Phe Asn Arg Asn Asp Leu Lys Asp
        195                 200                 205

Arg Glu Val Val Gly Arg Lys Leu Arg Asp His Val Gln Arg Pro Asp
    210                 215                 220

Asn Asn Pro Leu Leu Ile Phe Pro Glu Gly Thr Cys Val Asn Asn Gln
225                 230                 235                 240

Tyr Thr Val Met Phe Lys Lys Gly Ala Phe Glu Leu Gly Cys Ala Val
                245                 250                 255
```

```
Cys Pro Ile Ala Ile Lys Tyr Asn Lys Ile Phe Val Asp Ala Phe Trp
            260                 265                 270

Asn Ser Lys Lys Gln Ser Phe Thr Met His Leu Gly Arg Leu Met Thr
        275                 280                 285

Ser Trp Ala Val Val Cys Asp Val Trp Phe Leu Glu Pro Gln Tyr Leu
    290                 295                 300

Arg Glu Gly Glu Thr Ser Ile Ala Phe Thr Glu Arg Val Arg Asp Met
305                 310                 315                 320

Ile Ala Ala Arg Ala Gly Leu Lys Lys Val Leu Trp Asp Gly Tyr Leu
                325                 330                 335

Lys His Asn Arg Pro Ser Pro Lys His Thr Glu Glu Lys Gln Arg Ile
                340                 345                 350

Phe Ala Glu Ser Val Leu Lys Arg Leu Glu Glu Ser
            355                 360

<210> SEQ ID NO 113
<211> LENGTH: 371
<212> TYPE: PRT
<213> ORGANISM: Setaria italica

<400> SEQUENCE: 113

Met Ala Ser Ser Val Ala Ala Asp Met Glu Leu Asp Arg Pro Asn
1               5                   10                  15

Leu Glu Asp Tyr Leu Pro Pro Asp Ser Leu Pro Gln Glu Ala Pro Arg
                20                  25                  30

Asn Leu His Leu Arg Asp Leu Leu Asp Ile Ser Pro Val Leu Thr Glu
            35                  40                  45

Ala Ala Gly Ala Ile Val Asp Asp Ser Phe Thr Arg Cys Phe Lys Ser
        50                  55                  60

Asn Ser Pro Glu Pro Trp Asn Trp Asn Ile Tyr Leu Phe Pro Leu Trp
65                  70                  75                  80

Cys Leu Gly Val Val Ile Arg Tyr Gly Ile Leu Phe Pro Leu Arg Ser
                85                  90                  95

Leu Thr Leu Ala Ile Gly Trp Leu Ala Phe Phe Ala Ala Phe Phe Pro
            100                 105                 110

Val His Phe Leu Leu Lys Gly Gln Asp Lys Leu Arg Ser Lys Ile Glu
        115                 120                 125

Arg Lys Leu Val Glu Met Met Cys Ser Val Phe Val Ala Ser Trp Thr
    130                 135                 140

Gly Val Ile Lys Tyr His Gly Pro Arg Pro Ser Thr Arg Pro His Gln
145                 150                 155                 160

Val Phe Val Ala Asn His Thr Ser Met Ile Asp Phe Ile Ile Leu Glu
                165                 170                 175

Gln Met Thr Ala Phe Ala Val Ile Met Gln Lys His Pro Gly Trp Val
            180                 185                 190

Gly Phe Ile Gln Lys Thr Ile Leu Glu Ser Val Gly Cys Ile Trp Phe
        195                 200                 205

Asn Arg Asn Asp Leu Arg Asp Arg Glu Val Thr Ala Arg Lys Leu Arg
    210                 215                 220

Asp His Val Gln Gln Pro Asp Lys Asn Pro Leu Leu Ile Phe Pro Glu
225                 230                 235                 240

Gly Thr Cys Val Asn Asn Gln Tyr Thr Val Met Phe Lys Lys Gly Ala
                245                 250                 255

Phe Glu Leu Gly Cys Ala Val Cys Pro Ile Ala Ile Lys Tyr Asn Lys
```

```
              260                 265                 270
Ile Phe Val Asp Ala Phe Trp Asn Ser Lys Lys Gln Ser Phe Thr Met
            275                 280                 285

His Leu Val Arg Leu Met Thr Ser Trp Ala Val Val Cys Asp Val Trp
            290                 295                 300

Tyr Leu Pro Pro Gln Tyr Leu Arg Glu Gly Glu Thr Ala Ile Ala Phe
305                 310                 315                 320

Ala Glu Arg Val Arg Asp Met Ile Ala Ala Arg Ala Gly Leu Lys Lys
                325                 330                 335

Val Pro Trp Asp Gly Tyr Leu Lys His Asn Arg Pro Ser Pro Lys His
            340                 345                 350

Thr Glu Glu Lys Gln Arg Ile Phe Ala Glu Ser Val Leu Met Arg Leu
            355                 360                 365

Glu Glu Lys
    370

<210> SEQ ID NO 114
<211> LENGTH: 376
<212> TYPE: PRT
<213> ORGANISM: Cicer arietinum

<400> SEQUENCE: 114

Met Asn Ser Thr Gly Thr Leu Lys Ser Ser Ser Glu Leu Asp Leu
1               5                   10                  15

Asp Arg Pro Asn Ile Glu Asp Tyr Leu Pro Ser Gly Ala Ala Ile Gln
            20                  25                  30

Gln Glu Pro Arg Gly Lys Leu Arg Leu His Asp Leu Leu Asp Ile Ser
        35                  40                  45

Pro Thr Leu Ser Glu Ala Ala Gly Ala Ile Val Asp Asp Ser Phe Thr
    50                  55                  60

Arg Cys Phe Lys Ser Asn Pro Pro Glu Pro Trp Asn Trp Asn Ile Tyr
65                  70                  75                  80

Leu Phe Pro Leu Trp Cys Phe Gly Val Val Val Arg Tyr Leu Ile Leu
                85                  90                  95

Phe Pro Thr Arg Val Leu Gly Leu Thr Leu Gly Trp Ile Ile Phe Leu
            100                 105                 110

Ser Ala Phe Ile Pro Val His Leu Leu Leu Lys Gly His Asp Lys Leu
        115                 120                 125

Arg Arg Asn Ile Glu Arg Ser Leu Val Glu Met Met Cys Gly Phe Phe
130                 135                 140

Val Ala Ser Trp Thr Gly Val Val Lys Tyr His Gly Pro Lys Pro Ser
145                 150                 155                 160

Arg Arg Pro Lys Gln Val Phe Val Ala Asn His Thr Ser Met Ile Asp
                165                 170                 175

Phe Ile Ile Leu Glu Gln Met Thr Ala Phe Ala Val Ile Met Gln Lys
            180                 185                 190

His Pro Gly Trp Val Gly Leu Leu Gln Ser Thr Ile Leu Glu Ser Val
        195                 200                 205

Gly Cys Ile Trp Phe Asn Arg Thr Glu Ala Lys Asp Arg Glu Ile Val
    210                 215                 220

Ala Arg Lys Leu Arg Glu His Val Gln Gly Ala Asp Asn Asn Pro Leu
225                 230                 235                 240

Leu Ile Phe Pro Glu Gly Thr Cys Val Asn Asn His Tyr Thr Val Met
                245                 250                 255
```

Phe Lys Lys Gly Ala Phe Glu Leu Gly Cys Thr Val Cys Pro Val Ala
                260                 265                 270

Ile Lys Tyr Asn Lys Ile Phe Val Asp Ala Phe Trp Asn Ser Arg Lys
            275                 280                 285

Gln Ser Phe Thr Lys His Leu Leu Gln Leu Met Thr Ser Trp Ala Val
        290                 295                 300

Val Cys Asp Val Trp Tyr Leu Glu Pro Gln Asn Leu Lys Pro Gly Glu
305                 310                 315                 320

Thr Pro Ile Glu Phe Ala Glu Arg Val Arg Asp Ile Ile Ser His Arg
                325                 330                 335

Ala Gly Leu Lys Lys Val Pro Trp Asp Gly Tyr Leu Lys Tyr Ser Arg
            340                 345                 350

Pro Ser Pro Lys His Arg Glu Arg Lys Gln Gln Asn Phe Ala Glu Ser
        355                 360                 365

Val Leu Arg Arg Leu Glu Glu Lys
    370                 375

<210> SEQ ID NO 115
<211> LENGTH: 371
<212> TYPE: PRT
<213> ORGANISM: Zea mays

<400> SEQUENCE: 115

Met Ala Ser Ser Ser Val Ala Ala Asp Met Glu Leu Asp Arg Pro Asn
1               5                   10                  15

Leu Glu Asp Tyr Leu Pro Pro Asp Ser Leu Pro Gln Glu Ala Pro Arg
            20                  25                  30

Asn Leu His Leu Arg Asp Leu Asp Ile Ser Pro Val Leu Thr Glu
        35                  40                  45

Ala Ala Gly Ala Ile Val Asp Asp Ser Phe Thr Arg Cys Phe Lys Ser
    50                  55                  60

Asn Ser Pro Glu Pro Trp Asn Trp Asn Ile Tyr Leu Phe Pro Leu Trp
65                  70                  75                  80

Cys Phe Gly Val Val Ile Arg Tyr Gly Leu Leu Phe Pro Leu Arg Ser
                85                  90                  95

Leu Thr Leu Ala Ile Gly Trp Leu Ala Phe Phe Ala Ala Phe Phe Pro
            100                 105                 110

Val His Phe Leu Leu Lys Gly Gln Asp Lys Leu Arg Asn Lys Ile Glu
        115                 120                 125

Arg Lys Leu Val Glu Met Met Cys Ser Val Phe Val Ala Ser Trp Thr
    130                 135                 140

Gly Val Ile Lys Tyr His Gly Pro Arg Pro Ser Thr Arg Pro His Gln
145                 150                 155                 160

Val Phe Val Ala Asn His Thr Ser Met Ile Asp Phe Ile Ile Leu Glu
                165                 170                 175

Gln Met Thr Ala Phe Ala Val Ile Met Gln Lys His Pro Gly Trp Val
            180                 185                 190

Gly Phe Ile Gln Lys Thr Ile Leu Glu Ser Val Gly Cys Ile Trp Phe
        195                 200                 205

Asn Arg Asn Asp Leu Arg Asp Arg Glu Val Thr Ala Arg Lys Leu Arg
    210                 215                 220

Asp His Val Gln His Pro Asp Lys Asn Pro Leu Leu Ile Phe Pro Glu
225                 230                 235                 240

Gly Thr Cys Val Asn Asn Gln Tyr Thr Val Met Phe Lys Lys Gly Ala
                245                 250                 255

```
Phe Glu Leu Gly Cys Ala Val Cys Pro Ile Ala Ile Lys Tyr Asn Lys
            260                 265                 270

Ile Phe Val Asp Ala Phe Trp Asn Ser Lys Lys Gln Ser Phe Thr Met
        275                 280                 285

His Leu Val Arg Leu Met Thr Ser Trp Ala Val Val Cys Asp Val Trp
    290                 295                 300

Tyr Leu Glu Pro Gln Tyr Leu Arg Glu Gly Glu Thr Ala Ile Ala Phe
305                 310                 315                 320

Ala Glu Arg Val Arg Asp Met Ile Ala Ala Arg Ala Gly Leu Lys Lys
                325                 330                 335

Val Pro Trp Asp Gly Tyr Leu Lys His Asn Arg Pro Ser Pro Lys His
            340                 345                 350

Thr Glu Glu Lys Gln Arg Ile Phe Ala Glu Ser Val Leu Arg Arg Leu
        355                 360                 365

Glu Glu Lys
    370

<210> SEQ ID NO 116
<211> LENGTH: 378
<212> TYPE: PRT
<213> ORGANISM: Gossypium hirsutum

<400> SEQUENCE: 116

Met Asn Ser Ser Glu Gly Lys Leu Lys Ser Ser Ser Glu Leu Asp
1               5                   10                  15

Leu Asp Arg Pro Asn Ile Glu Asp Tyr Leu Pro Ser Gly Ser Ser Ile
            20                  25                  30

Gln Glu Pro His Gly Lys Leu Arg Leu Arg Asp Leu Leu Asp Ile Ser
        35                  40                  45

Pro Ala Leu Thr Glu Ala Ala Gly Ala Ile Val Asp Asp Ser Phe Thr
    50                  55                  60

Arg Cys Phe Lys Ser Asn Pro Pro Glu Pro Trp Asn Trp Asn Val Tyr
65                  70                  75                  80

Leu Phe Pro Leu Trp Cys Cys Gly Val Val Phe Arg Tyr Leu Ile Leu
                85                  90                  95

Phe Pro Met Arg Ala Leu Ile Leu Thr Ile Gly Trp Ile Ile Phe Leu
            100                 105                 110

Ser Cys Phe Ile Pro Val His Phe Leu Leu Lys Gly Asn Asp Asn Leu
        115                 120                 125

Arg Lys Lys Met Glu Arg Ala Leu Val Glu Leu Ile Cys Ser Phe Phe
    130                 135                 140

Val Ala Ser Trp Thr Gly Val Val Lys Tyr His Gly Pro Arg Pro Ser
145                 150                 155                 160

Met Arg Pro Lys Gln Val Phe Val Ala Asn His Thr Ser Met Ile Asp
                165                 170                 175

Phe Ile Ile Leu Glu Gln Met Thr Ala Phe Ala Val Ile Met Gln Lys
            180                 185                 190

His Pro Gly Trp Val Gly Leu Leu Gln Ser Thr Ile Leu Glu Ser Val
        195                 200                 205

Gly Cys Ile Trp Phe Asn Arg Ser Glu Ala Lys Asp Arg Glu Ile Val
    210                 215                 220

Thr Arg Lys Leu Arg Glu His Ser Gln Gly Ala Asp Asn Asn Pro Leu
225                 230                 235                 240

Leu Ile Phe Pro Glu Gly Thr Cys Val Asn Asn Gln Tyr Ser Val Met
```

```
                        245                 250                 255
Phe Lys Lys Gly Ala Phe Glu Leu Gly Cys Thr Val Cys Pro Ile Ala
                260                 265                 270

Ile Lys Tyr Asn Lys Ile Phe Val Asp Ala Phe Trp Asn Ser Arg Lys
            275                 280                 285

Gln Ser Phe Thr Met His Leu Leu Gln Leu Met Thr Ser Trp Ala Val
        290                 295                 300

Val Cys Asp Val Trp Tyr Leu Glu Pro Gln Asn Leu Arg Pro Gly Glu
305                 310                 315                 320

Thr Pro Ile Glu Phe Ala Glu Arg Ile Arg Asp Ile Ser Val Arg
                325                 330                 335

Ala Gly Leu Lys Lys Val Pro Trp Asp Gly Tyr Leu Lys Tyr Ser Arg
                340                 345                 350

Pro Ser Pro Lys His Arg Glu Arg Lys Gln Gln Ser Phe Ala Glu Ser
            355                 360                 365

Val Leu Arg Gly Leu Glu Leu Glu Glu Lys
        370                 375

<210> SEQ ID NO 117
<211> LENGTH: 375
<212> TYPE: PRT
<213> ORGANISM: Eucalyptus grandis

<400> SEQUENCE: 117

Met Ala Ser Pro Arg Lys Leu Pro Thr Ser Ser Glu Leu Asp Leu
1               5                   10                  15

Asp Arg Leu Asn Ile Glu Asp Tyr Leu Pro Ser Gly Ser Ser Ile His
                20                  25                  30

Glu Pro Pro Gly Gln Leu Arg Leu Arg Asp Leu Leu Asp Ile Thr Pro
            35                  40                  45

Thr Leu Thr Glu Ala Ala Gly Ala Ile Val Asp Asp Ser Phe Thr Arg
        50                  55                  60

Cys Phe Lys Ser Asn Ser Gln Glu Pro Trp Asn Trp Asn Val Tyr Leu
65                  70                  75                  80

Phe Pro Leu Trp Cys Phe Gly Val Val Arg Tyr Leu Ile Leu Phe
                85                  90                  95

Pro Ala Arg Val Leu Val Leu Thr Ile Gly Trp Ile Ile Phe Leu Ser
            100                 105                 110

Ser Phe Ala Ile Val His Phe Met Leu Lys Ala His Asp Ala Leu Arg
        115                 120                 125

Arg Lys Leu Glu Arg Leu Leu Val Glu Leu Ile Cys Ser Phe Phe Val
    130                 135                 140

Ala Ser Trp Thr Gly Val Val Lys Tyr His Gly Pro Arg Pro Ser Ile
145                 150                 155                 160

Arg Pro Lys Gln Val Phe Val Ala Asn His Thr Ser Met Ile Asp Phe
                165                 170                 175

Ile Ile Leu Glu Gln Met Thr Ala Phe Ala Val Ile Met Gln Lys His
            180                 185                 190

Pro Gly Trp Val Gly Leu Leu Gln Ser Thr Ile Leu Glu Ser Val Gly
        195                 200                 205

Cys Ile Trp Phe Asn Arg Ser Glu Ala Lys Asp Arg Glu Ile Val Ala
    210                 215                 220

Arg Lys Leu Arg Asp His Val Leu Gly Thr Asp Asn Asn Pro Leu Leu
225                 230                 235                 240
```

```
Ile Phe Pro Glu Gly Thr Cys Val Asn Asn His Tyr Thr Val Met Phe
                245                 250                 255

Lys Lys Gly Ala Phe Glu Leu Gly Cys Thr Val Cys Pro Ile Ala Ile
            260                 265                 270

Lys Tyr Asn Lys Ile Phe Val Asp Ala Phe Trp Asn Ser Arg Lys Gln
            275                 280                 285

Ser Phe Thr Met His Leu Leu Gln Leu Met Thr Ser Trp Ala Val Val
            290                 295                 300

Cys Asp Val Trp Tyr Leu Glu Pro Gln Thr Leu Lys Pro Gly Glu Thr
305                 310                 315                 320

Pro Ile Glu Phe Ala Glu Arg Val Arg Asp Ile Ile Ser Val Arg Ala
                325                 330                 335

Gly Leu Lys Lys Val Pro Trp Asp Gly Tyr Leu Lys Tyr Ser Arg Pro
            340                 345                 350

Ser Pro Lys His Arg Glu Gly Lys Gln Arg Ser Phe Ala Glu Trp Val
            355                 360                 365

Leu Gln Arg Leu Glu Arg
            370                 375

<210> SEQ ID NO 118
<211> LENGTH: 375
<212> TYPE: PRT
<213> ORGANISM: Cucumis sativus

<400> SEQUENCE: 118

Met Ser Gly Ala Ala Leu Leu Lys Ser Ser Ala Ser Glu Leu Asp Leu
1               5                   10                  15

Asp Arg Pro Asn Ile Glu Asp Tyr Leu Pro Ser Gly Ser Ser Ile Gln
            20                  25                  30

Gln Pro Thr Ala Lys Leu Arg Leu Arg Asp Leu Leu Asp Ile Ser Pro
        35                  40                  45

Thr Leu Thr Glu Ala Ala Gly Ala Ile Val Asp Asp Ser Phe Thr Arg
    50                  55                  60

Cys Phe Lys Ser Asn Pro Pro Glu Pro Trp Asn Trp Asn Ile Tyr Leu
65                  70                  75                  80

Phe Pro Leu Trp Cys Cys Gly Val Val Ile Arg Tyr Leu Phe Leu Phe
                85                  90                  95

Pro Ala Arg Val Leu Ile Leu Thr Ile Gly Trp Ile Ile Phe Leu Ser
            100                 105                 110

Thr Phe Ile Pro Val Asn Leu Leu Lys Gly His Pro Lys Leu Arg
            115                 120                 125

Ala Lys Leu Glu Arg Phe Leu Val Glu Leu Ile Cys Ser Phe Phe Val
            130                 135                 140

Ala Ser Trp Thr Gly Val Val Lys Tyr His Gly Pro Arg Pro Ser Ile
145                 150                 155                 160

Arg Pro Lys Gln Val Phe Val Ala Asn His Thr Ser Met Ile Asp Phe
                165                 170                 175

Ile Val Leu Glu Gln Met Thr Ala Phe Ala Val Ile Met Gln Lys His
            180                 185                 190

Pro Gly Trp Val Gly Leu Leu Gln Ser Thr Ile Leu Glu Ser Ile Gly
            195                 200                 205

Cys Ile Trp Phe Asn Arg Thr Glu Leu Lys Asp Arg Glu Ile Val Ala
            210                 215                 220

Lys Lys Leu Asn Asp His Val Gln Gly Ala Asp Asn Asn Pro Leu Leu
225                 230                 235                 240
```

```
Ile Phe Pro Glu Gly Thr Cys Val Asn Asn His Tyr Ser Val Met Phe
                245                 250                 255

Lys Lys Gly Ala Phe Glu Leu Gly Cys Ser Val Cys Pro Ile Ala Ile
            260                 265                 270

Lys Tyr Asn Lys Ile Phe Val Asp Ala Phe Trp Asn Ser Arg Lys Gln
            275                 280                 285

Ser Phe Thr Met His Leu Leu Gln Leu Met Thr Ser Trp Ala Val Val
            290                 295                 300

Cys Asp Val Trp Tyr Leu Glu Pro Gln Val Leu Lys Pro Gly Glu Thr
305                 310                 315                 320

Pro Ile Glu Phe Ala Glu Arg Val Arg Asp Ile Ile Cys Ala Arg Ala
                325                 330                 335

Gly Leu Lys Lys Val Pro Trp Asp Gly Tyr Leu Lys His Ser Arg Pro
            340                 345                 350

Ser Pro Lys Tyr Arg Glu Arg Lys Gln Gln Ser Phe Ala Glu Ser Val
            355                 360                 365

Leu Gln Leu Leu Asp Asn Lys
    370                 375

<210> SEQ ID NO 119
<211> LENGTH: 375
<212> TYPE: PRT
<213> ORGANISM: Gossypium arboreum

<400> SEQUENCE: 119

Met Ser Gly Ala Ala Leu Leu Lys Ser Ser Ala Ser Glu Leu Asp Leu
1               5                   10                  15

Asp Arg Pro Asn Ile Glu Asp Tyr Leu Pro Ser Gly Ser Ser Ile Gln
            20                  25                  30

Gln Pro Thr Ala Lys Leu Arg Leu Arg Asp Leu Leu Asp Ile Ser Pro
            35                  40                  45

Thr Leu Thr Glu Ala Ala Gly Ala Ile Val Asp Asp Ser Phe Thr Arg
    50                  55                  60

Cys Phe Lys Ser Asn Pro Pro Glu Pro Trp Asn Trp Asn Ile Tyr Leu
65                  70                  75                  80

Phe Pro Leu Trp Cys Cys Gly Val Val Ile Arg Tyr Leu Phe Leu Phe
                85                  90                  95

Pro Ala Arg Val Leu Ile Leu Thr Ile Gly Trp Ile Ile Phe Leu Ser
            100                 105                 110

Thr Phe Ile Pro Val Asn Leu Leu Leu Lys Gly His Pro Lys Leu Arg
            115                 120                 125

Ala Lys Leu Glu Arg Phe Leu Val Glu Leu Ile Cys Ser Phe Phe Val
            130                 135                 140

Ala Ser Trp Thr Gly Val Val Lys Tyr His Gly Pro Arg Pro Ser Ile
145                 150                 155                 160

Arg Pro Lys Gln Val Phe Val Ala Asn His Thr Ser Met Ile Asp Phe
                165                 170                 175

Ile Val Leu Glu Gln Met Thr Ala Phe Ala Val Ile Met Gln Lys His
            180                 185                 190

Pro Gly Trp Val Gly Leu Leu Gln Ser Thr Ile Leu Glu Ser Ile Gly
            195                 200                 205

Cys Ile Trp Phe Asn Arg Thr Glu Leu Lys Asp Arg Glu Ile Val Ala
            210                 215                 220

Lys Lys Leu Asn Asp His Val Gln Gly Ala Asp Asn Asn Pro Leu Leu
```

```
               225                 230                 235                 240
Ile Phe Pro Glu Gly Thr Cys Val Asn Asn His Tyr Ser Val Met Phe
                245                 250                 255

Lys Lys Gly Ala Phe Glu Leu Gly Cys Ser Val Cys Pro Ile Ala Ile
                260                 265                 270

Lys Tyr Asn Lys Ile Phe Val Asp Ala Phe Trp Asn Ser Arg Lys Gln
                275                 280                 285

Ser Phe Thr Met His Leu Leu Gln Leu Met Thr Ser Trp Ala Val Val
        290                 295                 300

Cys Asp Val Trp Tyr Leu Glu Pro Gln Val Leu Lys Pro Gly Glu Thr
305                 310                 315                 320

Pro Ile Glu Phe Ala Glu Arg Val Arg Asp Ile Ile Cys Ala Arg Ala
                325                 330                 335

Gly Leu Lys Lys Val Pro Trp Asp Gly Tyr Leu Lys His Ser Arg Pro
                340                 345                 350

Ser Pro Lys Tyr Arg Glu Arg Lys Gln Gln Ser Phe Ala Glu Ser Val
                355                 360                 365

Leu Gln Leu Leu Asp Asn Lys
        370                 375

<210> SEQ ID NO 120
<211> LENGTH: 1116
<212> TYPE: DNA
<213> ORGANISM: Cocos nucifera

<400> SEQUENCE: 120
atggttgagc tgcggtcatc gagctcggag atggatctgg accgcccaa  catcgaggag      60 tacctcacca cggactccat ccaagaatcc cccaagaagc tccacctgag ggacttgctc     120
gacatttctc ccacgctgac ggaggccacc ggcgccatcg ttgatgattc cttcactcgc     180
tgctttaaat cgaatcctcc agagccctgg aattggaatg tctatttatt tcccttatgg     240
tgcttgggag tgattattag atatggaatt ctttttcccc taagagttgc aatcttgaca     300
gcaggttggc tagtgttctt tgcagccttc attcctgtac atttcttgtt gacagcacat     360
aataagtgga ggcgtaaaat agagaggaag ttggttgaga tgatatgcag tgtctttgtt     420
gcttcatgga caggggtagt caagtatcat gggcctcgtc ctagcatgcg ccctcagcag     480
gtatttgttg ccaaccacac ttccatgatt gatttcatca tactagagca gatgacagca     540
tttgctgtta taatgcaaaa gcatcctgga tgggttggat ttattcaaaa gaccatattg     600
gaaggtgttg ttgtatttg gttcaaccgt acagaatcaa aggatcgtga agttgtggca     660
cgaaagttaa gagaacatat tcatggagct gacaacaacc ctcttctgat atttccagaa     720
ggaacttgtg ttaacaacca ttacactgtc atgttcaaga agggtgcttt tgaacttggt     780
tgtgctgttt gcccggttgc aataaagtac aacaaaattt ttgtggatgc cttctggaac     840
agtaagaagc aatcttttac aatgcatttg tttcacctta tgacatcgtg ggctgttgtt     900
tgcgatgttt ggtacctgga gcctcagtac ataagacctg agagacgcc  cattgaattt     960 gctgaaaggg ttagagacat gatatctgtt cgagctggtc tcaaaaaggt cccgtgggat    1020
ggatatttga agtacttccg cccccagtcct aagctaacag agaggaagca gcagatcttt    1080
gcggagtcgg tcttgcagag gttggaggaa aaataa                              1116

<210> SEQ ID NO 121
<211> LENGTH: 1131
<212> TYPE: DNA
```

<213> ORGANISM: Arabidopsis thaliana

<400> SEQUENCE: 121

| | | | | | |
|---|---|---|---|---|---|
| atgagcagta | cggcagggag | gctcgtgact | tcaaaatccg | agcttgacct | cgatcaccct | 60 |
| aacatcgaag | attaccttcc | ttctggttct | tccatcaatg | aacctcgcgg | caagctcagc | 120 |
| ctgcgtgatt | tgctagacat | ctctccaacg | ctcactgaag | ctgctggtgc | cattgttgat | 180 |
| gactcgttca | agatgtttt | caaatcaaat | cctccagaac | cttggaactg | gaatatttac | 240 |
| ttattcccac | tatactgctt | tggggttgtt | gttagatact | gtatcctctt | tcccttgagg | 300 |
| tgcttcactt | tagcttttgg | gtggattatt | ttcctttcat | tgtttatccc | tgtaaatgcg | 360 |
| ttgctgaaag | gtcaagatag | gttgaggaaa | agatagaga | gggtcttggt | ggaaatgatt | 420 |
| tgcagctttt | ttgtcgcctc | atggaccgga | gttgtcaaat | atcacgggcc | acgtcctagc | 480 |
| atccgtccta | agcaggtcta | tgttgccaac | catacttcaa | tgattgattt | catcgtattg | 540 |
| gagcagatga | ccgcatttgc | tgttataatg | cagaagcatc | ctggttgggt | tggtcttctg | 600 |
| caaagcacaa | tattagagag | tgtgggatgt | atctggttca | atcgttcaga | ggcaaaggat | 660 |
| cgtgaaattg | tagcaaaaaa | gttaagggac | catgtccaag | gagctgacag | taatcctctt | 720 |
| ctcatatttc | ccgaagggac | atgtgtaaat | aataattaca | cagtgatgtt | taagaagggt | 780 |
| gcttttgaat | ggactgcac | tgtttgtcca | attgcaatta | aatacaacaa | gatttttgtt | 840 |
| gacgccttct | ggaatagcag | aaaacaatca | tttactatgc | acttgctgca | actcatgaca | 900 |
| tcatgggctg | ttgtatgtga | agtgtggtac | ttggaaccac | aaaccataag | gcccggtgaa | 960 |
| acaggaattg | aatttgcaga | gagggtcaga | gacatgatat | ctcttcgggc | gggtctcaaa | 1020 |
| aaggtccctt | gggatggata | cttgaagtat | tcgagaccaa | gccccaagca | tagtgaacgc | 1080 |
| aagcaacaga | gtttcgcaga | gtcgatcctg | gctagattgg | aagagaagtg | a | 1131 |

<210> SEQ ID NO 122
<211> LENGTH: 1116
<212> TYPE: DNA
<213> ORGANISM: Elaeis guineensis

<400> SEQUENCE: 122

| | | | | | |
|---|---|---|---|---|---|
| atggttgagc | tgcggtcatc | gagctcggag | atggatctgg | accgcccaa | catcgaggag | 60 |
| tacctcccac | cgactccatc | caagaatccc | cccaagaagc | tccacctgag | ggacttgctc | 120 |
| gacatttctc | ccacgctgac | ggaggccgcc | ggcgccatcg | ttgatgattc | cttcactcgc | 180 |
| tgctttaaat | cgaatcctcc | agagccctgg | aattggaatg | tctatttatt | tcccttatgg | 240 |
| tgcttgggag | tgattattag | atacggaatt | ctttttcccc | taagagttgc | aatcttgaca | 300 |
| gcagggtggc | tagtattctt | tgcagccttt | attcctgtac | atttcttgtt | gacagcacat | 360 |
| aataagtgga | ggcgtaaaat | agagaggaag | ttggttgaga | tgatatgcag | tgtctttgtt | 420 |
| gcttcatgga | caggggtggt | caagtatcat | gggcctcgtc | ctagcatgcg | ccctcagcag | 480 |
| gtatttgttg | ccaaccacac | ttccatgatt | gatttcatca | tactagagca | gatgacagca | 540 |
| tttgctgtta | taatgcaaaa | gcatcctgga | tgggtcggat | ttattcaaaa | gactattttg | 600 |
| gaaggtgttg | ttgtatttg | gttcaaccgt | acagaatcaa | aggatcgtga | agttgtggca | 660 |
| cgaaagttaa | gagaacatat | tcacggagct | gacaacaacc | ctcttctgat | atttccagaa | 720 |
| ggaacctgcg | tcaacaacca | ttacactgtc | atgttcaaga | agggtgcttt | tgaacttggt | 780 |
| tgtgctgttt | gcccagtcgc | aataaagtac | aacaaaattt | ttgtggatgc | cttctggaac | 840 |
| agtaagaagc | aatcttttac | aatgcatttg | tttcacctta | tgacatcgtg | ggctgttgtt | 900 |

| | |
|---|---|
| tgcgatgttt ggtacctgga gcctcagtac ataagacctg agagacgcc tattgaattt | 960 |
| gctgaaaggg ttagggacat gatttccatt cgagctggtc tcaaaaaggt gccgtgggat | 1020 |
| ggatatttga aatacttccg ccccagtcct aagctcactg aaagaaagca gcagatattt | 1080 |
| gcagagtcag tcttgcagcg gttggaggaa aaataa | 1116 |

<210> SEQ ID NO 123
<211> LENGTH: 1057
<212> TYPE: DNA
<213> ORGANISM: Phoenix dactylifera

<400> SEQUENCE: 123

| | |
|---|---|
| atggttggac tgcggtcatc gagctcggag atggatcttg accggccgaa cattgaggag | 60 |
| tacctcacca ccgactccat cgaagaatcc cccaagaagc tccacttgag ggacttgctc | 120 |
| gacatttctc ccacgctgac ggaggccgct ggtgctatcg ttgatgattc tttcactcgg | 180 |
| tgctttaaat cgaatcctcc agaacccggg aattggaatg tctatttatt tcccttatgg | 240 |
| tgcttgggag tgattattag atacggaatt ctttttcccc taagagttgc agtcttgaca | 300 |
| gcagggtggc tagtattctt tgcagccttt attcctgcac atttcctgtt gacagctcat | 360 |
| aataagtgga ggcgtaaaat agagaggaag ttggttgaga tgatatgcag tgtctttgtt | 420 |
| gcttcatgga caggggtggt caagtatcat gggcctcgtc ctagcatgcg cccccagcag | 480 |
| gtatttgttg ccaaccacac ttcaatgatt gatttcatca tactagagca gatgacagca | 540 |
| tttgctgtta tcatgcaaaa gcatcctgga tgggtcggat ttattcagaa gactattttg | 600 |
| gaaggtgttg gttgtatttg gttcaaccgt acagaatcaa aggatcgtga agttgtggca | 660 |
| cgaaagttaa gagaacatat tcaaggagct gacaacaacc ctcttctgat atttccagaa | 720 |
| ggaacctgcg ttaacaacca ttacactgtc atgttcaaga agggtgcttt tgaacttggt | 780 |
| tgtgctgttt gcccagttgc aataaagtac aacaaaattt ttgtggatgc tttctggaac | 840 |
| agtaagaagc aatcttttac gatgcatttg tttcacctta tgacatcatg ggctgttgtt | 900 |
| tgtgatgttt ggtatctgga gcctcagtac ataagacctg agagacgcc cattgaattt | 960 |
| gctgaaaggg ttagagacat gatttctgtt cgagctggtc tcagaaaggt cccatgggat | 1020 |
| ggatatttga aatacttccg cccgagtcct aagctaa | 1057 |

<210> SEQ ID NO 124
<211> LENGTH: 1116
<212> TYPE: DNA
<213> ORGANISM: Musa acuminata

<400> SEQUENCE: 124

| | |
|---|---|
| atggctgggt ggctaccctc gagcacggag atggatctcg accgcccaa catcgacgag | 60 |
| tacctcaccg tggagtcgat ccgggaggcc cccaagaagc tccacctgag ggacctcctc | 120 |
| gacatttctc ctactctcaa agaagctgcc ggcgccatcg tggacgactc cttcactcgt | 180 |
| tgctttaagt cgaatccttc agaaccctgg aattggaata tctatttgtt ccctttatgg | 240 |
| tgcttgggag tagttattag atatgggatt ctttttccat tcagagttat aatcttggtt | 300 |
| gcaggatgga tagtattctt tgcagccttt tcactggtgc atttccttt aggagaacat | 360 |
| aataagtgga agcgtgaaat agagaggaaa ctggttgaga tgatatgcag cgtatttgtt | 420 |
| gcttcatgga cggcagtgat taaataccat ggacctcgtc ccagcatgcg ccctcaacag | 480 |
| gtcttcgttg ccaaccacac ttctatgatt gatttcatca tcttagaaca gatgacagca | 540 |

```
tttgctgtca ttatgcaaaa gcatcctggt tgggttggat ttatccagaa gatcatcgta        600
gaaagtttag gttgtatatg gttcaaccgt acagaggcta aggaccgtga aattgttgct        660
agaaagttga gagaacacat tcaaggagtt gacaacaacc ctcttctgat atttcctgag        720
ggaacttgcg ttaacaacca ttatactgtt atgttcaaga agggtgcttt tgaacttggt        780
tgtgctgttt gtcctgtagc aatcaagtac aacaagattt tgtggatgc tttctggaac         840 agcaaaaagc aatctttcac gatgcactta gtacagctta tgacatcatg ggctgttgtt        900
tgtgatgttt ggtacctgga gcctcagtat ataaggcctg agagactcc tattgaattt         960 gctgaagggg ttcaagacat gatctctgtt cgagctggtc tcaaaaaggt cccatgggat       1020
ggctatctaa agtacttccg ccccagtccc aagctcatag agcgcaagca gcagatcttt       1080
gcggagtcag tcttacagcg attggaggag aaatga                                 1116
```

```
<210> SEQ ID NO 125
<211> LENGTH: 1119
<212> TYPE: DNA
<213> ORGANISM: Ananas comosus

<400> SEQUENCE: 125
atggctgaag ctctgggctc gtcgagcgcg gagatggatc tcgaccgtcc caacctcgag         60
gagtacctcc ccaccgactc catccaagac tcccccaaaa acctccacct gagggacctg        120
ctcgatatct cccccacgct caccgaggcc gcggcgcca tcgttgatga ctcattcact         180
cgctgcttta aatcaaatcc tccagaacca tggaattgga atatatattt gttccctcta        240
tggtgcctcg agtcgttgt aagatatggg attctttttc cactcagagt tgcagtcttg         300
gcgatagggt ggatagtatt tttttctgcc ttcttccctg tacatttctt attgaaaggg        360
tatcccaagt ggaggcgcaa actagagaga aaattggttg agatgatgtg cagtgtattt        420
gttgcttcat ggactggagt cgtaaaatat catggaccac gcccaagcac gcgccctcat        480
caggtatttg ttgctaatca cacctccatg atcgatttca tcattttaga acaaatgact       540
gcatttgctg ttatcatgca aaacatcct ggatggggttg gatttattca gaagaccatc        600
ttagaaagtg taggatgtat ttggttcaac cgaacggagt ctaaggatcg cggagttgtc        660
gggcggaagc taagagaaca tgttcaagga gtagacaaca accctcttct gatatttcca        720
gaaggaacct gcgtaaacaa tcactacact gtcatgttta agaagggtgc ttttgagctt        780
ggatgtgctg tttgcccaat agcaatcaaa tacaacaaaa ttttttgtgga tgccttctgg        840 aacagtaaga agcaatcttt taccatgcat ctggtccgcc tcatgacgtc gtgggctgtt        900
gtctgtgatg tgtggtactt ggagcctcag tacctgagac ctggggagac gccaattgaa        960
tttgctgaaa gggttagaga catgatttct gctcgagctg gtctaaagaa ggttccatgg       1020
gatgggtatc tgaagtactt cgtcctagc cccaagcata cagaacggaa gcagcagatc        1080
tttgcagagt caatcttgcg gcggttggag aggaaatga                              1119
```

```
<210> SEQ ID NO 126
<211> LENGTH: 1113
<212> TYPE: DNA
<213> ORGANISM: Asparagus officinalis

<400> SEQUENCE: 126
atggcggggc tggagtcctc gagcgcaggg atcgacgtcg accctccaaa tattgaagac         60
tatctcacat ccgatgccct ccatcaacct cataagaagc ttcaattgaa ggatttactc        120
gatatttctc ctacactaac tgaggctgca ggagcaattg ttgatgactc atttacacga        180
```

```
tgtttcaagt caaatcctcc cgaaccctgg aattggaatg tctacctatt tcccttgtgg     240
tgcttgggag tggttgttcg atatgggatc cttttccct tgagagttat gactctggca      300
gctggatgga ttgtgttctt ttcagccttt cttcctgttc attatctaat gaaagggcag     360
aacaaatgga aaataatat agagagaaaa ttggtggaga tgatatgtag tgttttgtt       420 gcttcttgga ctggtgttgt caggtatcac ggacctcgtc ctagcatgcg ccctcaacag     480
gtatttgtgg cgaatcatac ttcgatgatt gatttcatca ttttagagca gatggctgca    540
tttgctgtaa tcatgcagaa gcatcctgga tgggttggtt ccttcagac gacaattttg     600 gaaagcatag gttctatttg gttcaatcgt accgaggcca aggatcgcga agttgtagca    660
agaaagttaa gagaacatac tgaagggac aacaatcctt tactaatatt tccggaagga    720
acttgtgtga acaatgacta cactgttatg ttcaaaaagg gcgcatttga actgggatgt   780
gctgtttgtc ctgtagccat caagtacaat aaaattttcg tggacgcctt ctggaacagc   840
aagaagcaat cttttacgat gcatctgatg cgccttatga catcatgggc tgtggtatgt   900
gatgtttggt atcttgaacc acagtatctg aaaccgggag agacttctat tgaattcgct   960
gaaagggtca gggatatgat ttcggtccga gctggtctca gaaaggtccc gtgggatgga   1020
tatttgaagt acttccgccc aagtcctaag cttacagagc gcaagcagca aatatttgcg   1080
gaatcagtcc tacggcggct ggaagaaaag tga                                  1113

<210> SEQ ID NO 127
<211> LENGTH: 1113
<212> TYPE: DNA
<213> ORGANISM: Oryza brachyantha

<400> SEQUENCE: 127
atggcgtcct catcggtggc gggggacatc gagctggacc ggccgaacct ggaggattac     60
ctcccgcccg actcgctgcc gcaggaatcc cccgggaatc tccatctgcg cgatctgctt    120
gacatctcgc cggtgctcac tgaagcggcg ggggcggccg tcgatgattc attcacacgt    180
tgctttaagt ccaattctcc agagccatgg aattggaaca tttatttatt cccactatgg    240
tgcttgggag tagtgataag atatggaata ctcttcccac taagggggctt aactcttcta   300 gttggatgga tagcttttctt cgctgccttt ttctctgtgc atttcttatt taaagggcaa    360
aagatgagaa gtaaaataga gagaaaactg gttgaaatga tgtgcagtgt ttttgttgct    420
tcttggactg gagtgatcaa gtatcatgga cctcgcccaa gcacacggcc tcatcaggta    480
tttgttgcaa accacacatc gatgatagac ttcattattc tggagcagat gacagcattt    540
gctgtcatta tgcaaaagca tcctggatgg gttggattta ttcagaagac tatattggaa    600
agtgtgggtt gcatctggtt caatcgtaac gatctcaagg atcgtgaagt agtagcaaaa    660
aagttacgag atcatgttca acatccagac aacaatcctc tcctaattt ccctgaagga    720 acttgtgtta acaaccagta cactgtcatg ttcaagaagg gtgcttttga gcttggctgt    780
gctgtatgcc caatagctat caaatacaat aaaatatttg ttgatgcctt ctggaatagt    840
aagaagcaat cttttacaat gcacttggtt cggcttatga catcatgggc agttgtgtgt   900
gatgtatggt acttggagcc gcaatatcta aaggaggag aaacagcaat tcaatttgct    960
gaaagagtaa gagacatgat agctgctaga gctggtctta agaaggttcc atgggacgga   1020
tatctgaaac acaaccgccc tagccccaaa cacactgaag agaagcagcg catctttgct   1080
gattctgtgt tgcagagact ggaggaaagc taa                                  1113
```

<210> SEQ ID NO 128
<211> LENGTH: 1113
<212> TYPE: DNA
<213> ORGANISM: Oryza sativa

<400> SEQUENCE: 128

| | | | | | |
|---|---|---|---|---|---|
| atggcgacct | cgtcggtggc | ggggggacatc | gagctggacc | ggccgaacct | ggaggactac | 60 |
| ctcccatccg | actcgctgcc | gcaggagttc | cccaggaatc | tccatctgcg | cgatctgctg | 120 |
| gacatctcgc | cggtgctcac | tgaagcggcg | ggcgccatcg | tcgatgattc | attcacacgt | 180 |
| tgctttaagt | caaattctcc | agagccatgg | aattggaaca | tttatttatt | cccattgtgg | 240 |
| tgcttgggag | tagtgataag | atacggaata | ctattcccgc | tgaggggcct | aactcttcta | 300 |
| gttggatggt | tagcattctt | tgctgccttt | tttcctgtac | atttcttatt | gaaaggtcaa | 360 |
| aagatgagaa | gtaaaataga | gagaaagctg | gttgaaatga | tgtgcagtgt | ttttgttgct | 420 |
| tcttggactg | gagtgatcaa | gtatcatggg | cctcgcccaa | gcacacggcc | tcatcaggta | 480 |
| tttgttgcaa | accatacatc | gatgatagat | ttcattattc | tggagcagat | gacagcattt | 540 |
| gctgtcatta | tgcaaaagca | tcctggatgg | gttggattta | tcagaagac | tatcttggaa | 600 |
| agtgttggtt | gcatctggtt | taatcgcaat | gatctcaagg | atcgtgaagt | ggttgcaaaa | 660 |
| aagttacgag | atcatgttca | acatccagac | agcaatcctc | tcctgatttt | ccctgaagga | 720 |
| acttgtgtta | caaccagta | cactgtcatg | ttcaagaagg | gtgcttttga | gcttggctgt | 780 |
| gctgtatgcc | aatagctat | caaatacaat | aaaatatttg | ttgatgcctt | ctggaatagt | 840 |
| aagaagcaat | cgtttacaat | gcacttggtt | aggcttatga | catcatgggc | agttgtgtgt | 900 |
| gatgtatggt | acttggagcc | tcagtatctg | agggatggag | aaacagcaat | tgaatttgct | 960 |
| gaaagagtaa | gagacatgat | agctgctaga | gctggtctta | agaaggttcc | gtgggacggg | 1020 |
| tatctgaaac | acaaccgccc | tagtcccaaa | cacactgaag | agaagcagcg | catctttgct | 1080 |
| gactctgtgt | tgcggagact | ggaggaaagc | taa | | | 1113 |

<210> SEQ ID NO 129
<211> LENGTH: 1092
<212> TYPE: DNA
<213> ORGANISM: Nelumbo nucifera

<400> SEQUENCE: 129

| | | | | | |
|---|---|---|---|---|---|
| atggacttgg | atcgaccaaa | catagaggaa | tatttacctt | cagaagccat | tcaagagtct | 60 |
| aacgagaagc | ttcacttgcg | tgatttgctc | gacatttcgc | ctactctaac | cgaggctgct | 120 |
| ggtgccattg | ttgatgattc | tttcactcgt | tgtttcaagt | caaatccgtc | agaaccttgg | 180 |
| aattggaatg | tatatttatt | tccactttgg | tgctttggag | tggtggtaag | atatgggatt | 240 |
| ctttttcctg | ttagagttct | agtgttaaca | attgggtgga | taatattcct | ttcatccttc | 300 |
| attcctgcac | atttcctatt | gagaagtcat | gataagtgga | ggaagaagat | agagagatat | 360 |
| ctggtggagt | taatatgcag | cttctttgtt | gcatcatgga | ctgggggttgt | caaatatcat | 420 |
| gggccacggc | caagcatgcg | acccaagcag | gttttttgtgg | ccaatcatac | ttccatgata | 480 |
| gattttattg | ttttagaaca | gatgactgca | tttgctgtaa | ttatgcagaa | gcatcctgga | 540 |
| tgggttgggc | ttttgcaaag | cactattttg | gagagtgtag | gttgtatctg | gttcaatcgt | 600 |
| gcagaagcaa | aggaccgtga | aattgtagca | agaaagttaa | gagaccacat | tcaaggggtt | 660 |
| gacaacaatc | ctcttcttat | atttccagaa | ggaacatgtg | taaataacca | ctatacagtc | 720 |
| atgttcaaga | agggtgcatt | tgaacttgga | tgcactgttt | gtccaatagc | aatcaagtac | 780 |

```
aataaaattt tgttgatgc cttctggaat agtaagaagc aatctttttac catgcactta     840 ctgcacctta tgacttcatg ggctgttgtt tgtgatgttt ggtatttgga ccgcaaaat     900 attagacctg gagagacacc catagaattt gcagagaggg tacgagacat aatttctgtt     960
cgagcaggtc ttaaaaaggt tccatgggat ggatatttga aatattctcg tcctagcccc    1020
aaacacagag aaagaaagca acaaaggttt gtagagtcgg tattgcagcg cttggagaaa    1080
aagggaaaat ga                                                        1092

<210> SEQ ID NO 130
<211> LENGTH: 1131
<212> TYPE: DNA
<213> ORGANISM: Vitis vinifera

<400> SEQUENCE: 130
atggccaacg ctcccgataa taagctcact tcctcaagct ccgagctcga cttggatcgc      60
cccaatctcg aagactacct tccctccgga tccatgcaag aacctcgcgg caagcttcgc     120
ctgcgtgatt tattggacat ttcgccgacc ctaaccgagg ctgctggggc cattgttgac     180 gactcttttca cacgatgttt caagtcgaac cctccggagc cttggaactg gaatgtgtat     240
ttgtttcctc tttggtgttt gggagtggta attcgatatg gaattttatt tcccacaagg     300
gttctagtac tcacactggg gtggataata ttcctttcat cctttattcc agtacatttt     360
ctattgaagg gaaacgataa gttgaggaaa agttggagaa gatgtctagt ggagttaatt     420
tgcagcttct tgttgcatc atggactgga gttgtcaagt accatgggcc acggcctagc     480
aggaggcctc agcaggtttt tgttgccaat catacttcca tgattgattt tatcgtttta     540
gaacagatga ctgcatttgc agttattatg cagaagcatc ctggctgggt tggattgctg     600
caaagtacca ttttggagag tgtaggatgt atctggttca atcgtacaga agcaaaggac     660
cgtgaaattg ttgctaggaa gctaagggat catgttcagg gggctgacaa caaccctctt     720
ctcatattcc cagaaggaac ttgtgtgaat aaccactaca ctgtcatgtt caagaagggc     780
gcattcgaac ttggctgcac tgtttgccct attgcaataa agtacaataa gattttcgtt     840
gatgctttct ggaacagtaa gaagcaatcc tttacaatgc atcttctgca gcttatgaca     900
tcctgggctg tcgtttgtga tgtttggtac ttagagcccc aaacattgaa gccaggagag     960
acacccattg aatttgcaga gagggtcagg gacataattt ctcttcgagc tggtttgaaa    1020
aaggttcctt gggatggata tttgaagtac tctcgcccta gcccaaagca tagagagcag    1080
aagcagcaga gctttgctga ttcagtgtta cggcgcctgg aagagaagtg a             1131

<210> SEQ ID NO 131
<211> LENGTH: 1122
<212> TYPE: DNA
<213> ORGANISM: Nicotiana tomentosiformis

<400> SEQUENCE: 131
atgaatatga ataagctaaa aacatcaagc tccgaattgg acttggatcg acccaatctc      60
gaagattatc ttccaactgg atccatccca gaaccccatg gcaagcttcg cctgcgtgat     120
ttaattgata tttctcccac cctaactgag gctgctggtg ccattgttga cgattctttc     180
accagatgct tcaagtcaaa tccaccagag ccttggaact ggaacattta tttgttccct     240
ttatggtgct tgggggttgt tgttagatat gggattcttt tccctataag agttattgtc     300
ttgacaatag gatggataat attcctctct tgctatatcc cggtgcattt cctgctgaaa     360
```

```
ggacacgata agttcaggaa aaagcttgag agatgtctgg tggagctgat atgcagtttc    420
tttgttgcat cttggactgg ggttgtcaaa taccatggtc cacggcctag catacgacct    480
aagcaggttt ttgtggcgaa tcacacgtca atgatagatt ttattgtcct agagcagatg    540
actgcatttg cagtgatcat gcagaagcat cctggatggg ttggactact gcagagtacc    600
attttagaag gtgttggatg tatctggttc aaccgctcag aagccaagga tcgtgaaatt    660
gtagcacgaa agttgaggca acatgttgaa ggggccgata caacccctct tcttatattc    720
cccgagggaa cttgcgtaaa taaccactac actgtcatgt tcaaaaaggg agcatttgaa    780
ctcggttgca ctgtttgtcc tgttgcaatc aagtacaaca aaattttgt tgacgccttt    840
tggaatagta gaaaacaatc cttcacaatg cacctcttgc agctcatgac atcttgggct    900
gttgtctgtg atgtttggta cctggagcct cagaacataa gacctgggga gactccaatc    960
gagtttgcag agagggtgag ggacatcatt tctgctagag caggtcttaa aaaggttcct   1020
tgggatggat atttaaaata ctctcgtcct agccccaagc atcgagagag gaagcaacag   1080
agttttgcag aatcagtgct gcgtcgcctg gaagagaagt ag                      1122

<210> SEQ ID NO 132
<211> LENGTH: 1128
<212> TYPE: DNA
<213> ORGANISM: Jatropha curcas

<400> SEQUENCE: 132
atggctactc caggtaagct aaagacctcg agctctgaat tggacttgga tcgacccaat     60
atcgaagact accttccttc tggagtctct attcaagaac ctcgtggcaa gcttcgtctg    120
cgtgatttgc ttgacatttc gccgacccta acggaggctg ctggtgccat tgttgatgac    180
acctttacaa ggtgtttcaa gtcaaatcct ccagaaccat ggaattggaa catatatcta    240
tttccccttt ggtgctgcgg tgtggtgtgt cgatatggga ttttgtttcc catcagggtt    300
ctagtactga caatagggtg gataatttc ctttcatgct acattcctgt gcatttccta    360
cttaaaggac atgacaagtt gagaaaaaag cttgagagat gtttggtgga gttaatttgc    420
agcttctttg tggcatcatg gaccggagtt gtcaagtacc atggtccacg gcctagcatc    480
cgacctaaac aggttttgt ggccaatcat acctccatga ttgattttat catcttggaa    540
cagatgactg catttgctgt tattatgcag aagcatcctg gatgggttgg actactgcaa    600
agcactatat tagagagtgt cggatgtatc tggttcaatc gttcagaggc aaaggatcgt    660
gaaattgtaa caaaaaagtt aagggatcat gtacaggggg ctgacaataa ccctcttctc    720
atatttcctg aaggaacttg tgtaaataat cactatactg taatgttcaa gaagggtgca    780
ttcgaactgg gatgtactgt ttgtccaatt gcaatcaaat acaacaaaat ttttgttgat    840
gcttttgga acagccggaa gcagtcattt acaacgcatt gctgcaact catgacttcc    900
tgggctgttg tttgtgatgt atggtacttg gagcccacaa atctgaaacc tggagagaca    960
cccattgagt ttgctgagag ggtcagggac ataatatctg tacgagcagg tctcaaaaag   1020
gttccttggg atggatatct aaagtattct cgccctagcc caaagcatag agagcgaaag   1080
caacaaagct tgctgagtc agtgctgcag cgactggagg agaaatga                1128

<210> SEQ ID NO 133
<211> LENGTH: 1131
<212> TYPE: DNA
<213> ORGANISM: Glycine max

<400> SEQUENCE: 133
```

```
atgaataact cagggacacc caagtcttca agttctgaat tggatcttga tcgacccaac    60
attgaggatt acctcccttc agggtccacc attcaacaag aacctcatgg aaagcttttc   120
ctgcatgatt tgctcaatat ttctcctact ttgtctgagg ctgcaggtgc tattgtagat   180
gactcattca caagatgctt caagtcaaat cctccagaac catggaattg gaatgtttat   240
ttgtttcctt tgtggtgttt tggagttgtg attcgatact tgattctgtt cccaatcagg   300
gttatagggt taacaatagg atggataata tttctttcat ccttcattcc ggtgcacttc   360
ctattgaaag gacatgacaa gttaaggaga agtattgaga ggtctttggt agagatgatg   420
tgcagtttct tgttgcatc ttggactggg gttgttaagt atcatggacc caggcctagc   480
aggagaccaa agcaggtttt tgtagccaac catacttcca tgattgattt cattatctta   540
gaacagatga ctgcttttgc tgttattatg cagaagcatc ctggatgggt tggattattg   600
cagagtacca ttttggagag tctaggatgc atctggttca accgtacaga ggcaaaggat   660
cgggaaatag tagcaaggaa attgagggat catgtccagg gagctgataa caacccctt   720
ctcatatttc ctgaaggaac ttgtgtaaat aatcactata cagtcatgtt caagaagggt   780
gcatttgaac ttggctgcac agtttgccca gttgcaatca agtacaataa gattttgta   840
gatgcttttt ggaatagtcg aaagcaatca ttcactatgc atctgttgca gctaatgacg   900
tcttgggcag ttgtttgtga tgtttggtac ttggagccac aaaatctgaa gccaggagag   960
acgcctattg agttcgcaga gagggtgaga gacataatct cagttcgtgc tggccttaaa  1020
aaggttcctt gggatggata tctgaagtat tctcgtccta gcccaaagca tagagaaagg  1080
aagcaacaga actttgctga gtcagtgctg cggcgatggg aggaaaagtg a           1131

<210> SEQ ID NO 134
<211> LENGTH: 1116
<212> TYPE: DNA
<213> ORGANISM: Sesamum indicum

<400> SEQUENCE: 134
atgagtaagc ttaacacatc cagctccgaa ttggattttg atcgcccaa catcgaggac    60
tatctcccat ccggatccat tcaagagcct cacggcaaac tccgcctgcg tgatttgctc   120
gatatttcac caactctcac tgaggccgct ggtgcaattg ttgatgactc tttcaccaga   180
tgcttcaagt caaatcctcc agaacctgg aactggaaca tatacttgtt tcctttatgg   240
tgcttgggag tggtcatcag atatggcctt cttttcccat aagggtaat agtgttgaca   300
ataggatgga ttatatttct atcatgctat tttcctgtgc atttcctgtt aagagggcac   360
gacaaattga ggaaaagatt agagagaggt ctagtggagt tgatttgcag tttcttcgtt   420
gcatcatgga caggggttgt caagtatcat ggtccacggc cgtccatgcg acctaagcag   480
gtttttgtgg cgaatcacac atccatgatt gatttcattg ttttggaaca aatgactgct   540
tttgcagtga ttatgcagaa gcatcctggg tgggttggat tattgcagag cacaattttg   600
gaaagtctag gatgtatctg gttcaaccgc tcagagtcca aggatcgtga aattgttgca   660
aaaaagctaa gggaacatgt ccatgatgct gataacaatc ctcttcttat attcccggaa   720
ggaacttgtg tgaataacca ttacactgtt atgtttaaga agggtgcatt tgaacttggc   780
tgcactgtct gtccaatagc aatcaagtac aacaagatat tgttgatgc cttctggaat   840
agccgaaagc aatccttcac tacacacttg ttgcagctta tgacatcctg gctgttgtt   900
tgtgacgttt ggtacctaga gcctcaaaat ctgaacctg gggaacacc cattgaattt   960
```

```
gcagagaggg tgagggacat tatttctgtt cgggccggcc tcagaaaggt gccttgggat   1020
ggatatttga agtactctcg gcctagtccg aagcatcgtg aacgcaagca acaaagcttt   1080
gcagagtcaa ttctccgtcg cttggaagag aaatag                             1116

<210> SEQ ID NO 135
<211> LENGTH: 1095
<212> TYPE: DNA
<213> ORGANISM: Brachypodium distachyon

<400> SEQUENCE: 135
atggcgtcgt cgctcgacgc gccgaaccct gatgattacc tccccacgga ctcgctcccg     60
caggaacccc ccaggagcct caatctgcgc gatctgctgg acatctcgcc agtgctcact    120
gaagcggcgg cgccatcgt ggatgattcg ttcacacgct gctttaagtc aaattctcca    180
gagccatgga actggaacat ttatttgttc ccgttatggt gcttcggagt agtcgtaaga    240
tacggactac tgtttccact cagggtatta acgcttggat taggatggat ggtattcttt    300
gctgcctttt ttcccgtgca tttcctattg aaagggcaaa ataaactgag aagtaaaata    360
gagagaaagc tcgttgaaat gatgtgcagt gttttttgttg cttcttggac tggagtaatc    420
aagtaccatg gaccacgccc aagctcacgg ccttatcagg tatttgttgc aaaccataca    480
tcaatgatag atttcattat tctggagcag atgacagcat tgctgtcat tatgcaaaag    540 catcctggat gggttggatt tattcagaag actattttgg aaagtgtggg ttgcatctgg    600
tttaatcgta atgatcttaa ggatcgtgaa gtagttggca aaagttacg tgatcatgtt    660 caacgtccag acaacaaccc tctcttgatt ttcccagaag aacttgtgt taacaaccag    720 tacactgtaa tgttcaagaa gggtgctttt gagcttgggt gtgctgtatg tccgatagct    780
atcaagtata taaaatatt tgttgatgcc ttctggaata gtaagaagca atctttcaca    840
atgcacttgg gtcggcttat gacatcatgg gctgtagtgt gtgatgtttg gttcttggaa    900
cctcaatatc tcagggaagg agagacatcg attgcattta ctgaaagagt aagggacatg    960
atagctgctc gagccggtct taagaaggtt ctgtgggatg gtatctgaa gcataaccgt   1020 cctagcccca aacacactga ggagaagcag cgcatatttg cagaatcggt gttgaagaga   1080
ctagaggaaa gctaa                                                    1095

<210> SEQ ID NO 136
<211> LENGTH: 1116
<212> TYPE: DNA
<213> ORGANISM: Setaria italica

<400> SEQUENCE: 136
atggcgagct cctcggtggc ggcggacatg gagctggacc gccccaatct ggaggactac     60
ctcccgcccg actcgctccc gcaggaggcg ccccggaatc tccatctgcg cgatttgctg    120
gacatctcgc cagtgctcac cgaggcagca ggcgccatcg tcgatgactc cttcacgcgt    180
tgctttaagt caaattctcc agagccatgg aattggaaca tatatctgtt ccccttatgg    240
tgcttgggtg tagtaataag atatggaata ctcttcccac tgaggtcctt aacgcttgca    300
ataggatggt tagcatttt tgctgccttt ttcctgtcc atttcctatt gaaagggcaa    360
gacaagttga gaagtaaaat tgagaggaag ttggttgaaa tgatgtgcag tgtttttgtt    420
gcttcatgga ctggagtgat caagtatcat ggaccacgcc caagcacacg acctcatcag    480
gtattcgttg caaaccatac atcaatgata gatttcatta ttctggagca aatgacagca    540
tttgctgtca tcatgcagaa gcatcctgga tgggttggat ttattcagaa gactatcttg    600
```

```
gaaagtgtcg gttgcatctg gtttaatcgt aatgatcttc gggatcgtga agttacggca    660
cggaagttac gtgatcatgt tcaacaacca gacaaaaatc ctctcttgat ttttccggaa    720
ggaacttgtg ttaacaacca gtacacggtc atgttcaaga agggtgcctt tgagcttggc    780
tgcgctgtct gtccaatagc tatcaagtac aataaaatat ttgttgatgc cttttggaac    840
agtaagaagc aatcttttac aatgcacttg gtccggctga tgacatcatg ggctgttgtg    900
tgtgatgttt ggtacttacc tcctcaatat ctgagggagg gagagacggc aattgcattt    960
gctgagagag taagggacat gatagccgct agagctggac taaaaaaggt tccgtgggat   1020
ggctatctga aacacaaccg tcctagtccc aaacacactg aagagaaaca acgcatattt   1080
gccgaatctg tcctgatgag actggaggag aaatga                             1116
```

<210> SEQ ID NO 137
<211> LENGTH: 1131
<212> TYPE: DNA
<213> ORGANISM: Cicer arietinum

<400> SEQUENCE: 137

```
atgaatagca ctggaacact taagtcttca agttctgagt tggatcttga tcgacccaac     60
attgaggatt atctcccttc aggagccgcc attcaacaag aacctcgcgg caagcttcgc    120
ctgcatgact tgcttgatat ttctcctaca ctatctgagg cagctggtgc tattgtagat    180
gactcattca agatgttt caagtcaaat cctccagaac catggaattg aatatatat    240 ttgtttcctt tgtggtgttt tggagttgtt gttcgatatt tgatactgtt ccctacaagg    300
gttcttgggt taacattagg atggataata tttctttctg ctttcattcc agtgcacctc    360
ctattgaaag acatgacaa gttgaggaga aatattgaga ggtctttggt agagatgatg    420
tgcggtttct ttgttgcatc ttggactggg gttgtcaagt accatgggcc aaagcccagc    480
aggcgaccaa acaggtttt tgttgccaac cacacttcca tgattgattt cattatctta    540
gaacagatga ctgcttttgc tgttattatg cagaagcatc ctggatgggt tggattgttg    600
caaagcacca ttttggagag tgtaggatgt atctggttca atcgcacaga ggcaaaggat    660
cgagaaattg tggcaagaaa attgagggaa catgtccagg gagctgacaa caatcctctt    720
ctcatatttc cagagggaac ttgtgtaaat aatcactaca cagtcatgtt taagaagggt    780
gcatttgaac ttggctgcac agtttgccct gttgcaatca aatacaacaa aatttttgtc    840
gatgcatttt ggaatagtcg aaagcaatca ttcactaaac atctgttgca gctaatgaca    900
tcatgggctc ttgtttgtga tgtttggtac ttggagccac aaaaacctaaa gccaggagag    960 acaccaattg agtttgccga aagggtgaga gacataatct cacatcgtgc tggtcttaaa   1020
aaggttcctt gggatggata tctgaagtat tcgcgtccta gcccaaagca tagagaaaga   1080
aagcaacaga actttgctga gtcggtgctg cggcgtttgg aagaaaaata a            1131
```

<210> SEQ ID NO 138
<211> LENGTH: 1116
<212> TYPE: DNA
<213> ORGANISM: Zea mays

<400> SEQUENCE: 138

```
atggcgagct cgtctgtggc ggcggacatg gagctggacc gccccaacct ggaggactac     60
ctcccgcccg actcgctccc gcaggaggcg cccaggaatc tccatctgcg cgatctgctt    120
gacatctcgc cggtgctaac cgaggcagcg ggtgccatag tcgatgattc attcacgcgc    180
```

-continued

| | |
|---|---|
| tgctttaagt cgaattctcc agaaccatgg aactggaaca tatatttgtt ccctttatgg | 240 |
| tgcttcggtg tagtaattcg atatggatta ctcttcccac tgaggtcctt aacgcttgca | 300 |
| ataggatggt tagcattttt tgctgccttt ttccccgtgc atttcctatt gaaaggtcaa | 360 |
| gacaagttga gaataaaat tgagaggaag ttggttgaaa tgatgtgcag tgttttttgtt | 420 |
| gcttcatgga ctggagtgat caagtaccat ggaccacgcc aagcacacg acctcatcag | 480 |
| gtatttgttg caaccatac atcaatgata gatttcatta ttctggagca aatgacagca | 540 |
| tttgctgtca tcatgcagaa gcatcctgga tgggttggat ttattcagaa gactatcttg | 600 |
| gaaagtgtgg gttgcatctg gtttaaccgt aatgatctcc gggatcgtga agttacggca | 660 |
| cggaagttgc gtgatcatgt tcaacatcca gacaaaaacc ctctcttgat tttcccagaa | 720 |
| ggaacttgtg ttaacaacca gtatacggtc atgttcaaga agggtgcctt tgagcttggg | 780 |
| tgtgctgtct gtccaatagc tatcaaatac aataaaatat tgttgatgc cttttggaac | 840 |
| agtaagaagc aatcttttac gatgcacttg gtccggttga tgacatcatg ggctgttgtg | 900 |
| tgtgatgttt ggtacttgga gcctcaatat ctgagggagg gagagactgc aattgcgttt | 960 |
| gctgagagag taagggacat gatagcagct agagctggtc ttaagaaggt cccgtgggat | 1020 |
| ggctatctga aacacaaccg ccctagtccc aaacacaccg aagagaagca acgcatattc | 1080 |
| gccgaatctg tcttgaggag actagaggag aaatga | 1116 |

<210> SEQ ID NO 139
<211> LENGTH: 1137
<212> TYPE: DNA
<213> ORGANISM: Gossypium hirsutum

<400> SEQUENCE: 139

| | |
|---|---|
| atgaacagta gtgaagggaa gttgaaatca tcgagttccg aattggattt ggatcgaccc | 60 |
| aacatcgaag attatctccc ttctggatct tccattcaag aaccacatgg caagcttcgc | 120 |
| ctgcgggatt tgcttgatat ttctcccgct ttaactgaag ctgctggtgc tattgttgat | 180 |
| gattctttca cacggtgttt taagtcgaat cccccggaac cgtggaactg gaatgtgtat | 240 |
| cttttttcctc tctggtgttg tggtgtggta tttcggtact tgattttgtt ccctatgagg | 300 |
| gctttaattt tgacaatagg atggataata tttctgtcat gcttcattcc tgtgcacttt | 360 |
| cttctcaaag ggaacgataa cttgcggaaa aagatggaga gggcgttggt ggagctaatc | 420 |
| tgcagcttct tgttgcatc ctggactgga gttgttaagt accatggacc gcggcctagc | 480 |
| atgcggccca gcaggtgtt tgtggccaat catacttcta tgattgattt catcatatta | 540 |
| gaacagatga ctgcatttgc tgtcattatg cagaagcacc ctggatgggt tggactgcta | 600 |
| cagagcacta ttttagagag tgtagggtgt atttggttta accgttcaga ggccaaagat | 660 |
| cgtgaaattg taacaaggaa gttaagggag catagtcagg gagctgacaa taaccctctt | 720 |
| ctcatatttc ccgaagggac atgtgtaaac aatcaataca gcgttatgtt caagaagggt | 780 |
| gcattcgaac ttggttgcac tgtttgcccg attgcaataa agtacaataa aatttttgtt | 840 |
| gatgcctttt ggaatagccg gaagcagtcc tttacaatgc atttattgca gcttatgaca | 900 |
| tcctgggctc ttgtttgcga tgtttggtac ctagagcccc aaaatctaag gcctggagaa | 960 |
| acacccatcg agtttgcaga gaggatcaga gacataatct ctgttcgagc aggtcttaaa | 1020 |
| aaggttccat gggacggata tttgaagtat tctcgcccga gccctaagca tagagagcga | 1080 |
| aaacaacaaa gttttgccga atctgttctt cggggactgg aactggaaga aaatga | 1137 |

```
<210> SEQ ID NO 140
<211> LENGTH: 1128
<212> TYPE: DNA
<213> ORGANISM: Eucalyptus grandis

<400> SEQUENCE: 140
atggcgagcc ccaggaagct gccgacctcg agctccgagc tggacctgga tcgcctcaac      60
atcgaggatt acctcccttc cggatcctcc atccacgagc ccccggcca gctccgcctg     120
cgcgatttgc ttgatatcac gccgactctg accgaggccg ccggtgctat cgtcgatgac     180
tcgttcacgc ggtgcttcaa gtcgaattcg caggaaccgt ggaactggaa cgtgtacctc     240
ttcccgctgt ggtgcttcgg ggtggtggtt cggtacttga tcctgttccc ggcaagggtt     300
ttagtgttga caattggatg gataatattc ctctcatcat tgccattgt tcactttatg      360
cttaaagcac atgatgcact gagaaggaag ctggagaggt gctggtgga gttaatttgc      420
agcttctttg ttgcttcatg gactggtgtc gtcaaatacc atgggccacg gcctagcatt     480
cggcctaaac aagttttgt tgccaaccac acttccatga ttgatttcat catcttagag      540
caaatgactg ccttcgctgt tattatgcaa aagcatcctg gatggttgg actactgcaa      600
agcactattt tggagagtgt aggatgcatc tggtttaatc gttctgaggc caaagatcgt     660
gaaattgtgg caagaaagtt gagagatcac gtactgggaa ctgataacaa tcctcttctc     720
atatttcctg aagggacttg tgtgaacaat cactatactg tcatgttcaa aaagggtgca     780
tttgagcttg ggtgcactgt ttgccctatc gcaatcaagt acaataagat cttcgtggat     840
gccttttgga acagcaggaa acaatctttc acaatgcatc tactgcaact tatgacatct     900
tgggctgttg tttgtgacgt ctggtacttg aaccccaaa ccttgaaacc tggtgaaacg      960
ccaattgaat ttgcagagag ggtccgtgac atcatatctg ttcgagctgg tttgaagaag    1020
gttccttggg atggatatct gaagtactct cgccctagcc ccaagcatag agaagggaag    1080
caacgaagct tgctgagtg ggtgctgcag cgacttgagg agaggtga                  1128

<210> SEQ ID NO 141
<211> LENGTH: 1128
<212> TYPE: DNA
<213> ORGANISM: Cucumis sativus

<400> SEQUENCE: 141
atgagtggtg ctgctcttct caaatcctcc gcctctgaat tggacttaga tcgacccaat      60
atcgaagatt acttgccttc cggatcctct atccaacaac ccactgccaa gcttcgcctt     120
cgtgatttgc tcgatatttc gccgaccctt accgaggctg ctggtgctat tgttgatgat     180
tcgtttacaa ggtgtttcaa atcaaaccca ccagagccat ggaattggaa tatttatttg     240
ttcccttttgt ggtgctgtgg agtggtgatt cggtatttgt ttctcttccc ggcaagggtt     300
ctcatattga cgataggatg gataattttc cttttcaacgt tcattccagt gaatctcctt    360
ctgaaagggc atcctaaact gagagctaag ttagagaggt ttttggtgga gttgatttgc    420
agcttctttg ttgcatcttg gactggagtt gttaagtatc atgggccacg gcctagcatc     480
agaccaaaac aggttttcgt ggccaaccac acttccatga ttgatttcat agtcttggag     540
caaatgactg cctttgctgt tattatgcaa aaacatcctg ggtggttgg actgttgcaa     600
agcactatat tggagagtat aggatgtata tggttcaacc gtacagagtt gaaggaccgt     660
gaaattgtag caagaaagtt aaatgaccac gttcaagggg ctgacaacaa tcctcttctt     720
atatttcctg aaggaacttg tgtaaataac cactactctg ttatgttcaa gaagggtgca     780
```

```
tttgaacttg gatgctctgt tgcccaatt gcaatcaaat acaataaaat tttcgttgat    840
gcttttgga acagcaggaa gcagtcgttc actatgcatc tgctgcagct catgacctct    900
tgggctgttg tttgtgatgt ttggtacctg gagccccaag ttttgaagcc tggagaaaca    960
cccattgagt ttgcagaaag ggtcagggac ataatatgtg ctcgagcagg tcttaagaag   1020
gttccatggg atggatattt gaagcactcc cgtccgagcc caaataccg agaacgtaaa    1080
caacaaagct cgcggagtc agtgctgcag ctattggaca ataagtga               1128
```

```
<210> SEQ ID NO 142
<211> LENGTH: 1137
<212> TYPE: DNA
<213> ORGANISM: Gossypium arboreum

<400> SEQUENCE: 142
atgaacagta gtgaagggaa gttgaaatca tcgagttccg aattggattt ggatcgaccc     60
aacatcgaag attatctccc ttctggatct tccattcaag aaccacatgg caagcttcgc    120
ctgcgggatt tgcttgatat ttctcccgct ttaactgaag ctgctggtgc tattgttgat    180
gattcattca cacggtgttt taagtcgaat ccccggaac cgtggaactg aatgtgtat     240
ctgtttcctc tctggtgttg tggtgtggta tttcggtact tgattttgtt ccctatgagg    300
gctttagttt tgacaatagg atggataata tttctgtcat gcttcattcc tgtgcacttt    360
cttctcaaag ggaacgataa cttgcggaaa aagatggaga gggcgttggt ggagctaatc    420
tgtagcttct tgttgcgtc ctggactgga gttgttaagt accatggacc acggcctagc    480
atgcggccca gcaggtgtt tgtggccaat catacttcta tgattgattt catcatatta    540
gaacagatga ctgcatttgc tgtcattatg cagaagcacc ctggatgggt tggactgcta    600
cagagcacta ttttagagag tgtagggtgt atttggttta accgttcaga ggccaaagat    660
cgtgaaattg taacaaggaa gttaagggag catagtcagg gagctgacaa taaccctctt    720
ctcatatttc ccgaagggac atgtgtaaac aatcaataca gcgttatgtt caagaagggt    780
gcattcgaac ttggttgcac tgtttgcccg attgcaataa agtacaataa aatttttgtt    840
gatgcctttt ggaatagccg gaagcagtcc tttacaatgc atttattgca gctaatgaca    900
tcctgggctg ttgtttgcga tgtttggtac ctagagcccc aaaatctaag gcctggagaa    960
acacccatcg agtttgcaga gaggatcaga gacataatct ctgttcgagc aggtcttaaa   1020
aaggttccat gggacggata tttgaagtat tctcgcccga gccctaagca tagagagcga   1080
aaacaacaaa gttttgccga atctgttctt cggggactgg aactggaaga aaaatga      1137
```

```
<210> SEQ ID NO 143
<211> LENGTH: 215
<212> TYPE: PRT
<213> ORGANISM: Elaeis guineensis

<400> SEQUENCE: 143

Met Pro Asp Ser Asp Asn Glu Ser Gly Gly Gln Asn Asn Ser His Asn
1               5                   10                  15

Asn Asn Val Gly Glu Tyr Ser Ser Ser Arg Glu Gln Asp Arg Phe Leu
            20                  25                  30

Pro Ile Ala Asn Val Ser Arg Ile Met Lys Lys Ala Leu Pro Ala Asn
        35                  40                  45

Ala Lys Ile Ser Lys Asp Ala Lys Glu Thr Val Gln Glu Cys Val Ser
    50                  55                  60

Glu Phe Ile Ser Phe Ile Thr Gly Glu Ala Ala Asp Lys Cys Gln Arg
```

```
                65                  70                  75                  80
        Glu Lys Arg Lys Thr Ile Asn Gly Asp Asp Leu Leu Trp Ala Met Thr
                            85                  90                  95

Thr Leu Gly Phe Glu Asp Tyr Val Asp Pro Leu Lys Val Tyr Leu His
                        100                 105                 110

Arg Phe Arg Glu Met Glu Gly Asp Lys Cys Ser Ala Gly Ala Ser Ala
                    115                 120                 125

Ser Ser Gln Pro Gln His Lys Asp Gly Asp Gly Gly Gly Gly
            130                 135                 140

Gly Gly Gly Ala Pro Ser Met Gly Asn Asn Val Val Gly Leu Gly Gly
        145                 150                 155                 160

Gly Gly Gly Gly Ala Gly Gly Met Met Met Met Gly Gln Gln Met
                        165                 170                 175

Tyr Ala Thr Pro Pro Ser Tyr His His His Met Ser Thr Met Ser Gly
                        180                 185                 190

Lys Ser Ser Met Gly Gly Gly Ser Ser Ala Ser Ser Ser Ser Pro Gly
                        195                 200                 205

Phe Gly Arg Gln Gly Arg Val
                    210                 215

<210> SEQ ID NO 144
<211> LENGTH: 133
<212> TYPE: PRT
<213> ORGANISM: Elaeis guineensis

<400> SEQUENCE: 144

Met Glu Pro Glu Asn Pro Glu Leu Asn Leu Asp Leu Ala Leu Gln Pro
        1               5                   10                  15

Ser Ser Pro Pro Glu Pro Ala Arg Val Phe Ser Cys Asn Tyr Cys Gln
                        20                  25                  30

Lys Lys Phe Tyr Ser Ser Gln Ala Leu Gly Gly His Gln Asn Ala His
                    35                  40                  45

Lys Leu Glu Arg Ser Leu Ala Lys Arg Ser Trp Glu Leu Ala Thr Ala
            50                  55                  60

Leu Arg Pro His Ala Gly Ser Thr Ile Gly Gln His Thr Ser Thr Val
        65                  70                  75                  80

Val Leu Val Glu Arg Gln Arg Glu Glu Cys Cys Tyr Asn Gly Val Gly
                        85                  90                  95

Leu Ala Thr Arg Gly Arg Glu Ala Ser Arg Ala Ser Ile Arg Leu Gly
                        100                 105                 110

Ser Arg Lys Glu Ser Asp Asp Lys Arg Glu Leu Ala Asp Gly Ile Asp
                    115                 120                 125

Leu Ser Leu Arg Leu
            130

<210> SEQ ID NO 145
<211> LENGTH: 190
<212> TYPE: PRT
<213> ORGANISM: Arabidopsis thaliana

<400> SEQUENCE: 145

Met Gly Asp Ser Asp Arg Asp Ser Gly Gly Gly Gln Asn Gly Asn Asn
        1               5                   10                  15

Gln Asn Gly Gln Ser Ser Leu Ser Pro Arg Glu Gln Asp Arg Phe Leu
                        20                  25                  30

Pro Ile Ala Asn Val Ser Arg Ile Met Lys Lys Ala Leu Pro Ala Asn
```

```
                35                  40                  45
Ala Lys Ile Ser Lys Asp Ala Lys Glu Thr Met Gln Glu Cys Val Ser
 50                  55                  60

Glu Phe Ile Ser Phe Val Thr Gly Glu Ala Ser Asp Lys Cys Gln Lys
 65                  70                  75                  80

Glu Lys Arg Lys Thr Ile Asn Gly Asp Asp Leu Leu Trp Ala Met Thr
                 85                  90                  95

Thr Leu Gly Phe Glu Asp Tyr Val Glu Pro Leu Lys Val Tyr Leu Gln
                100                 105                 110

Arg Phe Arg Glu Ile Glu Gly Glu Arg Thr Gly Leu Gly Arg Pro Gln
            115                 120                 125

Thr Gly Gly Glu Val Gly Glu His Gln Arg Asp Ala Val Gly Asp Gly
        130                 135                 140

Gly Gly Phe Tyr Gly Gly Gly Gly Met Gln Tyr His Gln His His
145                 150                 155                 160

Gln Phe Leu His Gln Gln Asn His Met Tyr Gly Ala Thr Gly Gly
                165                 170                 175

Ser Asp Ser Gly Gly Gly Ala Ala Ser Gly Arg Thr Arg Thr
            180                 185                 190

<210> SEQ ID NO 146
<211> LENGTH: 161
<212> TYPE: PRT
<213> ORGANISM: Arabidopsis thaliana

<400> SEQUENCE: 146

Met Ala Asp Ser Asp Asn Asp Ser Gly Gly His Lys Asp Gly Gly Asn
 1               5                  10                  15

Ala Ser Thr Arg Glu Gln Asp Arg Phe Leu Pro Ile Ala Asn Val Ser
                 20                  25                  30

Arg Ile Met Lys Lys Ala Leu Pro Ala Asn Ala Lys Ile Ser Lys Asp
             35                  40                  45

Ala Lys Glu Thr Val Gln Glu Cys Val Ser Glu Phe Ile Ser Phe Ile
 50                  55                  60

Thr Gly Glu Ala Ser Asp Lys Cys Gln Arg Glu Lys Arg Lys Thr Ile
 65                  70                  75                  80

Asn Gly Asp Asp Leu Leu Trp Ala Met Thr Thr Leu Gly Phe Glu Asp
                 85                  90                  95

Tyr Val Glu Pro Leu Lys Val Tyr Leu Gln Lys Tyr Arg Glu Val Glu
                100                 105                 110

Gly Glu Lys Thr Thr Thr Ala Gly Arg Gln Gly Asp Lys Glu Gly Gly
            115                 120                 125

Gly Gly Gly Gly Ala Gly Ser Gly Ser Gly Ala Pro Met Tyr
        130                 135                 140

Gly Gly Gly Met Val Thr Thr Met Gly His Gln Phe Ser His Phe
145                 150                 155                 160

Ser

<210> SEQ ID NO 147
<211> LENGTH: 150
<212> TYPE: PRT
<213> ORGANISM: Arabidopsis thaliana

<400> SEQUENCE: 147

Met Asp Tyr Gln Pro Asn Thr Ser Leu Arg Leu Ser Leu Pro Ser Tyr
 1               5                  10                  15
```

```
Lys Asn His Gln Leu Asn Leu Glu Leu Val Leu Glu Pro Ser Ser Met
             20                  25                  30

Ser Ser Ser Ser Ser Ser Ser Thr Asn Ser Ser Ser Cys Leu Glu Gln
         35                  40                  45

Pro Arg Val Phe Ser Cys Asn Tyr Cys Gln Arg Lys Phe Tyr Ser Ser
 50                  55                  60

Gln Ala Leu Gly Gly His Gln Asn Ala His Lys Leu Glu Arg Thr Leu
 65                  70                  75                  80

Ala Lys Lys Ser Arg Glu Leu Phe Arg Ser Ser Asn Thr Val Asp Ser
                 85                  90                  95

Asp Gln Pro Tyr Pro Phe Ser Gly Arg Phe Glu Leu Tyr Gly Arg Gly
            100                 105                 110

Tyr Gln Gly Phe Leu Glu Ser Gly Gly Ser Arg Asp Phe Ser Ala Arg
            115                 120                 125

Arg Val Pro Glu Ser Gly Leu Asp Gln Asp Gln Glu Lys Ser His Leu
130                 135                 140

Asp Leu Ser Leu Arg Leu
145                 150

<210> SEQ ID NO 148
<211> LENGTH: 398
<212> TYPE: PRT
<213> ORGANISM: Elaeis guineensis

<400> SEQUENCE: 148

Met Ala Ser Ala Ser Glu Ser Arg Asn Val Thr Ser Glu Glu Thr Glu
1               5                   10                  15

Val Thr Ser Glu Arg Arg Pro Glu Glu Gly Lys Glu Glu Arg Glu Leu
             20                  25                  30

Gly Leu Glu Phe Pro Leu Met Arg Gln Ser Ser Ile Tyr Ser Leu Thr
         35                  40                  45

Leu Asp Glu Ile Gln Asn Thr Val Cys Glu Pro Gly Lys Ser Phe Gly
 50                  55                  60

Ser Met Asn Met Asp Glu Phe Leu Thr Asn Ile Trp Asn Val Glu Glu
 65                  70                  75                  80

Gly Gln Ile Ala Ser Ala Asn Ala Gln Asn Gln His Ile Gly Gly
                 85                  90                  95

Gly Gly Pro Pro Ala Ala Pro Pro Leu Gln Arg Gln Gly Ser Ile Ala
            100                 105                 110

Val Pro Ala Pro Leu Cys Arg Lys Thr Val Asp Glu Val Trp Ser Asp
            115                 120                 125

Ile His Arg Gly Gln Asn Ala Arg Arg Gln Asn Val Asp Arg Pro Pro
130                 135                 140

Pro Pro Ser Gln Gln Gln Glu Ser Asn Cys Ala Ala Pro Arg Lys Pro
145                 150                 155                 160

Thr Phe Gly Glu Ile Thr Leu Glu Asp Phe Leu Val Lys Ala Gly Val
                165                 170                 175

Val Arg Glu Gly Tyr Gln Pro Gly Ser Ala Pro Ser Ala His Ala Pro
            180                 185                 190

Val Pro Pro Ala Thr Gln Tyr Gly Met Pro Ala Gly Tyr Gln Met Val
            195                 200                 205

Gly Thr Glu Gly Ala Pro Val Phe Gly His Val Val Gly Val Gln Ala
210                 215                 220

Tyr Gly Asp His Gln Val Thr Ala Ala Asn Ala Met Tyr Pro Val Val
```

```
                225                 230                 235                 240

Gly Asp Gly Gly Gly Pro Gly Tyr Ala Val Gly Asn Gly Phe Gly Gly
                        245                 250                 255

Arg Val Gly Asn Gly Tyr Gly Ala Val Ala Ala Val Gly Gly Ser Pro
                        260                 265                 270

Ala Ser Pro Gly Ser Ser Glu Gly Val Gly Gly Gln Val Glu Asn
                    275                 280                 285

Ser Gly Ala Ala Glu Gly Gly Gly Gly Lys Gly Gly Arg Lys Arg
            290                 295                 300

Pro Leu Asp Gly Thr Val Glu Lys Val Val Glu Arg Gln Arg Arg
    305                 310                 315                 320

Met Ile Lys Asn Arg Glu Ser Ala Ala Arg Ser Arg Ala Arg Lys Gln
                        325                 330                 335

Ala Tyr Thr Val Glu Leu Glu Ala Glu Leu Asn Gln Leu Lys Glu Glu
                        340                 345                 350

Asn Ala Arg Leu Lys Glu Ala Glu Lys Lys Met Leu Ala Leu Lys Lys
                        355                 360                 365

Gln Leu Leu Met Glu Ala Met Ala Glu Arg Ala Arg Val Asn Ala Gln
            370                 375                 380

Lys Thr Ile Leu Thr Met Arg Arg Cys Asn Ser Ser Lys Trp
    385                 390                 395
```

<210> SEQ ID NO 149
<211> LENGTH: 272
<212> TYPE: PRT
<213> ORGANISM: Elaeis guineensis

<400> SEQUENCE: 149

```
    Met Glu Gln Ser Thr Gln Pro Ser His Pro Val Met Gly Ile Val Thr
    1                   5                   10                  15

Gly Ala Ala Gln Ile Ala Tyr Ala Ala Pro Thr Tyr Gln Ser Ala Ala
                        20                  25                  30

Met Val Thr Gly Ala Pro Ala Val Ile Gly Ala Ile Pro Ser Pro Ala
                        35                  40                  45

Gln Pro Thr Ser Thr Phe Pro Thr Ser Pro Ala Gln Leu Thr Ser Gln
                    50                  55                  60

His Gln Leu Ala Tyr Gln Gln Val Arg Gln Phe His His Gln Gln
    65                  70                  75                  80

Gln Gln Gln Gln Gln Gln Leu Gln Thr Phe Trp Ala Asn Gln Met Leu
                        85                  90                  95

Glu Ile Glu His Ala Thr Asp Phe Lys Asn His Ser Leu Pro Leu Ala
                        100                 105                 110

Arg Ile Lys Lys Ile Met Lys Ala Asp Glu Asp Val Arg Met Ile Ser
                        115                 120                 125

Ala Glu Ala Pro Val Ile Phe Ala Lys Ala Cys Glu Met Phe Ile Leu
            130                 135                 140

Glu Leu Thr Leu Arg Ser Trp Ile His Thr Glu Asn Lys Arg Arg
    145                 150                 155                 160

Thr Leu Gln Lys Asn Asp Ile Ala Ala Ala Ile Thr Arg Thr Asp Ile
                        165                 170                 175

Phe Asp Phe Leu Val Asp Ile Val Pro Arg Asp Glu Leu Lys Glu Glu
                        180                 185                 190

Gly Ile Gly Ile Ala Arg Ala Ala Leu Pro Thr Met Gly Ala Pro Ala
                        195                 200                 205
```

```
Asp Ser Gly Pro Tyr Tyr Val Pro Ala Gln His Gln Leu Ala Gly
    210                 215                 220

Pro Gly Met Ile Met Gly Lys Pro Val Asp Gln Ala Thr Thr Ala Ala
225                 230                 235                 240

Met Tyr Thr Ala Gln Pro Pro His Pro Val Ala Tyr Met Trp Gln Gln
                245                 250                 255

Pro Gln Gln Gln Gln Ala Gln Gln Gln Gln Gln Met Pro Asp Ser Gly
                260                 265                 270
```

<210> SEQ ID NO 150
<211> LENGTH: 352
<212> TYPE: PRT
<213> ORGANISM: Elaeis guineensis

<400> SEQUENCE: 150

```
Met Pro Leu Asp Asn Ala Asn Ala Phe Asp Thr Gln His Phe Ser Asn
1               5                   10                  15

Lys Asp Ser Glu His Ser Ser Val Thr Ser Val His Ser Ala Ser Asn
                20                  25                  30

Cys Val Asp Asn Phe Pro Ser Leu Trp Lys Gln Ser Gly Ser His Phe
            35                  40                  45

Pro Gln Ser Thr Tyr Phe Lys Asn Phe Cys Met Asn Met Gly Phe Leu
        50                  55                  60

Ala Gln Pro Asp Asn Gln Met Lys Gln Leu Gly Gly Gln Met Pro Asp
65                  70                  75                  80

Gln Asp Ser Ser Ser Gln Ser Thr Gly Gln Ser His Gln Glu Val
                85                  90                  95

Ser Gly Thr Ser Glu Gly Asn Leu His Glu Gln Ser Ile Ser Ala Gln
                100                 105                 110

Ala Gly Asn Asp Lys Thr Cys Gly Lys Gln Val Glu Gly His Val Asn
            115                 120                 125

Ser Val Leu Phe Leu Gly Thr Pro Glu Ala Ala Phe Val Ser Pro Arg
        130                 135                 140

Leu Asp Tyr Gly Gln Ser Phe Ala Cys Val Pro Tyr Thr Tyr Ala Asp
145                 150                 155                 160

Pro Ser Phe Gly Gly Val Leu Ala Ala Tyr Gly Ser Pro Ala Ile Ile
                165                 170                 175

His Pro Gln Met Val Gly Val Pro Pro Ser Ser Arg Val Pro Leu Pro
            180                 185                 190

Leu Glu Pro Ala Ala Glu Pro Ile Tyr Val Asn Ala Lys Gln Tyr
        195                 200                 205

Arg Ala Ile Leu Arg Arg Arg Gln Leu Arg Ala Lys Leu Glu Ala Gln
210                 215                 220

Asn Lys Leu Ile Lys Ala Arg Lys Pro Tyr Leu His Glu Ser Arg His
225                 230                 235                 240

Leu His Ala Met Lys Arg Ala Arg Gly Ser Gly Gly Arg Phe Leu Asn
                245                 250                 255

Thr Lys Gln Leu Glu Gln Gln Gln Arg Pro Leu Pro Pro Pro
            260                 265                 270

Pro Ser Val Ser Thr Gly Leu Gly Asn Leu Ser Ala Ser Asn Leu His
        275                 280                 285

Phe Glu Asn Gly Pro Ser Gly Ser Ser Ala Ala Pro Thr Ser Ser Ala
    290                 295                 300

Asp Val Val Arg Val Ser Thr Ser Gly Gly Met Leu Glu Gln Gln Gly
305                 310                 315                 320
```

```
His Leu Ser Phe Leu Ser Ala Asp Phe His Ser His Val Arg Ser Thr
                325                 330                 335

Gln Gly Gly Gly Asp Ser Gly Ser Gln Pro Arg Ile Thr Ile Met Arg
            340                 345                 350
```

<210> SEQ ID NO 151
<211> LENGTH: 300
<212> TYPE: PRT
<213> ORGANISM: Glycine max

<400> SEQUENCE: 151

```
Met Gln Gln Ile His Ser Met Pro Gly Gly Arg Phe Phe Ser Gly Ser
1               5                   10                  15

Gly Ser Ala Asp Arg Arg Leu Arg Pro His His Gln Asn Gln Gln Ala
            20                  25                  30

Leu Lys Cys Pro Arg Cys Asp Ser Leu Asn Thr Lys Phe Cys Tyr Tyr
        35                  40                  45

Asn Asn Tyr Asn Leu Ser Gln Pro Arg His Phe Cys Lys Asn Cys Arg
    50                  55                  60

Arg Tyr Trp Thr Lys Gly Gly Val Leu Arg Asn Val Pro Val Gly Gly
65                  70                  75                  80

Gly Cys Arg Lys Ser Lys Arg Ser Ser Lys Pro Asn Lys Ile Thr Pro
                85                  90                  95

Ser Glu Thr Ala Ser Pro Pro Pro Pro His Pro Asp His Asn Asn
            100                 105                 110

Asn Ser Asn Ser His Ser Ser Ser Glu Ser Ser Ser Leu Thr Ala Ala
        115                 120                 125

Val Ala Thr Thr Thr Glu Ala Val Ser Ala Pro Glu Thr Leu Asn Ser
    130                 135                 140

Asp Ser Asn Asn Asn Asn Met Gln Glu Ser Lys Leu Leu Ile Pro
145                 150                 155                 160

Ala Leu Glu Thr Asn Asn Pro Leu Glu Gln Gly Thr Gly Asp Cys Gly
                165                 170                 175

Gly Ile Phe Ser Glu Ile Gly Pro Phe Thr Ser Leu Ile Thr Thr Thr
            180                 185                 190

Thr Ser Thr Asn Glu Pro Leu Gly Ser Gly Phe Gly Phe Asn Ser
        195                 200                 205

Thr Leu Pro Asp Ala Ser Ser Phe Gln Trp His Tyr Gln Lys Val Ser
    210                 215                 220

Ser Asn Asn Glu Glu Leu Lys Leu Pro Glu Asn Ser Phe Leu Asp His
225                 230                 235                 240

Thr Val Asp Leu Ser Gly Met His Ser Lys Thr Ser His Gly Gly Gly
                245                 250                 255

Phe Gly Ser Leu Asp Trp Gln Gly Gly Ala Asp Gln Gly Leu Phe Asp
            260                 265                 270

Leu Pro Asn Thr Val Asp His Ala Tyr Trp Ser His Thr His Trp Ser
        275                 280                 285

Asp His Asp Asn Ser Ser Ser Leu Phe His Leu Pro
    290                 295                 300
```

<210> SEQ ID NO 152
<211> LENGTH: 351
<212> TYPE: PRT
<213> ORGANISM: Glycine max

<400> SEQUENCE: 152

-continued

```
Met Ser Ser Val Phe Ser Glu His Lys Phe Gln Leu Gln Pro Ser His
1               5                   10                  15
Gln Leu Leu Ser Leu Lys Lys Ser Leu Gly Asp Ile Asp Ile Pro Val
            20              25              30
Pro Pro Arg Lys Leu Leu Thr Arg Arg Ser Ala Ala Val His Asp Gly
        35              40                      45
Ser Gly Asp Ile Tyr Leu Pro His Ser Gly Ser Thr Asp Ser Ser Thr
    50                  55                  60
Asp Asp Asp Ser Asp Gly Asp Pro Tyr Ala Ser Asp Gln Phe Arg Met
65                  70              75                      80
Phe Glu Phe Lys Val Arg Arg Cys Ser Arg Ser Arg Ser His Asp Trp
                85                  90                  95
Thr Asp Cys Pro Phe Val His Pro Gly Glu Lys Ala Arg Arg Arg Asp
                100                 105                 110
Pro Arg Arg Phe Tyr Tyr Ser Gly Thr Val Cys Pro Glu Phe Arg Arg
            115                 120                 125
Gly Gln Cys Asp Arg Gly Asp Ala Cys Glu Phe Ser His Gly Val Phe
130                 135                 140
Glu Cys Trp Leu His Pro Ser Arg Tyr Arg Thr Glu Ala Cys Lys Asp
145                 150                 155                 160
Gly Lys Asn Cys Lys Arg Lys Val Cys Phe Phe Ala His Thr Pro Arg
                165                 170                 175
Gln Leu Arg Val Phe His Ser Asn Asp Asn Ser Asn Lys Lys Lys Cys
                180                 185                 190
Thr Asp Ile Ser Pro His Asn Asn Asn Cys Cys Leu Val Cys His
                195                 200                 205
Cys Ser Asn Ser Thr Arg Ser Pro Thr Ser Thr Leu Phe Gly Met Ser
    210                 215                 220
His Phe Ser Pro Pro Leu Ser Pro Pro Ser Pro Ser Ser Pro Ser Met
225                 230                 235                 240
Phe Glu Thr Asn Asn His His His Gly Val Val Lys Tyr Asn Lys Asp
                245                 250                 255
Val Phe Ser Glu Leu Val Cys Ser Met Glu Gly Leu Asn Phe Asp Glu
            260                 265                 270
Ala Ser Ser Leu Leu Ser Ala Ala Ser Lys Pro His His His Asn Asn
        275                 280                 285
Leu Ser Ser Trp Leu Asp Val Ser Lys Asp His Asn Gln Lys Gln Phe
    290                 295                 300
Asn Thr Leu Asn Ser Pro Thr Ile Thr Ala Cys Gly Ser Phe Ser Asn
305                 310                 315                 320
Asn Gly Asn Gly Gly Phe Leu Arg Ala Glu Asn Gly Val Val Val Asp
                325                 330                 335
Asp Val Ile Ala Pro Asp Leu Ala Trp Val Asn Glu Leu Leu Met
                340                 345                 350
```

PLANTS PRODUCING MODIFIED LEVELS OF MEDIUM CHAIN FATTY ACIDS

The present application claims priority from Australian Patent Application No 2018201932 filed on 16 Mar. 2018 and Canadian Patent Application No 2,998,211 filed on 16 Mar. 2018, the content of which is incorporated herein by reference.

REFERENCE TO A SEQUENCE LISTING

This application incorporates-by-reference nucleotide and/or amino acid sequences which are present in the file named "190315_5938_90904_Sequence_Listing_SC.txt", which is 373 kilobytes in size, and which was created Mar. 15, 2019 in the IBM-PC machine format, having an operating system compatibility with MS-Windows, which is contained in the text file filed Mar. 15, 2019 as part of this application.

FIELD OF THE INVENTION

The present invention relates to methods of producing industrial products from plant lipids, particularly from vegetative parts of plants. In particular, the present invention provides oil products such as biofuel, and processes for producing these products, as well as plants having an increased level medium chain fatty acids such as lauric acid and myristic acid. In one particular embodiment, the present invention relates to combinations of modifications in a fatty acid thioesterase and one or more acyltransferases. In an embodiment, the present invention relates to a process for extracting lipids. In another embodiment, the lipid is converted to one or more hydrocarbon products in harvested plant vegetative parts to produce alkyl esters of the fatty acids which are suitable for use as a renewable biofuel.

BACKGROUND OF THE INVENTION

Over recent years the global production of vegetable oils has experienced constant growth, with over 179 million metric tons (MMT) being produced in 2015 (OECD/FAO, 2015), with the four major oil production crops being oil palm, soybean, canola and sunflower. An important component of global oil consumption is medium-chain fatty acids (MCFA), here defined as fatty acids in the range of 6-14 carbons in length. As well as their application within the food industry MCFAs are an ideal source for biodiesel and also for a wide range of oleochemical feedstocks including pharmaceuticals, personal care products, lubricants and detergents (Arkcoll, 1988; Basiron and Weng, 2004). Currently, the predominant crop sources of MCFA-enriched oils are coconut palm and oil palm (both palm oil and palm kernel oil) (Arkcoll, 1988). The production of these crops is limited to tropical and subtropical climates. The development of new crops that can produce MCFA-enriched oils in temperate climates has been proposed (Dehesh, 2001; Eccleston et al., 1996; Reynolds et al., 2015; Tjellstrom et al., 2013; Voelker et al., 1992; Wiberg et al., 2000) as a way to meet the growing global demand for MCFA in oleochemical production, pharmaceutical applications, and personal care products.

Many studies have investigated the modification of seed oils to contain increased MCFA content, predominantly focused on the engineering of lauric acid (C12:0) (Eccleston and Ohlrogge, 1998; Knutzon et al., 1999; Voelker et al., 1992). In oilseeds the engineered pathway begins with the overexpression of a specialised thioesterase (FATB) that prematurely truncates the standard fatty acid elongation cycle within the plastid allowing export into the cytoplasm. The MCFA in the cytoplasm is available for incorporation into triacylglycerols (TAG) via the endogenous oilseed pathways which can occur via the acyl-CoA dependent reactions of the Kennedy pathway (glycerol-3-phosphate acyltransferase (GPAT), lysophosphatidic acid acyltransferase (LPAAT) and diacylglycerol acyltransferase (DGAT). Previous studies have investigated the incorporation of MCFA into seed oils following the coordinated over-expression of FATB and LPAAT, achieving up to 67% of laurate (C12:0) in seed oil (Knutzon et al., 1999). More recently, transcriptomic analyses have enabled the identification of new FATB and LPAAT genes from many *Cuphea* species, which have been used to both modify the fatty acid profiles and improve the incorporation of MCFA into the TAG, respectively, of transgenic *C. amelina sativa* seeds (Kim et al., 2015a; Kim et al., 2015b).

Evidence, although, has found that endogenous TAG synthesis pathways in developing oilseeds are not ideal for incorporating MCFA into TAG (Wiberg et al., 1997; Wiberg et al., 2000), and that newly-synthesised MCFA becomes incorporated into membrane bound lipids, impeding lipid flux, agronomic performance and can even result in cell death through chlorosis (Bates et al., 2014; Voelker et al., 1996). Therefore it would seem that although MCFA can be produced in plant cells there is a poor pathway for incorporation into seed TAG. It has also been recognised that the accumulation of unusual fatty acids in PC appears to be a bottleneck for their enriched incorporation into TAG (Bates and Browse, 2011; Reynolds et al., 2015). In the example of engineering ricinoleic acid into oilseeds it has been demonstrated that the endogenous pathways need to be removed in conjunction with the ectopic expression of the specialised pathway counterpart (Adhikari et al., 2016; Bates and Browse, 2011; Burgal et al., 2008; Chen et al., 2016; van Erp et al., 2011; van Erp et al., 2015).

Recent work has demonstrated that engineering high oil levels in plant biomass is a realistic proposition (Vanhercke et al., 2014a; Vanhercke et al., 2013; Vanhercke et al., 2014b) with the accumulation of levels of TAG in *Nicotiana tabacum* leaves of up to 15% being attained by the coordinated transgenic expression of genes normally involved in oil production in seeds (Vanhercke et al., 2014a). Such approaches have uncovered a synergism involving an increase in the production of fatty acids in the plastid (WRINKLED1 (WRI1)), improving the assembly of fatty acids into leaf oils (DGAT) and slowing the catabolism of these oils (OLEOSIN, OLE1 (Winichayakul et al., 2013)); and sugar-dependent-1, SDP1 (Fan et al., 2014; Kelly et al., 2013a and b; Kim et al., 2014b; Vanhercke, 2014a). Although the production of TAG in biomass offers a new source of common vegetable oils, these new expression platforms could also be adapted to produce high levels of novel fatty acids, such as MCFA (Reynolds et al., 2015; Wood, 2014).

The inventors first steps in this direction involved the overexpression of thioesterases from *Umbellularia californica, Cinnamomum camphora* and *Cocos nucifera* which resulted in the production of MCFA in leaf tissues (Reynolds et al., 2015). However, these metabolic pathways also resulted in high levels of MCFA in PC resulting in severe chlorosis and cell death (Bates et al., 2014; Wiberg et al., 2000), similar to conclusions drawn from oilseed engineering. The incorporation of MCFA into the membrane lipids of vegetative tissues is therefore particularly problematic.

The inventors have improved the MCFA metabolic pathway by combining a series of gene ensembles with three different DGAT1 genes isolated from *Elaeis guineensis* (African oil palm). A functional GPAT9 from *C. nucifera* was identified that was included in the metabolic pathway for improving the incorporation of MCFA into seed oils. An improvement in MCFA utilisation was demonstrated in vegetative plant cells such as leaf cells, which resulted in more efficient sequestering of MCFA in TAG while also effectively limiting the accumulation of MCFA in membrane lipids.

SUMMARY OF THE INVENTION

In a first aspect, the present invention provides a process for producing extracted plant lipid, comprising the steps of:
 a) obtaining one or more plant parts comprising lipid, preferably vegetative plant parts, the lipid comprising a total fatty acid content which comprises fatty acids in an esterified form, the fatty acids comprising a level of total, or new, medium chain fatty acids (MCFA) that is at least 25% of the total fatty acid content on a weight basis, and
 b) extracting lipid from the plant part(s),
thereby producing the extracted plant lipid.

In an embodiment, the plant part comprises one or more exogenous polynucleotides which encode polypeptides having fatty acid thioesterase (TE) activity, and either glycerol-3-phosphate acyltransferase (GPAT) activity, preferably GPAT9 activity, or diacylglycerol acyltransferase (DGAT) activity, preferably DGAT1 activity, or both GPAT and DGAT,
wherein the exogenous polynucleotide is operably linked to a promoter which is capable of directing expression of the polynucleotide in a cell of the plant part.

In a further embodiment, the plant part further comprises one or more or all of:
 i. an exogenous polynucleotide which encodes a second polypeptide having glycerol-3-phosphate acyltransferase (GPAT) activity, preferably GPAT9 activity, or diacylglycerol acyltransferase (DGAT) activity, preferably DGAT1 activity;
 ii. an exogenous polynucleotide which encodes a third polypeptide having 1-acyl-glycerol-3-phosphate acyltransferase (LPAAT) activity;
 iii. an exogenous polynucleotide which encodes a transcription factor polypeptide that increases the expression of one or more glycolytic and/or fatty acid biosynthetic genes in a cell of the plant part compared to a corresponding cell lacking the exogenous polynucleotide;
 iv. an exogenous polynucleotide which encodes a polypeptide which increases the export of fatty acids out of plastids of a cell in the plant part when compared to a corresponding cell lacking the exogenous polynucleotide; and
 v. an exogenous polynucleotide which encodes an oil body coating (OBC) polypeptide,
wherein each exogenous polynucleotide is operably linked to a promoter which is capable of directing expression of the polynucleotide in a cell of the plant part.

In an embodiment, the OBC polypeptide is an oleosin, such as a polyoleosin or a caleosin, or a lipid droplet associated protein (LDAP).

In an embodiment, the transcription factor polypeptide is selected from the group consisting of Wrinkled 1 (WRI1), Leafy Cotyledon 1 (LEC1), LEC1-like, Leafy Cotyledon 2 (LEC2), BABY BOOM (BBM), FUS3, ABI3, ABI4, ABI5, Dof4 and Dof11, preferable WRI1, or the group consisting of MYB73, bZIP53, AGL15, MYB115, MYB118, TANMEI, WUS, GFR2a1, GFR2a2 and PHR1.

In an embodiment, the polypeptide which increases the export of fatty acids out of plastids of the cell is a fatty acid thioesterase such as a FATA polypeptide or a FATB polypeptide, a fatty acid transporter such as an ABCA9 polypeptide or a long-chain acyl-CoA synthetase (LACS), preferably a FATB polypeptide.

In an embodiment, the fatty acid thioesterase is capable of hydrolysing a substrate which is an acyl carrier protein (ACP) esterified to a medium chain fatty acid and/or a C16:0, preferably wherein the MCFA is a C10, C12 and/or C14.

In an embodiment, the plant part further comprises one or more or all of:
 i. a genetic modification which down-regulates endogenous production and/or activity of a polypeptide involved in the catabolism of triacylglycerols (TAG) in a cell of the plant part when compared to a corresponding cell lacking the genetic modification;
 ii. a genetic modification which down-regulates endogenous production and/or activity of a polypeptide involved in importing fatty acids into plastids of a cell in the plant part when compared to a corresponding cell lacking the genetic modification; and
 iii. a genetic modification which down-regulates endogenous production and/or activity of a polypeptide involved in diacylglycerol (DAG) production in the plastid when compared to a corresponding cell in the plant part lacking the genetic modification.

In an embodiment, the polypeptide involved in the catabolism of triacylglycerols (TAG) in the plant, or part thereof, is an SDP1 lipase, a Cgi58 polypeptide, an acyl-CoA oxidase such as ACX1 or ACX2, or a polypeptide involved in β-oxidation of fatty acids in the plant or part thereof such as a PXA1 peroxisomal ATP-binding cassette transporter, preferably an SDP1 lipase.

In an embodiment, the polypeptide involved in importing fatty acids into plastids of the cell is a fatty acid transporter, or subunit thereof, preferably a TGD polypeptide.

In an embodiment, the polypeptide involved in diacylglycerol (DAG) production in the plastid is a plastidial GPAT, a plastidial LPAAT or a plastidial PAP.

In another embodiment, the plant part further comprises one or both of:
 i. an exogenous polynucleotide which encodes a second transcription factor polypeptide that increases the expression of one or more glycolytic and/or fatty acid biosynthetic genes in the cell; and
 ii. a second genetic modification which down-regulates endogenous production and/or activity of a polypeptide involved in importing fatty acids into plastids of the cell when compared to a corresponding cell lacking the second genetic modification.

In a preferred embodiment, the presence of a) a genetic modification which down-regulates endogenous production and/or activity of a polypeptide involved in the catabolism of triacylglycerols (TAG) in a cell of the plant part when compared to a corresponding cell lacking the genetic modification, b) an exogenous polynucleotide which encodes a polypeptide which increases the export of fatty acids out of plastids of a cell in the plant part when compared to a corresponding cell lacking the exogenous polynucleotide, or c) an exogenous polynucleotide which encodes a second transcription factor polypeptide that increases the expression of one or more glycolytic and/or fatty acid biosynthetic genes in the cell, together with an exogenous polynucleotide which encodes a WRI1 polypeptide and an exogenous polynucleotide which encodes a polypeptide having DGAT1 activity, increases the total non-polar lipid content of the plant part, preferably a vegetative plant part such as a leaf or stem, relative to a corresponding plant part comprising the exogenous polynucleotides encoding the WRI1 and DGAT1 polypeptides but lacking each of the other exogenous polynucleotide and genetic modifications. Most preferably, at least the promoter that directs expression of the exogenous polynucleotide which encodes the transcription factor is a promoter other than a constitutive promoter. Alternatively for *Sorghum* or *Zea mays*, the promoter is preferably a constitutive promoter such as, for example a ubiquitin gene promoter.

In an embodiment, the addition of one or more of the exogenous polynucleotides or genetic modifications, preferably the exogenous polynucleotide encoding an OBC or a fatty acyl thioesterase or the genetic modification which down-regulates endogenous production and/or activity of a polypeptide involved in the catabolism of triacylglycerols (TAG) in the plant or part thereof, more preferably the exogenous polynucleotide which encodes a FATA thioesterase or an LDAP or which decreases expression of an endogenous TAG lipase such as a SDP1 TAG lipase in the plant or part thereof, results in a synergistic increase in the total non-polar lipid content of the plant or part thereof when added to the pair of transgenes WRI1 and DGAT, particularly before the plant flowers and even more particularly in the stems and/or roots of the plant.

In a preferred embodiment, the increase in the TAG content of a stem or root is at least 2-fold, more preferably at least 3-fold, relative to a corresponding plant part transformed with genes encoding WRI1 and DGAT1 but lacking the FATA thioesterase, LDAP and the genetic modification which down-regulates endogenous production and/or activity of a polypeptide involved in the catabolism of triacylglycerols (TAG) in the plant part. Most preferably, at least the promoter that directs expression of the exogenous polynucleotide which encodes the transcription factor is a promoter other than a constitutive promoter. Alternatively for *Sorghum* or *Zea mays*, the promoter is preferably a constitutive promoter such as, for example a ubiquitin gene promoter.

In an embodiment, each genetic modification is, independently, a mutation of an endogenous gene which partially or completely inactivates the gene, such as a point mutation, an insertion, or a deletion, or an exogenous polynucleotide encoding an RNA molecule which inhibits expression of the endogenous gene, wherein the exogenous polynucleotide is operably linked to a promoter which is capable of directing expression of the polynucleotide in the plant, or part thereof. The point mutation may be a premature stop codon, a splice-site mutation, a frame-shift mutation or an amino acid substitution mutation that reduces activity of the gene or the encoded polypeptide. The deletion may be of one or more nucleotides within a transcribed exon or promoter of the gene, or extend across or into more than one exon, or extend to deletion of the entire gene. Preferably the deletion is introduced by use of ZF, TALEN or CRISPR technologies. In an alternate embodiment, one or more or all of the genetic modifications is an exogenous polynucleotide encoding an RNA molecule which inhibits expression of the endogenous gene, wherein the exogenous polynucleotide is operably linked to a promoter which is capable of directing expression of the polynucleotide in the plant, or part thereof.

Examples of exogenous polynucleotide which reduces expression of an endogenous gene are selected from the group consisting of an antisense polynucleotide, a sense polynucleotide, a microRNA, a polynucleotide which encodes a polypeptide which binds the endogenous enzyme, a double stranded RNA molecule and a processed RNA molecule derived therefrom. In an embodiment, the plant or part thereof comprises genetic modifications which are an introduced mutation in an endogenous gene and an exogenous polynucleotide encoding an RNA molecule which reduces expression of another endogenous gene. In an alternate embodiment, all of the genetic modifications that provide for the increased TTQ and or TAG levels are mutations of endogenous genes.

In an embodiment, the activity of PDCT or CPT in a cell in the plant part is increased relative to a wild-type plant part. Alternatively, the activity of PDCT or CPT is decreased, for example by mutation in the endogenous gene encoding the enzyme or by downregulation of the gene through an RNA molecule which reduces its expression.

In an embodiment, when present, the two transcription factors are WRI1 and LEC2, or WRI1 and LEC1.

In the above embodiments, the plant part preferably comprises an exogenous polynucleotide which encodes a DGAT and a genetic modification which down-regulates production of an endogenous SDP1 lipase. More preferably, the plant part does not comprise an exogenous polynucleotide encoding a PDAT, and/or is a plant part other than a *Nicotiana benthamiana* or part thereof, and/or the WRI1 is a WRI1 other than *Arabidopsis thaliana* WRI1 and/or is a plant part other than a *Brassica napus* or part thereof. In an embodiment, at least one of the exogenous polynucleotides in the plant part is expressed from a promoter which is not a constitutive promoter such as, for example, a promoter which is expressed preferentially in green tissues or stems of the plant or that is up-regulated after commencement of flowering or during senescence.

In an embodiment, the plant part comprises an increased level or activity of polypeptides which are:
  i. a GPAT, a LPAAT, and a WRI1 polypeptide;
    ii. a GPAT, a LPAAT, a DGAT and a WRI1 polypeptide;
    iii. a GPAT9, a LPAAT, and a WRI1 polypeptide;
    iv. a GPAT9, a LPAAT, a DGAT, and a WRI1 polypeptide;
    v. a GPAT, a LPAAT, a DGAT1, and a WRI1 polypeptide;
    vi. a GPAT9, a LPAAT, a DGAT1, and a WRI1 polypeptide;
    vii. a GPAT, a LPAAT, a WRI1 polypeptide, and a fatty acid thioesterase, preferably a FATB polypeptide;
    viii. a GPAT, a LPAAT, a DGAT, a WRI1 polypeptide, and a fatty acid thioesterase, preferably a FATB polypeptide;
    ix. a GPAT9, a LPAAT, a WRI1 polypeptide, and a fatty acid thioesterase, preferably a FATB polypeptide;
    x. a GPAT9, a LPAAT, a DGAT, a WRI1 polypeptide, and a fatty acid thioesterase, preferably a FATB polypeptide;
    xi. a GPAT, a LPAAT, a DGAT1, a WRI1 polypeptide, and a fatty acid thioesterase, preferably a FATB polypeptide;
    xii. a GPAT9, a LPAAT, a DGAT1, a WRI1 polypeptide, and a fatty acid thioesterase, preferably a FATB polypeptide;
    xiii. a GPAT, a LPAAT, a WRI1 polypeptide, a fatty acid thioesterase, preferably a FATB polypeptide, and an OBC polypeptide such as an oleosin, preferably a caleosin or a LDAP;
xiv. a GPAT, a LPAAT, a DGAT, a WRI1 polypeptide, a fatty acid thioesterase, preferably a FATB polypeptide, and an OBC polypeptide such as an oleosin, preferably a caleosin or a LDAP;
xv. a GPAT9, a LPAAT, a WRI1 polypeptide, a fatty acid thioesterase, preferably a FATB polypeptide, and an OBC polypeptide such as an oleosin, preferably a caleosin or a LDAP;
xvi. a GPAT9, a LPAAT, a DGAT, a WRI1 polypeptide, a fatty acid thioesterase, preferably a FATB polypeptide, and an OBC polypeptide such as an oleosin, preferably a caleosin or a LDAP;
xvii. a GPAT, a LPAAT, a DGAT1, a WRI1 polypeptide, a fatty acid thioesterase, preferably a FATB polypeptide, and an OBC polypeptide such as an oleosin, preferably a caleosin or a LDAP;
xviii. a GPAT9, a LPAAT, a DGAT1, a WRI1 polypeptide, a fatty acid thioesterase, preferably a FATB polypeptide, and an OBC polypeptide such as an oleosin, preferably a caleosin or a LDAP;
xix. a GPAT, a LPAAT, a WRI1 polypeptide, a fatty acid thioesterase, preferably a FATB polypeptide, and a silencing RNA which reduces the expression of an endogenous gene which encodes a SDP1 lipase;
xx. a GPAT, a LPAAT, a DGAT, a WRI1 polypeptide, a fatty acid thioesterase, preferably a FATB polypeptide, and a silencing RNA which reduces the expression of an endogenous gene which encodes a SDP1 lipase;
xxi. a GPAT9, a LPAAT, a WRI1 polypeptide, a fatty acid thioesterase, preferably a FATB polypeptide, and a silencing RNA which reduces the expression of an endogenous gene which encodes a SDP1 lipase;
xxii. a GPAT9, a LPAAT, a DGAT, a WRI1 polypeptide, a fatty acid thioesterase, preferably a FATB polypeptide, and a silencing RNA which reduces the expression of an endogenous gene which encodes a SDP1 lipase;
xxiii. a GPAT, a LPAAT, a DGAT1, a WRI1 polypeptide, a fatty acid thioesterase, preferably a FATB polypeptide, and a silencing RNA which reduces the expression of an endogenous gene which encodes a SDP1 lipase;
xxiv. a GPAT9, a LPAAT, a DGAT1, a WRI1 polypeptide, a fatty acid thioesterase, preferably a FATB polypeptide, and a silencing RNA which reduces the expression of an endogenous gene which encodes a SDP1 lipase;
xxv. a GPAT, a LPAAT, a DGAT, a WRI1 polypeptide, a fatty acid thioesterase, preferably a FATB polypeptide, an OBC polypeptide such as an oleosin, preferably a caleosin or a LDAP, and a silencing RNA which reduces the expression of an endogenous gene which encodes a SDP1 lipase;
xxvi. a GPAT9, a LPAAT, a WRI1 polypeptide, a fatty acid thioesterase, preferably a FATB polypeptide, an OBC polypeptide such as an oleosin, preferably a caleosin or a LDAP, and a silencing RNA which reduces the expression of an endogenous gene which encodes a SDP1 lipase;
xxvii. a GPAT9, a LPAAT, a DGAT, a WRI1 polypeptide, a fatty acid thioesterase, preferably a FATB polypeptide, an OBC polypeptide such as an oleosin, preferably a caleosin or a LDAP, and a silencing RNA which reduces the expression of an endogenous gene which encodes a SDP1 lipase;
xxviii. a GPAT, a LPAAT, a DGAT1, a WRI1 polypeptide, a fatty acid thioesterase, preferably a FATB polypeptide, an OBC polypeptide such as an oleosin, preferably a caleosin, or a LDAP, and a silencing RNA which reduces the expression of an endogenous gene which encodes a SDP1 lipase; or a GPAT9, a LPAAT, a DGAT1, a WRI1 polypeptide, a fatty acid thioesterase, preferably a FATB polypeptide, an OBC polypeptide such as an oleosin, preferably a caleosin, or a LDAP, and a silencing RNA which reduces the expression of an endogenous gene which encodes a SDP1 lipase.

In an embodiment, the one or more or all of the polypeptides are encoded by one or more exogenous polynucleotides in the plant parts.

In a second aspect, the present invention provides a process for producing extracted plant lipid, comprising the steps of:
a) obtaining one or more plant parts comprising lipid, preferably vegetative plant parts, the lipid comprising a total fatty acid content which comprises fatty acids in an esterified form, the fatty acids comprising an increased level of medium chain fatty acids (MCFA) relative to a corresponding wild-type plant part, wherein the plant part comprises an increased level or activity of polypeptides which are:
i. a GPAT, a LPAAT, and a WRI1 polypeptide;
ii. a GPAT, a LPAAT, a DGAT and a WRI1 polypeptide;
iii. a GPAT9, a LPAAT, and a WRI1 polypeptide;
iv. a GPAT9, a LPAAT, a DGAT, and a WRI1 polypeptide;
v. a GPAT, a LPAAT, a DGAT1, and a WRI1 polypeptide;
vi. a GPAT9, a LPAAT, a DGAT1, and a WRI1 polypeptide;
vii. a GPAT, a LPAAT, a WRI1 polypeptide, and a fatty acid thioesterase, preferably a FATB polypeptide;
viii. a GPAT, a LPAAT, a DGAT, a WRI1 polypeptide, and a fatty acid thioesterase, preferably a FATB polypeptide;
ix. a GPAT9, a LPAAT, a WRI1 polypeptide, and a fatty acid thioesterase, preferably a FATB polypeptide;
x. a GPAT9, a LPAAT, a DGAT, a WRI1 polypeptide, and a fatty acid thioesterase, preferably a FATB polypeptide;
xi. a GPAT, a LPAAT, a DGAT1, a WRI1 polypeptide, and a fatty acid thioesterase, preferably a FATB polypeptide;
xii. a GPAT9, a LPAAT, a DGAT1, a WRI1 polypeptide, and a fatty acid thioesterase, preferably a FATB polypeptide;
xiii. a GPAT, a LPAAT, a WRI1 polypeptide, a fatty acid thioesterase, preferably a FATB polypeptide, and an OBC polypeptide such as an oleosin, preferably a caleosin or a LDAP;
xiv. a GPAT, a LPAAT, a DGAT, a WRI1 polypeptide, a fatty acid thioesterase, preferably a FATB polypeptide, and an OBC polypeptide such as an oleosin, preferably a caleosin or a LDAP;
xv. a GPAT9, a LPAAT, a WRI1 polypeptide, a fatty acid thioesterase, preferably a FATB polypeptide, and an OBC polypeptide such as an oleosin, preferably a caleosin or a LDAP;
xvi. a GPAT9, a LPAAT, a DGAT, a WRI1 polypeptide, a fatty acid thioesterase, preferably a FATB polypeptide, and an OBC polypeptide such as an oleosin, preferably a caleosin or a LDAP;

xvii. a GPAT, a LPAAT, a DGAT1, a WRI1 polypeptide, a fatty acid thioesterase, preferably a FATB polypeptide, and an OBC polypeptide such as an oleosin, preferably a caleosin or a LDAP;

xviii. a GPAT9, a LPAAT, a DGAT1, a WRI1 polypeptide, a fatty acid thioesterase, preferably a FATB polypeptide, and an OBC polypeptide such as an oleosin, preferably a caleosin or a LDAP;

xix. a GPAT, a LPAAT, a WRI1 polypeptide, a fatty acid thioesterase, preferably a FATB polypeptide, and a silencing RNA which reduces the expression of an endogenous gene which encodes a SDP1 lipase;

xx. a GPAT, a LPAAT, a DGAT, a WRI1 polypeptide, a fatty acid thioesterase, preferably a FATB polypeptide, and a silencing RNA which reduces the expression of an endogenous gene which encodes a SDP1 lipase;

xxi. a GPAT9, a LPAAT, a WRI1 polypeptide, a fatty acid thioesterase, preferably a FATB polypeptide, and a silencing RNA which reduces the expression of an endogenous gene which encodes a SDP1 lipase;

xxii. a GPAT9, a LPAAT, a DGAT, a WRI1 polypeptide, a fatty acid thioesterase, preferably a FATB polypeptide, and a silencing RNA which reduces the expression of an endogenous gene which encodes a SDP1 lipase;

xxiii. a GPAT, a LPAAT, a DGAT1, a WRI1 polypeptide, a fatty acid thioesterase, preferably a FATB polypeptide, and a silencing RNA which reduces the expression of an endogenous gene which encodes a SDP1 lipase;

xxiv. a GPAT9, a LPAAT, a DGAT1, a WRI1 polypeptide, a fatty acid thioesterase, preferably a FATB polypeptide, and a silencing RNA which reduces the expression of an endogenous gene which encodes a SDP1 lipase;

xxv. a GPAT, a LPAAT, a DGAT, a WRI1 polypeptide, a fatty acid thioesterase, preferably a FATB polypeptide, an OBC polypeptide such as an oleosin, preferably a caleosin or a LDAP, and a silencing RNA which reduces the expression of an endogenous gene which encodes a SDP1 lipase;

xxvi. a GPAT9, a LPAAT, a WRI1 polypeptide, a fatty acid thioesterase, preferably a FATB polypeptide, an OBC polypeptide such as an oleosin, preferably a caleosin or a LDAP, and a silencing RNA which reduces the expression of an endogenous gene which encodes a SDP1 lipase;

xxvii. a GPAT9, a LPAAT, a DGAT, a WRI1 polypeptide, a fatty acid thioesterase, preferably a FATB polypeptide, an OBC polypeptide such as an oleosin, preferably a caleosin or a LDAP, and a silencing RNA which reduces the expression of an endogenous gene which encodes a SDP1 lipase;

xxviii. a GPAT, a LPAAT, a DGAT1, a WRI1 polypeptide, a fatty acid thioesterase, preferably a FATB polypeptide, an OBC polypeptide such as an oleosin, preferably a caleosin, or a LDAP, and a silencing RNA which reduces the expression of an endogenous gene which encodes a SDP1 lipase; or xxix. a GPAT9, a LPAAT, a DGAT1, a WRI1 polypeptide, a fatty acid thioesterase, preferably a FATB polypeptide, an OBC polypeptide such as an oleosin, preferably a caleosin, or a LDAP, and a silencing RNA which reduces the expression of an endogenous gene which encodes a SDP1 lipase, and b) extracting lipid from the plant part(s), thereby producing the extracted plant lipid.

In an embodiment, the one or more or all of the polypeptides are encoded by one or more exogenous polynucleotides in the plant parts.

In an embodiment, the level of total, or new, MCFA is increased relative to a corresponding wild-type plant part, preferably the level is at least 25% of the total fatty acid content on a weight basis.

In an embodiment of the first and second aspects, the one or more or all of the encoded GPAT, LPAAT and DGAT have a preference for utilising medium chain fatty acid substrates. GPAT, LPAAT and DGAT each use an acyl-CoA substrate, with a second substrate that is G3P, LPA or DAG, respectively.

In an embodiment of the first and second aspects, the extracted lipid has one or more or all of the following features:

i. the level of medium chain fatty acids in the total fatty acid content of the extracted lipid, and/or in the total fatty acid content of the TAG of the extracted lipid, is at least about 30%, at least about 35%, at least about 40%, at least about 50%, at least about 55%, or between about 25% and about 55%, between about 25% and about 50%, between about 30% and about 50%, between about 35% and about 50%, between about 25% and about 40%, or between about 30% and about 40%;

ii. the level of lauric acid (C12:0) in the total fatty acid content of the extracted lipid, and/or in the total fatty acid content of the TAG of the extracted lipid, is, or is increased by, at least about 15%, at least about 20%, at least about 25%, at least about 30%, at least about 35%, at least about 40%, at least about 50%, at least or about 55%, or between about 15% and about 55%, between about 20% and about 50%, between about 30% and about 50%, between about 35% and about 50%, between about 15% and about 25%, or between about 20% and about 30%;

iii. the level of myristic acid (C14:0) in the total fatty acid content of the extracted lipid, and/or in the total fatty acid content of the TAG of the extracted lipid, is, or is increased by, at least about 25%, at least about 30%, at least about 35%, at least about 40%, at least about 45%, or between about 25% and about 45%, between about 20% and about 50%, between about 30% and about 50%, between about 35% and about 50%, between about 30% and about 40%, between about 15% and about 25%, or between about 20% and about 30%;

iv. the level of palmitic acid (C16:0) in the total fatty acid content of the extracted lipid, and/or in the total fatty acid content of the TAG of the extracted lipid, is, or is increased by, between about 2% and about 18%, or between about 2% and about 16%, or between about 2% and about 15%, or between about 15% and about 50%;

v. the level of lauric acid (C12:0) in the total fatty acid content of the extracted lipid, and/or in the total fatty acid content of the TAG of the extracted lipid is, or is increased by, at least about 25%, at least about 30%, at least about 40%, at least about 45%, or at least about 50%, and the level of myristic acid (C14:0) in the total fatty acid content of the extracted lipid and/or in the total fatty acid content of the TAG of the extracted lipid is, or is increased by, at least about 1%, at least about 2%, at least about 5%, or at least about 10%, or between about 1% and about 10%, or between about 2% and 10%, or between about 2% and about 6%, or less than about 10%, or less than about 8% or less than about 5%, or less than about 2%;

vi. the level of myristic acid (C14:0) in the total fatty acid content of the extracted lipid, and/or in the total fatty acid content of the TAG of the extracted lipid is, or is increased by, at least about 20%, at least about 25%, at least about 30%, or at least about 40%, and the level of lauric acid (C12:0) in the total fatty acid content of the extracted lipid and/or in the total fatty acid content of the TAG of the extracted lipid is, or is increased by, at least about 1%, at least about 2%, at least about 5%, or at least about 10%, or between about 1% and about 10%, or between about 2% and about 10%, or between about 2% and about 6%, or less than about 10%, or less than about 8% or less than about 5%, or less than about 2%;

vii. the level of myristic acid (C14:0) in the total fatty acid content of the extracted lipid, and/or in the total fatty acid content of the TAG of the extracted lipid is, or is increased by, at least about 20%, at least about 25%, at least about 30%, and the level of palmitic acid (C16:0) in the total fatty acid content of the extracted lipid and/or in the total fatty acid content of the TAG of the extracted lipid is, or is increased by, at least about 2%, at least about 3%, at least about 4%, or at least about 5%.

viii. the ratio of lauric acid (C12:0):myristic acid (C14:0) in the fatty acid content of the extracted lipid, and/or in the total fatty acid content of the TAG of the extracted lipid, is increased, or is about 1:4, about 1:5, about 1:10, about 1:15, about 1:20, about 1:25, or about 4:1, about 5:1, about 10:1, about 15:1, about 20:1, about 30:1, about 40:1, or about 45:1;

ix. the ratio of lauric acid (C12:0):palmitic acid (C16:0) in the fatty acid content of the extracted lipid, and/or in the total fatty acid content of the TAG of the extracted lipid, is increased, or is about 1:2, about 1:3, about 1:4, about 1:5, about 1:10, about 1:15, about 10:1, about 20:1, about 30:1, about 40:1, or about 45:1;

x. the ratio of myristic acid (C14:0):palmitic acid (C16:0) in the fatty acid content of the extracted lipid, and/or in the total fatty acid content of the TAG of the extracted lipid, is increased, or is about 1:2, about 1:3, about 1:4, about 1:5, about 1:10, about 1:15, about 10:1, about 20:1, about 30:1, or about 40:1;

xi. the level of oleic acid in the total fatty acid content of the extracted lipid, and/or in the total fatty acid content of the TAG of the extracted lipid, is decreased, or is less than about 10%, less than about 8%, less than about 6%, less than about 5%, less than about 4%, less than about 3%, less than about 2%, less than about 1%;

xii. the level of linoleic acid (LA) in the total fatty acid content of the extracted lipid, and/or in the total fatty acid content of the TAG of the extracted lipid, is increased or decreased, or is less than about 20%, less than about 15%, less than about 10%, less than about 5%, less than about 4%, less than about 3%, less than about 2%, or less than about 1%;

xiii. the level of α-linolenic acid (ALA) in the total fatty acid content of the extracted lipid, or in the total fatty acid content of the TAG of the extracted lipid, is decreased or is less than about 50%, less than about 40%, less than about 30%, less than about 20%, less than about 10%, less than about 8%, less than about 6%, less than about 5%, less than about 2%, or less than about 1%;

xiv. the level of total unsaturated fatty acids in the total fatty acid content of the extracted lipid, and/or in the total fatty acid content of the TAG of the extracted lipid, is decreased, or is less than about 50%, less than about 40%, less than about 30%, less than about 20%, less than about 15%, less than about 10%, less than about 8%, less than about 6%, less than about 5%, less than about 2%, or less than about 1%;

xv. the level of total monounsaturated fatty acids in the total fatty acid content of the extracted lipid, and/or in the total fatty acid content of the TAG of the extracted lipid, is decreased, or is less than about 10%, less than about 5%, less than about 4%, less than about 3%, less than about 2%, or less than about 1%;

xvi. the level of total polyunsaturated fatty acids in the total fatty acid content of the extracted lipid, and/or in the total fatty acid content of the TAG of the extracted lipid, is less than about 50%, less than about 40%, less than about 30%, less than about 20%, less than about 15%, less than about 10%, less than about 8%, less than about 6%, less than about 5%, less than about 2%, or less than about 1%;

xvii. the triacylglycerol (TAG) content of the extracted lipid is at least about 80%, at least about 85%, at least about 90%, or least about 95%, and about 98%, or between about 95% and about 98%, by weight of the extracted lipid;

xviii. the TAG content of the extracted lipid comprises, or is increased in a level of, one or more or all of the TAG species 36:0, 38:0, 40:0 and 42:0;

xix. the extracted lipid comprises tri-laurin (tri-C12:0) and/or tri-myristin (tri-C14:0); and xx. the phosphocholine (PC) content of the extracted lipid comprises one or both of the PC species 28:0 and 30:0, wherein any increase or decrease is relative to a corresponding wild-type plant part.

In an embodiment, the plant part comprises one or more of the features defined with respect to the first aspect.

In an embodiment of the first and second aspects, the plant part has one or more or all of the following features:

a) an increased soluble protein content relative to a corresponding wild-type plant part, b) an increased nitrogen content in plant part relative to a corresponding wild-type plant part, f) decreased carbon:nitrogen ratio relative to a corresponding wild-type plant part, g) increased photosynthetic gene expression relative to a corresponding wild-type plant part, h) increased photosynthetic capacity relative to a corresponding wild-type plant part, i) decreased total dietary fibre (TDF) content relative to a corresponding wild-type plant part, j) increased carbon content relative to a corresponding wild-type plant part, and k) increased energy content relative to a corresponding wild-type plant part, wherein each exogenous polynucleotide is operably linked to a promoter which is capable of directing expression of the polynucleotide in the cell.

In an embodiment, the plant part, preferably a *Sorghum* sp. or *Zea mays* plant part, further comprises:

1) an increased TTQ relative to a corresponding wild-type plant part, wherein each exogenous polynucleotide is operably linked to a promoter which is capable of directing expression of the polynucleotide in the plant, or part thereof.

In an embodiment, the plant part is derived from an ancestor plant, for example, as described herein.

In an embodiment, the plant part has one or more or all of:

i) the plant part has an increased soluble protein relative to the corresponding wild-type plant part of at least about 10%, at least about 25%, at least about 50%, at least about 75%, at least about 100%, between about 10% and about 200%, between about 50% and about 150%, or between about 50% and about 125%, ii) the plant part has an increased nitrogen content relative to the corresponding wild-type plant part of at least about 10%, at least about 25%, at least about 50%, at least about 75%, at least about 100%, between about 10% and about 200%, between about 50% and about 150% or between about 50% and about 125%, iii) the plant part is a leaf which has an increased soluble protein content relative to a corresponding wild-type leaf of at least about 10%, at least about 25%, at least about 50%, at least about 75%, at least about 100%, between about 10% and about 200%, between about 50% and about 150%, or between about 50% and about 125%, iv) the plant part is a leaf which has an increased nitrogen content relative to a corresponding wild-type leaf of at least about 10%, at least about 25%, at least about 50%, at least about 75%, at least about 100%, between about 10% and about 200%, between about 50% and about 150%, or between about 50% and about 125%, v) the plant part has a decreased carbon:nitrogen content relative to the corresponding wild-type plant or part thereof of at least about 10%, at least about 25%, at least about 40%, between about 10% and about 50%, or between about 25% and about 50%, vi) expression of one or more genes involved in photosynthesis is increased in the plant part relative to the corresponding wild-type plant part, vii) the plant part has an increased carbon content relative to the corresponding wild-type plant part of at least about 10%, at least about 25%, at least about 50%, at least about 75%, at least about 100%, at least about 125%, at least about 150%, between about 10% and about 300%, between about 50% and about 250%, or between about 100% and about 200%, viii) the plant part has an increased energy content in the plant part relative to the corresponding wild-type plant part of at least about 10%, at least about 25%, at least about 50%, at least about 75%, at least about 100%, at least about 125%, at least about 150%, at least about 200%, at least about 250%, between about 10% and about 400%, between about 50% and about 300%, or between about 200% and about 300%, ix) the plant part has a decreased starch content relative to the corresponding wild-type plant part of at least about 2 fold, at least about 5 fold, at least about 10 fold, at least about 15 fold, at least about 20 fold, at least about 25 fold, between about 5 fold and about 35 fold, between about 10 fold and about 30 fold, or between about 20 fold and about 30 fold, x) the plant part has a decreased TDF content relative to the corresponding wild-type plant part of at least about 10%, at least about 30%, at least about 50%, between about 10% and about 70%, or between about 30% and about 65%, and xi) the plant part has a soluble sugar content relative to the corresponding wild-type plant part which is about 0.5 fold to 2 fold.

In an embodiment of the first and second aspects, plant part has one or more or all of;

i) the plant part comprises a total non-polar lipid content of at least about 8%, at least about 10%, at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight), preferably before flowering, ii) the plant part is a vegetative part that comprises a TAG content of at least about 8%, at least about 10%, at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight), preferably before flowering, iii) one or more or all of the promoters are selected from a tissue-specific promoter such as a leaf and/or stem specific promoter, a developmentally regulated promoter such as a senescence-specific promoter such as a SAG12 promoter, an inducible promoter, or a circadian-rhythm regulated promoter, iv) the plant part is one member of a population or collection of at least about 1,500, at least about 3,000 or at least about 5,000 such plant parts, preferably vegetative plant parts.

In a further embodiment, the plant part is:

i) a 16:3 plant part, and which comprises one or more or all of the following:

a) an exogenous polynucleotide which encodes a polypeptide which increases the export of fatty acids out of plastids of the plant when compared to a corresponding plant lacking the exogenous polynucleotide, b) a first genetic modification which down-regulates endogenous production and/or activity of a polypeptide involved in importing fatty acids into plastids of the plant when compared to a corresponding plant lacking the first genetic modification, and c) a second genetic modification which down-regulates endogenous production and/or activity of a polypeptide involved in diacylglycerol (DAG) production in the plastid when compared to a corresponding plant lacking the second genetic modification, wherein the exogenous polynucleotide is operably linked to a promoter which is capable of directing expression of the polynucleotide in the plant part, or ii) a 18:3 plant part.

In an embodiment, the plant part has one or more or all of:

i) the plant part, preferably a vegetative plant part which has an increased synthesis of total fatty acids relative to a corresponding plant part lacking the exogenous polynucleotide(s) and/or genetic modification(s), ii) the plant part, preferably a vegetative plant part which has an increased expression and/or activity of a fatty acyl acyltransferase which catalyses the synthesis of TAG, DAG or MAG, preferably TAG, relative to a corresponding plant part lacking the exogenous polynucleotide(s) and/or genetic modification(s), iii) the plant part, preferably a vegetative plant part which has a decreased production of lysophosphatidic acid (LPA) from acyl-ACP and G3P in its plastids relative to a corresponding plant part lacking the exogenous polynucleotide(s) and/or genetic modification(s), iv) the plant part, preferably a vegetative plant part which has an altered ratio of C16:3 to C18:3 fatty acids in its total fatty acid content and/or its galactolipid content relative to a corresponding part lacking the exogenous polynucleotide(s) and/or genetic modification(s), preferably a decreased ratio, v) one or more or all of the promoters are selected from promoter other than a constitutive promoter, preferably a tissue-specific promoter such as a leaf and/or stem specific promoter, a developmentally regulated promoter such as a senescense-specific promoter such as a SAG12 promoter, an inducible promoter, or a circadian-rhythm regulated promoter, preferably wherein at least one of the promoters operably linked to an exogenous polynucleotide which encodes a transcription factor polypeptide is a promoter other than a constitutive promoter, vi) the plant part, preferably a vegetative plant part, comprises a total fatty acid content whose oleic acid level and/or palmitic acid level is increased by at least 2% relative to a corresponding plant, or part thereof, lacking the exogenous polynucleotide(s) and/or genetic modification(s), and/or whose α-linolenic acid (ALA) level and/or linoleic acid level is decreased by at least 2% relative to a corresponding plant part lacking the exogenous polynucleotide(s) and/or genetic modification(s), vii) non-polar lipid in the plant part, preferably a vegetative plant part, comprises a modified level of total sterols, preferably free (non-esterified) sterols, steroyl esters, steroyl glycosides, relative to the non-polar lipid in a corresponding plant, or part thereof, lacking the exogenous polynucleotide(s) and/or genetic modification(s), viii) non-polar lipid in the plant part comprises waxes and/or wax esters, ix) the plant part comprises an exogenous polynucleotide encoding a silencing suppressor, wherein the exogenous polynucleotide is operably linked to a promoter which is capable of directing expression of the polynucleotide in the plant, x) the level of one or more non-polar lipid(s) and/or the total non-polar lipid content of the plant or part thereof, preferably a vegetative plant part, is at least 2% greater on a weight basis than in a corresponding plant or part, respectively, which comprises exogenous polynucleotides encoding an *Arabidposis thaliana* WRI1 and an *Arabidopsis thaliana* DGAT1 (SEQ ID NO:1), xi) a total polyunsaturated fatty acid (PUFA) content which is decreased relative to the total PUFA content of a corresponding plant lacking the exogenous polynucleotide(s) and/or genetic modification(s), xii) if the plant part is a seed, the seed germinates at a rate substantially the same as for a corresponding wild-type seed or when sown in soil produces a plant whose seed germinate at a rate substantially the same as for corresponding wild-type seed, and xiii) the plant is an algal plant such as from diatoms (bacillariophytes), green algae (chlorophytes), blue-green algae (cyanophytes), golden-brown algae (chrysophytes), haptophytes, brown algae or heterokont algae.

In an embodiment, the plant part comprises a first exogenous polynucleotide encoding a WRI1, a second exogenous polynucleotide encoding a DGAT or a PDAT, preferably a DGAT1, a third exogenous polynucleotide encoding an RNA which reduces expression of a gene encoding an SDP1 polypeptide, and a fourth exogenous polynucleotide encoding an oleosin. In preferred embodiments, the plant part has one or more or all of the following features:

i) a total lipid content of at least 8%, at least 10%, at least 12%, at least 14%, or at least 15.5% (% weight), ii) at least a 3 fold, at least a 5 fold, at least a 7 fold, at least an 8 fold, or least a 10 fold, at higher total lipid content in the plant part relative to a corresponding the plant part lacking the exogenous polynucleotides and/or genetic modifications, iii) a total TAG content of at least 5%, at least 6%, at least 6.5% or at least 7% (% weight of dry weight or seed weight), iv) at least a 40 fold, at least a 50 fold, at least a 60 fold, or at least 70 fold, at least 100 fold, or at least a 120-fold higher total TAG content relative to a corresponding the plant part lacking the exogenous polynucleotides and/or genetic modifications, v) palmitic acid comprises at least 20%, at least 25%, at least 30% or at least 33% (% weight) of the fatty acids in TAG, vi) at least a 1.5 fold higher level of palmitic acid in TAG relative to a corresponding the plant part lacking the exogenous polynucleotides and/or genetic modifications, vii) linoleic acid comprises at least 22%, at least 25%, at least 30% or at least 34% (% weight) of the fatty acids in TAG, and viii) α-linolenic acid comprises less than 20%, less than 15%, less than 11% or less than 8% (% weight) of the fatty acids in TAG.

ix) at least a 5 fold, or at least an 8 fold, lower level of α-linolenic acid in TAG relative to a corresponding the plant or part thereof lacking the exogenous polynucleotides and/or genetic modifications, In the above embodiments, a preferred plant part is a leaf piece having a surface area of at least 1 cm² or a stem piece having a length of at least 1 cm.

In an embodiment of the above aspects, the plant part has been treated so it is no longer able to be propagated or give rise to a living plant, i.e. it is dead (for example a brown leaf or stem). For example, the plant part has been dried and/or ground. In another embodiment, the plant part is alive (for example, a green leaf or stem).

In an embodiment, the part is a seed, fruit, or a vegetative part such as an aerial plant part or a green part such as a leaf or stem.

In the above embodiments, it is preferred that the plant part is a vegetative plant part which is growing in soil or which was grown in soil and the plant part was subsequently harvested, and wherein the vegetative part comprises at least 8% TAG on a weight basis (% dry weight) such as for example between 8% and 75% or between 8% and 30%. More preferably, the TAG content is at least 10%, such as for example between 10% and 75% or between 10% and 30%. Preferably, these TAG levels are present in the vegetative parts prior to or at flowering of the plant or prior to seed setting stage of plant development. In these embodiments, it is preferred that the ratio of the TAG content in the leaves to the TAG content in the stems of the plant is between 1:1 and 10:1, and/or the ratio is increased relative to a corresponding vegetative part comprising the first and second exogenous polynucleotides and lacking the first genetic modification. Preferably, the vegetative plant part has an increased soluble protein content relative to the corresponding wild-type vegetative plant part of at least about 100%, or between about 50% and about 125%. Preferably, the vegetative plant part has an increased nitrogen content relative to the corresponding wild-type vegetative part of at least about 100%, or between about 50% and about 125%. Preferably, the vegetative plant part has an decreased carbon:nitrogen content relative to the corresponding wild-type vegetative part of at least about 40%, or between about 25% and about 50%. Preferably, the vegetative plant part has a decreased TDF content in the part or at least a part of the transgenic plant relative to the corresponding wild-type vegetative plant part of at least about 30%, or between about 30% and about 65%.

In an embodiment, the plant part, preferably a leaf, a grain, a stem, a root or an endosperm is from a monocotyledonous plant, which has a total fatty acid content or TAG content which is increased at least 5-fold on a weight basis when compared to a corresponding non-transgenic monocotyledonous plant. Alternatively, the transgenic monocotyledonous plant has endosperm comprising a TAG content which is at least 2.0%, preferably at least 3%, more preferably at least 4% or at least 5%, on a weight basis. In an embodiment, the endosperm has a TAG content of at least 2% which is increased at least 5-fold relative to a corresponding non-transgenic endosperm. Preferably, the plant is fully male and female fertile, its pollen is essentially 100% viable, and its grain has a germination rate which is between 70% and 100% relative to corresponding wild-type grain. In an embodiment, the transgenic plant is a progeny plant at least two generations derived from an initial transgenic wheat plant, and is preferably homozygous for the transgenes. In embodiments, the monocotyledonous plant, or part thereof, preferably a leaf, stem, grain or endosperm, is further characterised by one or more features as defined in the context of a plant or part thereof of the invention. In embodiments, the monocotyledonous plant, or part thereof, preferably a leaf, a grain, stem or an endosperm of the invention preferably has an increased level of monounsaturated fatty acids (MUFA) and/or a lower level of polyunsaturated fatty acids (PUFA) in both the total fatty acid content and in the TAG fraction of the total fatty acid content, such as for example an increased level of oleic acid and a reduced level of LA (18:2), when compared to a corresponding plant or part thereof lacking the genetic modifications and/or exogenous polynucleotide(s). Preferably, the linoleic acid (LA, 18:2) level in the total fatty acid content of the grain or endosperm of the monocotyledonous plant is reduced by at least 5% and/or the level of oleic acid in the total fatty acid content is increased by at least 5% relative to a corresponding wild-type plant or part thereof, preferably at least 10% or more preferably at least 15%, when compared to a corresponding plant or part thereof lacking the genetic modifications and/or exogenous polynucleotide(s).

In an embodiment of the first and second aspects, the extracted lipid is in the form of an oil, wherein at least about 90%, or least about 95%, at least about 98%, or between about 95% and about 98%, by weight of the oil is the lipid.

In an embodiment of the first and second aspects, the plant part is a vegetative plant part such as a plant leaf or stem, or the plant part is a seed or a fruit.

In an embodiment of the first and second aspects the plant part is from a species selected from a group consisting of a *Acrocomia aculeata* (macauba palm), *Arabidopsis thaliana*, *Aracinis hypogaea* (peanut), *Astrocaryum murumuru* (murumuru), *Astrocaryum vulgare* (tucumã), *Attalea geraensis* (Indaiá-rateiro), *Attalea humilis* (American oil palm), *Attalea oleifera* (andaiá), *Attalea phalerata* (uricuri), *Attalea speciosa* (babassu), *Avena sativa* (oats), *Beta vulgaris* (sugar beet), *Brassica* sp. such as *Brassica carinata*, *Brassica juncea*, *Brassica napobrassica*, *Brassica napus* (canola), *Camelina sativa* (false flax), *Cannabis sativa* (hemp), *Carthamus tinctorius* (safflower), *Caryocar brasiliense* (pequi), *Cocos nucifera* (Coconut), *Crambe abyssinica* (Abyssinian kale), *Cucumis melo* (melon), *Elaeis guineensis* (African palm), *Glycine max* (soybean), *Gossypium hirsutum* (cotton), *Helianthus* sp. such as *Helianthus annuus* (sunflower), *Hordeum vulgare* (barley), *Jatropha curcas* (physic nut), *Joannesia princeps* (arara nut-tree), *Lemna* sp. (duckweed) such as *Lemna aequinoctialis*, *Lemna disperma*, *Lemna ecuadoriensis*, *Lemna gibba* (swollen duckweed), *Lemna japonica*, *Lemna minor*, *Lemna minuta*, *Lemna obscura*, *Lemna paucicostata*, *Lemna perpusilla*, *Lemna tenera*, *Lemna trisulca*, *Lemna turionifera*, *Lemna valdiviana*, *Lemna yungensis*, *Licania rigida* (oiticica), *Linum usitatissimum* (flax), *Lupinus angustifolius* (lupin), *Mauritia flexuosa* (buriti palm), *Maximiliana maripa* (inaja palm), *Miscanthus* sp. such as *Miscanthus* x *giganteus* and *Miscanthus sinensis*, *Nicotiana* sp. (tabacco) such as *Nicotiana tabacum* or *Nicotiana benthamiana*, *Oenocarpus bacaba* (bacaba-do-azeite), *Oenocarpus bataua* (patauã), *Oenocarpus distichus* (bacaba-de-leque), *Oryza* sp. (rice) such as *Oryza sativa* and *Oryza glaberrima*, *Panicum virgatum* (switchgrass), *Paraqueiba paraensis* (mari), *Persea amencana* (avocado), *Pongamia pinnata* (Indian beech), *Populus trichocarpa*, *Ricinus communis* (castor), *Saccharum* sp. (sugarcane), *Sesamum indicum* (sesame), *Solanum tuberosum* (potato), *Sorghum* sp. such as *Sorghum bicolor*, *Sorghum vulgare*, *Theobroma grandiforum* (cupuassu), *Trifolium* sp., *Trithrinax brasiliensis* (Brazilian needle palm), *Triticum* sp. (wheat) such as *Triticum aestivum* and *Zea mays* (corn). For example, the plant part is from a monocotyledonous plant, preferably a plant from the family Poaceae, more preferably a *Sorghum* sp., a *Zea mays*, *Miscanthus* sp. such as *Miscanthus* x *giganteus* and *Miscanthus sinensis*, and/or a *Panicum virgatum* (switchgrass) plant.

In an embodiment of the first and second aspects, the one or more or all of the promoters are expressed at a higher level in a vegetative plant part relative to seed of a plant.

In another aspect, the present invention provides extracted plant lipid produced by the process of both the first and second aspects, preferably comprising plant leaf lipid.

In another aspect, the present invention provides extracted plant lipid, comprising fatty acids in an esterified form, wherein the level of medium chain fatty acids in the total fatty acid content of the lipid in the vegetative plant part is at least about 25%. In an embodiment, the lipid has one or more of the features defined above in relation to the first or second aspects.

In another aspect, the present invention provides a cell comprising an increased level or activity of polypeptides which are:
  i. a GPAT, a LPAAT, and a WRI1 polypeptide;
    ii. a GPAT, a LPAAT, a DGAT and a WRI1 polypeptide;
    iii. a GPAT9, a LPAAT, and a WRI1 polypeptide;
    iv. a GPAT9, a LPAAT, a DGAT, and a WRI1 polypeptide;
    v. a GPAT, a LPAAT, a DGAT1, and a WRI1 polypeptide;
    vi. a GPAT9, a LPAAT, a DGAT1, and a WRI1 polypeptide;
    vii. a GPAT, a LPAAT, a WRI1 polypeptide, and a fatty acid thioesterase, preferably a FATB polypeptide;

viii. a GPAT, a LPAAT, a DGAT, a WRI1 polypeptide, and a fatty acid thioesterase, preferably a FATB polypeptide;
ix. a GPAT9, a LPAAT, a WRI1 polypeptide, and a fatty acid thioesterase, preferably a FATB polypeptide;
x. a GPAT9, a LPAAT, a DGAT, a WRI1 polypeptide, and a fatty acid thioesterase, preferably a FATB polypeptide;
xi. a GPAT, a LPAAT, a DGAT1, a WRI1 polypeptide, and a fatty acid thioesterase, preferably a FATB polypeptide;
xii. a GPAT9, a LPAAT, a DGAT1, a WRI1 polypeptide, and a fatty acid thioesterase, preferably a FATB polypeptide;
xiii. a GPAT, a LPAAT, a WRI1 polypeptide, a fatty acid thioesterase, preferably a FATB polypeptide, and an OBC polypeptide such as an oleosin, preferably a caleosin or a LDAP;
xiv. a GPAT, a LPAAT, a DGAT, a WRI1 polypeptide, a fatty acid thioesterase, preferably a FATB polypeptide, and an OBC polypeptide such as an oleosin, preferably a caleosin or a LDAP;
xv. a GPAT9, a LPAAT, a WRI1 polypeptide, a fatty acid thioesterase, preferably a FATB polypeptide, and an OBC polypeptide such as an oleosin, preferably a caleosin or a LDAP;
xvi. a GPAT9, a LPAAT, a DGAT, a WRI1 polypeptide, a fatty acid thioesterase, preferably a FATB polypeptide, and an OBC polypeptide such as an oleosin, preferably a caleosin or a LDAP;
xvii. a GPAT, a LPAAT, a DGAT1, a WRI1 polypeptide, a fatty acid thioesterase, preferably a FATB polypeptide, and an OBC polypeptide such as an oleosin, preferably a caleosin or a LDAP;
xviii. a GPAT9, a LPAAT, a DGAT1, a WRI1 polypeptide, a fatty acid thioesterase, preferably a FATB polypeptide, and an OBC polypeptide such as an oleosin, preferably a caleosin or a LDAP;
xix. a GPAT, a LPAAT, a WRI1 polypeptide, a fatty acid thioesterase, preferably a FATB polypeptide, and a silencing RNA which reduces the expression of an endogenous gene which encodes a SDP1 lipase;
xx. a GPAT, a LPAAT, a DGAT, a WRI1 polypeptide, a fatty acid thioesterase, preferably a FATB polypeptide, and a silencing RNA which reduces the expression of an endogenous gene which encodes a SDP1 lipase;
xxi. a GPAT9, a LPAAT, a WRI1 polypeptide, a fatty acid thioesterase, preferably a FATB polypeptide, and a silencing RNA which reduces the expression of an endogenous gene which encodes a SDP1 lipase;
xxii. a GPAT9, a LPAAT, a DGAT, a WRI1 polypeptide, a fatty acid thioesterase, preferably a FATB polypeptide, and a silencing RNA which reduces the expression of an endogenous gene which encodes a SDP1 lipase;
xxiii. a GPAT, a LPAAT, a DGAT1, a WRI1 polypeptide, a fatty acid thioesterase, preferably a FATB polypeptide, and a silencing RNA which reduces the expression of an endogenous gene which encodes a SDP1 lipase;
xxiv. a GPAT9, a LPAAT, a DGAT1, a WRI1 polypeptide, a fatty acid thioesterase, preferably a FATB polypeptide, and a silencing RNA which reduces the expression of an endogenous gene which encodes a SDP1 lipase;
xxv. a GPAT, a LPAAT, a DGAT, a WRI1 polypeptide, a fatty acid thioesterase, preferably a FATB polypeptide, an OBC polypeptide such as an oleosin, preferably a caleosin or a LDAP, and a silencing RNA which reduces the expression of an endogenous gene which encodes a SDP1 lipase;
xxvi. a GPAT9, a LPAAT, a WRI1 polypeptide, a fatty acid thioesterase, preferably a FATB polypeptide, an OBC polypeptide such as an oleosin, preferably a caleosin or a LDAP, and a silencing RNA which reduces the expression of an endogenous gene which encodes a SDP1 lipase;
xxvii. a GPAT9, a LPAAT, a DGAT, a WRI1 polypeptide, a fatty acid thioesterase, preferably a FATB polypeptide, an OBC polypeptide such as an oleosin, preferably a caleosin or a LDAP, and a silencing RNA which reduces the expression of an endogenous gene which encodes a SDP1 lipase;
xxviii. a GPAT, a LPAAT, a DGAT1, a WRI1 polypeptide, a fatty acid thioesterase, preferably a FATB polypeptide, an OBC polypeptide such as an oleosin, preferably a caleosin, or a LDAP, and a silencing RNA which reduces the expression of an endogenous gene which encodes a SDP1 lipase; or
xxix. a GPAT9, a LPAAT, a DGAT1, a WRI1 polypeptide, a fatty acid thioesterase, preferably a FATB polypeptide, an OBC polypeptide such as an oleosin, preferably a caleosin, or a LDAP, and a silencing RNA which reduces the expression of an endogenous gene which encodes a SDP1 lipase.

In an embodiment, the one or more or all of the polypeptides are encoded by one or more exogenous polynucleotides in the plant parts.

In an embodiment, the level of total, or new, MCFA is increased relative to a corresponding wild-type plant part, preferably at least 25% of the total fatty acid content on a weight basis.

In an embodiment, the one or more or all of the encoded GPAT, LPAAT and/or DGAT have a preference for utilising medium chain fatty acid substrates.

In an embodiment, the cell further comprises one or more or all of:
i. a genetic modification which down-regulates endogenous production and/or activity of a polypeptide involved in the catabolism of triacylglycerols (TAG) in the cell when compared to a corresponding cell lacking the genetic modification;
ii. a genetic modification which down-regulates endogenous production and/or activity of a polypeptide involved in importing fatty acids into plastids of the cell when compared to a corresponding cell lacking the genetic modification; and
iii. a genetic modification which down-regulates endogenous production and/or activity of a polypeptide involved in diacylglycerol (DAG) production in the plastid when compared to a corresponding cell lacking the genetic modification.

In an embodiment, the genetic modification is a mutation of an endogenous gene which partially or completely inactivates the gene, such as a point mutation, an insertion, or a deletion, or the genetic modification is an exogenous polynucleotide encoding an RNA molecule which inhibits expression of the endogenous gene, wherein the exogenous polynucleotide is operably linked to a promoter which is capable of directing expression of the polynucleotide in the cell.

In an embodiment, the one or more or all of the promoters are expressed at a higher level in a vegetative plant part relative to seed of a plant.

In an embodiment, the cell has one or more or all of the following features:
  i. the level of medium chain fatty acids in the total fatty acid content of the cell, and/or in the total fatty acid content of the TAG of the cell, is at least about 30%, at least about 35%, at least about 40%, at least about 50%, at least about 55%, or between about 25% and about 55%, between about 25% and about 50%, between about 30% and about 50%, between about 35% and about 50%, between about 25% and about 40%, or between about 30% and about 40%;
  ii. the level of lauric acid (C12:0) in the total fatty acid content of the cell, and/or in the total fatty acid content of the TAG of the cell, is, or is increased by, at least about 15%, at least about 20%, at least about 25%, at least about 30%, at least about 35%, at least about 40%, at least about 50%, at least or about 55%, or between about 15% and about 55%, between about 20% and about 50%, between about 30% and about 50%, between about 35% and about 50%, between about 15% and about 25%, or between about 20% and about 30%;
  iii. the level of myristic acid (C14:0) in the total fatty acid content of the cell, and/or in the total fatty acid content of the TAG of the cell, is, or is increased by, at least about 25%, at least about 30%, at least about 35%, at least about 40%, at least about 45%, or between about 25% and about 45%, between about 20% and about 50%, between about 30% and about 50%, between about 35% and about 50%, between about 30% and about 40%, between about 15% and about 25%, or between about 20% and about 30%;
  iv. the level of palmitic acid (C16:0) in the total fatty acid content of the cell, and/or in the total fatty acid content of the TAG of the cell, is, or is increased by, between about 2% and about 18%, or between about 2% and about 16%, or between about 2% and about 15%, or between about 15% and about 50%;
  v. the level of lauric acid (C12:0) in the total fatty acid content of the cell, and/or in the total fatty acid content of the TAG of the cell is, or is increased by, at least about 25%, at least about 30%, at least about 40%, at least about 45%, or at least about 50%, and the level of myristic acid (C14:0) in the total fatty acid content of the cell and/or in the total fatty acid content of the TAG of the cell is, or is increased by, at least about 1%, at least about 2%, at least about 5%, or at least about 10%, or between about 1% and about 10%, or between about 2% and 10%, or between about 2% and about 6%, or less than about 10%, or less than about 8% or less than about 5%, or less than about 2%;
  vi. the level of myristic acid (C14:0) in the total fatty acid content of the cell, and/or in the total fatty acid content of the TAG of the cell is, or is increased by, at least about 20%, at least about 25%, at least about 30%, or at least about 40%, and the level of lauric acid (C12:0) in the total fatty acid content of the cell and/or in the total fatty acid content of the TAG of the cell is, or is increased by, at least about 1%, at least about 2%, at least about 5%, or at least about 10%, or between about 1% and about 10%, or between about 2% and about 10%, or between about 2% and about 6%, or less than about 10%, or less than about 8% or less than about 5%, or less than about 2%;
  vii. the level of myristic acid (C14:0) in the total fatty acid content of the cell, and/or in the total fatty acid content of the TAG of the cell is, or is increased by, at least about 20%, at least about 25%, at least about 30%, and the level of palmitic acid (C16:0) in the total fatty acid content of the cell and/or in the total fatty acid content of the TAG of the cell is, or is increased by, at least about 2%, at least about 3%, at least about 4%, or at least about 5%.
  viii. the ratio of lauric acid (C12:0):myristic acid (C14:0) in the fatty acid content of the cell, and/or in the total fatty acid content of the TAG of the cell, is increased, or is about 1:4, about 1:5, about 1:10, about 1:15, about 1:20, about 1:25, or about 4:1, about 5:1, about 10:1, about 15:1, about 20:1, about 30:1, about 40:1, or about 45:1;
  ix. the ratio of lauric acid (C12:0):palmitic acid (C16:0) in the fatty acid content of the cell, and/or in the total fatty acid content of the TAG of the cell, is increased, or is about 1:2, about 1:3, about 1:4, about 1:5, about 1:10, about 1:15, about 10:1, about 20:1, about 30:1, about 40:1, or about 45:1;
  x. the ratio of myristic acid (C14:0):palmitic acid (C16:0) in the fatty acid content of the cell, and/or in the total fatty acid content of the TAG of the cell, is increased, or is about 1:2, about 1:3, about 1:4, about 1:5, about 1:10, about 1:15, about 10:1, about 20:1, about 30:1, or about 40:1;
  xi. the level of oleic acid in the total fatty acid content of the cell, and/or in the total fatty acid content of the TAG of the cell, is decreased, or is less than about 10%, less than about 8%, less than about 6%, less than about 5%, less than about 4%, less than about 3%, less than about 2%, less than about 1%;
  xii. the level of linoleic acid (LA) in the total fatty acid content of the cell, and/or in the total fatty acid content of the TAG of the cell, is increased or decreased, or is less than about 20%, less than about 15%, less than about 10%, less than about 5%, less than about 4%, less than about 3%, less than about 2%, or less than about 1%;
  xiii. the level of α-linolenic acid (ALA) in the total fatty acid content of the cell, or in the total fatty acid content of the TAG of the cell, is decreased or is less than about 50%, less than about 40%, less than about 30%, less than about 20%, less than about 10%, less than about 8%, less than about 6%, less than about 5%, less than about 2%, or less than about 1%;
  xiv. the level of total unsaturated fatty acids in the total fatty acid content of the cell, and/or in the total fatty acid content of the TAG of the cell, is decreased, or is less than about 50%, less than about 40%, less than about 30%, less than about 20%, less than about 15%, less than about 10%, less than about 8%, less than about 6%, less than about 5%, less than about 2%, or less than about 1%;
  xv. the level of total monounsaturated fatty acids in the total fatty acid content of the cell, and/or in the total fatty acid content of the TAG of the cell, is decreased, or is less than about 10%, less than about 5%, less than about 4%, less than about 3%, less than about 2%, or less than about 1%;
  xvi. the level of total polyunsaturated fatty acids in the total fatty acid content of the cell, and/or in the total fatty acid content of the TAG of the cell, is less than about 50%, less than about 40%, less than about 30%, less than about 20%, less than about 15%, less than about 10%, less than about 8%, less than about 6%, less than about 5%, less than about 2%, or less than about 1%; xvii. the triacylglycerol (TAG) content of the cell is at least about 80%, at least about 85%, at least about 90%, or least about 95%, and about 98%, or between about 95% and about 98%, by weight of the cell;

xviii. the TAG content of the cell comprises, or is increased in a level of, one or more or all of the TAG species 36:0, 38:0, 40:0 and 42:0;

xix. the cell comprises tri-laurin (tri-C12:0) and/or tri-myristin (tri-C14:0);

xx. the phosphocholine (PC) content of the cell comprises one or both of the PC species 28:0 and 30:0, xxi. the cell has a reduced level of medium chain fatty acids, preferably C14:0, in membrane lipids relative to a corresponding cell;

xxii. the cell has less chlorosis relative to a corresponding cell which comprises the exogenous polynucleotide encoding the thioesterase but lacks the exogenous polynucleotide encoding the DGAT; and xxiii. the cell is in a vegetative plant part and the part has an alleviated chlorosis phenotype relative to a corresponding vegetative plant part, wherein any increase or decrease is relative to a corresponding wild-type cell.

In another aspect, the present invention provides a plant or a part thereof comprising the cell of the invention, or which is transgenic for one or more exogenous polynucleotides defined above.

In an embodiment, before the plant flowers, a vegetative part of the plant comprises a total non-polar lipid content of at least about 8%, at least about 10%, about 11%, between 8% and 15%, or between 9% and 12% (w/w dry weight).

In an embodiment, the plant is a monocotyledonous plant, or part thereof preferably a leaf, a grain, a stem, a root or an endosperm, which has a total fatty acid content or TAG content which is increased at least 5-fold on a weight basis when compared to a corresponding non-transgenic monocotyledonous plant, or part thereof. Alternatively, the transgenic monocotyledonous plant has endosperm comprising a TAG content which is at least 2.0%, preferably at least 3%, more preferably at least 4% or at least 5%, on a weight basis, or part of the plant, preferably a leaf, a stem, a root, a grain or an endosperm. In an embodiment, the endosperm has a TAG content of at least 2% which is increased at least 5-fold relative to a corresponding non-transgenic endosperm. Preferably, the plant is fully male and female fertile, its pollen is essentially 100% viable, and its grain has a germination rate which is between 70% and 100% relative to corresponding wild-type grain. In an embodiment, the transgenic plant is a progeny plant at least two generations derived from an initial transgenic wheat plant, and is preferably homozygous for the transgenes. In embodiments, the monocotyledonous plant, or part thereof, preferably a leaf, stem, grain or endosperm, is further characterised by one or more features as defined in the context of a plant or part thereof of the invention. In embodiments, the monocotyledonous plant, or part thereof preferably a leaf, a grain, stem or an endosperm of the invention preferably has an increased level of mono-unsaturated fatty acids (MUFA) and/or a lower level of polyunsaturated fatty acids (PUFA) in both the total fatty acid content and in the TAG fraction of the total fatty acid content, such as for example an increased level of oleic acid and a reduced level of LA (18:2), when compared to a corresponding plant or part thereof lacking the genetic modifications and/or exogenous polynucleotide(s). Preferably, the linoleic acid (LA, 18:2) level in the total fatty acid content of the grain or endosperm of the monocotyledonous plant is reduced by at least 5% and/or the level of oleic acid in the total fatty acid content is increased by at least 5% relative to a corresponding wild-type plant or part thereof, preferably at least 10% or more preferably at least 15%, when compared to a corresponding plant or part thereof lacking the genetic modifications and/or exogenous polynucleotide(s).

In an embodiment, the plant, or part thereof, is a member of a population or collection of at least about 1,500, at least about 3,000 or at least about 5,000 such plants or parts.

In an embodiment, the TFA content, the TAG content, the total non-polar lipid content, or the one or more non-polar lipids, and/or the level of the oleic acid or a PUFA in the plant or part thereof is determinable by analysis by using gas chromatography of fatty acid methyl esters obtained from the plant or vegetative part thereof.

In a further embodiment, wherein the plant part is a leaf and the total non-polar lipid content of the leaf is determinable by analysis using Nuclear Magnetic Resonance (NMR).

In each of the above embodiments, it is preferred that the plant is a transgenic progeny plant at least two generations derived from an initial transgenic plant, and is preferably homozygous for the transgenes.

In an embodiment, the plant or the part thereof is phenotypically normal, in that it is not significantly reduced in its ability to grow and reproduce when compared to an unmodified plant or part thereof. In an embodiment, the biomass, growth rate, germination rate, storage organ size, seed size and/or the number of viable seeds produced is not less than 70%, not less than 80% or not less than 90% of that of a corresponding wild-type plant when grown under identical conditions. In an embodiment, the plant is male and female fertile to the same extent as a corresponding wild-type plant and its pollen (if produced) is as viable as the pollen of the corresponding wild-type plant, preferably at least about 75%, or at least about 90%, or close to 100% viable. In an embodiment, the plant produces seed which has a germination rate of at least about 75% or at least about 90% relative to the germination rate of corresponding seed of a wild-type plant, where the plant species produces seed. In an embodiment, the plant of the invention has a plant height which is at least about 75%, or at least about 90% relative to the height of the corresponding wild-type plant grown under the same conditions. A combination of each of these features is envisaged. In an alternative embodiment, the plant of the invention has a plant height which is between 60% and 90% relative to the height of the corresponding wild-type plant grown under the same conditions. In an embodiment, the plant or part thereof of the invention, preferably a plant leaf, does not exhibit increased necrosis, i.e. the extent of necrosis, if present, is the same as that exhibited by a corresponding wild-type plant or part thereof grown under the same conditions and at the same stage of plant development. This feature applies in particular to the plant or part thereof comprising an exogenous polynucleotide which encodes a fatty acid thioesterase such as a FATB thioesterase.

In another aspect, the present invention provides a population of at least about 1,500, at least about 3,000 or at least about 5,000 plants, each being a plant of the invention, growing in a field.

In an embodiment, the exogenous polynucleotides are inserted at the same chromosomal location in the genome of each of the plants, preferably in the nuclear genome of each of the plants.

In another aspect, the present invention provides a population of at least about 1000 plants, each being a plant according to the invention, growing in a field, or a collection of at least about 1000 plant parts, each being a plant part according to the invention, wherein the plant parts have been harvested from plants growing in a field.

Also provided is a storage bin comprising a collection of plants or plant parts of the invention.

In another aspect, the present invention provides an extract of a plant or a part thereof of the invention. The extract preferably has a different fatty acid composition relative to a corresponding wild-type extract.

In an embodiment, the extract is lacking at least 50% or at least 90% of the chlorophyll and/or soluble sugars of the plant or part thereof.

In a further aspect, the present invention provides a process for selecting a plant or a part thereof with a desired phenotype, the process comprising
- i) obtaining a plurality of candidate plants, or parts thereof, which each comprise
  - a) a first exogenous polynucleotide which encodes a transcription factor polypeptide that increases the expression of one or more glycolytic and/or fatty acid biosynthetic genes in a plant or part thereof, and
  - b) a second exogenous polynucleotide which encodes a polypeptide involved in the biosynthesis of one or more non-polar lipids, wherein each exogenous polynucleotide is operably linked to a promoter which is capable of directing expression of the polynucleotide in the plant, or part thereof,
- ii) analysing lipid in the plurality of parts, or at least a part of each plant in the plurality of candidate plants, from step i),
- iii) analysing the plurality of parts, or at least a part of each plant in the plurality of candidate plants, from step i) for one or more or all of;
  - a) soluble protein content,
  - b) nitrogen content,
  - c) carbon:nitrogen ratio,
  - d) photosynthetic gene expression,
  - e) photosynthetic capacity,
  - f) total dietary fibre (TDF) content,
  - g) carbon content, and
  - h) energy content, and
- iv) selecting a plant or part thereof which comprises an increased triacylglycerol (TAG) content in the part or at least a part of the plant relative to a corresponding wild-type plant or part thereof and a desired phenotype selected from one or more or all of the following;
  - A) an increased soluble protein content in the part or at least a part of the plant relative to a corresponding wild-type plant or part thereof,
  - B) an increased nitrogen content in the part or at least a part of the plant relative to a corresponding wild-type plant or part thereof,
  - C) decreased carbon:nitrogen ratio in the part or at least a part of the plant relative to a corresponding wild-type plant or part thereof,
  - D) increased photosynthetic gene expression in the part or at least a part of the plant relative to a corresponding wild-type plant or part thereof,
  - E) increased photosynthetic capacity in the part or at least a part of the plant relative to a corresponding wild-type plant or part thereof,
  - F) decreased total dietary fibre (TDF) content in the part or at least a part of the plant relative to a corresponding wild-type plant or part thereof,
  - G) increased carbon content in the part or at least a part of the plant relative to a corresponding wild-type plant or part thereof, and
  - H) increased energy content in the part or at least a part of the plant relative to a corresponding wild-type plant or part thereof.

In an embodiment, the process further comprises a step of obtaining seed or a progeny plant from the transgenic plant, wherein the seed or progeny plant comprises the exogenous polynucleotides.

In an embodiment, the increased triacylglycerol (TAG) content is determined by analysing one or more of the total fatty acid content, TAG content, fatty acid composition, by any means, which might or might not involve first extracting the lipid.

In yet another embodiment, the selected plant or part thereof has one or more of the features as defined herein.

In another aspect, the present invention provides seed of, or obtained from, a plant according to the invention.

In another aspect, the present invention provides a process for obtaining a cell according to the invention, the process comprising the steps of:
- i) introducing into a cell at least one exogenous polynucleotide and/or at least one genetic modification as defined above to produce a cell as defined above,
- ii) expressing the exogenous polynucleotide(s) in the cell or a progeny cell thereof,
- iii) analysing the lipid content of the cell or progeny cell, and
- iv) selecting a cell according to the invention.

In another aspect, the present invention provides a method of producing a plant which has integrated into its genome a set of exogenous polynucleotides and/or genetic modifications as defined above, the method comprising the steps of:
- i) crossing two parental plants, wherein one plant comprises at least one of the exogenous polynucleotides and/or at least one genetic modifications as defined in any one of claims 24 to 31; and the other plant comprises at least one of the exogenous polynucleotides and/or at least one genetic modifications as defined in any one of claims 24 to 31, and wherein between them the two parental plants comprise a set of exogenous polynucleotides and/or genetic modifications as defined in any one of claims 24 to 31,
- ii) screening one or more progeny plants from the cross for the presence or absence of the set of exogenous polynucleotides and/or genetic modifications as defined in any one of claims 24 to 31, and
- iii) selecting a progeny plant which comprise the set of exogenous polynucleotides and/or genetic modifications as defined in any one of claims 24 to 31, thereby producing the plant.

In another aspect, the present invention provides a process for producing an industrial product, the process comprising the steps of:
- i) obtaining a cell of the invention, a plant or a part thereof of the invention, or seed the invention, and
- ii) either
  - a) converting at least some of the lipid in the cell, plant or part thereof, or seed, of step i) to the industrial product by applying heat, chemical, or enzymatic means, or any combination thereof, to the lipid in situ in the cell, or plant or vegetative part thereof, or seed, or
  - b) physically processing the cell, plant or part thereof, or seed, of step i), and subsequently or simultaneously converting at least some of the lipid in the processed cell, plant or part thereof, or seed, to the industrial product by applying heat, chemical, or enzymatic means, or any combination thereof, to the lipid in the processed cell, plant or part thereof, or seed, and iii) recovering the industrial product, thereby producing the industrial product.

In an embodiment, the step of physically processing the cell, plant or part thereof, or seed, of step i), comprises one or more of rolling, pressing, crushing or grinding the plant or part thereof, or seed.

In an embodiment, the invention further comprises steps of:
(a) extracting at least some of the non-polar lipid content of the cell, or plant or part thereof, or seed, as non-polar lipid, and
(b) recovering the extracted non-polar lipid, wherein steps (a) and (b) are performed prior to the step of converting at least some of the lipid in the cell, plant or part thereof, or seed, to the industrial product.

In another aspect, the present invention provides a process for producing extracted lipid, the process comprising the steps of:
i) obtaining a plant cell of the invention, or a plant or a part thereof of the invention, or seed of the invention,
ii) extracting lipid from the cell, or plant or part thereof, or seed, and
iii) recovering the extracted lipid, thereby producing the extracted lipid.

In an embodiment, a process of extraction comprises one or more of drying, rolling, pressing crushing or grinding the plant or part thereof, or seed, and/or purifying the extracted lipid or seedoil.

In an embodiment, the process uses an organic solvent in extraction process to extract the oil.

In an embodiment, the process comprises recovering the extracted lipid by collecting it in a container and/or one or more of degumming, deodorising, decolourising, drying, fractionating the extracted lipid, removing wax esters from the extracted lipid, or analysing the fatty acid composition of the extracted lipid.

In an embodiment, the volume of the extracted lipid or oil is at least 1 litre.

In a further embodiment, one or more or all of the following features apply:
(i) the extracted lipid or oil comprises triacylglycerols, wherein the triacylglycerols comprise at least 90%, preferably at least 95% or at least 96%, of the extracted lipid or oil,
(ii) the extracted lipid or oil comprises free sterols, steroyl esters, steroyl glycosides, waxes or wax esters, or any combination thereof, and
(iii) the total sterol content and/or composition in the extracted lipid or oil is significantly different to the sterol content and/or composition in the extracted lipid or oil produced from a corresponding plant or part thereof, or seed.

In an embodiment, the process further comprises converting the extracted lipid to an industrial product.

In an embodiment, the industrial product is a hydrocarbon product such as fatty acid esters, preferably fatty acid methyl esters and/or a fatty acid ethyl esters, an alkane such as methane, ethane or a longer-chain alkane, a mixture of longer chain alkanes, an alkene, a biofuel, carbon monoxide and/or hydrogen gas, a bioalcohol such as ethanol, propanol, or butanol, biochar, or a combination of carbon monoxide, hydrogen and biochar.

In a further embodiment, the plant part is an aerial plant part or a green plant part, preferably a vegetative plant part such as a plant leaf or stem.

In yet a further embodiment, the process further comprises a step of harvesting the plant or part thereof such as a vegetative plant part, tuber or beet, or seed, preferably with a mechanical harvester.

In another embodiment, the level of a lipid in the plant or part thereof, or seed and/or in the extracted lipid or oil is determinable by analysis by using gas chromatography of fatty acid methyl esters prepared from the extracted lipid or oil.

In yet another embodiment, the process further comprises harvesting the part from a plant.

In an embodiment, the plant part is a vegetative plant part which comprises a total non-polar lipid content of at least about 18%, at least about 20%, at least about 25%, at least about 30%, at least about 35%, at least about 40%, at least about 45%, at least about 50%, at least about 55%, at least about 60%, at least about 65%, at least about 70%, between 18% and 75%, between about 20% and 75%, between about 30% and 75%, between about 40% and 75%, between about 50% and 75%, between about 60% and 75%, or between about 25% and 50% (w/w dry weight).

In a further embodiment, the plant part is a vegetative plant part which comprises a total TAG content of at least about 18%, at least about 20%, at least about 25%, at least about 30%, at least about 35%, at least about 40%, at least about 45%, at least about 50%, at least about 55%, at least about 60%, at least about 65%, at least about 70%, between 18% and 75%, between about 20% and 75%, between about 30% and 75%, between about 40% and 75%, between about 50% and 75%, between about 60% and 75%, or between about 25% and 50% (w/w dry weight).

In another embodiment, the plant part is a vegetative plant part which comprises a total non-polar lipid content of at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight), and wherein the vegetative plant part is from a 16:3 plant.

In yet another embodiment, the plant part is a vegetative plant part which comprises a total TAG content of at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight), and wherein the vegetative plant part is from a 16:3 plant.

In an embodiment, the vegetative plant parts have a TAG/TFA Quotient (TTQ) of between 0.01 and 0.6. In an embodiment, the vegetative plant parts have a TTQ of between 0.01 and 0.55, or between 0.01 and 0.5, or about 0.1, or about 0.2 or about 0.3, or about 0.4 or about 0.5. Preferably, the TTQ is between 0.60 and 0.84, which corresponds to a TAG:TFA ratio of between 1.5:1 and 5:1, or between 0.84 and 0.95 which corresponds to a TAG:TFA ratio of between 5:1 and 20:1.

In an embodiment, the vegetative plant parts comprise an average TFA content of about 6%, or about 8%, or about 9% or about 10% (w/w dry weight).

In an embodiment, the TFA content of the vegetative plant parts comprises a palmitic acid content which is increased by at least 2% or at least 3% relative to the palmitic acid content of a corresponding wild-type vegetative plant part.

In an embodiment, the TFA content of the vegetative plant parts comprises a α-linoleic acid (ALA) content which is decreased by at least 2% or at least 3% relative to the ALA content of a corresponding wild-type vegetative plant part.

In an embodiment, one or more or all of the following features apply:
  (i) the vegetative plant parts are leaves and/or stems or parts thereof which comprise one or more of an increased carbon content, an increased energy content, an increased soluble protein content, a reduced starch content, a reduced total dietary fibre (TDF) content and an increased nitrogen content, each on a weight basis relative to a corresponding wild-type leaf or stem or parts thereof from a wild-type *Sorghum* sp. or *Zea mays* plant at the same stage of growth,
  (ii) the TFA content of the vegetative plant parts is at least about 6%, at least about 7%, at least about 8%, at least about 9%, at least about 10%, at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between about 6% and about 20%, between 8% and 75%, between 10% and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight) TFA,
  (iii) the fatty acids esterified in the form of TAG in the vegetative plant parts is at least about 1%, at least about 2%, at least about 3%, at least about 4%, at least about 5%, at least about 6%, at least about 7%, at least about 8%, at least about 9%, at least about 10%, at least about 11%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, between about 6% and about 20%, between 8% and 75%, between 10%, and 75%, between 11% and 75%, between about 15% and 75%, between about 20% and 75%, between about 30% and 75%, between about 40% and 75%, between about 50% and 75%, between about 60% and 75%, or between about 25% and 50% (w/w dry weight),
  (iv) the vegetative plant parts comprise an increased content of a WRI1 polypeptide, an increased content of a DGAT polypeptide, and a decreased content of a SDP1 polypeptide, each relative to a corresponding wild-type vegetative plant part,
  (v) the vegetative plant parts comprise an increased content of a WRI1 polypeptide, an increased content of a DGAT polypeptide, and an increased content of a LEC2 polypeptide, each relative to a corresponding wild-type vegetative plant part,
  (vi) the vegetative plant parts comprise an increased content of a PDAT or DGAT polypeptide, a decreased content of a TGD polypeptide, and a decreased content of a SDP1 polypeptide, each relative to a corresponding wild-type vegetative plant part, and
  (vii) the vegetative plant parts comprise a decreased content of a TAG lipase such as a SDP1 TAG lipase, a decreased content of a TGD polypeptide such as a TGD5 polypeptide, and optionally a decreased content of a TST polypeptide such as a TST1 polypeptide, each decrease being relative to a corresponding wild-type vegetative plant part.

In an embodiment, one or more or all of the following features apply:
  (i) the vegetative plant parts are harvested from the plant between the time of first flowering of the plant and first maturity of seed,
  (ii) the *Sorghum* sp. plant is a *Sorghum bicolor* plant,
  (iii) the vegetative plant parts include leaves and/or stems or parts thereof,
  (iv) the vegetative plant parts comprise an average total fatty acid content of about 8% or about 10% (w/w dry weight), In another aspect, the present invention provides a process for producing seed, the process comprising:
  i) growing a plant according to the invention, and
  ii) harvesting seed from the plant.

In an embodiment, the above process comprises growing a population of at least about 1,500, at least about 3,000 or at least about 5,000 plants, each being a plant of the invention, and harvesting seed from the population of plants.

In another aspect, the present invention provides recovered or extracted lipid obtainable from a cell according to the invention, a plant or a part thereof of the invention, seed of the invention, or obtainable by the process of the invention.

In another aspect, the present invention provides an industrial product produced by the process according to the invention, which is a hydrocarbon product such as fatty acid esters, preferably fatty acid methyl esters and/or a fatty acid ethyl esters, an alkane such as methane, ethane or a longer-chain alkane, a mixture of longer chain alkanes, an alkene, a biofuel, carbon monoxide and/or hydrogen gas, a bioalcohol such as ethanol, propanol, or butanol, biochar, or a combination of carbon monoxide, hydrogen and biochar. In an embodiment the industrial product comprises MCFA, preferably an increased level of MCFA relative to a corresponding industrial product produced from a wild-type plant or part thereof.

In a further aspect, the present invention provides for the use of a transgenic plant or part thereof of the invention, seed of the invention, extract of the invention or the recovered or extracted lipid or soluble protein of the invention for the manufacture of an industrial product.

Examples of industrial products of the invention include, but are not limited to, a hydrocarbon product such as fatty acid esters, preferably fatty acid methyl esters and/or a fatty acid ethyl esters, an alkane such as methane, ethane or a longer-chain alkane, a mixture of longer chain alkanes, an alkene, a biofuel, carbon monoxide and/or hydrogen gas, a bioalcohol such as ethanol, propanol, or butanol, biochar, or a combination of carbon monoxide, hydrogen and biochar.

In another aspect, the present invention provides use of a cell according to the invention, a plant or part thereof of the invention, seed of the invention, or the lipid of the invention, for the manufacture of an industrial product.

In another aspect, the present invention provides a process for producing fuel, the process comprising:

i) reacting the lipid of the invention with an alcohol, optionally, in the presence of a catalyst, to produce alkyl esters, and ii) optionally, blending the alkyl esters with petroleum based fuel.

In another aspect, the present invention provides a process for producing a synthetic diesel fuel, the process comprising:

i) converting the lipid in a cell of the invention, or a plant or a part thereof of the invention, or seed of the invention, to a bio-oil by a process comprising pyrolysis or hydrothermal processing or to a syngas by gasification, and ii) converting the bio-oil to synthetic diesel fuel by a process comprising fractionation, preferably selecting hydrocarbon compounds which condense between about 150° C. to about 200° C. or between about 200° C. to about 300° C., or converting the syngas to a biofuel using a metal catalyst or a microbial catalyst.

In another aspect, the present invention provides a process for producing a biofuel, the process comprising converting the lipid in a cell of the invention, a plant or a part thereof of the invention, or seed of the invention, to bio-oil by pyrolysis, a bioalcohol by fermentation, or a biogas by gasification or anaerobic digestion.

In another aspect, the present invention provides a process for producing a feedstuff, the process comprising admixing a plant cell of the invention, a plant or a part thereof of the invention, seed of the invention, or the lipid of any one of claims the invention, or an extract or portion thereof, with at least one other food ingredient.

In another aspect, the present invention provides feedstuffs, cosmetics or chemicals comprising a plant cell of the invention, a plant or a part thereof of the invention, seed of the invention, or the lipid of the invention, or an extract or portion thereof.

In an embodiment, the feedstuff is silage, pellets or hay.

In another aspect, the present invention provides a process for feeding an animal, the process comprising providing to the animal a plant or a part thereof of the invention, seed of the invention, or the lipid of the invention.

In an embodiment, the animal ingests an increased amount of MCFA, nitrogen, protein, carbon and/or energy potential relative to when the animal ingests the same amount on a dry weight basis of a corresponding wild-type plant or part thereof, seed or extract or feedstuff produced from the corresponding wild-type plant or part thereof.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. A representation of lipid synthesis in eukaryotic cells, showing export of some of the fatty acids synthesized in the plastids to the Endoplasmic Reticulum (ER) via the Plastid Associated Membrane (PLAM), and import of some of the fatty acids into the plastid from the ER for eukaryotic galactolipid synthesis. Abbreviations:

Acetyl-CoA and Malonyl-CoA: acetyl-coenzyme A and malonyl-coenzymeA;
ACCase: Acetyl-CoA carboxylase;
FAS: fatty acid synthase complex;
16:0-ACP, 18:0-ACP and 18:1-ACP: C16:0-acyl carrier protein (ACP), C18:0-acyl carrier protein, C18:1-acyl carrier protein;
KAS II: ketoacyl-ACP synthase II (EC 2.3.1.41);
PLPAAT: plastidial LPAAT;
PGPAT: plastidial GPAT;
PAP: PA phosphorylase (EC 3.1.3.4);
G3P: glycerol-3-phosphate;
LPA: lysophosphatidic acid;
PA: phosphatidic acid;
DAG: diacylglycerol;
TAG: triacylglycerol;
Acyl-CoA and Acyl-PC: acyl-coenzyme A and acyl-phosphatidylcholine;
PC: phosphatidylcholine;
GPAT: glycerol-3-phosphate acyltransferase;
LPAAT: lysophosphatidic acid acyltransferase (EC 2.3.1.51);
LPCAT: acyl-CoA: lysophosphatidylcholine acyltransferase; or synonyms 1-acylglycerophosphocholine 0-acyltransferase; acyl-CoA:1-acyl-sn-glycero-3-phosphocholine O-acyltransferase (EC 2.3.1.23);
CPT: CDP-choline:diacylglycerol cholinephosphotransferase; or synonyms 1-alkyl-2-acetylglycerol cholinephosphotransferase; alkylacylglycerol cholinephosphotransferase; cholinephosphotransferase; phosphorylcholine-glyceride transferase (EC 2.7.8.2);
PDCT: phosphatidylcholine:diacylglycerol cholinephosphotransferase;
PLC: phospholipase C (EC 3.1.4.3);
PLD: Phospholipase D; choline phosphatase; lecithinase D; lipophosphodiesterase II (EC 3.1.4.4);
PDAT: phospholipid: diacylglycerol acyltransferase; or synonym phospholipid:1,2-diacyl-sn-glycerol O-acyltransferase (EC 2.3.1.158);
FAD2: fatty acid Δ12-desaturase; FAD3, fatty acid Δ15-desaturase;
UDP-Gal: Uridine diphosphate galactose;
MGDS: monogalactosyldiacylglycerol synthase;
MGDG: monogalactosyldiacylglycerol; DGDG: digalactosyldiacylglycerol
FADE, 7, 8: plastidial fatty acid Δ12-desaturase, plastidial ω3-desaturase, plastidial ω3-desaturase induced at low temperature, respectively.

Figure 2:
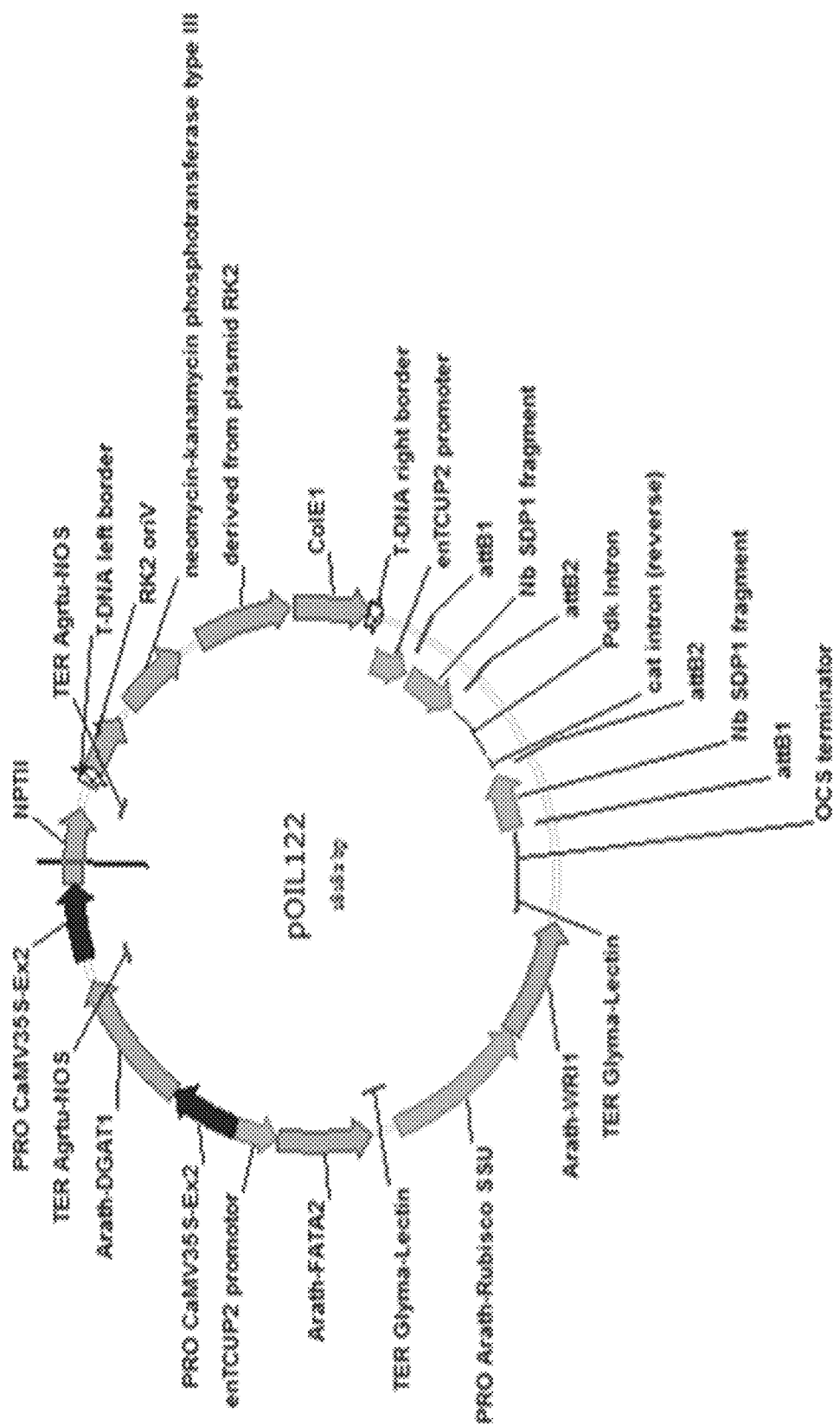

FIG. 2. Schematic diagram of vector pOIL122. Abbreviations: TER Agrtu-Nos, *Agrobacterium tumefaciens* nopaline synthase terminator; NPTII, neomycin phosphotransferase protein coding region; PRO CaMV35S-Ex2, Cauliflower Mosaic Virus 35S promoter with double enhancer region; Arath-DGAT1, *Arabidopsis thaliana* DGAT1 acyltransferase protein coding region; PRO Arath-Rubisco SSU, *A. thaliana* Rubisco small subunit promoter; Arath-FATA2, *A. thaliana* FATA2 thioesterase protein coding region; Arath-WRI, *A. thaliana* WRI1 transcription factor protein coding region; TER Glyma-Lectin, *Glycine max* lectin terminator; enTCUP2 promoter, *Nicotiana tabacum* cryptic constitutive promoter; attB1 and attB2, Gateway recombination sites; NB SDP1 fragment, *Nicotiana benthamiana* SDP1 region targeted for hpRNAi silencing; OCS terminator, *A. tumefaciens* octopine synthase terminator. Backbone features outside the T-DNA region are derived from pORE04 (Coutu et al., 2007).

Figure 3:
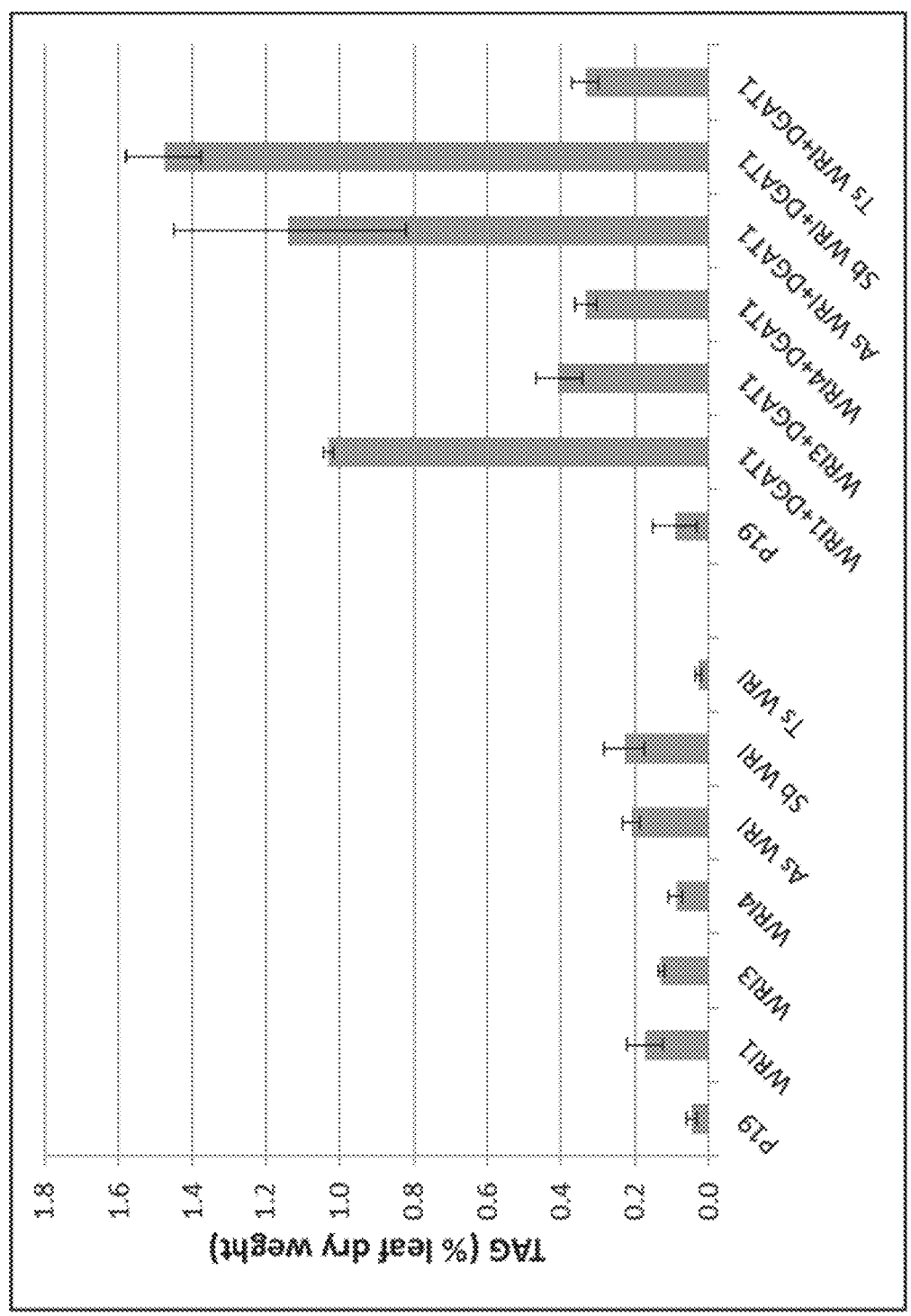

FIG. 3. TAG levels (% leaf dry weight) in *N. benthamiana* leaf tissue, infiltrated with genes encoding different WRI1 polypeptides either with (right hand bars) or without (left hand bars) co-expression of DGAT1 (n=3). All samples were infiltrated with the P19 construct as well.

Figure 4:
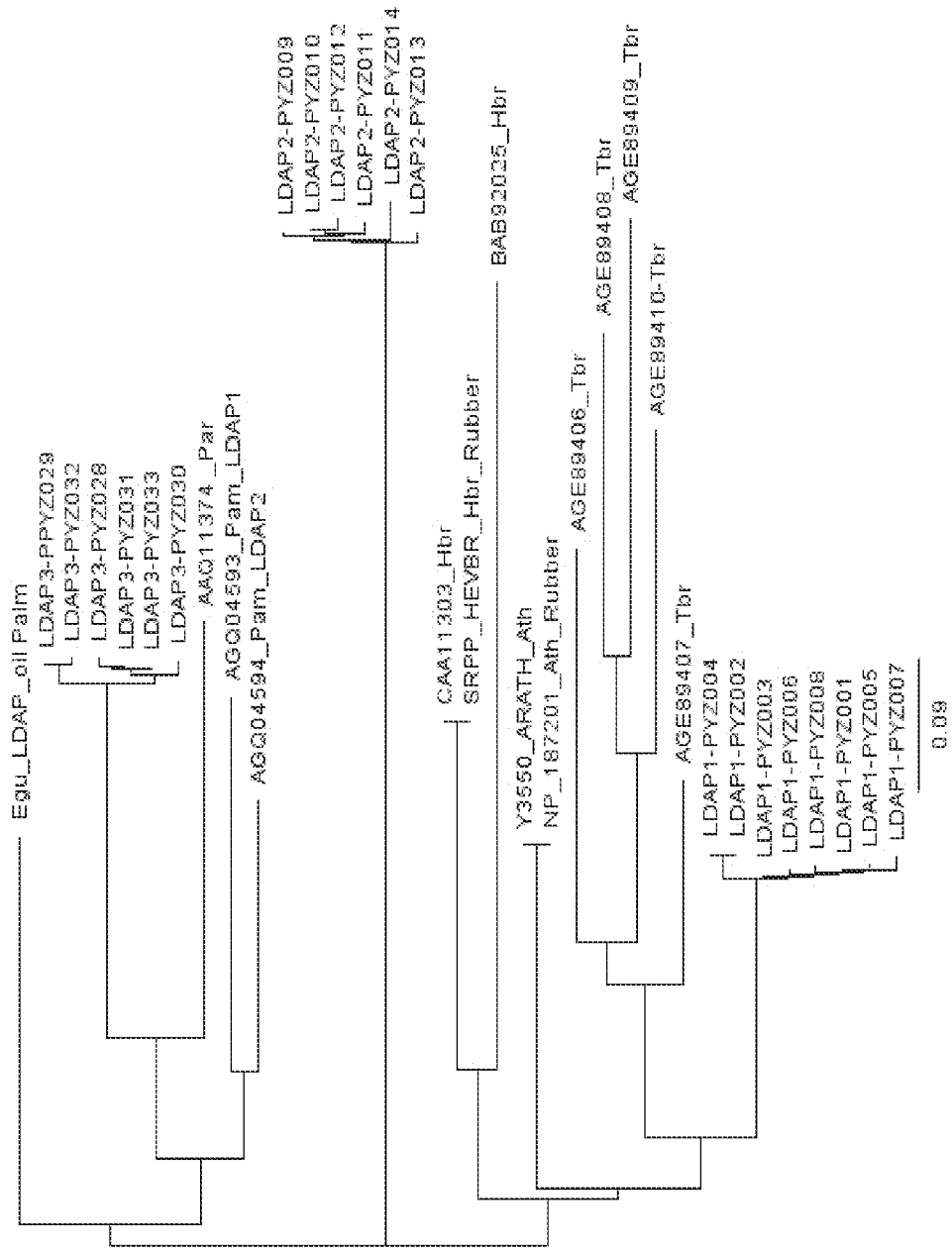

FIG. 4. Phylogenetic tree of LDAP polypeptides (Example 6).

Figure 5:
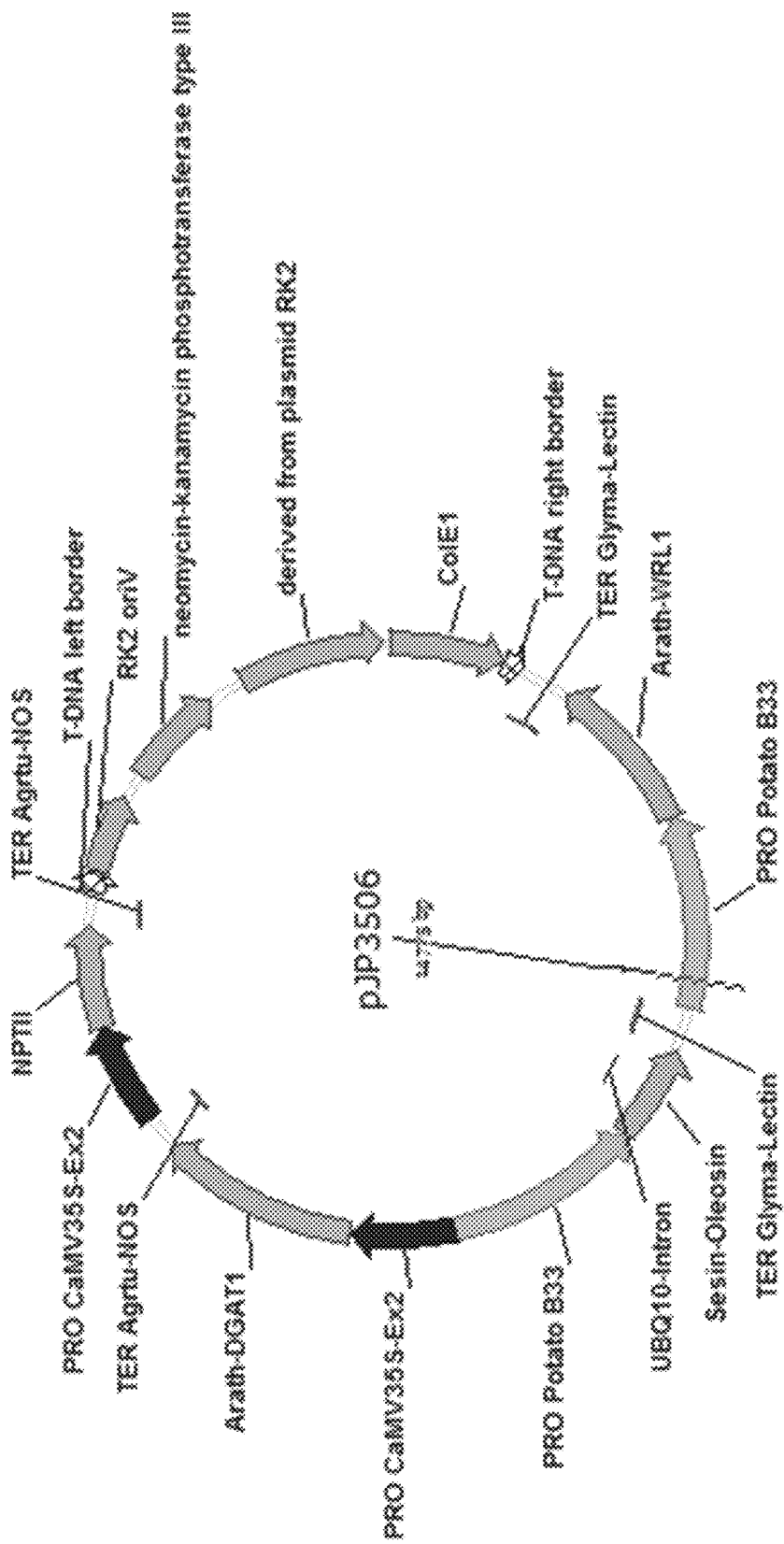

FIG. 5. Schematic representation of the genetic construct pJP3506 including the T-DNA region between the left and right borders. TAG, triacylglycerol; FFA, free fatty acids; DAG, diacylglycerol; Sesin-Oleosin, *Sesame indicum* oleosin protein coding region.

Figure 6:
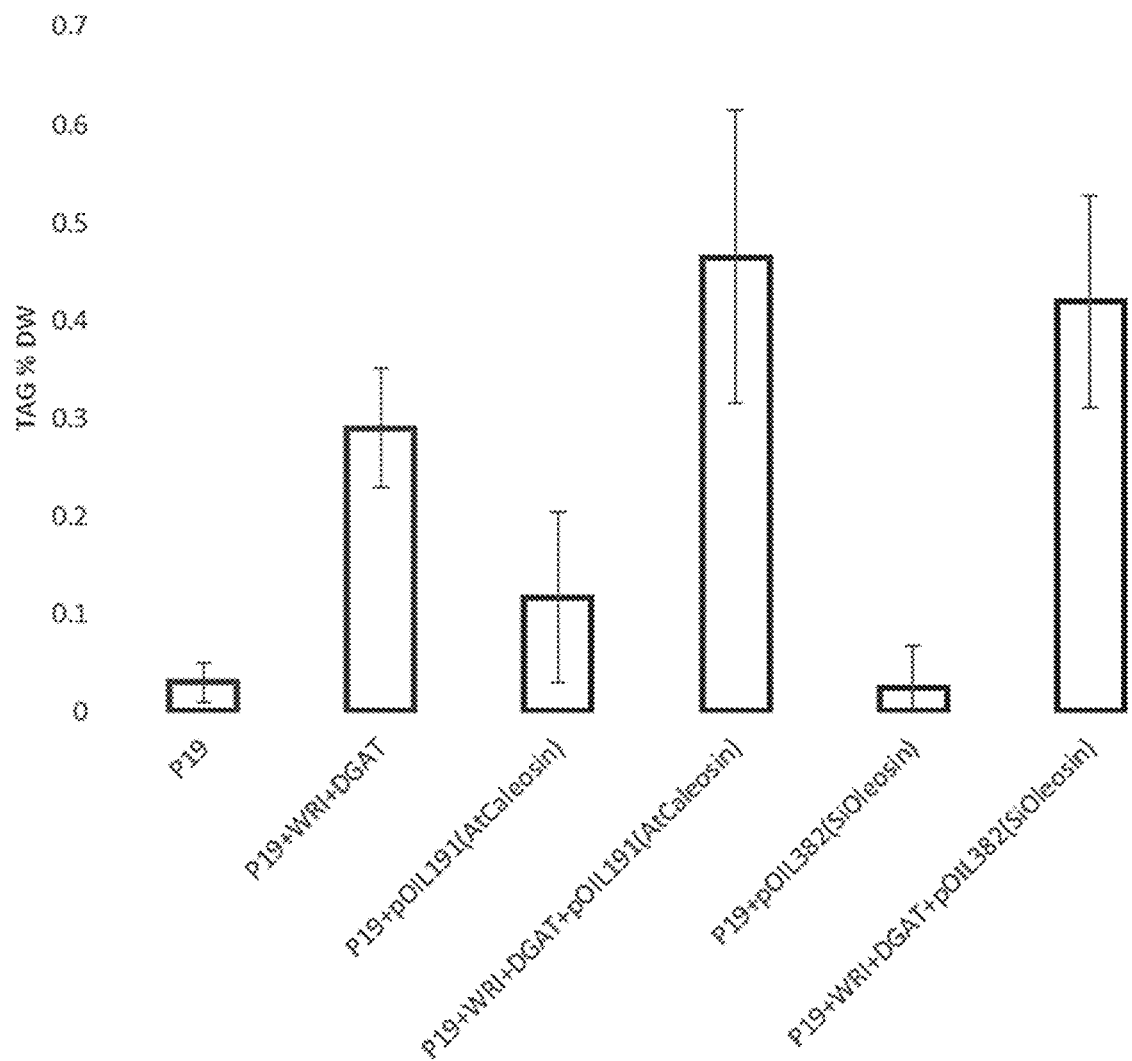

FIG. 6. Triacylglycerol accumulation upon the expression of AtCaleosin 3 and SiOleosin L.

Figure 7:
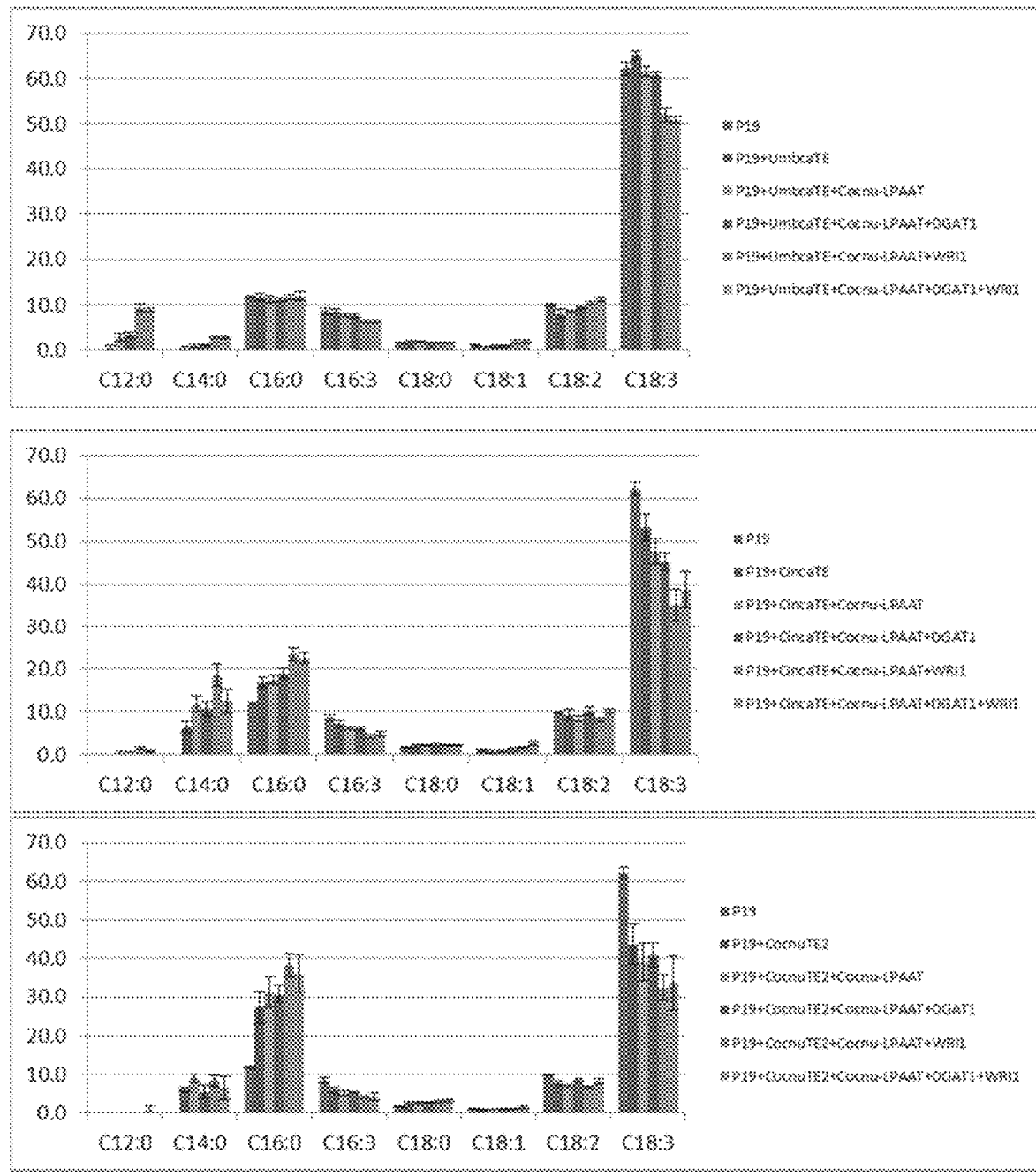

FIG. 7. Total fatty acid methyl ester (FAME) profiles (weight %) illustrating the effect of WRI1+DGAT1-mediated high oil background on MCFA production in *Nicotiana benthamiana* leaf (n=4). Highest MCFA production was observed after the addition of Arath-WRI1.

Figure 8:
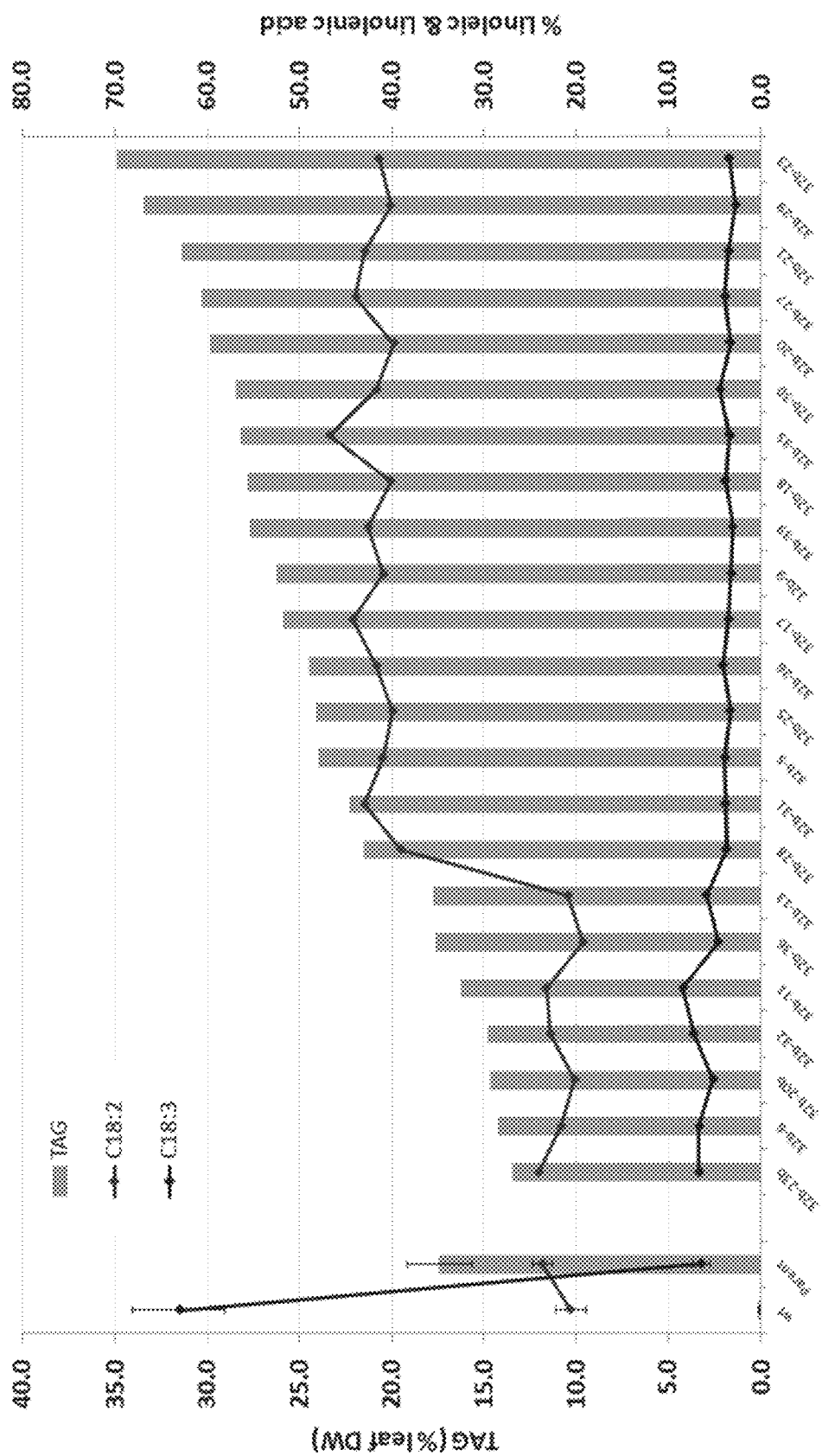

FIG. 8. TAG content in leaf samples of transformed tobacco plants at seed-setting stage of growth, transformed with the T-DNA from pOIL049, lines #23c and #32b. The controls (parent) samples were from plants transformed with the T-DNA from pJP3502. The upper line shows 18:2 percentage in the TAG and the lower line shows the 18:3 (ALA) percentage in the fatty acid content.

Figure 9:
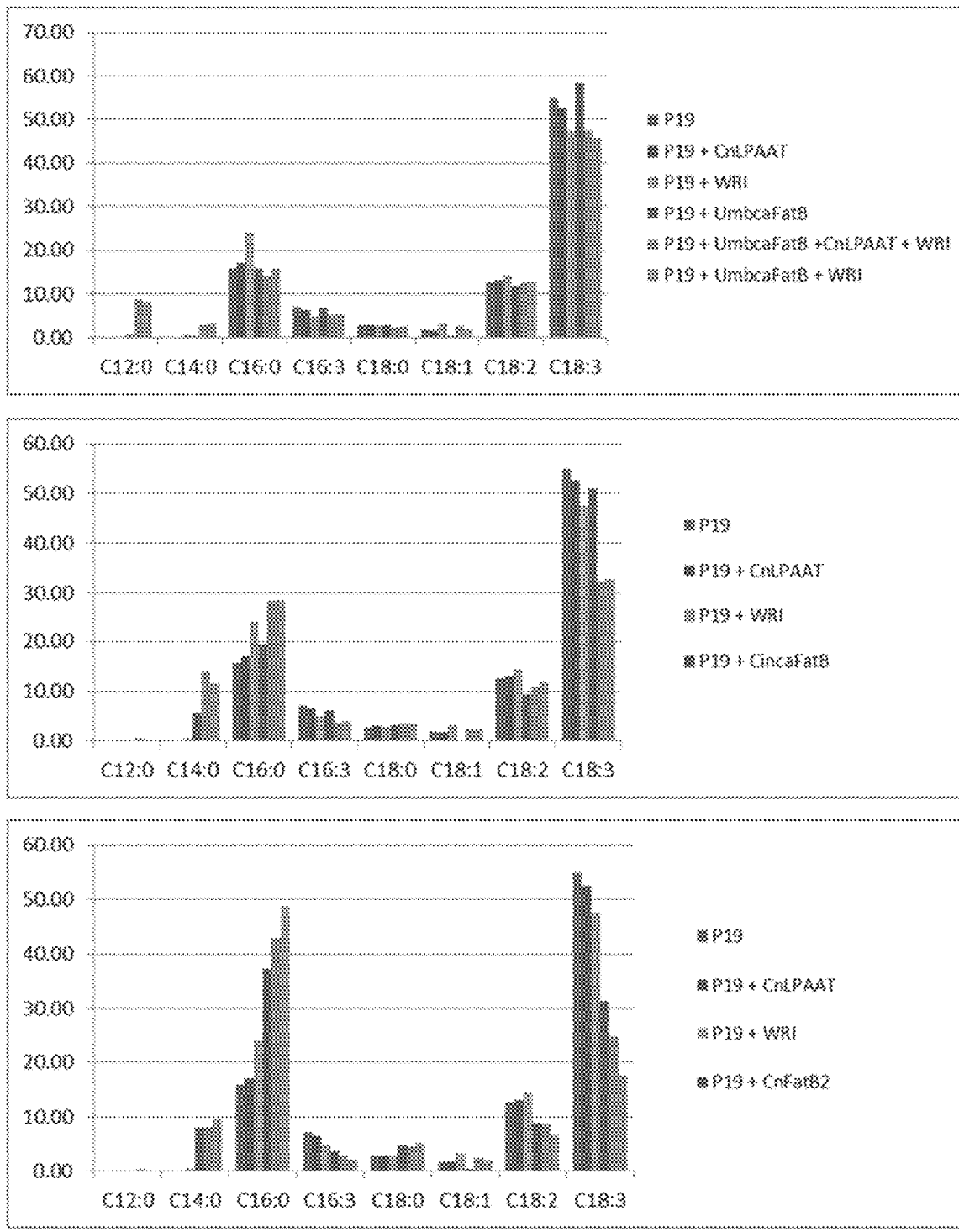

FIG. 9. Leaf total FAME profiles (weight %) elucidating the effect of WRI1 on MCFA accumulation (n=4). Addition of Arath-WRI1 greatly increased the production of the relevant fatty acid (C12:0, C14:0 or C16:0) relative to the previous addition of Cocnu-LPAAT alone.

Figure 10:
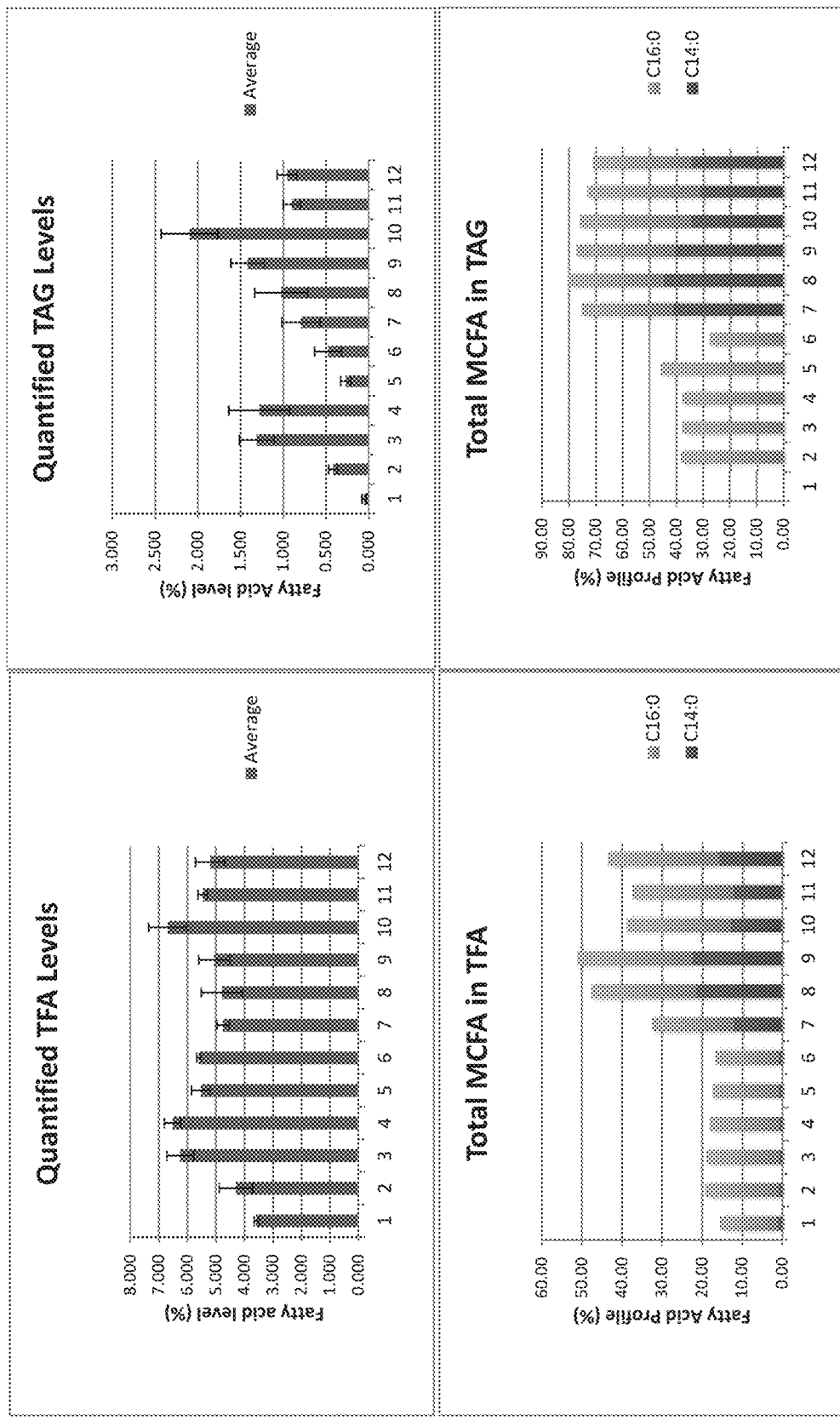

FIG. 10. TFA levels (% weight), TAG levels, levels of MCFA (C16:0 and C14:0, % of total fatty acids) in TFA and MCFA in TAG (% of total fatty acid content in TAG) in plant cells after expression of combinations of three oil palm DGATs with FATB, LPAAT and WRI1. Numbers 1-10 are as listed in the text (Example 10).

Figure 11:
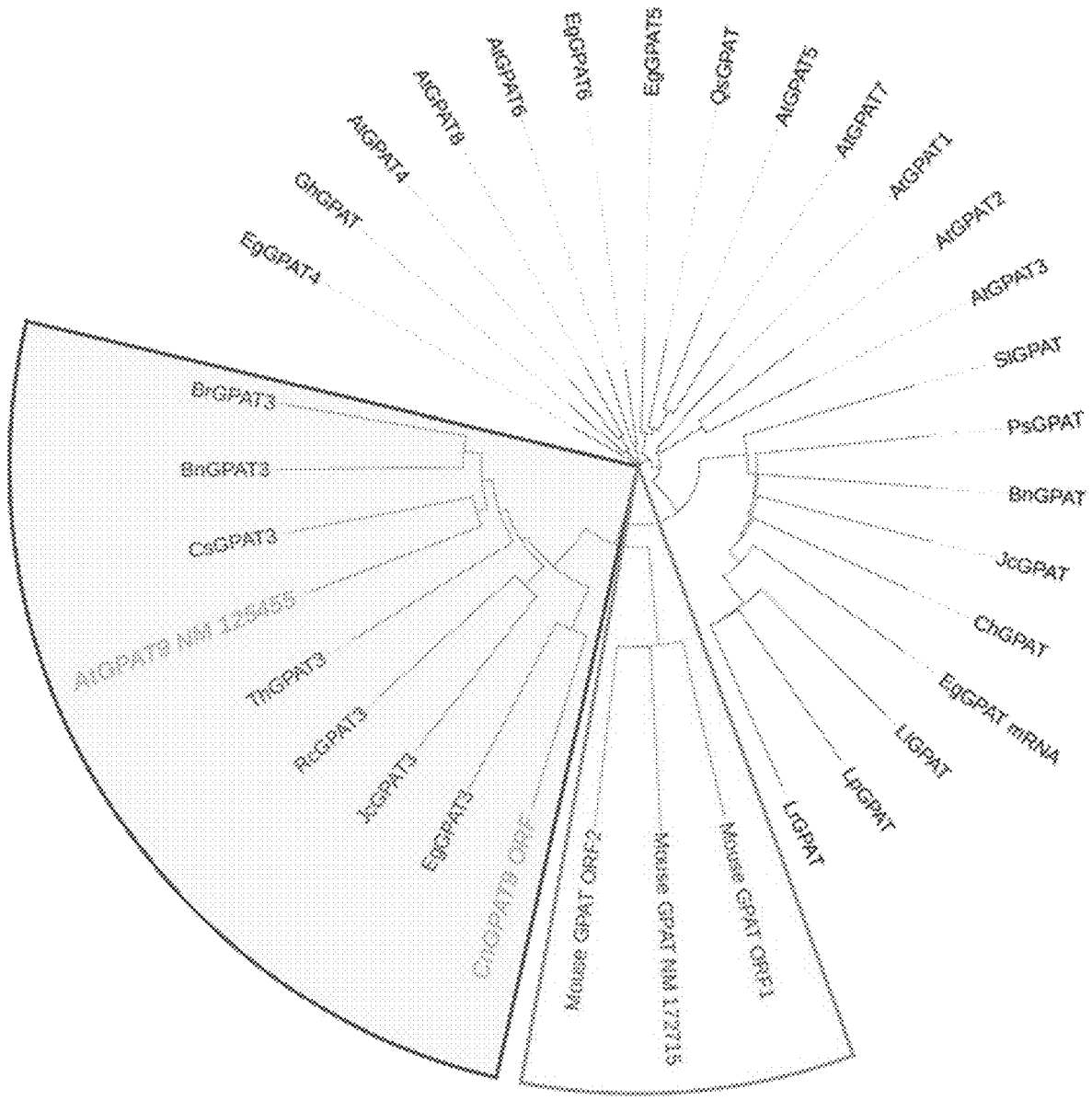

FIG. 11. Phylogenetic relationship of glycerol-3-phosphate acyltransferase (GPAT) genes from various species including the *Arabidopsis thaliana* (AtGPAT9) and *Cocos nucifera* (CnGPAT9) genes used in this study. The plant GPAT9 cluster is shaded in grey. BrGPAT3=*Brassica rapa* glycerol-3-phosphate acyltransferase 3-like (Accession: XM_009105753); BnGPAT3=*Brassica napus* glycerol-3-phosphate acyltransferase 3-like (Accession: XM_013896062); CsGPAT3=*Camelina sativa* glycerol-3-phosphate acyltransferase 3 (Accession: XM_010458322); AtGPAT9=*A. thaliana* glycerol-3-phosphate acyltransferase 9 (Accession: NM_125455); ThGPAT3=*Tarenaya hassleriana* glycerol-3-phosphate acyltransferase 3-like (Accession: XM_010549847); RcGPAT3=*Ricinus communis* glycerol-3-phosphate acyltransferase 3 (Accession: NM_001323761); JcGPAT3=*Jatropha curcas* glycerol-3-phosphate acyltransferase 3 (Accession: NM_001308751); EgGPAT3=*Elaeis guineensis* glycerol-3-phosphate acyltransferase 3-like (Accession: XM_010913693); CnGPAT9=*C. nucifera* GPAT9 (Accession: KX235871); Mouse GPAT=*Mus musculus* 1-acylglycerol-3-phosphate O-acyltransferase 9 (Accession: NM_172715); LrGPAT=*Lilium regale* GPAT (Accession: JX524740); LpGPAT=*Lilium pensylvanicum* GPAT (Accession: JX524741); LlGPAT=*Lilium longiflorum* GPAT (Accession: JX524738); EgGPAT mRMA=*E. guineensis* mRNA for acylation enzyme (Accession: AJ272082); ChGPAT=*Corylus heterophylla* GPAT (Accession: JF428134); JcGPAT=*J. curcas* glycerol-3-phosphate acyltransferase, chloroplastic (Accession: NM_001305998); BnGPAT=*B. napus* glycerol-3-phosphate acyltransferase gene (Accession: KM243174); PsGPAT=*Pisum sativum* chloroplast mRNA for acyl-ACP:sn-glycerol-3-phosphate-acyltransferase (Accession: X59041); SlGPAT=*Solanum lycopersicum* glycerol-3-phosphate acyltransferase (Accession: NM_001306067); AtGPAT3=*A. thaliana* putative sn-glycerol-3-phosphate 2-O-acyltransferase (Accession: NM_116426); AtGPAT2=*A. thaliana* glycerol-3-phosphate sn-2-acyltransferase 2 (Accession: NM_100120); AtGPAT1=*A. thaliana* sn-glycerol-3-phosphate 2-O-acyltransferase (Accession: NM_100531); AtGPAT7=*A. thaliana* glycerol-3-phosphate acyltransferase 7 (Accession: NM_120691); AtGPAT5=*A. thaliana* glycerol-3-phosphate acyltransferase 5 (Accession: NM 111976); QsGPAT=*Quercus suber* glycerol-3-phosphate acyltransferase (Accession: JN819185); EgGPAT5=*E. guineensis* glycerol-3-phosphate acyltransferase 5 (Accession: XM_010923983); EgGPAT6=*E. guineensis* glycerol-3-phosphate 2-O-acyltransferase 6 (Accession: XM_010924793); AtGPAT6=*A. thaliana* bifunctional sn-glycerol-3-phosphate 2-O-acyltransferase/phosphatase (Accession: NM_129367); AtGPAT8=*A. thaliana* bifunctional sn-glycerol-3-phosphate 2-O-acyltransferase/phosphatase (Accession: NM_116264); AtGPAT4=*A. thaliana* glycerol-3-phosphate sn-2-acyltransferase (Accession: NM_100043); GhGPAT=*Gossypium hirsutum* probable glycerol-3-phosphate acyltransferase 3 (Accession: XM_016838669); EgGPAT4=*E. guineensis* glycerol-3-phosphate 2-O-acyltransferase 4-like (Accession: XM_010942191).

Figure 12:
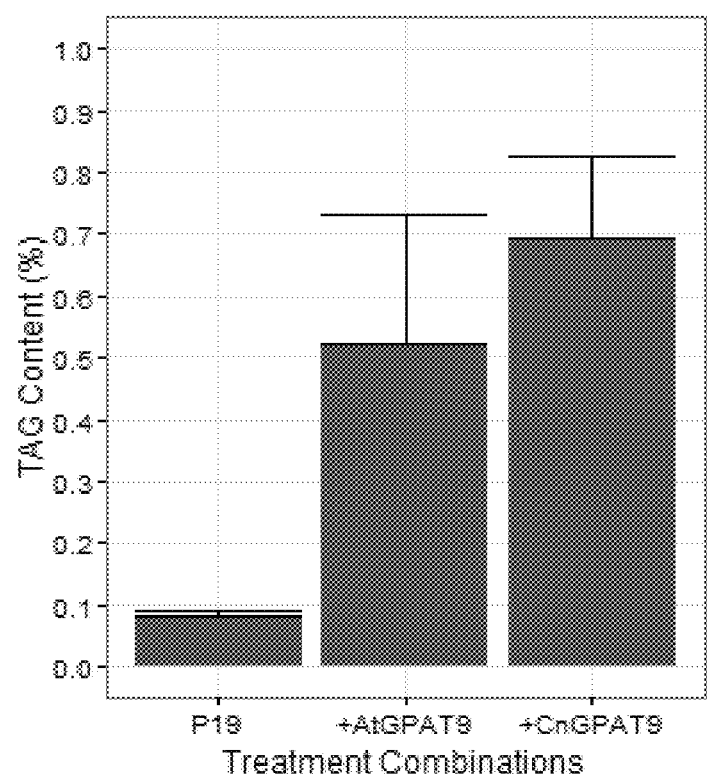

FIG. 12. Testing the effect of GPAT9 genes from *Arabidopsis thaliana* (AtGPAT9) and from *Cocos nucifera* (CnGPAT9) expression on TAG content, determined by transient *Nicotiana benthamiana* leaf expression (n=4).

Figure 13:
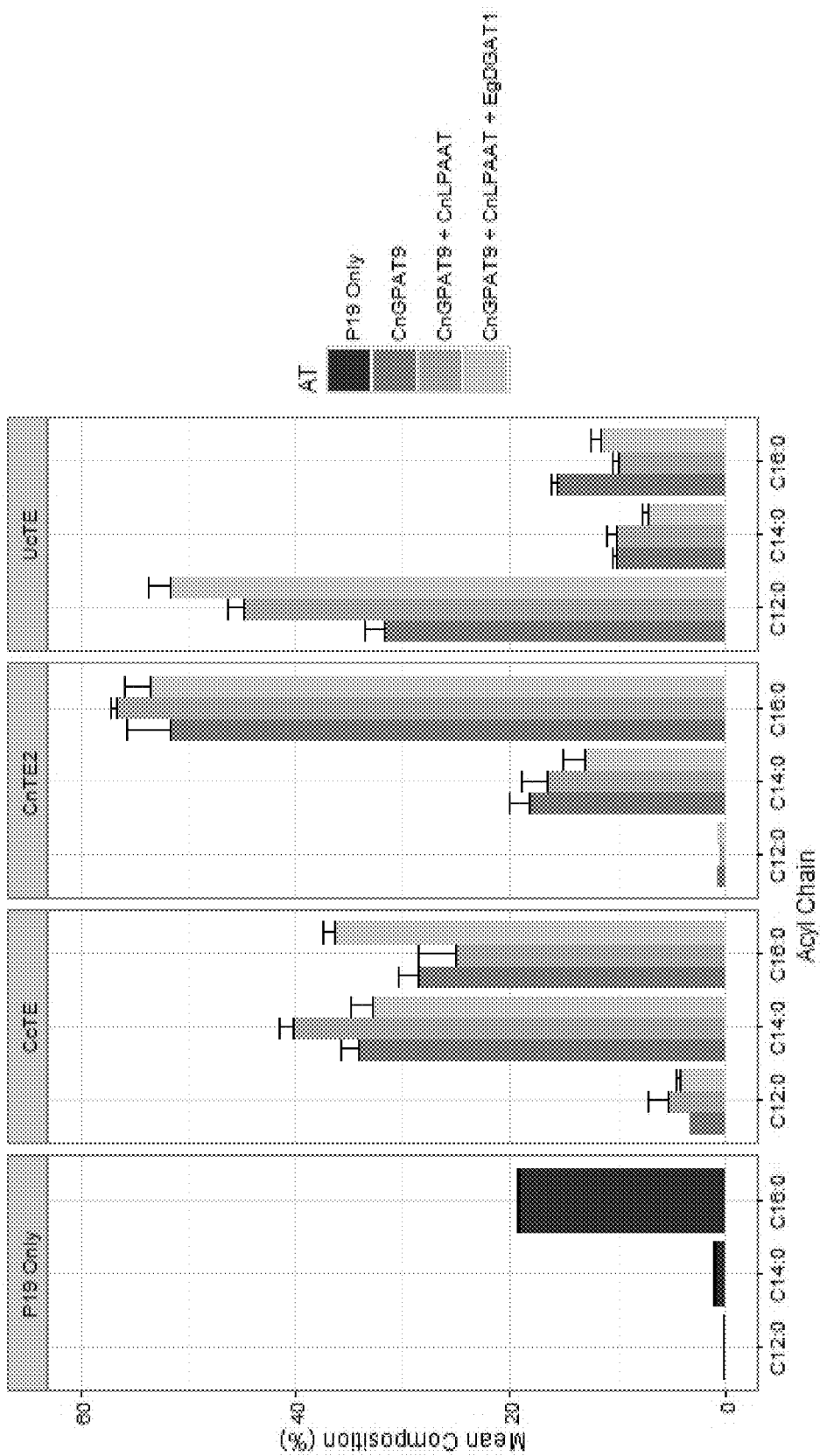

FIG. 13. Fatty acid composition analysis of triacylglycerol (TAG), determined by the analysis of fatty acid methyl esters (FAME) via gas chromatography-flame ionisation detection (GC-FID) (n=3). Each thioesterase was infiltrated in combination with CnGPAT9 alone, CnGPAT9+CnLPAAT or CnGPAT9+CnLPAAT+EgDGAT1, with all treatments including expression of AtWRI1 (*Arabidopsis thaliana* WRINKLED1). CcTE=*Cinnamomum camphora* thioesterase; CnTE2=*Cocos nucifera* thioesterase; UcTE=*Umbellularia californica* thioesterase; CnGPAT9=*C. nucifera* glycerol-3-phosphate acyltransferase 9; CnLPAAT=*C. nucifera* lysophosphatidic acid acyltransferase; EgDGAT1=*Elaeis guineensis* diacylglycerol acyltransferase.

KEY TO THE SEQUENCE LISTING

SEQ ID NO:1 *Arabidopsis thaliana* DGAT1 polypeptide (CAB44774.1)
SEQ ID NO:2 YFP tripeptide—conserved DGAT2 and/or MGAT1/2 sequence motif
SEQ ID NO:3 HPHG tetrapeptide—conserved DGAT2 and/or MGAT1/2 sequence motif
SEQ ID NO:4 EPHS tetrapeptide—conserved plant DGAT2 sequence motif SEQ ID NO:5 RXGFX(K/R)XAXXXGXXX(L/V) VPXXXFG(E/Q)—long conserved sequence motif of DGAT2 which is part of the putative glycerol phospholipid domain SEQ ID NO:6 FLXLXXXN—conserved sequence motif of mouse DGAT2 and MGAT1/2 which is a putative neutral lipid binding domain SEQ ID NO:7 Conserved GPAT amino acid sequence GDLVICPEGTTCREP SEQ ID NO:8 Conserved GPAT/phosphatase amino acid sequence (Motif I)

SEQ ID NO:9 Conserved GPAT/phosphatase amino acid sequence (Motif III)

SEQ ID NO:10 Sorbi-WRL1

SEQ ID NO:11 Lupan-WRL1

SEQ ID NO:12 Ricco-WRL1

SEQ ID NO:13 *Lupin angustifolius* WRI1 polypeptide

```
SEQ ID NO: 14 WRI1 motif (R G V T/S R H R W T G R)

SEQ ID NO: 15 WRI1 motif (F/Y E A H L W D K)

SEQ ID NO: 16 WRI1 motif (D L A A L K Y W G)

SEQ ID NO: 17 WRI1 motif (S X G F S/A R G X)

SEQ ID NO: 18 WRI1 motif (H H H/Q N G R/K W E A R
I G R/K V)

SEQ ID NO: 19 WRI1 motif (Q E E A A A X Y D)
```

SEQ ID NO:20 pJP3502 TDNA (inserted into genome) sequence

SEQ ID NO:21 pJP3507 vector sequence

SEQ ID NO:22 Linker sequence

SEQ ID NO:23 Partial *Nicotiana benthamiana* CGI-58 sequence selected for hpRNAi silencing (pTV46)

SEQ ID NO:24 Partial *N. tabacum* AGPase sequence selected for hpRNAi silencing (pTV35)

SEQ ID NO:25 GXSXG lipase motif

SEQ ID NO:26 HX(4)D acyltransferase motif

SEQ ID NO:27 VX(3)HGF probable lipid binding motif

SEQ ID NO:28 *Arabidopsis thaliana* BBM polypeptide (NP_197245.2)

SEQ ID NO:29 Inducible *Aspergillus niger* alcA promoter

SEQ ID NO:30 AlcR inducer that activates the AlcA promotor in the presence of ethanol SEQ ID NO:31 *Arabidopsis thaliana* LEC1; (AAC39488)

SEQ ID NO:32 *Zea mays* LEC1 (AAK95562)

SEQ ID NO:33 *Arabidopsis thaliana* LEC1-like (AAN15924)

SEQ ID NO:34 *Arabidopsis thaliana* FUS3 (AAC35247)

SEQ ID NO:35 *Brassica napus* FUS3

SEQ ID NO:36 *Medicago truncatula* FUS3

SEQ ID NO:37 *Arabidopsis thaliana* SDP1 cDNA sequence, Accession No. NM_120486, 3275 nt SEQ ID NO:38 *Sorghum bicolor* SDP1 cDNA XM_002458486; 2724 nt SEQ ID NO:39 *Nicotiana benthamiana* SDP1 cDNA, Nbv5tr6404201SEQ ID NO:40 *Nicotiana benthamiana* SDP1 cDNA region targeted for hpRNAi silencing SEQ ID NO:41 Promoter of *Arabidopsis thaliana* SDP1 gene, 1.5 kb SEQ ID NO:42 Nucleotide sequence of the complement of the pSSU-Oleosin gene in the T-DNA of pJP3502. In order (complementary sequences): *Glycine max* Lectin terminator 348nt, 3' exon 255nt, UBQ10 intron 304nt, 5' exon 213nt, SSU promoter 1751nt SEQ ID NO:43 *Arabidopsis thaliana* FATA1

SEQ ID NO:44 *Arabidopsis thaliana* FATA2

SEQ ID NO:45 *Arabidopsis thaliana* FATB

SEQ ID NO:46 *Arabidopsis thaliana* WRI3

SEQ ID NO:47 *Arabidopsis thaliana* WRI4

SEQ ID NO:48 *Avena sativa* WRI1

SEQ ID NO:49 *Sorghum bicolor* WRI1

SEQ ID NO:50 *Zea mays* WRI1

SEQ ID NO:51 *Triadica sebifera* WRI1

SEQ ID NO:52 *S. tuberosum* Patatin B33 promoter sequence

SEQ ID NO:53 *Z. mays* SEE1 promoter region (1970nt from Accession number AJ494982)

SEQ ID NO:54 *A. littoralis* A1SAP promoter sequence, Accession No DQ885219

SEQ ID NO:55 *A. rhizogenes* ArRo1C promoter sequence, Accession No. DQ160187

SEQ ID NO:56 *Elaeis guineensis* (oil palm) DGAT1

SEQ ID NO:57 *G. max* MYB73, Accession No. ABH02868

SEQ ID NO:58 *A. thaliana* bZIP53, Accession No. AAM14360

SEQ ID NO:59 *A. thaliana* AGL15, Accession No NP_196883

SEQ ID NO:60 *A. thaliana* MYB118, Accession No. AAS58517

SEQ ID NO:61 *A. thaliana* MYB115, Accession No. AAS10103

SEQ ID NO:62 *A. thaliana* TANMEI, Accession No. BAE44475

SEQ ID NO:63 *A. thaliana* WUS, Accession No. NP_565429

SEQ ID NO:64 *B. napus* GFR2a1, Accession No. AFB74090

SEQ ID NO:65 *B. napus* GFR2a2, Accession No. AFB74089

SEQ ID NO:66 *A. thaliana* PHR1, Accession No. AAN72198

SEQ ID NO:67 *Sapium sebiferum* LDAP-1 nucleotide sequence

SEQ ID NO:68 *Sapium sebiferum* LDAP-1 amino acid sequence

SEQ ID NO:69 *Sapium sebiferum* LDAP-2 nucleotide sequence

SEQ ID NO:70 *Sapium sebiferum* LDAP-2 amino acid sequence

SEQ ID NO:71 *Sapium sebiferum* LDAP-3 nucleotide sequence

SEQ ID NO:72 *Sapium sebiferum* LDAP-3 amino acid sequence

SEQ ID NO:73 *S. bicolor* SDP1 (accession number XM_002463620)

SEQ ID NO:74 *T. aestivum* SDP1 nucleotide sequence (Accession number AK334547)

SEQ ID NO:75 *S. bicolor* SDP1 hpRNAi fragment.

SEQ ID NO's 76 to 81 Oligonucleotide primer sequence

SEQ ID NO:82 *Saccharum* hybrid DIRIGENT (DIR16) promoter sequence

SEQ ID NO:83 *Saccharum* hybrid 0-Methyl transferase (OMT) promoter sequence

SEQ ID NO:84 Sequence of the A1 promoter allele of the *Saccharum* hybrid R1MYB1 gene SEQ ID NO:85 *Saccharum* hybrid Loading Stem Gene 5 (LSG5) promoter sequence SEQ ID NO:86 Amino acid sequence of *Sesamum indicum* oleosinL polypeptide (Accession No. AF091840)

SEQ ID NO:87 Amino acid sequence of *Cinnamomum camphora* 14:0-ACP thioesterase (Accession No. Q39473.1)

SEQ ID NO:88 Amino acid sequence of *Cocos nucifera* acyl-ACP thioesterase FatB1 (Accession No. AEM72519.1)

SEQ ID NO:89 Amino acid sequence of *Cocos nucifera* acyl-ACP thioesterase FatB2 (Accession No. AEM72520.1)

SEQ ID NO:90 Amino acid sequence of *Cocos nucifera* acyl-ACP thioesterase FatB3 (Accession No. AEM72521.1)

SEQ ID NO:91 Amino acid sequence of *Cuphea lanceolata* acyl-(ACP) thioesterase type B (Accession No. CAB60830.1)

SEQ ID NO:92 Amino acid sequence of *Cuphea viscosissima* FatB1 (Accession No. AEM72522.1)

SEQ ID NO:93 Amino acid sequence of and *Umbellularia californica* 12:0-ACP thioesterase (Accession No. Q41635.1)

SEQ ID NO:94 Amino acid sequence of *C. nucifera* LPAAT (Accession No. Q42670.1)

SEQ ID NO:95 Amino acid sequence of *A. thaliana* plastidial LPAAT1 (Accession No. AEE85783.1)

SEQ ID NO:96 Codon optimised nucleotide sequence of *Elaeis guineensis* DGAT1

SEQ ID NO:97 Amino acid sequence of *Cocos nucifera* GPAT9

SEQ ID NO:98 Amino acid sequence of *Arabidopsis thaliana* GPAT9

SEQ ID NO:99 Amino acid sequence of *Elaeis guineensis* GPAT9

SEQ ID NO:100 Amino acid sequence of *Phoenix dactylifera* GPAT9

SEQ ID NO:101 Amino acid sequence of *Musa acuminata* GPAT9

SEQ ID NO:102 Amino acid sequence of *Ananas comosus* GPAT9

SEQ ID NO:103 Amino acid sequence of *Asparagus officinalis* GPAT9

SEQ ID NO:104 Amino acid sequence of *Oryza brachyantha* GPAT9

SEQ ID NO:105 Amino acid sequence of *Oryza sativa* GPAT9

SEQ ID NO:106 Amino acid sequence of *Nelumbo nucifera* GPAT9

SEQ ID NO:107 Amino acid sequence of *Vitis vinifera* GPAT9

SEQ ID NO:108 Amino acid sequence of *Nicotiana tomentosiformis* GPAT9

SEQ ID NO:109 Amino acid sequence of *Jatropha curcas* GPAT9

SEQ ID NO:110 Amino acid sequence of *Glycine max* GPAT9

SEQ ID NO:111 Amino acid sequence of *Sesamum indicum* GPAT9

SEQ ID NO:112 Amino acid sequence of *Brachypodium distachyon* GPAT9

SEQ ID NO:113 Amino acid sequence of *Setaria italica* GPAT9

SEQ ID NO:114 Amino acid sequence of *Cicer arietinum* GPAT9

SEQ ID NO:115 Amino acid sequence of *Zea mays* GPAT9

SEQ ID NO:116 Amino acid sequence of *Gossypium hirsutum* GPAT9

SEQ ID NO:117 Amino acid sequence of *Eucalyptus grandis* GPAT9

SEQ ID NO:118 Amino acid sequence of *Cucumis sativus* GPAT9

SEQ ID NO:119 Amino acid sequence of *Gossypium arboreum* GPAT9

SEQ ID NO:120 Nucleotide sequence of *Cocos nucifera* GPAT9

SEQ ID NO:121 Nucleotide sequence of *Arabidopsis thaliana* GPAT9

SEQ ID NO:122 Nucleotide sequence of *Elaeis guineensis* GPAT9

SEQ ID NO:123 Nucleotide sequence of *Phoenix dactylifera* GPAT9

SEQ ID NO:124 Nucleotide sequence of *Musa acuminata* GPAT9

SEQ ID NO:125 Nucleotide sequence of *Ananas comosus* GPAT9

SEQ ID NO:126 Nucleotide sequence of *Asparagus officinalis* GPAT9

SEQ ID NO:127 Nucleotide sequence of *Oryza brachyantha* GPAT9

SEQ ID NO:128 Nucleotide sequence of *Oryza sativa* GPAT9

SEQ ID NO:129 Nucleotide sequence of *Nelumbo nucifera* GPAT9

SEQ ID NO:130 Nucleotide sequence of *Vitis vinifera* GPAT9

SEQ ID NO:131 Nucleotide sequence of *Nicotiana tomentosiformis* GPAT9

SEQ ID NO:132 Nucleotide sequence of *Jatropha curcas* GPAT9

SEQ ID NO:133 Nucleotide sequence of *Glycine max* GPAT9

SEQ ID NO:134 Nucleotide sequence of *Sesamum indicum* GPAT9

SEQ ID NO:135 Nucleotide sequence of *Brachypodium distachyon* GPAT9

SEQ ID NO:136 Nucleotide sequence of *Setaria italica* GPAT9

SEQ ID NO:137 Nucleotide sequence of *Cicer arietinum* GPAT9

SEQ ID NO:138 Nucleotide sequence of *Zea mays* GPAT9

SEQ ID NO:139 Nucleotide sequence of *Gossypium hirsutum* GPAT9

SEQ ID NO:140 Nucleotide sequence of *Eucalyptus grandis* GPAT9

SEQ ID NO:141 Nucleotide sequence of *Cucumis sativus* GPAT9

SEQ ID NO:142 Nucleotide sequence of *Gossypium arboreum* GPAT9

SEQ ID NO:143 Amino acid sequence of *E. guineensis* NF-YB1

SEQ ID NO:144 Amino acid sequence of *E. guineensis* ZFP1

SEQ ID NO:145 Amino acid sequence of *A. thaliana* NF-YB2

SEQ ID NO:146 Amino acid sequence of *A. thaliana* NF-YB3

SEQ ID NO:147 Amino acid sequence of *A. thaliana* ZFP2

SEQ ID NO:148 Amino acid sequence of *E. guineensis* ABI5

SEQ ID NO:149 Amino acid sequence of *E. guineensis* NF-YC2

SEQ ID NO:150 Amino acid sequence of *E. guineensis* NF-YA3

SEQ ID NO:151 Amino acid sequence of *G. max* DOF4

SEQ ID NO:152 Amino acid sequence of *G. max* ZF351

DETAILED DESCRIPTION OF THE INVENTION

General Techniques

Unless specifically defined otherwise, all technical and scientific terms used herein shall be taken to have the same meaning as commonly understood by one of ordinary skill in the art (e.g., in cell culture, molecular genetics, plant biology, cell biology, protein chemistry, lipid and fatty acid chemistry, animal nutrition, biofeul production, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

Selected Definitions

The term "exogenous" in the context of a polynucleotide or polypeptide refers to the polynucleotide or polypeptide when present in a cell or a plant or part thereof which does not naturally comprise the polynucleotide or polypeptide. Such a cell is referred to herein as a "recombinant cell" or a "transgenic cell" and a plant comprising the cell as a "transgenic plant". In an embodiment, the exogenous polynucleotide or polypeptide is from a different genus to the cell of the plant or part thereof comprising the exogenous polynucleotide or polypeptide. In another embodiment, the exogenous polynucleotide or polypeptide is from a different species. In one embodiment, the exogenous polynucleotide or polypeptide expressed in the plant cell is from a different species or genus. The exogenous polynucleotide or polypeptide may be non-naturally occurring, such as for example, a synthetic DNA molecule which has been produced by recombinant DNA methods. The DNA molecule may, preferably, include a protein coding region which has been codon-optimised for expression in the plant cell, thereby producing a polypeptide which has the same amino acid sequence as a naturally occurring polypeptide, even though the nucleotide sequence of the protein coding region is non-naturally occurring. The exogenous polynucleotide may encode, or the exogenous polypeptide may be, for example: a diacylglycerol acyltransferase (DGAT) such as a DGAT1 or a DGAT2, a Wrinkled 1 (WRI1) transcription factor, on OBC such as an Oleosin or preferably an LDAP, a fatty acid thioesterase such as a FATA or FATB polypeptide, or a silencing suppressor polypeptide. In an embodiment, a cell of the invention is a recombinant cell.

As used herein, the term "triacylglycerol (TAG) content" or variations thereof refers to the amount of TAG in the cell, plant or part thereof. TAG content can be calculated using techniques known in the art such as the sum of glycerol and fatty acyl moieties using a relation: % TAG by weight=100× ((41×total mol FAME/3)+(total g FAME−(15× total mol FAME)))/g, where 41 and 15 are molecular weights of glycerol moiety and methyl group, respectively (where FAME is fatty acid methyl esters) (see Examples such as Example 1).

As used herein, the term "total fatty acid (TFA) content" or variations thereof refers to the total amount of fatty acids in the cell, plant or part thereof on a weight basis, as a percentage of the weight of the cell, plant or part thereof. Unless otherwise specified, the weight of the cell, plant or part thereof is the dry weight of the cell, plant or part thereof. TFA content is measured as described in Example 1 herein. The method involves conversion of the fatty acids in the sample to FAME and measurement of the amount of FAME by GC, using addition of a known amount of a distinctive fatty acid standard such as C17:0 as a quantitation standard in the GC. TFA therefore represents the weight of just the fatty acids, not the weight of the fatty acids and their linked moieties in the plant lipid.

As used herein, the "TAG/TFA Quotient" or "TTQ" parameter is calculated as the level of TAG (%) divided by the level of TFA (%), each as a percentage of the dry weight of the plant material. For example, a TAG level of 6% comprised in a TFA level of 10% yields a TTQ of 0.6. The TAG and TFA levels are measured as described herein. It is understood that, in this context, the TFA level refers to the weight of the total fatty acid content and the TAG level refers to the weight of TAG, including the glycerol moiety of TAG.

As used herein, the term "soluble protein content" or variations thereof refers to the amount of soluble protein in the plant or part thereof. Soluble protein content can be calculated using techniques known in the art. For instance, fresh tissue can be ground, chlorophyll and soluble sugars extracted by heating to 80° C. in 50-80% (v/v) ethanol in 2.5 mM HEPES buffer at pH 7.5, centriguation, washing pellet in distilled water, resuspending the pellet 0.1 M NaOH and heating to 95° C. for 30 min, and then the Bradford assay (Bradford, 1976) is used determined soluble protein content. Alternatively, fresh tissue can be ground in buffer containing 100 mM Tris-HCl pH 8.0 and 10 mM $MgCl_2$.

As used herein, the term "nitrogen content" or variations thereof refers to the amount of nitrogen in the plant or part thereof. Nitrogen content can be calculated using techniques known in the art. For example, freeze-dried tissue can be analysed using a Europa 20-20 isotope ratio mass spectrometer with an ANCA preparation system, comprising a combustion and reduction tube operating at 1000° C. and 600° C., respectively, to determine nitrogen content.

As used herein, the term "carbon content" or variations thereof refers to the amount of carbon in the plant or part thereof. Carbon content can be calculated using techniques known in the art. For example, organic carbon levels can be determined using the method described by Shaw (1959), or as described in Example 1 of WO 2016/004473.

As used herein, the term "carbon:nitrogen ratio" or variations thereof refers to the relative amount of carbon in the cell, plant or part thereof when compared to the amount of nitrogen in the cell, plant or part thereof. Carbon and nitrogen contents can be calculated as described above and represented as a ratio.

As used herein, the term "photosynthetic gene expression" or variations thereof refers to one or more genes expressing proteins involved in photosynthetic pathways in the plant of part thereof. Examples of photosynthetic genes which may be upregulated in plants or parts thereof of the invention include, but are not limited to, one or more of the genes listed in Table 10 of WO 2016/004473.

As used herein, the term "photosynthetic capacity" or variations thereof refers to the ability of the plant or part thereof to photosynthesize (convert light energy to chemical energy). Photosynthetic capacity ($A_{max}$) is a measure of the maximum rate at which leaves are able to fix carbon during photosynthesis. It is typically measured as the amount of carbon dioxide that is fixed per metre squared per second, for example as $\mu mol\ m^{-2}\ sec^{-1}$. Photosynthetic capacity can be calculated using techniques known in the art.

As used herein, the term "total dietary fibre (TDF) content" or variations thereof refers to the amount of fiber (including soluble and insoluble fibre) in the cell, plant or part thereof. As the skilled person would understand, dietary fiber includes non-starch polysaccharides such as arabinoxylans, cellulose, and many other plant components such as resistant starch, resistant dextrins, inulin, lignin, chitins, pectins, β-glucans, and oligosaccharides. TDF can be calculated using techniques known in the art. For example, using the Prosky method (Prosky et al. 1985), the McCleary method (McCleary et al., 2007) or the rapid integrated total dietary fiber method (McCleary et al., 2015).

As used herein, the term "energy content" or variations thereof refers to the amount of food energy in the plant or part thereof. More specifically, the amount of chemical energy that animals (including humans) derive from their food. Energy content can be calculated using techniques known in the art. For example, energy content can be determined based on heats of combustion in a bomb calorimeter and corrections that take into consideration the efficiency of digestion and absorption and the production of urea and other substances in the urine. As another example, energy content can be calculated as described in Example 1 of WO 2016/004473.

As used herein, the term "extracted lipid" refers to a composition extracted from a cell, plant or part thereof of the invention, such as a transgenic cell, plant or part thereof of the invention, which comprises at least 60% (w/w) lipid.

As used herein, the term "non-polar lipid" refers to fatty acids and derivatives thereof which are soluble in organic solvents but insoluble in water. The fatty acids may be free fatty acids and/or in an esterified form. Examples of esterified forms of non-polar lipid include, but are not limited to, triacylglycerol (TAG), diacylglycerol (DAG), monoacylglycerol (MAG). Non-polar lipids also include sterols, sterol esters and wax esters. Non-polar lipids are also known as "neutral lipids". Non-polar lipid is typically a liquid at room temperature. In an embodiment, at least 50%, more preferably at least 70%, more preferably at least 80%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% of the fatty acids in non-polar lipid of the invention are present as TAG. The non-polar lipid may be further purified or treated, for example by hydrolysis with a strong base to release the free fatty acid, or by fractionation, distillation, or the like. Non-polar lipid may be present in or obtained from plant parts such as seed, leaves, tubers, beets or fruit. Non-polar lipid of the invention may form part of "seedoil" if it is obtained from seed.

The free and esterified sterol (for example, sitosterol, campesterol, stigmasterol, brassicasterol, Δ5-avenasterol, sitostanol, campestanol, and cholesterol) concentrations in the extracted lipid may be as described in Phillips et al. (2002). Sterols in plant oils are present as free alcohols, esters with fatty acids (esterified sterols), glycosides and acylated glycosides of sterols. Sterol concentrations in naturally occurring vegetable oils (seedoils) ranges up to a maximum of about 1100 mg/100 g. Hydrogenated palm oil has one of the lowest concentrations of naturally occurring vegetable oils at about 60 mg/100 g. The recovered or extracted seedoils of the invention preferably have between about 100 and about 1000 mg total sterol/100 g of oil. For use as food or feed, it is preferred that sterols are present primarily as free or esterified forms rather than glycosylated forms. In the seedoils of the present invention, preferably at least 50% of the sterols in the oils are present as esterified sterols, except for soybean seedoil which has about 25% of the sterols esterified. The canola seedoil and rapeseed oil of the invention preferably have between about 500 and about 800 mg total sterol/100 g, with sitosterol the main sterol and campesterol the next most abundant. The corn seedoil of the invention preferably has between about 600 and about 800 mg total sterol/100 g, with sitosterol the main sterol. The soybean seedoil of the invention preferably has between about 150 and about 350 mg total sterol/100 g, with sitosterol the main sterol and stigmasterol the next most abundant, and with more free sterol than esterified sterol. The cottonseed oil of the invention preferably has between about 200 and about 350 mg total sterol/100 g, with sitosterol the main sterol. The coconut oil and palm oil of the invention preferably have between about 50 and about 100 mg total sterol/100 g, with sitosterol the main sterol. The safflower seedoil of the invention preferably has between about 150 and about 250 mg total sterol/100 g, with sitosterol the main sterol. The peanut seedoil of the invention preferably has between about 100 and about 200 mg total sterol/100 g, with sitosterol the main sterol. The sesame seedoil of the invention preferably has between about 400 and about 600 mg total sterol/100 g, with sitosterol the main sterol. The sunflower seedoil of the invention preferably has between about 200 and 400 mg total sterol/100 g, with sitosterol the main sterol. Oils obtained from vegetative plant parts according to the invention preferably have less than 200 mg total sterol/100 g, more preferably less than 100 mg total sterol/100 g, and most preferably less than 50 mg total sterols/100 g, with the majority of the sterols being free sterols. In an embodiment, the lipid or oil is from a vegetative plant part which comprises one or more or all of sitosterol, campesterol, stigmasterol and cholesterol. In an embodiment, the lipid or oil is from a vegetative plant part and has more galactosylglycerides than phosphoglycerides. In an embodiment, the lipid or oil is from a seed and has more phosphoglycerides than galactosylglycerides. Further guidance regarding sterols and other lipids components of plant cells can be found in Gunstone et al. (2007) The Lipid Handbook, Third Edition, CRC Press.

As used herein, the term "vegetative oil" refers to a composition obtained from vegetative parts of a plant which comprises at least 60% (w/w) lipid, or obtainable from the vegetative parts if the oil is still present in the vegetative part. That is, vegetative oil of the invention includes oil which is present in the vegetative plant part, as well as oil which has been extracted from the vegetative part (extracted oil). The vegetative oil is preferably extracted vegetative oil. Vegetative oil is typically a liquid at room temperature. The fatty acids are typically in an esterified form such as for example, TAG, DAG, acyl-CoA, galactolipid or phospholipid. The fatty acids may be free fatty acids and/or in an esterified form. In an embodiment, at least 50%, more preferably at least 70%, more preferably at least 80%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% of the fatty acids in vegetative oil of the invention can be found as TAG. In an embodiment, vegetative oil of the invention is "substantially purified" or "purified" oil that has been separated from one or more other lipids, nucleic acids, polypeptides, or other contaminating molecules with which it is associated in the vegetative plant part or in a crude extract. It is preferred that the substantially purified vegetative oil is at least 60% free, more preferably at least 75% free, and more preferably, at least 90% free from other components with which it is associated in the vegetative plant part or extract. Vegetative oil of the invention may further comprise non-fatty acid molecules such as, but not limited to, sterols. In an embodiment, the vegetative oil is canola oil (*Brassica* sp. such as *Brassica carinata, Brassica juncea, Brassica napobrassica, Brassica napus*) mustard oil (*Brassica juncea*), other *Brassica* oil (e.g., *Brassica napobrassica, Brassica camelina*), sunflower oil (*Helianthus* sp. such as *Helianthus annuus*), linseed oil (*Linum usitatissimum*), soybean oil (*Glycine max*), safflower oil (*Carthamus tinctorius*), corn oil (*Zea mays*), tobacco oil (*Nicotiana* sp. such as *Nicotiana tabacum* or *Nicotiana benthamiana*), peanut oil (*Arachis hypogaea*), palm oil (*Elaeis guineensis*), cotton oil (*Gossypium hirsutum*), coconut oil (*Cocos nucifera*), avocado oil (*Persea americana*), olive oil (*Olea europaea*), cashew oil (*Anacardium occidentale*), macadamia oil (*Macadamia intergrifolia*), almond oil (*Prunus amygdalus*), oat oil (*Avena sativa*), rice oil (*Oryza* sp. such as *Oryza sativa* and *Oryza glaberrima*), *Arabidopsis* oil (*Arabidopsis thaliana*), *Aracinis hypogaea* (peanut), *Beta vulgaris* oil (sugar beet), *Camelina sativa* oil (false flax), *Crambe abyssinica* oil (Abyssinian kale), *Cucumis melo* oil (melon), *Hordeum vulgare* oil (barley), *Jatropha curcas* oil (physic nut), *Joannesia princeps* oil (arara nut-tree), *Licania rigida* oil (oiticica), *Lupinus angustifolius* oil (lupin), *Miscanthus* sp. oil such as *Miscanthus* x *giganteus* oil and *Miscanthus sinensis* oil, *Panicum virgatum* (switchgrass) oil, Pongamia pinnata oil (Indian beech), *Populus trichocarpa* oil, *Ricinus communis* oil (castor), *Saccharum* sp. oil (sugarcane), *Sesamum indicum* oil (sesame), *Solanum tuberosum* oil (potato), *Sorghum* sp. oil such as *Sorghum bicolor* oil, *Sorghum vulgare* oil, *Theobroma grandiforum* oil (cupuassu), *Trifolium* sp. oil, and *Triticum* sp. oil (wheat) such as *Triticum aestivum*. oil Vegetative oil may be extracted from vegetative plant parts by any method known in the art, such as for extracting seedoils. This typically involves extraction with nonpolar solvents such as diethyl ether, petroleum ether, chloroform/methanol or butanol mixtures, generally associated with first crushing of the seeds. Lipids associated with the starch or other polysaccharides may be extracted with water-saturated butanol. The seedoil may be "de-gummed" by methods known in the art to remove polar lipids such as phospholipids or treated in other ways to remove contaminants or improve purity, stability, or colour. The TAGs and other esters in the vegetative oil may be hydrolysed to release free fatty acids, or the oil hydrogenated, treated chemically, or enzymatically as known in the art. As used herein, the term "seedoil" has an analogous meaning except that it refers to a lipid composition obtained from seeds of plants of the invention.

As used herein, the term "fatty acid" refers to a carboxylic acid with an aliphatic tail of at least 6 carbon atoms in length, either saturated or unsaturated. Preferred fatty acids have a carbon-carbon bonded chain of at least 12 carbons in length, more preferably fatty acids having have a carbon-carbon bonded chain of 12 and/or 14 carbons in length. Most naturally occurring fatty acids have an even number of carbon atoms because their biosynthesis involves acetate which has two carbon atoms. The fatty acids may be in a free state (non-esterified) or in an esterified form such as part of a TAG, DAG, MAG, acyl-CoA (thio-ester) bound, acyl-ACP bound, or other covalently bound form. When covalently bound in an esterified form, the fatty acid is referred to herein as an "acyl" group. The fatty acid may be esterified as a phospholipid such as a phosphatidylcholine (PC), phosphatidylethanolamine (PE), phosphatidylserine (PS), phosphatidylglycerol (PG), phosphatidylinositol (PI), or diphosphatidylglycerol. Saturated fatty acids do not contain any double bonds or other functional groups along the chain. The term "saturated" refers to hydrogen, in that all carbons (apart from the carboxylic acid [—COOH] group) contain as many hydrogens as possible. In other words, the omega ($\omega$) end contains 3 hydrogens ($CH_3$—) and each carbon within the chain contains 2 hydrogens (—$CH_2$—). Unsaturated fatty acids are of similar form to saturated fatty acids, except that one or more alkene functional groups exist along the chain, with each alkene substituting a singly-bonded "—$CH_2$—$CH_2$—" part of the chain with a doubly-bonded "—CH=CH—" portion (that is, a carbon double bonded to another carbon). The two next carbon atoms in the chain that are bound to either side of the double bond can occur in a cis or trans configuration.

As used herein, a fatty acid with a "medium chain length", also referred to as "MCFA", comprises an acyl chain of 6 to 14 carbons. The acyl chain may be modified (for example it may comprise one or more double bonds, a hydroxyl group, an epoxy group, etc) or preferably is a saturated MCFA. This terms at least includes one or more or all of caproic acid (C6:0), caprylic acid (C8:0), capric acid (C10:0), lauric acid (C12:0), and myristic acid (C14:0). In an embodiment, the medium chain length fatty acids are lauric acid and/or myristic acid, or capric, lauric and myristic.

As used herein, "new medium chain fatty acids" or "new medium chain fatty acid content" or the like refers to the difference between the total MCFA content of the extracted lipid, oil, recombinant cell, plant or plant part, or seed, of the invention as the context determines, expressed as a percentage of the total fatty acid content, and the total MCFA content of a corresponding wild-type extracted lipid, oil, recombinant cell, plant or plant part, or seed, obtained from a wild-type plant. That is, the new MCFA refers to the increased MCFA of the product of the invention relative to the corresponding wild-type product. These new medium chain fatty acids are the fatty acids that are produced in the cells, plants and plant parts, or seeds, of the invention by the expression of the genetic constructs (exogenous polynucleotides) introduced into the cells, and include (if present) lauric acid and/or myristic acid. Exemplary total medium chain fatty acid contents and new medium chain fatty acid contents are determined by conversion of fatty acids in a sample to FAME and analysis by GC, as described in Example 1.

As used herein, "new medium chain fatty acids in the total fatty acid content of the TAG of the extracted lipid" or the like refers to the difference of the total MCFA content esterified in the form of triacylglycerols in the extracted lipid, oil, recombinant cell, plant or plant part, or seed, as the context determines, expressed as a percentage of the total fatty acid content esterified in TAG, and the total MCFA content esterified in the form of triacylglycerols in a corresponding wild-type extracted lipid, oil, recombinant cell, plant or plant part, or seed, obtained from a wild-type plant.

As used herein, the terms "monounsaturated fatty acid" or "MUFA" refer to a fatty acid which comprises at least 12 carbon atoms in its carbon chain and only one alkene group (carbon-carbon double bond), which may be in an esterified or non-esterified (free) form. As used herein, the terms "polyunsaturated fatty acid" or "PUFA" refer to a fatty acid which comprises at least 12 carbon atoms in its carbon chain and at least two alkene groups (carbon-carbon double bonds), which may be in an esterified or non-esterified form.

"Monoacylglyceride" or "MAG" is glyceride in which the glycerol is esterified with one fatty acid. As used herein, MAG comprises a hydroxyl group at an sn-⅓ (also referred to herein as sn-1 MAG or 1-MAG or ⅓-MAG) or sn-2 position (also referred to herein as 2-MAG), and therefore MAG does not include phosphorylated molecules such as PA or PC. MAG is thus a component of neutral lipids in a plant or part thereof.

"Diacylglyceride" or "DAG" is glyceride in which the glycerol is esterified with two fatty acids which may be the same or, preferably, different. As used herein, DAG comprises a hydroxyl group at a sn-1,3 or sn-2 position, and therefore DAG does not include phosphorylated molecules such as PA or PC. DAG is thus a component of neutral lipids in a plant or part thereof. In the Kennedy pathway of DAG synthesis (FIG. 1), the precursor sn-glycerol-3-phosphate (G3P) is esterified to two acyl groups, each coming from a fatty acid coenzyme A ester, in a first reaction catalysed by a glycerol-3-phosphate acyltransferase (GPAT) at position sn-1 to form LysoPA, followed by a second acylation at position sn-2 catalysed by a lysophosphatidic acid acyltransferase (LPAAT) to form phosphatidic acid (PA). This intermediate is then de-phosphorylated by PAP to form DAG. DAG may also be formed from TAG by removal of an acyl group by a lipase, or from PC essentially by removal of a choline headgroup by any of the enzymes PDCT, PLC or PLD (FIG. 1).

"Triacylglyceride" or "TAG" is a glyceride in which the glycerol is esterified with three fatty acids which may be the same (e.g. as in tri-olein) or, more commonly, different. In the Kennedy pathway of TAG synthesis, DAG is formed as described above, and then a third acyl group is esterified to the glycerol backbone by the activity of DGAT. Alternative pathways for formation of TAG include one catalysed by the enzyme PDAT (FIG. 1) and the MGAT pathway described herein.

As used herein, the term "wild-type" or variations thereof refers to a cell, plant or part thereof such as a cell, vegetative plant part, seed, tuber or beet, that has not been genetically modified, such as cells, plants or parts thereof that do not comprise the one or more exogenous polynucleotides, according to this invention.

The term "corresponding" refers to a cell, plant or part thereof such as a cell, vegetative plant part, seed, tuber or beet, that has the same or similar genetic background as a cell, plant or part thereof such as a vegetative plant part, seed, tuber or beet of the invention but which has not been modified as described herein (for example, a vegetative plant part or seed which lacks the defined exogenous polynucleotide(s)). In a preferred embodiment, the corresponding plant or part thereof such as a vegetative plant part is at the same developmental stage as the plant or part thereof such as a vegetative plant part of the invention. For example, if the plant is a flowering plant, then preferably the corresponding plant is also flowering. A corresponding cell, plant or part thereof such as a vegetative plant part, can be used as a control to compare levels of nucleic acid or protein expression, or the extent and nature of trait modification, for example MCFA and/or TAG content, with the cell, plant or part thereof such as a vegetative plant part of the invention which is modified as described herein. A person skilled in the art is readily able to determine an appropriate "corresponding" cell, plant or part thereof such as a vegetative plant part for such a comparison.

As used herein, "compared with" or "relative to" refers to comparing levels of, for example, MCFA or triacylglycerol (TAG) content, one or more or all of soluble protein content, nitrogen content, carbon:nitrogen ratio, photosynthetic gene expression, photosynthetic capacity, total dietary fibre (TDF) content, carbon content, and energy content, or non-polar lipid content or composition, total non-polar lipid content, total fatty acid content or other parameter of the cell, plant or part thereof comprising the one or more exogenous polynucleotides, genetic modifications or exogenous polypeptides with a cell, plant or part thereof such as a vegetative plant part lacking the one or more exogenous polynucleotides, genetic modifications or polypeptides.

As used herein, "synergism", "synergistic", "acting synergistically" and related terms are each a comparative term that means that the effect of a combination of elements present in a plant or part thereof of the invention, for example a combination of elements A and B, is greater than the sum of the effects of the elements separately in corresponding plants or parts thereof, for example the sum of the effect of A and the effect of B. Where more than two elements are present in the plant or part thereof, for example elements A, B and C, it means that the effect of the combination of all of the elements is greater than the sum of the effects of the individual effects of the elements. In a preferred embodiment, it means that the effect of the combination of elements A, B and C is greater than the sum of the effect of elements A and B combined and the effect of element C. In such a case, it can be said that element C acts synergistically with elements A and B. As would be understood, the effects are measured in corresponding cells, plants or parts thereof, for example grown under the same conditions and at the same stage of biological development.

As used herein, "germinate at a rate substantially the same as for a corresponding wild-type plant" or similar phrases refers to seed of a plant of the invention being relatively able to germinate when compared to seed of a wild-type plant lacking the defined exogenous polynucleotide(s) and genetic modifications. Germination may be measured in vitro on tissue culture medium or in soil as occurs in the field. In one embodiment, the number of seeds which germinate, for instance when grown under optimal greenhouse conditions for the plant species, is at least 75%, more preferably at least 90%, when compared to corresponding wild-type seed. In another embodiment, the seeds which germinate, for instance when grown under optimal glasshouse conditions for the plant species, produce seedlings which grow at a rate which, on average, is at least 75%, more preferably at least 90%, when compared to corresponding wild-type plants. This is referred to as "seedling vigour". In an embodiment, the rate of initial root growth and shoot growth of seedlings of the invention is essentially the same compared to a corresponding wild-type seedling grown under the same conditions. In an embodiment, the leaf biomass (dry weight) of the plants of the invention is at least 80%, preferably at least 90%, of the leaf biomass relative to a corresponding wild-type plant grown under the same conditions, preferably in the field. In an embodiment, the height of the plants of the invention is at least 70%, preferably at least 80%, more preferably at least 90%, of the plant height relative to a corresponding wild-type plant grown under the same conditions, preferably in the field and preferably at maturity.

As used herein, the term "an exogenous polynucleotide which down-regulates the production and/or activity of an endogenous polypeptide" or variations thereof, refers to a polynucleotide that encodes an RNA molecule, herein termed a "silencing RNA molecule" or variations thereof (for example, encoding an amiRNA or hpRNAi), that down-regulates the production and/or activity, or itself down-regulates the production and/or activity (for example, is an amiRNA or hpRNA which can be delivered directly to, for example, the plant or part thereof) of an endogenous polypeptide. This includes where the initial RNA transcript produced by expression of the exogenous polynucleotide is processed in the cell to form the actual silencing RNA molecule. The endogenous polypeptides whose production or activity are downregulated include, for example, SDP1 TAG lipase, plastidial GPAT, plastidial LPAAT, TGD polypeptide such as TGD5, TST such as TST1 or TST2, AGPase, PDCT, CPT or Δ12 fatty acid desturase (FAD2), or a combination of two or more thereof. Typically, the RNA molecule decreases the expression of an endogenous gene encoding the polypeptide. The extent of down-regulation is typically less than 100%, for example the production or activity is reduced by between 25% and 95% relative to the wild-type. The optimal level of remaining production or activity can be routinely determined.

As used herein, the term "on a weight basis" refers to the weight of a substance (for example, TAG, DAG, fatty acid, protein, nitrogen, carbon) as a percentage of the weight of the composition comprising the substance (for example, seed, leaf dry weight). For example, if a transgenic seed has 25 μg total fatty acid per 120 μg seed weight; the percentage of total fatty acid on a weight basis is 20.8%.

As used herein, the term "on a relative basis" refers to a parameter such as the amount of a substance in a composition comprising the substance in comparison with the parameter for a corresponding composition, as a percentage. For example, a reduction from 3 units to 2 units is a reduction of 33% on a relative basis.

As used herein, "plastids" are organelles in plants, including algae, which are the site of manufacture of carbon-based compounds from photosynthesis including sugars, starch and fatty acids. Plastids include chloroplasts which contain chlorophyll and carry out photosynthesis, etioplasts which are the predecessors of chloroplasts, as well as specialised plastids such as chromoplasts which are coloured plastids for synthesis and storage of pigments, gerontoplasts which control the dismantling of the photosynthetic apparatus during senescence, amyloplasts for starch synthesis and storage, elaioplasts for storage of lipids, and proteinoplasts for storing and modifying proteins.

As used herein, the term "biofuel" refers to any type of fuel, typically as used to power machinery such as automobiles, planes, boats, trucks or petroleum powered motors, whose energy is derived from biological carbon fixation. Biofuels include fuels derived from biomass conversion, as well as solid biomass, liquid fuels and biogases. Examples of biofuels include bioalcohols, biodiesel, synthetic diesel, vegetable oil, bioethers, biogas, syngas, solid biofuels, algae-derived fuel, biohydrogen, biomethanol, 2,5-Dimethylfuran (DMF), biodimethyl ether (bioDME), Fischer-Tropsch diesel, biohydrogen diesel, mixed alcohols and wood diesel.

As used herein, the term "bioalcohol" refers to biologically produced alcohols, for example, ethanol, propanol and butanol. Bioalcohols are produced by the action of microorganisms and/or enzymes through the fermentation of sugars, hemicellulose or cellulose.

As used herein, the term "biodiesel" refers to a composition comprising fatty acid methyl- or ethyl-esters derived from lipids by transesterification, the lipids being from living cells not fossil fuels.

As used herein, the term "synthetic diesel" refers to a form of diesel fuel which is derived from renewable feedstock rather than the fossil feedstock used in most diesel fuels.

As used herein, the term "vegetable oil" includes a pure plant oil (or straight vegetable oil) or a waste vegetable oil (by product of other industries), including oil produced in either a vegetative plant part or in seed. Vegetable oil includes vegetative oil and seedoil, as defined herein.

As used herein, the term "biogas" refers to methane or a flammable mixture of methane and other gases produced by anaerobic digestion of organic material by anaerobes.

As used herein, the term "syngas" refers to a gas mixture that contains varying amounts of carbon monoxide and hydrogen and possibly other hydrocarbons, produced by partial combustion of biomass. Syngas may be converted into methanol in the presence of catalyst (usually copper-based), with subsequent methanol dehydration in the presence of a different catalyst (for example, silica-alumina).

As used herein, the term "biochar" refers to charcoal made from biomass, for example, by pyrolysis of the biomass.

As used herein, the term "feedstock" refers to a material, for example, biomass or a conversion product thereof (for example, syngas) when used to produce a product, for example, a biofuel such as biodiesel or a synthetic diesel.

As used herein, the term "industrial product" refers to a hydrocarbon product which is predominantly made of carbon and hydrogen such as, for example, fatty acid methyl- and/or ethyl-esters or alkanes such as methane, mixtures of longer chain alkanes which are typically liquids at ambient temperatures, a biofuel, carbon monoxide and/or hydrogen, or a bioalcohol such as ethanol, propanol, or butanol, or biochar. The term "industrial product" is intended to include intermediary products that can be converted to other industrial products, for example, syngas is itself considered to be an industrial product which can be used to synthesize a hydrocarbon product which is also considered to be an industrial product. The term industrial product as used herein includes both pure forms of the above compounds, or more commonly a mixture of various compounds and components, for example the hydrocarbon product may contain a range of carbon chain lengths, as well understood in the art.

As used herein, "progeny" means the immediate and all subsequent generations of offspring produced from a parent, for example a second, third or later generation offspring.

As used herein, the term "ancestor" refers to any earlier generation of the plant comprising the first and second exogenous polynucleotides. The ancestor may be the parent plant, grandparent plant, great grandparent plant and so on.

As used herein, the term "selecting a plant" means actively selecting the plant on the basis that it has the desired phenotype, such as increased MCFA when compared to the corresponding wild-type plant.

As used herein, phrases such as "comprise a TFA content of about 5% (w/w dry weight)", or "comprise a total TAG content of about 6% (w/w dry weight)", or similarly structured phrases, mean that more than the defined level may be present. For instance, the phrase "comprise a TFA content of about 5% (w/w dry weight)" can be used interchangeably with "comprises at least about 5% TFA (w/w dry weight)". Extending this example further, a vegetative plant part which comprise a TFA content of about 5% (w/w dry weight) may have a 6%, or 7.5% or higher TFA content.

As used herein, unless the context indicates otherwise, the term "increased content" when used in reference to a polypeptide, or similar phrases including reference to specific polypeptide, refers to either an exogenous polypeptide or an endogenous polypeptide. For example, a vegetative plant part of the invention may comprise an increased content of a WRI1 polypeptide, am increased GPAT9 content, an increased LPAAT content, an increased content of a DGAT polypeptide, and a decreased content of a SDP1 polypeptide, each relative to a corresponding wild-type vegetative plant part, wherein each of the WRI1 and DGAT polypeptides is independently either an exogenous polypeptide or an endogenous polypeptide. As another example, a vegetative plant part of the invention may comprise an increased content of a WRI1 polypeptide, an increased content of a DGAT polypeptide, and an increased content of a LEC2 polypeptide, each relative to a corresponding wild-type vegetative plant part, wherein each of the WRI1, DGAT and LEC2 polypeptides is independently either an exogenous polypeptide or an endogenous polypeptide. As a further example, a vegetative plant part of the invention may comprise an increased content of a PDAT or DGAT polypeptide, a decreased content of a TGD polypeptide, and a decreased content of a SDP1 polypeptide, each relative to a corresponding wild-type vegetative plant part wherein the PDAT or DGAT is either an exogenous polypeptide or an endogenous polypeptide, and so on. An exogenous polypeptide may be the result of expression of a transgene encoding the polypeptide in the cell or plant or part thereof of the invention. The endogenous polypeptide may be the result of increased expression of an endogenous gene, such as inducing overexpression and/or providing increased levels of a transcription factor(s) for the gene.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, more preferably +/−5%, more preferably +/−2%, more preferably +/−1%, even more preferably +/−0.5%, of the designated value.

Production of Plants with Modified Traits

The present invention is based on the finding that plant traits, such as MFCA content and TAG content, in plants or parts thereof can be increased by a combination of two or more modifications selected from those designated herein as: (A). Push, (B). Pull, (C). Protect, (D). Package, (E). Plastidial Export, (F). Plastidial Import and (G). Prokaryotic Pathway.

Plants or parts thereof such as a vegetative plant parts of the invention therefore have a number of combinations of exogenous polynucleotides and/or genetic modifications each of which provide for one of the modifications. These exogenous polynucleotides and/or genetic modifications include:

(A) an exogenous polynucleotide which encodes a transcription factor polypeptide that increases the expression of one or more glycolytic and/or fatty acid biosynthetic genes in the plant or part thereof such as a vegetative plant part, providing the "Push" modification, (B) an exogenous polynucleotide which encodes a polypeptide involved in the biosynthesis of one or more non-polar lipids in the plant or part thereof such as a vegetative plant part, providing the "Pull" modification, (C) a genetic modification which down-regulates endogenous production and/or activity of a polypeptide involved in the catabolism of triacylglycerols (TAG) in the plant or part thereof such as a vegetative plant part when compared to a corresponding plant or part thereof such as a vegetative plant part lacking the genetic modification, providing the "Protect" modification, (D) an exogenous polynucleotide which encodes an oil body coating (OBC) polypeptide such as a lipid droplet associated polypeptide (LDAP), providing the "Package" modification, (E) an exogenous polynucleotide which encodes a polypeptide which increases the export of fatty acids out of plastids of the plant or part thereof such as a vegetative plant part, when compared to a corresponding plant or part thereof such as a vegetative plant part lacking the exogenous polynucleotide, providing the "Plastidial Export" modification, (F) a genetic modification which down-regulates endogenous production and/or activity of a polypeptide involved in importing fatty acids into plastids of the plant or part thereof such as a vegetative plant part when compared to a corresponding plant or part thereof such as a vegetative plant part lacking the genetic modification, providing the "Plastidial Import" modification, and G) a genetic modification which down-regulates endogenous production and/or activity of a polypeptide involved in diacylglycerol (DAG) production in the plastid of the plant or part thereof such as a vegetative plant part when compared to a corresponding plant or part thereof such as a vegetative plant part lacking the genetic modification, providing the "prokaryotic Pathway" modification.

Preferred combinations (also referred to herein as sets) of exogenous polynucleotides and/or genetic modifications of the invention are;

1) A, B and optionally one of C, D, E, F or G;
2) A, C and optionally one of D, E, F or G;
3) A, D and optionally one of E, F or G;
4) A, E and optionally F or G;
5) A, F and optionally G;
6) A and G;
7) A, B, C and optionally one of D, E, F or G;
8) A, B, D and optionally one of E, F or G;
9) A, B, E and optionally F or G;
10) A, B, F and optionally G;

11) A, B, C, D and optionally one of E, F or G;
12) A, B, C, E and optionally F or G;
13) A, B, C, F and optionally G;
14) A, B, D, E and optionally F or G;
15) A, B, D, F and optionally G;
16) A, B, E, F and optionally G;
17) A, C, D and optionally one of E, F or G;
18) A, C, E and optionally F or G;
19) A, C, F and optionally G;
20) A, C, D, E and optionally F or G;
21) A, C, D, F and optionally G;
22) A, C, E, F and optionally a fifth modification G;
23) A, D, E and optionally F or G;
24) A, D, F and optionally G;
25) A, D, E, F and optionally G;
26) A, E, F and optionally G;
27) Six of A, B, C, D, E, F and G omitting one of A, B, C, D, E, F or G, and
28) Any one of 1-26 above where there are two or more exogenous polynucleotides encoding two or more different transcription factor polypeptides that increases the expression of one or more glycolytic and/or fatty acid biosynthetic genes in the plant or part thereof, for example one exogenous polynucleotide encoding WRI1 and another exogenous polynucleotide encoding LEC2.

In each of the above preferred combinations there may be at least two different exogenous polynucleotides which encode at least two different transcription factor polypeptides that increases the expression of one or more glycolytic and/or fatty acid biosynthetic genes in the plant or part thereof such as a vegetative plant part.

These modifications are described more fully as follows:

A. The "Push" modification is characterised by an increased synthesis of total fatty acids in the plastids of the plant or part thereof. In an embodiment, this occurs by the increased expression and/or activity of a transcription factor which regulates fatty acid synthesis in the plastids. In one embodiment, this can be achieved by expressing in a transgenic plant or part thereof an exogenous polynucleotide which encodes a transcription factor polypeptide that increases the expression of one or more glycolytic and/or fatty acid biosynthetic genes in the plant or part thereof. In an embodiment, the increased fatty acid synthesis is not caused by the provision to the plant or part thereof of an altered ACCase whose activity is less inhibited by fatty acids, relative to the endogenous ACCase in the plant or part thereof. In an embodiment, the plant or part thereof comprises an exogenous polynucleotide which encodes the transcription factor, preferably under the control of a promoter other than a constitutive promoter. The transcription factor may be selected from the group consisting of WRI1, LEC1, LEC1-like, LEC2, BBM, FUS3, ABI3, ABI4, ABI5, Dof4, Dof11 or the group consisting of MYB73, bZIP53, AGL15, MYB115, MYB118, TANMEI, WUS, GFR2a1, GFR2a2 and PHR1, and is preferably WRI1, LEC1 or LEC2, or WRI1 alone. In a further embodiment, the increased synthesis of total fatty acids is relative to a corresponding wild-type plant or part thereof. In an embodiment, there are two or more exogenous polynucleotides encoding two or more different transcription factor polypeptides. The "Push" modification may also be achieved by increased expression of polypeptides which modulate activity of WRI1, such as MED15 or 14-3-3 polypeptides.

B. The "Pull" modification is characterised by increased expression and/or activity in the plant or part thereof of a fatty acyl acyltransferase which catalyses the synthesis of TAG, DAG or MAG in the plant or part thereof, such as a DGAT, PDAT, LPAAT, GPAT or MGAT, preferably a DGAT or a PDAT. In one embodiment, this can be achieved by expressing in a transgenic plant or part thereof an exogenous polynucleotide which encodes a polypeptide involved in the biosynthesis of one or more non-polar lipids. In an embodiment, the acyltransferase is a membrane-bound acyltransferase that uses an acyl-CoA substrate as the acyl donor in the case of DGAT, LPAAT, GPAT or MGAT, or an acyl group from PC as the acyl donor in the case of PDAT. The Pull modification can be relative to a corresponding wild-type plant or part thereof or, preferably, relative to a corresponding plant or part thereof which has the Push modification. In an embodiment, the plant or part thereof comprises an exogenous polynucleotide which encodes the fatty acyl acyltransferase. The "Pull" modification can also be achieved by increased expression of a PDCT, CPT or phospholipase C or D polypeptide which increases the production of DAG from PC.

In a preferred embodiment, the cell comprises an exogenous polynucleotide(s) encoding one or more or all of a GPAT, LPAAT and/or DGAT which have a preference for utilising medium chain fatty acid substrates, particularly for lauric acid and/or myristic acid. Such GPAT, LPAAT and/or DGAT having a preference for utilising medium chain fatty acid substrates include those described herein, as well as those which can be isolated from plants which naturally produce high levels of medium chain fatty acids, such as but not limited to, *Elaeis guineensis, Cocus nucifera, Attalea dubia, Orbignya phalerata, Astrocaryum murumuru, Bactris gasipaes, Pycnanthus angolensis, Cuphea wrightii, Attalea colenda, Laurus nobilis, Umbellularia californica, Qualea grandiflora* and *Actinodaphne hookeri*. The skilled person would appreciate that the sequences provided herein which readily be used to screen sequence databases to identify orthologous genes and proteins from the above species.

C. The "Protect" modification is characterised by a reduction in the catabolism of triacylglycerols (TAG) in the plant or part thereof. In an embodiment, this can be achieved through a genetic modification in the plant or part thereof which down-regulates endogenous production and/or activity of a polypeptide involved in the catabolism of triacylglycerols (TAG) in the plant or part thereof when compared to a corresponding plant or part thereof lacking the genetic modification. In an embodiment, the plant or part thereof has a reduced expression and/or activity of an endogenous TAG lipase in the plant or part thereof, preferably an SDP1 lipase, a Cgi58 polypeptide, an acyl-CoA oxidase such as the ACX1 or ACX2, or a polypeptide involved in β-oxidation of fatty acids in the plant or part thereof such as a PXA1 peroxisomal ATP-binding cassette transporter. This may occur by expression in the plant or part thereof of an exogenous polynucleotide which encodes an RNA molecule which reduces the expression of, for example, an endogenous gene encoding the TAG lipase such as the SDP1 lipase, acyl-CoA oxidase or the polypeptide involved in β-oxidation of fatty acids in the plant or part thereof, or by a mutation in an endogenous gene encoding, for example, the TAG lipase, acyl-CoA oxidase or polypeptide involved in β-oxidation of fatty acids. In an embodiment, the reduced expression and/or activity is relative to a corresponding wild-type plant or part thereof or relative to a corresponding plant or part thereof which has the Push modification.

D. The "Package" modification is characterised by an increased expression and/or accumulation of an oil body coating (OBC) polypeptide. In an embodiment, this can be achieved by expressing in a transgenic plant or part thereof an exogenous polynucleotide which encodes an oil body coating (OBC) polypeptide. The OBC polypeptide may be an oleosin, such as for example a polyoleosin, a caoleosin or a steroleosin, or preferably an LDAP. In an embodiment, the level of oleosin that is accumulated in the plant or part thereof is at least 2-fold higher relative to the corresponding plant or part thereof comprising the oleosin gene from the T-DNA of pJP3502. In an embodiment, the increased expression or accumulation of the OBC polypeptide is not caused solely by the Push modification. In an embodiment, the expression and/or accumulation is relative to a corresponding wild-type plant or part thereof or, preferably, relative to a corresponding plant or part thereof which has the Push modification.

E. The "Plastidial Export" modification is characterised by an increased rate of export of total fatty acids out of the plastids of the plant or part thereof. In one embodiment, this can be achieved by expressing in a plant or part thereof an exogenous polynucleotide which encodes a polypeptide which increases the export of fatty acids out of plastids of the plant or part thereof when compared to a corresponding plant or part thereof lacking the exogenous polynucleotide. In an embodiment, this occurs by the increased expression and/or activity of a fatty acid thioesterase (TE), a fatty acid transporter polypeptide such as an ABCA9 polypeptide, or a long-chain acyl-CoA synthetase (LACS). In an embodiment, the plant or part thereof comprises an exogenous polynucleotide which encodes the TE, fatty acid transporter polypeptide or LACS. The TE may be a FATB polypeptide or preferably a FATA polypeptide. In an embodiment, the TE is preferably a TE which has a preference for hydrolysing MCFA, or MCFA and C16:0 substrates. In an embodiment, the Plastidial Export modification is relative to a corresponding wild-type plant or part thereof or, preferably, relative to a corresponding plant or part thereof which has the Push modification.

F. The "Plastidial Import" modification is characterised by a reduced rate of import of fatty acids into the plastids of the plant or part thereof from outside of the plastids. In an embodiment, this can be achieved through a genetic modification in the plant or part thereof which down-regulates endogenous production and/or activity of a polypeptide involved in importing fatty acids into plastids of the plant or part thereof when compared to a corresponding plant or part thereof lacking the genetic modification. For example, this may occur by expression in the plant or part thereof of an exogenous polynucleotide which encodes an RNA molecule which reduces the expression of an endogenous gene encoding an transporter polypeptide such as a TGD polypeptide, for example a TGD1, TGD2, TGD3, TGD4 or preferably a TGD5 polypeptide, or by a mutation in an endogenous gene encoding the TGD polypeptide. In an embodiment, the reduced rate of import is relative to a corresponding wild-type plant or part thereof or relative to a corresponding plant or part thereof which has the Push modification.

G. The "Prokaryotic Pathway" modification is characterised by a decreased amount of DAG or rate of production of DAG in the plastids of the plant or part thereof. In an embodiment, this can be achieved through a genetic modification in the plant or part thereof which down-regulates endogenous production and/or activity of a polypeptide involved in diacylglycerol (DAG) production in the plastid when compared to a corresponding plant or part thereof lacking the genetic modification. In an embodiment, the decreased amount or rate of production of DAG occurs by a decreased production of LPA from acyl-ACP and G3P in the plastids. The decreased amount or rate of production of DAG may occur by expression in the plant or part thereof of an exogenous polynucleotide which encodes an RNA molecule which reduces the expression of an endogenous gene encoding a plastidial GPAT, plastidial LPAAT or a plastidial PAP, preferably a plastidial GPAT, or by a mutation in an endogenous gene encoding the plastidial polypeptide. In an embodiment, the decreased amount or rate of production of DAG is relative to a corresponding wild-type plant or part thereof or, preferably, relative to a corresponding plant or part thereof which has the Push modification.

The Push modification is highly desirable in the invention, and the Pull modification is preferred. The Protect and Package modifications may be complementary i.e. one of the two may be sufficient. The plant or part thereof may comprise one, two or all three of the Plastidial Export, Plastidial Import and Prokaryotic Pathway modifications. In an embodiment, at least one of the exogenous polynucleotides in the plant or part thereof, preferably at least the exogenous polynucleotide encoding the transcription factor which regulates fatty acid synthesis in the plastids, is expressed under the control of (H) a promoter other than a constitutive promoter such as, for example, a developmentally related promoter, a promoter that is preferentially active in photosynthetic cells, a tissue-specific promoter, a promoter which has been modified by reducing its expression level relative to a corresponding native promoter, or is preferably a senesence-specific promoter. More preferably, at least the exogenous polynucleotide encoding the transcription factor which regulates fatty acid synthesis in the plastids is expressed under the control of a promoter other than a constitutive promoter and the exogenous polynucleotide which encodes an RNA molecule which down-regulates endogenous production and/or activity of a polypeptide involved in the catabolism of triacylglycerols is also expressed under the control of a promoter other than a constitutive promoter, which promoters may be the same or different. Alternatively in monocotyledonous plants, the exogenous polynucleotide encoding the transcription factor which regulates fatty acid synthesis in the plastids is expressed under the control of a constitutive promoter such as, for example, a ubiquitin gene promoter or an actin gene promoter.

Plants produce some, but not all, of their membrane lipids such as MGDG in plastids by the so-called prokaryotic pathway (FIG. 1). In plants, there is also a eukaryotic pathway for synthesis of galactolipids and glycerolipids which synthesizes FA first of all in the plastid and then assembles the FA into glycerolipids in the ER. MGDG synthesised by the eukaryotic pathway contains C18:3 (ALA) fatty acid esterified at the sn-2 position of MGDG.

The DAG backbone including the ALA for the MGDG synthesis by this pathway is assembled in the ER and then imported into the plastid. In contrast, the MGDG synthesized by the prokaryotic pathway contains C16:3 fatty acid esterified at the sn-2 position of MGDG. The ratio of the contribution of the prokaryotic pathway relative to the eukaryotic pathway in producing MGDG (16:3) vs MGDG (18:3) is a characteristic and distinctive feature of different plant species (Mongrand et al. 1998). This distinctive fatty acid composition of MGDG allows all higher plants (angiosperms) to be classified as either so-called 16:3 or 18:3 plants. 16:3 species, exemplified by *Arabidopsis* and *Brassica napus*, generally have both of the prokaryotic and eukaryotic pathways of MGDG synthesis operating, whereas the 18:3 species exemplified by *Sorghum bicolor*, *Zea mays*, *Nicotiana tabacum*, *Pisum sativum* and *Glycine max* generally have only (or almost entirely) the eukaryotic pathway of MGDG synthesis, providing little or no C16:3 fatty acid accumulation in the vegetative tissues.

As used herein, a "16:3 plant" or "16:3 species" is one which has more than 2% C16:3 fatty acid in the total fatty acid content of its photosynthetic tissues. As used herein, a "18:3 plant" or "18:3 species" is one which has less than 2% C16:3 fatty acid in the total fatty acid content of its photosynthetic tissues. As described herein, a plant can be converted from being a 16:3 plant to an 18:3 plant by suitable genetic modifications. The proportion of flux between the prokaryote and eukaryote pathways is not conserved across different plant species or tissues. In 16:3 species up to 40% of flux in leaves occurs via the prokaryotic pathway (Browse et al., 1986), while in 18:3 species, such as pea and soybean, about 90% of FAs which are synthesized in the plastid are exported out of the plastid to the ER to supply the source of FA for the eukaryotic pathway (Ohlrogge and Browse, 1995; Somerville et al., 2000).

Therefore different amounts of 18:3 and 16:3 fatty acids are found within the glycolipids of different plant species. This is used to distinguish between 18:3 plants whose fatty acids with 3 double bonds are almost entirely C18 fatty acids and the 16:3 plants that contain both C16- and C18-fatty acids having 3 double bonds. In chloroplasts of 18:3 plants, enzymic activities catalyzing the conversion of phosphatidate to diacylglycerol and of diacylglycerol to monogalactosyl diacylglycerol (MGD) are significantly less active than in 16:3 chloroplasts. In leaves of 18:3 plants, chloroplasts synthesize stearoyl-ACP2 in the stroma, introduce the first double bond into the saturated hydrocarbon chain, and then hydrolyze the thioester by thioesterases (FIG. 1). Released oleate is exported across chloroplast envelopes into membranes of the cell, probably the endoplasmic reticulum, where it is incorporated into PC. PC-linked oleoyl groups are desaturated in these membranes and subsequently move back into the chloroplast. The MGD-linked acyl groups are substrates for the introduction of the third double bond to yield MGD with two linolenoyl residues. This galactolipid is characteristic of 18:3 plants such as Asteraceae and Fabaceae, for example. In photosynthetically active cells of 16:3 plants which are represented, for example, by members of Apiaceae and Brassicaceae, two pathways operate in parallel to provide thylakoids with MGD.

In one embodiment, the plant or part thereof such as a vegetative plant part of the invention produces higher levels of non-polar lipids such as TAG, or MFCA content, preferably both, than a corresponding plant or part thereof such as a vegetative plant part which lacks the genetic modifications or exogenous polynucleotides. In one example, plants of the invention produce seeds, leaves, or have leaf portions of at least 1 $cm^2$ in surface area, stems and/or tubers having an increased non-polar lipid content such as TAG or MCFA content, preferably both, when compared to corresponding seeds, leaves, leaf portions of at least 1 $cm^2$ in surface area, stems or tubers.

Preferably, the plant or part thereof such as a vegetative plant part of the invention is transformed with one or more exogenous polynucleotides such as chimeric DNAs. In the case of multiple chimeric DNAs, these are preferably covalently linked on one DNA molecule such as, for example, a single T-DNA molecule, and preferably integrated at a single locus in the host cell genome, preferably the host nuclear genome. Alternatively, the chimeric DNAs are on two or more DNA molecules which may be unlinked in the host genome, or the DNA molecule(s) is not integrated into the host genome, such as occurs in transient expression experiments. The plant or part thereof such as a vegetative plant part is preferably homozygous for the one DNA molecule inserted into its genome.

Transcription Factors

Various transcription factors are involved in plant cells in the synthesis of fatty acids and lipids incorporating the fatty acids such as TAG, and therefore can be manipulated for the Push modification. A preferred transcription factor is WRI1. As used herein, the term "Wrinkled 1" or "WRI1" or "WRL1" refers to a transcription factor of the AP2/ER-WEBP class which regulates the expression of several enzymes involved in glycolysis and de novo fatty acid biosynthesis. WRI1 has two plant-specific (AP2/EREB) DNA-binding domains. WRI1 in at least *Arabidopsis* also regulates the breakdown of sucrose via glycolysis thereby regulating the supply of precursors for fatty acid biosynthesis. In other words, it controls the carbon flow from the photosynthate to storage lipids. wri1 mutants in at least *Arabidopsis* have a wrinkled seed phenotype, due to a defect in the incorporation of sucrose and glucose into TAGs.

Examples of genes which are transcribed by WRI1 include, but are not limited to, one or more, preferably all, of genes encoding pyruvate kinase (At5 g52920, At3 g22960), pyruvate dehydrogenase (PDH) E1alpha subunit (At1 g01090), acetyl-CoA carboxylase (ACCase), BCCP2 subunit (At5 g15530), enoyl-ACP reductase (At2 g05990; EAR), phosphoglycerate mutase (At1 g22170), cytosolic fructokinase, and cytosolic phosphoglycerate mutase, sucrose synthase (SuSy) (see, for example, Liu et al., 2010; Baud et al., 2007; Ruuska et al., 2002).

WRI1 contains the conserved domain AP2 (cd00018). AP2 is a DNA-binding domain found in transcription regulators in plants such as APETALA2 and EREBP (ethylene responsive element binding protein). In EREBPs the domain specifically binds to the 11 bp GCC box of the ethylene response element (ERE), a promotor element essential for ethylene responsiveness. EREBPs and the C-repeat binding factor CBF1, which is involved in stress response, contain a single copy of the AP2 domain. APETALA2-like proteins, which play a role in plant development contain two copies.

Other sequence motifs which may be found in WRI1 and its functional homologs include:

```
                                        (SEQ ID NO: 14)
    1. R G V T/S R H R W T G R.

(SEQ ID NO: 15)
    2. F/Y E A H L W D K.

(SEQ ID NO: 16)
    3. D L A A L K Y W G.
```

```
                                                    (SEQ ID NO: 17)
4. S X G F S/A R G X.

(SEQ ID NO: 18)
5. H H H/Q N G R/K W E A R I G R/K V.

(SEQ ID NO: 19)
6. Q E E A A A X Y D.
```

As used herein, the term "Wrinkled 1" or "WRI1" also includes "Wrinkled 1-like" or "WRI1-like" proteins. Examples of WRI1 proteins include Accession Nos: A8MS57 (*Arabidopsis thaliana*), Q6X5Y6, (*Arabidopsis thaliana*), XP_002876251.1 (*Arabidopsis lyrata* subsp. *Lyrata*), ABD16282.1 (*Brassica napus*), ADO16346.1 (*Brassica napus*), XP_003530370.1 (*Glycine max*), AEO22131.1 (*Jatropha curcas*), XP_002525305.1 (*Ricinus communis*), XP_002316459.1 (*Populus trichocarpa*), CBI29147.3 (*Vitis vinifera*), XP_003578997.1 (*Brachypodium distachyon*), BAJ86627.1 (*Hordeum vulgare* subsp. *vulgare*), EAY79792.1 (*Oryza sativa*), XP_002450194.1 (*Sorghum bicolor*), ACG32367.1 (*Zea mays*), XP_003561189.1 (*Brachypodium distachyon*), ABL85061.1 (*Brachypodium sylvaticum*), BAD68417.1 (*Oryza sativa*), XP_002437819.1 (*Sorghum bicolor*), XP_002441444.1 (*Sorghum bicolor*), XP_003530686.1 (*Glycine max*), XP_003553203.1 (*Glycine max*), XP_002315794.1 (*Populus trichocarpa*), XP_002270149.1 (*Vitis vinifera*), XP_003533548.1 (*Glycine max*), XP_003551723.1 (*Glycine max*), XP_003621117.1 (*Medicago truncatula*), XP_002323836.1 (*Populus trichocarpa*), XP_002517474.1 (*Ricinus communis*), CAN79925.1 (*Vitis vinifera*), XP_003572236.1 (*Brachypodium distachyon*), BAD10030.1 (*Oryza sativa*), XP_002444429.1 (*Sorghum bicolor*), NP_001170359.1 (*Zea mays*), XP_002889265.1 (*Arabidopsis lyrata* subsp. *lyrata*), AAF68121.1 (*Arabidopsis thaliana*), NP_178088.2 (*Arabidopsis thaliana*), XP_002890145.1 (*Arabidopsis lyrata* subsp. *lyrata*), BAJ33872.1 (*Thellungiella halophila*), NP_563990.1 (*Arabidopsis thaliana*), XP_003530350.1 (*Glycine max*), XP_003578142.1 (*Brachypodium distachyon*), EAZ09147.1 (*Oryza sativa*), XP_002460236.1 (*Sorghum bicolor*), NP_001146338.1 (*Zea mays*), XP_003519167.1 (*Glycine max*), XP_003550676.1 (*Glycine max*), XP_003610261.1 (*Medicago truncatula*), XP_003524030.1 (*Glycine max*), XP_003525949.1 (*Glycine max*), XP_002325111.1 (*Populus trichocarpa*), CBI36586.3 (*Vitis vinifera*), XP_002273046.2 (*Vitis vinifera*), XP_002303866.1 (*Populus trichocarpa*), and CBI25261.3 (*Vitis vinifera*). Further examples include Sorbi-WRL1 (SEQ ID NO:10), Lupan-WRL1 (SEQ ID NO:11), Ricco-WRL1 (SEQ ID NO:12), and *Lupin angustifolius* WRI1 (SEQ ID NO:13). A preferred WRI1 is a maize WRI1 or a sorghum WRI1. In an embodiment, an exogenous polynucleotide of the invention which encodes a WRI1 which comprises one or more of the following:
  i) nucleotides encoding a polypeptide comprising amino acids whose sequence is set forth in any of the above mentioned accessions, or a biologically active fragment thereof, or a polypeptide whose amino acid sequence is at least 30% identical to that set forth in any of the above mentioned accessions,
  ii) nucleotides whose sequence is at least 30% identical to i), and
  iii) a polynucleotide which hybridizes to one or both of i) or ii) under stringent conditions.

More recently, a subset of WRI1-like transcription factors have been re-classified as WRI2, WRI3 or WRI4 transcription factors, which are characterised by preferential expression in stems and/or roots of plants rather than in developing seeds (To et al., 2012). Despite their re-classification, these are included in the definition of "WRI1" herein. Preferred WRI1-like transcription factors are those which can complement the function of a wri1 mutation in a plant, particularly the function in developing seed of the plant such as in an *A. thaliana* wri1 mutant. The function of a WRI1-like polypeptide can also be assayed in the *N. benthamiana* transient assays as described herein.

The WRI1 transcription factor may be endogenous to the plant or cell, or exogenous to the plant or cell, for example expressed from an exogenous polynucleotide. The WRI1 transcription factor may be a naturally occurring WRI1 polypeptide or a variant thereof, provided it retains transcription factor activity. The level or activity of an endogenous WRI1 polypeptide may also be increased by increased expression of a MED15 polypeptide (Kim et al., 2016), for example polypeptides whose amino acid sequences are provided in Accession No: NM_101446.4 or NM_001321633.1, or of a 14-3-3 polypeptide (Ma et al., 2016), for example Accession Nos: AY079350, AY079350, XM_002445734.1, XM_002445734.1, NM 001203346, NM 001203346, XM_002445734.1, or XM_002445734.1. MED15 polypeptide is thought to assist in directing WRI1 to its target promoters and expression of WRI1 expression itself, while 14-3-3 polypeptides are thought to interact with WRI1 polypeptide to increase the WRI1 effect.

As used herein, a "LEAFY COTYLEDON" or "LEC" polypeptide means a transcription factor which is a LEC1, LEC1-like, LEC2, ABI3 or FUS3 transcription factor which exhibits broad control on seed maturation and fatty acid synthesis. LEC2, FUS3 and ABI3 are related polypeptides that each contain a B3 DNA-binding domain of 120 amino acids (Yamasaki et al., 2004) that is only found in plant proteins. They can be distinguished by phylogenetic analysis to determine relatedness in amino acid sequence to the members of the *A. thaliana* polypeptides having the Accession Nos as follows: LEC2, Accession No. AAL12004.1; FUS3 (also known as FUSCA3), Accession No. AAC35247. LEC1 belongs to a different class of polypeptides and is homologous to a HAP3 polypeptide of the CBF binding factor class (Lee et al., 2003). The LEC1, LEC2 and FUS3 genes are required in early embryogenesis to maintain embryonic cell fate and to specify cotyledon identity and in later in initiation and maintenance of embryo maturation (Santos-Mendoza et al., 2008). They also induce expression of genes encoding seed storage proteins by binding to RY motifs present in the promoters, and oleosin genes. They can also be distinguished by their expression patterns in seed development or by their ability to complement the corresponding mutation in *A. thaliana*.

As used herein, the term "Leafy Cotyledon 1" or "LEC1" refers to a NF-YB-type transcription factor which participates in zygotic development and in somatic embryogenesis. The endogenous gene is expressed specifically in seed in both the embryo and endosperm. LEC1 activates the gene encoding WRI1 as well as a large class of fatty acid synthesis genes. Ectopic expression of LEC2 also causes rapid activation of auxin-responsive genes and may cause formation of somatic embryos. Examples of LEC1 polypeptides include proteins from *Arabidopsis thaliana* (AAC39488, SEQ ID NO:31), *Medicago truncatula* (AFK49653) and *Brassica napus* (ADF81045), *A. lyrata* (XP_002862657), *R. communis* (XP_002522740), *G. max*

(XP_006582823), *A. hypogaea* (ADC33213), *Z. mays* (AAK95562, SEQ ID NO:32). In an embodiment, an exogenous polynucleotide of the invention which encodes a LEC1 which comprises one or more of the following:
i) nucleotides encoding a polypeptide comprising amino acids whose sequence is set forth in any of the above mentioned accessions, or a biologically active fragment thereof, or a polypeptide whose amino acid sequence is at least 30% identical to that set forth in any of the above mentioned accessions,
ii) nucleotides whose sequence is at least 30% identical to i), and
iii) a polynucleotide which hybridizes to one or both of i) or ii) under stringent conditions.

LEC1-like (L1L) is closely related to LEC1 but has a different pattern of gene expression, being expressed earlier during embryogenesis (Kwong et al., 2003). Examples of LEC1-like polypeptides include proteins from *Arabidopsis thaliana* (AAN15924, SEQ ID NO:33), *Brassica napus* (AHI94922), and *Phaseolus coccineus* LEC1-like (AAN01148).

As used herein, the term "Leafy Cotyledon 2" or "LEC2" refers to a B3 domain transcription factor which participates in zygotic development and in somatic embryogenesis and which activates expression of a gene encoding WRI1. Its ectopic expression facilitates the embryogenesis from vegetative plant tissues (Alemanno et al., 2008). Examples of LEC2 polypeptides include proteins from *Arabidopsis thaliana* (Accession No. NP_564304.1), *Medicago truncatula* (Accession No. CAA42938.1) and *Brassica napus* (Accession No. ADO16343.1). In an embodiment, an exogenous polynucleotide of the invention which encodes a LEC2 which comprises one or more of the following:
i) nucleotides encoding a polypeptide comprising amino acids whose sequence is set forth in any of the above mentioned accessions, or a biologically active fragment thereof, or a polypeptide whose amino acid sequence is at least 30% identical to that set forth in any of the above mentioned accessions,
ii) nucleotides whose sequence is at least 30% identical to i), and
iii) a polynucleotide which hybridizes to one or both of i) or ii) under stringent conditions.

As used herein, the term "FUS3" refers to a B3 domain transcription factor which participates in zygotic development and in somatic embryogenesis and is detected mainly in the protodermal tissue of the embryo (Gazzarrini et al., 2004). Examples of FUS3 polypeptides include proteins from *Arabidopsis thaliana* (AAC35247, SEQ ID NO:34), *Brassica napus* (XP_006293066.1, SEQ ID NO:35) and *Medicago truncatula* (XP_003624470, SEQ ID NO:36). Over-expression of any of LEC1, L1L, LEC2, FUS3 and ABI3 from an exogenous polynucleotide is preferably controlled by a developmentally regulated promoter such as a senescence specific promoter, an inducible promoter, or a promoter which has been engineered for providing a reduced level of expression relative to a native promoter, particularly in plants other than *Arabidopsis thaliana* and *B. napus* cv. Westar, in order to avoid developmental abnormalities in plant development that are commonly associated with over-expression of these transcription factors (Mu et al., 2008). In an embodiment, an exogenous polynucleotide of the invention which encodes a FUS3 which comprises one or more of the following:
i) nucleotides encoding a polypeptide comprising amino acids whose sequence is set forth in any of the above mentioned accessions, or a biologically active fragment thereof, or a polypeptide whose amino acid sequence is at least 30% identical to that set forth in any of the above mentioned accessions,
ii) nucleotides whose sequence is at least 30% identical to i), and
iii) a polynucleotide which hybridizes to one or both of i) or ii) under stringent conditions.

As used herein, the term "BABY BOOM" or "BBM" refers an AP2/ERF transcription factor that induces regeneration under culture conditions that normally do not support regeneration in wild-type plants. Ectopic expression of *Brassica napus* BBM (BnBBM) genes in *B. napus* and *Arabidopsis* induces spontaneous somatic embryogenesis and organogenesis from seedlings grown on hormone-free basal medium (Boutilier et al., 2002). In tobacco, ectopic BBM expression is sufficient to induce adventitious shoot and root regeneration on basal medium, but exogenous cytokinin is required for somatic embryo (SE) formation (Srinivasan et al., 2007). Examples of BBM polypeptides include proteins from *Arabidopsis thaliana* (Accession No. NP_197245.2, SEQ ID NO:28), maize (U.S. Pat. No. 7,579, 529), *Sorghum bicolor* (Accession No. XP_002458927) and *Medicago truncatula* (Accession No. AAW82334.1). In an embodiment, an exogenous polynucleotide of the invention which encodes a BBM which comprises one or more of the following:
i) nucleotides encoding a polypeptide comprising amino acids whose sequence is set forth in any of the above mentioned accessions, or a biologically active fragment thereof, or a polypeptide whose amino acid sequence is at least 30% identical to that set forth in any of the above mentioned accessions,
ii) nucleotides whose sequence is at least 30% identical to i), and
iii) a polynucleotide which hybridizes to one or both of i) or ii) under stringent conditions.

An ABI3 polypeptide (*A. thaliana* Accession No. NP_189108) is related to the maize VP1 protein, is expressed at low levels in vegetative tissues and affects plastid development. An ABI4 polypeptide (*A. thaliana* Accession NP_181551) belongs to a family of transcription factors that contain a plant-specific AP2 domain (Finkelstein et al., 1998) and acts downstream of ABI3. ABI5 (*A. thaliana* Accession No. NP_565840) is a transcription factor of the bZIP family which affects ABA sensitivity and controls the expression of some LEA genes in seeds. It binds to an ABA-responsive element.

Each of the following transcription factors was selected on the basis that they functioned in embryogenesis in plants. Accession numbers are provided in Table 8. Homologs of each can be readily identified in many other plant species and tested as described in Example 4.

MYB73 is a transcription factor that has been identified in soybean, involved in stress responses.

bZIP53 is a transcription factor in the bZIP protein family, identified in *Arabidopsis*.

AGL15 (Agamous-like 15) is a MADS box transcription factor which is natively expressed during embryogenesis. AGL15 is also natively expressed in leaf primordia, shoot apical meristems and young floral buds, suggesting that AGL15 may also have a function during post-germinative development. AGL15 has a role in embryogenesis and gibberellic acid catabolism. It targets B3 domain transcription factors that are key regulators of embryogenesis.

MYB115 and MYB118 are transcription factors in the MYB family from *Arabidopsis* involved in embryo genesis.

TANMEI also known as EMB2757 encodes a WD repeat protein required for embryo development in *Arabidopsis*.

WUS, also known as Wuschel, is a homeobox gene that controls the stem cell pool in embryos. It is expressed in the stem cell organizing center of meristems and is required to keep the stem cells in an undifferentiated state. The transcription factor binds to a TAAT element core motif.

GFR2a1 and GFR2a2 are transcription factors at least from soybean.

Fatty Acyl Acyltransferases

As used herein, the term "fatty acyl acyltransferase" refers to a protein which is capable of transferring an acyl group from acyl-CoA, PC or acyl-ACP, preferably acyl-CoA or PC, onto a substrate to form TAG, DAG or MAG. These acyltransferases include DGAT, PDAT, MGAT, GPAT and LPAAT.

As used herein, the term "diacylglycerol acyltransferase" (DGAT) refers to a protein which transfers a fatty acyl group from acyl-CoA to a DAG substrate to produce TAG. Thus, the term "diacylglycerol acyltransferase activity" refers to the transfer of an acyl group from acyl-CoA to DAG to produce TAG. A DGAT may also have MGAT function but predominantly functions as a DGAT, i.e., it has greater catalytic activity as a DGAT than as a MGAT when the enzyme activity is expressed in units of nmoles product/min/mg protein (see for example, Yen et al., 2005). The activity of DGAT may be rate-limiting in TAG synthesis in seeds (Ichihara et al., 1988). DGAT uses an acyl-CoA substrate as the acyl donor and transfers it to the sn-3 position of DAG to form TAG. The enzyme functions in its native state in the endoplasmic reticulum (ER) of the cell.

There are three known types of DGAT, referred to as DGAT1, DGAT2 and DGAT3, respectively. DGAT1 polypeptides are membrane proteins that typically have 10 transmembrane domains, DGAT2 polypeptides are also membrane proteins but typically have 2 transmembrane domains, whilst DGAT3 polypeptides typically have none and are thought to be soluble in the cytoplasm, not integrated into membranes. Plant DGAT1 polypeptides typically have about 510-550 amino acid residues while DGAT2 polypeptides typically have about 310-330 residues. DGAT1 is the main enzyme responsible for producing TAG from DAG in most developing plant seeds, whereas DGAT2s from plant species such as tung tree (*Vernicia fordii*) and castor bean (*Ricinus communis*) that produce high amounts of unusual fatty acids appear to have important roles in the accumulation of the unusual fatty acids in TAG. Over-expression of AtDGAT1 in tobacco leaves resulted in a 6-7 fold increased TAG content (Bouvier-Nave et al., 2000).

Examples of DGAT1 polypeptides include DGAT1 proteins from *Aspergillus fumigatus* (XP_755172.1), *Arabidopsis thaliana* (CAB44774.1; SEQ ID NO:1), *Ricinus communis* (AAR11479.1), *Vernicia fordii* (ABC94472.1), *Vernonia galamensis* (ABV21945.1 and ABV21946.1), *Euonymus alatus* (AAV31083.1), *Caenorhabditis elegans* (AAF82410.1), *Rattus norvegicus* (NP_445889.1), *Homo sapiens* (NP_036211.2), as well as variants and/or mutants thereof. In an embodiment, an exogenous polynucleotide of the invention which encodes a DGAT1 which comprises one or more of the following:
  i) nucleotides encoding a polypeptide comprising amino acids whose sequence is set forth in any of the above mentioned accessions, or a biologically active fragment thereof, or a polypeptide whose amino acid sequence is at least 30% identical to that set forth in any of the above mentioned accessions,
  ii) nucleotides whose sequence is at least 30% identical to i), and
  iii) a polynucleotide which hybridizes to one or both of i) or ii) under stringent conditions.

Examples of DGAT2 polypeptides include proteins encoded by DGAT2 genes from *Arabidopsis thaliana* (NP_566952.1), *Ricinus communis* (AAY16324.1), *Vernicia fordii* (ABC94474.1), *Mortierella ramanniana* (AAK84179.1), *Homo sapiens* (Q96PD7.2) (Q58HT5.1), *Bos taurus* (Q70VZ8.1), *Mus musculus* (AAK84175.1), as well as variants and/or mutants thereof. DGAT1 and DGAT2 amino acid sequences show little homology. Expression in leaves of an exogenous DGAT2 was twice as effective as a DGAT1 in increasing oil content (TAG). Further, *A. thaliana* DGAT2 had a greater preference for linoleoyl-CoA and linolenoyl-CoA as acyl donors relative to oleoyl-CoA, compared to DGAT1. This substrate preference can be used to distinguish the two DGAT classes in addition to their amino acid sequences. In an embodiment, an exogenous polynucleotide of the invention which encodes a DGAT2 which comprises one or more of the following:
  i) nucleotides encoding a polypeptide comprising amino acids whose sequence is set forth in any of the above mentioned accessions, or a biologically active fragment thereof, or a polypeptide whose amino acid sequence is at least 30% identical to that set forth in any of the above mentioned accessions,
  ii) nucleotides whose sequence is at least 30% identical to i), and
  iii) a polynucleotide which hybridizes to one or both of i) or ii) under stringent conditions.

Examples of DGAT3 polypeptides include proteins encoded by DGAT3 genes from peanut (*Arachis hypogaea*, Saha, et al., 2006), as well as variants and/or mutants thereof. A DGAT has little or no detectable MGAT activity, for example, less than 300 pmol/min/mg protein, preferably less than 200 pmol/min/mg protein, more preferably less than 100 pmol/min/mg protein.

In a particularly preferred embodiment, the DGAT has a preference for medium chain fatty acids. For instance, the DGAT comprises one or more of the following:
  i) nucleotides encoding a polypeptide comprising amino acids whose sequence is set forth in SEQ ID NO:56, or a biologically active fragment thereof, or a polypeptide whose amino acid sequence is at least 30% identical to SEQ ID NO:56,
  ii) nucleotides whose sequence is at least 30% identical to i), and
  iii) a polynucleotide which hybridizes to one or both of i) or ii) under stringent conditions.

As used herein, the term "phospholipid:diacylglycerol acyltransferase" (PDAT; EC 2.3.1.158) or its synonym "phospholipid:1,2-diacyl-sn-glycerol O-acyltransferase" means an acyltransferase that transfers an acyl group from a phospholipid, typically PC, to the sn-3 position of DAG to form TAG. This reaction is different to DGAT and uses phospholipids as the acyl-donors. Increased expression of PDAT such as PDAT1, which may be exogenous or endogenous to the cell or plant of the invention, increases the production of TAG from PC. There are several forms of PDAT in plant cells including PDAT1, PDAT2 or PDAT3 (Ghosal et al., 2007). Sequences of exemplary PDAT coding regions and polypeptides are provided in Accession Nos: XM_002462417.1, (*Sorghum*), NM_001147943 (*Zea mays*), (Dahlqvist et al., 2000; Fan et al., 2013a and b; Fan et al., 2014) although any PDAT encoding gene can be used. The PDAT may be exogenous or endogenous to the plant or part thereof.

As used herein, the term "monoacylglycerol acyltransferase" or "MGAT" refers to a protein which transfers a fatty acyl group from acyl-CoA to a MAG substrate, for example sn-2 MAG, to produce DAG. Thus, the term "monoacylglycerol acyltransferase activity" at least refers to the transfer of an acyl group from acyl-CoA to MAG to produce DAG. The term "MGAT" as used herein includes enzymes that act on sn-1/3 MAG and/or sn-2 MAG substrates to form sn-1,3 DAG and/or sn-1,2/2,3-DAG, respectively. In a preferred embodiment, the MGAT has a preference for sn-2 MAG substrate relative to sn-1 MAG, or substantially uses only sn-2 MAG as substrate. As used herein, MGAT does not include enzymes which transfer an acyl group preferentially to LysoPA relative to MAG, such enzymes are known as LPAATs. That is, a MGAT preferentially uses non-phosphorylated monoacyl substrates, even though they may also have low catalytic activity on LysoPA. A preferred MGAT does not have detectable activity in acylating LysoPA. A MGAT may also have DGAT function but predominantly functions as a MGAT, i.e., it has greater catalytic activity as a MGAT than as a DGAT when the enzyme activity is expressed in units of nmoles product/min/mg protein (also see Yen et al., 2002). There are three known classes of MGAT, referred to as, MGAT1, MGAT2 and MGAT3, respectively. Examples of MGAT1, MGAT2 and MGAT3 polypeptides are described in WO2013/096993.

As used herein, an "MGAT pathway" refers to an anabolic pathway, different to the Kennedy pathway for the formation of TAG, in which DAG is formed by the acylation of either sn-1 MAG or preferably sn-2 MAG, catalysed by MGAT. The DAG may subsequently be used to form TAG or other lipids. WO2012/000026 demonstrated firstly that plant leaf tissue can synthesise MAG from G-3-P such that the MAG is accessible to an exogenous MGAT expressed in the leaf tissue, secondly MGAT from various sources can function in plant tissues, requiring a successful interaction with other plant factors involved in lipid synthesis and thirdly the DAG produced by the exogenous MGAT activity is accessible to a plant DGAT, or an exogenous DGAT, to produce TAG. MGAT and DGAT activity can be assayed by introducing constructs encoding the enzymes (or candidate enzymes) into *Saccharomyces cerevisiae* strain H1246 and demonstrating TAG accumulation.

Some of the motifs that have been shown to be important for catalytic activity in some DGAT2s are also conserved in MGAT acyltransferases. Of particular interest is a putative neutral lipid-binding domain with the concensus sequence FLXLXXXN (SEQ ID NO:6) where each X is independently any amino acid other than proline, and N is any nonpolar amino acid, located within the N-terminal transmembrane region followed by a putative glycerol/phospholipid acyltransferase domain. The FLXLXXXN motif (SEQ ID NO:6) is found in the mouse DGAT2 (amino acids 81-88) and MGAT1/2 but not in yeast or plant DGAT2s. It is important for activity of the mouse DGAT2. Other DGAT2 and/or MGAT1/2 sequence motifs include:

1. A highly conserved YFP tripeptide (SEQ ID NO:2) in most DGAT2 polypeptides and also in MGAT1 and MGAT2, for example, present as amino acids 139-141 in mouse DGAT2. Mutating this motif within the yeast DGAT2 with non-conservative substitutions rendered the enzyme non-functional.

2. HPHG tetrapeptide (SEQ ID NO:3), highly conserved in MGATs as well as in DGAT2 sequences from animals and fungi, for example, present as amino acids 161-164 in mouse DGAT2, and important for catalytic activity at least in yeast and mouse DGAT2. Plant DGAT2 acyltransferases have a EPHS (SEQ ID NO:4) conserved sequence instead, so conservative changes to the first and fourth amino acids can be tolerated.

3. A longer conserved motif which is part of the putative glycerol phospholipid domain. An example of this motif is RXGFX(K/R)XAXXXGXXX(L/V)VPXXXFG(E/Q) (SEQ ID NO:5), which is present as amino acids 304-327 in mouse DGAT2. This motif is less conserved in amino acid sequence than the others, as would be expected from its length, but homologs can be recognised by motif searching. The spacing may vary between the more conserved amino acids, i.e., there may be additional X amino acids within the motif, or less X amino acids compared to the sequence above.

One important component in glycerolipid synthesis from fatty acids esterified to ACP or CoA is the enzyme sn-glycerol-3-phosphate acyltransferase (GPAT), which is another of the polypeptides involved in the biosynthesis of non-polar lipids. This enzyme is involved in different metabolic pathways and physiological functions. It catalyses the following reaction: G3P+fatty acyl-ACP or -CoA→LPA+free-ACP or -CoA. The GPAT-catalyzed reaction occurs in three distinct plant subcellular compartments: plastid, endoplasmic reticulum (ER) and mitochondria. These reactions are catalyzed by three different types of GPAT enzymes, a soluble form localized in plastidial stroma which uses acyl-ACP as its natural acyl substrate (PGPAT in FIG. 1), and two membrane-bound foul's localized in the ER and mitochondria which use acyl-CoA and acyl-ACP as natural acyl donors, respectively (Chen et al., 2011).

As used herein, the term "glycerol-3-phosphate acyltransferase" (GPAT; EC 2.3.1.15) and its synonym "glycerol-3-phosphate O-acyltransferase" refer to a protein which acylates glycerol-3-phosphate (G-3-P) to form LysoPA and/or MAG, the latter product forming if the GPAT also has phosphatase activity on LysoPA. The acyl group that is transferred is from acyl-CoA if the GPAT is an ER-type GPAT (an "acyl-CoA:sn-glycerol-3-phosphate 1-O-acyltransferase" also referred to as "microsomal GPAT") or from acyl-ACP if the GPAT is a plastidial-type GPAT (PGPAT). Thus, the term "glycerol-3-phosphate acyltransferase activity" refers to the acylation of G-3-P to form LysoPA and/or MAG. The term "GPAT" encompasses enzymes that acylate G-3-P to form sn-1 LPA and/or sn-2 LPA, preferably sn-2 LPA. Preferably, the GPAT which may be over-expressed in the Pull modification is a membrane bound GPAT that functions in the ER of the cell, more preferably a GPAT9, and the plastidial GPAT that is down-regulated in the Prokaryotic Pathway modification is a soluble GPAT ("plastidial GPAT"). In a preferred embodiment, the GPAT has phosphatase activity. In a most preferred embodiment, the GPAT is a sn-2 GPAT having phosphatase activity which produces sn-2 MAG.

As used herein, the teen "sn-1 glycerol-3-phosphate acyltransferase" (sn-1 GPAT) refers to a protein which acylates sn-glycerol-3-phosphate (G-3-P) to preferentially form 1-acyl-sn-glycerol-3-phosphate (sn-1 LPA). Thus, the term "sn-1 glycerol-3-phosphate acyltransferase activity" refers to the acylation of sn-glycerol-3-phosphate to form 1-acyl-sn-glycerol-3-phosphate (sn-1 LPA).

As used herein, the term "sn-2 glycerol-3-phosphate acyltransferase" (sn-2 GPAT) refers to a protein which acylates sn-glycerol-3-phosphate (G-3-P) to preferentially form 2-acyl-sn-glycerol-3-phosphate (sn-2 LPA). Thus, the term "sn-2 glycerol-3-phosphate acyltransferase activity" refers to the acylation of sn-glycerol-3-phosphate to form 2-acyl-sn-glycerol-3-phosphate (sn-2 LPA).

The GPAT family is large and all known members contain two conserved domains, a plsC acyltransferase domain (PF01553) and a HAD-like hydrolase (PF12710) superfamily domain and variants thereof. In addition to this, at least in *Arabidopsis thaliana*, GPATs in the subclasses GPAT4-GPAT8 all contain a N-terminal region homologous to a phosphoserine phosphatase domain (PF00702), and GPATs which produce MAG as a product can be identified by the presence of such a homologous region. Some GPATs expressed endogenously in leaf tissue comprise the conserved amino acid sequence GDLVICPEGTTCREP (SEQ ID NO:7). GPAT4 and GPAT6 both contain conserved residues that are known to be critical to phosphatase activity, specifically conserved amino acids in Motif I (DXDX[T/V][L/V]; SEQ ID NO:8) and Motif III (K-[G/S][D/S]XXX[D/N]; SEQ ID NO:9) located at the N-terminus (Yang et al., 2010).

Homologues of *Arabidopsis* GPAT4 (Accession No. NP_171667.1) and GPAT6 (NP_181346.1) include AAF02784.1 (*Arabidopsis thaliana*), AAL32544.1 (*Arabidopsis thaliana*), AAP03413.1 (*Oryza sativa*), ABK25381.1 (*Picea sitchensis*), ACN34546.1 (*Zea Mays*), BAF00762.1 (*Arabidopsis thaliana*), BAH00933.1 (*Oryza sativa*), EAY84189.1 (*Oryza sativa*), EAY98245.1 (*Oryza sativa*), EAZ21484.1 (*Oryza sativa*), EEC71826.1 (*Oryza sativa*), EEC76137.1 (*Oryza sativa*), EEE59882.1 (*Oryza sativa*), EFJ08963.1 (*Selaginella moellendorffii*), EFJ11200.1 (*Selaginella moellendorffii*), NP_001044839.1 (*Oryza sativa*), NP_001045668.1 (*Oryza sativa*), NP_001147442.1 (*Zea mays*), NP_001149307.1 (*Zea mays*), NP_001168351.1 (*Zea mays*), AFH02724.1, (*Brassica napus*) NP_191950.2 (*Arabidopsis thaliana*), XP_001765001.1 (*Physcomitrella patens*), XP_001769671.1 (*Physcomitrella patens*), (*Vitis vinifera*), XP_002275348.1 (*Vitis vinifera*), XP_002276032.1 (*Vitis vinifera*), XP_002279091.1 (*Vitis vinifera*), XP_002309124.1 (*Populus trichocarpa*), XP_002309276.1 (*Populus trichocarpa*), XP_002322752.1 (*Populus trichocarpa*), XP_002323563.1 (*Populus trichocarpa*), XP_002439887.1 (*Sorghum bicolor*), XP_002458786.1 (*Sorghum bicolor*), XP_002463916.1 (*Sorghum bicolor*), XP_002464630.1 (*Sorghum bicolor*), XP_002511873.1 (*Ricinus communis*), XP_002517438.1 (*Ricinus communis*), XP_002520171.1 (*Ricinus communis*), ACT32032.1 (*Vernicia fordii*), NP_001051189.1 (*Oryza sativa*), AFH02725.1 (*Brassica napus*), XP_002320138.1 (*Populus trichocarpa*), XP_002451377.1 (*Sorghum bicolor*), XP_002531350.1 (*Ricinus communis*), and XP_002889361.1 (*Arabidopsis lyrata*).

In an embodiment, an exogenous polynucleotide of the invention which encodes a GPAT which comprises one or more of the following:
  i) nucleotides encoding a polypeptide comprising amino acids whose sequence is set forth in any of the above mentioned accessions, or a biologically active fragment thereof, or a polypeptide whose amino acid sequence is at least 30% identical to that set forth in any of the above mentioned accessions,
  ii) nucleotides whose sequence is at least 30% identical to i), and
  iii) a polynucleotide which hybridizes to one or both of i) or ii) under stringent conditions.

In a particularly preferred embodiment, the GPAT, preferably a GPAT9, has a preference for utilising medium chain fatty acid substrates. For instance, the GPAT9 comprises one or more of the following:
  i) nucleotides encoding a polypeptide comprising amino acids whose sequence is set forth in any of SEQ ID NO:97 to 119, preferably SEQ ID NO:97, or a biologically active fragment thereof, or a polypeptide whose amino acid sequence is at least 30% identical to any one of SEQ ID NO:97 to 119, preferably at least 30% identical to SEQ ID NO:97,
  ii) nucleotides whose sequence is at least 30% identical to i), and
  iii) a polynucleotide which hybridizes to one or both of i) or ii) under stringent conditions.

The soluble plastidial GPATs (PGPAT, also known as ATS1 in *Arabidopsis thaliana*) have been purified and genes encoding them cloned from several plant species such as pea (*Pisum sativum*, Accession number: P30706.1), spinach (*Spinacia oleracea*, Accession number: Q43869.1), squash (*Cucurbita moschate*, Accession number: P10349.1), cucumber (*Cucumis sativus*, Accession number: Q39639.1) and *Arabidopsis thaliana* (Accession number: Q43307.2). The soluble plastidial GPAT is the first committed step for what is known as the prokaryotic pathway of glycerolipid synthesis and is operative only in the plastid (FIG. 1). The so-called prokaryotic pathway is located exclusively in plant plastids and assembles DAG for the synthesis of galactolipids (MGDG and DGMG) which contain C16:3 fatty acids esterified at the sn-2 position of the glycerol backbone.

Conserved motifs and/or residues can be used as a sequence-based diagnostic for the identification of GPAT enzymes. Alternatively, a more stringent function-based assay could be utilised. Such an assay involves, for example, feeding labelled glycerol-3-phosphate to cells or microsomes and quantifying the levels of labelled products by thin-layer chromatography or a similar technique. GPAT activity results in the production of labelled LPA whilst GPAT/phosphatase activity results in the production of labelled MAG.

As used herein, the term "lysophosphatidic acid acyltransferase" (LPAAT; EC 2.3.1.51) and its synonyms "1-acyl-glycerol-3-phosphate acyltransferase", "acyl-CoA: 1-acyl-sn-glycerol-3-phosphate 2-O-acyltransferase" and "1-acylglycerol-3-phosphate O-acyltransferase" refer to a protein which acylates lysophosphatidic acid (LPA) to form phosphatidic acid (PA). The acyl group that is transferred is from acyl-CoA if the LPAAT is an ER-type LPAAT or from acyl-ACP if the LPAAT is a plastidial-type LPAAT (PLPAAT). Thus, the term "lysophosphatidic acid acyltransferase activity" refers to the acylation of LPA to form PA.

In a particularly preferred embodiment, the LPAAT has a preference for medium chain fatty acids. For instance, the LPAAT comprises one or more of the following:
  i) nucleotides encoding a polypeptide comprising amino acids whose sequence is set forth in SEQ ID NO:94, or a biologically active fragment thereof, or a polypeptide whose amino acid sequence is at least 30% identical to SEQ ID NO:94,
  ii) nucleotides whose sequence is at least 30% identical to i), and
  iii) a polynucleotide which hybridizes to one or both of i) or ii) under stringent conditions.

Oil Body Coating Polypeptides

TAGs are accumulated in plant tissues as subcellular spherical lipid droplets (LDs, also called oil bodies or lipid bodies) of approximately 0.5-2 µm in diameter. In seeds, each LD has a matrix of TAGs surrounded by a layer of phospholipids (PLs) and structural proteins termed oleosins (Chapman and Ohlrogge, 2012; Hsieh and Huang, 2004; Murphy, 2012). The small size of LDs provides a large surface area per unit TAG, which would facilitate lipase binding and lipolysis during germination (Huang and Huang, 2016). Recent proteomics and homology based studies have led to the identification of several new protein components involved in the formation, maintenance, and/or turnover of LDs (Pyc et al., 2017).

Regarding protein structural organization, oleosin comprises an N-terminal domain, a central hydrophobic domain, and a C-terminal domain (Hsiao and Tzen, 2011). Oleosin-H is distinguished from the other isoform oleosin-L by an extra 18-residue segment in its C-terminal domain (Tai et al., 2002). Ubiquitin is a highly-conserved regulatory protein that attaches to lysine ε-amino groups of target proteins by its C-terminal glycine residue (Hsiao and Tzen, 2011). Protein ubiquitination is integral to many biological pathways such as proteasomal degradation, stress responses, hormone biosynthesis and signaling, morphogenesis, chromatin structure, self-incompatibility, and battling pathogens (Sorokin et al., 2009). Some studies suggested that oleosin might be involved in storage lipid degradation after germination (Poxleitner et al., 2006). It has been noticed that protein ubiquitination is involved not only in the ubiquitin/26S proteasome pathway, but also in various biological functions possibly associated with different ubiquitin linkages (Weissman, 2001). Ectopic expression of several LD proteins, such as the plant oleosins and SEIPINs as well as the human perilipins, was shown to modulate LD morphology and accumulation in yeast (S. cerevisiae) (Cai et al., 2015). Lipid reserves are metabolized via the successive events of lipolysis, fatty acid (FA) transport to glyoxysomes, activation of acyl-CoA derivatives, β-oxidation, glyoxylate cycle, partial tricarboxylic acid cycle, and gluconeogenesis (Deruyffelaere et al., 2015).

In an embodiment, the oil body coating polypeptide is non-allergenic, or not known to be allergenic, such as to humans.

As used herein, the term "Oleosin" refers to an amphipathic protein present in the membrane of oil bodies in the storage tissues of seeds (see, for example, Huang, 1996; Tai et al., 2002; Lin et al., 2005; Capuano et al., 2007; Lui et al., 2009; Shimada and Hara-Nishimura, 2010) and artificially produced variants (see for example WO2011/053169 and WO2011/127118).

Oleosins are of low $M_r$ (15-26,000), corresponding to about 140-230 amino acid residues, which allows them to become tightly packed on the surface of oil bodies. Within each seed species, there are usually two or more oleosins of different $M_r$. Each oleosin molecule contains a relatively hydrophilic, variable N-terminal domain (for example, about 48 amino acid residues), a central totally hydrophobic domain (for example, of about 70-80 amino acid residues) which is particularly rich in aliphatic amino acids such as alanine, glycine, leucine, isoleucine and valine, and an amphipathic α-helical domain of about 30-40 amino acid residues at or near the C-terminus. The central hydrophobic domain typically contains a proline knot motif of about 12 residues at its center. Generally, the central stretch of hydrophobic residues is inserted into the lipid core and the amphipathic N-terminal and/or amphipathic C-terminal are located at the surface of the oil bodies, with positively charged residues embedded in a phospholipid monolayer and the negatively charged ones exposed to the exterior.

As used herein, the term "Oleosin" encompasses polyoleosins which have multiple oleosin polypeptides fused together in a head-to-tail fashion as a single polypeptide (WO2007/045019), for example 2×, 4× or 6× oleosin peptides, and caleosins which bind calcium and which are a minor protein component of the proteins that coat oil bodies in seeds (Froissard et al., 2009), and steroleosins which bind sterols (WO2011/053169). However, generally a large proportion (at least 80%) of the oleosins of oil bodies will not be caleosins and/or steroleosins. The term "oleosin" also encompasses oleosin polypeptides which have been modified artificially, such oleosins which have one or more amino acid residues of the native oleosins artificially replaced with cysteine residues, as described in WO2011/053169. Typically, 4-8 residues are substituted artificially, preferably 6 residues, but as many as between 2 and 14 residues can be substituted. Preferably, both of the amphipathic N-terminal and C-terminal domains comprise cysteine substitutions. The modification increases the cross-linking ability of the oleosins and increases the thermal stability and/or the stability of the proteins against degradation by proteases.

A substantial number of oleosin protein sequences, and nucleotide sequences encoding therefor, are known from a large number of different plant species. Examples include, but are not limited to, oleosins from sesame, Arabidposis, canola, corn, rice, peanut, castor, soybean, flax, grape, cabbage, cotton, sunflower, sorghum and barley. Examples of oleosins (with their Accession Nos) include Brassica napus oleosin (CAA57545.1), Brassica napus oleosin S1-1 (ACG69504.1), Brassica napus oleosin S2-1 (ACG69503.1), Brassica napus oleosin S3-1 (ACG69513.1), Brassica napus oleosin S4-1 (ACG69507.1), Brassica napus oleosin S5-1 (ACG69511.1), Arachis hypogaea oleosin 1 (AAZ20276.1), Arachis hypogaea oleosin 2 (AAU21500.1), Arachis hypogaea oleosin 3 (AAU21501.1), Arachis hypogaea oleosin 5 (ABC96763.1), Ricinus communis oleosin 1 (EEF40948.1), Ricinus communis oleosin 2 (EEF51616.1), Glycine max oleosin isoform a (P29530.2), Glycine max oleosin isoform b (P29531.1), Linum usitatissimum oleosin low molecular weight isoform (ABB01622.1), Linum usitatissimum oleosin high molecular weight isoform (ABB01624.1), Helianthus annuus oleosin (CAA44224.1), Zea mays oleosin (NP_001105338.1), Brassica napus steroleosin (ABM30178.1), Brassica napus steroleosin SLO1-1 (ACG69522.1), Brassica napus steroleosin SLO2-1 (ACG69525.1), Sesamum indicum steroleosin (AAL13315.1), Sesame indicum OleosinL (Tai et al., 2002; Accession number AF091840; SEQ ID NO:86), Ficus pumila var. awkeotsang oleosin L-isoform (Accession No. ABQ57397.1), Cucumis sativus oleosinL (Accession No. XP_004146901.1), Linum usitatissimum oleosinL (Accession No. ABB01618.1), Glycine max oleosinL (Accession No. XP_003556321.2), Ananas comosus oleosinL (Accession No. OAY72596.1), Setaria italica oleosinL (Accession No. XP_004956407.1), Fragaria vesca subsp. vesca oleosinL (Accession No. XP_004307777.1), Brassica napus oleosinL (Accession No. CDY03377.1), Solanum lycopersicum oleosinL (Accession No. XP_004240765.1), Sesame indicum OleosinH1 (Tai et al., 2002; Accession number AF302807), Vanilla planifolia leaf OleosinU1 (Huang and Huang, 2016; Accession number SRX648194), Persea americana mesocarp OleosinM lipid droplet associated protein (Huang and Huang, 2016; Accession number SRX627420), Arachis hypogaea Oleosin 3 (Parthibane et al., 2012a and b; Accession number AY722696), A. thaliana Caleosin3 (Shen et al., 2014; Laibach et al., 2015; Accession number AK317039), *A. thaliana* steroleosin (Accession number AT081653), *Zea mays* steroleosin (NP_001152614.1), *Brassica napus* caleosin CLO-1 (ACG69529.1), *Brassica napus* caleosin CLO-3 (ACG69527.1), *Sesamum indicum* caleosin (AAF13743.1), *Zea mays* caleosin (NP_001151906.1), *Glycine max* caleosin (AAB71227). Other lipid encapsulation polypeptides that are functionally equivalent are plastoglobulins and MLDP polypeptides (WO2011/127118). In an embodiment, an exogenous polynucleotide of the invention which encodes a oleosin (such as an OleosinL) or steroleosin which comprises one or more of the following:
 i) nucleotides encoding a polypeptide comprising amino acids whose sequence is set forth in any of the above mentioned accessions, or a biologically active fragment thereof, or a polypeptide whose amino acid sequence is at least 30% identical to that set forth in any of the above mentioned accessions,
 ii) nucleotides whose sequence is at least 30% identical to i), and
 iii) a polynucleotide which hybridizes to one or both of i) or ii) under stringent conditions.

In an embodiment, the oleosin is oleosinL or an ortholog thereof. OleosinL lacks the about 18 amino acid H-form insertion towards the C-terminus of other oleosins (see, for example, Tai et al., 2002). Thus, OleosinL's can readily be distinguished from other oleosins based on protein alignment.

As used herein, a "lipid droplet associated protein" or "LDAP" means a polypeptide which is associated with lipid droplets in plants in tissues or organs other than seeds, anthers and pollen, such as fruit tissues including pericarp and mesocarp. LDAPs may be associated with oil bodies in seeds, anthers or pollen as well as in the tissues or organs other than seeds, anthers and pollen. They are distinct from oleosins which are polypeptides associated with the surface of lipid droplets in seed tissues, anthers and pollen. LDAPs as used herein include LDAP polypeptides that are produced naturally in plant tissues as well as amino acid sequence variants that are produced artificially. The function of such variants can be tested as exemplified in Example 6.

Horn et al. (2013) identified two LDAP genes which are expressed in avocado pericarp. The encoded avocado LDAP1 and LDAP2 polypeptides were 62% identical in amino acid sequence and had homology to polypeptide encoded by *Arabidopsis* At3 g05500 and a rubber tree SRPP-like protein. Gidda et al. (2013) identified three LDAP genes that were expressed in oil palm (*Elaeis guineensis*) mesocarp but not in kernels and concluded that LDAP genes were plant specific and conserved amongst all plant species. LDAP polypeptides may contain additional domains (Gidda et al., (2013). Genes encoding LDAPs are generally up-regulated in non-seed tissues with abundant lipid and can be identified thereby, but are thought to be expressed in all non-seed cells that produce oil including for transient storage. Horn et al. (2013) shows a phylogenetic tree of SRPP-like proteins in plants. Exemplary LDAP polypeptides are described in Example 6 and Example 9 herein, such as *Rhodococcus opacus* TadA lipid droplet associated protein (MacEachran et al., 2010; Accession number HM625859), *Nannochloropsis oceanica* LSDP oil body protein (Vieler et al., 2012; Accession number JQ268559) and *Trichoderma reesei* HFBI hydrophobin (Linder et al., 2005; Accession number Z68124). Homologs of LDAPs in other plant species can be readily identified by those skilled in the art. In an embodiment, an exogenous polynucleotide of the invention which encodes an LDAP which comprises one or more of the following:
 i) nucleotides encoding a polypeptide comprising amino acids whose sequence is set forth in any of the above mentioned accessions, or a biologically active fragment thereof, or a polypeptide whose amino acid sequence is at least 30% identical to that set forth in any of the above mentioned accessions,
 ii) nucleotides whose sequence is at least 30% identical to i), and
 iii) a polynucleotide which hybridizes to one or both of i) or ii) under stringent conditions.

As used herein, the term a "polypeptide involved in starch biosynthesis" refers to any polypeptide, the downregulation of which in a plant cell below normal (wild-type) levels results in a reduction in the level of starch synthesis and a decrease in the levels of starch. This reduces the flow of carbon from sugars into starch. An example of such a polypeptide is AGPase.

As used herein, the term "ADP-glucose phosphorylase" or "AGPase" refers to an enzyme which regulates starch biosynthesis, catalysing conversion of glucose-1-phosphate and ATP to ADP-glucose which serves as the building block for starch polymers. The active form of the AGPase enzyme consists of 2 large and 2 small subunits.

The AGPase enzyme in plants exists primarily as a tetramer which consists of 2 large and 2 small subunits. Although these subunits differ in their catalytic and regulatory roles depending on the species (Kuhn et al., 2009), in plants the small subunit generally displays catalytic activity. The molecular weight of the small subunit is approximately 50-55 kDa. Sequences of exemplary AGPase small subunit polypeptides are provided in Accession Nos: XM_002462095.1 (*Sorghum*) and XM_008666513.1 (*Zea mays*) (Sanjaya et al., 2011; Zale et al., 2016). The molecular weight of the large subunit is approximately 55-60 kDa. The plant enzyme is strongly activated by 3-phosphoglycerate (PGA), a product of carbon dioxide fixation; in the absence of PGA, the enzyme exhibits only about 3% of its activity. Plant AGPase is also strongly inhibited by inorganic phosphate (Pi). In contrast, bacterial and algal AGPase exist as homotetramers of 50 kDa. The algal enzyme, like its plant counterpart, is activated by PGA and inhibited by Pi, whereas the bacterial enzyme is activated by fructose-1, 6-bisphosphate (FBP) and inhibited by AMP and Pi.

TAG Lipases and Beta-Oxidation

As used herein, the term "polypeptide involved in the degradation of lipid and/or which reduces lipid content" refers to any polypeptide which catabolises lipid, the down-regulation of which in a plant cell below normal (wild-type) levels results an increase in the level of oil, such as fatty acids and/or TAGs, in a cell of a transgenic plant or part thereof such as a vegetative part, tuber, beet or a seed. Examples of such polypeptides include, but are not limited to, lipases, or a lipase such as a CGi58 (Comparative Gene identifier-58-Like) polypeptide, a SUGAR-DEPENDENT) (SDP1) triacylglycerol lipase (see, for example, Kelly et al., 2011) and a lipase described in WO 2009/027335.

As used herein, the term "TAG lipase" (EC.3.1.1.3) refers to a protein which hydrolyzes TAG into one or more fatty acids and any one of DAG, MAG or glycerol. Thus, the term "TAG lipase activity" refers to the hydrolysis of TAG into glycerol and fatty acids.

As used herein, the term "CGi58" refers to a soluble acyl-CoA-dependent lysophosphatidic acid acyltransferase encoded by the At4 g24160 gene in *Arabidopsis thaliana* and its homologs in other plants and "Ict1p" in yeast and its homologs. The plant gene such as that from *Arabidopsis* gene locus At4 g24160 is expressed as two alternative transcripts: a longer full-length isoform (At4 g24160.1) and a smaller isoform (At4 g24160.2) missing a portion of the 3' end (see James et al., 2010; Ghosh et al., 2009; US 201000221400). Both mRNAs code for a protein that is homologous to the human CGI-58 protein and other orthologous members of this α/β hydrolase family (ABHD). In an embodiment, the CGI58 (At4 g24160) protein contains three motifs that are conserved across plant species: a GXSXG lipase motif (SEQ ID NO:25), a HX(4)D acyltransferase motif (SEQ ID NO:26), and VX(3)HGF, a probable lipid binding motif (SEQ ID NO:27). The human CGI-58 protein has lysophosphatidic acid acyltransferase (LPAAT) activity but not lipase activity. In contrast, the plant and yeast proteins possess a canonical lipase sequence motif GXSXG (SEQ ID NO:25), that is absent from vertebrate (humans, mice, and zebrafish) proteins, and have lipase and phospholipase activity (Ghosh et al., 2009). Although the plant and yeast CGI58 proteins appear to possess detectable amounts of TAG lipase and phospholipase A activities in addition to LPAAT activity, the human protein does not.

Disruption of the homologous CGI-58 gene in *Arabidopsis thaliana* results in the accumulation of neutral lipid droplets in mature leaves. Mass spectroscopy of isolated lipid droplets from cgi-58 loss-of-function mutants showed they contain triacylglycerols with common leaf-specific fatty acids. Leaves of mature cgi-58 plants exhibit a marked increase in absolute triacylglycerol levels, more than 10-fold higher than in wild-type plants. Lipid levels in the oil-storing seeds of cgi-58 loss-of-function plants were unchanged, and unlike mutations in β-oxidation, the cgi-58 seeds germinated and grew normally, requiring no rescue with sucrose (James et al., 2010).

Examples of nucleotides encoding CGi58 polypeptides include those from *Arabidopsis thaliana* (NM_118548.1 encoding NP_194147.2), *Brachypodium distachyon* (XP_003578450.1), *Glycine max* (XM_003523590.1 encoding XP_003523638.1), *Zea mays* (NM_001155541.1 encoding NP_001149013.1), *Sorghum bicolor* (XM_002460493.1 encoding XP_002460538.1), *Ricinus communis* (XM_002510439.1 encoding XP_002510485.1), *Medicago truncatula* (XM_003603685.1 encoding XP_003603733.1), and *Oryza sativa* (encoding EAZ09782.1). In an embodiment, a genetic modification of the invention down-regulates endogenous production of CGi58, wherein CGi58 is encoded by one or more of the following:
  i) nucleotides comprising a sequence set forth a the above mentioned accessions,
  ii) nucleotides whose sequence is at least 30% identical to i), and
  iii) a polynucleotide which hybridizes to one or both of i) or ii) under stringent conditions.

Other lipases which have lipase activity on TAG include SUGAR-DEPENDENT1 triacylglycerol lipase (SDP1, see for example Eastmond et al., 2006; Kelly et al., 2011) and SDP1-like polypeptides found in plant species as well as yeast (TGL4 polypeptide) and animal cells, which are involved in storage TAG breakdown. The SDP1 and SDP1-like polypeptides appear to be responsible for initiating TAG breakdown in seeds following germination (Eastmond et al., 2006). Plants that are mutant in SDP1, in the absence of exogenous WRI1 and DGAT1, exhibit increased levels of PUFA in their TAG. As used herein, "SDP1 polypeptides" include SDP1 polypeptides, SDP1-like polypeptides and their homologs in plant species. SDP1 and SDP1-like polypeptides in plants are 800-910 amino acid residues in length and have a patatin-like acylhydrolase domain that can associate with oil body surfaces and hydrolyse TAG in preference to DAG or MAG. SDP1 is thought to have a preference for hydrolysing the acyl group at the sn-2 position of TAG. *Arabidopsis* contains at least three genes encoding SDP1 lipases, namely SDP1 (Accession No. NP_196024, nucleotide sequence SEQ ID NO:37 and homologs in other species), SDP1L (Accession No. NM_202720 and homologs in other species, Kelly et al., 2011) and ATGLL (At1 g33270) (Eastmond et al, 2006). Of particular interest for reducing gene activity are SDP1 genes which are expressed in vegetative tissues in plants, such as in leaves, stems and roots. Levels of non-polar lipids in vegetative plant parts can therefore be increased by reducing the activity of SDP1 polypeptides in the plant parts, for example by either mutation of an endogenous gene encoding a SDP1 polypeptide or introduction of an exogenous gene which encodes a silencing RNA molecule which reduces the expression of an endogenous SDP1 gene. Such a reduction is of particular benefit in tuber crops such as sugarbeet and potato, and in "high sucrose" plants such as sweet sorghum, sugarcane and and sugarbeet.

Genes encoding SDP1 homologues (including SDP1-like homologues) in a plant species of choice can be identified readily by homology to known SDP1 gene sequences. Known SDP1 nucleotide or amino acid sequences include Accession Nos.: in *Brassica napus*, GN078290, GN078281, GN078283; *Capsella rubella*, XP_006287072; *Theobroma cacao*, XP_007028574.1; *Populus trichocarpa*, XP_002308909; *Prunus persica*, XP_007203312; *Prunus mume*, XP_008240737; *Malus domestica*, XP_008373034; *Ricinus communis*, XP_002530081; *Medicago truncatula*, XP_003591425; *Solanum lycopersicum*, XP_004249208; *Phaseolus vulgaris*, XP_007162133; *Glycine max*, XP_003554141; *Solanum tuberosum*, XP_006351284; *Glycine max*, XP_003521151; *Cicer arietinum*, XP_004493431; *Cucumis sativus*, XP_004142709; *Cucumis melo*, XP_008457586; *Jatropha curcas*, KDP26217; *Vitis vinifera*, CBI30074; *Oryza sativa*, Japonica Group BAB61223; *Oryza sativa*, Indica Group EAY75912; *Oryza sativa*, Japonica Group NP_001044325; *Sorghum bicolor*, XP_002458531 (SEQ ID NO:38); *Brachypodium distachyon*, XP_003567139; *Zea mays*, AFW85009; *Hordeum vulgare*, BAK03290; *Aegilops tauschii*, EMT32802; *Sorghum bicolor*, XP_002463665; *Zea mays*, NP_001168677; *Hordeum vulgare*, BAK01155; *Aegilops tauschii*, EMT02623; *Triticum urartu*, EMS67257; *Physcomitrella patens*, XP_001758169. Preferred SDP1 sequences for use in genetic constructs for inhibiting expression of the endogenous genes are from cDNAs corresponding to the genes which are expressed most highly in the plant cells, vegetative plant parts or the seeds, whichever is to be modified. Nucleotide sequences which are highly conserved between cDNAs corresponding to all of the SDP1 genes in a plant species are preferred if it is desired to reduce the activity of all members of a gene family in that species. In an embodiment, a genetic modification of the invention down-regulates endogenous production of SDP1, wherein SDP1 is encoded by one or more of the following:
  i) nucleotides comprising a sequence set forth a the above mentioned accessions,
  ii) nucleotides whose sequence is at least 30% identical to i), and
  iii) a polynucleotide which hybridizes to one or both of i) or ii) under stringent conditions.

As shown in the Examples, reduction of the expression and/or activity of SDP1 TAG lipase in plant leaves greatly increased the TAG content, both in terms of the amount of TAG that accumulated and the earlier timing of accumulation during plant development, in the context of co-expression of the transcription factor WRI1 and a fatty acyl acyltransferase. In particular, the increase was observed in plants prior to flowering, and was up to about 70% on a weight basis (% dry weight) at the onset of senescence. The increase was relative to the TAG levels observed in corresponding plant leaves transformed with exogenous polynucleotides encoding the WRI1 and fatty acyl acyltransferase but lacking the modification that reduced SDP1 expression and/or activity.

Reducing the expression of other TAG catabolism genes in plant parts can also increase TAG content, such as the ACX genes encoding acyl-CoA oxidases such as the Acx1 (At4 g16760 and homologs in other plant species) or Acx2 (At5 g65110 and homologs in other plant species) genes. Another polypeptide involved in lipid catabolism is PXA1 which is a peroxisomal ATP-binding cassette transporter that is requires for fatty acid import for β-oxidation (Zolman et al. 2001).

Export of Fatty Acids from Plastids

As used herein, the term "polypeptide which increases the export of fatty acids out of plastids of the cell" refers to any polypeptide which aids in fatty acids being transferred from within plastids of plant cells in a plant or part thereof to outside the plastid, which may be any other part of the cell such as for example the endoplasmic reticulum (ER). Examples of such polypeptides include, but are not limited to, a C16 or C18 fatty acid thioesterase such as a FATA polypeptide or a FATB polypeptide, a C6 to C14 fatty acid thioesterase (which is also a FATB polypeptide), a fatty acid transporter such as an ABCA9 polypeptide or a long-chain acyl-CoA synthetase (LACS).

As used herein, the term "fatty acid thioesterase" or "FAT" or "acyl-ACP thioesterase" refers to an enzyme which catalyses the hydrolysis of the thioester bond between an acyl moiety and acyl carrier protein (ACP) in acyl-ACP and the release of a free fatty acid. Such enzymes typically function in the plastids of an organism which is synthesizing de novo fatty acids. As used herein, the term "C16 or C18 fatty acid thioesterase" refers to an enzyme which catalyses the hydrolysis of the thioester bond between a C16 and/or C18 acyl moiety and ACP in acyl-ACP and the release of free C16 or C18 fatty acid in the plastid. The free fatty acid is then re-esterified to CoA in the plastid envelope as it is transported out of the plastid. The substrate specificity of the fatty acid thioesterase (FAT) enzyme in the plastid is involved in determining the spectrum of chain length and degree of saturation of the fatty acids exported from the plastid. FAT enzymes can be classified into two classes based on their substrate specificity and nucleotide sequences, FATA and FATB (EC 3.1.2.14) (Jones et al., 1995). FATA polypeptides prefer oleoyl-ACP as substrate, while FATB polypeptides show higher activity towards saturated acyl-ACPs of different chain lengths such as acting on palmitoyl-ACP to produce free palmitic acid. Examples of FATA polypeptides useful for the invention include, but are not limited to, those from *Arabidopsis thaliana* (NP_189147), *Arachis hypogaea* (GU324446), *Helianthus annuus* (AAL79361), *Carthamus tinctorius* (AAA33020), *Morus notabilis* (XP_010104178.1), *Brassica napus* (CDX77369.1), *Ricinus communis* (XP_002532744.1) and *Camelina sativa* (AFQ60946.1). Examples of FATB polypeptides useful for the invention include, but are not limited to, those from *Zea mays* (AIL28766), *Brassica napus* (ABH11710), *Helianthus annuus* (AAX19387), *Arabidopsis thaliana* (AEE28300), *Umbellularia californica* (AAC49001), *Arachis hypogaea* (AFR54500), *Ricinus communis* (EEF47013) and *Brachypodium sylvaticum* (ABL85052.1). In an embodiment, an exogenous polynucleotide of the invention which encodes a thioesterase which comprises one or more of the following:
  i) nucleotides encoding a polypeptide comprising amino acids whose sequence is set forth in any of the above mentioned accessions, or a biologically active fragment thereof, or a polypeptide whose amino acid sequence is at least 30% identical to that set forth in any of the above mentioned accessions,
  ii) nucleotides whose sequence is at least 30% identical to i), and
  iii) a polynucleotide which hybridizes to one or both of i) or ii) under stringent conditions.

A subclass of FATB polypeptides are fatty acid thioesterases which have hydrolysis activity on a C6C14 saturated acyl moiety linked by a thioester bond to ACP. Such enzymes are also referred to as medium chain fatty acid (MCFA) thioesterases or MC-FAT enzymes. Such enzymes may also have thioesterase activity on C16-ACP, indeed they may have greater thioesterase activity on a C16 acyl-ACP substrate than on a MCFA-ACP substrate, nevertheless they are considered herein to be an MCFA thioesterase if they produce at least 0.5% MCFA in the total fatty acid content when expressed exogenously in a plant cell. Examples of MCFA thioesterases are given in Example 10 herein. In a particularly preferred embodiment, the thioesterase has a preference for hydrolysing medium chain fatty acid substrates. For instance, the thioesterease comprises one or more of the following:
  i) nucleotides encoding a polypeptide comprising amino acids whose sequence is set forth in any one of SEQ ID NOs 87 to 93, or a biologically active fragment thereof, or a polypeptide whose amino acid sequence is at least 30% identical to any one or more of both of SEQ ID NOs 87 to 93,
  ii) nucleotides whose sequence is at least 30% identical to i), and
  iii) a polynucleotide which hybridizes to one or both of i) or ii) under stringent conditions.

More particularly preferred embodiment, the thioesterease is a C12:0-ACP thioesterase which comprises one or more of the following:
  i) nucleotides encoding a polypeptide comprising amino acids whose sequence is set forth in SEQ ID NO:93, or a biologically active fragment thereof, or a polypeptide whose amino acid sequence is at least 30% identical to SEQ ID NO:93,
  ii) nucleotides whose sequence is at least 30% identical to i), and
  iii) a polynucleotide which hybridizes to one or both of i) or ii) under stringent conditions.

As used herein, the term "fatty acid transporter" relates to a polypeptide present in the plastid membrane which is involved in actively transferring fatty acids from a plastid to outside the plastid. Examples of ABCA9 (ABC transporter A family member 9) polypeptides useful for the invention include, but are not limited to, those from *Arabidopsis thaliana* (Q9FLT5), *Capsella rubella* (XP_006279962.1), *Arabis alpine* (KFK27923.1), *Camelina sativa* (XP_010457652.1), *Brassica napus* (CDY23040.1) and *Brassica rapa* (XP_009136512.1).

As used herein, the term "acyl-CoA synthetase" or "ACS" (EC 6.2.1.3) means a polypeptide which is a member of a ligase family that catalyzes the formation of fatty acyl-CoA by a two-step process proceeding through an adenylated intermediate, using a non-esterified fatty acid, CoA and ATP as substrates to produce an acyl-CoA ester, AMP and pyrophosphate as products. As used herein, the term "long-chain acyl-CoA synthetase" (LACS) is an ACS that has activity on at least a C18 free fatty acid substrate although it may have broader activity on any of C14-C20 free fatty acids. The endogenous plastidial LACS enzymes are localised in the outer membrane of the plastid and function with fatty acid thioesterase for the export of fatty acids from the plastid (Schnurr et al., 2002). In *Arabidopsis*, there are at least nine identified LACS genes (Shockey et al., 2002). Preferred LACS polypeptides are of the LACS9 subclass, which in *Arabidopsis* is the major plastidial LACS. Examples of LACS polypeptides useful for the invention include, but are not limited to, those from *Arabidopsis thaliana* (Q9CAP8), *Camelina sativa* (XP_010416710.1), *Capsella rubella* (XP_006301059.1), *Brassica napus* (CDX79212.1), *Brassica rapa* (XP_009104618.1), *Gossypium raimondii* (XP_012450538.1) and *Vitis Vinifera* (XP_002285853.1). Homologs of the above mentioned polypeptides in other species can readily be identified by those skilled in the art.

Polypeptides Involved in Diacylglycerol (DAG) Production

Levels of non-polar lipids in, for example, vegetative plant parts can also be increased by reducing the activity of polypeptides involved in diacylglycerol (DAG) production in the plastid in the plant parts, for example by either mutation of an endogenous gene encoding such a polypeptide or introduction of an exogenous gene which encodes a silencing RNA molecule which reduces the expression of a target gene involved in diacylglycerol (DAG) production in the plastid.

As used herein, the term "polypeptide involved in diacylglycerol (DAG) production in the plastid" refers to any polypeptide in the plastid of plant cells in a plant or part thereof that is directly involved in the synthesis of diacylglycerol. Examples of such polypeptides include, but are not limited to, a plastidial GPAT, a plastidial LPAAT or a plastidial PAP.

GPATs are described elsewhere in the present document. Examples of plastidial GPAT polypeptides which can be targeted for down-regulation in the invention include, but are not limited to, those from *Arabidopsis thaliana* (BAA00575), *Capsella rubella* (XP_006306544.1), *Camelina sativa* (010499766.1), *Brassica napus* (CDY43010.1), *Brassica rapa* (XP_009145198.1), *Helianthus annuus* (ADV16382.1) and *Citrus unshiu* (BAB79529.1). Homologs in other species can readily be identified by those skilled in the art.

LPAATs are described elsewhere in the present document. As the skilled person would appreciate, plastidial LPAATs to be targeted for down-regulation for reducing DAG synthesis in the plastid are not endogenous LPAATs which function outside of the plastid such as those in the ER, for example being useful for producing TAG comprising medium chain length fatty acids. Examples of plastidial LPAAT polypeptides which can be targeted for down-regulation in the invention include, but are not limited to, those from *Brassica napus* (ABQ42862), =*Brassica rapa* (XP_009137939.1), *Arabidopsis thaliana* (NP_194787.2), *Camelina sativa* (XP_010432969.1), *Glycine max* (XP_006592638.1) and *Solanum tuberosum* (XP_006343651.1). Homologs in other species of the above mentioned polypeptides can readily be identified by those skilled in the art.

As used herein, the term "phosphatidic acid phosphatase" (PAP) (EC 3.1.3.4) refers to a protein which hydrolyses the phosphate group on 3-sn-phosphatidate to produce 1,2-diacyl-sn-glycerol (DAG) and phosphate. Examples of plastidial PAP polypeptides which can be targeted for down-regulation in the invention include, but are not limited to, those from *Arabidopsis thaliana* (Q6NLA5), *Capsella rubella* (XP_006288605.1), *Camelina sativa* (XP_010452170.1), *Brassica napus* (CDY10405.1), *Brassica rapa* (XP_009122733.1), *Glycine max* (XP_003542504.1) and *Solanum tuberosum* (XP_006361792.1). Homologs in other species of the above mentioned polypeptides can readily be identified by those skilled in the art.

Another enzyme that results in DAG production, but in the ER rather than the plastid, is PDCT. As used herein, the term "phosphatidylcholine:diacylglycerol cholinephosphotransferase" (PDCT; EC 2.7.8.2) means an cholinephosphotransferase that transfers a phospho-choline headgroup from a phospholipid, typically PC, to produce DAG, or the reverse reaction to produce PC from DAG. Thus, the two substrates of the forward reaction are cytidine monophosphate (CMP) and phosphatidylcholine and the two products are CDP-choline and DAG. PDCT belongs to the phosphatidic acid phosphatase-related protein family and typically possesses lipid phosphatase/phosphotransferase (LPT) domains. In *Arabidopsis thaliana*, PDCT is encoded by the ROD1 (At3 g15820) and ROD2 (At3 g15830) genes (Lu et al., 2009). Homologous genes are readily identified in other plant species (Guan et al., 2015). Sequences of exemplary PDCT coding regions and polypeptides are provided in, Accession Nos XM_002437214 and EU973573.1), although any PDCT encoding gene can be used. In an embodiment, the PDCT is other than *A. thaliana* PDCT (Lu et al., 2009). Increased expression of PDCT, which may be exogenous or endogenous to the cell or plant of the invention and which is preferably expressed from an exogenous polynucleotide, increases the flow of esterified acyl groups from PC to DAG and thereby increases the TTQ in the total fatty acid content and the level of TAG in vegetative plant parts or cells of the invention. Alternatively, decreasing the level of PDCT activity in the cell or plant by mutation in the gene or by a silencing RNA molecule reduces the production of PC from DAG, the reverse PDCT reaction.

Import of Fatty Acids into Plastids

Levels of non-polar lipids in vegetative plant parts can also be increased by reducing the activity of TGD polypeptides in the plant parts, for example by either mutation of an endogenous gene encoding a TGD polypeptide or introduction of an exogenous gene which encodes a silencing RNA molecule which reduces the expression of an endogenous TGD gene. As used herein, a "Trigalactosyldiacylglycerol (TGD) polypeptide" is one which is involved in the ER to chloroplast lipid trafficking (Xu et al., 2010; Fan et al., 2015) and involved in forming a protein complex which has permease function for lipids. Four such polypeptides are known to form or be associated with a TGD permease, namely TGD-1 (Accession No. At1 g19800 and homologs in other species), TGD-2 (Accession No At2 g20320 and homologs in other species), TGD-3 (Accession No. NM-105215 and homologs in other species) and TGD-4 (At3 g06960 and homologs in other species) (US 20120237949). TGD5 is also involved in ER to chloroplast lipid trafficking, and down-regulation of TGD5 is associated with increased oil production (US2015/337017; Fan et al., 2015). Sequences of exemplary TGD5 polypeptides are provided in Accession Nos XM_002442154 and EU972796.1). TGD-1, -2 and -3 polypeptides are thought to be components of an ATP-Binding Cassette (ABC) transporter associated with the inner envelope membrane of the chloroplast. TGD-2 and TGD-4 polypeptides bind to phosphatidic acid whereas TGD-3 polypeptide functions as an ATPase in the chloroplast stroma. As used herein, an "endogenous TGD gene" is a gene which encodes a TGD polypeptide in a plant. Mutations in TGD-1 gene in *A. thaliana* caused accumulation of triacylglycerols, oligogalactolipids and phosphatidic acid (PA) (Xu et al., 2005). Mutations in TGD genes or SDP1 genes, or indeed in any desired gene in a plant, can be introduced in a site-specific manner by artificial zinc finger nuclease (ZFN), TAL effector (TALEN) or CRISPR technologies (using a Cas9 type nuclease) as known in the art. Preferred exogenous genes encoding silencing RNAs are those encoding a double-stranded RNA molecule such as a hairpin RNA or an artificial microRNA precursor.

Sucrose Metabolism

The TAG levels and/or the TTQ of the total fatty content in the cells, plants and plant parts of the invention can also be increased by modifying sucrose metabolism, particularly in the stems of plants such as sugarcane, *Sorghum* and *Zea mays*. In an embodiment, this is achieved by increasing expression of a sucrose metabolism polypeptide such as invertase or sucrose synthase, or of a sucrose transport polypeptide such as SUS1, SUS4, SUT2, SUT4, or SWEET. The effect of these polypeptides is to increase the supply of sucrose and its monosaccharide components in the cytosol of the cells and/or to decrease the transfer and/or storage of sucrose in the vacuoles of the cells, particularly in stem cells. Sequences of examples of these polypeptides are provided in SEQ ID NOs:274-292 of WO 2016/004473. Invertase such as bCIN, INV2 or INV3 acts to convert sucrose into hexoses which can be exported from the vacuoles into the cytoplasm (McKinley et al., 2016). Increased expression of SUS1 or SUS4 breaks down cytosolic sucrose into hexoses for glycolysis and de novo fatty acid synthesis rather than transfer of the sucrose into vacuoles, such as in stem parenchyma cells (McKinley et al., 2016). Increased expression of sugar transport polypeptides such as tonoplast sucrose exporter, for example SUT2 or SUT4, or SWEET polypeptide releases vacuolar sucrose for cytosolic glycolysis and increases de novo fatty acid biosynthesis (Bihmidine et al., 2016; Qazi et al., 2012; Schneider et al., 2012; Hedrich et al., 2015; Klemens et al., 2013).

The TAG levels and/or the TTQ of the total fatty content in the cells, plants and plant parts of the invention can also be increased by reducing the level of TST polypeptides such as TST1 or TST2, particularly in the stems of plants such as sugarcane, *Sorghum* and *Zea mays*. TST polypeptide can be decreased by mutation of the endogenous genes encoding the polypeptide, or by introduction of an exogenous polynucleotide that encodes a silencing RNA molecule. Sequences of exemplary TST cDNAs and polypeptides are provided as SEQ ID NOs:266-273 of WO 2016/004473.

Fatty Acid Modifying Enzymes

As used herein, the term "FAD2" refers to a membrane bound delta-12 fatty acid desturase that desaturates oleic acid (C18:1$^{\Delta 9}$) to produce linoleic acid (C18:2$^{\Delta 9,12}$).

As used herein, the term "epoxygenase" or "fatty acid epoxygenase" refers to an enzyme that introduces an epoxy group into a fatty acid resulting in the production of an epoxy fatty acid. In preferred embodiment, the epoxy group is introduced at the 12th carbon on a fatty acid chain, in which case the epoxygenase is a Δ12-epoxygenase, especially of a C16 or C18 fatty acid chain. The epoxygenase may be a Δ9-epoxygenase, a Δ15 epoxygenase, or act at a different position in the acyl chain as known in the art. The epoxygenase may be of the P450 class. Preferred epoxygenases are of the mono-oxygenase class as described in WO98/46762. Numerous epoxygenases or presumed epoxygenases have been cloned and are known in the art. Further examples of expoxygenases include proteins comprising an amino acid sequence provided in SEQ ID NO:21 of WO 2009/129582, polypeptides encoded by genes from *Crepis paleastina* (CAA76156, Lee et al., 1998), *Stokesia laevis* (AAR23815) (monooxygenase type), *Euphorbia lagascae* (AAL62063) (P450 type), human CYP2J2 (arachidonic acid epoxygenase, U37143); human CYPIA1 (arachidonic acid epoxygenase, K03191), as well as variants and/or mutants thereof.

As used herein, the term, "hydroxylase" or "fatty acid hydroxylase" refers to an enzyme that introduces a hydroxyl group into a fatty acid resulting in the production of a hydroxylated fatty acid. In a preferred embodiment, the hydroxyl group is introduced at the 2nd, 12th and/or 17th carbon on a C18 fatty acid chain. Preferably, the hydroxyl group is introduced at the 12$^{th}$ carbon, in which case the hydroxylase is a Δ12-hydroxylase. In another preferred embodiment, the hydroxyl group is introduced at the 15th carbon on a C16 fatty acid chain. Hydroxylases may also have enzyme activity as a fatty acid desaturase. Examples of genes encoding Δ12-hydroxylases include those from *Ricinus communis* (AAC9010, van de Loo 1995); *Physaria lindheimeri*, (ABQ01458, Dauk et al., 2007); *Lesquerella fendleri*, (AAC32755, Broun et al., 1998); *Daucus carota*, (AAK30206); fatty acid hydroxylases which hydroxylate the terminus of fatty acids, for example: A, *thaliana* CYP86A1 (P48422, fatty acid ω-hydroxylase); *Vicia sativa* CYP94A1 (P98188, fatty acid ω-hydroxylase); mouse CYP2E1 (X62595, lauric acid co-1 hydroxylase); rat CYP4A1 (M57718, fatty acid co-hydroxylase), as well as as variants and/or mutants thereof.

As used herein, the term "conjugase" or "fatty acid conjugase" refers to an enzyme capable of forming a conjugated bond in the acyl chain of a fatty acid. Examples of conjugases include those encoded by genes from *Calendula officinalis* (AF343064, Qiu et al., 2001); *Vernicia fordii* (AAN87574, Dyer et al., 2002); *Punica granatum* (AY178446, Iwabuchi et al., 2003) and *Trichosanthes kirilowii* (AY178444, Iwabuchi et al., 2003); as well as as variants and/or mutants thereof.

As used herein, the term "acetylenase" or "fatty acid acetylenase" refers to an enzyme that introduces a triple bond into a fatty acid resulting in the production of an acetylenic fatty acid. In a preferred embodiment, the triple bond is introduced at the 2nd, 6th, 12th and/or 17th carbon on a C18 fatty acid chain. Examples acetylenases include those from *Helianthus annuus* (AAO38032, ABC59684), as well as as variants and/or mutants thereof.

Examples of such fatty acid modifying genes include proteins according to the following Accession Numbers which are grouped by putative function, and homologues from other species: Δ12-acetylenases ABC00769, CAA76158, AAO38036, AAO38032; Δ12 conjugases AAG42259, AAG42260, AAN87574; Δ12-desaturases P46313, ABS18716, AAS57577, AAL61825, AAF04093, AAF04094; Δ12 epoxygenases XP_001840127, CAA76156, AAR23815; Δ12-hydroxylases ACF37070, AAC32755, ABQ01458, AAC49010; and Δ12 P450 enzymes such as AF406732.

Silencing Suppressors

In an embodiment, a transgenic plant or part thereof of the invention may comprise a silencing suppressor.

As used herein, a "silencing suppressor" enhances transgene expression in a plant or part thereof of the invention.

For example, the presence of the silencing suppressor results in higher levels of a polypeptide(s) produced an exogenous polynucleotide(s) in a plant or part thereof of the invention when compared to a corresponding plant or part thereof lacking the silencing suppressor. In an embodiment, the silencing suppressor preferentially binds a dsRNA molecule which is 21 base pairs in length relative to a dsRNA molecule of a different length. This is a feature of at least the p19 type of silencing suppressor, namely for p19 and its functional orthologs. In another embodiment, the silencing suppressor preferentially binds to a double-stranded RNA molecule which has overhanging 5' ends relative to a corresponding double-stranded RNA molecule having blunt ends. This is a feature of the V2 type of silencing suppressor, namely for V2 and its functional orthologs. In an embodiment, the dsRNA molecule, or a processed RNA product thereof, comprises at least 19 consecutive nucleotides, preferably whose length is 19-24 nucleotides with 19-24 consecutive basepairs in the case of a double-stranded hairpin RNA molecule or processed RNA product, more preferably consisting of 20, 21, 22, 23 or 24 nucleotides in length, and preferably comprising a methylated nucleotide, which is at least 95% identical to the complement of the region of the target RNA, and wherein the region of the target RNA is i) within a 5' untranslated region of the target RNA, ii) within a 5' half of the target RNA, iii) within a protein-encoding open-reading frame of the target RNA, iv) within a 3' half of the target RNA, or v) within a 3' untranslated region of the target RNA.

Further details regarding silencing suppressors are well known in the art and described in WO 2013/096992 and WO 2013/096993.

Polynucleotides

The terms "polynucleotide", and "nucleic acid" are used interchangeably. They refer to a polymeric form of nucleotides of any length, either deoxyribonucleotides or ribonucleotides, or analogs thereof. A polynucleotide of the invention may be of genomic, cDNA, semisynthetic, or synthetic origin, double-stranded or single-stranded and by virtue of its origin or manipulation: (1) is not associated with all or a portion of a polynucleotide with which it is associated in nature, (2) is linked to a polynucleotide other than that to which it is linked in nature, or (3) does not occur in nature. The following are non-limiting examples of polynucleotides: coding or non-coding regions of a gene or gene fragment, exons, introns, messenger RNA (mRNA), transfer RNA (tRNA), ribosomal RNA (rRNA), ribozymes, cDNA, recombinant polynucleotides, plasmids, vectors, isolated DNA of any sequence, isolated RNA of any sequence, chimeric DNA of any sequence, nucleic acid probes, and primers. For in vitro use, a polynucleotide may comprise modified nucleotides such as by conjugation with a labeling component.

As used herein, an "isolated polynucleotide" refers to a polynucleotide which has been separated from the polynucleotide sequences with which it is associated or linked in its native state, or a non-naturally occurring polynucleotide.

As used herein, the term "gene" is to be taken in its broadest context and includes the deoxyribonucleotide sequences comprising the transcribed region and, if translated, the protein coding region, of a structural gene and including sequences located adjacent to the coding region on both the 5' and 3' ends for a distance of at least about 2 kb on either end and which are involved in expression of the gene. In this regard, the gene includes control signals such as promoters, enhancers, termination and/or polyadenylation signals that are naturally associated with a given gene, or heterologous control signals, in which case, the gene is referred to as a "chimeric gene". The sequences which are located 5' of the protein coding region and which are present on the mRNA are referred to as 5' non-translated sequences. The sequences which are located 3' or downstream of the protein coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns", "intervening regions", or "intervening sequences." Introns are segments of a gene which are transcribed into nuclear RNA (nRNA). Introns may contain regulatory elements such as enhancers. Introns are removed or "spliced out" from the nuclear or primary transcript; introns are therefore absent in the mRNA transcript. A gene which contains at least one intron may be subject to variable splicing, resulting in alternative mRNAs from a single transcribed gene and therefore polypeptide variants. A gene in its native state, or a chimeric gene may lack introns. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, "chimeric DNA" refers to any DNA molecule that is not naturally found in nature; also referred to herein as a "DNA construct" or "genetic construct". Typically, a chimeric DNA comprises regulatory and transcribed or protein coding sequences that are not naturally found together in nature. Accordingly, chimeric DNA may comprise regulatory sequences and coding sequences that are derived from different sources, or regulatory sequences and coding sequences derived from the same source, but arranged in a manner different than that found in nature. The open reading frame may or may not be linked to its natural upstream and downstream regulatory elements. The open reading frame may be incorporated into, for example, the plant genome, in a non-natural location, or in a replicon or vector where it is not naturally found such as a bacterial plasmid or a viral vector. The term "chimeric DNA" is not limited to DNA molecules which are replicable in a host, but includes DNA capable of being ligated into a replicon by, for example, specific adaptor sequences.

A "transgene" is a gene that has been introduced into the genome by a transformation procedure. The term includes a gene in a progeny plant or part thereof such as a vegetative plant part which was introducing into the genome of a progenitor cell thereof. Such progeny cells etc may be at least a $3^{rd}$ or $4^{th}$ generation progeny from the progenitor cell which was the primary transformed cell, or of the progenitor transgenic plant (referred to herein as a TO plant). Progeny may be produced by sexual reproduction or vegetatively such as, for example, from tubers in potatoes or ratoons in sugarcane. The term "genetically modified", "genetic modification" and variations thereof, is a broader term that includes introducing a gene into a cell by transformation or transduction, mutating a gene in a cell and genetically altering or modulating the regulation of a gene in a cell, or the progeny of any cell modified as described above.

A "genomic region" as used herein refers to a position within the genome where a transgene, or group of transgenes (also referred to herein as a cluster), have been inserted into a cell, or predecessor thereof. Such regions only comprise nucleotides that have been incorporated by the intervention of man such as by methods described herein.

A "recombinant polynucleotide" of the invention refers to a nucleic acid molecule which has been constructed or modified by artificial recombinant methods. The recombinant polynucleotide may be present in a cell of a plant or part thereof in an altered amount or expressed at an altered rate (e.g., in the case of mRNA) compared to its native state. In one embodiment, the polynucleotide is introduced into a cell that does not naturally comprise the polynucleotide. Typically an exogenous DNA is used as a template for transcription of mRNA which is then translated into a continuous sequence of amino acid residues coding for a polypeptide of the invention within the transformed cell. In another embodiment, the polynucleotide is endogenous to the plant or part thereof and its expression is altered by recombinant means, for example, an exogenous control sequence is introduced upstream of an endogenous gene of interest to enable the transformed plant or part thereof to express the polypeptide encoded by the gene, or a deletion is created in a gene of interest by ZFN, Talen or CRISPR methods.

A recombinant polynucleotide of the invention includes polynucleotides which have not been separated from other components of the cell-based or cell-free expression system, in which it is present, and polynucleotides produced in said cell-based or cell-free systems which are subsequently purified away from at least some other components. The polynucleotide can be a contiguous stretch of nucleotides or comprise two or more contiguous stretches of nucleotides from different sources (naturally occurring and/or synthetic) joined to form a single polynucleotide. Typically, such chimeric polynucleotides comprise at least an open reading frame encoding a polypeptide of the invention operably linked to a promoter suitable of driving transcription of the open reading frame in a cell of interest.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

A polynucleotide of, or useful for, the present invention may selectively hybridise, under stringent conditions, to a polynucleotide defined herein. As used herein, stringent conditions are those that: (1) employ during hybridisation a denaturing agent such as formamide, for example, 50% (v/v) formamide with 0.1% (w/v) bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (2) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS, and/or (3) employ low ionic strength and high temperature for washing, for example, 0.015 M NaCl/0.0015 M sodium citrate/0.1% SDS at 50° C.

Polynucleotides of the invention may possess, when compared to naturally occurring molecules, one or more mutations which are deletions, insertions, or substitutions of nucleotide residues. Polynucleotides which have mutations relative to a reference sequence can be either naturally occurring (that is to say, isolated from a natural source) or synthetic (for example, by performing site-directed mutagenesis or DNA shuffling on the nucleic acid as described above).

Polynucleotides for Reducing Expression of Genes
RNA Interference

RNA interference (RNAi) is particularly useful for specifically reducing the expression of a gene, which results in reduced production of a particular protein if the gene encodes a protein. Although not wishing to be limited by theory, Waterhouse et al. (1998) have provided a model for the mechanism by which dsRNA (duplex RNA) can be used to reduce protein production. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded RNA product(s) with homology to the target gene to be inactivated such as, for example, a SDP1, TGD, plastidial GPAT, plastidial LPAAT, plastidial PAP, AGPase gene. The DNA therefore comprises both sense and antisense sequences that, when transcribed into RNA, can hybridize to form the double stranded RNA region. In one embodiment of the invention, the sense and antisense sequences are separated by a spacer region that comprises an intron which, when transcribed into RNA, is spliced out. This arrangement has been shown to result in a higher efficiency of gene silencing (Smith et al., 2000). The double stranded region may comprise one or two RNA molecules, transcribed from either one DNA region or two. The presence of the double stranded molecule is thought to trigger a response from an endogenous system that destroys both the double stranded RNA and also the homologous RNA transcript from the target gene, efficiently reducing or eliminating the activity of the target gene.

The length of the sense and antisense sequences that hybridize should each be at least 19 contiguous nucleotides, preferably at least 50 contiguous nucleotides, more preferably at least 100 or at least 200 contiguous nucleotides. Generally, a sequence of 100-1000 nucleotides corresponding to a region of the target gene mRNA is used. The full-length sequence corresponding to the entire gene transcript may be used. The degree of identity of the sense sequence to the targeted transcript (and therefore also the identity of the antisense sequence to the complement of the target transcript) should be at least 85%, at least 90%, or 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ("siRNA") molecules comprise a nucleotide sequence that is identical to about 19-25 contiguous nucleotides of the target mRNA. Preferably, the siRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the organism in which it is to be introduced, for example, as determined by standard BLAST search.

microRNA

MicroRNAs (abbreviated miRNAs) are generally 19-25 nucleotides (commonly about 20-24 nucleotides in plants) non-coding RNA molecules that are derived from larger precursors that form imperfect stem-loop structures. miRNAs bind to complementary sequences on target messenger RNA transcripts (mRNAs), usually resulting in translational repression or target degradation and gene silencing. Artificial miRNAs (amiRNAs) can be designed based on natural miRNAs for reducing the expression of any gene of interest, as well known in the art.

In plant cells, miRNA precursor molecules are believed to be largely processed in the nucleus. The pri-miRNA (containing one or more local double-stranded or "hairpin" regions as well as the usual 5' "cap" and polyadenylated tail of an mRNA) is processed to a shorter miRNA precursor molecule that also includes a stem-loop or fold-back structure and is termed the "pre-miRNA". In plants, the pre-miRNAs are cleaved by distinct DICER-like (DCL) enzymes, yielding miRNA:miRNA* duplexes. Prior to transport out of the nucleus, these duplexes are methylated.

In the cytoplasm, the miRNA strand from the miRNA:miRNA duplex is selectively incorporated into an active RNA-induced silencing complex (RISC) for target recognition. The RISC-complexes contain a particular subset of Argonaute proteins that exert sequence-specific gene repression (see, for example, Millar and Waterhouse, 2005; Pasquinelli et al., 2005; Almeida and Allshire, 2005).

Cosuppression

Genes can suppress the expression of related endogenous genes and/or transgenes already present in the genome, a phenomenon termed homology-dependent
gene silencing. Most of the instances of homologydependent gene silencing fall into two classes—those that function at the level of transcription of the transgene, and those that operate post-transcriptionally.

Post-transcriptional homology-dependent gene silencing (i.e., cosuppression) describes the loss of expression of a transgene and related endogenous or viral genes in transgenic plants. Cosuppression often, but not always, occurs when transgene transcripts are abundant, and it is generally thought to be triggered at the level of mRNA processing, localization, and/or degradation. Several models exist to explain how cosuppression works (see in Taylor, 1997).

Cosuppression involves introducing an extra copy of a gene or a fragment thereof into a plant in the sense orientation with respect to a promoter for its expression. The size of the sense fragment, its correspondence to target gene regions, and its degree of sequence identity to the target gene can be determined by those skilled in the art. In some instances, the additional copy of the gene sequence interferes with the expression of the target plant gene. Reference is made to WO 97/20936 and EP 0465572 for methods of implementing co-suppression approaches.

Recombinant Vectors

One embodiment of the present invention includes a recombinant vector, which comprises at least one polynucleotide defined herein and is capable of delivering the polynucleotide into a host cell. Recombinant vectors include expression vectors. Recombinant vectors contain heterologous polynucleotide sequences, that is, polynucleotide sequences that are not naturally found adjacent to a polynucleotide defined herein, that preferably, are derived from a different species. The vector can be either RNA or DNA, and typically is a viral vector, derived from a virus, or a plasmid. Plasmid vectors typically include additional nucleic acid sequences that provide for easy selection, amplification, and transformation of the expression cassette in prokaryotic cells, e.g., pUC-derived vectors, pGEM-derived vectors or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

"Operably linked" as used herein, refers to a functional relationship between two or more nucleic acid (e.g., DNA) segments. Typically, it refers to the functional relationship of a transcriptional regulatory element (promoter) to a transcribed sequence. For example, a promoter is operably linked to a coding sequence of a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements such as enhancers need not be physically contiguous or located in close proximity to the coding sequences whose transcription they enhance.

When there are multiple promoters present, each promoter may independently be the same or different.

Recombinant vectors may also contain one or more signal peptide sequences to enable an expressed polypeptide defined herein to be retained in the endoplasmic reticulum (ER) in the cell, or transfer into a plastid, and/or contain fusion sequences which lead to the expression of nucleic acid molecules as fusion proteins. Examples of suitable signal segments include any signal segment capable of directing the secretion or localisation of a polypeptide defined herein.

To facilitate identification of transformants, the recombinant vector desirably comprises a selectable or screenable marker gene. By "marker gene" is meant a gene that imparts a distinct phenotype to cells expressing the marker gene and thus, allows such transformed cells to be distinguished from cells that do not have the marker. A selectable marker gene confers a trait for which one can "select" based on resistance to a selective agent (e.g., a herbicide, antibiotic). A screenable marker gene (or reporter gene) confers a trait that one can identify through observation or testing, that is, by "screening" (e.g., β-glucuronidase, luciferase, GFP or other enzyme activity not present in untransformed cells). Exemplary selectable markers for selection of plant transformants include, but are not limited to, a hyg gene which encodes hygromycin B resistance; a neomycin phosphotransferase (nptII) gene conferring resistance to kanamycin, paromomycin; a glutathione-S-transferase gene from rat liver conferring resistance to glutathione derived herbicides as for example, described in EP 256223; a glutamine synthetase gene conferring, upon overexpression, resistance to glutamine synthetase inhibitors such as phosphinothricin as for example, described in WO 87/05327; an acetyltransferase gene from *Streptomyces viridochromogenes* conferring resistance to the selective agent phosphinothricin as for example, described in EP 275957; a gene encoding a 5-enol-shikimate-3-phosphate synthase (EPSPS) conferring tolerance to N-phosphonomethylglycine as for example, described by Hinchee et al. (1988); a bar gene conferring resistance against bialaphos as for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS) which confers resistance to imidazolinone, sulfonylurea, or other ALS-inhibiting chemicals (EP 154,204); a mutated anthranilate synthase gene that confers resistance to 5-methyl tryptophan; or a dalapon dehalogenase gene that confers resistance to the herbicide.

Preferably, the recombinant vector is stably incorporated into the genome of the cell such as the plant cell. Accordingly, the recombinant vector may comprise appropriate elements which allow the vector to be incorporated into the genome, or into a chromosome of the cell.

Expression Vector

As used herein, an "expression vector" is a DNA vector that is capable of transforming a host cell and of effecting expression of one or more specified polynucleotides. Expression vectors of the present invention contain regulatory sequences such as transcription control sequences, translation control sequences, origins of replication, and other regulatory sequences that are compatible with the host cell and that control the expression of polynucleotides of the present invention. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. The choice of the regulatory sequences used depends on the target organism such as a plant and/or target organ or tissue of interest. Such regulatory sequences may be obtained from any eukaryotic organism such as plants or plant viruses, or may be chemically synthesized. A number of vectors suitable for stable transfection of plant cells or for the establishment of transgenic plants have been described in for example, Pouwels et al., Cloning Vectors: A Laboratory Manual, 1985, supp. 1987, Weissbach and Weissbach, Methods for Plant Molecular Biology, Academic Press, 1989, and Gelvin et al., Plant Molecular Biology Manual, Kluwer Academic Publishers, 1990. Typically, plant expression vectors include for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, a transcription termination site, and/or a polyadenylation signal.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the light-inducible promoter from the small subunit (SSU) of the ribulose-1,5-bis-phosphate carboxylase, the rice cytosolic triosephosphate isomerase promoter, the adenine phosphoribosyltransferase promoter of *Arabidopsis*, the rice actin 1 gene promoter, the mannopine synthase and octopine synthase promoters, the Adh promoter, the sucrose synthase promoter, the R gene complex promoter, and the chlorophyll α/β binding protein gene promoter. These promoters have been used to create DNA vectors that have been expressed in plants, see for example, WO 84/02913. All of these promoters have been used to create various types of plant-expressible recombinant DNA vectors.

For the purpose of expression in source tissues of the plant such as the leaf, seed, root or stem, it is preferred that the promoters utilized in the present invention have relatively high expression in these specific tissues. For this purpose, one may choose from a number of promoters for genes with tissue- or cell-specific, or -enhanced expression. Examples of such promoters reported in the literature include, the chloroplast glutamine synthetase GS2 promoter from pea, the chloroplast fructose-1,6-biphosphatase promoter from wheat, the nuclear photosynthetic ST-LS1 promoter from potato, the serine/threonine kinase promoter and the glucoamylase (CHS) promoter from *Arabidopsis thaliana*. Also reported to be active in photosynthetically active tissues are the ribulose-1,5-bisphosphate carboxylase promoter from eastern larch (*Larix laricina*), the promoter for the Cab gene, Cab6, from pine, the promoter for the Cab-1 gene from wheat, the promoter for the Cab-1 gene from spinach, the promoter for the Cab 1R gene from rice, the pyruvate, orthophosphate dikinase (PPDK) promoter from *Zea mays*, the promoter for the tobacco Lhcb1*2 gene, the *Arabidopsis thaliana* Suc2 sucrose-$H^{30}$ symporter promoter, and the promoter for the thylakoid membrane protein genes from spinach (PsaD, PsaF, PsaE, PC, FNR, AtpC, AtpD, Cab, RbcS). Other promoters for the chlorophyll α/β-binding proteins may also be utilized in the present invention such as the promoters for LhcB gene and PsbP gene from white mustard (*Sinapis alba*).

A variety of plant gene promoters that are regulated in response to environmental, hormonal, chemical, and/or developmental signals, also can be used for expression of RNA-binding protein genes in plant cells, including promoters regulated by (1) heat, (2) light (e.g., pea RbcS-3A promoter, maize RbcS promoter), (3) hormones such as abscisic acid, (4) wounding (e.g., WunI), or (5) chemicals such as methyl jasmonate, salicylic acid, steroid hormones, alcohol, Safeners (WO 97/06269), or it may also be advantageous to employ (6) organ-specific promoters.

As used herein, the term "plant storage organ specific promoter" refers to a promoter that preferentially, when compared to other plant tissues, directs gene transcription in a storage organ of a plant. For the purpose of expression in sink tissues of the plant such as the tuber of the potato plant, the fruit of tomato, or the seed of soybean, canola, cotton, *Zea mays*, wheat, rice, and barley, it is preferred that the promoters utilized in the present invention have relatively high expression in these specific tissues. The promoter for β-conglycinin or other seed-specific promoters such as the napin, zein, linin and phaseolin promoters, can be used. Root specific promoters may also be used. An example of such a promoter is the promoter for the acid chitinase gene. Expression in root tissue could also be accomplished by utilizing the root specific subdomains of the CaMV 35S promoter that have been identified.

In a particularly preferred embodiment, the promoter directs expression in tissues and organs in which lipid biosynthesis takes place. Such promoters may act in seed development at a suitable time for modifying lipid composition in seeds. Preferred promoters for seed-specific expression include: 1) promoters from genes encoding enzymes involved in lipid biosynthesis and accumulation in seeds such as desaturases and elongases, 2) promoters from genes encoding seed storage proteins, and 3) promoters from genes encoding enzymes involved in carbohydrate biosynthesis and accumulation in seeds. Seed specific promoters which are suitable are, the oilseed rape napin gene promoter (U.S. Pat. No. 5,608,152), the *Vicia faba* USP promoter (Baumlein et al., 1991), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980), or the legumin B4 promoter (Baumlein et al., 1992), and promoters which lead to the seed-specific expression in monocots such as maize, barley, wheat, rye, rice and the like. Notable promoters which are suitable are the barley lpt2 or lpt1 gene promoter (WO 95/15389 and WO 95/23230), or the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, the rye secalin gene). Other promoters include those described by Broun et al. (1998), Potenza et al. (2004), US 20070192902 and US 20030159173. In an embodiment, the seed specific promoter is preferentially expressed in defined parts of the seed such as the cotyledon(s) or the endosperm. Examples of cotyledon specific promoters include, but are not limited to, the FP1 promoter (Ellerstrom et al., 1996), the pea legumin promoter (Perrin et al., 2000), and the bean phytohemagglutnin promoter (Perrin et al., 2000). Examples of endosperm specific promoters include, but are not limited to, the maize zein-1 promoter (Chikwamba et al., 2003), the rice glutelin-1 promoter (Yang et al., 2003), the barley D-hordein promoter (Horvath et al., 2000) and wheat HMW glutenin promoters (Alvarez et al., 2000). In a further embodiment, the seed specific promoter is not expressed, or is only expressed at a low level, in the embryo and/or after the seed germinates.

In another embodiment, the plant storage organ specific promoter is a fruit specific promoter. Examples include, but are not limited to, the tomato polygalacturonase, E8 and Pds promoters, as well as the apple ACC oxidase promoter (for review, see Potenza et al., 2004). In a preferred embodiment, the promoter preferentially directs expression in the edible parts of the fruit, for example the pith of the fruit, relative to the skin of the fruit or the seeds within the fruit.

In an embodiment, the inducible promoter is the *Aspergillus nidulans* alc system. Examples of inducible expression systems which can be used instead of the *Aspergillus nidulans* alc system are described in a review by Padidam (2003) and Corrado and Karali (2009). In another embodiment, the inducible promoter is a safener inducible promoter such as, for example, the maize ln2-1 or ln2-2 promoter (Hershey and Stoner, 1991), the safener inducible promoter is the maize GST-27 promoter (Jepson et al., 1994), or the soybean GH2/4 promoter (Ulmasov et al., 1995).

In another embodiment, the inducible promoter is a senescence inducible promoter such as, for example, senescence-inducible promoter SAG (senescence associated gene) 12 and SAG 13 from *Arabidopsis* (Gan, 1995; Gan and Amasino, 1995) and LSC54 from *Brassica napus* (Buchanan-Wollaston, 1994). Such promoters show increased expression at about the onset of senescence of plant tissues, in particular the leaves.

For expression in vegetative tissue leaf-specific promoters, such as the ribulose biphosphate carboxylase (RBCS) promoters, can be used. For example, the tomato RBCS1, RBCS2 and RBCS3A genes are expressed in leaves and light grown seedlings (Meier et al., 1997). A ribulose bisphosphate carboxylase promoters expressed almost exclusively in mesophyll cells in leaf blades and leaf sheaths at high levels, described by Matsuoka et al. (1994), can be used. Another leaf-specific promoter is the light harvesting chlorophyll a/b binding protein gene promoter (see, Shiina et al., 1997). The *Arabidopsis thaliana* myb-related gene promoter (Atmyb5) described by Li et al. (1996), is leaf-specific. The Atmyb5 promoter is expressed in developing leaf trichomes, stipules, and epidermal cells on the margins of young rosette and cauline leaves, and in immature seeds. A leaf promoter identified in maize by Busk et al. (1997), can also be used.

In some instances, for example when LEC2 or BBM is recombinantly expressed, it may be desirable that the transgene is not expressed at high levels. An example of a promoter which can be used in such circumstances is a truncated napin A promoter which retains the seed-specific expression pattern but with a reduced expression level (Tan et al., 2011).

The 5' non-translated leader sequence can be derived from the promoter selected to express the heterologous gene sequence of the polynucleotide of the present invention, or may be heterologous with respect to the coding region of the enzyme to be produced, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. Nos. 5,362,865 and 5,859,347), and the TMV omega element.

The termination of transcription is accomplished by a 3' non-translated DNA sequence operably linked in the expression vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region, the 3' untranslated region from pea small subunit Rubisco gene, the 3' untranslated region from soybean 7S seed storage protein gene are commonly used in this capacity. The 3' transcribed, non-translated regions containing the polyadenylate signal of *Agrobacterium* tumor-inducing (Ti) plasmid genes are also suitable.

Recombinant DNA technologies can be used to improve expression of a transformed polynucleotide by manipulating, for example, the efficiency with which the resultant transcripts are translated by codon optimisation according to the host cell species or the deletion of sequences that destabilize transcripts, and the efficiency of post-translational modifications.

Transfer Nucleic Acids

Transfer nucleic acids can be used to deliver an exogenous polynucleotide to a cell and comprise one, preferably two, border sequences and one or more polynucleotides of interest. The transfer nucleic acid may or may not encode a selectable marker. Preferably, the transfer nucleic acid forms part of a binary vector in a bacterium, where the binary vector further comprises elements which allow replication of the vector in the bacterium, selection, or maintenance of bacterial cells containing the binary vector. Upon transfer to a eukaryotic cell, the transfer nucleic acid component of the binary vector is capable of integration into the genome of the eukaryotic cell or, for transient expression experiments, merely of expression in the cell.

As used herein, the term "extrachromosomal transfer nucleic acid" refers to a nucleic acid molecule that is capable of being transferred from a bacterium such as *Agrobacterium* sp., to a plant cell such as a plant leaf cell. An extrachromosomal transfer nucleic acid is a genetic element that is well-known as an element capable of being transferred, with the subsequent integration of a nucleotide sequence contained within its borders into the genome of the recipient cell. In this respect, a transfer nucleic acid is flanked, typically, by two "border" sequences, although in some instances a single border at one end can be used and the second end of the transferred nucleic acid is generated randomly in the transfer process. A polynucleotide of interest is typically positioned between the left border-like sequence and the right border-like sequence of a transfer nucleic acid. The polynucleotide contained within the transfer nucleic acid may be operably linked to a variety of different promoter and terminator regulatory elements that facilitate its expression, that is, transcription and/or translation of the polynucleotide. Transfer DNAs (T-DNAs) from *Agrobacterium* sp. such as *Agrobacterium tumefaciens* or *Agrobacterium rhizogenes*, and man made variants/mutants thereof are probably the best characterized examples of transfer nucleic acids. An example is P-DNA ("plant-DNA") which comprises T-DNA border-like sequences from plants.

As used herein, "T-DNA" refers to a T-DNA of an *Agrobacterium tumefaciens* Ti plasmid or from an *Agrobacterium rhizogenes* Ri plasmid, or variants thereof which function for transfer of DNA into plant cells. The T-DNA may comprise an entire T-DNA including both right and left border sequences, but need only comprise the minimal sequences required in cis for transfer, that is, the right T-DNA border sequence. The T-DNAs of the invention have inserted into them, anywhere between the right and left border sequences (if present), the polynucleotide of interest. The sequences encoding factors required in trans for transfer of the T-DNA into a plant cell such as vir genes, may be inserted into the T-DNA, or may be present on the same replicon as the T-DNA, or preferably are in trans on a compatible replicon in the *Agrobacterium* host. Such "binary vector systems" are well known in the art. As used herein, "P-DNA" refers to a transfer nucleic acid isolated from a plant genome, or man made variants/mutants thereof, and comprises at each end, or at only one end, a T-DNA border-like sequence.

As used herein, a "border" sequence of a transfer nucleic acid can be isolated from a selected organism such as a plant or bacterium, or be a man made variant/mutant thereof. The border sequence promotes and facilitates the transfer of the polynucleotide to which it is linked and may facilitate its integration in the recipient cell genome. In an embodiment, a border-sequence is between 10-80 bp in length. Border sequences from T-DNA from *Agrobacterium* sp. are well known in the art and include those described in Lacroix et al. (2008).

Whilst traditionally only *Agrobacterium* sp. have been used to transfer genes to plants cells, there are now a large number of systems which have been identified/developed which act in a similar manner to *Agrobacterium* sp. Several non-*Agrobacterium* species have recently been genetically modified to be competent for gene transfer (Chung et al., 2006; Broothaerts et al., 2005). These include *Rhizobium* sp. NGR234, *Sinorhizobium meliloti* and *Mezorhizobium loti*.

As used herein, the terms "transfection", "transformation" and variations thereof are generally used interchangeably. "Transfected" or "transformed" cells may have been manipulated to introduce the polynucleotide(s) of interest, or may be progeny cells derived therefrom.

Plants

The invention also provides a plant or part thereof comprising two or more exogenous polynucleotides and/or genetic modifications as described herein. The term "plant" when used as a noun refers to whole plants, whilst the term "part thereof" refers to plant organs (e.g., leaves, stems, roots, flowers, fruit), single cells (e.g., pollen), seed, seed parts such as an embryo, endosperm, scutellum or seed coat, plant tissue such as vascular tissue, plant cells and progeny of the same. As used herein, plant parts comprise plant cells.

As used herein, the terms "in a plant" and "in the plant" in the context of a modification to the plant means that the modification has occurred in at least one part of the plant, including where the modification has occurred throughout the plant, and does not exclude where the modification occurs in only one or more but not all parts of the plant. For example, a tissue-specific promoter is said to be expressed "in a plant", even though it might be expressed only in certain parts of the plant. Analogously, "a transcription factor polypeptide that increases the expression of one or more glycolytic and/or fatty acid biosynthetic genes in the plant" means that the increased expression occurs in at least a part of the plant.

As used herein, the term "plant" is used in it broadest sense, including any organism in the Kingdom Plantae. It also includes red and brown algae as well as green algae. It includes, but is not limited to, any species of flowering plant, grass, crop or cereal (e.g., oilseed, maize, soybean), fodder or forage, fruit or vegetable plant, herb plant, woody plant or tree. It is not meant to limit a plant to any particular structure. It also refers to a unicellular plant (e.g., microalga). The term "part thereof" in reference to a plant refers to a plant cell and progeny of same, a plurality of plant cells, a structure that is present at any stage of a plant's development, or a plant tissue. Such structures include, but are not limited to, leaves, stems, flowers, fruits, nuts, roots, seed, seed coat, embryos. The term "plant tissue" includes differentiated and undifferentiated tissues of plants including those present in leaves, stems, flowers, fruits, nuts, roots, seed, for example, embryonic tissue, endosperm, dermal tissue (e.g., epidermis, periderm), vascular tissue (e.g., xylem, phloem), or ground tissue (comprising parenchyma, collenchyma, and/or sclerenchyma cells), as well as cells in culture (e.g., single cells, protoplasts, callus, embryos, etc.). Plant tissue may be in planta, in organ culture, tissue culture, or cell culture.

As used herein, the term "vegetative tissue" or "vegetative plant part" is any plant tissue, organ or part other than organs for sexual reproduction of plants. The organs for sexual reproduction of plants are specifically seed bearing organs, flowers, pollen, fruits and seeds. Vegetative tissues and parts include at least plant leaves, stems (including bolts and tillers but excluding the heads), tubers and roots, but excludes flowers, pollen, seed including the seed coat, embryo and endosperm, fruit including mesocarp tissue, seed-bearing pods and seed-bearing heads. In one embodiment, the vegetative part of the plant is an aerial plant part. In another or further embodiment, the vegetative plant part is a green part such as a leaf or stem.

A "transgenic plant" or variations thereof refers to a plant that contains a transgene not found in a wild-type plant of the same species, variety or cultivar. Transgenic plants as defined in the context of the present invention include plants and their progeny which have been genetically modified using recombinant techniques to cause production of at least one polypeptide defined herein in the desired plant or part thereof. Transgenic plant parts has a corresponding meaning. The plant and plant parts of the invention may comprise genetic modifications, for example gene mutations, and be considered as "non-transgenic" provided they lack transgenes.

The terms "seed" and "grain" are used interchangeably herein. "Grain" refers to mature grain such as harvested grain or grain which is still on a plant but ready for harvesting, but can also refer to grain after imbibition or germination, according to the context. Mature grain commonly has a moisture content of less than about 18%. In a preferred embodiment, the moisture content of the grain is at a level which is generally regarded as safe for storage, preferably between 5% and 15%, between 6% and 8%, between 8% and 10%, or between 10% and 15%. "Developing seed" as used herein refers to a seed prior to maturity, typically found in the reproductive structures of the plant after fertilisation or anthesis, but can also refer to such seeds prior to maturity which are isolated from a plant. Mature seed commonly has a moisture content of less than about 12%.

As used herein, the term "plant storage organ" refers to a part of a plant specialized to store energy in the form of for example, proteins, carbohydrates, lipid. Examples of plant storage organs are seed, fruit, tuberous roots, and tubers. A preferred plant storage organ of the invention is seed.

As used herein, the term "phenotypically normal" refers to a genetically modified plant or part thereof, for example a plant such as a transgenic plant, or a storage organ such as a seed, tuber or fruit of the invention not having a significantly reduced ability to grow and reproduce when compared to an unmodified plant or part thereof. Preferably, the biomass, growth rate, germination rate, storage organ size, seed size and/or the number of viable seeds produced is not less than 90% of that of a plant lacking said genetic modifications or exogenous polynucleotides when grown under identical conditions. This term does not encompass features of the plant which may be different to the wild-type plant but which do not effect the usefulness of the plant for commercial purposes such as, for example, a ballerina phenotype of seedling leaves. In an embodiment, the genetically modified plant or part thereof which is phenotypically normal comprises a recombinant polynucleotide encoding a silencing suppressor operably linked to a plant storage organ specific promoter and has an ability to grow or reproduce which is essentially the same as a corresponding plant or part thereof not comprising said polynucleotide.

Plants go through a series of growing stages from sowing of a seed, germination and emergence of a seedling, through to flowering, seed setting, physiological maturity and ultimately senescence. These stages are well known and readily defined, for example for *Sorghum* plants as follows. Taking the day the seedling first emerges above the soil as day 0, the vegetative stage of growth is defined herein as from 10 days to initiation of flowering at about 60-70 days, and physiological maturity is reached at about 100 days, depending on the environmental conditions. The vegetative stage includes the boot leaf stage from about 45 days until the first flowering. The boot leaf is the last leaf formed on the plant, from which the panicle (head) emerges. The "boot leaf stage" is defined as from when the boot leaf has fully emerged to initiation of flowering.

As used herein, the term "commencement of flowering" or "initiation of flowering" with respect to a plant refers to the time that the first flower on the plant opens, or the time of onset of anthesis.

As used herein, the term "seed set" with respect to a seed-bearing plant refers to the time when the first seed of the plant reaches maturity. This is typically observable by the colour of the seed or its moisture content, well known in the art.

As used herein, the term "mature" as it relates to a plant leaf means that it has reached full size but has not begun to show signs of ageing or death such as yellowing and/or sensensce. The skilled person can readily determine whether a leaf of a particular plant can be considered as mature.

As used herein, the term "senescence" with respect to a whole plant refers to the final stage of plant development which follows the completion of growth, usually after the plant reaches maximum aerial biomass or height. Senescence begins when the plant aerial biomass reaches its maximum and begins to decline in amount and generally ends with death of most of the plant tissues. It is during this stage that the plant mobilises and recycles cellular components from leaves and other parts which accumulated during growth to other parts to complete its reproductive development. Senescence is a complex, regulated process which involves new or increased gene expression of some genes. Often, some plant parts are senescing while other parts of the same plant continue to grow. Therefore, with respect to a plant leaf or other green organ, the term "senescence" as used herein refers to the time when the amount of chlorophyll in the leaf or organ begins to decrease. Senescence is typically associated with dessication of the leaf or organ, mostly in the last stage of senescence. Senescence is usually observable by the change in colour of the leaf from green towards yellow and eventually to brown when fully dessicated. It is believed that cellular senescence underlies plant and organ senescence.

Plants provided by or contemplated for use in the practice of the present invention include both monocotyledons and dicotyledons. In preferred embodiments, the plants of the present invention are crop plants (for example, cereals and pulses, maize, wheat, potatoes, rice, sorghum, millet, cassava, barley) or legumes such as soybean, beans or peas. The plants may be grown for production of edible roots, tubers, leaves, stems, flowers or fruit. The plants may be vegetable plants whose vegetative parts are used as food. The plants of the invention may be: Acrocomia *aculeata* (macauba palm), *Arabidopsis thaliana, Aracinis hypogaea* (peanut), *Astrocaryum murumuru* (murumuru), *Astrocaryum vulgare* (tucumã), *Attalea geraensis* (Indaiá-rateiro), *Attalea humilis* (American oil palm), *Attalea oleifera* (andaiá), *Attalea phalerata* (uricuri), *Attalea speciosa* (babassu), *Avena sativa* (oats), *Beta vulgaris* (sugar beet), *Brassica* sp. such as *Brassica carinata, Brassica juncea, Brassica napobrassica, Brassica napus* (canola), *Camelina sativa* (false flax), *Can-* nabis sativa (hemp), *Carthamus tinctorius* (safflower), *Caryocar brasiliense* (pequi), *Cocos nucifera* (Coconut), *Crambe abyssinica* (Abyssinian kale), *Cucumis melo* (melon), *Elaeis guineensis* (African palm), *Glycine max* (soybean), *Gossypium hirsutum* (cotton), *Helianthus* sp. such as *Helianthus annuus* (sunflower), *Hordeum vulgare* (barley), *Jatropha curcas* (physic nut), *Joannesia princeps* (arara nut-tree), *Lemna* sp. (duckweed) such as *Lemna aequinoctialis, Lemna disperma, Lemna ecuadoriensis, Lemna gibba* (swollen duckweed), *Lemna japonica, Lemna minor, Lemna minuta, Lemna obscura, Lemna paucicostata, Lemna perpusilla, Lemna tenera, Lemna trisulca, Lemna turionifera, Lemna valdiviana, Lemna yungensis, Licania rigida* (oiticica), *Linum usitatissimum* (flax), *Lupinus angustifolius* (lupin), *Mauritia flexuosa* (buriti palm), *Maximiliana maripa* (inaja palm), *Miscanthus* sp. such as *Miscanthus* x *giganteus* and *Miscanthus sinensis*, *Nicotiana* sp. (tabacco) such as *Nicotiana tabacum* or *Nicotiana benthamiana*, *Oenocarpus bacaba* (bacaba-do-azeite), *Oenocarpus bataua* (patauã), *Oenocarpus distichus* (bacaba-de-leque), *Oryza* sp. (rice) such as *Oryza sativa* and *Oryza glaberrima*, *Panicum virgatum* (switchgrass), *Paraqueiba paraensis* (mari), *Persea amencana* (avocado), *Pongamia pinnata* (Indian beech), *Populus trichocarpa, Ricinus communis* (castor), *Saccharum* sp. (sugarcane), *Sesamum indicum* (sesame), *Solanum tuberosum* (potato), *Sorghum* sp. such as *Sorghum bicolor, Sorghum vulgare, Theobroma grandiforum* (cupuassu), *Trifolium* sp., *Trithrinax brasiliensis* (Brazilian needle palm), *Triticum* sp. (wheat) such as *Triticum aestivum, Zea mays* (corn), alfalfa (*Medicago sativa*), rye (*Secale cerale*), sweet potato (*Lopmoea batatus*), cassava (*Manihot esculenta*), coffee (*Cofea* spp.), pineapple (*Anana comosus*), citris tree (*Citrus* spp.), cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentals*), macadamia (*Macadamia intergrifolia*) and almond (*Prunus amygdalus*).

In an embodiment, the plant is not a *Nicotiana* sp.

Other preferred plants include C4 grasses such as, in addition to those mentioned above, *Andropogon gerardi, Bouteloua curtipendula, B. gracilis, Buchloe dactyloides, Schizachyrium scoparium, Sorghastrum nutans, Sporobolus cryptandrus*; C3 grasses such as *Elymus canadensis*, the legumes *Lespedeza capitata* and *Petalostemum villosum*, the forb *Aster azureus*; and woody plants such as *Quercus ellipsoidalis* and *Q. macrocarpa*. Other preferred plants include C3 grasses.

In a preferred embodiment, the plant is an angiosperm.

In an embodiment, the plant is an oilseed plant, preferably an oilseed crop plant. As used herein, an "oilseed plant" is a plant species used for the commercial production of lipid from the seeds of the plant. The oilseed plant may be, for example, oil-seed rape (such as canola), maize, sunflower, safflower, soybean, sorghum, flax (linseed) or sugar beet. Furthermore, the oilseed plant may be other Brassicas, cotton, peanut, poppy, rutabaga, mustard, castor bean, sesame, safflower, *Jatropha curcas* or nut producing plants. The plant may produce high levels of lipid in its fruit such as olive, oil palm or coconut. Horticultural plants to which the present invention may be applied are lettuce, endive, or vegetable Brassicas including cabbage, broccoli, or cauliflower. The present invention may be applied in tobacco, cucurbits, carrot, strawberry, tomato, or pepper.

In a preferred embodiment, the plant is a member of the family Fabaceae (or Leguminosae) such as alfalfa, clover, peas, lucerne, beans, lentils, lupins, mesquite, carob, soybeans, and peanuts, or a member of the family Poaceae such as corn, sorghum, wheat, barley and oats. In a particularly preferred embodiment, the plant is alfalfa, clover, corn or sorghum, each of which are particularly useful for forage or fodder for animals.

In a preferred embodiment, the transgenic plant is homozygous for each and every gene that has been introduced (transgene) so that its progeny do not segregate for the desired phenotype. The transgenic plant may also be heterozygous for the introduced transgene(s), preferably uniformly heterozygous for the transgene such as for example, in F1 progeny which have been grown from hybrid seed. Such plants may provide advantages such as hybrid vigour, well known in the art.

Transformation of Plants

Transgenic plants can be produced using techniques known in the art, such as those generally described in Slater et al., Plant Biotechnology—The Genetic Manipulation of Plants, Oxford University Press (2003), and Christou and Klee, Handbook of Plant Biotechnology, John Wiley and Sons (2004).

As used herein, the terms "stably transforming", "stably transformed" and variations thereof refer to the integration of the polynucleotide into the genome of the cell such that they are transferred to progeny cells during cell division without the need for positively selecting for their presence. Stable transformants, or progeny thereof, can be identified by any means known in the art such as Southern blots on chromosomal DNA, or in situ hybridization of genomic DNA, enablimg their selection.

*Agrobacterium*-mediated transfer is a widely applicable system for introducing genes into plant cells because DNA can be introduced into cells in whole plant tissues, plant organs, or explants in tissue culture, for either transient expression, or for stable integration of the DNA in the plant cell genome. For example, floral-dip (in planta) methods may be used. The use of *Agrobacterium*-mediated plant integrating vectors to introduce DNA into plant cells is well known in the art. The region of DNA to be transferred is defined by the border sequences, and the intervening DNA (T-DNA) is usually inserted into the plant genome. It is the method of choice because of the facile and defined nature of the gene transfer.

Acceleration methods that may be used include for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells, for example of immature embryos, by a propelling force. Exemplary particles include those comprised of tungsten, gold, platinum, and the like.

In another method, plastids can be stably transformed. Methods disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265). Other methods of cell transformation can also be used and include but are not limited to the introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polynucleotide is cultivated using methods well known to one skilled in the art.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Northern blot hybridisation, Western blot and enzyme assay. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics. Preferably, the vegetative plant parts are harvested at a time when the yield of non-polar lipids are at their highest. In one embodiment, the vegetative plant parts are harvested about at the time of flowering, or after flowering has initiated. Preferably, the plant parts are harvested at about the time senescence begins, usually indicated by yellowing and drying of leaves.

Transgenic plants formed using *Agrobacterium* or other transformation methods typically contain a single genetic locus on one chromosome. Such transgenic plants can be referred to as being hemizygous for the added gene(s). More preferred is a transgenic plant that is homozygous for the added gene(s), that is, a transgenic plant that contains two added genes, one gene at the same locus on each chromosome of a chromosome pair. A homozygous transgenic plant can be obtained by self-fertilising a hemizygous transgenic plant, germinating some of the seed produced and analyzing the resulting plants for the gene of interest.

It is also to be understood that two different transgenic plants that contain two independently segregating exogenous genes or loci can also be crossed (mated) to produce offspring that contain both sets of genes or loci. Selfing of appropriate F1 progeny can produce plants that are homozygous for both of the exogenous genes or loci. Back-crossing to a parental plant and out-crossing with a non-transgenic plant are also contemplated, as is vegetative propagation. Similarly, a transgenic plant can be crossed with a second plant comprising a genetic modification such as a mutant gene and progeny containing both of the transgene and the genetic modification identified. Descriptions of other breeding methods that are commonly used for different traits and crops can be found in Fehr, In: Breeding Methods for Cultivar Development, Wilcox J. ed., American Society of Agronomy, Madison Wis. (1987).

Tilling

In one embodiment, TILLING (Targeting Induced Local Lesions IN Genomes) can be used to produce plants in which endogenous genes comprise a mutation, for example genes encoding an SDP1 or TGD polypeptide, TST, a plastidial GPAT, plastidial LPAAT, phosphatidic acid phosphatase (PAP), or a combination of two or more thereof. In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time. For a TILLING assay, heteroduplex methods using specific endonucleases can be used to detect single nucleotide polymorphisms (SNPs). Alternatively, Next Generation Sequencing of DNA from pools of mutagenised plants can be used to identify mutants in the gene of choice. Typically, a mutation frequency of one mutant per 1000 plants in the mutagenised population is achieved. Using this approach, many thousands of plants can be screened to identify any individual with a single base change as well as small insertions or deletions (1-30 bp) in any gene or specific region of the genome. TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Genome Editing Using Site-Specific Nucleases

Genome editing uses engineered nucleases such as RNA guided DNA endonucleases or nucleases composed of sequence specific DNA binding domains fused to a non-specific DNA cleavage module. These engineered nucleases enable efficient and precise genetic modifications by inducing targeted DNA double stranded breaks that stimulate the cell's endogenous cellular DNA repair mechanisms to repair the induced break. Such mechanisms include, for example, error prone non-homologous end joining (NHEJ) and homology directed repair (HDR).

In the presence of donor plasmid with extended homology arms, HDR can lead to the introduction of single or multiple transgenes to correct or replace existing genes. In the absence of donor plasmid, NHEJ-mediated repair yields small insertion or deletion mutations of the target that cause gene disruption.

Engineered nucleases useful in the methods of the present invention include zinc finger nucleases (ZFNs), transcription activator-like (TAL) effector nucleases (TALEN) and CRISPR/Cas9 type nucleases, and related nucleases.

Typically nuclease encoded genes are delivered into cells by plasmid DNA, viral vectors or in vitro transcribed mRNA.

A zinc finger nuclease (ZFN) comprises a DNA-binding domain and a DNA-cleavage domain, wherein the DNA binding domain is comprised of at least one zinc finger and is operatively linked to a DNA-cleavage domain. The zinc finger DNA-binding domain is at the N-terminus of the protein and the DNA-cleavage domain is located at the C-terminus of said protein.

A ZFN must have at least one zinc finger. In a preferred embodiment, a ZFN would have at least three zinc fingers in order to have sufficient specificity to be useful for targeted genetic recombination in a host cell or organism. Typically, a ZFN having more than three zinc fingers would have progressively greater specificity with each additional zinc finger.

The zinc finger domain can be derived from any class or type of zinc finger. In a particular embodiment, the zinc finger domain comprises the $Cis_2His_2$ type of zinc finger that is very generally represented, for example, by the zinc finger transcription factors TFIIIA or Sp1. In a preferred embodiment, the zinc finger domain comprises three $Cis_2His_2$ type zinc fingers. The DNA recognition and/or the binding specificity of a ZFN can be altered in order to accomplish targeted genetic recombination at any chosen site in cellular DNA. Such modification can be accomplished using known molecular biology and/or chemical synthesis techniques. (see, for example, Bibikova et al., 2002).

The ZFN DNA-cleavage domain is derived from a class of non-specific DNA cleavage domains, for example the DNA-cleavage domain of a Type II restriction enzyme such as FokI (Kim et al., 1996). Other useful endonucleases may include, for example, HhaI, HindIII, Nod, BbvCI, EcoRI, BglI, and AlwI.

A transcription activator-like (TAL) effector nuclease (TALEN) comprises a TAL effector DNA binding domain and an endonuclease domain.

TAL effectors are proteins of plant pathogenic bacteria that are injected by the pathogen into the plant cell, where they travel to the nucleus and function as transcription factors to turn on specific plant genes. The primary amino acid sequence of a TAL effector dictates the nucleotide sequence to which it binds. Thus, target sites can be predicted for TAL effectors, and TAL effectors can be engineered and generated for the purpose of binding to particular nucleotide sequences.

Fused to the TAL effector-encoding nucleic acid sequences are sequences encoding a nuclease or a portion of a nuclease, typically a nonspecific cleavage domain from a type II restriction endonuclease such as FokI (Kim et al., 1996). Other useful endonucleases may include, for example, HhaI, HindIII, Nod, BbvCI, EcoRI, BglI, and AlwI. The fact that some endonucleases (e.g., FoId) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

A sequence-specific TALEN can recognize a particular sequence within a preselected target nucleotide sequence present in a cell. Thus, in some embodiments, a target nucleotide sequence can be scanned for nuclease recognition sites, and a particular nuclease can be selected based on the target sequence. In other cases, a TALEN can be engineered to target a particular cellular sequence.

Genome Editing Using Programmable RNA-Guided DNA Endonucleases

Distinct from the site-specific nucleases described above, the clustered regulatory interspaced short palindromic repeats (CRISPR)/Cas system provides an alternative to ZFNs and TALENs for inducing targeted genetic alterations, via RNA-guided DNA cleavage.

CRISPR systems rely on CRISPR RNA (crRNA) and transactivating chimeric RNA (tracrRNA) for sequence-specific cleavage of DNA. Three types of CRISPR/Cas systems exist: in type II systems, Cas9 serves as an RNA-guided DNA endonuclease that cleaves DNA upon crRNA-tracrRNA target recognition. CRISPR RNA base pairs with tracrRNA to form a two-RNA structure that guides the Cas9 endonuclease to complementary DNA sites for cleavage.

The CRISPR system can be portable to plant cells by co-delivery of plasmids expressing the Cas endonuclease and the necessary crRNA components. The Cas endonuclease may be converted into a nickase to provide additional control over the mechanism of DNA repair (Cong et al., 2013).

CRISPRs are typically short partially palindromic sequences of 24-40 bp containing inner and terminal inverted repeats of up to 11 bp. Although isolated elements have been detected, they are generally arranged in clusters (up to about 20 or more per genome) of repeated units spaced by unique intervening 20-58 bp sequences. CRISPRs are generally homogenous within a given genome with most of them being identical. However, there are examples of heterogeneity in, for example, the Archaea (Mojica et al., 2000).

Feedstuffs

The present invention includes compositions which can be used as feedstuffs. For purposes of the present invention, "feedstuffs" include any food or preparation for animal (including human) consumption and which serves to nourish or build up tissues or supply energy, and/or to maintain, restore or support adequate nutritional status or metabolic function. Feedstuffs of the invention include nutritional compositions for babies and/or young children.

As used herein, the term "animal" refers to any eukaryotic organism capable of ingesting plant derived material. In an embodiment, the animal is a ruminant animal (cattle, sheep, goats etc). Alternatively, the animal is a non-ruminant animal. In one embodiment, the animal is a mammal. In an embodiment, the animal is a human. In an embodiment, the animal is a livestock animal such, but not limited to, as cattle, goats, sheep, pigs, horses, poultry such as chickens and the like. In an embodiment, the cattle are diary cattle or beef cattle. In another embodiment, the animal is a fish, for instance fish bred using aquaculture including, but not limited to, salmon, trout, carp, bass, bream, turbot, sole, milkfish, grey mullet, grouper, flounder, sea bass, cod, haddock, Japanese flounder, catfish, char, whitefish, sturgeon, tench, roach, pike, pike-perch, yellowtail, tilapia, eel or tropical fish (such as the fresh, brackish, and salt water tropical fish). The animal may be a crustacean such as, but not limited to, krill, clams, shrimp (including prawns), crab, and lobster.

Feedstuffs of the invention may comprise for example, a plant or part thereof such as a vegetative plant part of the invention along with a suitable carrier(s). The term "carrier" is used in its broadest sense to encompass any component which may or may not have nutritional value. As the person skilled in the art will appreciate, the carrier must be suitable for use (or used in a sufficiently low concentration) in a feedstuff, such that it does not have deleterious effect on an organism which consumes the feedstuff. Feedstuffs may comprise plant parts which have been harvested and subsequently processed or treated, for example, by chopping, cutting, drying, pressing or pelleting the plant parts, into a form that is suitable for consumption by the animal, or altered by processes such as drying or fermentation to produce hay or silage.

The feedstuff of the present invention comprises a lipid and/or protein produced directly or indirectly by use of the methods, plants or parts thereof disclosed herein. The composition may either be in a solid or liquid form. Additionally, the composition may include edible macronutrients, vitamins, and/or minerals in amounts desired for a particular use. The amounts of these ingredients will vary depending on whether the composition is intended for use with normal individuals or for use with individuals having specialized needs such as individuals suffering from metabolic disorders and the like.

Examples of suitable carriers with nutritional value include, but are not limited to, macronutrients such as edible fats, carbohydrates and proteins. Examples of such edible fats include, but are not limited to, coconut oil, borage oil, fungal oil, black current oil, soy oil, and mono- and di-glycerides. Examples of such carbohydrates include, but are not limited to, glucose, edible lactose, and hydrolyzed starch. Additionally, examples of proteins which may be utilized in the nutritional composition of the invention include, but are not limited to, soy proteins, electrodialysed whey, electrodialysed skim milk, milk whey, or the hydrolysates of these proteins.

With respect to vitamins and minerals, the following may be added to the feedstuff compositions of the present invention, calcium, phosphorus, potassium, sodium, chloride, magnesium, manganese, iron, copper, zinc, selenium, iodine, and vitamins A, E, D, C, and the B complex. Other such vitamins and minerals may also be added.

A feedstuff composition of the present invention may also be added to food even when supplementation of the diet is not required. For example, the composition may be added to food of any type, including, but not limited to, margarine, butter, cheeses, milk, yogurt, chocolate, candy, snacks, salad oils, cooking oils, cooking fats, meats, fish and beverages.

Additionally, material produced in accordance with the present invention may also be used as animal food supplements to alter an animal's tissue or milk fatty acid composition to one more desirable for human or animal consumption, or to reduce methane production in ruminant animals. Furthermore, feedstuffs of the invention can be used in aquaculture to increase the levels of fatty acids and nutrition in fish for human or animal consumption.

Preferred feedstuffs of the invention are the plants, seed and other plant parts such as leaves, fruits and stems which may be used directly as food or feed for humans or other animals. For example, animals may graze directly on such plants grown in the field, or be fed more measured amounts in controlled feeding. The invention includes the use of such plants and plant parts as feed for increasing the polyunsaturated fatty acid levels in humans and other animals.

For consumption by non-human animals the feedstuff may be in any suitable form for such as, but not limited to, silage, hay or pasture growing in a field. In an embodiment, the feedstuff for non-human consumption is a leguminous plant, or part thereof, which is a member of the family Fabaceae family (or Leguminosae) such as alfalfa, clover, peas, lucerne, beans, lentils, lupins, mesquite, carob, soybeans, and peanuts.

In embodiment, the animal is in a feedlot and/or a shed.

In an embodiment, the plant or fraction thereof comprises at least about 5%, at least about 10%, at least about 50%, at least about 75%, at least about 90% or all of the feedstuff.

Silage

As used herein, "silage" is a relatively high-moisture fodder which has been produced and stored in a process called ensilage and which is typically fed to cattle, sheep or other ruminants. During the storage time, carbohydrates, lipids and proteins in the plant material ferment, producing organic acids, or are broken down oxidatively, or both. The plant material upon harvest and the post-fermentation plant materials are both included in silage as the term is used herein. Silage is typically made from grass crops such as maize, sorghum, oats or other cereals, or from mixed pasture grasses and legumes such as alfalfa or clover, using the green, above-ground parts of the plants. Silage is made either by placing cut vegetation (usually the whole above-ground plant biomass which can include reproductive tissues) in a pit or silo or other means for storage, and compressing it down so as to leave as little air as possible with the plant material. Oxygen is excluded to some extent by covering it with a plastic sheet or by wrapping the plant material tightly within plastic film (baling) to reduce air inflow. Silage is made from plant material with a suitable moisture content, generally about 50% to 60% of the fresh weight, depending on the means of storage and the degree of compression used and the amount of water that will be lost in storage, but not exceeding 75%. For sorghum and corn, harvest begins when the whole-plant moisture is at a suitable level, ideally a few days before it is ripe. For pasture-type crops, the plants are mowed and allowed to wilt for a day or so until the moisture content drops to a suitable level. Ideally the crop is mowed when in full flower and deposited in the pit or silo on the day of its cutting. At harvesting, or after, the plant material is shredded or chopped by the harvester into pieces typically about 1-5 cm long. The plant material may be placed in large heaps on the ground and compressed to reduce the amount of air, then covered with plastic, or into a silo. Alternatively, the plant material may be baled in plastic wrapping to exclude air, which typically requires a lower moisture content of about 30-40%, but still too damp to be stored as dry hay.

The cut or chopped, stored plant material undergoes mostly anaerobic fermentation, which starts about 48 hours after the pit or silo is filled. The fermentation process converts sugars and other carbohydrates such as hemicellulose to organic acids, mostly acetic, propionic, lactic and butyric acids. Fermentation starts after the trapped oxygen is consumed and is essentially complete after about two weeks of storage, or may continue for longer periods. When the plant material is closely packed, the supply of oxygen is limited and the fermentation results in the decomposition of the carbohydrates, some lipids and proteins in the material into the organic acids. This product is named sour silage. If, on the other hand, the fodder is more loosely packed, the main reaction is oxidation which proceeds more rapidly and the temperature rises. If the mass is compressed when the temperature is 60-75C, the reaction ceases and sweet silage results. Fermentation may be aided by inoculation with specific microorganisms such as lactic acid bacteria to speed fermentation or improve the resulting silage, e.g. with *Lactobacillus plantarum*.

Bulk silage is commonly fed to dairy cattle, while baled silage tends to be used for beef cattle, sheep and horses. The advantages of silage as animal feed are several. During fermentation, the silage bacteria act on the cellulose and other carbohydrates in the forage to produce the organic fatty acids, thereby lowering the pH. This inhibits competing bacteria that might cause spoilage and the organic acids thereby act as natural preservatives, improve digestibility and palatability. This preservative action is particularly important during winter in temperate regions, when green forage is unavailable.

Silage can be produced using techniques known in the art such as those described in CN 101940272 CN 103461658 CN 101946853, CN 101946853, CN 104381743, U.S. Pat. Nos. 3,875,304 and 6,224,916. Pellets for animal feed can be produced using techniques known in the art such as those described in U.S. Pat. Nos. 3,035,920, 3,573,924 and 5,871,802.

Plant Biomass

An increase in the total lipid content of plant biomass equates to greater energy content, making its use as a feed or forage or in the production of biofuel more economical.

The main components of naturally occurring plant biomass are carbohydrates (approximately 75%, dry weight) and lignin (approximately 25%), which can vary with plant type. The carbohydrates are mainly cellulose or hemicellulose fibers, which impart strength to the plant structure, and lignin, which holds the fibers together. Plant biomass typically has a low energy density as a result of both its physical form and moisture content. This also makes it inconvenient and inefficient for storage and transport without some kind of pre-processing. There are a range of processes available to convert it into a more convenient form including: 1) physical pre-processing (for example, grinding) or 2) conversion by thermal (for example, combustion, gasification, pyrolysis) or chemical (for example, anaerobic digestion, fermentation, composting, transesterification) processes. In this way, the biomass is converted into what can be described as a biomass fuel.

Combustion

Combustion is the process by which flammable materials are allowed to burn in the presence of air or oxygen with the release of heat. The basic process is oxidation. Combustion is the simplest method by which biomass can be used for energy, and has been used to provide heat. This heat can itself be used in a number of ways: 1) space heating, 2) water (or other fluid) heating for central or district, heating or process heat, 3) steam raising for electricity generation or motive force. When the flammable fuel material is a form of biomass the oxidation is of predominantly the carbon (C) and hydrogen (H) in the cellulose, hemicellulose, lignin, and other molecules present to form carbon dioxide ($CO_2$) and water ($H_2O$). The plants of the invention provide improved fuel for combustion by virtue of the increased lipid content.

Gasification

Gasification is a partial oxidation process whereby a carbon source such as plant biomass, is broken down into carbon monoxide (CO) and hydrogen ($H_2$), plus carbon dioxide ($CO_2$) and possibly hydrocarbon molecules such as methane ($CH_4$). If the gasification takes place at a relatively low temperature, such as 700° C. to 1000° C., the product gas will have a relatively high level of hydrocarbons compared to high temperature gasification. As a result it may be used directly, to be burned for heat or electricity generation via a steam turbine or, with suitable gas clean up, to run an internal combustion engine for electricity generation. The combustion chamber for a simple boiler may be close coupled with the gasifier, or the producer gas may be cleaned of longer chain hydrocarbons (tars), transported, stored and burned remotely. A gasification system may be closely integrated with a combined cycle gas turbine for electricity generation (IGCC—integrated gasification combined cycle). Higher temperature gasification (1200° C. to 1600° C.) leads to few hydrocarbons in the product gas, and a higher proportion of CO and H2. This is known as synthesis gas (syngas or biosyngas) as it can be used to synthesize longer chain hydrocarbons using techniques such as Fischer-Tropsch (FT) synthesis. If the ratio of H2 to CO is correct (2:1) FT synthesis can be used to convert syngas into high quality synthetic diesel biofuel which is compatible with conventional fossil diesel and diesel engines.

Pyrolysis

As used herein, the term "pyrolysis" means a process that uses slow heating in the absence of oxygen to produce gaseous, oil and char products from biomass. Pyrolysis is a thermal or thermo-chemical conversion of lipid-based, particularly triglyceride-based, materials. The products of pyrolysis include gas, liquid and a sold char, with the proportions of each depending upon the parameters of the process. Lower temperatures (around 400° C.) tend to produce more solid char (slow pyrolysis), whereas somewhat higher temperatures (around 500° C.) produce a much higher proportion of liquid (bio-oil), provided the vapour residence time is kept down to around 1s or less. Temperatures of about 275° C. to about 375° C. can be used to produce liquid bio-oil having a higher proportion of longer chain hydrocarbons. Pyrolysis involves direct thermal cracking of the lipids or a combination of thermal and catalytic cracking. At temperatures of about 400-500° C., cracking occurs, producing short chain hydrocarbons such as alkanes, alkenes, alkadienes, aromatics, olefins and carboxylic acid, as well as carbon monoxide and carbon dioxide.

Four main catalyst types can be used including transition metal catalysts, molecular sieve type catalysts, activated alumina and sodium carbonate (Maher and Bressler, 2007). Examples are given in U.S. Pat. No. 4,102,938. Alumina ($Al_2O_3$) activated by acid is an effective catalyst (U.S. Pat. No. 5,233,109). Molecular sieve catalysts are porous, highly crystalline structures that exhibit size selectivity, so that molecules of only certain sizes can pass through. These include zeolite catalysts such as ZSM-5 or HZSM-5 which are crystalline materials comprising $AlO_4$ and $SiO_4$ and other silica-alumina catalysts. The activity and selectivity of these catalysts depends on the acidity, pore size and pore shape, and typically operate at 300-500° C. Transition metal catalysts are described for example in U.S. Pat. No. 4,992,605. Sodium carbonate catalyst has been used in the pyrolysis of oils (Dandik and Aksoy, 1998).

As used herein, "hydrothermal processing", "HTP", also referred to as "thermal depolymerisation" is a form of pyrolysis which reacts the plant-derived matter, specifically the carbon-containing material in the plant-derived matter, with hydrogen to produce a bio-oil product comprised predominantly of paraffinic hydrocarbons along with other gases and solids. A significant advantage of HTP is that the vegetative plant material does not need to be dried before forming the composition for the conversion reaction, although the vegetative plant material can be dried beforehand to aid in transport or storage of the biomass. The biomass can be used directly as harvested from the field. The reactor is any vessel which can withstand the high temperature and pressure used and is resistant to corrosion. The solvent used in the HTP includes water or is entirely water, or may include some hydrocarbon compounds in the form of an oil. Generally, the solvent in HTP lacks added alcohols. The conversion reaction may occur in an oxidative, reductive or inert environment. "Oxidative" as used herein means in the presence of air, "reductive" means in the presence of a reducing agent, typically hydrogen gas or methane, for example 10-15% H2 with the remainder of the gas being $N_2$, and "inert" means in the presence of an inert gas such as nitrogen or argon. The conversion reaction is preferably carried out under reductive conditions. The carbon-containing materials that are converted include cellulose, hemicellulose, lignin and proteins as well as lipids. The process uses a conversion temperature of between 270° C. and 400° C. and a pressure of between 70 and 350 bar, typically 300° C. to 350° C. and a pressure between 100-170 bar. As a result of the process, organic vapours, pyrolysis gases and charcoal are produced. The organic vapours are condensed to produce the bio-oil. Recovery of the bio-oil may be achieved by cooling the reactor and reducing the pressure to atmospheric pressure, which allows bio-oil (organic) and water phases to develop and the bio-oil to be removed from the reactor.

The yield of the recovered bio-oil is calculated as a percentage of the dry weight of the input biomass on a dry weight basis. It is calculated according to the formula: weight of bio-oil×100/dry weight of the vegetative plant parts. The weight of the bio-oil does not include the weight of any water or solids which may be present in a bio-oil mixture, which are readily removed by filtration or other known methods.

The bio-oil may then be separated into fractions by fractional distillation, with or without additional refining processes. Typically, the fractions that condense at these temperatures are termed: about 370° C., fuel oil; about 300° C., diesel oil; about 200° C., kerosene; about 150° C., gasoline (petrol). Heavier fractions may be cracked into lighter, more desirable fractions, well known in the art. Diesel fuel typically is comprised of C13-C22 hydrocarbon compounds.

Transesterification

"Transesterification" as used herein is the conversion of lipids, principally triacylglycerols, into fatty acid methyl esters or ethyl esters by reaction with short chain alcohols such as methanol or ethanol, in the presence of a catalyst such as alkali or acid. Methanol is used more commonly due to low cost and availability, but ethanol, propanol or butanol or mixtures of the alcohols can also be used. The catalysts may be homogeneous catalysts, heterogeneous catalysts or enzymatic catalysts. Homogeneous catalysts include ferric sulphate followed by KOH. Heterogeneous catalysts include CaO, $K_3PO_4$, and $WO_3/ZrO_2$. Enzymatic catalysts include Novozyme 435 produced from *Candida antarctica.*

Transesterification can be carried out on extracted oil, or preferably directly in situ in the vegetative plant material. The vegetative plant parts may be dried and milled prior to being used to prepare the composition for the conversion reaction, but does not need to be. The advantage of direct conversion to fatty acid esters, preferably FAME, is that the conversion can use lower temperatures and pressures and still provide good yields of the product, for example, comprising at least 50% FAME by weight. The yield of recovered bio-oil by transesterification is calculated as for the HTP process.

Production of Non-Polar Lipids

Techniques that are routinely practiced in the art can be used to extract, process, purify and analyze the lipids such as the TAG produced by plants or parts thereof of the instant invention. Such techniques are described and explained throughout the literature in sources such as, Fereidoon Shahidi, Current Protocols in Food Analytical Chemistry, John Wiley & Sons, Inc. (2001) D1.1.1-D1.1.11, and Perez-Vich et al. (1998).

Production of Oil from Vegetative Plant Parts or Seed

Typically, vegetative plant parts or plant seeds are cooked, pressed, and/or extracted to produce crude vegetative oil or seedoil, which is then degummed, refined, bleached, and deodorized. Generally, techniques for crushing seed are known in the art. For example, oilseeds can be tempered by spraying them with water to raise the moisture content to, for example, 8.5%, and flaked using a smooth roller with a gap setting of 0.23 to 0.27 mm. Depending on the type of seed, water may not be added prior to crushing. Application of heat deactivates enzymes, facilitates further cell rupturing, coalesces the lipid droplets, and agglomerates protein particles, all of which facilitate the extraction process. Vegetative plant parts can be similarly treated, depending on the moisture content.

In an embodiment, the majority of the vegetative oil or seedoil is released by passage through a screw press. Cakes (vegetative plant meal, seedmeal) expelled from the screw press may then be solvent extracted for example, with hexane, using a heat traced column, or not be solvent treated, in which case it may be more suitable as animal feed. Alternatively, crude vegetative oil or seedoil produced by the pressing operation can be passed through a settling tank with a slotted wire drainage top to remove the solids that are expressed with the vegetative oil or seedoil during the pressing operation. The clarified vegetative oil or seedoil can be passed through a plate and frame filter to remove any remaining fine solid particles. Once the solvent is stripped from the crude oil, the pressed and extracted portions are combined and subjected to normal lipid processing procedures (i.e., degumming, caustic refining, bleaching, and deodorization).

Extraction of the lipid from vegetative plant parts of the invention uses analogous methods to those known in the art for seedoil extraction. One way is physical extraction, which often does not use solvent extraction. Expeller pressed extraction is a common type, as are the screw press and ram press extraction methods. Mechanical extraction is typically less efficient than solvent extraction where an organic solvent (e.g., hexane) is mixed with at least the plant biomass, preferably after the biomass is dried and ground. The solvent dissolves the lipid in the biomass, which solution is then separated from the biomass by mechanical action (e.g., with the pressing processes above). This separation step can also be performed by filtration (e.g., with a filter press or similar device) or centrifugation etc. The organic solvent can then be separated from the non-polar lipid (e.g., by distillation). This second separation step yields non-polar lipid from the plant and can yield a re-usable solvent if one employs conventional vapor recovery. In an embodiment, the oil and/or protein content of the plant part or seed is analysed by near-infrared reflectance spectroscopy as described in Hom et al. (2007) prior to extraction.

If the vegetative plant parts are not to be used immediately to extract the lipid it is preferably processed to ensure the lipid content is retained as much as possible (see, for example, Christie, 1993), such as by drying the vegetative plant parts.

Degumming

Degumming is an early step in the refining of oils and its primary purpose is the removal of most of the phospholipids from the oil, which may be present as approximately 1-2% of the total extracted lipid. Addition of ~2% of water, typically containing phosphoric acid, at 70-80° C. to the crude oil results in the separation of most of the phospholipids accompanied by trace metals and pigments. The insoluble material that is removed is mainly a mixture of phospholipids and triacylglycerols and is also known as lecithin. Degumming can be performed by addition of concentrated phosphoric acid to the crude oil to convert non-hydratable phosphatides to a hydratable form, and to chelate minor metals that are present. Gum is separated from the oil by centrifugation. The oil can be refined by addition of a sufficient amount of a sodium hydroxide solution to titrate all of the fatty acids and removing the soaps thus formed.

Alkali Refining

Alkali refining is one of the refining processes for treating crude oil, sometimes also referred to as neutralization. It usually follows degumming and precedes bleaching. Following degumming, the oil can treated by the addition of a sufficient amount of an alkali solution to titrate all of the fatty acids and phosphoric acids, and removing the soaps thus formed. Suitable alkaline materials include sodium hydroxide, potassium hydroxide, sodium carbonate, lithium hydroxide, calcium hydroxide, calcium carbonate and ammonium hydroxide. This process is typically carried out at room temperature and removes the free fatty acid fraction. Soap is removed by centrifugation or by extraction into a solvent for the soap, and the neutralised oil is washed with water. If required, any excess alkali in the oil may be neutralized with a suitable acid such as hydrochloric acid or sulphuric acid.

Bleaching

Bleaching is a refining process in which oils are heated at 90-120° C. for 10-30 minutes in the presence of a bleaching earth (0.2-2.0%) and in the absence of oxygen by operating with nitrogen or steam or in a vacuum. This step in oil processing is designed to remove unwanted pigments (carotenoids, chlorophyll, gossypol etc), and the process also removes oxidation products, trace metals, sulphur compounds and traces of soap.

Deodorization

Deodorization is a treatment of oils and fats at a high temperature (200-260° C.) and low pressure (0.1-1 mm Hg). This is typically achieved by introducing steam into the oil at a rate of about 0.1 ml/minute/100 ml of oil. Deodorization can be performed by heating the oil to 260° C. under vacuum, and slowly introducing steam into the oil at a rate of about 0.1 ml/minute/100 ml of oil. After about 30 minutes of sparging, the oil is allowed to cool under vacuum. The oil is typically transferred to a glass container and flushed with argon before being stored under refrigeration. If the amount of oil is limited, the oil can be placed under vacuum for example, in a Parr reactor and heated to 260° C. for the same length of time that it would have been deodorized. This treatment improves the colour of the oil and removes a majority of the volatile substances or odorous compounds including any remaining free fatty acids, monoacylglycerols and oxidation products.

Winterisation

Winterization is a process sometimes used in commercial production of oils for the separation of oils and fats into solid (stearin) and liquid (olein) fractions by crystallization at sub-ambient temperatures. It was applied originally to cottonseed oil to produce a solid-free product. It is typically used to decrease the saturated fatty acid content of oils.

Algae

Algae can produce 10 to 100 times as much mass as terrestrial plants in a year and can be cultured in open-ponds (such as raceway-type ponds and lakes) or in photobioreactors. The most common oil-producing algae can generally include the diatoms (bacillariophytes), green algae (chlorophytes), blue-green algae (cyanophytes), and golden-brown algae (chrysophytes). In addition a fifth group known as haptophytes may be used. Groups include brown algae and heterokonts. Specific non-limiting examples algae include the Classes: Chlorophyceae, Eustigmatophyceae, Prymnesiophyceae, Bacillariophyceae. Bacillariophytes capable of oil production include the genera *Amphipleura*, *Amphora*, *Chaetoceros*, *Cyclotella*, *Cymbella*, *Fragilaria*, *Hantzschia*, *Navicula*, *Nitzschia*, *Phaeodactylum*, and *Thalassiosira*. Specific non-limiting examples of chlorophytes capable of oil production include *Ankistrodesmus*, *Botryococcus*, *Chlorella*, *Chlorococcum*, *Dunaliella*, *Monoraphidium*, *Oocystis*, *Scenedesmus*, and *Tetraselmis*. In one aspect, the chlorophytes can be *Chlorella* or *Dunaliella*. Specific non-limiting examples of cyanophytes capable of oil production include *Oscillatoria* and *Synechococcus*. A specific example of chrysophytes capable of oil production includes Boekelovia. Specific non-limiting examples of haptophytes include Isochysis and Pleurochysis.

Specific algae useful in the present invention include, for example, *Chlamydomonas* sp. such as *Chlamydomonas reinhardtii*, *Dunaliella* sp. such as *Dunaliella salina*, *Dunaliella tertiolecta*, *D. acidophila*, *D. Lateralis*. *D. martima*. *D. parva*, *D. polmorpha*, *D. primolecta*, *D. pseudosalina*, *D. quartolecta*. *D. viridis*, *Haematococcus* sp., *Chlorella* sp. such as *Chlorella vulgaris*, *Chlorella sorokiniana* or *Chlorella protothecoides*, *Thraustochytrium* sp., *Schizochytrium* sp., *Volvox* sp, *Nannochloropsis* sp., *Botryococcus braunii* which can contain over 60 wt % lipid, *Phaeodactylum tricornutum*, *Thalassiosira pseudonana*, *Isochrysis* sp., *Pavlova* sp., *Chlorococcum* sp, *Ellipsoidion* sp., *Neochloris* sp., *Scenedesmus* sp.

Algae of the invention can be harvested using microscreens, by centrifugation, by flocculation (using for example, chitosan, alum and ferric chloride) and by froth flotation. Interrupting the carbon dioxide supply can cause algae to flocculate on its own, which is called "autoflocculation". In froth flotation, the cultivator aerates the water into a froth, and then skims the algae from the top. Ultrasound and other harvesting methods are currently under development.

Lipid may be extracted from the algae by mechanical crushing. When algal mass is dried it retains its lipid content, which can then be "pressed" out with an oil press. Osmotic shock may also be used to release cellular components such as lipid from algae, and ultrasonic extraction can accelerate extraction processes. Chemical solvents (for example, hexane, benzene, petroleum ether) are often used in the extraction of lipids from algae. Enzymatic extraction using enzymes to degrade the cell walls may also be used to extract lipids from algae. Supercritical $CO_2$ can also be used as a solvent. In this method, $CO_2$ is liquefied under pressure and heated to the point that it becomes supercritical (having properties of both a liquid and a gas), allowing it to act as a solvent.

Uses of Plant Lipids

The lipids produced by the methods described have a variety of uses. In some embodiments, the lipids are used as food oils. In other embodiments, the lipids are refined and used as lubricants or for other industrial uses such as the synthesis of plastics. In some preferred embodiments, the lipids are refined to produce biodiesel. Biodiesel can be made from oils derived from the plants, algae and fungi of the invention. Use of plant triacylglycerols for the production of biofuel is reviewed in Durrett et al. (2008). The resulting fuel is commonly referred to as biodiesel and has a dynamic viscosity range from 1.9 to 6.0 $mm^2s^{-1}$ (ASTM D6751). Bioalcohol may produced from the fermentation of sugars or the biomass other than the lipid left over after lipid extraction. General methods for the production of biofuel can be found in, for example, Maher and Bressler (2007), Greenwell et al. (2010), Karmakar et al. (2010), Alonso et al.

(2010), Liu et al. (2010). Gong and Jiang (2011), Endalew et al. (2011) and Semwal et al. (2011).

The present invention provides methods for increasing oil content in vegetative tissues. Plants of the present invention have increased energy content of leaves and/or stems such that the whole above-ground plant parts may be harvested and used to produce biofuel. Furthermore, the level of oleic acid is increased significantly while the polyunsaturated fatty acid alpha linolenic acid (ALA) was reduced. The plants, algae and fungi of the present invention thereby reduce the production costs of biofuel.

Biodiesel

The production of biodiesel, or alkyl esters, is well known. There are three basic routes to ester production from lipids: 1) Base catalysed transesterification of the lipid with alcohol; 2) Direct acid catalysed esterification of the lipid with methanol; and 3) Conversion of the lipid to fatty acids, and then to alkyl esters with acid catalysis. Any method for preparing fatty acid alkyl esters and glyceryl ethers (in which one, two or three of the hydroxy groups on glycerol are etherified) can be used. For example, fatty acids can be prepared, for example, by hydrolyzing or saponifying TAG with acid or base catalysts, respectively, or using an enzyme such as a lipase or an esterase. Fatty acid alkyl esters can be prepared by reacting a fatty acid with an alcohol in the presence of an acid catalyst. Fatty acid alkyl esters can also be prepared by reacting TAG with an alcohol in the presence of an acid or base catalyst. Glycerol ethers can be prepared, for example, by reacting glycerol with an alkyl halide in the presence of base, or with an olefin or alcohol in the presence of an acid catalyst. The alkyl esters can be directly blended with diesel fuel, or washed with water or other aqueous solutions to remove various impurities, including the catalysts, before blending.

Aviation Fuel

For improved performance of biofuels, thermal and catalytic chemical bond-breaking (cracking) technologies have been developed that enable converting bio-oils into bio-based alternatives to petroleum-derived diesel fuel and other fuels, such as jet fuel.

The use of medium chain fatty acid source, such produced by a cell of the invention, a plant or part thereof of the invention, a seed of of the invention, or a transgenic version of any one thereof, precludes the need for high-energy fatty acid chain cracking to achieve the shorter molecules needed for jet fuels and other fuels with low-temperature flow requirements. This method comprises cleaving one or more medium chain fatty acid groups from the glycerides to form glycerol and one or more free fatty acids. In addition, the method comprises separating the one or more medium chain fatty acids from the glycerol, and decarboxylating the one or more medium chain fatty acids to form one or more hydrocarbons for the production of the jet fuel.

Compositions

The present invention also encompasses compositions, particularly pharmaceutical compositions, comprising one or more plants, plant parts, lipids, proteins, nitrogen containing molecules, or carbon containing molecules, produced using the methods of the invention.

A pharmaceutical composition may additionally comprise an active ingredient and a standard, well-known, non-toxic pharmaceutically-acceptable carrier, adjuvant or vehicle such as phosphate-buffered saline, water, ethanol, polyols, vegetable oils, a wetting agent, or an emulsion such as a water/oil emulsion. The composition may be in either a liquid or solid form. For example, the composition may be in the form of a tablet, capsule, ingestible liquid, powder, topical ointment or cream. Proper fluidity can be maintained for example, by the maintenance of the required particle size in the case of dispersions and by the use of surfactants. It may also be desirable to include isotonic agents for example, sugars, sodium chloride, and the like. Besides such inert diluents, the composition can also include adjuvants such as wetting agents, emulsifying and suspending agents, sweetening agents, flavoring agents and perfuming agents.

A typical dosage of a particular fatty acid is from 0.1 mg to 20 g, taken from one to five times per day (up to 100 g daily) and is preferably in the range of from about 10 mg to about 1, 2, 5, or 10 g daily (taken in one or multiple doses). As known in the art, a minimum of about 300 mg/day of fatty acid, especially polyunsaturated fatty acid, is desirable. However, it will be appreciated that any amount of fatty acid will be beneficial to the subject.

Possible routes of administration of the pharmaceutical compositions of the present invention include for example, enteral and parenteral. For example, a liquid preparation may be administered orally. Additionally, a homogenous mixture can be completely dispersed in water, admixed under sterile conditions with physiologically acceptable diluents, preservatives, buffers or propellants to form a spray or inhalant.

The dosage of the composition to be administered to the subject may be determined by one of ordinary skill in the art and depends upon various factors such as weight, age, overall health, past history, immune status, etc., of the subject.

Additionally, the compositions of the present invention may be utilized for cosmetic purposes. The compositions may be added to pre-existing cosmetic compositions, such that a mixture is formed, or a fatty acid produced according to the invention may be used as the sole "active" ingredient in a cosmetic composition.

Polypeptides

The terms "polypeptide" and "protein" are generally used interchangeably herein.

A polypeptide or class of polypeptides may be defined by the extent of identity (% identity) of its amino acid sequence to a reference amino acid sequence, or by having a greater % identity to one reference amino acid sequence than to another. The % identity of a polypeptide to a reference amino acid sequence is typically determined by GAP analysis (Needleman and Wunsch, 1970; GCG program) with parameters of a gap creation penalty=5, and a gap extension penalty=0.3. The query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns two sequences over their entire length, and the extent of identity is determined over the full length of the reference sequence. The polypeptide or class of polypeptides may have the same enzymatic activity as, or a different activity than, or lack the activity of, the reference polypeptide. Preferably, the polypeptide has an enzymatic activity of at least 10% of the activity of the reference polypeptide.

As used herein a "biologically active fragment" is a portion of a polypeptide of the invention which maintains a defined activity of a full-length reference polypeptide for example, DGAT activity. Biologically active fragments as used herein exclude the full-length polypeptide. Biologically active fragments can be any size portion as long as they maintain the defined activity. Preferably, the biologically active fragment maintains at least 10% of the activity of the full length polypeptide.

With regard to a defined polypeptide or enzyme, it will be appreciated that % identity figures higher than those provided herein will encompass preferred embodiments. Thus, where applicable, in light of the minimum % identity figures, it is preferred that the polypeptide/enzyme comprises an amino acid sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides defined herein can be prepared by introducing appropriate nucleotide changes into a nucleic acid defined herein, or by in vitro synthesis of the desired polypeptide. Such mutants include for example, deletions, insertions, or substitutions of residues within the amino acid sequence. A combination of deletions, insertions and substitutions can be made to arrive at the final construct, provided that the final polypeptide product possesses the desired characteristics.

Mutant (altered) polypeptides can be prepared using any technique known in the art, for example, using directed evolution or rathional design strategies (see below). Products derived from mutated/altered DNA can readily be screened using techniques described herein to determine if they possess transcription factor, fatty acid acyltransferase or OBC activities.

In designing amino acid sequence mutants, the location of the mutation site and the nature of the mutation will depend on characteristic(s) to be modified. The sites for mutation can be modified individually or in series for example, by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide removed and a different residue inserted in its place. The sites of greatest interest for substitutional mutagenesis to inactivate enzymes include sites identified as the active site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

TABLE 1

| Exemplary substitutions. | |
|---|---|
| Original Residue | Exemplary Substitutions |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

In a preferred embodiment a mutant/variant polypeptide has only, or not more than, one or two or three or four conservative amino acid changes when compared to a naturally occurring polypeptide. Details of conservative amino acid changes are provided in Table 1. As the skilled person would be aware, such minor changes can reasonably be predicted not to alter the activity of the polypeptide when expressed in a transgenic plant or part thereof. Mutants with desired activity may be engineered using standard procedures in the art such as by performing random mutagenesis, targeted mutagenesis, or saturation mutagenesis on known genes of interest, or by subjecting different genes to DNA shuffling.

EXAMPLES

Example 1. General Materials and Methods

Expression of Genes in Plant Cells in a Transient Expression System

Genes were expressed in plant cells using a transient expression system essentially as described by Voinnet et al. (2003) and Wood et al. (2009). Binary vectors containing the coding region to be expressed by a strong constitutive e35S promoter containing a duplicated enhancer region were introduced into Agrobacterium tumefaciens strain AGL1. A chimeric binary vector, 35S:p19, for expression of the p19 viral silencing suppressor was separately introduced into AGL1, as described in WO2010/057246. A chimeric binary vector, 35S:V2, for expression of the V2 viral silencing suppressor was separately introduced into AGL1. The recombinant cells were grown to stationary phase at 28° C. in LB broth supplemented with 50 mg/L kanamycin and 50 mg/L rifampicin. The bacteria were then pelleted by centrifugation at 5000 g for 5 min at room temperature before being resuspended to OD600=1.0 in an infiltration buffer containing 10 mM MES pH 5.7, 10 mM $MgCl_2$ and 100 uM acetosyringone. The cells were then incubated at 28° C. with shaking for 3 hours after which the OD600 was measured and a volume of each culture, including the viral suppressor construct 35S:p19 or 35S:V2, required to reach a final concentration of OD600=0.125 added to a fresh tube. The final volume was made up with the above buffer. Leaves were then infiltrated with the culture mixture and the plants were typically grown for a further three to five days after infiltration before leaf discs were recovered for either purified cell lysate preparation or total lipid isolation.

Transformation of Sorghum bicolor L.

Plant Material

Sorghum plants of the inbred cultivar TX-430 (Miller, 1984) were grown in a plant growth chamber (Conviron, PGC-20 flex) at 28±1° C. "day" temperature and 20±1° C. "night" temperature, with a 16 hr photoperiod at a light intensity during the "day" of 900-1000 LUX. Panicles were covered with white translucent paper bags before flowering. Immature embryos were harvested from panicles 12-15 days after anthesis. Panicles were washed several times with water and developing seeds that were uniform in size were isolated and surface-sterilized using 20% commercial bleach mixed with 0.1% Tween-20 for 15-20 min. They were then washed with sterile distilled water 3 times each for 20 min, and blotted dry in a laminar flow hood. Immature embryos (IEs) ranging from 1.4 to 2.5 mm in length were aseptically isolated in the laminar flow hood and used as the starting tissue for preparation of green regenerative tissue.

Base Cultivation Media

Media used for plant transformation were based on MS (Murashige and Skoog, 1962), supplied by PhytoTechnology Laboratories (M519). The pH of the media was adjusted to 5.8 before sterilization at 121° C. for 15 min. Heat sensitive plant growth regulators and other additives such as Geneticin (G418, Sigma) used as a selection agent, were filter sterilized (0.2 μm) and added to the media after sterilization when the media had cooled to about 55° C. The optimized culture medium composition for the different stages of plant transformation from callus induction to plant regeneration from green tissue induced from immature embryos is presented in Table 2.

Cultivation Methods and Materials

The isolated IEs ranging from 1.4 to 2.5 mm in length were placed onto callus induction media-osmotic medium (CIM-osmotic medium, Table 2) with their scutellum facing upward. The CIM base medium was modified to improve callus quality and induction frequency from immature embryos, as well as callus regeneration media, by including α-Lipoic acid (1 to 5 mg/1), Melatonin (5 to 10 mg/1) and 2-Aminoidan-2-phosphonic acid HCl (1 to 2 mg/1) unless otherwise stated. For the development of green tissue, immature embryos were incubated under fluorescent light of approximately 45-50 μmol s$^{-1}$ m$^{-2}$ (16 h/day) in a tissue culture room at 24±2° C. After three days of culture, the root and shoot poles of the immature embryos were aseptically separated and re-inoculated on to the same CIM and maintained under the same conditions as described above. They were subcultured every two weeks onto the same CIM for 6 weeks and evaluated for callus quality, callus induction efficiency and transformation efficiency.

TABLE 2

Media used in DEC tissue induction and transformation of sorghum

| Name of the medium | Composition | Culture duration |
| --- | --- | --- |
| CIM-Osmotic Medium | MS medium powder with vitamins, 4.33 g/l; 2,4-D, 1 mg/l; BAP, 0.5 mg/l; L-proline, 0.7 g/l; L-Lipoic acid, 1 mg/l; peptone, 0.82 g/l; Myo-inositol, 150 mg/l; Copper sulfate, 0.8 mg/l; Manitol, 36.4 g/l; Sorbitol, 36.4 g/l; Agar, 8.5 g/l, pH 5.8 | 3-4 hrs before bombardment; o/n post bombardment |
| CIM- pre selection medium | MS medium powder with vitamins, 4.33 g/l; 2,4-D, 1 mg/l; BAP, 0.5 mg/l; L-proline, 0.7 g/l; L-Lipoic acid, 1 mg/l; peptone, 0.82 g/l; Myo-inosito, 1 150 mg/l; Copper sulfate, 0.8 mg/l; Maltose, 30 g/l; L-cysteine, 50 mg/l; Ascorbic acid, 15 mg/l; Agar, 9 g/l, pH 5.8 | 3-4 days |
| CIM-callus induction medium/G25 | MS medium powder with vitamins, 4.33 g/l; 2,4-D, 1 mg/l; BAP, 0.5 mg/l; L-proline, 0.7 g/l; L-Lipoic acid, 1 mg/l; peptone, 0.82 g/l; Myo-inositol, 150 mg/l; Copper sulfate, 0.8 mg/l; Maltose, 30 g/l; Geneticin, 25 mg/l; Agar, 9 g/l, pH 5.8 | 4 weeks |
| SIM-shoot induction medium/G25 | MS medium powder with vitamins, 4.33 g/l; BAP, 1.0 mg/l; 2,4-D, 0.5 mg/l; L-proline, 0.7 g/l; L-Lipoic acid, 1 mg/l; peptone, 0.82 g/l; Myo-inositol, 150 mg/l; Copper sulfate, 0.8 mg/l; Maltose, 30 g/l; Geneticin, 25 mg/l; Agar, 9 g/l, pH 5.8 | 2 weeks |
| SRM- shoot regeneration medium/G25 | MS medium powder with vitamins, 4.33 g/l; BAP, 1.0 mg/l; TDZ, 0.5 mg/l; L-proline, 0.7 g/l; L-Lipoic acid, 1 mg/l; peptone, 0.82 g/l; Myo-inositol, 150 mg/l; Copper sulfate, 0.8 mg/l; Maltose, 30 g/l; Geneticin, 25 mg/l; Agar, 9 g/l, pH 5.8 | 2 weeks |
| SOG-shoot out growth medium/G30 | MS medium powder with vitamins, 2.2 g/l; L-proline, 0.7 g/l; L-Lipoic acid, 1 mg/l; peptone, 0.82 g/l; Myo-inositol, 150 mg/l; Copper sulfate, 0.8 mg/l; Sucrose, 15 g/l; Geneticin, 30 mg/l; Agar, 9 g/l, pH 5.8 | 2 weeks |
| RIM-root induction medium/G15 | MS medium powder with vitamins, 4.33 g/l; L-proline, 0.7 g/l; L-Lipoic acid, 1 mg/l; peptone, 0.82 g/l; Myo-inositol, 150 mg/l; Copper sulfate, 0.8 mg/l; sucrose, 15 g/l; IAA, 1 mg/l; IBA, 1 mg/l; NAA, 1 mg/l; PVP, 2 g/l; Geneticin, 15 mg/l; Agar 9 g/l, pH 5.8 | 4 weeks |

Callus initiated from IEs in the first 3-4 weeks on CIM were mostly embryogenic and slowly differentiated into embryogenic callus with nodular structures which were coloured from pale to darker green. Embryogenic calli with green nodular structures were selected and maintained on the same medium (CIM) by subculturing every 2 weeks for up to 6 months or more, for use as explants for transformation. This type of tissue is termed herein as "differentiating embryogenic callus" tissue or "DEC" tissue, since this tissue forms nodular structures of differentiating cells which maintain embryogenic and organogenic potential, even though the tissues were really a mixture of callus cells, cells forming nodular structures and granular structures, and intermediate cells which the inventors understood were on the developmental pathway somewhere between callus (which is undifferentiated cells) and the nodular structures. Sometimes, the tissues included early stage (globular) somatic embryos.

Particle-Bombardment of Green Regenerative DEC Tissues

Plasmids containing a selectable marker gene encoding the neomycin phosphotransferase II (NptII) providing resistance to the antibiotic Geneticin, under the control of the pUbi promoter and terminated by the nos 3' region, were made or obtained for experiments to achieve stable transformation or for co-bombardment with other plasmids. Plasmid DNAs were isolated using a Zymopure™ Maxiprep kit (USA) according to the manufacturer's instructions. As a control vector for transformation, a genetic vector was obtained which contained uidA (GUS) and bar genes designed for expression in plant cells. The uidA gene was under the regulatory control of a maize polyubiquitin promoter (pUbi) and an *Agrobacterium tumefaciens* octopine synthase polyadenylation/terminator (ocs 3') sequence. The sequence between the promoter and the protein coding region included the 5' UTR and first intron of the Ubi gene. The uidA reporter gene also contained, within its protein coding region, an intron from a castor bean catalase gene which prevented translation of functional GUS protein in *Agrobacterium*, thereby reducing the background GUS gene expression in inoculated plant tissues. Therefore, any GUS expression would be due to expression of the uidA gene in the plant cells. The bar gene was also under the regulatory control of a pUbi promoter and terminated with an *Agrobacterium* nopaline synthase 3' regulatory sequence (nos 3'). The uidA/bar vector was initially used in experiments to detect transient gene expression in the sorghum DEC tissues.

Uniform healthy, green regenerative DEC tissues (4-5 mm in size), produced using methods described above and having been cultured for 6 weeks to 6 months from initiation, were used for microprojectile-mediated transformation (bombardment) with the plasmids. Approximately 15 uniform green DEC tissues (each 4-5 mm) were placed at the centre of a petri dish (90 mm diameter) containing CIM-osmotic medium (Table 2) and incubated in the dark for about 4 hrs prior to bombardment. Bombardment was performed with a PDS-1000 He device (Biorad, Hercules, CA) as described by Liu et al. (2014). Post bombardment, the tissues were kept on the same osmotic medium overnight and transferred to pre-selection medium the next morning Green DEC tissues bombarded with the genetic vector plasmid having a selectable marker encoding NptII were transferred to CIM-PS medium for 3-4 days before any selection, with addition to the medium of two compounds as antioxidants, L-cysteine (50 mg/l) and ascorbic acid (15 mg/l) (Table 2). Without the addition of these antioxidants in pre-selection medium, many of the bombarded tissues turned brown, some quite dark brown in colour, and many lost any ability to grow further. After 3-4 days on pre-selection medium, some of the bombarded tissues were subjected to GUS staining and viewed under a microscope to count the distinctive blue (GUS positive) spots, to check that genes had been transferred and could be expressed. The inclusion of the two antioxidants in the pre-selection medium improved the efficiency of the transformation as shown by the transient expression of the GUS gene.

Selection and Regeneration of Transgenic Plants with Optimised Conditions

Following bombardment and 3-4 days culture on pre-selection medium without selective agent (Geneticin), the bombarded tissues had increased in size from 4-5 mm to about 6-7 mm. These tissues were transferred to selective medium CIM/G25 containing 25 mg/l Geneticin (Table 2) and cultured for a further 4 weeks. When possible, the bombarded tissues were split into 2-6 pieces each, increasing the recovery of independent transformants. All of the tissues were cultured on the media as described in Table 2 and maintained in order to regenerate putative transgenic plants.

Plants were regenerated efficiently upon growth on these media. Each bombarded tissue and the shoots obtained from it were subcultured and maintained separately for calculation of the transformation efficiency. Positive transformation was confirmed by PCR on plant genomic DNA isolated from shoot samples, showing the presence of the selectable marker gene. The number of transformants was calculated per input DEC tissue. Transformation efficiencies of about 50% were obtained, expressed as independent transformants per input bombarded tissue.

Agrobacterium-Mediated Transformation of Green Regenerative DEC Tissues

Uniform healthy, green regenerative DEC tissues (4-5 mm in size) produced using methods described in the foregoing examples and which have been cultured for 6 weeks to 6 months from initiation, are used for *Agrobacterium*-mediated transformation.

Genetic vectors having T-DNA regions containing the genes for transformation were designed and made for transformation of green regenerative DEC tissues using *Agrobacterium*-mediated transformation. A control binary vector contained uidA (GUS) and bar genes designed for expression in plant cells. The uidA gene was under the regulatory control of a maize polyubiquitin promoter (pUbi) and an *Agrobacterium tumefaciens* octopine synthase polyadenylation/terminator (ocs 3') sequence. The sequence between the promoter and the protein coding region included the 5' UTR and first intron of the Ubi gene. The uidA reporter gene also contained, within its protein coding region, an intron from a castor bean catalase gene which prevented translation of functional GUS protein in *Agrobacterium*, thereby reducing the background GUS gene expression in inoculated plant tissues. Therefore, any GUS expression was due to expression of the uidA gene in the plant cells. The bar gene was also under the regulatory control of a pUbi promoter and terminated with an *Agrobacterium* nopaline synthase 3' regulatory sequence (nos 3').

A suitable *Agrobacterium tumefaciens* strain was obtained e.g., AGL1 as described in Lazo et al. (1991) and the genetic vector is introduced into the *Agrobacterium tumefaciens* strain by heat shock method.

*Agrobacterium* cultures harboring the genetic construct are grown in suitable medium e.g., LB medium, and under appropriate conditions to produce an *Agrobacterium* inoculum, after which time the uniform healthy, green regenerative DEC tissues are infected with *Agrobacterium* inoculum. The infected DEC tissues are blotted on sterile filter paper to remove excess *Agrobacterium* and transferred to co-cultivation medium, optionally supplemented with antioxidants, and incubated in the dark at approximately 22-24° C. for 2-4 days. Following incubation, the DEC tissues are treated with an appropriate agent to kill the *Agrobacterium*, washed in sterile water, transferred to an appropriate medium and allowed to grow. After 4-6 weeks, shoots are excised and cultured on shoot elongation medium, after which time putative transgenic shoots are then detected using appropriate assays.

Brassica napus Transformation

*Brassica napus* seeds were sterilized using chlorine gas as described by Kereszt et al. (2007) and germinated on tissue culture medium. Cotyledonary petioles with 2-4 mm stalk were isolated as described by Belide et al. (2013) and used as explants. *A. tumefaciens* AGL1 (Lazo et al., 1991) cultures containing the binary vector were prepared and cotyledonary petioles inoculated with the cultures as described by Belide et al. (2013). Infected cotyledonary petioles were cultured on MS medium supplemented with 1 mg/L TDZ+0.1 mg/L NAA+3 mg/L AgNO$_3$+250 mg/L cefotaxime, 50 mg/L timentin and 25 mg/L kanamycin and cultured for 4 weeks at 24° C. with 16 hr/8 hr light-dark photoperiod with a biweekly subculture on to the same medium. Explants with green callus were transferred to shoot initiation medium (MS+1 mg/L kinetin+3 mg/L AgNO$_3$+250 mg/L cefotaxime+50 mg/L timentin+25 mg/L kanamycin) and cultured for another 2-3 weeks. Small shoots (~1 cm) were isolated from the resistant callus and transferred to shoot elongation medium (MS medium with 0.1 mg/L gibberelic acid+3 mg/L AgNO$_3$+250 mg/L cefotaxime+25 mg/L kanamycin) and cultured for another two weeks. Healthy shoots with one or two leaves were selected and transferred to rooting media (½ MS with 1 mg/L NAA+20 mg/L ADS+3 mg/L AgNO$_3$+250 mg/L cefotaxime) and cultured for 2-3 weeks. DNA was isolated from small leaves of resistant shoots using the plant DNA isolation kit (Bioline, Alexandria, NSW, Australia) according to the manufacturer's protocol. Presence of T-DNA sequences was tested by PCR ampl. on genomic DNA. Positive, transgenic shoots with roots were transferred to pots with seedling raising mix and grown in a glasshouse at 24° C. daytime/16° C. night-time (stnd. conditions).

Purified Leaf Lysate—Enzyme Assays

*Nicotiana benthamiana* leaf tissues previously infiltrated as described above were ground in a solution containing 0.1 M potassium phosphate buffer (pH 7.2) and 0.33 M sucrose using a glass homogenizer. Leaf homogenate was centrifuged at 20,000 g for 45 minutes at 4° C. after which each supernatant was collected. Protein content in each supernatant was measured according to Bradford (1976) using a Wallac1420 multi-label counter and a Bio-Rad Protein Assay dye reagent (Bio-Rad Laboratories, Hercules, CA USA). Acyltransferase assays used 100 µg protein according to Cao et al. (2007) with some modifications. The reaction medium contained 100 mM Tris-HCl (pH 7.0), 5 mM MgCl$_2$, 1 mg/mL BSA (fatty acid-free), 200 mM sucrose, 40 mM cold oleoyl-CoA, 16.4 µM sn-2 monooleoylglycerol [$^{14}$C] (55 mCi/mmol, American Radiochemicals, Saint Louis, MO USA) or 6.0 µM [$^{14}$C]glycerol-3-phosphate (G-3-P) disodium salt (150 mCi/mmol, American Radiochemicals). The assays were carried out for 7.5, 15, or 30 minutes.

Lipid Analysis

Analysis of Oil Content in Seeds

When seed oil content or total fatty acid composition was to be determined in small seeds such as *Arabidopsis* seeds, fatty acids in the seeds were directly methylated without crushing of seeds. Seeds were dried in a desiccator for 24 hours and approximately 4 mg of seed was transferred to a 2 ml glass vial containing a Teflon-lined screw cap. 0.05 mg triheptadecanoin (TAG with three C17:0 fatty acids) dissolved in 0.1 ml toluene was added to the vial as internal standard. Seed fatty acids were methylated by adding 0.7 ml of 1N methanolic HCl (Supelco) to the vial containing seed material. Crushing of the seeds was not necessary for complete methylation with small seeds such as *Arabidopsis* seeds. The mixture was vortexed briefly and incubated at 80° C. for 2 hours. After cooling the mixtures to room temperature, 0.3 ml of 0.9% NaCl (w/v) and 0.1 ml hexane was added to the vial and mixed well for 10 minutes in a Heidolph Vibramax 110. The FAME were collected into 0.3 ml glass insert and analysed by GC with flame ionization detector (FID) as described below.

The peak area of individual FAME were first corrected on the basis of the peak area responses of a known amount of the same FAMEs present in a commercial standard GLC-411 (NU-CHEK PREP, INC., USA). GLC-411 contains equal amounts of 31 fatty acids (% by weight), ranging from C8:0 to C22:6. In case of fatty acids which were not present in the standard, the peak area responses of the most similar FAME was taken. For example, the peak area response of FAMEs of 16:1d9 was used for 16:1d7 and the FAME response of C22:6 was used for C22:5. The corrected areas were used to calculate the mass of each FAME in the sample by comparison to the internal standard mass. Oil is stored mainly in the form of TAG and its weight was calculated based on FAME weight. Total moles of glycerol was determined by calculating moles of each FAME and dividing total moles of FAMEs by three. TAG content was calculated as the sum of glycerol and fatty acyl moieties using a relation: % oil by weight=100×((41× total mol FAME/3)+(total g FAME−(15× total mol FAME)))/g seed, where 41 and 15 are molecular weights of glycerol moiety and methyl group, respectively.

Analysis of Fatty Acid Content in Larger Seeds

To determine fatty acid composition in single seeds that were larger, such as canola and Camelina seeds, or *Sorghum* or corn seeds, direct methylation of fatty acids in the seed was performed as for *Arabidopsis* seeds except with breaking of the seed coats. This method extracted sufficient oil from the seed to allow fatty acid composition analysis. To determine the fatty acid composition of total extracted lipid from seeds, seeds were crushed and lipids extracted with CHCl$_3$/MeOH. Aliquots of the extracted lipid were methylated and analysed by GC. Pooled seed-total lipid content (seed oil content) of canola was determined by two extractions of lipid using CHCl$_3$/MeOH from a known weight of desiccated seeds after crushing, followed by methylation of aliquots of the lipids together with the 17:0 fatty acids as internal standard. In the case of larger seeds such as Camelina, the lipid from a known amount of seeds was methylated together with known amount of 17:0 fatty acids as for the *Arabidopsis* oil analysis and FAME were analysed by GC. For TAG quantitation, TAG was fractionated from the extracted lipid using TLC and directly methylated in silica using 17:0 TAG as an internal standard. The methods are described as follows.

After harvest at plant maturity, seeds were desiccated by storing the seeds for 24 hours at room temperature in a desiccator containing silica gel as desiccant. Moisture content of the seeds was typically 6-8%. Total lipids were extracted from known weights of the desiccated seeds by crushing the seeds using a mixture of chloroform and methanol (2/1 v/v) in an eppendorf tube using a Reicht tissue lyser (22 frequency/seconds for 3 minutes) and a metal ball. One volume of 0.1M KCl was added and the mixture shaken for 10 minutes. The lower non-polar phase was collected after centrifuging the mixture for 5 minutes at 3000 rpm. The remaining upper (aqueous) phase was washed with 2 volumes of chloroform by mixing for 10 minutes. The second non-polar phase was also collected and pooled with the first. The solvent was evaporated from the lipids in the extract under nitrogen flow and the total dried lipid was dissolved in a known volume of chloroform.

To measure the amount of lipid in the extracted material, a known amount of 17:0-TAG was added as internal standard and the lipids from the known amount of seeds incubated in 1 N methanolic-HCl (Supelco) for 2 hours at 80° C. FAME thus made were extracted in hexane and analysed by GC. Individual FAME were quantified on the basis of the amount of 17:0 TAG-FAME. Individual FAME weights, after subtraction of weights of the esterified methyl groups from FAME, were converted into moles by dividing by molecular weights of individual FAME. Total moles of all FAME were divided by three to calculate moles of TAG and therefore glycerol. Then, moles of TAG were converted in to weight of TAG. Finally, the percentage oil content on a seed weight basis was calculated using seed weights, assuming that all of the extracted lipid was TAG or equivalent to TAG for the purpose of calculating oil content. This method was based on Li et al. (2006). Seeds other than Camelina or canola seeds that are of a similar size can also be analysed by this method.

Canola and other seed oil content can be measured by nuclear magnetic resonance techniques (Rossell and Pritchard, 1991) by a pulsed wave NMS 100 Minispec (Bruker Pty Ltd Scientific Instruments, Germany). The NMR method can simultaneously measured moisture content. Seed oil content can also be measured by near infrared reflectance (NIR) spectroscopy such as using a NIRSystems Model 5000 monochromator. Moisture content can also be measured on a sample from a batch of seeds by drying the seeds in the sample for 18 hours at about 100° C., according to Li et al. (2006).

Analysis of Lipids from Leaf Lysate Assays

Lipids from the lysate assays were extracted using chloroform:methanol:0.1 M KCl (2:1:1) and recovered. The different lipid classes in the samples were separated on Silica gel 60 thin layer chromatography (TLC) plates (MERCK, Dermstadt, Germany) impregnated with 10% boric acid. The solvent system used to fractionate TAG from the lipid extract was chloroform/acetone (90/10 v/v). Individual lipid classes were visualized by exposing the plates to iodine vapour and identified by running parallel authentic standards on the same TLC plate. The plates were exposed to phosphor imaging screens overnight and analysed by a Fujifilm FLA-5000 phosphorimager before liquid scintillation counting for DPM quantification.

Total Lipid Isolation and Fractionation of Lipids from Vegetative Tissues

Fatty acid composition of total lipid in leaf and other vegetative tissue samples was determined by direct methylation of the fatty acids in freeze-dried samples. For total lipid quantitation, fatty acids in a known weight of freeze-dried samples, with 17:0 FFA, were directly methylated. To determine total TAG levels in leaf samples, TAG was fractionated by TLC from extracted total lipids, and methylated in the presence of 17:0 TAG internal standard, because of the presence of substantial amounts of polar lipids in leaves. This was done as follows. Tissues including leaf samples were freeze-dried, weighed (dry weight) and total lipids extracted as described by Bligh and Dyer (1959) or by using chloroform:methanol:0.1 M KCl (CMK; 2:1:1) as a solvent. Total lipids were extracted from $N.$ $benthamiana$ leaf samples, after freeze dying, by adding 900 µL of a chloroform/methanol (2/1 v/v) mixture per 1 cm diameter leaf sample. 0.8 µg DAGE was added per 0.5 mg dry leaf weight as internal standard when TLC-FID analysis was to be performed. Samples were homogenized using an IKA ultra-turrax tissue lyser after which 500 µL 0.1 M KCl was added. Samples were vortexed, centrifuged for 5 min and the lower phase was collected. The remaining upper phase was extracted a second time by adding 600 µL chloroform, vortexing and centrifuging for 5 min. The lower phase was recovered and pooled into the previous collection. Lipids were dried under a nitrogen flow and resuspended in 2 µL chloroform per mg leaf dry weight. Total lipids of $N.$ $tabacum$ leaves or leaf samples were extracted as above with some modifications. If 4 or 6 leaf discs (each approx 1 cm² surface area) were combined, 1.6 ml of CMK solvent was used, whereas if 3 or less leaf discs were combined, 1.2 ml CMK was used. Freeze dried leaf tissues were homogenized in an eppendorf tube containing a metallic ball using a Reicht tissue lyser (Qiagen) for 3 minutes at 20 frequency/sec.

Separation of Neutral Lipids Via TLC and Transmethylation

Known volumes of total leaf extracts such as, for example, 30 µL were loaded on a TLC silica gel 60 plate (1×20 cm) (Merck KGaA, Germany). The neutral lipids were fractionated into the different types and separated from polar lipids via TLC in an equilibrated development tank containing a hexane/DEE/acetic acid (70/30/1 v/v/v/) solvent system. The TAG bands were visualised by primuline spraying, marked under UV, scraped from the TLC plate, transferred to 2 mL GC vials and dried with $N_2$. 750 µL of 1N methanolic-HCl (Supelco analytical, USA) was added to each vial together with a known amount of C17:0 TAG as an internal standard, depending on the amount of TAG in each sample. Typically, 30 µg of the internal standard was added for low TAG samples whilst up to 200 µg of internal standard was used in the case of high TAG samples.

Lipid samples for fatty acid composition analysis by GC were transmethylated by incubating the mixtures at 80° C. for 2 hours in the presence of the methanolic-HCl. After cooling samples to room temperature, the reaction was stopped by adding 350 µl $H_2O$. Fatty acyl methyl esters (FAME) were extracted from the mixture by adding 350 µl hexane, vortexing and centrifugation at 1700 rpm for 5 min. The upper hexane phase was collected and transferred into GC vials with 300 µl conical inserts. After evaporation, the samples were resuspended in 30 µl hexane. One µl was injected into the GC.

The amount of individual and total fatty acids (TFA) present in the lipid fractions was quantified by GC by determining the area under each peak and calculated by comparison with the peak area for the known amount of internal standard. TAG content in leaf was calculated as the sum of glycerol and fatty acyl moieties in the TAG fraction using a relation: % TAG by weigh=100×((41× total mol FAME/3)+(total g FAME−(15× total mol FAME)))/g leaf dry weight, where 41 and 15 are molecular weights of glycerol moiety and methyl group, respectively.

Capillary Gas-Liquid Chromatography (GC)

FAME were analysed by GC using an Agilent Technologies 7890A GC (Palo Alto, California, USA) equipped with an SGE BPX70 (70% cyanopropyl polysilphenylene-siloxane) column (30 m×0.25 mm i.d., 0.25 µm film thickness), an FID, a split/splitless injector and an Agilent Technologies 7693 Series auto sampler and injector. Helium was used as the carrier gas. Samples were injected in split mode (50:1 ratio) at an oven temperature of 150° C. After injection, the oven temperature was held at 150° C. for 1 min, then raised to 210° C. at 3° C.·min$^{-1}$ and finally to 240° C. at 50° C.·min$^{-1}$. Peaks were quantified with Agilent Technologies ChemStation software (Rev B.04.03 (16), Palo Alto, California, USA) based on the response of the known amount of the external standard GLC-411 (Nucheck) and C17:0-Me internal standard.

Quantification of TAG Via Iatroscan

One µL of lipid extract was loaded on one Chromarod-SII for TLC-FID Iatroscan™ (Mitsubishi Chemical Medience Corporation—Japan). The Chromarod rack was then transferred into an equilibrated developing tank containing 70 mL of a hexane/CHCl$_3$/2-propanol/formic acid (85/10.716/0.567/0.0567 v/v/v/v) solvent system. After 30 min of incubation, the Chromarod rack was dried for 3 min at 100° C. and immediately scanned on an Iatroscan MK-6s TLC-FID analyser (Mitsubishi Chemical Medience Corporation—Japan). Peak areas of DAGE internal standard and TAG were integrated using SIC-48011 integration software (Version: 7.0-E SIC System instruments Co., LTD—Japan).

TAG quantification was carried out in two steps. First, DAGE was scanned in all samples to correct the extraction yields after which concentrated TAG samples were selected and diluted. Next, TAG was quantified in diluted samples with a second scan according to the external calibration using glyceryl trilinoleate as external standard (Sigma-Aldrich).

Quantification of TAG in Leaf Samples by GC

The peak area of individual FAME were first corrected on the basis of the peak area responses of known amounts of the same FAMEs present in a commercial standard GLC-411 (NU-CHEK PREP, Inc., USA). The corrected areas were used to calculate the mass of each FAME in the sample by comparison to the internal standard. Since oil is stored primarily in the form of TAG, the amount of oil was calculated based on the amount of FAME in each sample. Total moles of glycerol were determined by calculating the number of moles of FAMEs and dividing total moles of FAMEs by three. The amount of TAG was calculated as the sum of glycerol and fatty acyl moieties using the formula: % oil by weight=100×((41× total mol FAME/3)+(total g FAME-(15× total mol FAME)))/g leaf dry weight, where 41 and 15 were the molecular weights of glycerol moiety and methyl group, respectively.

Total Lipid Extraction and Fatty Acid Profile Analysis

Total lipids were extracted from freeze-dried *N. benthamiana* leaves. During the extraction of total lipids, TAG 51:0 (tri-C17:0) was added as the internal standard for the quantification of both the TAG and total fatty acid (TFA) contents. Freeze dried leaf tissue was ground to powder in a microcentrifuge tube containing a metallic ball using Reicht tissue lyser (Qiagen) for 3 min at 20 frequency/s. Chloroform:methanol (2:1, v/v) was added and mixed for a further 3 min. on the tissue lyser before the addition of 1:3 (v/v) of 0.1 M KCl. The sample was then mixed for a further 3 min. before centrifugation (5 min. at 14,000 g), after which the lower lipid phase was collected. The remaining phase was washed once with chloroform, and the lower phase extracted and pooled with the earlier extract. Lipid phase solvent was then evaporated completely using N$_2$ gas flow and the lipids resuspended in 5 μL chloroform per mg of original dry leaf weight.

Fatty acid methyl esters (FAMEs) of total lipids (equivalent to 10 mg dry weight) were produced by incubating extracted lipid in 1 N methanolic-HCl (Supelco, Bellefonte, PA) at 80° C. for 3 hours. FAMEs were analyzed by an Agilent 7890A gas chromatograph coupled with flame ionisation detector (GC-FID, Agilent Technologies, Palo Alto, CA), on a BPX70 column (30 m, 0.25 mm inner diameter, 0.25 μm film thickness, SGE) essentially as described previously (Zhou et al., 2011), except the column temperature program. The column temperature was programmed as an initial temperature at 100° C. holding for 3 min, ramping to 240° C. at a rate of 7° C./min and holding for 1 min NuChek GLC-426 was used as the external reference standard. Peaks were integrated with Agilent Technologies ChemStation software (Rev B.04.03 (16)).

TLC Analysis

From the total lipid extracts (equivalent to 10 mg dry weight of plant tissue), TAG and polar lipids were fractionated by TLC (Silica gel 60, MERCK) using hexane:diethylether:acetic acid (70:30:1 v/v/v) and visualized by spraying Primuline (Sigma, 5 mg/100 ml acetone:water (80:20 v/v)) and exposing plate under UV. TLC analysis was primarily used for the identification of fatty acid composition of TAG and phospholipids from lipid extraction samples. This also enabled the determination of the total TAG content for each sample. The TAG and phospholipid fractions were scraped from the TLC plates and methylated according to the FAME preparation protocol described previously.

LC-MS Analysis

Lipids extracted from 1 mg dry leaf weight were dissolved and diluted to 1 mg/ml in mL butanol:methanol (1:1, v/v) and analyzed by liquid chromatography-mass spectrometry (LC-MS), based on previously described methods (Petrie et al., 2012). Briefly, lipids were chromatographically separated using a Waters BEH C8 (100 mm×2.1 mm, 2.7 μm) fitted to an Agilent 1290 series LC and 6490 triple quadrupole LC-MS with Jet Stream ionisation with a binary gradient flow rate of 0.2 mL/min. The mobile phases were: A. H$_2$O:acetonitrile (10:90, v/v) with 10 mM ammonium formate and 0.2% acetic acid; B. H$_2$O:acetonitrile:isopropanol (5:15:80, v/v) with 10 mM ammonium formate and 0.2% acetic acid. For the phosphatidylcholine (PC) and lysophosphatidylcholine (LPC) species hydrogen adducts were quantified by the characteristic 184 m/z phosphatidyl head group ion under positive ionisation mode. The ammonium adducts of monogalactosyl diacylglycerol (MGDG), digalactosyl diacylglycerol (DGDG), diacylglycerol (DAG) and TAG lipid species were analyzed by the neutral loss of singular fatty acids C$_{12}$ to C$_{18}$. Multiple reaction monitoring (MRM) lists were based on the following major fatty acids: 12:0, 14:0, 16:0, 16:3, 18:0, 18:1, 18:2, 18:3, using a collision energy of 28 V for all lipid classes except for DAG where a collision energy of 14 V was used. Individual MRM TAG was identified based on ammoniated precursor ion and product ion from neutral loss.

Example 2. Modifying Traits in Vegetative Parts of Monocotyledonous Plants

Chimeric DNA constructs were designed to increase oil content in monocotyledonous plants, for example the C4 plant *S. bicolor* (sorghum), by expressing a combination of genes encoding WRI1, *Z. mays* LEC1 (Accession number AAK95562; SEQ ID NO:32), DGAT and Oleosin in the transgenic plants. Several pairs of constructs for biolistic co-transformation were designed and produced by restriction enzyme-ligation cloning, as follows.

The genetic construct pOIL136 was a binary vector containing three monocot expression cassettes, namely a selectable marker gene encoding phosphinothricin acetyltransferase (PAT) for plant selection, a second cassette for expressing DGAT and a third for expressing Oleosin. pJP136 was first produced by amplifying an Actin-1 gene promoter from *Oryza sativa* (McElroy et al., 1990) and inserting it as a blunt-ClaI fragment into pORE04 (Coutu et al., 2007) to produce pOIL094. pOIL095 was then produced by inserting a version of the *Sesamum indicum* Oleosin L gene which had been codon optimised for monocot expression into pOIL094 at the KpnI site. pOIL093 was produced by cloning a monocot (*Triticum aestivum*) codon optimised version of the *Umbelopsis ramanniana* DGAT2a gene (Lardizabal et al., 2008) as a SmaI-KpnI fragment into a vector already containing a *Zea mays* Ubiquitin gene promoter. pOIL134 was then produced by cloning the NotI DGAT2a expression cassette from pOIL093 into pOIL095 at the NotI sites. pOIL141 was produced by inserting the selectable marker gene coding for PAT as a BamHI-SacI fragment into a vector containing the Z. mays Ubiquitin-1 promoter. Finally, pOIL136 was produced by cloning the Z. mays Ubiquitin::PAT expression cassette as a blunt-AscI fragment into the ZraI-AscI of pOIL096. The genetic construct pOIL136 therefore contained the following expression cassettes: promoter O. sativa Actin::S. indicum Oleosin, promoter Z. mays Ubiquitin::U. ramanniana DGAT2a and promoter Z. mays Ubiquitin::PAT.

A similar vector pOIL197, containing NPTII instead of PAT was constructed by subcloning of the Z. mays Ubiquitin::NPTII cassette from pUKN (Liu and Godwin, 2012) as a HindIII-SmaI fragment into the AscI (blunted) and HindIII sites of pJP3343. The resulting vector, pOIL196, was then digested with HindIII (blunted) and AgeI. The resulting 3358 bp fragment was cloned into the ZraI-AgeI sites of pOIL134, yielding pOIL197.

A set of constructs containing genes encoding the Z. mays WRI1 (ZmWRI) or the LEC1 (ZmLEC1) transcription factors under the control of different promoters were designed and produced for biolistic co-transformation in combination with pOIL136 or pOIL197 to test the effect of promoter strength and cell specificity on the function of WRI1 or LEC1, or both if combined, when expressed in vegetative tissues of a C4 plant such as sorghum. This separate set of constructs did not contain a selectable marker gene, except for pOIL333 which contained NPTII as selectable marker. The different promoters tested were as follows. The Z. mays Ubiquitin gene promoter (pZmUbi) was a strong constitutive monocot promoter while the enhanced CaMV 35S promoter (e35S) having a duplicated enhancer region was reported to result in lower transgene expression levels (reviewed in Girijashankar and Swathisree, 2009). Whilst the Z. mays phosphoenolpyruvate carboxylase (pZmPEPC) gene promoter was active in leaf mesophyl cells (Matsuoka and Minami, 1989), the site of photosynthesis in C4 plant species, the Z. mays Rubisco small subunit (pZmSSU) gene promoter was specific for the bundle sheath cell layer (Nomura et al., 2000; Lebrun et al., 1987), the cells where carbon fixation takes place in C4 plants.

The expression of the Z. mays gene encoding the SEE1 cysteine protease (Accession number AJ494982) was identified as similar to that of the A. thaliana SAG12 senescence-specific promoter during plant development. Therefore a 1970 bp promoter from the SEE1 gene (SEQ ID NO:53) was also selected to drive expression of the genes encoding the Z. mays WRI1 and LEC1 transcription factors. Further, the promoter from the gene encoding Aeluropus littoralis zinc finger protein A1SAP (Ben Saad et al., 2011; Accession number DQ885219; SEQ ID NO:54), the promoter from the gene encoding the Saccharum hybrid DIRIGENT (DIR16) (Damaj et al., 2010; Accession number GU062718; SEQ ID NO:82), the promoter from the gene encoding the Saccharum hybrid 0-Methyl transferase (OMT) (Damaj et al., 2010; Accession number GU062719; SEQ ID NO:83), the A1 promoter allel from the gene encoding the Saccharum hybrid R1MYB1 (Mudge et al., 2013; Accession number JX514703.1; SEQ ID NO:84), the promoter from the gene encoding the Saccharum hybrid Loading Stem Gene 5 (LSG5) (Moyle and Birch, 2013; Accession number JX514698.1; SEQ ID NO:85) and the promoter from the sucrose-responsive ArRolC gene from A. rhizogenes (Yokoyama et al., 1994; Accession number DQ160187; SEQ ID NO:55) were also selected for expression of ZmWRI1 expression in stem tissue. Therefore, each of these promoters was individually joined upstream of the ZmWRI1 or ZmLEC1 coding regions, as follows.

An intermediate vector, pOIL100, was first produced by cloning the Z. mays WRI1 coding sequence and a Glycine max lectin gene transcription terminator/polyadenylation region, flanked by AscI-NcoI sites, into the same sites in the binary vector pJP3343. The WRI1 coding sequence was codon optimized using T. aestivum codon preferences. The different versions of the constructs for WRI1 expression were based on pOIL100 and were produced by cloning the various promoters into pOIL100. pOIL101 was produced by cloning a XhoI-SalI fragment containing the e35S promoter with duplicated enhancer region into the XhoI site of pOIL100. pOIL102 was produced by cloning a HindIII-AvrII fragment containing the Z. mays Ubiquitin gene promoter (Christensen et al., 1992) into the HindIII-XbaI sites of pOIL100. pOIL103 was produced by cloning a HindIII-NcoI fragment containing a Z. mays PEPC gene promoter (Matsuoka and Minami, 1989) into the HindIII-NcoI sites of pOIL100. pOIL104 was produced by cloning a HindIII-AvrII fragment containing a Z. mays SSU gene promoter into the HindIII-AvrII sites of pOIL100.

A synthetic fragment containing the Z. mays SEE1 promoter region flanked by HindIII-XhoI unique sites was synthesized. This fragment was cloned upstream of the Z. mays WRI1 protein coding region using the HindIII-XhoI sites in pOIL100. The resulting vector was designated pOIL329. A synthetic fragment containing the A. littoralis A1SAP promoter region flanked by XhoI-XbaI unique sites was synthesized. This fragment was cloned upstream of the Z. mays WRI1 coding region using the XbaI-XhoI sites in pOIL100. The resulting vector was designated pOIL330. A synthetic fragment containing the A. rhizogenes ArRolC promoter region flanked by PspOMI-XhoI unique sites was synthesized. This fragment was cloned upstream of the Z. mays WRI1 coding region using the PspOMI-XhoI sites in pOIL100. The resulting vector was designated pOIL335. Finally, a binary vector (pOIL333) containing the Z. mays SEE1::ZmLEC1 expression cassette was obtained in three steps. First, a 35S::GUS expression vector was constructed by amplifying the GUS coding region with flanking primers containing AvrII and KpnI sites. The resulting fragment was subsequently cloned into the SpeI-KpnI sites of pJP3343. The resulting vector was designated pTV111. Next, the 35S promoter region of pTV111 was replaced by the Z. mays SEE1 promoter. To this end, the Z. mays SEE1 sequence was amplified using flanking primers containing HindIII and XhoI unique sites. The resulting fragment was cut with the respective restriction enzymes and subcloned into the SalI-HindIII sites of pTV111. The resulting vector was designated pOIL332. Next the ZmLEC1 coding sequence was amplified using flanking primers containing NotI and EcoRV sites. This resulting fragment was subcloned into the respective sites of pOIL332, yielding pOIL333.

A 2673 bp synthetic fragment containing the Saccharum DIR16 promoter region flanked by HindIII-XbaI sites was synthesized. This fragment was cloned upstream of the Z. mays WRI1 protein coding region using the HindIII-XbaI sites in pOIL100. The resulting vector was designated pOIL337. A 2947 bp synthetic fragment containing the Saccharum OMT promoter region flanked by XhoI-XbaI sites was synthesized. This fragment was cloned upstream of the Z. mays WRI1 protein coding region using the XhoI-XbaI sites in pOIL100. The resulting vector was designated pOIL339. A 1181 bp synthetic fragment containing the Saccharum R1MYB1 promoter region flanked by HindIII- XhoI sites was synthesized. This fragment was cloned upstream of the Z. mays WRI1 protein coding region using the HindIII-XhoI sites in pOIL100. The resulting vector was designated pOIL341. A 4482 bp synthetic fragment containing the Saccharum LSG5 promoter region flanked by XbaIII-SmaI sites was synthesized. This fragment was cloned as an XbaIII-SmaI fragment upstream of the Z. mays WRI1 protein coding region using the StuI-NheI sites in pOIL100. The resulting vector was designated pOIL343.

Two putative S. bicolor SDP1 genes were identified by a BLASTn search using an A. thaliana SDP1 nucleotide sequence (Accession number NM_120486; SEQ ID NO:37) as query. The Accession numbers of the two S. bicolor SDP1 homologs are XM_002458486 (SEQ ID NO:38) and XM_002463620 (SEQ ID NO:73). A 7991 bp synthetic fragment was synthesized and contained the following genetic components in order: a matrix association region (MAR), a Z. mays promoter, a TMV 5' UTR sequence, a 2198 bp hairpin RNA encoding region (SEQ ID NO:75) directed against both S. bicolor SDP1 genes, an OCS gene polyadenylation/transcription terminator, an O. sativa Actin-1 gene promoter, TMV 5' UTR sequence, and a NOS gene polyadenylation/transcription terminator. The hairpin RNA encoding region contained a Pdk intron (Wesley et al., 2001) and a Cat intron, the second in reverse orientation. The entire fragment was synthesized and inserted into an E. coli expression vector. The resulting vector was designated pOIL385.

Whole plasmid DNA was prepared from pOIL101, pOIL102, pOIL103, pOIL104, pOIL197, pOIL136, pOIL329 and pOIL385 for biolistic transformation. pOIL197 DNA was then mixed with DNA from either pOIL101, pOIL102, pOIL103, pOIL104, pOIL329 or pOIL385 and introduced by biolistics into S. bicolor (TX430) differentiating embryonic calli (DEC) cells to produced transformed plants as described in Example 1. Alternatively, constructs for expression of the same combinations of genes are introduced separately or co-transformed by Agrobacterium-mediated methods (Gurel et al., 2009; Wu et al., 2014) into DEC tissues.

Between 9 and 47 transgenic plants were regenerated and selected by antibiotic resistance for the pairs of constructs including pOIL197 with each of pOIL101 (p35SSWRI1); pOIL102 (pZmUbi::WRI1), pOIL103 (pZmPEPC::WRI1), pOIL104 (pSSU::WRI1) and pOIL329 (pSEE1::WRI1). Transformations were also carried out with pOIL197 or pOIL102 alone, and for the transformation vector without an insert (empty vector control). The presence of the introduced transgenes in plants that were resistant to the selective agent was demonstrated by PCR. The copy number of each transgene was also determined by digital droplet PCR (ddPCR).

Total leaf lipids were quantified in a first subset of transgenic S. bicolor plants prior to their transfer from MS medium to soil. This preliminary screening suggested slightly elevated total lipid levels in leaf tissue of some events at this very early stage. The line with the highest total lipid content, pOIL136 (2), was further analyzed by thin layer chromatography (TLC) to determine the effect of transgene expression on TAG accumulation. Leaf tissue of this particular line was sampled at vegetative stage following transfer to soil in the glasshouse. When compared to the wildtype and empty vector negative controls, pOIL136 (2) exhibited increased TAG levels in leaf tissue after TLC separation and iodine staining. Subsequent quantification revealed 10-fold increased TAG in the transgenic line compared to the negative controls. The TAG profile was dominated by the polyunsaturated fatty acids linoleic and α-linolenic acid. The presence or absence of all three transgenes was determined by digital PCR analysis. Of note, up to 30% mortality rate was observed for plantlets at rooting stage during tissue culture following transformation with the pOIL103 and pOIL197 combination due to unknown reasons.

Confirmed transgenic plants were transferred to soil in pots in the glasshouse and leaves were sampled from primary transformants at vegetative stage of growth (i.e. prior to the appearance of the boot leaf), at the boot leaf stage (defined as when the boot leaf has fully emerged, the boot leaf is the last leaf formed on the plant and from which the panicle (head) emerges) and at the mature seed-setting stage. Total fatty acid (TFA) and triacylglycerol (TAG) contents (% leaf dry weight) were quantified by TLC-GC as described in Example 1.

TFA levels in wild-type and empty vector negative controls decreased during plant development and were in the range 0.05-2.9% (weight/dry weight). The highest TFA levels were detected prior to the appearance of the boot leaf (termed the vegetative stage of growth) and were below 3%. TAG levels in the same plants were consistently low in the range 0-0.2% during the entire plant life cycle. Both the TFA content and the TAG content had fatty acid compositions of predominantly C16:0, C18:2$^{\Delta9,12}$ (LA) and C18:3$^{\Delta9,12,15}$ (ALA). In particular, ALA was present at >70% of the TFA content, reflecting use of this fatty acid in wild-type plastid membranes. ALA also was the predominant fatty acid in the small amount of TAG present in the wild-type leaves. 27 confirmed transgenic plants which had been transformed with pOIL197 or pOIL136, comprising both pZmUbi:DGAT and pZmUbi:Oleosin genes in addition to the selectable marker genes, were analysed at the vegetative, boot leaf and mature seed setting stages. Some data are presented in Table 5. Generally, the pOIL197 and pOIL136 primary transformants displayed increased TFA and TAG accumulation compared to the negative control lines, but only to about triple for the TFA level compared to the controls. The highest TFA levels were detected at the vegetative stage of growth. Similar to the wild-type and negative control lines, TFA levels decreased as the plants grew and developed. Maximum TFA levels at vegetative, boot leaf and mature seed setting stages equalled 4.3%, 3.3% and 2.2%, respectively. The highest TAG levels detected varied between 0.8 and 1.4% depending on the age of the plant at the time of sampling (Table 3), so were increased up to 7-fold relative to the very low levels in the wild-type leaves. The TFA composition remained largely unchanged at the different stages and was dominated by ALA. The TAG composition displayed a higher degree of variation between the different transgenic lines. Compared to the fatty acid composition of the TFA content, the level of LA (18:2$^{\Delta9,12}$) was consistently increased in TAG throughout all plant stages investigated.

Nine primary regenerated plants made by transformation with the single vector pOIL102 (pZmUbi:WRI1) were generated by co-bombardment of pOIL102 and pUKN, containing the NPTII selectable marker gene. Table 4 shows some of the data for TFA and TAG contents and fatty acid compositions were measured at the three growth stages. When compared to the plants transformed with the constructs encoding DGAT2 and Oleosin (pOIL197 or pOIL136), TFA and TAG levels in the pOIL102 transgenic events were generally lower. Indeed, levels of TFA and TAG were similar to the levels in the wild-type and negative control plants at vegetative stage. Maximum TFA levels at vegetative, boot leaf and mature seed setting stages were 2.6%, 2.5% and 2.0%, respectively (Table 4). Maximum TAG levels observed were 0.2%, 0.4% and 0.9% at vegetative, boot leaf and mature seed setting stages, respectively.

Thirty-seven primary regenerated plants were obtained after co-bombardment with both pOIL197 (pZmUbi:DGAT and pZmUbi:Oleosin) and pOIL102 (pZmUbi:WRI1). Four of the regenerated events were found to be non-transgenic. In addition, 2 plants did not contain pOIL102 while 2 other plants did not contain the DGAT2 transgene. All of the transgenic plants were analysed for TFA and TAG contents and fatty acid composition at the three growth stages, as above. Representative data are presented in Table 5. Some of the plants exhibited greatly increased TFA and TAG levels compared to the plants transformed with single vectors pOIL197, pOIL136 or pOIL102. The maximum TFA levels at vegetative, boot leaf and mature seed setting stages in the pOIL102+pOIL197 transformed plants equalled 7.2%, 6.4% and 8.7% (w/dry weight), respectively. Importantly, the maximum observed TAG levels increased during plant development from 2.7% (vegetative stage) to 3.5% (boot leaf stage) and 6.1% (mature seed setting stage). Compared with the data obtained for the separate transformations with the DGAT and WRI1 transgenes, this exemplified the synergism for co-expressing DGAT and WRI1 transgenes to increase non-polar lipid accumulation in vegetative plant tissues. High levels of TAG and TFA were in most cases associated with a substantial reduction in the $C18:3^{\Delta9,12,15}$ content, which was reduced by about 50% in the lines with the highest levels of TAG.

Forty-seven primary transformants were obtained following transformation with both pOIL197 (pZmUbi:DGAT and pZmUbi:Oleosin) and pOIL103 (pZmPEPC:WRI1). Copy number analysis by ddPCR revealed one non-transgenic plant and 3 plants that did not contain DGAT2 and/or OLEOSIN transgenes. All events were subsequently analysed for TFA and TAG contents and fatty acid composition during the three stages of plant development. Some plants with this gene combination exhibited the highest TFA and TAG levels detected in this experimental series. TFA levels were observed at vegetative, boot leaf and mature seed setting stages in the pOIL103+pOIL197 population at 8.3%, 8.3% and 9.7%, respectively. Maximum TAG levels observed at vegetative, boot leaf and mature seed setting stages were at 2.3%, 6.6% and 7.6%, respectively. Of note, the highest TAG (6.6%) and TFA (8.3%) levels amongst all transgenic lines were detected in event TX-03-31 at mature seed setting stage. While $C18:3^{\Delta9,12,15}$ typically dominated the TFA fraction other than TAG, the TAG in this population of transgenic plants displayed a high degree of variability in fatty acid composition. Of note, some plants exhibited increases in levels of palmitic acid (C16:0) and/or linoleic acid (LA, $C18:2^{\Delta9,12}$) at the expense of ALA. Indeed, the ALA level in both TFA and TAG contents was reduced below 40% in some plants as a percentage of the total fatty acid content, while less than 30% in other selected events. The ALA level in TAG was even less than 20% in some selected plants, as a percentage of the total fatty acid content.

Due to the use of biolistic transformation in this experiment, many of the transgenic sorghum plants contained high transgene copy numbers as determined by digital PCR. In addition, varying degrees of male and female sterility were observed amongst the transgenic lines, likely a result of the multiple transgene insertions. The inventors therefore did not pursue homozygosity of the transgenes in subsequent generations but rather performed a detailed analysis on vegetative progeny plants obtained from selected primary transformants. To this end, tillers were propagated allowing for triplicate analyses of TAG and TFA levels. Furthermore, the analyses focussed on the boot leaf stage of growth as this was a distinct and easily identified time point during development that allowed for good comparison between the different transgenic lines, grown under the same environmental conditions. Plants containing the higher levels of TFA and TAG were propagated by separating tillers and transplanting them into soil in new pots. The tillers produced new roots and continued to grow.

Quantitation of the total lipid content in triplicate leaves from established tillers confirmed elevated TAG and TFA contents in several independent lines co-transformed with either pOIL102+pOIL197 or pOIL103+pOIL197. The highest levels were observed in progeny plants of line 03-31, confirming the earlier results. Leaves of this line contained on average 6.9% TFA and 4.6% TAG (% DW) at boot leaf stage. This corresponded to an 89.4-fold increase in TAG content compared to wild-type control leaves at the same developmental stage.

Twenty primary regenerated plants were obtained following transformation with both pOIL197 (pZmUbi:DGAT and pZmUbi:Oleosin) and pOIL104 (pSSU:WRI1). Five plants were found to be non-transgenic and four other plants had only the gene(s) from one of the genetic constructs. All plants were analysed for TFA and TAG contents and fatty acid composition. Leaves of primary transformants containing both pOIL197 and pOIL104 T-DNA regions, sampled at vegetative, mature and seed setting stages of growth contained up to 4.1%, 5.9% and 5.89% TFA, respectively. Surprisingly, the highest TFA levels detected in this population were accompanied by a relatively low TAG content. TAG levels in pOIL104+pOIL197 transgenic plants at vegetative, boot leaf and seed setting stages reached only to 0.7%, 2.8% and 3.4%. Increased TAG levels were typically associated with a reduction in $C18:3^{\Delta9,12,15}$ and an increase in both palmitic acid and LA.

Forty-three primary regenerated plants were obtained following transformation with both pOIL197 (pZmUbi:DGAT and pZmUbi:Oleosin) and pOIL101 (p35S:WRI1). One plant was non-transgenic, another lacked the WRI1 transgene and another lacked the DGAT1 transgene. All plants were analysed for TFA and TAG contents and fatty acid composition at boot leaf stage. Leaves of primary transformants containing both pOIL197 and pOIL104 T-DNA regions contained up to 4% TFA while TAG levels were low with a maximum of 1.4%. Increased TAG levels were associated with a reduction in $C18:3^{\Delta9,12,15}$ as a percentage of the total fatty acid content.

Twenty primary transformants were obtained following transformation with both pOIL197 (pZmUbi:DGAT and pZmUbi:Oleosin) and pOIL329 (pSEE1:WRI1). All plants were confirmed to be transgenic by ddPCR. TFA and TAG levels in leaves of 10 plants at vegetative growth stage were increased up to 3.6% and 0.3%, respectively. Maximum TFA and TAG levels at boot leaf stage equalled 3.8% and 1.5%, respectively. The low TFA and TAG levels were likely the result of the senescence-specific expression patterns of the SEE1 promoter used to drive WRI1 transgene expression. Increased TAG levels were typically associated with a reduction in $C18:3^{\Delta9,12,15}$ as a percentage of the total fatty acid content.

Thirty-six primary regenerated plants were obtained following transformation with both pOIL197 (pZmUbi:DGAT and pZmUbi:Oleosin) and pOIL385 (SDP1hpRNAi). Two plants lacked pOIL197 and another two lacked pOIL385. The highest TFA level detected in transgenic leaves at the vegetative growth stage was 4.2%. TAG levels in this particular event at the same growth stage was only 1.0%. TFA and TAG levels in leaves sampled at boot leaf stage were increased up to 3.9% and 1.6%, respectively. The lower TFA and TAG levels could be due to the absence of a WRI1 transgene in this transgenic population. No changes in TAG or TFA fatty acid composition were detected relative to the wild-type plants.

Transgene expression levels were determined in propagated tillers of selected lines by RT-PCR. In the majority of transgenic lines, the DGAT2a transgene was typically expressed at a higher levels than the WRI1 transgene. Oleosin L gene expression was either low or not detected. Total lipid and TAG contents at the boot leaf stage were used to calculate correlation coefficients with gene expression. Both WRI1 and DGAT2a gene expression showed a significant positive correlation with TAG levels amongst pOIL102+pOIL197 and pOIL103+pOIL197 transgenic populations. Significant, albeit slightly weaker, correlation was observed for TFA content and WRI1 or DGAT2a expression. Oleosin L expression was not correlated with either TAG or TFA accumulation in transgenic leaf tissues. It was observed that plant TX-03-31 which had a relatively high TTQ had the highest level of expression of DGAT amongst the tested plants. It was concluded that high levels of DGAT expression were beneficial for increasing the TAG level and also the TTQ.

The most surprising and unexpected observation made in these experiments was the relatively high level of TFA accompanied by the low levels of TAG in most of the transformed sorghum plants, except in a few exceptional plants such as plant TX-03-31. That is, although fatty acid synthesis and accumulation were significantly increased, much of the fatty acid was appearing as TFA but not as TAG. This observation was the opposite of what had been seen with the WRI1+DGAT transgenic plants for Nicotiana including tobacco. To quantitate this in the sorghum plants, the quotient of the TAG to TFA level was calculated for all of the above mentioned transgenic sorghum populations (Tables 3-6). The TAG/TFA Quotient (TTQ) parameter was calculated as the level of TAG (%) divided by the level of TFA (%), each as a percentage of the dry weight of the plant material (leaf in this case). It was observed that for many of the sorghum lines, the TTQ was in the range of 0.01 to 0.6, i.e. less than 60% of the TFA was present as TAG. Addition of one or more further genetic modifications to the combination of WRI1 and DGAT genes such as, for example, which provide for a reduction in the expression of endogenous SDP1, TGD or TST genes, or an increase in the levels of one or more of PDAT, PDCT or CPT polypeptides increases the TTQ to above 0.6 for a larger proportion of the plant lines. In particular, reduction in TAG lipase in combination with at least WRI1 and DGAT increases the TTQ to up to 0.95.

Due to the large difference in absolute TFA and TAG levels in many transgenic lines, the inventors selected two pOIL102+pOIL197 events (02-10, 02-19) and two pOIL103+pOIL197 events (03-31 and 03-48) for quantitation of the major neutral and polar lipid classes, to determine the type of lipid other than TAG in which the high level of fatty acids was present. The types of lipid were separated by TLC and quantitated. The propagated tillers were smaller compared to tillers obtained from wild-type controls plants grown under the same conditions with the exception of line 03-48. Quantitation by GC-FID of TAG and TFA levels in triplicate leaves confirmed increases in both lipid fractions. Maximum average TAG levels in triplicate leaves (% DW) of lines 02-19 and 03-31 sampled at boot leaf stage were 2.8% and 5.2%, respectively. For all of the transgenic lines, linoleic acid was increased at the expense of α-linolenic acid. However, differences were observed in the levels of palmitic acid and oleic acid. Lines 02-10 and 02-19 contained increased proportions of oleic acid, whereas palmitic acid was elevated in the TFA and TAG fractions of 03-31 and 03-48 leaves. Lipid quantitation in leaf and stem tissues at seed setting stage revealed considerable leaf-to-leaf variation. Lower TFA and TAG contents were observed in older leaves of wild-type and transgenic propagated tillers. The TFA and TAG levels in the flag leaf of line 03-31 at seed setting equalled 9.9% and 8.4% on a DW basis, respectively. Transgenic stem tissues contained up to about 3% total lipids on a dry weight basis compared to 0.3% in wild-type stems.

Total lipid extracts from the wild-type and transgenic leaves sampled at boot leaf stage were subjected to LC-MS to analyse different neutral and polar lipid classes in more detail. Plants of all four transgenic lines exhibited elevated TAG, amounting to a 100-fold increase in line 03-31 compared to the wild-type control leaves. Small increases in levels of PC were detected in plants of the 03-31 and 03-48 transgenic lines while levels of the plastidial galactolipids MGDG and DGDG were variable, increased in some, decreased in other plants. Both LPC and DAG constituted minor lipid classes. TAG molecular species in plants of lines 03-31 and 03-48 were enriched in palmitic acid and linoleic acid. Major TAG species included TAG (50:2) and TAG (50:3) which contained two palmityl groups and TAG (52:4) and TAG (52:5) which contained palmitoyl and linoloyl groups. In contrast, plants of lines 02-10 and 02-19 exhibited distinctly different TAG profiles. Leaf tissues of both lines preferentially accumulated TAG comprising one or more linolyl chains such as TAG (52:3-5) and TAG (54:4-8). The distinct differences in TAG profiles between the two transgenic populations were consistent with earlier GC-FID results.

Changes in TAG compositions were also reflected in the precursor DAG. Dominant DAG (34:2) and DAG (34:3) molecular species in plants 03-31 and 03-48 were enriched in palmitic acid while both 02-10 and 02-19 plants had DAG molecules containing two C18 acyl chains (DAG 36:2-6). Abundant eukaryotic galactolipid species such as MGDG (36:6) and DGDG (36:6) were either reduced or not significantly affected. Two prokaryotic galactolipid species, MGDG (34:3) and DGDG (34:2) were increased slightly in plants 03-31 and 03-48. The dominant prokaryotic DGDG species (34:3) was either unchanged or reduced in transgenic leaves. PC molecular species containing palmitic or linoleic acid including PC (34:1-2) and PC (36:4) were elevated, particularly in lines 03-31 and 03-48. Di-palmitoyl PC (32:0) was increased in line 03-31, reflecting the higher levels of palmitic acid as detected by GC-FID.

Taken together, these results indicated an increased flux of acyl chains into TAG from PC in the transgenic lines whilst galactolipid biosynthesis mainly occurred via the eukaryotic pathway. These data also led the inventors to understand that reduction of TGD activity or increases in PDCT and/or CPT in the plants in addition to the present transgenes would likely enhance the TFA and TAG levels.

TAG Accumulation Affects Starch and Amino Acid Content

Transitory starch levels in transgenic leaves of lines 03-31 and 03-48 were reduced 7.4- and 15.3-fold on average, respectively. In contrast, starch levels in leaves of 02-10 and 02-19 plants were not significantly affected. Sucrose constituted the dominant leaf soluble sugar in all plants. Sucrose levels were 2-fold lower in line 03-48 while similar to the wild-type control in line 02-19. Raffinose was reduced by 19.6-fold in line 03-48 while monosaccharides such as glucose, fructose and galactose displayed smaller reductions.

A metabolite quantitation by GC-MS identified 36 compounds that were significantly different in leaves of wild-type and transgenic plants. Twenty metabolites were detected at higher levels in TAG-accumulating leaves, including multiple amino acids, urea and the citric acid cycle (TCA) intermediate, α-ketoglutarate. Several dicarboxylic acids, sugar alcohols, fructose, xylose and shikimate were amongst the metabolites that were less abundant in transgenic leaves. Principle component analysis revealed clear separations of both transgenic events and the wild-type control.

Sorghum Leaves Accumulate TAG as Cytosolic Lipid Droplets

To examine transgenic leaves microscopically to see whether the increased TAG was accumulated in oil droplets, flag leaves of re-established side tillers from transgenic *S. bicolor* plants were harvested at the beginning of flowering and kept on ice until sections were prepared for imaging. Fresh, thin hand sections were stained for 10 min with a solution of 50 mM PIPES pH7 supplemented with 2 µg/ml of BODIPY 505-515 (4,4-Difluoro-1,3,5,7-Tetramethyl-4-Bora-3a,4a-Diaza-s-Indacene, ThermoFisher Scientific). They were then rinsed in a solution of PIPES pH7 and imaged right away. Control sections were placed directly in PIPES pH7 for 10 min before being mounted on slides and imaged.

All samples were imaged with a confocal laser scanning microscope (Leica TCS SP8) equipped with a white light laser and a 40× water immersion objective ([NA]=1.1), and controlled by the LAS X software (Leica Microsystems). Imaging was done in a sequential manner: BODIPY excited at 505 nm and its emission was collected at 520-540 nm, while in a separate track, chloroplasts were excited at 633 nm and their auto-fluorescence was collected at 650-690 nm. Maximum projections were generated with the LAS X software. Confocal imaging settings were optimized to distinguish cell types in which oil accumulated by minimizing chloroplast auto-fluorescence in the bundle sheath cells as opposed to the surrounding mesophyll cells.

Leaf cross sections of line 03-10 revealed an abundance of small lipid droplets that preferentially accumulated in the cytosol of mesophyll cells. The unequal distribution likely reflected the tissue specificity of the PEPC promoter used to generate this particular transgenic line. Some lipid accumulation was also visible in the bundle sheath cells of transgenic lines and the wild-type control. Line 02-10 contained an intermediate number of lipid droplets, confirming previous LC-MS and GC-FID TAG quantitation results. Transmission electron micrographs showed densely packed small lipid droplets in the cytosol of mesophyll cells in line 03-31. Mesophyll cells of the wild-type control plants were largely devoid of cytosolic oil droplets.

The chimeric DNA constructs for *Agrobacterium*-mediated transformation are used to transform *Zea mays* (corn) as described by Gould et al. (1991). Briefly, shoot apex explants are co-cultivated with transgenic *Agrobacterium* for two days before being transferred onto a MS salt media containing kanamycin and carbenicillin. After several rounds of sub-culture, transformed shoots and roots spontaneously form and are transplanted to soil. The constructs are similarly used to transform *Hordeum vulgare* (barley) and *Avena sativa* (oats) using transformation methods known for these species. Briefly, for barley, the *Agrobacterium* cultures are used to transform cells in immature embryos of barley (cv. Golden Promise) according to published methods (Tingay et al., 1997; Bartlett et al., 2008) with some modifications in that embryos between 1.5 and 2.5 mm in length are isolated from immature caryopses and the embryonic axes removed. Resulting explants are co-cultivated for 2-3 days with the transgenic *Agrobacterium* and then cultured in the dark for 4-6 weeks on media containing timentin and hygromycin to generate embryogenic callus then moved to transition media in low light conditions for two weeks. Calli are then transferred to regeneration media to allow for the regeneration of shoots and roots before transfer of the regenerated plantlets to soil. Transformed plants are obtained and grown to maturity in the glasshouse.

TABLE 3

TFA and TAG levels, fatty acid composition and TTQ in *sorghum* leaves transformed with pOIL197 or pOIL136 (pZmUbi:DGAT; pZmUbi:Oleosin) during the boot leaf stage of growth. The lines are listed in order of increasing TFA levels.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-197-14 | TFA | 12.7 | 5.2 | 2.0 | 14.4 | 57.7 | 8.1 | 1.2 | | |
| TX-197-14 | TAG | 8.8 | 7.1 | 3.1 | 22.7 | 54.7 | 3.6 | | 0.3 | 0.266 |
| TX-197-15 | TFA | 14.5 | 5.0 | 2.3 | 14.7 | 55.8 | 7.7 | 1.2 | | |
| TX-197-15 | TAG | 12.7 | 7.1 | 3.2 | 21.0 | 51.7 | 4.3 | | 0.3 | 0.262 |
| TX-197-19 | TFA | 13.1 | 3.2 | 2.0 | 14.3 | 60.9 | 6.4 | 1.2 | | |
| TX-197-19 | TAG | 10.6 | 4.3 | 3.4 | 24.4 | 54.0 | 3.2 | | 0.2 | 0.203 |
| TX-136-03 | TFA | 14.1 | 1.8 | 1.7 | 12.6 | 65.0 | 4.8 | 1.2 | | |
| TX-136-03 | TAG | 14.5 | 4.3 | 4.5 | 32.9 | 42.2 | 1.6 | | 0.1 | 0.045 |
| TX-197-08 | TFA | 14.4 | 3.5 | 1.3 | 14.2 | 62.2 | 4.4 | 1.2 | | |
| TX-197-08 | TAG | 13.7 | 5.2 | 2.7 | 22.4 | 50.5 | 5.5 | | 0.3 | 0.211 |
| TX-197-11 | TFA | 14.1 | 3.8 | 2.0 | 15.0 | 57.0 | 8.2 | 1.3 | | |
| TX-197-11 | TAG | 10.3 | 4.8 | 3.0 | 22.8 | 55.9 | 3.1 | | 0.3 | 0.267 |
| TX-136-24 | TFA | 15.5 | 2.2 | 2.2 | 16.9 | 58.1 | 5.2 | 1.3 | | |
| TX-136-24 | TAG | 14.7 | 3.3 | 4.0 | 32.4 | 42.9 | 2.7 | | 0.2 | 0.164 |
| TX-136-02 | TFA | 12.3 | 1.5 | 1.4 | 14.7 | 65.7 | 4.4 | 1.5 | | |
| TX-136-02 | TAG | 13.9 | 2.7 | 3.0 | 28.7 | 46.6 | 5.1 | | 0.7 | 0.444 |
| TX-197-30 | TFA | 13.1 | 2.3 | 1.3 | 9.3 | 65.1 | 8.8 | 2.0 | | |
| TX-197-30 | TAG | 10.0 | 3.0 | 2.2 | 15.0 | 65.3 | 4.5 | | 0.4 | 0.223 |
| TX-197-46 | TFA | 13.2 | 2.5 | 0.8 | 7.9 | 71.2 | 4.5 | 2.0 | | |
| TX-197-46 | TAG | 17.3 | 18.6 | 3.2 | 14.7 | 42.5 | 3.7 | | 0.1 | 0.033 |
| TX-197-45 | TFA | 13.6 | 2.7 | 0.6 | 6.7 | 71.7 | 4.5 | 2.1 | | |

TABLE 3-continued

TFA and TAG levels, fatty acid composition and TTQ in *sorghum* leaves transformed with pOIL197 or pOIL136 (pZmUbi:DGAT; pZmUbi:Oleosin) during the boot leaf stage of growth. The lines are listed in order of increasing TFA levels.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-197-45 | TAG | 22.7 | 17.7 | 4.4 | 12.9 | 38.6 | 3.6 | | 0.1 | 0.030 |
| TX-197-39 | TFA | 12.6 | 3.6 | 1.1 | 9.0 | 66.2 | 7.4 | 2.1 | | |
| TX-197-39 | TAG | 9.5 | 4.0 | 1.6 | 12.8 | 66.7 | 5.5 | | 0.6 | 0.291 |
| TX-197-22 | TFA | 13.6 | 2.0 | 0.8 | 7.3 | 71.3 | 4.9 | 2.1 | | |
| TX-197-22 | TAG | 13.8 | 3.3 | 1.8 | 14.2 | 64.6 | 2.3 | | 0.1 | 0.056 |
| TX-197-34 | TFA | 12.0 | 3.2 | 1.2 | 9.6 | 67.9 | 5.9 | 2.2 | | |
| TX-197-34 | TAG | 9.1 | 4.6 | 2.3 | 18.4 | 63.2 | 2.3 | | 0.4 | 0.190 |
| TX-197-50 | TFA | 13.0 | 2.5 | 1.1 | 9.1 | 66.8 | 7.5 | 2.5 | | |
| TX-197-50 | TAG | 11.4 | 4.6 | 2.1 | 15.3 | 59.8 | 6.9 | | 0.5 | 0.183 |
| TX-197-43 | TFA | 12.4 | 2.3 | 0.7 | 8.0 | 71.9 | 4.7 | 2.5 | | |
| TX-197-43 | TAG | 11.0 | 4.4 | 1.8 | 15.7 | 62.3 | 4.8 | | 0.2 | 0.065 |
| TX-197-32 | TFA | 12.5 | 2.1 | 1.1 | 9.0 | 70.0 | 5.3 | 2.5 | | |
| TX-197-32 | TAG | 12.8 | 3.7 | 2.1 | 16.1 | 60.3 | 5.0 | | 0.6 | 0.220 |
| TX-197-33 | TFA | 12.1 | 2.7 | 0.7 | 7.9 | 71.0 | 5.6 | 2.5 | | |
| TX-197-33 | TAG | 11.1 | 4.8 | 1.4 | 15.4 | 62.4 | 4.9 | | 0.3 | 0.130 |
| TX-197-41 | TFA | 12.8 | 1.9 | 0.7 | 8.1 | 72.8 | 3.7 | 2.6 | | |
| TX-197-41 | TAG | 15.1 | 5.9 | 2.4 | 16.7 | 53.7 | 6.3 | | 0.2 | 0.065 |
| TX-197-36 | TFA | 12.2 | 2.0 | 0.8 | 7.7 | 71.6 | 5.6 | 2.6 | | |
| TX-197-36 | TAG | 11.4 | 3.4 | 1.6 | 13.9 | 65.6 | 4.1 | | 0.4 | 0.158 |
| TX-197-42 | TFA | 12.4 | 2.1 | 0.8 | 8.2 | 70.3 | 6.3 | 2.7 | | |
| TX-197-42 | TAG | 12.4 | 5.4 | 2.3 | 17.8 | 57.1 | 5.0 | | 0.2 | 0.060 |
| TX-197-51 | TFA | 13.6 | 2.1 | 1.0 | 9.9 | 66.8 | 6.6 | 2.7 | | |
| TX-197-51 | TAG | 13.1 | 4.6 | 3.0 | 18.8 | 53.4 | 7.0 | | 0.5 | 0.175 |
| TX-197-49 | TFA | 15.2 | 2.9 | 1.0 | 9.3 | 65.3 | 6.3 | 2.7 | | |
| TX-197-49 | TAG | 17.3 | 5.0 | 2.0 | 16.7 | 52.7 | 6.3 | | 0.5 | 0.192 |
| TX-197-48 | TFA | 13.0 | 2.3 | 1.0 | 8.8 | 68.5 | 6.4 | 2.8 | | |
| TX-197-48 | TAG | 13.0 | 4.7 | 2.2 | 16.1 | 58.0 | 6.0 | | 0.4 | 0.144 |
| TX-197-38 | TFA | 12.2 | 2.0 | 1.0 | 7.7 | 72.1 | 5.0 | 2.9 | | |
| TX-197-38 | TAG | 11.2 | 3.4 | 2.2 | 14.9 | 63.8 | 4.5 | | 0.5 | 0.160 |
| TX-197-35 | TFA | 12.8 | 1.8 | 0.9 | 8.5 | 69.4 | 6.6 | 2.9 | | |
| TX-197-35 | TAG | 12.7 | 2.9 | 1.7 | 14.5 | 63.3 | 4.9 | | 0.7 | 0.227 |
| TX-197-40 | TFA | 12.7 | 1.9 | 0.7 | 7.7 | 73.9 | 3.1 | 2.9 | | |
| TX-197-40 | TAG | 16.3 | 4.7 | 3.3 | 20.8 | 52.4 | 2.6 | | 0.1 | 0.031 |
| TX-197-47 | TFA | 13.9 | 2.4 | 0.6 | 6.9 | 72.2 | 3.9 | 2.9 | | |
| TX-197-47 | TAG | 24.6 | 19.8 | 5.2 | 10.7 | 34.8 | 4.9 | | 0.0 | 0.017 |
| TX-136-01 | TFA | 11.6 | 1.4 | 1.3 | 14.1 | 67.2 | 4.3 | 3.3 | | |
| TX-136-01 | TAG | 14.6 | 2.9 | 3.0 | 29.5 | 44.1 | 5.9 | | 0.7 | 0.199 |
| TX-197-44 | TFA | 13.5 | 2.1 | 1.4 | 14.7 | 63.1 | 5.1 | 3.4 | | |
| TX-197-44 | TAG | 14.4 | 4.3 | 3.1 | 25.0 | 45.0 | 8.2 | | 0.8 | 0.245 |
| TX-136-25 | TFA | 13.6 | 2.2 | 0.7 | 10.8 | 67.4 | 5.2 | 3.4 | | |
| TX-136-25 | TAG | 16.6 | 4.2 | 1.4 | 20.1 | 51.5 | 6.1 | | 1.0 | 0.286 |
| TX-197-28 | TFA | 11.5 | 1.3 | 0.4 | 7.8 | 75.3 | 3.6 | 3.4 | | |
| TX-197-28 | TAG | 17.4 | 4.5 | 1.6 | 19.5 | 50.2 | 6.9 | | 0.1 | 0.035 |
| TX-197-37 | TFA | 12.6 | 3.4 | 6.3 | 17.4 | 54.1 | 6.2 | 4.5 | | |
| TX-197-37 | TAG | 13.4 | 5.0 | 10.1 | 27.4 | 40.2 | 3.9 | | 1.9 | 0.426 |

TABLE 4

TFA and TAG levels, fatty acid composition and TTQ in *sorghum* leaves transformed with pOIL102 (pZmUbi:WRI1) during the boot leaf stage of growth.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-102-8 | TFA | 16.9 | 4.2 | 2.3 | 12.3 | 57.7 | 6.5 | 0.9 | | |
| TX-102-8 | TAG | 14.5 | 6.2 | 13.5 | 25.7 | 36.8 | 3.4 | | 0.2 | 0.243 |
| TX-102-4 | TFA | 17.1 | 4.2 | 2.0 | 12.5 | 57.5 | 6.7 | 0.9 | | |
| TX-102-4 | TAG | 10.5 | 4.4 | 3.0 | 20.0 | 59.6 | 2.6 | | 0.2 | 0.182 |
| TX-102-1 | TFA | 16.6 | 4.3 | 3.9 | 15.4 | 50.7 | 9.1 | 1.1 | | |
| TX-102-1 | TAG | 10.7 | 4.4 | 5.3 | 21.9 | 54.1 | 3.6 | | 0.3 | 0.273 |
| TX-102-5 | TFA | 16.7 | 4.1 | 1.7 | 11.6 | 60.2 | 5.8 | 1.1 | | |
| TX-102-5 | TAG | 11.7 | 5.5 | 2.8 | 21.4 | 56.1 | 2.5 | | 0.1 | 0.118 |
| TX-102-6 | TFA | 17.8 | 3.8 | 15.9 | 17.0 | 38.8 | 6.6 | 1.5 | | |
| TX-102-6 | TAG | 19.6 | 7.0 | 29.4 | 25.4 | 13.9 | 4.7 | | 0.4 | 0.267 |
| TX-102-2 | TFA | 15.0 | 1.9 | 1.7 | 19.1 | 56.5 | 5.9 | 1.7 | | |
| TX-102-2 | TAG | 10.6 | 1.9 | 2.7 | 30.2 | 51.2 | 3.4 | | 0.4 | 0.258 |
| TX-102-7 | TFA | 15.0 | 3.1 | 7.0 | 13.9 | 56.1 | 4.9 | 2.4 | | |
| TX-102-7 | TAG | 16.1 | 6.5 | 20.5 | 28.0 | 24.4 | 4.5 | | 0.3 | 0.111 |

TABLE 4-continued

TFA and TAG levels, fatty acid composition and TTQ in *sorghum* leaves transformed with pOIL102 (pZmUbi:WRI1) during the boot leaf stage of growth.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-102-3 | TFA | 14.4 | 3.5 | 9.5 | 13.4 | 50.9 | 8.2 | 2.5 | | |
| TX-102-3 | TAG | 16.9 | 6.7 | 23.9 | 24.7 | 22.5 | 5.2 | | 0.4 | 0.150 |

TABLE 5

TFA and TAG levels, fatty acid composition and TTQ in sorghum leaves transformed with pOIL102 (pZmUbi:WRI1) and pOIL197 (pZmUbi:DGAT and pZmUbi:Oleosin) during the boot leaf stage of growth. The lines are listed in order of increasing TFA levels.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-02-27 | TFA | 17.3 | 3.8 | 1.4 | 10.1 | 60.1 | 7.2 | 1.0 | | |
| TX-02-27 | TAG | 11.9 | 4.4 | 2.1 | 19.4 | 61.2 | 0.8 | | 0.2 | 0.164 |
| TX-02-21 | TFA | 15.9 | 2.3 | 2.0 | 19.3 | 53.3 | 7.3 | 1.2 | | |
| TX-02-21 | TAG | 12.6 | 3.7 | 2.7 | 27.0 | 51.0 | 3.0 | | 0.4 | 0.318 |
| TX-02-01 | TFA | 15.2 | 4.2 | 5.1 | 14.7 | 53.2 | 7.5 | 1.3 | | |
| TX-02-01 | TAG | 11.7 | 5.6 | 9.3 | 26.1 | 42.9 | 4.5 | | 0.3 | 0.199 |
| TX-02-12 | TFA | 15.3 | 3.2 | 2.0 | 13.6 | 58.9 | 6.9 | 1.3 | | |
| TX-02-12 | TAG | 13.7 | 4.2 | 3.6 | 25.1 | 50.4 | 2.9 | | 0.1 | 0.111 |
| TX-02-33 | TFA | 15.9 | 4.3 | 1.0 | 10.1 | 59.7 | 9.1 | 1.4 | | |
| TX-02-33 | TAG | 14.3 | 5.4 | 2.7 | 18.9 | 54.7 | 4.0 | | 0.1 | 0.107 |
| TX-02-13 | TFA | 15.4 | 5.1 | 11.4 | 19.4 | 39.1 | 9.5 | 1.4 | | |
| TX-02-13 | TAG | 12.9 | 6.5 | 20.3 | 25.2 | 28.6 | 6.4 | | 0.5 | 0.389 |
| TX-02-36 | TFA | 16.2 | 3.4 | 1.8 | 12.3 | 58.5 | 7.8 | 1.4 | | |
| TX-02-36 | TAG | 15.4 | 5.8 | 3.3 | 21.5 | 48.9 | 5.1 | | 0.3 | 0.209 |
| TX-02-37 | TFA | 13.3 | 3.5 | 1.3 | 9.9 | 65.3 | 6.7 | 1.4 | | |
| TX-02-37 | TAG | 9.6 | 3.6 | 3.8 | 20.4 | 60.6 | 2.1 | | 0.2 | 0.137 |
| TX-02-18 | TFA | 14.6 | 3.0 | 1.4 | 9.8 | 65.5 | 5.7 | 1.4 | | |
| TX-02-18 | TAG | 12.5 | 5.6 | 4.3 | 20.6 | 54.8 | 2.3 | | 0.1 | 0.077 |
| TX-02-34 | TFA | 16.6 | 2.2 | 2.2 | 17.6 | 54.7 | 6.7 | 1.4 | | |
| TX-02-34 | TAG | 14.1 | 2.8 | 4.1 | 30.3 | 44.7 | 4.1 | | 0.3 | 0.231 |
| TX-02-31 | TFA | 13.3 | 3.1 | 1.8 | 10.1 | 64.7 | 7.0 | 1.5 | | |
| TX-02-31 | TAG | 5.4 | 1.8 | 3.2 | 17.8 | 71.1 | 0.7 | | 0.3 | 0.171 |
| TX-02-29 | TFA | 13.2 | 3.2 | 1.1 | 8.2 | 68.6 | 5.6 | 1.6 | | |
| TX-02-29 | TAG | 10.5 | 4.7 | 2.9 | 18.1 | 62.0 | 1.8 | | 0.1 | 0.082 |
| TX-02-35 | TFA | 17.8 | 3.4 | 6.5 | 14.0 | 50.3 | 8.0 | 1.6 | | |
| TX-02-35 | TAG | 18.8 | 5.3 | 19.1 | 28.4 | 22.4 | 6.1 | | 0.2 | 0.108 |
| TX-02-09 | TFA | 14.0 | 3.3 | 0.9 | 9.9 | 66.0 | 6.0 | 1.6 | | |
| TX-02-09 | TAG | 11.2 | 4.7 | 1.9 | 19.6 | 58.7 | 3.9 | | 0.1 | 0.036 |
| TX-02-24 | TFA | 12.9 | 3.5 | 0.6 | 7.9 | 67.3 | 7.7 | 1.8 | | |
| TX-02-24 | TAG | 10.7 | 3.5 | 1.6 | 11.8 | 69.0 | 3.4 | | 0.1 | 0.044 |
| TX-02-126 | TFA | 13.8 | 2.7 | 1.1 | 9.9 | 66.4 | 6.0 | 1.8 | | |
| TX-02-126 | TAG | 12.8 | 4.3 | 2.1 | 17.0 | 58.6 | 5.2 | | 0.5 | 0.247 |
| TX-02-23 | TFA | 13.6 | 2.7 | 0.7 | 8.9 | 68.3 | 5.8 | 1.9 | | |
| TX-02-23 | TAG | 10.0 | 3.3 | 2.2 | 18.2 | 63.9 | 2.4 | | 0.1 | 0.047 |
| TX-02-07 | TFA | 17.5 | 2.3 | 10.9 | 17.5 | 44.5 | 7.3 | 1.9 | | |
| TX-02-07 | TAG | 21.0 | 3.9 | 24.5 | 27.4 | 15.2 | 8.0 | | 0.4 | 0.225 |
| TX-02-28 | TFA | 12.8 | 2.9 | 0.5 | 7.7 | 68.4 | 7.8 | 2.0 | | |
| TX-02-28 | TAG | 13.0 | 5.5 | 1.2 | 11.1 | 64.3 | 4.8 | | 0.1 | 0.063 |
| TX-02-04 | TFA | 13.6 | 2.9 | 1.2 | 12.1 | 65.3 | 4.9 | 2.1 | | |
| TX-02-04 | TAG | 12.0 | 4.4 | 2.4 | 21.6 | 55.9 | 3.6 | | 0.4 | 0.206 |
| TX-02-25 | TFA | 12.2 | 2.8 | 0.5 | 9.4 | 68.8 | 6.3 | 2.5 | | |
| TX-02-25 | TAG | 10.3 | 4.2 | 1.0 | 15.4 | 62.5 | 6.6 | | 0.4 | 0.159 |
| TX-02-05 | TFA | 13.6 | 3.6 | 3.2 | 14.7 | 59.8 | 5.1 | 2.5 | | |
| TX-02-05 | TAG | 12.2 | 5.5 | 7.0 | 26.8 | 43.4 | 5.1 | | 0.6 | 0.220 |
| TX-02-14 | TFA | 15.9 | 5.7 | 30.9 | 12.7 | 26.0 | 8.9 | 2.8 | | |
| TX-02-14 | TAG | 17.9 | 8.5 | 42.6 | 14.9 | 7.8 | 8.4 | | 1.4 | 0.514 |
| TX-02-131 | TFA | 12.6 | 1.4 | 0.6 | 8.3 | 73.1 | 3.9 | 2.9 | | |
| TX-02-131 | TAG | 16.0 | 3.9 | 1.9 | 18.0 | 53.9 | 6.3 | | 0.2 | 0.061 |
| TX-02-129 | TFA | 12.1 | 1.6 | 1.0 | 10.4 | 70.5 | 4.3 | 2.9 | | |
| TX-02-129 | TAG | 12.8 | 3.6 | 2.5 | 22.0 | 53.6 | 5.5 | | 0.3 | 0.106 |
| TX-02-08 | TFA | 17.6 | 2.6 | 5.6 | 17.2 | 51.2 | 5.8 | 3.0 | | |
| TX-02-08 | TAG | 24.4 | 5.9 | 15.8 | 29.3 | 15.8 | 8.8 | | 0.6 | 0.183 |
| TX-02-02 | TFA | 17.9 | 3.1 | 7.2 | 15.5 | 49.6 | 6.7 | 3.1 | | |
| TX-02-02 | TAG | 23.7 | 6.5 | 17.7 | 22.8 | 19.6 | 9.7 | | 0.6 | 0.194 |
| TX-02-11 | TFA | 25.1 | 4.1 | 9.0 | 16.3 | 36.3 | 9.1 | 3.2 | | |
| TX-02-11 | TAG | 33.3 | 6.6 | 13.9 | 20.9 | 16.0 | 9.3 | | 1.1 | 0.341 |
| TX-02-127 | TFA | 11.4 | 1.6 | 0.3 | 8.9 | 75.4 | 2.4 | 3.5 | | |
| TX-02-127 | TAG | 21.0 | 5.8 | 1.4 | 20.6 | 47.4 | 3.9 | | 0.1 | 0.016 |
| TX-02-30 | TFA | 16.4 | 3.1 | 3.7 | 17.1 | 53.8 | 5.9 | 4.0 | | |
| TX-02-30 | TAG | 21.3 | 5.0 | 7.6 | 27.1 | 30.5 | 8.5 | | 0.9 | 0.236 |
| TX-02-19 | TFA | 13.5 | 2.7 | 25.4 | 22.6 | 30.8 | 5.0 | 4.2 | | |

TABLE 5-continued

TFA and TAG levels, fatty acid composition and TTQ in sorghum leaves transformed with
pOIL102 (pZmUbi:WRI1) and pOIL197 (pZmUbi:DGAT and pZmUbi:Oleosin) during the
boot leaf stage of growth. The lines are listed in order of increasing TFA levels.

| Line | TAG or TFA | C16:0 | C18:0 | C18:1 | C18:2 | C18:3n3 | Other | TFA | TAG | TTQ |
|---|---|---|---|---|---|---|---|---|---|---|
| TX-02-19 | TAG | 14.0 | 3.3 | 34.3 | 27.0 | 16.6 | 4.8 | | 2.3 | 0.548 |
| TX-02-06 | TFA | 24.0 | 4.8 | 14.3 | 19.6 | 29.7 | 7.7 | 4.8 | | |
| TX-02-06 | TAG | 29.7 | 6.9 | 19.2 | 23.0 | 13.4 | 7.7 | | 2.7 | 0.555 |
| TX-02-10 | TFA | 22.0 | 3.3 | 10.3 | 22.7 | 33.7 | 7.9 | 6.3 | | |
| TX-02-10 | TAG | 24.8 | 4.1 | 12.9 | 27.0 | 22.4 | 8.8 | | 3.5 | 0.551 |
| TX-02-38 | TFA | 24.8 | 4.4 | 13.9 | 24.5 | 23.7 | 8.7 | 6.4 | | |
| TX-02-38 | TAG | 21.5 | 5.3 | 8.6 | 25.2 | 39.3 | 0.0 | | 2.5 | 0.392 |

TABLE 6

TFA and TAG levels, fatty acid composition and TTQ in pOIL103 +
pOIL197 primary transformants at boot leaf stage.

| Line | TFA or TAG | C16:0 | C18:0 | C18:1 | C18:2 | C18:3n3 | Other | TFA | TAG | TTQ |
|---|---|---|---|---|---|---|---|---|---|---|
| TX-03-20 | TFA | 12.2 | 2.6 | 1.7 | 10.3 | 67.5 | 5.7 | 2.1 | | |
| TX-03-20 | TAG | 9.4 | 3.6 | 3.3 | 18.1 | 63.0 | 2.5 | | 0.4 | 0.217 |
| TX-03-54 | TFA | 13.6 | 3.5 | 3.0 | 12.1 | 61.5 | 6.4 | 2.1 | | |
| TX-03-54 | TAG | 14.1 | 6.9 | 7.0 | 22.5 | 43.5 | 6.0 | | 0.4 | 0.207 |
| TX-03-61 | TFA | 23.9 | 3.1 | 1.7 | 19.0 | 43.9 | 8.3 | 2.2 | | |
| TX-03-61 | TAG | 31.4 | 6.6 | 3.4 | 28.3 | 19.6 | 10.8 | | 0.4 | 0.159 |
| TX-03-02 | TFA | 14.9 | 3.0 | 2.8 | 12.1 | 60.6 | 6.6 | 2.2 | | |
| TX-03-02 | TAG | 14.8 | 5.5 | 5.6 | 20.6 | 46.7 | 6.8 | | 0.5 | 0.222 |
| TX-03-53 | TFA | 18.5 | 3.7 | 8.9 | 15.4 | 43.1 | 10.4 | 2.3 | | |
| TX-03-53 | TAG | 20.1 | 6.8 | 16.7 | 24.5 | 23.3 | 8.6 | | 0.6 | 0.275 |
| TX-03-01 | TFA | 13.4 | 3.0 | 3.0 | 12.5 | 61.8 | 6.4 | 2.3 | | |
| TX-03-01 | TAG | 13.9 | 5.5 | 7.5 | 23.0 | 42.6 | 7.4 | | 0.4 | 0.164 |
| TX-03-47 | TFA | 12.8 | 2.1 | 1.6 | 7.5 | 70.7 | 5.3 | 2.4 | | |
| TX-03-47 | TAG | 14.8 | 5.1 | 5.0 | 19.3 | 52.1 | 3.7 | | 0.1 | 0.050 |
| TX-03-07 | TFA | 18.4 | 2.8 | 7.6 | 15.6 | 47.1 | 8.5 | 2.5 | | |
| TX-03-07 | TAG | 25.8 | 6.4 | 18.7 | 25.5 | 15.2 | 8.5 | | 0.3 | 0.127 |
| TX-03-05 | TFA | 21.4 | 2.3 | 1.4 | 9.7 | 59.1 | 6.1 | 2.6 | | |
| TX-03-05 | TAG | 36.4 | 5.6 | 3.9 | 17.1 | 28.4 | 8.6 | | 0.4 | 0.168 |
| TX-03-49 | TFA | 18.1 | 3.7 | 8.2 | 13.2 | 52.0 | 4.9 | 2.6 | | |
| TX-03-49 | TAG | 24.1 | 8.2 | 18.3 | 20.9 | 18.8 | 9.7 | | 0.5 | 0.212 |
| TX-03-34 | TFA | 19.0 | 2.7 | 6.0 | 15.4 | 50.6 | 6.4 | 2.6 | | |
| TX-03-34 | TAG | 24.8 | 10.5 | 10.9 | 23.9 | 20.6 | 9.3 | | 0.8 | 0.287 |
| TX-03-32 | TFA | 18.2 | 2.2 | 1.6 | 12.4 | 60.2 | 5.4 | 2.8 | | |
| TX-03-32 | TAG | 20.8 | 14.6 | 3.2 | 21.4 | 31.5 | 8.5 | | 0.6 | 0.204 |
| TX-03-04 | TFA | 18.8 | 3.1 | 5.8 | 13.4 | 50.3 | 8.6 | 2.9 | | |
| TX-03-04 | TAG | 26.7 | 7.5 | 14.6 | 23.1 | 19.0 | 9.1 | | 0.3 | 0.118 |
| TX-03-23 | TFA | 18.9 | 1.7 | 1.0 | 7.9 | 63.2 | 7.3 | 2.9 | | |
| TX-03-23 | TAG | 25.0 | 4.6 | 2.5 | 18.1 | 39.6 | 10.2 | | 0.2 | 0.070 |
| TX-03-25 | TFA | 14.5 | 1.8 | 0.4 | 6.4 | 73.5 | 3.4 | 3.0 | | |
| TX-03-25 | TAG | 20.3 | 5.1 | 1.0 | 12.3 | 53.6 | 7.7 | | 0.3 | 0.110 |
| TX-03-18 | TFA | 21.1 | 2.9 | 1.2 | 17.8 | 46.3 | 10.7 | 3.0 | | |
| TX-03-18 | TAG | 22.6 | 5.9 | 4.5 | 31.1 | 22.6 | 13.3 | | 0.4 | 0.143 |
| TX-03-50 | TFA | 16.5 | 2.6 | 6.1 | 12.9 | 53.9 | 8.0 | 3.0 | | |
| TX-03-50 | TAG | 20.2 | 19.9 | 12.9 | 19.6 | 20.6 | 6.8 | | 0.7 | 0.217 |
| TX-03-60 | TFA | 20.2 | 2.9 | 0.8 | 14.1 | 55.7 | 6.2 | 3.1 | | |
| TX-03-60 | TAG | 30.5 | 6.2 | 1.6 | 21.6 | 30.2 | 9.9 | | 0.6 | 0.202 |
| TX-03-21 | TFA | 12.3 | 1.7 | 0.5 | 6.8 | 74.4 | 4.4 | 3.2 | | |
| TX-03-21 | TAG | 16.1 | 4.7 | 1.6 | 13.1 | 57.0 | 7.5 | | 0.2 | 0.067 |
| TX-03-40 | TFA | 17.1 | 1.4 | 0.4 | 8.0 | 68.2 | 4.9 | 3.2 | | |
| TX-03-40 | TAG | 34.5 | 4.4 | 0.9 | 14.5 | 39.8 | 5.9 | | 0.4 | 0.112 |
| TX-03-62 | TFA | 25.3 | 2.9 | 1.7 | 14.7 | 47.9 | 7.6 | 3.3 | | |
| TX-03-62 | TAG | 40.3 | 5.6 | 3.5 | 22.3 | 18.7 | 9.5 | | 0.6 | 0.171 |
| TX-03-36 | TFA | 19.5 | 2.0 | 2.0 | 11.4 | 58.3 | 6.8 | 3.5 | | |
| TX-03-36 | TAG | 31.2 | 4.0 | 4.4 | 20.0 | 29.4 | 11.0 | | 0.6 | 0.160 |
| TX-03-63 | TFA | 25.4 | 3.6 | 2.6 | 18.2 | 42.0 | 8.2 | 3.5 | | |
| TX-03-63 | TAG | 33.1 | 6.1 | 3.8 | 24.9 | 21.6 | 10.4 | | 1.4 | 0.383 |
| TX-03-45 | TFA | 16.4 | 1.4 | 0.5 | 8.1 | 69.1 | 4.5 | 3.5 | | |
| TX-03-45 | TAG | 30.8 | 4.6 | 1.4 | 16.2 | 40.7 | 6.3 | | 0.2 | 0.058 |
| TX-03-17 | TFA | 14.2 | 1.8 | 0.8 | 6.9 | 71.2 | 5.2 | 3.6 | | |
| TX-03-17 | TAG | 18.7 | 4.5 | 2.2 | 13.5 | 52.8 | 8.3 | | 0.4 | 0.120 |
| TX-03-57 | TFA | 18.7 | 3.4 | 1.5 | 13.8 | 55.8 | 6.8 | 3.6 | | |
| TX-03-57 | TAG | 23.4 | 6.3 | 3.0 | 21.0 | 36.2 | 10.1 | | 1.2 | 0.330 |
| TX-03-11 | TFA | 29.1 | 6.4 | 2.1 | 22.4 | 33.0 | 7.1 | 3.6 | | |
| TX-03-11 | TAG | 30.6 | 8.5 | 2.8 | 27.0 | 19.7 | 11.4 | | 1.9 | 0.510 |
| TX-03-48 | TFA | 27.1 | 3.7 | 3.7 | 20.6 | 37.2 | 7.6 | 3.7 | | |
| TX-03-48 | TAG | 31.2 | 5.0 | 5.5 | 27.1 | 23.0 | 8.1 | | 2.1 | 0.569 |

TABLE 6-continued

TFA and TAG levels, fatty acid composition and TTQ in pOIL103 + pOIL197 primary transformants at boot leaf stage.

| Line | TFA or TAG | C16:0 | C18:0 | C18:1 | C18:2 | C18:3n3 | Other | TFA | TAG | TTQ |
|---|---|---|---|---|---|---|---|---|---|---|
| TX-03-29 | TFA | 20.1 | 2.3 | 1.7 | 13.4 | 55.5 | 7.1 | 3.7 | | |
| TX-03-29 | TAG | 33.0 | 5.0 | 4.1 | 24.3 | 26.4 | 7.2 | | 0.4 | 0.104 |
| TX-03-26 | TFA | 15.3 | 1.6 | 0.4 | 5.9 | 71.3 | 5.5 | 3.9 | | |
| TX-03-26 | TAG | 25.2 | 4.6 | 1.7 | 13.3 | 49.7 | 5.5 | | 0.3 | 0.074 |
| TX-03-10 | TFA | 28.6 | 6.8 | 2.1 | 21.8 | 33.0 | 7.7 | 3.9 | | |
| TX-03-10 | TAG | 31.0 | 8.5 | 2.9 | 26.7 | 18.6 | 12.2 | | 1.9 | 0.491 |
| TX-03-58 | TFA | 16.3 | 2.6 | 1.3 | 14.5 | 60.3 | 5.0 | 4.1 | | |
| TX-03-58 | TAG | 20.4 | 5.2 | 2.8 | 24.3 | 39.2 | 8.2 | | 1.1 | 0.278 |
| TX-03-08 | TFA | 19.8 | 2.0 | 0.7 | 6.6 | 64.9 | 5.9 | 4.1 | | |
| TX-03-08 | TAG | 34.8 | 5.2 | 2.7 | 14.3 | 34.5 | 8.5 | | 0.2 | 0.051 |
| TX-03-33 | TFA | 27.4 | 2.4 | 1.5 | 16.3 | 46.0 | 6.4 | 4.2 | | |
| TX-03-33 | TAG | 39.2 | 5.4 | 2.3 | 21.9 | 20.8 | 10.5 | | 1.6 | 0.386 |
| TX-03-22 | TFA | 19.8 | 2.8 | 3.1 | 11.8 | 53.4 | 9.1 | 4.2 | | |
| TX-03-22 | TAG | 28.4 | 5.3 | 5.4 | 19.4 | 38.3 | 3.2 | | 1.2 | 0.287 |
| TX-03-41 | TFA | 18.1 | 2.6 | 3.1 | 11.1 | 58.0 | 7.1 | 4.8 | | |
| TX-03-41 | TAG | 27.8 | 6.0 | 6.8 | 19.3 | 34.9 | 5.3 | | 0.7 | 0.139 |
| TX-03-46 | TFA | 24.6 | 2.0 | 0.6 | 7.9 | 57.4 | 7.4 | 4.9 | | |
| TX-03-46 | TAG | 44.7 | 4.2 | 1.3 | 13.4 | 31.4 | 5.0 | | 1.1 | 0.220 |
| TX-03-28 | TFA | 28.5 | 2.1 | 1.3 | 23.4 | 33.7 | 11.0 | 6.2 | | |
| TX-03-28 | TAG | 36.0 | 2.9 | 3.1 | 29.6 | 18.5 | 10.0 | | 3.7 | 0.596 |
| TX-03-31 | TFA | 33.4 | 2.9 | 4.3 | 28.6 | 25.5 | 5.5 | 8.3 | | |
| TX-03-31 | TAG | 38.0 | 3.6 | 4.9 | 30.6 | 14.8 | 8.1 | | 6.6 | 0.789 |

Example 3. Increasing Expression of Thioesterase in Plant Cells

De novo fatty acid synthesis takes place in the plastids of eukaryotic cells where the fatty acids are synthesized while bound to acyl carrier protein as acyl-ACP conjugates. Following chain elongation to C16:0 and C18:0 acyl groups and then desaturation to C18:1 while linked to ACP, the fatty acids are cleaved from the ACP by thioesterases and enter the eukaryotic pathway by export from the plastids and transport to the ER where they participate in membrane and storage lipid biogenesis. In chloroplasts, the export process has two steps: firstly, acyl chains are released as free fatty acids by the enzymatic activity of acyl-ACP thioesterases (fatty acyl thioesterase; FAT), secondly by reaction with CoA to form acyl-CoA esters which is catalysed by long chain acyl-CoA synthetases (LACS). *A. thaliana* contains 3 fatty acyl thioesterases which can be distinguished based on their acyl chain specificity. FATA1 and FATA2 preferentially hydrolyze unsaturated acyl-ACPs while saturated acyl-ACP chains are typically cleaved by FATB.

To explore the effect upon total fatty acid content, TAG content, and fatty acid composition of the co-expression of a thioesterase and genes encoding the WRI1 and/or DGAT polypeptides, chimeric genes were made for each of the three *A. thaliana* thioesterases by insertion of the coding regions into the pJP3343 binary expression vector for transient expression in *N. benthamiana* leaf cells from the 35S promoter. Protein coding regions for the *A. thaliana* FATA1 (Accession No. NP_189147.1, SEQ ID NO:43) and FATA2 (Accession No. NP_193041.1, SEQ ID NO:44) thioesterases were amplified from silique cDNA using primers containing EcoRI and PstI sites and subsequently cloned into pJP3343 using the same restriction sites. The resulting expression vectors were designated pOIL079 and pOIL080, respectively. The protein coding region of the *A. thaliana* FATB gene (Accession No. NP_172327.1, SEQ ID NO:45) was amplified using primers containing NotI and SacI flanking sites and cloned into the corresponding restriction sites of pJP3343, resulting in pOIL081. Constructs pOIL079, pOIL080 and pOIL081 are infiltrated into *N. benthamiana* leaf tissue, either individually or in combination with constructs containing the genes for the *A. thaliana* WRI1 transcription factor (AtWRI1) (pJP3414) and/or DGAT1 acyltransferase (AtDGAT1) (pJP3352). For comparison, chimeric genes encoding the *Cocos nucifera* FatB1 (Cn-FATB1) (pJP3630), *C. nucifera* FatB2 (CnFATB2) (pJP3629) were introduced into *N. benthamiana* leaf tissue in parallel with the *Arabidopsis* thioesterases, to compare the effect of the FatB polypeptides having MCFA specificity to the *Arabidopsis* thioesterases which do not have MCFA specificity. All of the infiltrations included a chimeric gene for expression of the p19 silencing suppressor as described in Example 1. The negative control infiltrated only the p19 T-DNA.

A synergistic effect was observed between thioesterase expression and WRI1 and/or DGAT over-expression on TAG levels in *N. benthamiana* leaves. Expression of the thioesterase genes without the WRI1 or DGAT genes significantly increased TAG levels above the low level in the negative control (p19 alone). For example, expression of the coconut FATB2 thioesterase resulted in an 8.2-fold increase in TAG levels in the leaves compared to the negative control. Co-expression of the *A. thaliana* WRI1 transcription factor with each of the thioesterases further increased TAG levels compared to the AtWRI1 control. Co-expression of each of the coconut thioesterases CnFATB1 and CnFATB2 with WRI1 resulted in higher TAG levels than each of the three *A. thaliana* thioesterases with WRI1. Interestingly, the converse was observed when the *A. thaliana* DGAT1 acyltransferase was co-expressed in combination with a thioesterase and WRI1. This suggested a better match in acyl-chain specificity of the *A. thaliana* thioesterases and the *A. thaliana* DGAT1 acyltransferase, resulting in a greater flux of acyl-chains from the acyl-ACP into TAG. The non-MCFA thioesterases were also considerably more effective in elevating the percentage of oleic acid in the total fatty acid content in the leaves. Co-expression of the AtWRI1, AtDGAT1 and AtFATA2 resulted in the greatest level of TAG in the leaves, providing a level which was 1.6-fold greater than when AtWRI1 and AtDGAT1 were co-expressed without the thioesterase. In another experiment, transient overexpression of FATA2 in combination with WRI1 and DGAT1 led to a 2.5-fold increase in TAG level relative to a p19+WRI1+DGAT1 control, which represented a 50-fold increase in TAG levels relative to p19 alone. Addition of FATA1 increased TAG levels 2-fold compared to p19+WRI1+DGAT1, a 40-fold increase compared to p19 alone. Addition of FATB increased TAG levels by 1.6-fold relative to p19+WRI1+DGAT1, a 32-fold increase relative to p19 control.

Co-expression of thioesterase FATA or FATB together with WRI1 and DGAT1 resulted in modified leaf fatty acid composition relative to WRI1 and DGAT1 without thioesterase. Addition of FATAL increased the percentages of C16:0 and C18:0 at the expense of saturated fatty acids. Addition of FATA2 also increased the proportion of C18:0 but did not have as great an effect on C16:0. In contrast, addition of FATB increased C16:0 but not C18:0 levels. In each case, addition of FATA1, FATA2 and FATB reduced C18:1 levels. Notably, the C16:0 percentage increased from 28.4% in p19+WRI1+DGAT1 without thioesterase to 43.8% with the addition of FATA1, to 34.4% with the addition of FATA2 and to 46.3% with the addition of FATB.

These experiments confirmed the synergistic increase in oil synthesis and accumulation when both WRI1 and DGAT were co-expressed as well as showing the further synergistic increase obtained by adding a thioesterase to the combination.

Effect of Transient Thioesterase Expression in a High Oil Background

The three A. thaliana thioesterase genes were also tested by transient expression in leaves of N. benthamiana plants (transgenic line AT001) which were transgenic for and stably expressing WRI1, DGAT1 and OLEOSIN genes (El Tahchy et al., 2017). Thirty plants from homozygous, T2 generation, transgenic AT001 seeds were grown in a randomised design alongside wild-type (WT) controls. At a vegetative stage of growth, 53 days after sowing (DAS), the transgenic leaves contained about 8.7% (DW) TAG compared to about 0.03% (DW) TAG in the wild-type plants. After further growth of the transgenic plants, TAG levels increased from about 11.2% to about 21.3% (DW) during flowering stages. They continued to increase, reaching about 31.4% (DW) TAG at maturity (late seed development stage). As the plants senesced, the TAG level in at least some plants decreased to about 19.6% DW.

The genes encoding the thioesterases were introduced into leaves of young plants (49 DAS) when the leaves typically had about 3.1% (DW) TAG, and sampled 5 days after infiltration with the Agrobacterium strains. Leaf samples were harvested and analyzed for TAG content. FATA2 overexpression in AT001 N. benthamiana leaves significantly increased TAG to 4.4% (DW) compared to the p19 control (3.1% TAG). FATA1 increased TAG content to 3.9% (DW). FATB transient expression did not appear to increase TAG accumulation in this experiment.

Samples were also used in radiolabel feeding assays with [$^{14}$C]-acetate. [$^{14}$C]-acetate was added in a 10 minute pulse to leaf discs of AT001 leaves, infiltrated previously with genes encoding p19 and one of FATA1, FATA2 and FATB. This pulse was followed by a 20 minute chase. Lipid extracts were prepared at each time point followed by separation of labelled lipid classes on TLC. Quantitation of the labelled reaction products showed increases in the rate of TAG production in the AT001 leaves transiently expressing FATA1 (602 DPM), FATA2 (762 DPM) and FATB (559 DPM) compared to the p19 control (283 DPM).

Three different binary expression vectors were constructed to test the effect of co-expression of genes encoding WRI1, DGAT1 and FATA on TAG levels and fatty acid composition in stably transformed N. tabacum leaves. The vector pOIL121 contained an SSU::AtWRI1 gene for expression of AtWRI1 from the SSU promoter, a 35S::AtDGAT1 gene for expression of AtDGAT from the 35S promoter, and an enTCUP2::AtFATA2 gene for expression of AtFATA2 from the enTCUP2 promoter which is a constitutive promoter. These genetic constructs were derived from pOIL38 by first digesting the DNA with NotI to remove the gene coding for the S. indicum oleosin. The protein coding region of the A. thaliana FATA2 gene was amplified and flanked with NotI sites using pOIL80 DNA as template. This fragment was then inserted into the NotI site of pOIL38. pOIL121 then served as a parent vector for pOIL122 which contained an additional enTCUP2::SDP1 hairpin RNA cassette for RNAi-mediated silencing of the endogenous SDP1 gene in the transgenic plants. To do this, the entire N. benthamiana SDP1 hairpin cassette was isolated from pOIL51 (Vanhercke et al., 2017) as an SfoI-SmaI fragment and cloned into the SfoI site of pOIL121, producing pOIL122 (FIG. 2). A third vector, pOIL123, containing the SSU::WRI1 and 35S::DGAT1 genes and the enTCUP2::SDP1 hairpin RNA gene was obtained in a similar way by cloning the enTCUP2::SDP1 hairpin RNA cassette as a SfoI-SmaI fragment into the SfoI site of pOIL36.

In summary, the vectors contained the gene combinations:

pOIL121: SSU::AtWRI1, 35S::AtDGAT1, enTCUP2::AtFATA2.

pOIL122: SSU::AtWRI1, 35S::AtDGAT1, enTCUP2::AtFATA2, enTCUP2::SDP1 hairpin.

pOIL123: SSU::AtWRI1, 35S::AtDGAT1, enTCUP2::SDP1 hairpin.

The three constructs were each used to produce transformed N. tabacum plants (cultivar Wi38) by Agrobacterium-mediated transformation. Co-expression of the A. thaliana FATA2 thioesterase or silencing of the endogenous SDP1 TAG lipase in combination with AtWRI1 and AtDGAT1 expression each resulted in further elevated TAG levels compared to expression of AtWRI1 and AtDGAT1 in the absence of both of the thioesterase gene and the SDP1-silencing gene. The greatest TAG yields were obtained using pOIL122 by the combined action of all four chimeric genes. In absence of SDP1, pOIL121 lines yielded 13.3% TAG which was included increased palmitate (16:0) levels (36%) and reduced ALA (18:3ω3) levels (7%).

It is noted that N. benthamiana is an 18:3 plant. The same constructs pOIL079, pOIL080 and pOIL081 are used to transform A. thaliana, a 16:3 plant.

The inventors conceived of the model that increasing plastidial fatty acid export such as by increased fatty acyl thioesterase activity reduces acyl-ACP accumulation in the plastids, thereby increasing fatty acid biosynthesis as a result of reduced feedback inhibition on the acetyl-CoA carboxylase (ACCase) (Andre et al., 2012; Moreno-Perez et al., 2012). Thioesterase over-expression increases export of acyl chains from the plastids into the ER, thereby providing an efficient link between so-called 'Push' and 'Pull' metabolic engineering strategies.

Example 4. The Effect of Different Transcription Factor Polypeptides on Plant Traits Previously reported experiments with WRI1 and DGAT (Vanhercke et al., 2013) used a synthetic gene encoding A. thaliana AtWRI1 (Accession No. AAP80382.1) and a synthetic gene encoding AtDGAT1, also from *A. thaliana* (Accession No. AAF19262; SEQ ID NO: 1). To compare other WRI polypeptides with AtWRI1 for their ability to combine with DGAT to increase oil content, other WRI coding sequences were identified and used to generate constructs for expression in *N. benthamiana* leaves. Nucleotide sequences encoding the *A. thaliana* WRI3 (Accession No. AAM91814.1, SEQ ID NO:46) and WRI4 (Accession No. NP_178088.2, SEQ ID NO:47) transcription factors (To et al., 2012) were synthesized and inserted as EcoRI fragments into pJP3343 under the control of the 35S promoter. The resulting binary expression vectors were designated pOIL027 and pOIL028, respectively. The coding sequence for the oat (*Avena sativa*) WRI1 (AsWRI1, SEQ ID NO:48) was PCR amplified from a vector provided by Prof. Sten Stymne (Swedish University of Agricultural Sciences) using flanking primers containing additional EcoRI sites. The amplified fragment was inserted into pJP3343 resulting in pOIL055. A WRI1 candidate sequence from *S. bicolor* (Accession No. XP_002450194.1, SEQ ID NO:49) was identified by a BLASTp search on the NCBI server using the *Zea mays* WRI1 amino acid sequence (Accession No. NP_001137064.1, SEQ ID NO:50) as query. The protein coding region of the *S. bicolor* WRI1 gene (SbWRI1) was synthesized and inserted as an EcoRI fragment into pJP3343, yielding pOIL056. A gene candidate encoding a WRI1 was identified from the Chinese tallow (*Triadica sebifera*; TsWRI1, SEQ ID NO:51) transcriptome (Uday et al., submitted). The protein coding region was synthesized and inserted as an EcoRI fragment into pJP3343 resulting in pOIL070. The pJP3414 and pJP3352 binary vectors containing the coding sequences for expression of the *A. thaliana* WRI1 and DGAT1 polypeptides were as described by Vanhercke et al. (2013).

Plasmids containing the various WRI coding sequences were introduced into *N. benthamiana* leaf tissue for transient expression using a gene encoding the p19 viral suppressor protein in all inoculations as described in Example 1. The genes encoding the WRI polypeptides were either tested alone or in combination with the DGAT1 acyltransferase gene, the latter to provide greater TAG biosynthesis and accumulation. The positive control in this experiment was the combination of the genes encoding *A. thaliana* WRI1 transcription factor and AtDGAT1. All infiltrations were done in triplicate using three different plants and TAG levels were analyzed as described in Example 1. Expression of most of the individual WRI polypeptides in the absence of exogenously added DGAT1 resulted in increased, yet still low, TAG levels (<0.23% on dry weight basis) in infiltrated leaf spots, compared to the control which had only the p19 construct (FIG. 3). The exception was TsWRI1 which, by itself, did not appear to increase TAG levels significantly. In addition, differences in TAG levels produced by expression of the different WRI transcription factors on their own were not great. Both AsWRI1 and SbWRI1 yielded TAG levels similar to AtWRI1 on its own. Analysis of the TAG fatty acid composition revealed only minor changes except for increased C18:1Δ9 levels from expression of AtWRI3 in the infiltrated leaf tissues (Table 7).

In contrast, differences in0 TAG yields from expression of the different WRI polypeptides were more pronounced upon co-expression with the AtDGAT1 acyltransferase. This again demonstrated the synergistic effect of WRI1 and DGAT co-expression on TAG biosynthesis in infiltrated *N. benthamiana* leaf tissue, as reported by Vanhercke et al. (2013). Intermediate TAG levels were observed upon co-expression of DGAT1 with AtWRI3, AtWRI4 and TsWRI1 expressing vectors while levels obtained with the AsWRI1 and AtWRI1 were significantly lower. In a result that could not have been predicted beforehand, the highest TAG yields were obtained with co-expression of DGAT with SbWRI1, even though the assay was done in dicotyledonous cells. TAG fatty acid composition analysis revealed increased levels of $C18:1^{\Delta 9}$ and decreased levels of $C18:3^{\Delta 9,12,15}$ (ALA) in the case of SbWRI1, AsWRI1 and the AtWRI1 positive control. Unlike AtWRI1, however, expression of AsWRI1 and SbWRI1 both displayed increased C16:0 levels compared to the p19 negative control. Interestingly, AtWRI3 infiltrated leaf samples exhibited a distinct TAG profile with $C18:1^{\Delta 9}$ being enriched while C16:0 and ALA were only slightly affected.

This experiment showed that the *S. bicolor* WRI1 transcription factor, SbWRI1, was superior to AtWRI1 when co-expressed with DGAT to increase TAG levels in vegetative plant parts. The inventors also concluded that a transcription factor, for example a WRI1, from a monocotyledonous plant could function well in a dicotyledonous plant cell, indeed might even have superior activity compared to a corresponding transcription factor from a dicotyledonous plant. Likewise, a transcription factor from a dicotyledonous plant could function well in a monocotyledonous plant cell.

TABLE 7

TAG fatty acid composition in *N. benthamiana* leaf samples infiltrated with different chimeric genes for expression of WRI (n = 3). All samples were also infiltrated with the P19 construct. The TAG samples also contained 0.1-0.4% C14:0; 0.5-1.2% C16:3 and; 0.1-0.7% C18:1Δ11.

| Infiltrated genes | C16:0 | C16:1 | C18:0 | C18:1 | C18:2 | C18:3n3 | C20:0 | C20:1 | C22:0 | C24:0 |
|---|---|---|---|---|---|---|---|---|---|---|
| Control (P19) | 33.6 ± 4.7 | 0.5 ± 0.4 | 8.9 ± 2.2 | 4.7 ± 0.6 | 16.9 ± 1.0 | 32.2 ± 7.8 | 1.1 ± 0.2 | 0.8 ± 1.5 | 0.0 | 0.0 |
| WRI1 | 35.5 ± 3.4 | 0.7 ± 0.2 | 5.2 ± 0.8 | 5.4 ± 1.3 | 17.1 ± 1.0 | 33.1 ± 2.7 | 0.8 ± 0.1 | 0.5 ± 0.6 | 0.3 ± 0.0 | 0.0 |
| WRI3 | 27.3 ± 1.6 | 0.9 ± 0.2 | 4.8 ± 0.3 | 10.2 ± 1.5 | 16.1 ± 1.0 | 37.8 ± 1.2 | 0.8 ± 0.1 | 0.6 ± 0.7 | 0.1 ± 0.2 | 0.0 |
| WRI4 | 30.1 ± 0.4 | 1.0 ± 0.4 | 5.2 ± 0.8 | 4.6 ± 0.6 | 17.2 ± 0.4 | 38.1 ± 1.6 | 0.8 ± 0.1 | 1.3 ± 1.3 | 0.0 | 0.0 |
| AsWRI | 35.7 ± 3.0 | 1.7 ± 0.4 | 5.3 ± 0.7 | 6.5 ± 0.3 | 15.4 ± 0.4 | 31.6 ± 1.6 | 0.8 ± 0.1 | 0.4 ± 0.7 | 0.3 ± 0.1 | 0.0 |
| SbWRI | 37.4 ± 0.8 | 1.9 ± 0.3 | 4.8 ± 0.3 | 7.0 ± 1.2 | 15.2 ± 0.3 | 30.8 ± 0.3 | 0.8 ± 0.1 | 0.4 ± 0.6 | 0.3 ± 0.0 | 0.0 |
| TsWRI | 34.5 ± 4.8 | 0.0 | 9.4 ± 8.2 | 5.9 ± 1.7 | 16.0 ± 0.7 | 29.3 ± 12.4 | 0.0 | n.d. | 0.0 | 0.0 |
| Control (P19) | 31.0 ± 2.1 | 0.9 ± 0.1 | 8.7 ± 1.3 | 8.0 ± 2.3 | 24.9 ± 1.5 | 22.1 ± 4.7 | 2.0 ± 0.1 | 0.0 | 0.6 ± 0.6 | 0.2 ± 0.4 |
| WRI1 + DGAT | 27.7 ± 0.1 | 0.3 ± 0.0 | 7.0 ± 0.1 | 17.2 ± 0.7 | 27.9 ± 0.9 | 14.7 ± 0.3 | 2.4 ± 0.2 | 0.3 ± 0.0 | 1.1 ± 0.1 | 0.8 ± 0.2 |
| WRI3 + DGAT | 30.0 ± 0.8 | 0.6 ± 0.1 | 5.9 ± 0.4 | 13.9 ± 2.9 | 21.5 ± 1.1 | 21.3 ± 0.8 | 2.8 ± 0.1 | 0.2 ± 0.0 | 1.8 ± 0.1 | 1.0 ± 0.2 |
| WRI4 + DGAT | 27.0 ± 0.5 | 0.2 ± 0.1 | 8.5 ± 0.2 | 5.8 ± 0.7 | 23.9 ± 0.8 | 25.2 ± 1.3 | 3.5 ± 0.1 | 0.2 ± 0.0 | 2.1 ± 0.2 | 1.7 ± 0.2 |
| AsWRI + DGAT | 33.8 ± 0.5 | 1.1 ± 0.1 | 5.5 ± 0.9 | 12.2 ± 1.6 | 26.0 ± 1.9 | 16.3 ± 1.3 | 2.2 ± 0.2 | 0.2 ± 0.0 | 1.2 ± 0.1 | 0.8 ± 0.1 |
| SbWRI + DGAT | 34.6 ± 0.5 | 1.3 ± 0.1 | 5.6 ± 0.4 | 13.9 ± 1.6 | 23.6 ± 1.3 | 15.8 ± 0.6 | 2.2 ± 0.1 | 0.2 ± 0.0 | 1.2 ± 0.1 | 0.9 ± 0.1 |
| TsWRI + DGAT | 25.4 ± 0.5 | 0.2 ± 0.0 | 9.4 ± 0.1 | 7.7 ± 1.0 | 27.0 ± 1.3 | 22.1 ± 2.4 | 3.6 ± 0.2 | 0.2 ± 0.0 | 1.8 ± 0.2 | 1.3 ± 0.2 |

Use of Other Transcription Factors

Genetic constructs were prepared for expression of each of 24 different transcription factors in plant cells to test their ability to function for increasing TAG levels in combination with other genes involved in TAG biosynthesis and accumulation. These transcription factors were candidates as alternatives for WRI1 or for addition to combinations including one or more of WRI1, LEC1 and LEC2 transcription factors for use in plant cells, particularly in vegetative plant parts. Their selection was largely based on their reported involvement in embryogenesis (reviewed in Baud and Lepiniec (2010), and Ikeda et al. (2006)), similar to LEC2, or plant storage lipid metabolism. Experiments were therefore carried out to assay their function, using the N. benthamiana expression system (Example 1), as follows.

Nucleotide sequences of the protein coding regions of the following transcription factors were codon optimized for expression in N. benthamiana and N. tabacum, synthesized and subcloned as NotI-SacI fragments into the respective sites of pJP3343: A. thaliana FUS3 (pOIL164) (Luerssen et al., 1998; Accession number AAC35247; SEQ ID NO:34), A. thaliana LEC1L (pOIL165) (Kwong et al. 2003; Accession number AAN15924; SEQ ID NO:33), A. thaliana LEC1 (pOIL166) (Lotan et al., 1998; Accession number AAC39488; SEQ ID NO:31), G. max MYB73 (pOIL167) (Liu et al., 2014; Accession number ABH02868; SEQ ID NO:57), A. thaliana bZIP53 (pOIL168) (Alonso et al., 2009; Accession number AAM14360; SEQ ID NO:58), A. thaliana AGL15 (pOIL169) (Zheng et al., 2009; Accession number NP_196883; SEQ ID NO:59), A. thaliana MYB118 (Accession number AAS58517; pOIL170; SEQ ID NO:60), MYB115 (Wang et al., 2002; Accession number AAS10103; pOIL171; SEQ ID NO:61), A. thaliana TANMEI (pOIL172) (Yamagishi et al., 2005; Accession number BAE44475; SEQ ID NO:62), A. thaliana WUS (pOIL173) (Laux et al., 1996; Accession number NP_565429; SEQ ID NO:63), A. thaliana BBM (pOIL174) (Boutilier et al., 2002; Accession number AAM33893, SEQ ID NO:64), B. napus GFR2a1 (Accession number AFB74090; pOIL177; SEQ ID NO:64), GFR2a2 (Accession number AFB74089; pOIL178; SEQ ID NO:65) (Liu et al. (2012)), E. guineensis NF-YB1 (pOIL405) (Geurin et al., 2016; Accession number XM_010907896; SEQ ID NO:143, E. guineensis ZFP1 (pOIL406) (Geurin et al., 2016; Accession number XM_010930940; SEQ ID NO:144), A. thaliana NF-YB2 (pOIL407) (Geurin et al., 2016; Accession number NM_124138; SEQ ID NO:145), A. thaliana NF-YB3 (pOIL408) (Geurin et al., 2016; Accession number NM_117534; SEQ ID NO:146), A. thaliana ZFP2 (pOIL409) (Geurin et al, 2016; Accession number NM_125133; SEQ ID NO:147), E. guineensis ABI5 (pOIL410) (Yeap et al., 2017; Accession number XM_010909282; SEQ ID NO:148), E. guineensis NF-YC2 (pOIL411) (Yeap et al., 2017; Accession number XM_010911913; SEQ ID NO:149), and E. guineensis NF-YA3 (pOIL412) (Yeap et al., 2017; Accession number XM_010941630; SEQ ID NO:150). In addition, a codon optimized version of the A. thaliana PHR1 transcription factor involved in adaptation to high light phosphate starvation conditions was similarly subcloned into pJP3343 (pOIL189) (Nilsson et al (2012); Accession number AAN72198; SEQ ID NO:221). The sequence coding for the G. max DOF4 (Wang et al., 2007; Accession number DQ857254; SEQ ID NO:151) was codon optimized for expression in N. benthamiana and N. tabacum, synthesized as a NotI-SpeI fragment and subcloned into pJP3343. The resulting vector was designated pOIL379. Finally, the gene coding for the G. max ZF351 transcription factor (Li et al., 2017; Accession number XM_003526219; SEQ ID NO:152) was synthesized as a NotI-EcoRI fragment and cloned into pJP3343, resulting in pOIL420. These transcription factors are summarised in Table 8.

As a screening assay to determine the function of these transcription factors, the genetic constructs and a gene encoding DGAT1 were co-infiltrated into N. benthamiana leaf cells as described in Example 1, either with or without a gene encoding WRI1. Total lipid content and fatty acid composition of the leaf cells were analysed 5 days post-infiltration. Among the various embryogenic transcription factors tested, only overexpression of FUS3 resulted in significantly increased TAG levels in N. benthamiana leaf tissue when compared to DGAT and DGAT1+WRI1 control infiltrations (Table 9).

TABLE 8

Additional transcription factors and the genetic constructs for their expression

| Plasmid | Transcription factor | Species | Length (amino acid) | Accession number |
|---|---|---|---|---|
| pOIL164 | FUS3 | A. thaliana | 312 | AAC35247 |
| pOIL165 | LEC1L | A. thaliana | 234 | AAN15924 |
| pOIL166 | LEC1 | A. thaliana | 208 | AAC39488 |
| pOIL167 | MYB73 | G. max | 74 | ABH02868 |
| pOIL168 | bZIP53 | A. thaliana | 146 | AAM14360 |
| pOIL169 | AGL15 | A. thaliana | 268 | NP_196883 |
| pOIL170 | MYB118 | A. thaliana | 437 | AAS58517 |
| pOIL171 | MYB115 | A. thaliana | 359 | AAS10103 |
| pOIL172 | TANMEI | A. thaliana | 386 | BAE44475 |
| pOIL173 | WUS | A. thaliana | 292 | NP_565429 |
| pOIL174 | BBM | A. thaliana | 584 | AAM33803 |
| pOIL177 | GFR2a1 | B. napus | 453 | AFB74090 |
| pOIL178 | GFR2a2 | B. napus | 461 | AFB74089 |
| pOIL189 | PHR1 | A. thaliana | 409 | AAN72198 |
| pOIL379 | DOF4 | G. max | 300 | DQ857254 |
| pOIL405 | NF-YB1 | E. guineensis | 215 | XM_010907896 |
| pOIL406 | ZFP1 | E. guineensis | 142 | XM_010930940 |
| pOIL407 | NF-YB2 | A. thaliana | 190 | NM_124138 |
| pOIL408 | NF-YB3 | A. thaliana | 161 | NM_117534 |
| pOIL409 | ZFP2 | A. thaliana | 150 | NM_125133 |
| pOIL410 | ABI5 | E. guineensis | 398 | XM_010909282 |
| pOIL411 | NF-YC2 | E. guineensis | 272 | XM_010911913 |
| pOIL412 | NF-YA3 | E. guineensis | 352 | XM_010941630 |
| pOIL420 | ZF351 | G. max | 351 | 003526219 |

TABLE 9

TAG level (% leaf dry weight) and fatty acid profile of infiltrated N. benthamiana leaves.

| | C16:0 | C16:1 | C18:0 | C18:1 | C18:2 | C18:3 | TAG |
|---|---|---|---|---|---|---|---|
| P19 | 27.1 ± 1.5 | 0.3 ± 0.1 | 9.6 ± 1.7 | 4.4 ± 1.2 | 22.4 ± 4.0 | 30.5 ± 0.9 | 0.0 |
| P19 + DGAT1 | 26.3 ± 1.0 | 0.1 ± 0.0 | 10.7 ± 0.6 | 3.7 ± 0.7 | 26.1 ± 1.6 | 26.4 ± 1.4 | 0.2 ± 0.0 |
| P19 + DGAT1 + FUS3 | 24.1 ± 1.0 | 0.1 ± 0.0 | 6.3 ± 0.4 | 5.2 ± 1.6 | 27.9 ± 1.8 | 30.0 ± 1.8 | 0.6 ± 0.1 |
| P19 + DGAT1 + LEC1L | 26.0 ± 1.4 | 0.1 ± 0.0 | 10.3 ± 0.8 | 3.9 ± 1.0 | 26.6 ± 2.1 | 26.4 ± 0.7 | 0.2 ± 0.0 |
| P19 | 30.3 ± 0.7 | 0.0 | 12.4 ± 0.7 | 6.8 ± 0.9 | 22.9 ± 0.2 | 26.0 ± 0.9 | 0.0 |

TABLE 9-continued

TAG level (% leaf dry weight) and fatty acid profile of infiltrated *N. benthamiana* leaves.

| | C16:0 | C16:1 | C18:0 | C18:1 | C18:2 | C18:3 | TAG |
|---|---|---|---|---|---|---|---|
| P19 + DGAT1 | 25.8 ± 1.1 | 0.0 | 10.1 ± 0.4 | 4.4 ± 0.9 | 26.1 ± 1.3 | 26.2 ± 1.4 | 0.2 ± 0.0 |
| P19 + DGAT1 + WRI1 | 22.7 ± 0.9 | 0.0 | 10.1 ± 0.4 | 14.9 ± 0.5 | 27.9 ± 1.3 | 18.5 ± 0.8 | 0.3 ± 0.1 |
| P19 + DGAT1 + FUS3 | 23.9 ± 0.7 | 0.2 ± 0.1 | 7.6 ± 0.4 | 5.3 ± 0.7 | 29.1 ± 0.8 | 26.8 ± 0.7 | 0.4 ± 0.1 |
| P19 + DGAT1 + LEC1 | 24.9 ± 0.4 | 0.1 ± 0.2 | 11.1 ± 0.2 | 4.0 ± 0.1 | 25.9 ± 0.5 | 26.1 ± 0.6 | 0.1 ± 0.0 |
| P19 + DGAT1 + MYB73 | 25.8 ± 0.3 | 0.0 | 10.9 ± 0.7 | 4.3 ± 1.0 | 26.2 ± 0.8 | 25.2 ± 1.8 | 0.1 ± 0.0 |
| P19 | 34.2 ± 4.9 | 0.0 | 10.6 ± 3.1 | 8.3 ± 4.1 | 19.5 ± 1.4 | 23.2 ± 0.8 | 0.1 ± 0.1 |
| P19 + DGAT1 | 27.7 ± 0.1 | 0.3 ± 0.1 | 9.9 ± 1.1 | 4.2 ± 0.3 | 26.4 ± 1.8 | 22.5 ± 0.4 | 0.2 ± 0.1 |
| P19 + DGAT1 + WRI1 | 24.8 ± 1.0 | 0.2 ± 0.0 | 8.8 ± 1.0 | 14.7 ± 0.6 | 27.6 ± 1.0 | 17.2 ± 0.3 | 0.4 ± 0.1 |
| P19 + DGAT1 + bZIP53 | 29.3 ± 0.8 | 0.1 ± 0.2 | 8.7 ± 0.4 | 2.9 ± 0.3 | 22.0 ± 0.5 | 25.9 ± 0.5 | 0.1 ± 0.1 |
| P19 + DGAT1 + AGL15 | 29.2 ± 1.4 | 0.2 ± 0.0 | 4.9 ± 0.9 | 7.0 ± 1.9 | 19.8 ± 0.8 | 30.0 ± 1.3 | 0.3 ± 0.1 |
| P19 + DGAT1 + MYB118 | 31.6 ± 1.7 | 0.2 ± 0.1 | 5.8 ± 1.2 | 4.8 ± 0.8 | 20.7 ± 0.3 | 28.2 ± 1.6 | 0.2 ± 0.1 |
| P19 | 27.4 ± 1.2 | 0.0 | 6.9 ± 1.0 | 4.8 ± 2.6 | 20.0 ± 1.5 | 39.0 ± 4.1 | 0.1 ± 0.0 |
| P19 + DGAT1 | 26.0 ± 1.1 | 0.0 | 8.0 ± 0.6 | 4.2 ± 1.6 | 22.3 ± 2.4 | 33.9 ± 4.3 | 0.2 ± 0.0 |
| P19 + DGAT1 + WRI1 | 23.4 ± 0.8 | 0.1 ± 0.1 | 8.5 ± 0.6 | 17.0 ± 2.4 | 23.3 ± 1.8 | 23.3 ± 4.3 | 0.5 ± 0.1 |
| P19 + DGAT1 + MYB115 | 26.3 ± 0.4 | 0.1 ± 0.1 | 6.6 ± 0.3 | 2.8 ± 0.4 | 22.5 ± 1.8 | 35.7 ± 2.9 | 0.2 ± 0.0 |
| P19 + DGAT1 + TANMEI | 25.6 ± 0.9 | 0.1 ± 0.2 | 8.5 ± 1.2 | 2.6 ± 0.5 | 21.9 ± 2.0 | 35.3 ± 3.8 | 0.2 ± 0.0 |
| P19 + DGAT1 + WUS | 24.3 ± 0.9 | 0.1 ± 0.1 | 5.5 ± 0.6 | 1.7 ± 0.2 | 16.8 ± 1.6 | 47.9 ± 3.3 | 0.2 ± 0.0 |
| P19 | 30.5 ± 1.3 | 0.0 | 8.1 ± 0.9 | 8.2 ± 6.0 | 21.8 ± 1.2 | 28.3 ± 7.3 | 0.1 ± 0.1 |
| P19 + DGAT1 + WRI1 | 25.9 ± 1.7 | 0.2 ± 0.0 | 8.3 ± 0.7 | 19.9 ± 2.8 | 24.5 ± 1.1 | 16.0 ± 0.6 | 0.8 ± 0.1 |
| P19 + DGAT1 + WRI1 + BBM | 27.7 ± 0.7 | 0.2 ± 0.0 | 6.7 ± 0.2 | 21.2 ± 0.7 | 19.8 ± 0.5 | 18.5 ± 0.6 | 0.5 ± 0.1 |
| P19 + DGAT1 + WRI1 + GFR2a1 | 29.2 ± 1.3 | 0.4 ± 0.0 | 6.1 ± 0.1 | 12.9 ± 1.5 | 24.3 ± 0.4 | 20.9 ± 0.5 | 0.4 ± 0.1 |
| P19 + DGAT1 + WRI1 + GFR2a2 | 29.9 ± 2.4 | 0.4 ± 0.1 | 5.5 ± 0.6 | 13.5 ± 2.7 | 23.0 ± 0.5 | 21.3 ± 1.2 | 0.5 ± 0.1 |
| P19 + DGAT1 + WRI1 + PHR1 | 26.2 ± 0.3 | 0.2 ± 0.0 | 4.9 ± 0.0 | 7.6 ± 0.2 | 19.2 ± 0.3 | 36.0 ± 0.7 | 0.3 ± 0.0 |
| P19 | 32.0 ± 1.9 | 1.6 ± 2.7 | 11.1 ± 2.7 | 5.5 ± 2.2 | 23.3 ± 1.1 | 25.4 ± 3.3 | 0.0 |
| P19 + DGAT1 + WRI1 | 27.5 ± 1.2 | 0.7 ± 0.8 | 6.8 ± 0.4 | 16.6 ± 2.1 | 26.7 ± 0.8 | 16.5 ± 0.3 | 1.2 ± 0.2 |
| P19 + DGAT1 + WRI1 + FUS3 | 23.6 ± 1.1 | 2.1 ± 3.5 | 6.5 ± 0.5 | 13.3 ± 0.9 | 32.1 ± 2.6 | 15.6 ± 1.5 | 1.6 ± 0.1 |
| P19 + GFP | 35.8 ± 1.8 | 0.0 ± 0.0 | 8.5 ± 0.8 | 2.0 ± 1.3 | 19.7 ± 1.2 | 32.1 ± 2.2 | 0.03 ± 0.0 |
| P19 + GFP + DGAT1 + WRI1 | 24.6 ± 1.4 | 0.2 ± 0.0 | 10.3 ± 0.5 | 22.7 ± 2.7 | 23.0 ± 1.7 | 14.0 ± 0.6 | 0.99 ± 0.2 |
| P19 + GFP + DGAT1 + NF-YB2 | 27.6 ± 0.6 | 0.1 ± 0.0 | 10.2 ± 0.2 | 3.0 ± 0.2 | 24.1 ± 1.1 | 27.1 ± 1.2 | 0.25 ± 0.0 |
| P19 + GFP + DGAT1 + NF-YB3 | 27.4 ± 0.5 | 0.1 ± 0.0 | 10.8 ± 0.5 | 3.1 ± 1.0 | 24.6 ± 0.9 | 26.0 ± 0.7 | 0.27 ± 0.1 |
| P19 + GFP + DGAT1 + NF-YA3 | 28.9 ± 0.8 | 0.2 ± 0.0 | 8.3 ± 0.4 | 3.6 ± 0.5 | 22.7 ± 1.0 | 29.2 ± 0.9 | 0.17 ± 0.0 |
| P19 + GFP | 38.3 ± 1.3 | 0.0 ± 0.0 | 11.1 ± 1.2 | 2.9 ± 1.4 | 21.3 ± 1.0 | 26.4 ± 3.8 | 0.0 ± 0.0 |
| P19 + GFP + DGAT1 + WRI1 | 29.8 ± 1.1 | 0.3 ± 0.0 | 7.6 ± 1.7 | 18.3 ± 0.6 | 23.9 ± 1.4 | 15.0 ± 0.7 | 1.1 ± 0.5 |
| P19 + GFP + DGAT1 + DOF4 | 32.5 ± 0.5 | 0.0 ± 0.0 | 5.1 ± 0.7 | 3.6 ± 0.2 | 20.5 ± 0.9 | 32.6 ± 1.2 | 0.2 ± 0.1 |
| P19 + GFP + DGAT1 + NF-YB1 | 27.9 ± 0.7 | 0.0 ± 0.0 | 10.8 ± 0.5 | 2.9 ± 0.5 | 27.0 ± 1.3 | 23.7 ± 1.4 | 0.3 ± 0.1 |
| P19 + GFP + DGAT1 + ZFP1 | 25.4 ± 1.4 | 0.1 ± 0.2 | 4.1 ± 0.3 | 5.2 ± 1.2 | 22.8 ± 0.8 | 36.2 ± 0.8 | 0.3 ± 0.1 |
| P19 + GFP | 37.7 ± 1.7 | 0.0 ± 0.0 | 11.5 ± 1.5 | 2.6 ± 2.3 | 22.2 ± 1.9 | 24.1 ± 4.7 | 0.0 ± 0.0 |
| P19 + GFP + DGAT1 + WRI1 | 28.0 ± 2.1 | 0.2 ± 0.0 | 9.3 ± 1.0 | 17.2 ± 3.1 | 27.3 ± 1.2 | 13.0 ± 0.3 | 0.8 ± 0.3 |
| P19 + GFP + DGAT1 + ZF351 | 30.8 ± 0.5 | 0.2 ± 0.1 | 9.5 ± 0.7 | 2.6 ± 1.5 | 25.4 ± 1.1 | 25.4 ± 2.1 | 0.2 ± 0.0 |
| P19 | 18.9 ± 2.9 | 0.4 ± 0.3 | 5.6 ± 1.7 | 6.1 ± 4.8 | 18.3 ± 1.7 | 45.8 ± 9.5 | 0.4 ± 0.1 |
| P19 + DGAT1 + WRI1 | 21.4 ± 2.3 | 0.2 ± 0.0 | 9.9 ± 0.8 | 19.4 ± 0.9 | 20.5 ± 0.9 | 23.8 ± 2.7 | 1.7 ± 0.6 |
| P19 + DGAT1 + WRI1 + ZFP2 | 23.1 ± 1.2 | 0.3 ± 0.1 | 5.3 ± 0.5 | 9.3 ± 1.7 | 16.2 ± 0.7 | 40.5 ± 4.1 | 1.0 ± 0.4 |
| P19 + DGAT1 + WRI1 + ABI5 | 21.4 ± 1.1 | 0.2 ± 0.0 | 8.4 ± 0.7 | 11.4 ± 1.3 | 23.2 ± 1.4 | 29.9 ± 2.9 | 1.2 ± 0.4 |
| P19 + DGAT1 + WRI1 + NF-YC2 | 20.5 ± 0.7 | 0.2 ± 0.1 | 9.6 ± 0.4 | 18.1 ± 0.6 | 21.2 ± 0.6 | 25.4 ± 1.5 | 1.6 ± 0.4 |

For stable transformation of plants using genes encoding the alternative transcription factors, the following binary constructs are made. The genes for expression of the transcription factors use either the SSU promoter or the SAG12 promoter. Over-expression of embryogenic transcription factors such as LEC1 and LEC2 has been shown to induce a variety of pleotropic effects, undesirable in the present context, including somatic embryogenesis (Feeney et al. (2012); Santos-Mendoza et al. (2005); Stone et al. (2008); Stone et al. (2001); Shen et al. (2010)). To minimize possible negative impact on plant development and biomass yield, tissue or developmental-stage specific promoters are preferred over constitutive promoters to drive the ectopic expression of master regulators of embryogenesis.

Example 5. Stem-Specific Expression of a Gene Encoding a Transcription Factor

Leaves of *N. tabacum* plants expressing transgenes encoding WRI1, DGAT and Oleosin contain about 16% TAG at seed setting stage of development. However, the TAG levels were much lower in stems (1%) and roots (1.4%) of the plants (Vanhercke et al., 2014a and b). The inventors considered whether the lower TAG levels in stems and roots were due to poor promoter activity of the Rubisco SSU promoter used to express the gene encoding WRI1 in the transgenic plants. The DGAT transgene in the T-DNA of pJP3502 was expressed by the CaMV35S promoter which is expressed more strongly in stems and roots and therefore was unlikely to be the limiting factor for TAG accumulation in stems and roots.

In an attempt to increase TAG biosynthesis in stem tissue, a construct was designed in which the gene encoding WRI1 was placed under the control of an *A. thaliana* SDP1 promoter. A 3.156 kb synthetic DNA fragment was synthesized comprising 1.5 kb of the *A. thaliana* SDP1 promoter (SEQ ID NO:41) (Kelly et al., 2013a and b), followed by the coding region for the *A. thaliana* WRI1 polypeptide and the *G. max* lectin terminator/polyadenylation region. This fragment was inserted between the SacI and NotI sites of pJP3303. The resulting vector was designated pOIL050, which was then used to transform cells from the *N. tabacum* plants homozygous for the T-DNA from pJP3502 by *Agrobacterium*-mediated transformation. Transgenic plants were selected for hygromycin resistance and a total of 86 independent transgenic plants were grown to maturity in the glasshouse. Samples were taken from transgenic leaf and stem tissue at seed setting stage and contain increased TAG levels compared to the N. tabacum parental plants transformed with pJP3502.

Example 6. Effect of Oil Body Protein Expression on Plant Traits

N. tabacum plants transformed with the T-DNA of pJP3502 and expressing transgenes encoding A. thaliana WRI1, DGAT1 and S. indicum Oleosin had increased TAG levels in vegetative tissues. As shown in Example 2 above, when the endogenous gene encoding SDP1 TAG lipase was silenced in those plants, the leaf TAG levels further increased, which indicated to the inventors that substantial TAG turnover was occurring in the plants that retained SDP1 activity. Therefore, the level of expression of the transgenes in the plants was determined. While Northern hybridisation blotting confirmed strong WRI1 and DGAT1 expression and some oleosin mRNA expression, expression analysis by digital PCR and qRT-PCR detected only very low levels of oleosin transcripts. The expression analysis revealed that the gene encoding the Oleosin was poorly expressed compared to the WRI1 and DGAT1 transgenes. From these experiments, the inventors concluded that the oil bodies in the leaf tissue were not completely protected from TAG breakdown because of inadequate production of Oleosin protein when encoded by the T-DNA in pJP3502. To improve stable accumulation of TAG throughout plant development, several pJP3502 modifications were designed in which the Oleosin gene was substituted. These modified constructs were as follows.
1. pJP3502 contains a gene (SEQ ID NO:42 provides the sequence of its complement) encoding the S. indicum oleosin which was poorly expressed. That gene has an internal UBQ10 intron which might be reducing the expression level. To test this, a 502 bp synthetic DNA fragment containing the S. indicum oleosin gene and lacking the internal UBQ10 intron was synthesized and inserted into pJP3502 as a NotI fragment, to substitute the oleosin gene containing the intron in pJP3502. The resultant plasmid was designated pOIL040.
2. The Rubisco small subunit (SSU) promoter driving expression of the oleosin gene in pJP3502 was replaced by the constitutive enTCUP2 promoter. To this end, a 2321 bp fragment containing the enTCUP2 promoter, Oleosin protein coding region, G. max lectin terminator/polyadenylation region and the first 643 bp of the downstream SSU promoter driving wri1 expression was synthesized and subcloned into the AscI and SpeI sites of pJP3502 resulting in pOIL038.
3. A similar strategy was followed for the expression of an engineered version of the S. indicum oleosin gene containing 6 introduced cysteine residues (o3-3) under the control of the enTCUP2 promoter (Winichayakul et al., 2013). A 2298 bp fragment containing the enTCUP2 promoter, Oleosin o3-3 protein coding region, G. max lectin terminator/polyadenylation region and the first 643 bp of the downstream SSU promoter driving wri1 expression was synthesized and subcloned into the AscI and SpeI sites of pJP3502 resulting in pOIL037.
4. The NotI sites flanking the S. indicum oleosin gene in pJP3502 were used to exchange the protein coding region for one encoding peanut Oleosin3 (Accession No. AAU21501.1) (Parthibane et al., 2012a and b). A 528 bp fragment containing the oleosin3 gene, flanked by NotI sites, was synthesized and subcloned into the respective site of pJP3502. The resulting vector was designated pOIL041.
5. Similarly, a 1077 bp NotI flanked fragment containing the gene coding for the A. thaliana steroleosin (Arab-1) (Accession No. AAM10215.1) (Jolivet et al., 2014) was synthesized and subcloned into the NotI site of pJP3502, resulting in pOIL043.
6. The Nannochloropsis oceanic lipid droplet surface protein (LDSP) (Accession No. AFB75402.1) (Vieler et al., 2012) was synthesized as a 504 bp NotI-flanked fragment and subcloned into the NotI site of pJP3502, yielding pOIL044.
7. Finally, the A. thaliana caleosin (CLO3) (Accession No. 022788.1) (Shimada et al., 2014) was synthesized as a 612 bp NotI flanked fragment and subcloned into pJP3502, resulting in pOIL042.

Each of these constructs was introduced into N. benthamiana leaf cells as described in Example 1. Transient expression of both pJP3502 and pOIL040 in N. benthamiana leaf tissue resulted in elevated TAG levels and similar changes in the TAG fatty acid profile but pOIL040 increased the TAG level more (1.3% compared to 0.9%). Each of the constructs pOIL037, pOIL038, pOIL041, pOIL042 and pOIL043 were used to stably transform N. tabacum plants (cultivar W38) by Agrobacterium-mediated methods. Transgenic plants were selected on the basis of kanamycin resistance and are grown to maturity in the glasshouse. Samples are taken from transgenic leaf tissue at different stages during plant development and contain increased TAG levels compared to wild-type N. tabacum and N. tabacum plants transformed with pJP3502.

Cloning and Characterisation of LDAP Polypeptides from Sapium sebifera

Oleosins are not highly expressed in non-seed oil accumulating plant tissues such as the mesocarp of olive, oil palm, and avocado (Murphy, 2012). Instead, lipid droplet associated proteins (LDAP) have been identified in these tissues that may play a similar role to that of oleosin in seed tissues (Horn et al., 2013). The inventors therefore considered it possible that oleosin might not be the optimal packaging protein to protect the accumulated oil from TAG lipase or other cytosolic enzyme activities in vegetative tissues of plants. LDAP polypeptides were therefore identified and evaluated for enhancement of TAG accumulation, as follows.

The fruit of Chinese tallow tree, Sapium sebifera, a member of the family Euphorbiaceae, was of particular interest to the inventors as it contains an oil-rich tissue outside of the seed. A recent study (Divi et al, submitted for publication) indicated that this oleoginous tissue, called a tallow layer, might be derived from the mesocarp of its fruit. Therefore, the inventors queried the transcriptome of S. sebifera for LDAP sequences. A comparative analysis of expressed genes in the fruit coat and seed tissues revealed a group of three previously unidentified LDAP genes which were highly expressed in the tallow layer.

Nucleotide sequences encoding the three LDAPs were obtained by RT-PCR using RNAs derived from tallow tissue using three pairs of primers. The primer sequences were based on the DNA sequences flanking the entire coding region of each of the three genes. The primer sequences were: for LDAP1, 5'-TTTTAACGATATCCGCTAAAGG-3' (SEQ ID NO:76) and 5'-AATGAATGAACAAGAAT-TAAGTC-3' (SEQ ID NO:77) AT-3'; LDAP2, 5'-CTTTTCT-CACACCGTATCTCCG-3' (SEQ ID NO:78) and 5'-AG-CATGATATA CTTGTCGAGAAAGC-3' (SEQ ID NO:79);

LDAP3, 5'-GCGACAGTGTAGCGTTTT-3' (SEQ ID NO:80) and 5'-ATACATAAAATGAAAACTATTGTGC-3' (SEQ ID NO:81).

Analysis of the *S. sebifera* transcriptome revealed multiple orthologs for each of the LDAP genes, including eight LDAP1, six LDAP2, and six LDAP3 genes, with less than 10% sequence divergence within each gene family. The putative peptide sequences were aligned and a phylogenetic tree was constructed using Genious software (FIG. 4), together with LDAPs homologs from other plant species, including two from avocado (Pam), one from oil palm, one from *Parthenium argentatum* (Par), two from *Arabidopsis* (Ath), five from *Taraxacum brevicorniculatum* (Tbr), three from *Hevea brasiliensis* (Hbr), as presented in FIG. 4. The phylogenetic tree was revealed that the SsLDAP3 shared greater amino acid sequence identity to the LDAP1 and LDAP2 polypeptides from avocado and the LDAP from oil palm, while the SsLDAP1 and SsLDAP2 polypeptides were more divergent.

Genetic Constructs for Over-Expression of LDAP

In order to test the function of the LDAPs from *S. sebifera*, expression vectors were made to express each of these polypeptides under the control of the 35S promoter in leaf cells. The full length SsLDAP cDNA sequences were inserted into the pDONR207 destination vector by recombination reactions, replacing the CcdB and Cm(R) regions of the destination vector with the SsLDAP cDNA fragments. Following confirmation by restriction digestion analysis and DNA sequencing, the constructs were introduced into *Agrobacterium tumefaciens* strain AGL1 and used for both transient expression in *N. benthamiana* leaf cells and stable transformation of *N. tabacum*.

The expression of each of the three SsLDAP genes under the transcriptional control of the 35S promoter in *N. benthamiana* leaves in combination with the expression of 35S::AtDGAT1 and 35S::AtWRI1 yielded substantially higher levels of TAG accumulation relative to the cells infiltrated with the 35S::AtDGAT1 and 35S::AtWRI1 genes without the LDAP construct. The TAG level was increased about 2-fold above the TAG level in the control cells. A significant increase in the level of α-linolenic acid (ALA) and a reduced level of saturated fatty acids was observed in the cells receiving the combination of genes, relative to the control cells.

Co-Localisation of YFP-Fused LDAP Polypeptides with Lipid Droplets in Leaf Cells In order to characterise SsLDAPs in vivo and observe their dynamic behaviour, expression constructs were made for expression of fusion polypeptides consisting of the LDAP polypeptides fused to yellow fluorescent protein (YFP). For each fusion polypeptide, the YFP was fused in-frame to the C-terminus of the SsLDAP. The full open reading frame of each of the three LDAP genes without a stop codon, at its 3' end, was fused to the YFP sequence and the chimeric genes inserted into pDONR207. Following confirmation of the resultant constructs by restriction digestion and DNA sequencing, the constructs were introduced into *A. tumefaciens* strain AGL1 and used for both transient expression in *N. benthamiana* leaf cells and stable transformation of *N. tabacum*. Three days following infiltration of the leaf cells with the LDAP-YFP constructs, leaf discs from the infiltrated zones were stained with Nile Red, which positively stained lipid droplets, and observed under a confocal microscope to detect both the red stain (lipid droplets) and fluorescence from the YFP polypeptide. Co-localisation of LDAP-YFP with the lipid droplets was observed, indicating that the LDAP associated with the lipid droplets in the leaf cells.

Example 7. Modifying Traits in Monocotyledonous Plants—Expression in Leaves and Stems A series of binary expression vectors was designed for *Agrobacterium*-mediated transformation of sorghum (*S. bicolor*) and wheat (*Triticum aestivum*) to increase the oil content in vegetative tissues. The starting vectors for the constructions were pOIL093-095, pOIL134 and pOIL100-104 (see Example 5 of WO 2016/004473). Firstly, a DNA fragment encoding the *Z. mays* WRI1 polypeptide was amplified by PCR using pOIL104 as a template and primers containing KpnI restriction sites. This fragment was subcloned downstream of the constitutive *Oryza sativa* Actin1 promoter of pOIL095, using the KpnI site. The resulting vector was designated pOIL154. The DNA fragment encoding the *Umbelopsis ramanniana* DGAT2a under the control of the *Z. mays* ubiquitin promoter (pZmUbi) was isolated from pOIL134 as a NotI fragment and inserted into the NotI site of pOIL154, resulting in pOIL155. An expression cassette consisting of the PAT coding region under the control of the pZmUbi promoter and flanked at the 3' end by the *A. tumefaciens* NOS terminator/polyadenylation region was constructed by amplifying the PAT coding region using pJP3416 as a template. Primers were designed to incorporate BamHI and SacI restriction sites at the 5' and 3' ends, respectively. After BamHI+SacI double digestion, the PAT fragment was cloned into the respective sites of pZLUbi1casNK. The resulting intermediate was designated pOIL141. Next, the PAT selectable marker cassette was introduced into the pOIL155 backbone. To this end, pOIL141 was first cut with NotI, blunted with Klenow fragment of DNA polymerase I and subsequently digested with AscI. This 2622 bp fragment was then subcloned into the ZraI-AscI sites of pOIL155, resulting in pOIL156. Finally, the Actin1 promoter driving WRI1 expression in pOIL156 was exchanged for the *Z. mays* Rubisco small subunit promoter (pZmSSU) resulting in pOIL157. This vector was obtained by PCR amplification of the *Z. mays* SSU promoter using pOIL104 as a template and flanking primers containing AsiSI and PmlI restriction sites. The resulting amplicon was then cut with SpeI+MluI and subcloned into the respective sites of pOIL156.

These Vectors Therefore Contained the Following Expression Cassettes:

pOIL156: promoter *O. sativa* Actin1::*Z. mays* WRI1, promoter *Z. mays* Ubiquitin::*U. rammaniana* DGAT2a and promoter *Z. mays* Ubiquitin::PAT pOIL157: promoter *Z. mays* SSU::*Z. mays* WRI1, promoter *Z. mays* Ubiquitin::*U. rammaniana* DGAT2a and *Z. mays* Ubiquitin::PAT.

A second series of binary expression vectors containing the *Z. mays* SEE1 senescence promoter (Robson et al., 2004, see Example 5 of WO 2016/004473), *Z. mays* LEC1 transcription factor (Shen et al., 2010) and a *S. bicolor* SDP1 hpRNAi fragment were constructed as follows. First, a matrix attachment region (MAR) was introduced into pORE04 by AatII+SnaBI digest of pDCOT and subcloning into the AatII+EcoRV sites of pORE04. The resulting intermediate vector was designated pOIL158. Next, the PAT selectable marker gene under the control of the *Z. mays* Ubiquitin promoter was subcloned into pOIL158. To this end, pOIL141 was first digested with NotI, treated with Klenow fragment of DNA polymerase I and finally digested with AscI. The resulting fragment was inserted into the AscI+ZraI sites of pOIL158, resulting in pOIL159. The original RK2 oriV origin of replication in pOIL159 was exchanged for the RiA4 origin by SwaI+SpeI restriction digestion of pJP3416, followed by subcloning into the SwaI+AvrII sites of pOIL159. The resulting vector was designated pOIL160. A 10.019 kb 'Monocot senescence part1' fragment containing the following expression cassettes was synthesized: *O. sativa* Actin1::*A. thaliana* DGAT1, codon optimized for *Z. mays* expression, *Z. mays* SEE1::*Z. mays* WRI1, *Z. mays* SEE1::*Z. mays* LEC1. This fragment was subcloned as a SpeI-EcoRV fragment into the SpeI-StuI sites of pOIL160, resulting in pOIL161. A second 7.967 kb 'Monocot senescence part2' fragment was synthesized and contains the following elements: MAR, *Z. mays* Ubiquitin::hpRNAi fragment targeted against *S. bicolor/T. aestivum* SDP1, empty cassette under the control of the *O. sativa* Actin1 promoter. The sequences of two *S. bicolor* SDP1 TAG lipases (Accession Nos. XM_002463620; SEQ ID NO:73 and XM_002458486; SEQ ID NO:38) and one *T. aestivum* SDP1 sequence (Accession No. AK334547) (SEQ ID NO:74) were obtained by a BLAST search with the *A. thaliana* SDP1 sequence (Accession No. NM_120486). A synthetic hairpin construct (SEQ ID NO:75) was designed including four fragments (67 bp, 90 bp, 50 bp, 59 bp) of the *S. bicolor* XM_002458486 sequence that showed highest degree of identity with the *T. aestivum* SDP1 sequence. In addition, a 278 bp fragment originating from the *S. bicolor* XM_002463620 SDP1 lipase was included to increase silencing efficiency against both *S. bicolor* SDP1 sequences. The 'Monocot senescence part2' fragment is subcloned as a BsiWI-EcoRV fragment into the BsiWI-FspI sites of pOIL161. The resulting vector is designated pOIL162.

The genetic constructs pOIL156 pOIL157, pOIL161 and pOIL162 are used to transform *S. bicolor* and *T. aestivum* using *Agrobacterium*-mediated transformation. Transgenic plants are selected for hygromycin resistance and contain elevated levels of TAG and TFA in vegetative tissues compared to untransformed control plants. Such plants are useful for providing feed for animals as hay or silage, as well as producing grain, or may be used to extract oil.

Further genetic constructs are made for expression of combinations of polypeptides in leaves and stems of monocotyledonous plants, including the C4-photosynthesis plants *S. bicolor* and *Z. mays*. Several constructs are made containing genes for expression of WRI1, DGAT and oleosin, with each gene under the control of a constitutive promoter such as a maize Ubiquitin gene promoter or a rice actin gene promoter, and containing an NPTII gene as selectable marker gene. In one particular construct, the WRI1 is sorghum WRI1. In another, the oleosin is SiOleosinL (see Example 9). In other particular constructs, the oleosin gene is replaced with a gene encoding either LDAP2 or LDAP3 from *S. sebifera* (Example 6). These constructs are used as the "core constructs" for transformation of *S. bicolor* and *Z. mays* and are deployed on their own or in combination with genetic constructs for expression of a hairpin RNA targeting one or more SDP1 genes in sorghum or maize (see above), a construct encoding Lec2 under the control of a SEE1 promoter (senescence specific), or both. Another construct is made comprising three genes, namely for expression of a hairpin RNA targeting the endogenous TGD5 gene to reduce its expression, a FatA fatty acyl thioesterase and a PDAT, which is used to increase the level of TAG and/or the TTQ parameter for plants transformed with this construct.

Example 8. Extraction of Oil

Extraction of Lipid from Leaves

Transgenic tobacco leaves which had been transformed with the T-DNA from pJP3502 were harvested from plants grown in a glasshouse during the summer months. The leaves were dried and then ground to 1-3 mm sized pieces prior to extraction. The ground material was subject to soxhlet (refluxing) extraction over 24 hours with selected solvents, as described below. 5 g of dried tobacco leaf material and 250 ml of solvent was used in each extraction experiment.

Hexane Solvent Extraction

Hexane is commonly used as a solvent commercially for oil extraction from pressed oil seeds such as canola, extracting neutral (non-polar) lipids, and was therefore tried first. The extracted lipid mass was 1.47 g from 5 g of leaf material, a lipid recovery of 29% by weight. 1H NMR analysis of the hexane extracted lipid in DMSO was preformed. The analysis showed typical signals for long chain triglyceride fatty acids, with no aromatic products being present. The lipid was then subjected to GCMS for identification of major components. Direct GCMS analysis of the hexane extracted lipid proved to be difficult as the boiling point was too high and the material decomposed in the GCMS. In such situations, a common analysis technique is to first make methyl esters of the fatty acids, which was done as follows: 18 mg lipid extract was dissolved in 1 mL toluene, 3 mL of dry 3N methanolic HCL was added and stirred overnight at 60° C. 5 mL of 5% NaCl and 5 mL of hexane were added to the cooled vial and shaken. The organic layer was removed and the extraction was repeated with another 5 mL of hexane. The combined organic fractions were neutralized with 8 mL of 2% KHCO3, separated and dried with Na2SO4. Solvent was evaporated under a stream of N2 and then made up to a concentration of 1 mg/mL in hexane for GCMS analysis. Main fatty acids present were 16:0 (palmitic, 38.9%) and 18:1 (oleic, 31.3%) (Table 10).

TABLE 10

| Fatty acid composition in transgenic tobacco leaves | | | | | | |
|---|---|---|---|---|---|---|
| FA | | | | | | |
| 16:0 | 16:1 | 18:0 | 18:1 | 18:2 | 20:0 | 22:0 |
| % wt 38.9 | 4.6 | 6.4 | 31.3 | 2.5 | 1.5 | 0.6 |

Acetone Solvent Extraction

Acetone was used as an extraction solvent because its solvent properties should extract almost all lipid from the leaves, i.e. both non-polar and polar lipids. The acetone extracted oil looked similar to the hexane extracted lipid. The extracted lipid mass was 1.59 g from 5 g of tobacco leaf, i.e. 31.8% by weight. 1H NMR analysis of the lipid in DMSO was performed. Signals typical of long chain triglyceride fatty acids were observed, with no signal for aromatic products.

Hot Water Solvent Extraction

Hot water was attempted as an extraction solvent to see if it was suitable to obtain oil from the tobacco leaves. The water extracted material was gel like in appearance and gelled when cooled. The extracted mass was 1.9 g, or 38% by weight. This material was like a thick gel and was likely to have included polar compounds from the leaves such as sugars and other carbohydrates. The 1H NMR analysis of the material in DMSO was preformed. The analysis showed typical signals for long chain triglyceride fatty acids, with no aromatic products being extracted. The left over solid material was extracted with hexane, yielding 20% of lipid by weight, indicating that the water extraction had not efficiently extracted non-polar lipids.

Ethanol Solvent Extraction

Ethanol was used as an extraction solvent to see if it was suitable to obtain oil from the tobacco leaves. The ethanol extracted lipid was similar in appearance to both the water- and hexane-extracted lipid, being yellow-red in colour, had a gel-like appearance and gelled when cooled. The extracted lipid mass was 1.88 g from 5 g tobacco, or 37.6% by weight. The ethanol solvent would also have extracted some of the polar compounds in the tobacco leaves.

Ether Solvent Extraction

Diethyl ether was attempted as an extraction solvent since it was thought that it might extract less impurities than other solvents. The extraction yielded 1.4 g, or 28% by weight. The ether extracted lipid was similar to the hexane extracted material in appearance, was yellowish in colour, and it did appeared a little cleaner than the hexane extract. While the diethyl ether extraction appeared to have given the cleanest oil, the NMR analysis showed a mixture of more organic compounds.

Example 9. Expression of Oil Body Proteins in Plant Vegetative Tissues

A protein coding region encoding a *Rhodococcus opacus* TadA lipid droplet associated protein (MacEachran et al. 2010; Accession number HM625859), codon optimized for expression in dicotyledonous plants such as *Nicotiana benthamiana*, was synthesized as a NotI-SpeI DNA fragment. The fragment was inserted downstream of the 35S promoter in pJP3343 using the NotI-SpeI sites. The resultant plasmid was designated pOIL380. A protein coding region encoding a *Sesame indicum* OleosinL lipid droplet associated protein (Tai et al. 2002; Accession number AF091840; SEQ ID NO:86) was synthesized as a NotI-SacI DNA fragment and inserted downstream of the 35S promoter in pJP3343 using the same sites. The resultant plasmid was designated pOIL382. A protein coding region encoding a *Sesame indicum* OleosinH1 lipid droplet associated protein (Tai et al., 2002; Accession number AF302807) was synthesized as a NotI-SacI DNA fragment and cloned downstream of the 35S promoter in pJP3343 using the same sites. The resultant plasmid was designated pOIL383. A variant of the protein coding region encoding S. indicum OleosinH1 having three amino acid substitutions to remove ubiquitination sites (K130R, K143R, K145R) (Hsiao and Tzen, 2011) was generated by targeted mutagenesis. The coding region was inserted downstream of the 35S promoter in pJP3343 as a NotI-SacI fragment. The resultant plasmid was designated pOIL384. A protein coding region encoding a *Vanilla planifolia* leaf OleosinU1 lipid droplet associated protein (Huang and Huang, 2016; Accession number SRX648194) was codon optimized for expression in *N. benthamiana*, synthesized as a SpeI-EcoRI DNA fragment and inserted downstream of the 35S promoter in pJP3343 using the same sites. The resultant plasmid was designated pOIL386. A protein coding region encoding a *Persea americana* mesocarp OleosinM lipid droplet associated protein (Huang and Huang 2016; Accession number SRX627420) was codon optimized for expression in *N. benthamiana*, synthesized as a SpeI-EcoRI DNA fragment and inserted downstream of the 35S promoter in pJP3343 using the same restriction sites. The resultant plasmid was designated pOIL387. A protein coding region encoding an *Arachis hypogaea* Oleosin 3 lipid droplet associated protein (Parthibane et al., 2012a; Accession number AY722696) was codon optimized for expression in *N. benthamiana*, flanked by NotI sites and inserted into the binary expression vector pJP3502. The resulting plasmid, pOIL041, was digested with NotI and the resultant 520 bp DNA fragment was inserted downstream of the 35S promoter of pJP3343. The resultant plasmid was designated pOIL190. Similarly, the protein coding region for the *A. thaliana* Caleosin3 lipid droplet associated protein (Shen et al., 2014; Laibach et al., 2015; Accession number AK317039) was codon optimized for expression in *N. benthamiana*, flanked by NotI sites and inserted into pJP3502. The resulting plasmid, pOIL042, was digested with NotI and the resulting 604 bp DNA fragment was inserted downstream of the 35S promoter of pJP3343. The resultant plasmid was designated pOIL191. A protein coding region encoding an *A. thaliana* steroleosin lipid droplet associated protein (Accession number AT081653) was codon optimized for expression in *N. benthamiana*, flanked by NotI sites and inserted into pJP3502. The resultant plasmid, pOIL043, was digested with NotI and the resultant 1069 bp DNA fragment was inserted downstream of the 35S promoter of pJP3343. The resultant plasmid was designated pOIL192. A protein coding region encoding a *Nannochloropsis oceanica* LSDP oil body protein (Vieler et al., 2012; Accession number JQ268559) was codon optimized for expression in *N. benthamiana*, flanked by NotI sites and inserted into the pJP3502 binary expression vector. The resultant plasmid, pOIL044, was digested with NotI and the 496 bp DNA fragment was inserted downstream of the 35S promoter of pJP3343. The resultant plasmid was designated pOIL193. A protein coding region encoding a *Trichoderma reesei* HFBI hydrophobin (Linder et al., 2005; Accession number Z68124) was codon optimized for expression in *N. benthamiana*, flanked by NotI sites and inserted into pJP3502. The resultant plasmid, pOIL045, was digested with NotI and the 313 bp DNA fragment was inserted downstream of the 35S promoter of pJP3343. The resultant plasmid was designated pOIL194. An ER-targeted variant of the *Trichoderma reesei* HFBI hydrophobin was created by amending the KDEL ER retention peptide to the C-terminus (Gutierrew et al., 2013). This variant was codon optimized for expression in *N. benthamiana* and cloned as a NotI fragment into pJP3502, resulting in pOIL046. Subsequently, pOIL046 was digested with NotI and the 325 bp fragment was inserted into pJP3343. The resulting vector was designated pOIL195.

Each of the genetic constructs encoding the lipid droplet associated polypeptides were introduced into *N. benthamiana* leaves in combination with genetic constructs encoding WRI1, DGAT1 and p19 as described in Example 1 with some minor modifications. *Agrobacterium tumefaciens* cultures containing the gene coding for the p19 silencing suppressor protein and the chimeric genes of interest were mixed such that the final OD600 of each culture was equal to 0.125 prior to infiltration. Samples being compared were located on the same leaf After infiltration, *N. benthamiana* plants were grown for a further five days before leaf discs were harvested, pooled across three leaves from the same plant, freeze-dried, weighed and stored at −80° C. Total lipids were extracted from freeze-dried tissues using chloroform:methanol:0.1 M KCl (2:1:1 v/v/v) and aliquots loaded on a thin layer chromatography (TLC) plate and developed in hexane:diethyl ether:acetic acid (70:30:1, v/v/v). TAG was recovered, converted to FAME in the presence of a known amount of triheptadecanoin (Nu-Chek PREP, Inc. USA) as internal standard for lipid quantitation, and analyzed by GC-FID.

The assays showed a range of TAG levels compared to the WRI1+DGAT1 control. Some constructs encoding lipid droplet associated polypeptides increased the TAG level relative to the control in some assays whereas others did not. A consistent and statistically significant increase in TAG content was observed when the construct expressing SiOleosinL (pOIL382) was introduced (FIG. 5); this construct was superior to all the others tested in these assays. In one experiment, the increase was 2.27-fold compared to p19+WRI+DGAT and 121.7-fold compared to the p19 control. An increase in the levels of C18:2 and C18:1 (about 22% increased) and a decrease in C16:0 (about 23% decreased) was also observed in the TAG for this construct, relative to the p19+WRI1+DGAT1 control (FIG. 5). Microscopic analyses to visualise lipid droplets in the leaf cells expressing SiOleosinL showed a decrease in lipid droplet size and an increase in abundance compared to the control.

The lipid droplets in leaf cells transiently expressing the genes encoding SiOleosinL together with p19+WRI1+DGAT1 were examined by microscopy. *N. benthamiana* treated leaf discs were collected 4 days after infiltration. Each leaf sample was prepared, stained and imaged within 30-45 minutes, to ensure the samples were imaged fresh. More specifically, immediately after collection, the abaxial epidermis was peeled off in 50 mM PIPES pH7. One half of each disc was stained for 10 minutes in 2 µg/ml BODIPY505/515 in 50 mM PIPES pH7, followed by 2-3 washes in 50 mM PIPES pH7. During this time, the other disc half was kept in 50 mM PIPES pH7. Leaf tissue was mounted in 50 mM PIPES pH7 and imaged immediately, using a Leica SP8 Laser-Scanning Confocal Microscope, a 20× objective (NA=0.75), and the LAS X software. Lipid droplets and chloroplasts were imaged by exciting the leaf discs with a 505 nm laser. BODIPY 505/515 signal was collected between 510 and 540 nm, while chloroplast signal was collected between 650 nm and 690 nm. Unstained half discs were imaged to determine tissue auto-fluorescence.

Microscopy of cells in the leaf discs having the introduced SiOleosinL showed an accumulation of smaller lipid droplets compared to the discs having the p19+WRI1+DGAT1 without SiOleosinL. In contrast, leaf cells expressing genes encoding the p19+WRI1+DGAT1+SiOleosinH combination showed larger lipid droplets which looked about the same as those observed in leaves expressing p19+WRI1+DGAT1 without an oleosin. Finally, when genes encoding both SiOleosinH and SiOleosinL were co-expressed with p19+WRI1+DGAT1, the lipid droplets were smaller and looked similar to those observed in leaves expressing p19+WRI1+DGAT1+SiOleosinL. Interestingly, expression of the vanilla leaf oleosin (pOIL386) resulted in a different pattern in which lipid droplets appeared compacted in a smear form.

Further assays were carried out using radiolabelled [$^{14}$C]-acetate to measure the rate of TAG synthesis for the different gene combinations including each of the lipid droplet associated polypeptides. The [$^{14}$C]-acetate was infiltrated into the same leaf tissues at 3 days post-infiltration of the genetic constructs i.e. after the genes had been expressed for three days. Leaf discs were sampled after 5 min, 10 min and 3 hr after addition of the radiolabel, and total lipids in the tissues were extracted and fractionated by TLC. The amount of radioactivity in different lipid types was quantitated using a Fujifilm FLA-5000 phosphorimager or using a Beckman-Coulter LS 6500 Multipurpose Scintillation Counter.

These assays demonstrated an increase in TAG synthesis rates in the leaves expressing SiOleosinL (pOIL382) as well as an increase in PC and PA synthesis rates over the three hours in leaves expressing SiOleosinL. SiOleosinL expression increased TAG accumulation already at 15 minutes (789 dpm) compared to p19 (198 dpm). In *N. benthamiana* leaf cells expressing genes encoding the p19+WRI1+DGAT1 combination, TAG accumulated rapidly, reaching 3865 dpm after 5 min of [$^{14}$C]-acetate incorporation compared to 293 dpm in the p19 control. This accumulation reached a maximum at 10 minutes after [$^{14}$C]-acetate addition (4519 dpm). However, the radiolabel in TAG quickly reduced thereafter to reach 1013 dpm at 15 minutes, indicating TAG catabolism. When the gene encoding SiOleosinL was added, the TAG was stabilised, indicating protection (i.e. TAG packaging) in the leaf cells. TAG rapidly accumulated at 5 minutes of infiltration (2855 dpm) and the level remained the same at 10 and 15 min after [$^{14}$C]-acetate addition. At the 15 min timepoint, TAG accumulation was equivalent to 2690 dpm for the p19+WRI1+DGAT1+SiOleosinL combination compared to 1013 dpm for the p19+WRI1+DGAT1 combination.

TAG degradation was not correlated with free fatty acid (FFA) levels, presumably because of further catabolism or of incorporation into lipids other that TAG. In order to study TAG degradation and chase the resulting derivatives, [$^{14}$C]-acetate incorporation into TAG and and its stability at 3 hr post-addition was studied. This experiment showed an increase in [$^{1}$V] in PC (2579 dpm) and PA (1270 dpm) in leaf cells expressing the SiOleosinL construct compared to 1495 dpm PC and 899 PA in both p19 and p19+WRI1+DGAT1 controls.

In another experiment, pOIL191 (AtCaleosin 3) was transiently expressed in *N. benthamiana* leaves. The expression of this gene increased TAG content by 3.6 fold (FIG. 6) compared to p19 control. The expression of AtCaleosin3 with WRI1 and DGAT1 resulted in a further increase in TAG content by up to 15.3 fold compared p19 control, and up to 1.6 fold compared to WRI1 and DGAT1 control. TAG yields are comparable with SiOleosin co-expression with WRI1 and DGAT1.

Example 10. Medium-Chain Fatty Acid Production in Vegetative Plant Cells

Eccleston et al. (1996) studied the accumulation of C12:0 and C14:0 fatty acids in both seeds and leaves of transgenic *Brassica napus* plants transformed with a constitutively expressed gene encoding California Bay Laurel 12:0-ACP thioesterase (*Umbellularia californica*). That study reported that substantial levels of C12:0 accumulated in mature *B. napus* seeds but only very low levels of C12:0 were observed in leaf tissue, despite high levels of 12:0-ACP thioesterase expression and activity. The same results were obtained when the gene was transformed into *A. thaliana* (Voelker et al., 1992). That research was extended by the co-expression of the *Cocos nucifera* LPAAT and *Umbellularia californica* thioesterase which resulted in an increased accumulation of total C12:0 as well as an increased fraction of trilaurin in the seeds of *B. napus* (Knutzon et al., 1999). The prior art therefore indicated that medium chain fatty acids (MCFA) synthesis in vegetative plant cells was problematic.

To test the effect of introducing thioesterases having specificity for MCFA in combination with other genes described herein, chimeric DNAs for expressing several different thioesterases were synthesized and introduced into plant cells either singly or in combinations. The protein coding regions for thioesterases from organisms known to produce MCFAs (Jing et al., 2011) were synthesised and inserted as EcoRI fragments into the binary vector pJP3343 which contained a 35S-promoter expression cassette (Vanhercke et al., 2013). The thioesterases were: *Cinnamomum camphora* 14:0-ACP thioesterase (referred to as Cinca-TE) (Yuan et al., 1995; Accession No. Q39473.1; SEQ ID NO:43), *Cocos nucifera* acyl-ACP thioesterase FatB1 (Cocnu-TE1; Accession No. AEM72519.1; SEQ ID NO:88), *Cocos nucifera* acyl-ACP thioesterase FatB2 (Cocnu-TE2; Accession No. AEM72520.1; SEQ ID NO: 89), *Cocos nucifera* acyl-ACP thioesterase FatB3 (Cocnu-TE3; Accession No. AEM72521.1; SEQ ID NO: 90), *Cuphea lanceolata* acyl-(ACP) thioesterase type B (Cupla-TE) (Topfer et al., 1995; Accession No. CAB60830.1; SEQ ID NO: 91), *Cuphea viscosissima* FatB1 (Cupvi-TE; Accession No. AEM72522.1; SEQ ID NO: 92) and *Umbellularia californica* 12:0-ACP thioesterase (Umbca-TE) (Voelker et al., 1992; Accession No. Q41635.1; SEQ ID NO: 93). These thioesterases were all in the FATB class and had specificity for MCFA. The protein coding regions for *C. nucifera* LPAAT (Cocnu-LPAAT, MCFA type) (Knutzon et al., 1995; Accession No. Q42670.1; SEQ ID NO:94) and *A. thaliana* plastidial LPAAT1 (Arath-PLPAAT; Accession No. AEE85783.1; SEQ ID NO:95), were also cloned. Cocnu-LPAAT had previously been shown to increase MCFA incorporation on the sn-2 position of TAG in seeds (Knutzon et al., 1995) whilst *A. thaliana* plastidial LPAAT (Arath-PLPAAT) (Kim et al., 2014) was used as a control LPAAT to determine the effect of any MCFA specificity that the Cocnu-LPAAT might have. The former LPAAT uses acyl-CoA as one substrate and operates in the ER in its native context, whereas the latter PLPAAT uses acyl-ACP as substrate and works in the plastid.

The thioesterase genes were introduced into *Nicotiana benthamiana* leaves by *Agrobacterium*-mediated infiltration as described in Example 1 along with the gene for co-expression of the p19 silencing suppressor and either the Cocnu-LPAAT or Arath-PLPAAT to determine whether MCFA could be produced in *N. benthamiana* leaf tissue. Infiltrated leaf zones were harvested and freeze-dried five days after infiltration with the *Agrobacterium* mixtures, after which the total fatty acid content and composition were determined by GC as described in Example 1 (Table 11). For the data shown in Table 11, errors are the standard deviation of triplicate infiltrations. The infiltrated zones of control leaves contained only trace (<0.1%) or zero levels of fatty acids C12:0 and C14:0 whereas C16:0 was present at 14.9%±0.6 of the TFA in the total leaf lipids. C12:0 levels were only increased significantly by expression of the Cocnu-TE3 (1.2%±0.1) and Umbca-TE (1.6%±0.1). Expression of each of the tested thioesterases resulted in the accumulation of C14:0 in the *N. benthamiana* leaves, with Cinca-TE giving the highest level of 11.3%±1.0. Similarly, expression of each of the thioesterases with the exception of Umbca-TE resulted in increased C16:0 levels. The highest level of C16:0 accumulation (35.4%±4.7) was observed with expression of Cocnu-TE1. Substantial necrosis of the infiltrated zones was observed in the leaves when the FATB genes were expressed alone, which appeared to correlate with the level of MCFA production. The inventors considered that the necrosis was probably due to levels of free fatty acids (FFA) greater than optimum, and also due to the extensive accumulation of MCFA in phospholipid lipid pools rather than in TAG.

TABLE 11

Total leaf fatty acid composition (% total leaf fatty acid) of selected fatty acids in *Nicotiana benthamiana* leaves infiltrated with various thioesterases (TE) and LPAATs. Results are grouped by the co-infiltrated gene (single genes (other than p19 present in all samples), Arath-LPAAT + various TE, Cocnu-LPAAT + various TE). 'Control' denotes uninfiltrated *N. benthamiana* leaf whereas 'p19 only' contains the silencing suppressor gene alone. 16:3 is $16:3^{\Delta 7,10,13}$; 18:3 is $18:3^{\Delta 9,12,15}$. Gene identities are defined in the text.

|  |  | 12:0 | 14:0 | 16:0 | 16:3 | 18:3 |
|---|---|---|---|---|---|---|
| Single-gene tests | Control | 0.2 ± 0 | 0.1 ± 0 | 14.0 ± 0.2 | 8.1 ± 0.1 | 57.2 ± 0 |
|  | p19 only | 0.2 ± 0 | 0.1 ± 0 | 14.9 ± 0.6 | 7.0 ± 0.8 | 53.1 ± 0.7 |
|  | Cinca-TE | 0.4 ± 0 | 11.3 ± 1.0 | 21.9 ± 0.7 | 5.0 ± 0.2 | 38.5 ± 1.0 |
|  | Cocnu-TE1 | 0.2 ± 0 | 6.3 ± 0.6 | 35.4 ± 4.7 | 4.2 ± 1.4 | 29.9 ± 5.5 |
|  | Cocnu-TE2 | 0.2 ± 0 | 7.1 ± 0.3 | 31.9 ± 2.2 | 4.7 ± 0.5 | 32.9 ± 2.8 |
|  | Cocnu-TE3 | 1.2 ± 0.1 | 7.2 ± 1.3 | 19.6 ± 1.6 | 5.7 ± 0.5 | 44.8 ± 2.9 |
|  | Cupla-TE | 0.2 ± 0 | 1.1 ± 0.2 | 21.8 ± 2.9 | 6.0 ± 0.6 | 48.2 ± 3.1 |
|  | Cupvi-TE | 0.2 ± 0 | 0.6 ± 0.1 | 17.3 ± 1.3 | 6.4 ± 0.4 | 52.9 ± 2.1 |
|  | Umbca-TE | 1.6 ± 0.1 | 1.1 ± 0.2 | 14.4 ± 0.8 | 6.5 ± 0.3 | 52.7 ± 0.1 |
|  | Arath-LPAAT | 0.2 ± 0 | 0.4 ± 0.5 | 17.4 ± 1.0 | 6.2 ± 0.3 | 51.4 ± 1.3 |
|  | Cocnu-LPAAT | 0.1 ± 0.1 | 0.1 ± 0 | 15.1 ± 1.5 | 6.7 ± 0.5 | 52.2 ± 4.2 |
| +Arath-LPAAT | Cinca-TE | 0.2 ± 0 | 7.8 ± 0.1 | 24.6 ± 0.4 | 5.3 ± 0.2 | 39.2 ± 1.5 |
|  | Cocnu-TE1 | 0.2 ± 0 | 4.6 ± 1.3 | 35.3 ± 1.4 | 4.4 ± 0.7 | 32.7 ± 2.0 |
|  | Cocnu-TE2 | 0.2 ± 0 | 6.1 ± 0.4 | 32.5 ± 1.8 | 4.7 ± 0.1 | 34.1 ± 0.6 |
|  | Cocnu-TE3 | 0.9 ± 0.2 | 8.5 ± 0.4 | 21.4 ± 1.9 | 5.6 ± 0.2 | 41.7 ± 0.6 |
|  | Cupla-TE | 0.2 ± 0 | 1.0 ± 0.1 | 23.4 ± 2.7 | 5.9 ± 0.5 | 47.3 ± 1.2 |
|  | Cupvi-TE | 0.2 ± 0 | 0.6 ± 0 | 19.0 ± 0.2 | 6.3 ± 0.1 | 51.4 ± 1.0 |
|  | Umbca-TE | 1.2 ± 0.2 | 1.1 ± 0.1 | 15.4 ± 0.2 | 6.5 ± 0.2 | 52.3 ± 1.3 |
| +Cocnu-LPAAT | Cinca-TE | 0.7 ± 0.2 | 14.9 ± 1.6 | 23.0 ± 3.7 | 4.8 ± 1.4 | 35.4 ± 3.3 |
|  | Cocnu-TE1 | 0.2 ± 0 | 5.4 ± 0.9 | 40.2 ± 2.8 | 3.3 ± 0 | 27.8 ± 1.1 |
|  | Cocnu-TE2 | 0.2 ± 0 | 6.6 ± 1.0 | 38.3 ± 1.1 | 3.7 ± 0.2 | 28.2 ± 1.1 |
|  | Cocnu-TE3 | 2.0 ± 0.3 | 10.9 ± 1.0 | 24.4 ± 1.8 | 4.9 ± 0.5 | 37.7 ± 0.9 |
|  | Cupla-TE | 0.5 ± 0.1 | 1.6 ± 0.3 | 22.2 ± 0.6 | 6.0 ± 0.3 | 46.9 ± 2.0 |
|  | Cupvi-TE | 0.5 ± 0 | 1.1 ± 0 | 19.6 ± 0.8 | 6.0 ± 0.2 | 49.8 ± 0.3 |
|  | Umbca-TE | 3.3 ± 0.5 | 1.2 ± 0.1 | 13.9 ± 0.4 | 6.4 ± 0.2 | 51.3 ± 1.7 |

Co-infiltration of the chimeric gene for expressing Arath-PLPAAT with the thioesterases tended to reduce the accumulation of both C12:0 and C14:0 compared to the absence of the LPAAT, whilst slightly increasing the accumulation of C16:0. In contrast, co-infiltration of the genes for expressing Cocnu-LPAAT or Umbca-TE increased the accumulation of C12:0 to 3.3%±0.5 whilst C14:0 was found to accumulate to 14.9%±1.6 in the Cinca-TE+Cocnu-LPAAT sample. The highest C16:0 levels were observed after co-expression of Cocnu-TE1 and Cocnu-LPAAT (40.2%±2.8). Addition of an LPAAT to each inoculated zone decreased the degree of necrosis of the leaf tissue. Surprisingly, both C8:0 and C10:0 fatty acids were also produced in the plant cells in the transient expression studies. The accumulation of C8:0 and C10:0 was not observed when the thioesterase was expressed alone. However, when thioesterase expression was combined with the co-expression of CuphoFatB with CnLPAAT and AtWRI1, C8:0 was found to be present at a concentration of 0.27±0.09% of the total fatty acid content in the plant cells. Similarly, when CuplaFatB was co-expressed with CnLPAAT and AtWRI1, C10:0 was found to be present at 0.54±0.16% of the total fatty acid content.

These results indicated that the previously-reported acyl specificities of the thioesterases, observed from seed expression, were essentially maintained in *N. benthamiana* leaves and that this expression system was a valid system for testing acyl specificity. The addition of the plastidial *A. thaliana* PLPAAT did not increase the accumulation of MCFAs although it did result in slightly increased accumulation of C16:0 in *A. thaliana* cells. In contrast, the *C. nucifera* LPAAT increased the accumulation of C12:0, C14:0 and C16:0 in *N. benthamiana* leaves, which fatty acids are found in *C. nucifera* oil (Laureles et al., 2002). This indicated that the native *N. benthamiana* LPAAT was either not highly expressed in leaf tissue or did not have high activity on C12:0, C14:0 and C16:0 substrates.

Medium-Chain Fatty Acid Production in Vegetative Plant Cells Accumulating High Levels of TAG The inventors previously obtained the production of 15% TAG in *N. tabacum* leaves by the coordinate expression of chimeric genes encoding *A. thaliana* WRI1, *A. thaliana* DGAT1 and *S. indicum* Oleosin (Vanhercke et al., 2014a and b). To test whether the accumulation of MCFA that was observed after expression of thioesterases in combination with an LPAAT would also occur or be increased in plant cells producing high levels of TAG (Vanhercke et al., 2013), these genes were co-expressed. The best performing C12:0, C14:0 and C16:0 thioesterase/LPAAT combinations (Cocnu-LPAAT plus Umbca-TE, Cinca-TE and Cocnu-TE2 thioesterases, respectively) were infiltrated with and without the Arath-WRI1+DGAT combinations previously described (Vanhercke et al., 2013). The data are shown in FIG. 7.

The accumulation of the relevant MCFA (C12:0 for Umbca-TE, C14:0 for Cinca-TE and C16:0 for Cocnu-TE2) was consistently and substantially increased most by the addition of Arath-WRI1 to the combinations: C12:0 comprised 9.5%±0.9 of total leaf fatty acids in the Umbca-TE+Cocnu-LPAAT+Arath-WRI1 samples, the C14:0 level was 18.5%±2.6 in the Cinca-TE+Cocnu-LPAAT+Arath-WRI1 samples and the C16:0 level was 38.3%±3.0 in the Cocnu-TE2+Cocnu-LPAAT+Arath-WRI1 samples. Thioesterase plus Arath-WRI1 infiltrations were found to have a significantly greater effect on C12:0 in the presence of Umbca-TE, C14:0 in the presence of Cinca-TE and C16:0 in the presence of Cocnu-TE2 relative to infiltration with thioesterase plus Cocnu-LPAAT in the absence of WRI1 (FIG. 8). The addition of the Cocnu-LPAAT to the thioesterase plus Arath-WRI1 mixtures did have an effect on the fatty acid composition with relatively small increases in C12:0 and C14:0 observed in the Umbca-TE and Cinca-TE sets and a small decrease in C16:0 in the Cocnu-TE2 set. The maximum levels observed were: 8.8%±1.1 of C12:0 in total leaf fatty acids observed in the Umbca-TE+Arath-WRI1+Cocnu-LPAAT samples, 14.1%±3.5 of C14:0 in the Cinca-TE+Arath-WRI1+Cocnu-LPAAT samples and 48.6%±3.7 of C16:0 in the Cocnu-TE2+Arath-WRI1 sample.

Interestingly, the only thioesterase in which the Arath-WRI1 did not increase MCFA accumulation as much was the Cocnu-TE2, although it still increased significantly. The addition of this gene alone resulted in the increased accumulation of C16:0 from 16.0%±0.4 to 37.3%±0.6 whereas the further addition of Arath-WRI1 only increased this to 48.6%±1.7. This may have been due to the C12:0 and C14:0 intermediates being relatively transient during plastidial fatty acid synthesis compared to C16:0.

Other effects that were noted included the increase in C16:0 and C18:1$^{\Delta9}$ and decrease in C18:3$^{\Delta9,12,15}$ levels in the presence of Arath-WRI1. The further addition of the Cinca-TE and Cocnu-TE2 decreased C18:3$^{\Delta9,12,15}$ levels further still. In contrast, the extra C12:0 produced following the addition of Arath-WRI1 to Umbca-TE appeared to come at the cost of C16:0 rather than additional C18:3$^{\Delta9,12,15}$ (FIG. 9).

A subset of samples were also analysed by LC-MS to gain a better understanding of MCFA accumulation. The plastidial galactolipids monogalactosyl diacylglycerol (MGDG) and digalactosyl diacylglycerol (DGDG) contained only low levels of C12:0 and C14:0 and reduced levels of C16:0 relative to the p19 control infiltration. The major C12:0-containing MGDG species in the Umbca-TE samples was 30:3 indicating that one C18:3 and one C12:0 were co-located on the monogalactosyl backbone. The other main C12:0-containing MGDG species was 28:0, indicating that the second fatty acid was C16:0. The major C14:0-containing MGDG species in the Cinca-TE samples were 28:0 and 30:0, indicating that a significant proportion of the C14:0 in MGDG was either di-C14:0 or with C16:0. The C12:0-containing and C14:0-containing MGDG species were not detected in the p19 control sample. In contrast, C16:0-containing MGDG species tended to be reduced in the Cocnu-TE2 samples. The major MGDG species in the wildtype samples (C16:3-containing 34:6, C18:3-containing 34:6, and C18:3-containing 36:6) all tended to be reduced by the expression of the transgenes. This reduction was greatest in the presence of the WRI+DGAT combination.

Only trace levels of C12:0-containing DGDG species were observed in the Umbca-TE samples. The major C14:0-containing species observed in the Cinca-TE samples were 28:0 and 30:0, both of which were absent in the control. These species were also observed at elevated levels in the Cocnu-TE2 samples but only at trace levels in the Umbca-TE samples. The major DGDG species in the wildtype samples (C16:0-containing 34:3, C18:3-containing 34:3, and C18:3-containing 36:6) all tended to be reduced by the expression of the transgenes. This reduction was greatest in the presence of WRI.

Similarly, TAG species were generally increased considerably in all the samples containing WRI+DGAT as previously described (Vanhercke et al., 2013). C12:0 species were found to be dominant in the high TAG Umbca-TE sample, C14:0 in the high TAG Cinca-TE sample and C16:0 in the high TAG Cocnu-TE2 sample. LC-MS analysis of the TAG fraction showed that the C12:0-containing 36:0 was found to be the dominant TAG species, twice the level of TAG species containing C18:3, in all Umbca-TE samples containing the WRI transcription factor. Similarly, C14:0-containing 42:0 was the dominant TAG species in the Cinca-TE samples co-transformed with either LPAAT, DGAT, WRI or WRI+DGAT, although the response was considerably higher in the case of the samples containing WRI. Several C16:0-containing TAG species were significantly elevated in both the high TAG Cinca-TE (e.g. 44:0 and 50:3) and Cocnu-TE2 (e.g. 46:0, 48:0, 50:2 and 50:3) samples. Again, the greatest C16:0 increases were observed in the presence of WRI.

Stable Transformation for Production of MCFA in Vegetative Tissues.

A series of genetic constructs were made in a binary vector in order to stably transform plants such as tobacco with combinations of genes for production of MCFA in vegetative tissues, to identify optimal combinations of genes. These constructs included a gene for expression of WRI1 under the control of either the SSU promoter (see Example 3, pOIL121) or the senescence-specific SAG12 promoter, a gene encoding an oil palm DGAT (below), a gene encoding the coconut LPAAT (CocnuLPAAT, see above) under the control of an enTCUP promoter and several genes expressing a variety of fatty acyl thioesterases (FATB) expressed from either a 35S promoter or a SAG12 promoter. These are described below.

Cloning of a Gene Encoding *Elaeis guineensis* (Oil Palm) DGAT

In order to firstly test different DGAT enzymes, including representative DGAT1, DGAT2 and DGAT3 enzymes, candidate oil palm DGAT sequences were identified from the published transcriptome (Dussert et al., 2013) and codon optimised for expression in *Nicotiana tabacum*. The protein coding regions were then each cloned individually into binary expression vectors under the control of the 35S promoter for testing in transient *N. benthamiana* leaf assays as described in Example 1. The gene combinations tested were as follows:

1 P19 (negative control)
2 P19+CnLPAAT+WRI1
3 P19+CnLPAAT+AtWRI1+AtDGAT1
4 P19+CnLPAAT+AtWRI1+EgDGAT1
5 P19+CnLPAAT+AtWRI1+EgDGAT2
6 P19+CnLPAAT+AtWRI1+EgDGAT3
7 P19+CincaFatB
8 P19+CincaFatB+CnLPAAT+WRI1
9 P19+CincaFatB+CnLPAAT+AtWRI1+AtDGAT1
10 P19+CincaFatB+CnLPAAT+AtWRI1+EgDGAT1
11 P19+CincaFatB+CnLPAAT+AtWRI1+EgDGAT2
12 P19+CincaFatB+CnLPAAT+AtWRI1+EgDGAT3

The results for the TFA and TAG levels, and the levels of total MCFA in the TFA or the TAG contents, are shown in FIG. 10. Compared to AtDGAT1, the expression of EgDGAT1 led to greater accumulation of total fatty acids and increased TAG levels. The total MCFA content in the total fatty acid content was reduced with the expression of EgDGAT1 relative to AtDGAT1, but the levels of MCFA present in TAG remained about the same (FIG. 10).

Preparation of Genetic Constructs

Genetic constructs for stable transformation (Table 12) were assembled through the sequential insertion of gene cassettes through the use of compatible restriction enzyme sites. The four gene constructs (Table 12) each contained a gene encoding the oil palm DGAT1 (EgDGAT1) expressed from the 35S promoter, a gene encoding the *C. nucifera* LPAAT (CnLPAAT) expressed from the constitutive enTCUP2 promoter, and a gene encoding AtWRI1 expressed from either the SSU promoter or the SAG12 promoter in addition to one of a series of genes encoding FATB enzymes.

The five gene constructs also contained a gene for expression of a hairpin RNA for reducing expression of an endogenous gene encoding acyl-activating enzyme (AAE). The hairpin was constructed based on sequence similarity with the identified AAE15 from *Arabidopsis lyrata* (EFH44575.1) and the *N. benthamiana* genome. AAE has been shown to be involved in the reactivation of MCFA, and hence further elongation. It was considered that silencing of AAE might increase MCFA accumulation. The hairpin cassette was constructed in the vector pKANNIBAL and then subcloned into the expression vector pWBVec2 with the expression of the hairpin being driven by the 35S promoter.

TABLE 12

Summary of assembled genetic constructs.

| | Construct | Gene Combination |
|---|---|---|
| Single Gene Constructs | pKR1 | 35S::UmbcaFATB |
| | pKR2 | 35S::CincaFATB |
| | pKR3 | 35S::CocnuFATB2 |
| | pOIL115 | SAG12::CincaFATB |
| | pOIL116 | SAG12::UmbcaFATB |
| | pOIL117 | SAG12::CocnuFATB2 |
| Construction Components | pOIL300 | 35S::EgDGAT1 |
| | pOIL301 | enTCUP::CnLPAAT inFATBrmediaFATB construct |
| | pOIL302 | 35S::EgDGAT1 + enTCUP::CnLPAAT |
| | pOIL303 | 35S::EgDGAT1 + enTCUP::CnLPAAT + SSU:AtWRI1 |
| | pOIL304 | 35S::EgDGAT1 + enTCUP::CnLPAAT + SAG12:AtWRI1 |
| Four Gene Constructs | pOIL305 | 35S::EgDGAT1 + enTCUP::CnLPAAT + SSU:AtWRI1 + 35S::UmbcaFATB |
| | pOIL306 | 35S::EgDGAT1 + enTCUP::CnLPAAT + SSU:AtWRI1 + 35S::CincaFATB |
| | pOIL307 | 35S::EgDGAT1 + enTCUP::CnLPAAT + SSU:AtWRI1 + 35S::CocnuFATB2 |
| | pOIL308 | 35S::EgDGAT1 + enTCUP::CnLPAAT + SSU:AtWRI1 + SAG12::UmbcaFATB |
| | pOIL309 | 35S::EgDGAT1 + enTCUP::CnLPAAT + SSU:AtWRI1 + SAG12::CincaFATB |
| | pOIL310 | 35S::EgDGAT1 + enTCUP::CnLPAAT + SSU:AtWRI1 + SAG12::CocnuFATB2 |

TABLE 12-continued

Summary of assembled genetic constructs.

|   | Construct | Gene Combination |
|---|---|---|
|  | pOIL311 | 35S::EgDGAT1 + enTCUP::CnLPAAT + SAG12:AtWRI1 + 35S::UmbcaFATB |
|  | pOIL312 | 35S::EgDGAT1 + enTCUP::CnLPAAT + SAG12:AtWRI1 + 35S::CincaFATB |
|  | pOIL313 | 35S::EgDGAT1 + enTCUP::CnLPAAT + SAG12:AtWRI1 + 35S::CocnuFATB2 |
|  | pOIL314 | 35S::EgDGAT1 + enTCUP::CnLPAAT + SAG12:AtWRI1 + SAG12::UmbcaFATB |
|  | pOIL315 | 35S::EgDGAT1 + enTCUP::CnLPAAT + SAG12:AtWRI1 + SAG12::CincaFATB |
|  | pOIL316 | 35S::EgDGAT1 + enTCUP::CnLPAAT + SAG12:AtWRI1 + SAG12::CocnuFATB2 |
| Five Gene Constructs | pOIL317 | 35S::EgDGAT1 + enTCUP::CnLPAAT + SSU:AtWRI1 + 35S::UmbcaFATB + 35S::hpNbAAE |
|  | pOIL318 | 35S::EgDGAT1 + enTCUP::CnLPAAT + SSU:AtWRI1 + 35S::CincaFATB + 35S::hpNbAAE |
|  | pOIL319 | 35S::EgDGAT1 + enTCUP::CnLPAAT + SSU:AtWRI1 + 35S::CocnuFATB2 + 35S::hpNbAAE |
|  | pOIL320 | 35S::EgDGAT1 + enTCUP::CnLPAAT + SSU:AtWRI1 + SAG12::UmbcaFATB + 35S::hpNbAAE |
|  | pOIL321 | 35S::EgDGAT1 + enTCUP::CnLPAAT + SSU:AtWRI1 + SAG12::CincaFATB + 35S::hpNbAAE |
|  | pOIL322 | 35S::EgDGAT1 + enTCUP::CnLPAAT + SSU:AtWRI1 + SAG12::CocnuFATB2 + 35S::hpNbAAE |
|  | pOIL323 | 35S::EgDGAT1 + enTCUP::CnLPAAT + SAG12:AtWRI1 + 35S::UmbcaFATB + 35S::hpNbAAE |
|  | pOIL324 | 35S::EgDGAT1 + enTCUP::CnLPAAT + SAG12:AtWRI1 + 35S::CincaFATB + 35S::hpNbAAE |
|  | pOIL325 | 35S::EgDGAT1 + enTCUP::CnLPAAT + SAG12:AtWRI1 + 35S::CocnuFATB2 + 35S::hpNbAAE |
|  | pOIL326 | 35S::EgDGAT1 + enTCUP::CnLPAAT + SAG12:AtWRI1 + SAG12::UmbcaFATB + 35S::hpNbAAE |
|  | pOIL327 | 35S::EgDGAT1 + enTCUP::CnLPAAT + SAG12:AtWRI1 + SAG12::CincaFATB + 35S::hpNbAAE |
|  | pOIL328 | 35S::EgDGAT1 + enTCUP::CnLPAAT + SAG12:AtWRI1 + SAG12::CocnuFATB2 + 35S::hpNbAAE |

These genetic constructs were used to produce transformed tobacco plants of cultivars Wisconsin 38 and a high oil line transformed with the T-DNA from pJP3502. It was observed that plants transformed with the single gene FATB constructs expressed from the 35S promoter were significantly smaller than those transformed with the corresponding FATB construct expressed from the SAG12 promoter or from the four gene constructs. The smaller plant size was considered to be caused by a buildup of MCFA which was not incorporated efficiently into TAG.

Discussion

The present study found that C12:0 production in leaf cells was only about 1.6% of the total fatty acid content after expression of Umbca-TE alone (Table 11). The addition of a gene for expression of Arath-WRI had a much stronger effect on C12:0 and C14:0 accumulation in leaf tissue than the addition of the coconut LPAAT (FIGS. 7 and 9). This indicated that WRI1 in combination with the thioesterase greatly increased MCFA accumulation in leaf cells, acting synergistically. Importantly, much of the C12:0, C14:0 and C16:0 was found to accumulate in the leaves in TAG, which lipid does not accumulate at substantial levels in wild-type leaves. These experiments showed that the cells in the vegetative parts of plants could be modified to produce MCFA, particularly C12:0 and C14:0 in TAG at high levels. C16:0 levels were also increased substantially.

Example 11: Gene Selection and Vector Construction

Fatty acyl thioesterases were identified from *Cinnamomum camphora* 14:0-ACP thioesterase (referred to as 'CcTE', Accession No. Q39473.1, (Yuan et al., 1995)), *Umbellularia californica* 12:0-ACP thioesterase (UcTE, Accession No. Q41635.1, (Voelker et al., 1992)), and *Cocos nucifera* acyl-ACP thioesterase FatB2 (CnTE2, Accession No. AEM72520.1, (Jing et al., 2011)). A *C. nucifera* LPAAT (CnLPAAT, Accession No. Q42670.1, (Knutzon et al., 1995)) was also identified. Coding regions were synthesized using codon optimised nucleotide sequences for expression in *Nicotiana* plant cells. Expression vectors encoding WRI1 and DGAT were produced as previously described by Vanhercke et al. (2013).

Three DGAT candidate sequences were identified in the transcriptome of African oil palm (*Elaeis guineensis*) (Dussert et al., 2013) and selected to be tested in their utilisation of MCFA for the assembly of leaf lipids. The DGATs from oil palm were selected based on the fatty acid compositions of palm oil and palm kernel oil (Edem, 2002), being high in MCFA content.

A gene encoding glycerol-3-phosphate acyltransferase 9 (GPAT9) from *C. nucifera* (coconut, CnGPAT9) was identified from a transcriptome. A genetic construct to express this enzyme was made from RNA isolated from developing coconut endosperm, as described below.

Each gene was cloned into the EcoRI site of the binary vector pJP3343 which contained a constitutive 35S promoter with duplicated enhancer region (Vanhercke et al., 2013) for expression in plant cells. *Agrobacterium tumefaciens* strain AGL1 was transformed with each of the constructs.

Example 12: Increasing Medium Chain Fatty Acid Production in Vegetative Plant Cells GPAT9 has recently been identified as functioning in *Arabidopsis thaliana* seed to transfer acyl groups from acyl-CoA to the sn-1 position of glycerol-3-phosphate (G3P) (Shockey et al., 2016; Singer et al., 2016). The inventors hypothesized that a GPAT9 from coconut might assist in increasing the MCFA content of transgenic oils produced in vegetative plant cells. A GPAT9 gene from coconut was identified by searching an assembled coconut endosperm transcriptome using the *Arabidopsis thaliana* GPAT9 nucleotide sequence (AtGPAT9) (Shockey et al., 2016) as the BLAST query. A candidate for GPAT9 from coconut was identified, namely NCBI Accession number KX235871. High fidelity PCR was used to amplify the full length CnGPAT9 cDNA sequence from coconut. Following isolation and sequencing of the full length transcript of interest, the open reading frame for the predicted CnGPAT9 was identified. The predicted amino acid sequence was aligned with the sequence of AtGPAT9, revealing that the sequences were 78% identical. Sequence alignment with other annotated GPAT nucleotide sequences showed that the identified CnGPAT9 nucleotide sequence clustered with other GPAT9 sequences (FIG. 11).

A nucleotide sequence encoding the candidate CnGPAT9 was synthesized and inserted into pJP3343 in order to test its enzymatic function using the transient *N. benthamiana* infiltration assay as described in Example 1, in particular to test its ability to increase TAG content. AtGPAT9 was used as a positive control. Total lipids were extracted from infiltrated leaf zones and analysed to determine the effect of the GPAT9s on TAG content (FIG. 12). From comparison with the samples where p19 alone was infiltrated, which provided a TAG level of about 0.1%, expression of either AtGPAT9 or CnGPAT9 provided significant increases in the TAG content in the leaf, to 0.5±0.2% and 0.7±0.1% on a dry weight basis, respectively. There was no significant difference in the TAG levels between the two GPAT9s. It was concluded from these data and the phylogeny (FIG. 11) that the isolated CnGPAT9 sequence from coconut encoded a functional GPAT9.

Example 13: DGAT1 Promotes Production of MCFA-Enriched Oils

It has been previously demonstrated that MCFA-containing oils could be produced in the leaves of *N. benthamiana* (Reynolds et al., 2015). However, chlorosis of the leaves was observed with some gene combinations when MCFA accumulated in membrane lipids such as PC. The inventors wanted to test whether the introduction of a DGAT capable of esterifying MCFA into TAG might increase the MCFA content and perhaps reduce the chlorosis phenotype.

Gene candidates that might be involved in lipid synthesis pathways were identified in the *Elaeis guineensis* (African oil palm) transcriptome (Dussert et al., 2013) as described above. The fatty acid profile of the oils from oil palm (palm oil and palm kernel oil) (Edem, 2002) suggested that some DGATs from oil palm might exhibit preference for MCFA substrates. Sequences for three candidate DGAT1 cDNAs were identified from the *E. guineensis* transcriptome. Alignment of the predicted amino acid sequences after translation of the cDNAs revealed that the isoforms designated EgDGAT1.2 and EgDGAT1.3 lacked highly conserved C- and N-terminal motifs (Cao, 2011) which are responsible for the catalytic and regulatory activities of DGAT1, respectively (Liu et al., 2012; Xu et al., 2008), suggesting these isoforms would be non-functional. The third candidate EgDGAT1.1 had these conserved motifs and was further tested.

A genetic construct with codon optimization for expressing EgDGAT1.1 in *N. tabacum* was synthesized and infiltrated into *N. benthamiana* in combination with genetic constructs to express *Arabidopsis thaliana* WRI1 and CnLPAAT. The infiltrations were either with or without a gene for co-expression of a thioesterase from *Cinnamomum camphora* (CcTE), to measure levels of both TAG production and the incorporation of MCFA into TAG. Five days after infiltration, a strong chlorosis phenotype was observed to be associated with several gene combinations, correlated in particular with the presence of CcTE. Surprisingly, the chlorosis phenotype was alleviated by the addition of the gene encoding EgDGAT1.1 (hereinafter referred to as EgDGAT1) more so than with AtDGAT1. It was hypothesized that the alleviation of the negative chlorosis phenotype was due to the increased capacity of EgDGAT1 to sequester MCFA into TAG relative to AtDGAT1.

Total lipids were extracted and analysed in order to better understand the relationship between chlorosis and the particular gene combinations. The total fatty acid profile revealed that in the absence of CcTE, the TFA content was similar in the presence of either AtDGAT1 or EgDGAT1. In the presence of CcTE, the TFA content was significantly greater for treatments including EgDGAT1 relative to AtDGAT1. The same correlation was observed for TAG content. Although the TAG content was similar for the AtWRI1+AtDGAT1 and AtWRI1+EgDGAT1.1 samples, the TAG content was significantly increased for samples expressing CcTE and EgDGAT1, compared to samples expressing AtDGAT1. These results suggested that following CcTE expression, in the presence of AtDGAT1, fatty acid synthesis was inhibited due to inefficient assembly of the MCFA into glycerolipids. Conversely, there appeared to be no inhibition of fatty acid synthesis following the addition of EgDGAT highlighted by increases in both the TFA and TAG content, implying improved incorporation efficiency for MCFAs.

The fatty acid composition of the phospholipid fraction in the infiltrated leaf zones was also analysed. Total phospholipids were fractionated by TLC and prepared for analysis by the preparation of FAME. Analysis of the fatty acid composition of the phospholipids revealed a significant reduction in the accumulation of MCFA, particularly C14:0 and C16:0, following the expression of the EgDGAT1 construct, compared to AtDGAT1. This suggested that the reduced accumulation of MCFA into membrane lipids assisted in reducing the chlorosis phenotype.

Example 14: Reconfiguration of Kennedy Pathway for Efficient MCFA Accumulation Following confirmation of CnGPAT9 activity, its capability to use various MCFA acyl-CoAs as substrates for TAG assembly was tested. This was done in the context of the Kennedy pathway components LPAAT and DGAT1, as well as WRI1 to increase the level of fatty acid synthesis. The fatty acid composition of TAG and the TAG content were determined by GC-FID (FIG. 13, Tables 13-15). When combined with co-expression of UcTE, the sequential addition of each acyltransferase resulted in both significantly increased total TAG content, and a significantly increased accumulation of laurate (C12:0) in the TAG as a percentage of the total fatty acid content of the TAG. C12:0 levels were up to 51.6±2.0% in the presence of the combined expression of UcTE+AtWRI1+CnGPAT9+CnLPAAT+EgDGAT1, at a total TAG content in the leaf tissue of 2.4±0.7%. It was also observed that this combination was associated with a reduction of the chlorosis phenotype, thought by the inventors to be a result of efficient sequestering of laurate into TAG, i.e. less inclusion in membrane lipids such as PC. Similar results were observed with the co-expression of CcTE. C14:0 accumulated to 40.3±1.2% in the presence of the combination of CcTE+AtWRI1+CnGPAT9+CnLPAAT. There was an increase in the TAG content but not significantly compared to CcTE+CnGPAT9. The greatest TAG production was achieved following the further addition of the EgDGAT1, with a total TAG content of 2.8±0.2%. The fatty acid composition of TAG was altered following the additional combination with EgDGAT1, with a significant reduction in C14:0 and a significant increase in C16:0 content, each as a percentage of the total fatty acid content of the TAG. This shift in profile suggested that EgDGAT1 exhibited a stronger substrate preference for C16:0 compared to C14:0. Consistent with the observations with UcTE, a significant improvement in the chlorotic phenotype was observed following the addition of EgDGAT1. When CnTE2 was used, the sequential addition of the acyltransferases did not result in any significant differences in either the fatty acid profile of TAG, or the total TAG content. This may have been due to the native acyltransferases' ability to efficiently utilise the increased flux of C16:0 acyl-CoA associated with the activity of CnTE2.

Further investigations into the effects of the sequential addition of acyltransferases on the utilization of acyl-CoAs for the assembly of MCFA-enriched glycerolipids was performed using QQQ-LCMS as described in Example 1, to reveal any differences in MCFA assembly and distribution. The integrated analysis including DAG, PC and TAG revealed much information about the assembly process of lipids in the leaf cells. When CnGPAT9 was expressed with UcTE+AtWRI1, it was observed that CnGPAT9 used C12:0 substrate for assembly, based on the presence of PC 30:3 (C12:0 plus C18:3). It was reasoned that the sn-2 position of the PC was most likely occupied by C18:3, due to either the esterification of C12:0 to the sn-1 position via CnGPAT9 or from the absence of CnLPAAT. The presence of some TAG 42:3 suggested that the native DGATs exhibited some capability of utilising C12:0 for TAG assembly (12:0/18:3/12:0). With the addition of CnLPAAT, a significant amount of PC 24:0 (di-C12:0) was produced, indicating that C12:0 was efficiently esterified to both the sn-1 and sn-2 positions of the G3P backbone. However, without a strong substrate preference for C12:0, most of the produced laurate remains sequestered in membrane lipids. However, further addition of EgDGAT1 increased laurate accumulation. This shift involved the reduction of MCFAs accumulating in PC and increased production of MCFA-enriched TAG. Most notable was the shift from PC 24:0 (without EgDGAT1) to the accumulation of TAG 36:0 (tri-C12:0) (with EgDGAT1), highlighting that laurate was being efficiently incorporated into all three position of the G3P backbone in the presence of EgDGAT1. Significant increases were also observed for other MCFA-enriched TAG species including TAG 38:0, TAG 40:0 and TAG 42:0. These results confirmed that the expression of an appropriate DGAT1 was effective for the efficient incorporation of the unusual fatty acids of interest (in this instance, C12:0 and other MCFA) into TAG. These results highlighted that the expression of the EgDGAT1 in the enzyme combination effectively relieved the accumulation of MCFA in PC and promoted efficient production of MCFA-enriched TAG in plant leaf lipids.

A similar pattern was also observed in the case study involving combinations including CcTE. When CnGPAT9 was combined with CcTE+AtWRI1, it was observed that CnGPAT9 utilised C14:0 substrate, based on the accumulation of PC 28:0 (di-C14:0) and PC 30:0 (C14:0 plus C16:0). It appeared that the native LPAAT genes were somewhat capable of utilising C14:0-CoA as substrate based on the presence of PC 28:0, indicating that C14:0 was being esterified at both the sn-1 and sn-2 positions of the PC. Similarly, the native DGATs also appeared capable of utilising C14:0-CoA for TAG assembly, based on the production of TAG 42:0 (tri-C14:0). However, the subsequent addition of CnLPAAT to the system increased utilisation of C14:0 acyl-CoA, evident from the significantly increased abundance of PC 28:0, which indicated an increased efficiency of esterification to the sn-2 position of PC. This increased accumulation of MCFA was also correlated with a more severe chlorosis phenotype then compared to the CnGPAT9 alone, most likely attributed to the increased accumulation in the membrane lipids. The further addition of the EgDGAT1 to the combination resulted in almost complete absence of MCFA from PC. This was associated with an increased production of MCFA-enriched TAG species, particularly TAG 40:0, TAG 42:0, TAG 44:0 and TAG 46:0, all of which include the incorporation of C14:0.

When CnGPAT9 was combined with CnTE2+AtWRI1, it was observed that CnGPAT9 also utilised C16:0-CoA as substrate, based on the accumulation of PC 32:0 (di-C16:0). Based on the fatty acid profile of N. benthamiana leaves, it was expected that the native LPAATs and DGATs would exhibit substrate preference for the incorporation of C16:0 into glycerolipids, evidenced from the increased production of C16:0-enriched TAG species, through simply over-expressing a thioesterase with C16:0 specificity. Although the subsequent additions of the CnLPAAT and EgDGAT1 did not appear to significantly affect the overall TAG composition, there was a significant reduction in the total MCFA accumulation in PC lipids. Importantly, the addition of the EgDGAT1 to CnTE2 was associated with a reduction in the degree of leaf chlorosis, although not as complete as in the presence of the other TEs.

It was concluded that a GPAT9 like CnGPAT9 having a preference for MCFA substrates was an important factor in contributing towards both MCFA accumulation and increasing the total production of TAG in plant leaves. In the absence of a DGAT having substrate preference for MCFA, the low abundance of MCFA-containing DAG species suggested that DAG containing the MCFA was efficiently converted to PC through the activities of either PDCT or CPT (Bates and Browse, 2011; Bates and Browse, 2012; Bates et al., 2012). The addition of EgDGAT1 changed the metabolic flux of the system, pushing MCFA towards TAG accumulation via the Kennedy pathway, and thus away from incorporation of the MCFA into membrane lipids through reducing conversion of DAG to PC.

TABLE 13

Total leaf fatty acid composition of TAG (% total TAG) of C6:0, C8:0 and C10:0 fatty acids in *Nicotiana benthamiana* leaves infiltrated with various constructs.

| Genotype | C6:0 | C8:0 | C10:0 |
|---|---|---|---|
| REPLICATE 1 | | | |
| P19 | 0.000 | 0.000 | 4.317 |
| P19 + CincaTE + CnGPAT9 + AtWRI | 0.000 | 0.000 | 0.000 |
| P19 + CuplaTE + CnGPAT9 + AtWRI | 0.000 | 0.000 | 5.687 |
| P19 + UmbcaTE + CnGPAT9 + AtWRI | 0.000 | 0.000 | 0.000 |
| P19 + CocnuTE2 + CnGPAT9 + AtWRI | 0.000 | 0.000 | 0.000 |
| P19 + CincaTE + CnGPAT9 + AtWRI + CnLPAAT | 0.000 | 0.000 | 0.000 |
| P19 + CuplaTE + CnGPAT9 + AtWRI + CnLPAAT | 0.000 | 0.000 | 0.947 |
| P19 + UmbcaTE + CnGPAT9 + AtWRI + CnLPAAT | 0.000 | 0.000 | 0.000 |
| P19 + CocnuTE2 + CnGPAT9 + AtWRI + CnLPAAT | 0.000 | 0.000 | 0.000 |
| P19 + CincaTE + CnGPAT9 + AtWRI + CnLPAAT + EgDGAT | 0.000 | 0.000 | 0.000 |
| P19 + CuplaTE + CnGPAT9 + AtWRI + CnLPAAT + EgDGAT | 0.000 | 0.000 | 1.533 |
| P19 + UmbcaTE + CnGPAT9 + AtWRI + CnLPAAT + EgDGAT | 0.000 | 0.000 | 0.000 |
| P19 + CocnuTE2 + CnGPAT9 + AtWRI + CnLPAAT + EgDGAT | 0.000 | 0.000 | 0.000 |
| P19 + CincaTE + AtGPAT9 + AtWRI + CnLPAAT + EgDGAT | 0.000 | 0.000 | 0.000 |
| P19 + CuplaTE + AtGPAT9 + AtWRI + CnLPAAT + EgDGAT | 0.000 | 0.000 | 1.643 |
| P19 + UmbcaTE + AtGPAT9 + AtWRI + CnLPAAT + EgDGAT | 0.000 | 0.000 | 0.000 |
| REPLICATE 2 | | | |
| P19 | 0.000 | 0.000 | 0.000 |
| P19 + CincaTE + CnGPAT9 + AtWRI | 0.000 | 0.000 | 0.000 |
| P19 + CuplaTE + CnGPAT9 + AtWRI | 0.000 | 0.000 | 4.368 |
| P19 + UmbcaTE + CnGPAT9 + AtWRI | 0.000 | 0.000 | 0.000 |
| P19 + CocnuTE2 + CnGPAT9 + AtWRI | 0.000 | 0.000 | 0.000 |
| P19 + CincaTE + CnGPAT9 + AtWRI + CnLPAAT | 0.000 | 0.000 | 0.000 |
| P19 + CuplaTE + CnGPAT9 + AtWRI + CnLPAAT | 0.000 | 0.000 | 3.523 |
| P19 + UmbcaTE + CnGPAT9 + AtWRI + CnLPAAT | 0.000 | 0.000 | 0.000 |
| P19 + CocnuTE2 + CnGPAT9 + AtWRI + CnLPAAT | 0.000 | 0.000 | 0.000 |
| P19 + CincaTE + CnGPAT9 + AtWRI + CnLPAAT + EgDGAT | 0.000 | 0.000 | 0.000 |
| P19 + CuplaTE + CnGPAT9 + AtWRI + CnLPAAT + EgDGAT | 0.000 | 0.000 | 0.000 |
| P19 + UmbcaTE + CnGPAT9 + AtWRI + CnLPAAT + EgDGAT | 0.000 | 0.000 | 0.000 |
| P19 + CocnuTE2 + CnGPAT9 + AtWRI + CnLPAAT + EgDGAT | 0.000 | 0.000 | 0.000 |
| P19 + CincaTE + AtGPAT9 + AtWRI + CnLPAAT + EgDGAT | 0.000 | 0.000 | 0.000 |
| P19 + CuplaTE + AtGPAT9 + AtWRI + CnLPAAT + EgDGAT | 0.000 | 0.000 | 0.000 |
| P19 + UmbcaTE + AtGPAT9 + AtWRI + CnLPAAT + EgDGAT | 0.000 | 0.000 | 0.000 |
| REPLICATE 3 | | | |
| P19 | 0.000 | 0.000 | 0.000 |
| P19 + CincaTE + CnGPAT9 + AtWRI | 0.000 | 0.000 | 0.000 |
| P19 + CuplaTE + CnGPAT9 + AtWRI | 0.000 | 0.000 | 0.000 |
| P19 + UmbcaTE + CnGPAT9 + AtWRI | 0.000 | 0.000 | 0.000 |
| P19 + CocnuTE2 + CnGPAT9 + AtWRI | 0.000 | 0.000 | 0.000 |
| P19 + CincaTE + CnGPAT9 + AtWRI + CnLPAAT | 0.000 | 0.000 | 0.000 |
| P19 + CuplaTE + CnGPAT9 + AtWRI + CnLPAAT | 0.000 | 0.000 | 0.000 |
| P19 + UmbcaTE + CnGPAT9 + AtWRI + CnLPAAT | 0.000 | 0.000 | 0.000 |
| P19 + CocnuTE2 + CnGPAT9 + AtWRI + CnLPAAT | 0.000 | 0.000 | 0.000 |
| P19 + CincaTE + CnGPAT9 + AtWRI + CnLPAAT + EgDGAT | 0.000 | 0.000 | 0.000 |
| P19 + CuplaTE + CnGPAT9 + AtWRI + CnLPAAT + EgDGAT | 0.000 | 0.000 | 0.000 |
| P19 + UmbcaTE + CnGPAT9 + AtWRI + CnLPAAT + EgDGAT | 0.000 | 0.000 | 0.000 |
| P19 + CocnuTE2 + CnGPAT9 + AtWRI + CnLPAAT + EgDGAT | 0.000 | 0.000 | 0.000 |
| P19 + CincaTE + AtGPAT9 + AtWRI + CnLPAAT + EgDGAT | 0.000 | 0.000 | 0.000 |
| P19 + CuplaTE + AtGPAT9 + AtWRI + CnLPAAT + EgDGAT | 0.000 | 0.000 | 0.000 |
| P19 + UmbcaTE + AtGPAT9 + AtWRI + CnLPAAT + EgDGAT | 0.000 | 0.000 | 0.000 |

TABLE 14

Total leaf fatty acid composition of TAG (% total TAG) of 12:0, C14:0, C14;1, C15:0, C16:0 and C16:1 fatty acids in *Nicotiana benthamiana* leaves infiltrated with various constructs.

| Genotype | C12:0 | C14:0 | C14:1 | C15:0 | C16:0 | C16:1 |
|---|---|---|---|---|---|---|
| REPLICATE 1 | | | | | | |
| P19 | 3.882 | 11.116 | 0.000 | 1.380 | 41.258 | 0.000 |
| P19 + CincaTE + CnGPAT9 + AtWRI | 3.332 | 35.333 | 0.000 | 0.226 | 27.276 | 0.203 |
| P19 + CuplaTE + CnGPAT9 + AtWRI | 2.119 | 10.647 | 0.000 | 0.000 | 47.322 | 0.000 |
| P19 + UmbcaTE + CnGPAT9 + AtWRI | 32.957 | 9.794 | 0.000 | 0.000 | 16.217 | 0.000 |
| P19 + CocnuTE2 + CnGPAT9 + AtWRI | 0.000 | 17.998 | 0.000 | 0.343 | 56.230 | 0.578 |
| P19 + CincaTE + CnGPAT9 + AtWRI + CnLPAAT | 7.219 | 41.154 | 0.000 | 0.261 | 24.586 | 0.334 |
| P19 + CuplaTE + CnGPAT9 + AtWRI + CnLPAAT | 1.491 | 7.331 | 0.000 | 0.241 | 57.931 | 0.315 |
| P19 + UmbcaTE + CnGPAT9 + AtWRI + CnLPAAT | 44.742 | 10.476 | 0.000 | 0.000 | 10.207 | 0.270 |

TABLE 14-continued

Total leaf fatty acid composition of TAG (% total TAG) of 12:0, C14:0, C14;1, C15:0, C16:0 and C16:1 fatty acids in *Nicotiana benthamiana* leaves infiltrated with various constructs.

| Genotype | C12:0 | C14:0 | C14:1 | C15:0 | C16:0 | C16:1 |
|---|---|---|---|---|---|---|
| P19 + CocnuTE2 + CnGPAT9 + AtWRI + CnLPAAT | 0.465 | 14.889 | 0.000 | 0.335 | 56.250 | 0.481 |
| P19 + CincaTE + CnGPAT9 + AtWRI + CnLPAAT + EgDGAT | 4.620 | 30.554 | 0.000 | 0.177 | 37.511 | 0.475 |
| P19 + CuplaTE + CnGPAT9 + AtWRI + CnLPAAT + EgDGAT | 4.598 | 5.250 | 0.000 | 0.221 | 51.742 | 0.320 |
| P19 + UmbcaTE + CnGPAT9 + AtWRI + CnLPAAT + EgDGAT | 53.604 | 7.690 | 0.000 | 0.157 | 11.120 | 0.094 |
| P19 + CocnuTE2 + CnGPAT9 + AtWRI + CnLPAAT + EgDGAT | 0.654 | 14.116 | 0.000 | 0.256 | 53.942 | 0.306 |
| P19 + CincaTE + AtGPAT9 + AtWRI + CnLPAAT + EgDGAT | 4.499 | 35.151 | 0.000 | 0.196 | 33.202 | 0.314 |
| P19 + CuplaTE + AtGPAT9 + AtWRI + CnLPAAT + EgDGAT | 4.943 | 5.716 | 0.000 | 0.262 | 50.177 | 0.542 |
| P19 + UmbcaTE + AtGPAT9 + AtWRI + CnLPAAT + EgDGAT | 49.589 | 7.781 | 0.000 | 0.105 | 12.284 | 0.252 |
| REPLICATE 2 | | | | | | |
| P19 | 6.485 | 10.998 | 0.000 | 0.000 | 46.160 | 0.000 |
| P19 + CincaTE + CnGPAT9 + AtWRI | 0.000 | 0.000 | 0.000 | 0.000 | 0.000 | 0.000 |
| P19 + CuplaTE + CnGPAT9 + AtWRI | 1.758 | 10.767 | 0.000 | 0.000 | 49.728 | 0.583 |
| P19 + UmbcaTE + CnGPAT9 + AtWRI | 32.530 | 10.553 | 0.000 | 0.000 | 15.254 | 0.544 |
| P19 + CocnuTE2 + CnGPAT9 + AtWRI | 0.628 | 16.693 | 0.000 | 0.327 | 49.863 | 0.466 |
| P19 + CincaTE + CnGPAT9 + AtWRI + CnLPAAT | 3.660 | 40.701 | 0.000 | 0.264 | 28.736 | 0.333 |
| P19 + CuplaTE + CnGPAT9 + AtWRI + CnLPAAT | 2.472 | 10.374 | 0.000 | 0.364 | 49.195 | 0.635 |
| P19 + UmbcaTE + CnGPAT9 + AtWRI + CnLPAAT | 43.462 | 10.775 | 0.000 | 0.206 | 10.328 | 0.225 |
| P19 + CocnuTE2 + CnGPAT9 + AtWRI + CnLPAAT | 0.000 | 0.000 | 0.000 | 0.000 | 0.000 | 0.000 |
| P19 + CincaTE + CnGPAT9 + AtWRI + CnLPAAT + EgDGAT | 4.101 | 33.380 | 0.000 | 0.000 | 35.431 | 0.000 |
| P19 + CuplaTE + CnGPAT9 + AtWRI + CnLPAAT + EgDGAT | 8.061 | 5.606 | 0.000 | 0.000 | 47.901 | 0.000 |
| P19 + UmbcaTE + CnGPAT9 + AtWRI + CnLPAAT + EgDGAT | 49.552 | 6.800 | 0.000 | 0.000 | 12.602 | 0.000 |
| P19 + CocnuTE2 + CnGPAT9 + AtWRI + CnLPAAT + EgDGAT | 0.000 | 14.374 | 0.000 | 0.000 | 50.723 | 0.000 |
| P19 + CincaTE + AtGPAT9 + AtWRI + CnLPAAT + EgDGAT | 2.758 | 26.757 | 0.000 | 0.000 | 38.082 | 0.000 |
| P19 + CuplaTE + AtGPAT9 + AtWRI + CnLPAAT + EgDGAT | 2.672 | 4.771 | 0.000 | 0.000 | 53.725 | 0.000 |
| P19 + UmbcaTE + AtGPAT9 + AtWRI + CnLPAAT + EgDGAT | 49.847 | 6.988 | 0.000 | 0.000 | 11.945 | 0.000 |
| REPLICATE 3 | | | | | | |
| P19 | 0.000 | 0.000 | 0.000 | 0.000 | 55.478 | 0.000 |
| P19 + CincaTE + CnGPAT9 + AtWRI | 0.000 | 32.975 | 0.000 | 0.000 | 29.893 | 0.000 |
| P19 + CuplaTE + CnGPAT9 + AtWRI | 0.000 | 9.743 | 0.000 | 0.000 | 55.084 | 0.000 |
| P19 + UmbcaTE + CnGPAT9 + AtWRI | 29.807 | 9.939 | 0.000 | 0.000 | 15.215 | 0.000 |
| P19 + CocnuTE2 + CnGPAT9 + AtWRI | 0.000 | 20.098 | 0.000 | 0.000 | 48.646 | 0.000 |
| P19 + CincaTE + CnGPAT9 + AtWRI + CnLPAAT | 4.924 | 38.894 | 0.000 | 0.000 | 22.078 | 0.000 |
| P19 + CuplaTE + CnGPAT9 + AtWRI + CnLPAAT | 0.000 | 9.483 | 0.000 | 0.000 | 57.458 | 0.000 |
| P19 + UmbcaTE + CnGPAT9 + AtWRI + CnLPAAT | 46.258 | 8.809 | 0.000 | 0.000 | 9.487 | 0.000 |
| P19 + CocnuTE2 + CnGPAT9 + AtWRI + CnLPAAT | 0.000 | 18.294 | 0.000 | 0.000 | 56.968 | 0.000 |
| P19 + CincaTE + CnGPAT9 + AtWRI + CnLPAAT + EgDGAT | 3.909 | 34.512 | 0.000 | 0.000 | 36.091 | 0.000 |
| P19 + CuplaTE + CnGPAT9 + AtWRI + CnLPAAT + EgDGAT | 0.000 | 4.605 | 0.000 | 0.000 | 56.818 | 0.000 |
| P19 + UmbcaTE + CnGPAT9 + AtWRI + CnLPAAT + EgDGAT | 51.506 | 7.067 | 0.000 | 0.000 | 11.083 | 0.000 |
| P19 + CocnuTE2 + CnGPAT9 + AtWRI + CnLPAAT + EgDGAT | 0.000 | 10.744 | 0.000 | 0.000 | 55.660 | 0.000 |
| P19 + CincaTE + AtGPAT9 + AtWRI + CnLPAAT + EgDGAT | 3.697 | 26.670 | 0.000 | 0.000 | 37.159 | 0.000 |
| P19 + CuplaTE + AtGPAT9 + AtWRI + CnLPAAT + EgDGAT | 1.737 | 4.336 | 0.000 | 0.000 | 54.136 | 0.000 |
| P19 + UmbcaTE + AtGPAT9 + AtWRI + CnLPAAT + EgDGAT | 49.371 | 6.898 | 0.000 | 0.000 | 10.168 | 0.000 |

TABLE 15

Total leaf fatty acid composition of TAG (% total TAG) of C17:0, C17:1, C18:0, C18:1, C19:0, C18:2, C18:3, C20:0, C20:1, C22:0 and C24:0 fatty acids in *Nicotiana benthamiana* leaves infiltrated with various constructs.

| Genotype | C17:0 | C17:1 | C18:0 | C18:1 | C19:0 | C18:2 | C18:3 | C20:0 | C20:1 | C22:0 | C24:0 |
|---|---|---|---|---|---|---|---|---|---|---|---|
| REPLICATE 1 | | | | | | | | | | | |
| P19 | 0.000 | 0.000 | 7.003 | 3.505 | 0.000 | 7.516 | 13.827 | 1.204 | 1.260 | 1.303 | 2.428 |
| P19 + CincaTE + CnGPAT9 + AtWRI | 0.000 | 0.381 | 2.160 | 1.542 | 0.363 | 6.795 | 21.636 | 0.382 | 0.000 | 0.208 | 0.163 |
| P19 + CuplaTE + CnGPAT9 + AtWRI | 0.000 | 0.768 | 3.491 | 1.051 | 0.000 | 7.046 | 20.841 | 0.607 | 0.000 | 0.000 | 0.421 |
| P19 + UmbcaTE + CnGPAT9 + AtWRI | 0.000 | 1.251 | 2.658 | 1.439 | 0.000 | 9.993 | 25.690 | 0.000 | 0.000 | 0.000 | 0.000 |
| P19 + CocnuTE2 + CnGPAT9 + AtWRI | 0.000 | 0.485 | 3.864 | 1.427 | 0.000 | 5.547 | 13.027 | 0.503 | 0.000 | 0.000 | 0.000 |
| P19 + CincaTE + CnGPAT9 + AtWRI + CnLPAAT | 0.000 | 0.296 | 1.824 | 2.156 | 0.000 | 4.653 | 17.211 | 0.307 | 0.000 | 0.000 | 0.000 |
| P19 + CuplaTE + CnGPAT9 + AtWRI + CnLPAAT | 0.000 | 0.242 | 2.812 | 5.820 | 0.616 | 6.643 | 14.892 | 0.515 | 0.000 | 0.203 | 0.000 |
| P19 + UmbcaTE + CnGPAT9 + AtWRI + CnLPAAT | 0.000 | 0.191 | 1.359 | 3.790 | 0.514 | 8.779 | 19.329 | 0.204 | 0.000 | 0.140 | 0.000 |
| P19 + CocnuTE2 + CnGPAT9 + AtWRI + CnLPAAT | 0.000 | 0.333 | 3.431 | 2.297 | 0.000 | 4.517 | 16.271 | 0.552 | 0.000 | 0.179 | 0.000 |
| P19 + CincaTE + CnGPAT9 + AtWRI + CnLPAAT + EgDGAT | 0.000 | 0.244 | 2.274 | 6.967 | 0.414 | 7.193 | 8.577 | 0.560 | 0.000 | 0.297 | 0.137 |

TABLE 15-continued

Total leaf fatty acid composition of TAG (% total TAG) of C17:0, C17:1, C18:0, C18:1, C19:0, C18:2, C18:3, C20:0, C20:1, C22:0 and C24:0 fatty acids in *Nicotiana benthamiana* leaves infiltrated with various constructs.

| Genotype | C17:0 | C17:1 | C18:0 | C18:1 | C19:0 | C18:2 | C18:3 | C20:0 | C20:1 | C22:0 | C24:0 |
|---|---|---|---|---|---|---|---|---|---|---|---|
| P19 + CuplaTE + CnGPAT9 + AtWRI + CnLPAAT + EgDGAT | 0.000 | 0.283 | 3.698 | 7.203 | 0.473 | 9.780 | 13.198 | 0.895 | 0.000 | 0.535 | 0.272 |
| P19 + UmbcaTE + CnGPAT9 + AtWRI + CnLPAAT + EgDGAT | 0.000 | 0.237 | 1.704 | 6.638 | 0.460 | 8.261 | 8.641 | 0.521 | 0.117 | 0.470 | 0.286 |
| P19 + CocnuTE2 + CnGPAT9 + AtWRI + CnLPAAT + EgDGAT | 0.000 | 0.457 | 3.117 | 1.071 | 0.324 | 4.844 | 20.248 | 0.459 | 0.000 | 0.205 | 0.000 |
| P19 + CincaTE + AtGPAT9 + AtWRI + CnLPAAT + EgDGAT | 0.000 | 0.299 | 2.232 | 4.203 | 0.290 | 5.963 | 12.828 | 0.500 | 0.000 | 0.233 | 0.089 |
| P19 + CuplaTE + AtGPAT9 + AtWRI + CnLPAAT + EgDGAT | 0.000 | 0.321 | 4.172 | 5.766 | 0.479 | 8.508 | 15.845 | 0.902 | 0.000 | 0.501 | 0.224 |
| P19 + UmbcaTE + AtGPAT9 + AtWRI + CnLPAAT + EgDGAT | 0.000 | 0.185 | 1.873 | 6.977 | 0.608 | 9.240 | 9.823 | 0.532 | 0.095 | 0.425 | 0.230 |
| REPLICATE 2 | | | | | | | | | | | |
| P19 | 0.000 | 0.000 | 5.724 | 0.000 | 0.000 | 9.527 | 21.105 | 0.000 | 0.000 | 0.000 | 0.000 |
| P19 + CincaTE + CnGPAT9 + AtWRI | 0.000 | 0.000 | 0.000 | 0.000 | 0.000 | 0.000 | 0.000 | 0.000 | 0.000 | 0.000 | 0.000 |
| P19 + CuplaTE + CnGPAT9 + AtWRI | 0.000 | 0.450 | 4.115 | 0.919 | 0.000 | 7.307 | 18.646 | 0.635 | 0.000 | 0.440 | 0.285 |
| P19 + UmbcaTE + CnGPAT9 + AtWRI | 0.000 | 0.432 | 3.015 | 2.565 | 0.000 | 10.355 | 23.801 | 0.580 | 0.000 | 0.370 | 0.000 |
| P19 + CocnuTE2 + CnGPAT9 + AtWRI | 0.000 | 0.324 | 3.210 | 1.170 | 0.467 | 5.649 | 20.593 | 0.447 | 0.000 | 0.163 | 0.000 |
| P19 + CincaTE + CnGPAT9 + AtWRI + CnLPAAT | 0.000 | 0.206 | 2.042 | 3.281 | 0.299 | 4.527 | 15.495 | 0.334 | 0.000 | 0.122 | 0.000 |
| P19 + CuplaTE + CnGPAT9 + AtWRI + CnLPAAT | 0.000 | 0.342 | 3.649 | 1.568 | 0.000 | 6.412 | 20.615 | 0.553 | 0.000 | 0.298 | 0.000 |
| P19 + UmbcaTE + CnGPAT9 + AtWRI + CnLPAAT | 0.000 | 0.197 | 1.653 | 3.620 | 0.431 | 8.552 | 20.205 | 0.201 | 0.000 | 0.145 | 0.000 |
| P19 + CocnuTE2 + CnGPAT9 + AtWRI + CnLPAAT | 0.000 | 0.000 | 0.000 | 0.000 | 0.000 | 0.000 | 0.000 | 0.000 | 0.000 | 0.000 | 0.000 |
| P19 + CincaTE + CnGPAT9 + AtWRI + CnLPAAT + EgDGAT | 0.000 | 1.023 | 2.522 | 4.695 | 0.000 | 7.688 | 11.161 | 0.000 | 0.000 | 0.000 | 0.000 |
| P19 + CuplaTE + CnGPAT9 + AtWRI + CnLPAAT + EgDGAT | 0.000 | 0.000 | 3.790 | 5.402 | 0.000 | 11.197 | 17.104 | 0.939 | 0.000 | 0.000 | 0.000 |
| P19 + UmbcaTE + CnGPAT9 + AtWRI + CnLPAAT + EgDGAT | 0.000 | 0.000 | 1.950 | 6.434 | 0.000 | 10.572 | 10.877 | 0.615 | 0.000 | 0.598 | 0.000 |
| P19 + CocnuTE2 + CnGPAT9 + AtWRI + CnLPAAT + EgDGAT | 0.000 | 2.364 | 2.998 | 1.381 | 0.000 | 6.570 | 21.589 | 0.000 | 0.000 | 0.000 | 0.000 |
| P19 + CincaTE + AtGPAT9 + AtWRI + CnLPAAT + EgDGAT | 0.000 | 0.962 | 2.526 | 6.126 | 0.000 | 9.898 | 12.288 | 0.603 | 0.000 | 0.000 | 0.000 |
| P19 + CuplaTE + AtGPAT9 + AtWRI + CnLPAAT + EgDGAT | 0.000 | 1.141 | 3.660 | 6.542 | 0.000 | 11.577 | 14.693 | 0.794 | 0.000 | 0.424 | 0.000 |
| P19 + UmbcaTE + AtGPAT9 + AtWRI + CnLPAAT + EgDGAT | 0.000 | 0.000 | 1.909 | 6.636 | 0.000 | 11.998 | 10.677 | 0.000 | 0.000 | 0.000 | 0.000 |
| REPLICATE 3 | | | | | | | | | | | |
| P19 | 0.000 | 0.000 | 0.000 | 0.000 | 0.000 | 19.966 | 24.557 | 0.000 | 0.000 | 0.000 | 0.000 |
| P19 + CincaTE + CnGPAT9 + AtWRI | 0.000 | 1.600 | 2.296 | 2.966 | 0.000 | 10.225 | 20.046 | 0.000 | 0.000 | 0.000 | 0.000 |
| P19 + CuplaTE + CnGPAT9 + AtWRI | 0.000 | 0.000 | 3.044 | 2.041 | 0.000 | 10.711 | 19.376 | 0.000 | 0.000 | 0.000 | 0.000 |
| P19 + UmbcaTE + CnGPAT9 + AtWRI | 0.000 | 0.000 | 2.821 | 3.186 | 0.000 | 14.113 | 24.919 | 0.000 | 0.000 | 0.000 | 0.000 |
| P19 + CocnuTE2 + CnGPAT9 + AtWRI | 0.000 | 1.637 | 2.992 | 1.264 | 0.000 | 6.611 | 18.753 | 0.000 | 0.000 | 0.000 | 0.000 |
| P19 + CincaTE + CnGPAT9 + AtWRI + CnLPAAT | 0.000 | 2.465 | 1.645 | 1.269 | 0.000 | 6.427 | 22.298 | 0.000 | 0.000 | 0.000 | 0.000 |
| P19 + CuplaTE + CnGPAT9 + AtWRI + CnLPAAT | 0.000 | 0.000 | 2.864 | 3.499 | 0.000 | 7.993 | 18.702 | 0.000 | 0.000 | 0.000 | 0.000 |
| P19 + UmbcaTE + CnGPAT9 + AtWRI + CnLPAAT | 0.000 | 0.000 | 1.356 | 4.320 | 0.000 | 10.699 | 19.070 | 0.000 | 0.000 | 0.000 | 0.000 |
| P19 + CocnuTE2 + CnGPAT9 + AtWRI + CnLPAAT | 0.000 | 0.000 | 3.467 | 0.000 | 0.000 | 6.091 | 15.180 | 0.000 | 0.000 | 0.000 | 0.000 |
| P19 + CincaTE + CnGPAT9 + AtWRI + CnLPAAT + EgDGAT | 0.000 | 0.875 | 2.053 | 5.925 | 0.000 | 7.047 | 9.165 | 0.422 | 0.000 | 0.000 | 0.000 |
| P19 + CuplaTE + CnGPAT9 + AtWRI + CnLPAAT + EgDGAT | 0.000 | 1.103 | 3.685 | 8.285 | 0.000 | 10.471 | 15.034 | 0.000 | 0.000 | 0.000 | 0.000 |
| P19 + UmbcaTE + CnGPAT9 + AtWRI + CnLPAAT + EgDGAT | 0.000 | 0.631 | 1.506 | 6.663 | 0.000 | 11.367 | 9.290 | 0.462 | 0.000 | 0.425 | 0.000 |
| P19 + CocnuTE2 + CnGPAT9 + AtWRI + CnLPAAT + EgDGAT | 0.000 | 1.705 | 3.665 | 2.985 | 0.000 | 7.058 | 18.182 | 0.000 | 0.000 | 0.000 | 0.000 |
| P19 + CincaTE + AtGPAT9 + AtWRI + CnLPAAT + EgDGAT | 0.000 | 0.816 | 2.447 | 7.987 | 0.000 | 9.927 | 10.359 | 0.598 | 0.000 | 0.339 | 0.000 |
| P19 + CuplaTE + AtGPAT9 + AtWRI + CnLPAAT + EgDGAT | 0.000 | 1.020 | 3.588 | 7.767 | 0.000 | 11.969 | 14.237 | 0.765 | 0.000 | 0.445 | 0.000 |
| P19 + UmbcaTE + AtGPAT9 + AtWRI + CnLPAAT + EgDGAT | 0.000 | 0.647 | 1.538 | 8.125 | 0.000 | 12.136 | 10.070 | 0.433 | 0.000 | 0.377 | 0.236 |

Discussion

In the seeds of native plants, the incorporation of unusual fatty acids is almost exclusively confined to TAG and typically excluded from membrane lipids, most likely because they interfere with proper membrane functions and are often deleterious to the plant cells (Millar et al., 2000). A different scenario has been observed in transgenic plants that have attempted to modify the oil fatty acid profiles, such as increasing the lauric acid content (Knutzon et al., 1999). Although high levels of laurate accumulation in plant oils have been achieved in the seeds of transgenic canola, there was a significant level of laurate being sequestered in PC during seed development (Wiberg et al., 1997). In that work, de novo DAG containing laurate was not efficiently converted to TAG by the resident DGAT but was instead converted to the membrane lipid PC. The native canola LPCAT lacked the capability to handle MCFAs (Zhang et al., 2015) so the route to PC could be through PDCT or CPT activities. Consequently, this inefficient utilization of laurate for TAG synthesis was also associated with a negatively correlated penalty in total oil yields (Knutzon et al., 1999).

Similar to the expression of MCFA in seed oil, the over expression of MCFA in the leaf cells described here with the co-expression of CnGPAT9 and CnLPAAT identified a metabolic bottleneck through the sequestering of MCFA in PC. The low abundance of MCFA-containing DAG species suggested that de novo DAG containing MCFA was quickly converted to PC through the activities of PDCT or CPT or both, due to the absence of a DGAT capable of using the MCFA-containing DAG for TAG assembly. The inventors showed that the addition to the enzyme combination of a DGAT with a preference for MCFA as substrate, relative to one or more C18 substrates such as oleic acid, LA or ALA, promoted synthesis of MCFA-enriched TAG and relieved this bottleneck. Endogenous PDAT may also be involved in the maintenance of membrane homeostasis, through the removal of unusual fatty acids from the membrane lipids and sequestering them into TAG (Fan et al., 2014; Fan et al., 2013a and b). This study demonstrated that the expression of the DGAT from a species such as *E. guineensis* (EgDGAT1) was sufficient to restore membrane homeostasis by reducing the accumulation of MCFA in PC. The expression of EgDGAT1 proved that a DGAT with MCFA substrate preference was beneficial for the efficient assembly of TAG and increased TAG content in the plant cells. The reconfigured Kennedy pathway for improving MCFA incorporation into TAG is expected to benefit seedoil composition and TAG content as well.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

The references listed below are incorporated by reference where cited in the Specification:
Adhikari et al. (2016) Plant Physiol 171:179-191.
Alemanno et al. (2008) Planta 227:853-866.
Almeida and Allshire (2005) TRENDS Cell Biol. 15:251-258.
Alonso et al. (2009) Plant Cell 21: 1747-1761.
Alonso et al. (2010) Green Chem. 12:1493-1513.
Alvarez et al. (2000) Theor. Appl. Genet. 100:319-327.
Andre et al. (2012) Proc. Natl. Acad. Sci. U.S.A. 109:10107-10112.
Arkcoll (1988) Lauric Oil Resources. Economic Botany 42:195-205.
Bartlett et al. (2008) Plant Methods 4:22.
Basiron and Weng (2004) Journal of Oil Palm Research 16.
Bates et al. (2014) PNAS USA 111:1204-1209.
Bates and Browse (2011) Plant J 68:387-399.
Bates and Browse (2012) Frontiers in Plant Science 3:147.
Baud et al. (2007) Plant J. 50:825-838.
Baud and Lepiniec (2010) Progr. Lipid Res. 49: 235-249.
Baumlein et al. (1991) Mol. Gen. Genet. 225:459-467.
Baumlein et al. (1992) Plant J. 2:233-239.
Belide et al. (2013) Plant Cell Tiss. Org. Cult. DOI 10.1007/s11240-013-0295-1.
Ben Saad et al. (2011) Transgenic Res 20: 1003-1018.
Bibikova et al. (2002) Genetics 161:1169-1175.
Bihmidine et al. (2015) BMC Plant Biology 15:186.
Bihmidine et al. (2016) Plant Signaling & Behaviour 11: e1117721.
Bligh and Dyer (1959) Canadian Journal of Biochemistry and Physiology 37:911-917.
Boutilier et al. (2002) Plant Cell 14:1737-1749.
Bouvier-Nave et al. (2000) European Journal of Biochemistry/FEBS 267:85-96.
Bradford (1976) Anal. Biochem. 72:248-254.
Broothaerts et al. (2005) Nature 433:629-633.
Broun et al. (1998) Plant J. 13:201-210.
Browse et al. (1986) Biochem J 235: 25-31.
Buchanan-Wollaston (1994) Plant Physiol. 105:839-846.
Burgal et al. (2008) Plant Biotechnol J 6:819-831.
Busk et al. (1997) Plant J. 11:1285-1295.
Cai et al. (2015) Plant Cell 27:2616-2636.
Cao (2011) BMC Research Notes 4:249.
Cao et al. (2007) J. Lipid Res. 48:583-591.
Capuano et al. (2007) Biotechnol. Adv. 25:203-206.
Chapman and Ohlogge (2012) J. Biol. Chem. 287:2288-2294.
Chen et al (2011) Plant Physiol. 155:851-865.
Chen et al. (2016) International Journal of Molecular Sciences 17:507.
Chikwamba et al. (2003) Proc. Natl. Acad. Sci. U.S.A. 100:11127-11132.
Christensen et al. (1992) Plant Mol Biol 18:675-689.
Christie (1993) Advances in Lipid Methodology-Two, Oily Press, Dundee, pp 195-213.
Chung et al. (2006) BMC Genomics 7:120.
Comai et al. (2004) Plant J 37: 778-786.
Cong et al. (2013) Science 339:819-823.
Corrado and Karali (2009) Biotechnol. Adv. 27:733-743.
Coutu et al. (2007) Transgenic Res. 16:771-781.
Dahlqvist et al. (2000), Proc. Natl. Acad. Sci. U.S.A. 97: 6487-6492.
Damaj et al., (2010) Planta 231:1439-1458.
Dandik and Aksoy (1998) Fuel Process Technol. 57: 81-92.
Dauk et al (2007) Plant Sci. 173:43-49.

Deruyffelaere et al. (2015) Plant Cell Physiol 56:1374-1387.
Dehesh (2001) European Journal of Lipid Science and Technology 103:688-697.
Durrett et al. (2008) Plant J. 54:593-607.
Dussert et al. (2013) Plant Physiol 162:1337-1358.
Dyer et al. (2002) Plant Physiol. 130:2027-2038.
Eastmond et al. (2006) Plant Cell 18: 665-675.
Eccleston et al. (1996) Planta 198:46-53.
Eccleston and Ohlrogge (1998) The Plant Cell Online 10:613-621.
Edem (2002) Plant Foods for Human Nutrition 57:319-341.
Ellerstrom et al. (1996) Plant Mol. Biol. 32:1019-1027.
El Tahchy et al. (2017) FEBS Letters 591:448-456.
Endalew et al. (2011) Biomass and Bioenergy 35:3787-3809.
Fan et al. (2013a) Plant Cell 25: 3506-3518.
Fan et al. (2013b) Plant Journal 76: 930-942.
Fan et al. (2014) Plant Cell 26: 4119-4134.
Fan et al. (2015) Plant Cell 27: 2941-2955.
FAO Animal Production and Health Proceedings (2002) Protein sources for the animal feed
industry, Expert Consultation and Workshop, Bangkok.
Feeney et al. (2012) Plant Physiol 162: 1881-1896.
Finkelstein et al. (1998) Plant Cell 10:1043-1054.
Froissard et al. (2009) FEMS Yeast Res 9:428-438.
Gan (1995) Molecular characterization and genetic manipulation of plant senescence. PhD thesis. University of Wisconsin, Madison.
Gan and Amasino (1995) Science 270:1986-1988.
Gazzarrini et al. (2004) Dev. Cell 7:373-385.
Geurin et al. (2016) Plant Biotech. J 87: 423-441.
Ghosal et al. (2007) Biochimica et Biophysica Acta 1771: 1457-1463.
Ghosh et al. (2009) Plant Physiol. 151:869-881.
Gidda et al (2013) Plant Signaling Behav. 8:e27141.
Girijashankar and Swathisree, (2009) Physiol. Mol. Biol. Plants 15: 287-302.
Gong and Jiang (2011) Biotechnol. Lett. 33:1269-1284.
Gould et al. (1991) Plant Physiol. 95:426-434.
Greenwell et al. (2010) J. R. Soc. Interface 7:703-726.
Guan et al. (2015) Lipids 50:407-416.
Gurel et al. (2009) Plant Cell Rep. 28:429-444.
Gutierrew et al. (2013) BMC Biotechnol. 13: 40.
Hedrich et al. (2015) Curr Opin Plant Biol 25: 63-70.
Henikoff et al. (2004) Plant Physiol. 135:630-636.
Hershey and Stoner (1991) Plant Mol. Biol. 17:679-690.
Hinchee et al. (1988) Biotechnology 6:915-922.
Horn et al. (2007) Euphytica 153:27-34.
Horn et al. (2013). Plant Physiol 162:1926-1936.
Horvath et al. (2000) Proc. Natl. Acad. Sci. U.S.A. 97:1914-1919.
Hsiao and Tzen (2011) Plant Physiol. Biochem. 49: 77-81.
Hsieh and Huang (2004) Plant Physiol 136:3427-3434.
Huang (1996) Plant Physiol. 110:1055-1061.
Huang and Huang (2016) Plant Physiol. 171: 1867-1878.
Ichihara et al (1988) Biochim. Biophys. Acta 958:125-129.
Ikeda et al. (2006) Pl Biotech J. 23: 153-161.
Iwabuchi et al. (2003) J. Biol. Chem. 278:4603-4610.
James et al. (2010) Proc. Natl. Acad. Sci. USA 107:17833-17838.
Jepson et al. (1994) Plant Mol. Biol. 26:1855-1866.
Jing et al. (2011) BMC Biochemistry 12:44.
Jolivet et al. (2014) Plant Physiol. Biochem. 42:501-509.
Jones et al. (1995) Plant Cell 7: 359-371.
Karmakar et al. (2010) Bioresource Technology 101:7201-7210.
Kelly et al. (2011) Plant Physiol. 157: 866-875.
Kelly et al (2013a) Plant Biotech. J. 11:355-361.
Kelly et al. (2013b) Plant Physiol. 162:1282-1289.
Kereszt et al. (2007) Nature Protocols 2:948-952.
Knutzon et al. (1995) Plant Physiol 109:999-1006.
Knutzon et al. (1999) Plant Physiology 120:739-746.
Kim et al. (2014) Biotechnology for Biofuels 7:36.
Kim et al. (2015a) Plant J 84:1021-1033.
Kim et al. (2015b) Journal of Experimental Botany 66:4251-4265.
Kim et al. (1996) Proc. Natl. Acad. Sci. USA 93:1156-1160.
Kim et al. (2016) Plant Physiol 171: 1951-1964.
Klemens et al. (2013) Plant Physiol 163: 1338-1352.
Koziel et al. (1996) Plant Mol. Biol. 32:393-405.
Kuhn et al. (2009) J. Biol. Chem. 284:34092-102.
Kunst et al. (1988) Proc. Natl. Acad. Sci. U.S.A. 85:4143-4147.
Kwong et al. (2003) Plant Cell 15:5-18.
Lacroix et al. (2008) Proc. Natl. Acad. Sci. U.S.A. 105: 15429-15434.
Laibach et al. (2015). J. Biotechnol. 201: 15-27.
Lardizabal et al. (2008) Plant Physiol. 148: 89-96.
Laureles et al. (2002) J Agric Food Chem 50:1581-1586.
Lebrun et al. (1987) Nucl. Acids Res. 15:4360.
Laux et al. (1996) Development 122: 87-96.
Lazo et al. (1991) Bio/Technology 9:963-967.
Lee et al. (1998) Science 280:915-918.
Lee et al. (2003) Proc. Natl. Acad. Sci. U.S.A. 100:2152-2158.
Li et al. (1996) FEBS Lett. 379:117-121.
Li et al. (2006) Phytochemistry 67: 904-915.
Li et al. (2017) Plant Physiol 173:2208-2224.
Lin et al. (2005) Plant Physiol. Biochem. 43:770-776.
Linder et al. (2005). FEMS Microbiol. Rev. 29: 877-896.
Liu and Godwin (2012). Plant Cell Reports 31, 999-1007.
Liu et al. (2010) Plant Physiol. Biochem. 48: 9-15.
Liu et al. (2012) Prog Lipid Res 51:350-377.
Liu et al. (2012) J Exp Bot 63: 3727-3740.
Liu et al. (2014) BMC Plant Biol. 14: 73.
Lotan et al. (1998) Cell 93: 1195-1205.
Lu et al. (2009) Proc Natl Acad of Sci USA 106:18837-18842.
Luerssen et al. (1998) Plant J. 15: 755-764.
Lui et al. (2009) J. Agric. Food Chem. 57: 2308-2313.
Ma et al. (2016) Plant Journal doi: 10.1111/tpj.13244.
MacEachran et al. (2010). Appl. Environ. Microbiol. 76: 7217-7225.
Maher and Bressler (2007) Bioresource Technology 98:2351-2368.
Matsuoka et al. (1994) Plant J. 6:311-319.
Matsuoka and Minami (1989) Eur. J. Biochem. 181: 593-598.
McCleary et al. (2013) J AOAC Int 93:221-233.
McCleary et al. (2015) Starch 67:860-883.
McElroy et al. (1990) Plant Cell 2: 163-171.
McKinley et al. (2016) Plant Journal: doi:10.1111/tpj.13269.
Meier et al. (1997) FEBS Lett. 415:91-95.
Millar et al. (2000) Trends in Plant Science 5:95-101.
Millar and Waterhouse (2005). Funct Integr Genomics 5:129-135.
Miller (1984). Crop Sci 24:1224-1224.
Mojica et al. (2000) Mol Microbiol 36:244-246.
Moreno-Perez (2012) PNAS 109:10107-10112.
Mongrand et al. (1998) Phytochemistry 49:1049-1064.
Moyle and Birch (2013) Theor. Appl. Genet. 126:1775-1782.
Mu et al. (2008) Plant Physiol. 148:1042-1054.
Mudge et al. (2013) Plant Biotechnol. J. 11:502-509.

Murashige and Skoog (1962). Physiol Plant 15:473-497.
Murphy et al. (2012). Protoplasma 249:541-585.
Needleman and Wunsch (1970) J. Mol Biol. 45: 443-453.
Nilsson et al. (2012) Physiol. Plantarum 144: 35-47.
Nomura et al. (2000) Plant Mol. Biol. 44: 99-106.
OECD/FAO (2015) OECD-FAO Agricultural Outlook (Edition 2015). Paris: OECD Publishing.
Ohlrogge and Browse (1995) Plant Cell 7: 957-970.
Padidam (2003) Curr. Opin. Plant Biol. 6:169-77.
Padidam et al. (2003) Transgenic Res. 12:101-9.
Parthibane et al. (2012a) J. Biol. Chem. 287:1946-1965.
Parthibane et al. (2012b) Plant Physiol. 159:95-104.
Pasquinelli et al. (2005). Curr. Opin. Genet. Develop. 15:200-205.
Perez-Vich et al. (1998) J.A.O.C.S. 75:547-555.
Perrin et al. (2000) Mol. Breed. 6:345-352.
Petrie et al. (2012) PLOS One 7: e35214.
Phillips et al. (2002) Journal of Food Composition and Analysis 12:123-142.
Potenza et al. (2004) In Vitro Cell Dev. Biol. Plant 40:1-22.
Poxleitner et al. (2006) Plant J. 47:917-933.
Prosky et al. (1985) J AOAC Chem 68:677-679.
Pyc et al. (2017) Trends in Plant Sci. 22:596-609.
Qazi et al. (2012) Journal of Plant Physiology 169: 605-613.
Qiu et al. (2001) J. Biol. Chem. 276:31561-3156.
Reynolds et al. (2015) Frontiers in Plant Science 6.
Robson et al. (2004) Plant Biotechnol J 2:101-112.
Rossell and Pritchard (1991) Analysis of Oilseeds, Fats and Fatty Foods. Elsevier
Ruuska et al. (2002) Plant Cell 14:1191-1206.
Saha et al. (2006) Plant Physiol. 141:1533-1543.
Sanjaya et al. (2011) Plant Biotechnol J 9:874-883.
Santos-Mendoza et al. (2005) FEBS Lett. 579:4666-4670.
Santos-Mendoza et al. (2008) Plant J. 54:608-620.
Schneider et al. (2012) Plant Biol 14: 325-336.
Schnurr et al. (2002) Plant Physiol 129:1700-1709.
Shaw et al. (1959) J Soil Sci 10:316-326.
Shen et al. (2010) Plant Phys. 153: 980-987.
Shen et al. (2014). Biochem. Biophys. Res. Comm. 448: 365-371.
Semwal et al. (2011) Bioresource Technology 102:2151-2161.
Shen et al. (2010) Plant Physiol. 153:980-987.
Shiina et al. (1997) Plant Physiol. 115:477-483.
Shimada and Hara-Nishimura (2010) Biol. Pharm. Bull. 33:360-363.
Shimada et al. (2014) Plant Physiol. 164:105-118.
Shockey et al. (2002) Plant Physiol 129:1710-1722.
Shockey et al. (2016) Plant Physiol 170:163-179.
Singer et al. (2016) Journal of Experimental Botany 67:4627-4638.
Slade and Knauf (2005) Transgenic Res. 14: 109-115.
Smith et al. (2000) Nature 407:319-320.
Somerville et al. (2000) Lipids. In BB Buchanan, W Gruissem, R L Jones, eds, Biochemisty and Molecular Biology of Plants. American Society of Plant Physiologists, Rockville, MD, pp 456-527.
Sorokin et al. (2009) Biochemistry Biokhimiia 74:1411-1442.
Srinivasan et al. (2007) Planta 225:341-51.
Stalker et al. 1988 Science 242: 419-423.
Stone et al. (2001) Proc. Natl. Acad. Sci. U.S.A. 98: 11806-11811.
Stone et al. (2008) Proc. Natl. Acad. Sci. U.S.A. 105: 3151-3156.
Tai et al. (2002). Biosci. Biotechnol. Biochem. 66: 2146-2153.
Tan et al. (2011) Plant Physiol. 156:1577-1588.
Taylor (1997) The Plant Cell 9:1245-1249.
Thillet et al. (1988) J. Biol. Chem 263:12500-12508.
Tingay et al. (1997) Plant J. 11:1369-1376.
Tjellstrom et al. (2013) FEBS Lett 587:936-942.
To et al. (2012) Plant Cell 24:5007-5023.
Ulmasov et al. (1995) Plant Physiol. 108:919-927.
van de Loo et al. (1995) Proc Natl Acad Sci USA. 92:6743-6747.
van Erp et al. (2011) Plant Physiol 155:683-693.
van Erp et al. (2015) Plant Physiol 168:36-46.
Vanhercke et al. (2013) FEBS Letters 587:364-369.
Vanhercke et al. (2014a). Plant Biotech. J. 12:231-239.
Vanhercke et al. (2014b) Biocatalysis and Agricultural Biotechnology 3:75-80.
Vanhercke et al. (2017) Metabolic Engineering 39:237-246.
Vieler et al. (2012) Plant Physiol. 158:1562-1569.
Voinnet et al. (2003) Plant J. 33:949-956.
Voelker et al. (1992) Science 257:72-74.
Voelker et al. (1996) Plant J 9:229-241.
Wang et al. (2002) Plant J 32:831-843.
Wang et al. (2007) Plant J 52: 716-729.
Waterhouse et al. (1998). Proc. Natl. Acad. Sci. U.S.A. 95:13959-13964.
Weissbach and Weissbach, (1989) Methods for Plant Mol Biol, Academic Press.
Weissbach et al., In: Methods for Plant Molecular Biology, Academic Press, San Diego, Calif., (1988).
Weissman (2001) Molec Cell Biol. 2:169-178.
Wesley et al. (2001) Plant J. 27:581-590.
Wiberg et al. (1997) Planta 203:341-348.
Wiberg et al. (2000) Planta 212:33-40.
Winichayakul et al. (2013) Plant Physiol. 162:626-639.
Wood (2014) EMBO Reports 15:201-202.
Wood et al. (2009) Plant Biotech. J. 7: 914-924.
Wu et al. (2014) In Vitro Cellular and Dev. Biol.-Plant 50:9-18.
Xu et al. (2008) Plant Biotechnol J 6:799-818.
Xu et al (2010) Plant and Cell Physiol. 51:1019-1028.
Xu et al (2005) Plant Cell 17:3094-3110.
Xu et al (2008) Plant Cell 20:2190-2204.
Yamagishi et al. (2005) Pl Physiol 139: 163-173.
Yamasaki et al. (2004) Plant Cell 16:3448-3459.
Yang et al. (2003) Planta 216:597-603.
Yang et al. (2010) Proc. Natl. Acad. Sci. U.S.A. 107:12040-12045.
Yeap et al. (2017) Plant Journal 91: 97-113.
Yen et al. (2002) Proc. Natl. Acad. Sci. U.S.A. 99:8512-8517.
Yen et al. (2005) J. Lipid Res. 46: 1502-1511.
Yokoyama et al. (1994) Mol Gen Genet 244: 15-22.
Yuan et al. (1995) Proc. Natl. Acad. Sci. U.S.A. 92:10639-10643.
Zale et al. (2016) Plant Biotech J. 14: 661-669.
Zhang et al. (2015) PLoS ONE 10, e0144653.
Zheng et al. (2009) Pl Physiol 21: 2563-2577.
Zhou et al. (2011) J Biol Chem 286:43644-43650.
Zolman et al. (2001) Plant Physiol. 127:1266-1274.

The invention claimed is:

1. A process for producing extracted plant lipid, comprising the steps of:
   a) obtaining one or more vegetative plant parts comprising lipid, the lipid comprising a total fatty acid content which comprises fatty acids in an esterified form, the fatty acids comprising a level of total medium chain fatty acids (MCFA) that is at least 25% of the total fatty acid content on a weight basis, wherein the MCFA comprises a level of lauric acid (C12:0), wherein the level of lauric acid is between 15% and 55% of the total fatty acid content on a weight basis, and
   b) extracting lipid from the vegetative plant part(s), thereby producing the extracted plant lipid.

2. The process of claim 1, wherein the extracted plant lipid is in the form of an oil, wherein between 95% and 98% by weight of the oil is the lipid.

3. The process of claim 1, wherein the vegetative plant part is a plant leaf or stem.

4. The process of claim 1, wherein the vegetative plant part is from a monocotyledonous plant.

5. Extracted plant lipid which was extracted from a vegetative plant part, comprising a total fatty acid content which comprises fatty acids in an esterified form, the fatty acids comprising a level of medium chain fatty acids in the total fatty acid content of the extracted plant lipid that is at least 25% on a weight basis, wherein the medium chain fatty acids comprise a level of lauric acid (C12:0), wherein the level of lauric acid in the total fatty acid content of the extracted plant lipid is between 15% and 55% on a weight basis.

6. The process of claim 1, wherein the level of medium chain fatty acids in the total fatty acid content of the vegetative plant parts is between 25% and 55% of the total fatty acid content on a weight basis.

7. The process of claim 6, wherein the process further comprises converting the extracted plant lipid to a hydrocarbon product.

8. The process of claim 7, wherein the hydrocarbon product is selected from fatty acid esters, an alkane, an alkene, and a biofuel.

9. A process for producing an industrial product, the process comprising the steps of:
  i) obtaining extracted plant lipid which was produced by the process of claim 6,
  ii) converting at least some of the extracted plant lipid to the industrial product by applying heat, chemical, or enzymatic means, or any combination thereof, to the extracted plant lipid, and
  iii) recovering the industrial product,
thereby producing the industrial product.

10. A process for producing fuel, the process comprising the steps of:
  i) obtaining extracted plant lipid which was produced by the process of claim 6, and
  ii) reacting the extracted plant lipid with an alcohol, optionally in the presence of a catalyst, to produce alkyl esters.

11. The process of claim 10, further comprising a step of blending the alkyl esters with petroleum based fuel.

12. A process for producing a synthetic diesel fuel, the process comprising:
  i) obtaining extracted plant lipid which was produced by the process of claim 6, and
  ii) converting the extracted plant lipid to a synthetic diesel fuel by a process comprising fractionation.

13. The process of claim 12, wherein step ii) comprises selecting hydrocarbon compounds which condense between 150° C. and 200° C. or between 200° C. and 300° C.

14. The process of claim 4, wherein vegetative plant part is from a plant from the family Poaceae.

15. The process of claim 14, wherein the vegetative plant part is from a Sorghum species, a *Zea mays*, a *Miscanthus* species, or a *Panicum virgatum* plant.

16. The process of claim 6 which further comprises recovering the extracted plant lipid by collecting it in a container and/or one or more of degumming, deodorising, decolourising, drying, fractionating the extracted plant lipid, removing wax esters from the extracted plant lipid, or analysing the fatty acid composition of the extracted plant lipid.

17. The process of claim 4, wherein the level of medium chain fatty acids in the total fatty acid content of the vegetative plant parts is between 25% and 55% of the total fatty acid content on a weight basis.

18. The process of claim 14, wherein the level of medium chain fatty acids in the total fatty acid content of the vegetative plant parts is between 25% and 55% of the total fatty acid content on a weight basis.

19. The process of claim 15, wherein the level of medium chain fatty acids in the total fatty acid content of the vegetative plant parts is between 25% and 55% of the total fatty acid content on a weight basis.

20. The process of claim 6, wherein the total fatty acid content of the extracted plant lipid and/or the total fatty acid content of triacylglycerol of the extracted plant lipid comprises a level of lauric acid (C12:0) of at least 30% and a level of myristic acid (C14:0) of between 2% and 10%.

21. The process of claim 6, wherein the total fatty acid content of the extracted plant lipid and/or the total fatty acid content of triacylglycerol of the extracted plant lipid comprises a level of lauric acid (C12:0) of at least 40% and a level of myristic acid (C14:0) of between 2% and 10%.

22. The process of claim 6, wherein the total fatty acid content of the extracted plant lipid and/or the total fatty acid content of triacylglycerol of the extracted plant lipid comprises a level of lauric acid (C12:0) of at least 45% and a level of myristic acid (C14:0) of between 2% and 10%.

23. The extracted plant lipid of claim 5, wherein the level of medium chain fatty acids in the total fatty acid content of the vegetative plant parts is between 25% and 55% of the total fatty acid content on a weight basis.

24. The extracted plant lipid of claim 23, wherein the total fatty acid content of the extracted plant lipid, and/or the total fatty acid content of triacylglycerol of the extracted plant lipid comprises a level of palmitic acid (C16:0) of between 2% and 18%.

25. The extracted plant lipid of claim 23, wherein the total fatty acid content of the extracted plant lipid, and/or the total fatty acid content of triacylglycerol of the extracted plant lipid comprises a level of myristic acid (C14:0) of between 1% and 10%.

26. The extracted plant lipid of claim 23, wherein the total fatty acid content of the extracted plant lipid, and/or the total fatty acid content of triacylglycerol of the extracted plant lipid comprises a ratio of lauric acid (C12:0):myristic acid (C14:0) of about 4:1.

27. The extracted plant lipid of claim 23, wherein the total fatty acid content of the extracted plant lipid, and/or the total fatty acid content of triacylglycerol of the extracted plant lipid comprises
  i) a level of oleic acid of less than 10%;
  ii) a level of linoleic acid (LA) of less than 20%; and
  iii) a level of α-linolenic acid (ALA) of less than 20%.

28. The extracted plant lipid of claim 23, wherein the extracted plant lipid comprises tri-laurin.

29. The process of claim 6, wherein the total fatty acid content of the extracted lipid, and/or the total fatty acid content of triacylglycerol of the extracted plant lipid comprises a level of palmitic acid (C16:0) of between 2% and 18%.

30. The process of claim 6, wherein the total fatty acid content of the extracted plant lipid and/or the total fatty acid content of the triacylglycerol of the extracted plant lipid comprises a level of myristic acid (C14:0) of between 1% and 10%.

31. The process of claim 6, wherein the fatty acid content of the extracted plant lipid, and/or the total fatty acid content of the triacylglycerol of the extracted plant lipid comprises a ratio of lauric acid (C12:0):myristic acid (C14:0) of about 4:1.

32. The process of claim 6, wherein the total fatty acid content of the extracted plant lipid, and/or the total fatty acid content of triacylglycerol of the extracted plant lipid comprises:
  i) a level of oleic acid of less than 10%;
  ii) a level of linoleic acid (LA) of less than 20%; and
  iii) a level of α-linolenic acid (ALA) of less than 20%.

33. The process of claim 6, wherein the extracted plant lipid comprises tri-laurin.

* * * * *